US012533424B2

(12) United States Patent
Thomas et al.

(10) Patent No.: US 12,533,424 B2
(45) Date of Patent: Jan. 27, 2026

(54) SUPPLEMENTATION OF LIVER ENZYME EXPRESSION

(71) Applicant: Metagenomi, Inc., Emeryville, CA (US)

(72) Inventors: Brian C. Thomas, Berkeley, CA (US); Alan Brooks, Clayton, CA (US)

(73) Assignee: Metagenomi, Inc., Emeryville, CA (US)

( * ) Notice: Subject to any disclaimer, the term of this patent is extended or adjusted under 35 U.S.C. 154(b) by 0 days.

(21) Appl. No.: 18/959,371

(22) Filed: Nov. 25, 2024

(65) Prior Publication Data

US 2025/0161491 A1 May 22, 2025

Related U.S. Application Data

(63) Continuation of application No. PCT/US2023/067509, filed on May 25, 2023.

(60) Provisional application No. 63/396,421, filed on Aug. 9, 2022, provisional application No. 63/359,288, filed on Jul. 8, 2022, provisional application No. 63/345,526, filed on May 25, 2022.

(51) Int. Cl.

| | |
|---|---|
| ***A61K 48/00*** | (2006.01) |
| ***A61K 9/1272*** | (2025.01) |
| ***A61K 9/51*** | (2006.01) |
| ***A61K 38/37*** | (2006.01) |
| ***C12N 5/071*** | (2010.01) |
| ***C12N 9/22*** | (2006.01) |
| ***C12N 15/11*** | (2006.01) |
| ***C12N 15/86*** | (2006.01) |
| ***C12N 15/88*** | (2006.01) |
| ***C12N 15/90*** | (2006.01) |

(52) U.S. Cl.

CPC .......... *A61K 48/005* (2013.01); *A61K 9/1272* (2013.01); *A61K 9/5123* (2013.01); *A61K 38/37* (2013.01); *C12N 5/067* (2013.01); *C12N 9/22* (2013.01); *C12N 15/111* (2013.01); *C12N 15/86* (2013.01); *C12N 15/88* (2013.01); *C12N 15/907* (2013.01); *C12N 2310/20* (2017.05); *C12N 2750/14143* (2013.01)

(58) Field of Classification Search

None

See application file for complete search history.

(56) References Cited

U.S. PATENT DOCUMENTS

| | | | | |
|---|---|---|---|---|
| 9,394,545 | B2 * | 7/2016 | Rebar | C12N 9/96 |
| 11,529,427 | B2 * | 12/2022 | Brooks | C12N 9/647 |
| 11,713,471 | B2 | 8/2023 | Thomas et al. | |
| 12,123,014 | B2 | 10/2024 | Thomas et al. | |
| 2018/0371498 | A1 | 12/2018 | Gill et al. | |
| 2019/0264186 | A1 | 8/2019 | Yamano et al. | |
| 2020/0102577 | A1 | 4/2020 | Lee et al. | |
| 2020/0149009 | A1 | 5/2020 | Regev et al. | |
| 2020/0384125 | A1 * | 12/2020 | Brooks | C12N 15/113 |
| 2021/0115474 | A1 * | 4/2021 | McCoy | C07K 16/28 |
| 2022/0080055 | A9 | 3/2022 | Brooks | |
| 2023/0108784 | A1 | 4/2023 | Zhang et al. | |
| 2023/0190809 | A1 | 6/2023 | Bedoya et al. | |
| 2023/0227857 | A1 | 7/2023 | Thomas et al. | |
| 2023/0416710 | A1 * | 12/2023 | Thomas | C12N 15/907 |
| 2024/0218339 | A1 | 7/2024 | Thomas et al. | |

FOREIGN PATENT DOCUMENTS

| | | | | |
|---|---|---|---|---|
| CN | 110684823 | A | 1/2020 | |
| CN | 110904239 | A | 3/2020 | |
| EP | 3617311 | A1 | 3/2020 | |
| WO | WO-2016205711 | A1 | 12/2016 | |
| WO | WO-2017127807 | A1 | 7/2017 | |
| WO | WO-2017189308 | A1 | 11/2017 | |
| WO | WO-2019191495 | A1 | 10/2019 | |
| WO | WO-2020030984 | A2 | 2/2020 | |
| WO | WO-2020077135 | A1 | 4/2020 | |
| WO | WO-2020172343 | A2 | 8/2020 | |
| WO | WO-2020227307 | A1 | 11/2020 | |
| WO | WO-2021046442 | A1 | 3/2021 | |
| WO | WO-2021067788 | A1 | 4/2021 | |
| WO | WO-2021178933 | A2 | 9/2021 | |
| WO | WO-2021178934 | A1 | 9/2021 | |
| WO | WO-2022056489 | A1 | 3/2022 | |
| WO | WO-2022159758 | A1 | 7/2022 | |
| WO | WO-2022159892 | A1 | 7/2022 | |
| WO | WO 2022/256462 | A1 * | 12/2022 | C12N 9/22 |
| WO | WO-2023019227 | A1 | 2/2023 | |
| WO | WO-2023019263 | A1 | 2/2023 | |
| WO | 2023028348 | A1 | 3/2023 | |
| WO | WO-2023039378 | A1 | 3/2023 | |
| WO | WO-2024026499 | A2 | 2/2024 | |
| WO | WO-2024187140 | A2 | 9/2024 | |
| WO | 2025097031 | A1 | 5/2025 | |
| WO | WO-2025117858 | A1 | 6/2025 | |

OTHER PUBLICATIONS

Bu, X., et al., CD38 knockout suppresses tumorigenesis in mice and clonogenic growth of human lung cancer cells, Carcinogenesis, 39(2): 242-251 (2018).

Database Registry, Genbank, Accession No. OD003705 (Entered Dec. 11, 2020) retrieved on Feb. 14, 2025 from <https://ncbi.nlm.nih.gov/nuccore/OD003705>.

Database Registry, Genbank, Accession No. OU696696 (Entered Feb. 9, 2022) retrieved on Feb. 14, 2025 from <https://ncbi.nlm.nih.gov/nuccore/OU696696>.

Goltsman, D.S.A., et al., Novel Type V-A CRISPR Effectors Are Active Nucleases with Expanded Targeting Capabilities, CRISPR J, 3(6): 454-461 (2020).

Harms, M.J., et al., Analyzing protein structure and function using ancestral gene reconstruction, Curr Opin Struct Biol, 20(3): 360-366 (2010).

(Continued)

*Primary Examiner* — Nancy J Leith

(74) *Attorney, Agent, or Firm* — Antheros Legal Advisors LLP

(57) ABSTRACT

Described herein are methods, compositions, and systems derived from uncultivated microorganisms useful supplementing liver enzyme deficiencies.

7 Claims, 29 Drawing Sheets

Specification includes a Sequence Listing.

(56) References Cited

OTHER PUBLICATIONS

Kararoudi, M.N., et al., CD38 deletion of human primary NK cells eliminates daratumumab-induced fratricide and boosts their effector activity, Blood, 136(21): 2416-2427 (2020).
Liu, Y., et al., Designer lipids advance systemic siRNA delivery, Mol Ther, 18(4): 669-670 (2010).
Love, K.T., et al., Lipid-like materials for low-dose, in vivo gene silencing, Proc Natl Acad Sci USA, 107(5): 1864-1869 (2010).
Moon, S.B., et al., Recent advances in the CRISPR genome editing tool set, Exp Mol Med, 51:130, pp. 1-11 (2019).
PCT/US2023/067509 International Search Report and Written Opinion mailed Nov. 21, 2023.
PCT/US2023/071286 International Search Report and Written Opinion mailed Feb. 16, 2024.
PCT/US2024/019205 International Search Report and Written Opinion mailed Aug. 8, 2024.
Price, M.N., et al., FastTree 2—approximately maximum-likelihood trees for large alignments, PLoS One, 5(3): e9490 (2010).
Singh, R.K., et al., Protein Engineering Approaches in the Post-Genomic Era, Curr Protein Pept Sci, 19(1): 5-15 (2017).
Stamatakis, A., RAxML version 8: a tool for phylogenetic analysis and post-analysis of large phylogenies, Bioinformatics, 30(9): 1312-1313 (2014).
Stella, S., et al., Class 2 CRISPR-Cas RNA-guided endonucleases: Swiss Army knives of genome editing, Nat Struct Mol Biol, 24: 882-892 (2017).
Tang, Y., et al., Class 2 CRISPR/Cas: an expanding biotechnology toolbox for and beyond genome editing, Cell Biosci, 8:59, pp. 1-13 (2018).
Yang, Z., PAML 4: phylogenetic analysis by maximum likelihood, Mol Biol Evol, 24(8): 1586-1591 (2007).
Zetsche, B., et al., Cpf1 is a single RNA-guided endonuclease of a class 2 CRISPR-Cas system, Cell, 163(3): 759-771 (2015).
Zetsche, B., et al., Multiplex gene editing by CRISPR-Cpf1 using a single crRNA array, Nat Biotechnol, 35(1): 31-34 (2017).
Zhang, M., et al., Propagated Perturbations from a Peripheral Mutation Show Interactions Supporting WW Domain Thermostability, Structure, 26(11): 1474-1485 (2018).
Zhang, Y., et al., CRISPR-Cpf1 correction of muscular dystrophy mutations in human cardiomyocytes and mice, Sci Adv, 3(4): e1602814 (2017).
Cancellieri, S., et al., CRISPRitz: rapid, high-throughput and variant-aware in silico off-target site identification for CRISPR genome editing, Bioinformatics, 36(7): 2001-2008 (2020).
Edgar, R.C., Search and clustering orders of magnitude faster than BLAST, Bioinformatics, 26(19): 2460-2461 (2010).
Jumper, J., et al., Highly accurate protein structure prediction with AlphaFold, Nature, 596(7873): 583-589 (2021).
Katoh, K., et al., MAFFT multiple sequence alignment software version 7: improvements in performance and usability, Mol Biol Evol, 30(4): 772-780 (2013).
Kondo, M., et al., Expansion of human peripheral blood yo T cells using zoledronate, J Vis Exp, 55: e3182 (2011).
Lorenz, P., et al., Transcriptional repression mediated by the KRAB domain of the human C2H2 zinc finger protein Kox1/ZNF10 does not require histone deacetylation, Biol Chem, 382(4): 637-644 (2001).
Nuñez, J.K., et al., Genome-wide programmable transcriptional memory by CRISPR-based epigenome editing, Cell, 184(9): 2503-2519.e17 (2021).
O'Geen, H., et al., Ezh2-dCas9 and KRAB-dCas9 enable engineering of epigenetic memory in a context-dependent manner, Epigenetics Chromatin, 12(1): 26 (2019).
O'Leary, N.A., et al., Reference sequence (RefSeq) database at NCBI: current status, taxonomic expansion, and functional annotation, Nucleic Acids Res, 44(D1): D733-D745 (2016).
PCT/US2024/057905 International Search Report and Written Opinion mailed Mar. 24, 2025.
Ribeiro, S.T., et al., Five Layers of Receptor Signaling in γδ T-Cell Differentiation and Activation, Front Immunol, 6(15): pp. 1-9, (2015).
Sánchez Martínez, D., et al., Generation and proof-of-concept for allogeneic CD123 CAR-Delta One T (DOT) cells in acute myeloid leukemia, J Immunother Cancer, 10(9): e005400 (2022).
Sievers, N.M., et al., CARs: Beyond T Cells and T Cell-Derived Signaling Domains, Int J Mol Sci, 21(10): 3525 (2020).
Silva-Santos, B., et al., γδ T cells in cancer, Nat Rev Immunol, 15(110): 683-691 (2015).
Steinegger, M., et al., MMseqs2 enables sensitive protein sequence searching for the analysis of massive data sets, Nat Biotechnol, 35(11): 1026-1028 (2017).
International Search Report and Written Opinion for International Application No. PCT/US2024/054231 dated Feb. 24, 2025, 19 pages.

* cited by examiner

Animal 2502 excluded (outlier with 3% INDELS that exhibited injection site reaction and exacerbated cytokine response)

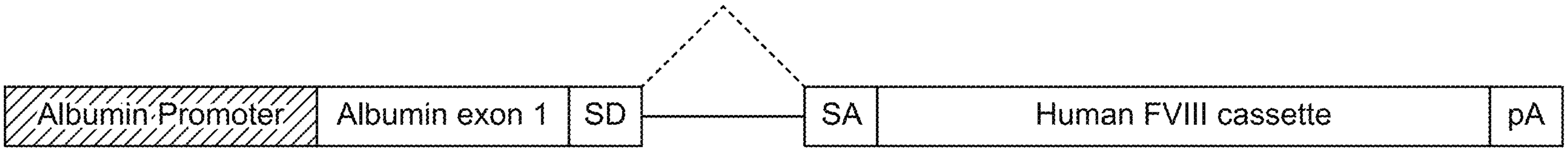

Predicted mRNA sequence of the Albumin exon 1- human FVIII junction (albumin exon 1 in italics, FVIII in normal text, junction created by correct splicing shown by |, GCC in bold is the first codon of mature FVIII that encodes Alanine. GCA underlined is the last codon of albumin exon 1 encoding Alanine)

*ATGAAGTGGGTAACCTTTCTCCTCCTCCTCTTCGTCTCCGGCTCTGCTTTTTCCAGGGGTGTGTTTCGCCGAGAAGCAC*|TGGCCACCAGAAGATATTACCTGGGAGC
TGTGGAACTGAGCTGGGACTACAT

The sequences of the primers are probe are:

- MG101-set1-FWD: TAACCTTTCTCCTCCTCCTCTT
- MG101-set1-REV: TCCACAGCTCCCAGGTAATA
- MG101-set1-Probe: TCTTCTGGTGGCCAGTGCTTCTC FAM, ZEN/3'IBFQ

FIG. 13

| | | | | | | SQ LINK N TERM | | | | | | | | | | | | | | | | | | | | | | | | | | | | | | | | | | PROTEASE | | | | | | # of Nglycan | # AA CHANGES |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| WT FVIII | A | I | E | P | R | S | F | S | Q | N | S | R | H | P | S | T | R | Q | K | B-DOMAIN | A | K | Q | G | R | T | E | R | L | C | S | Q | N | P | P | V | L | K | R | H | Q | R | E | I | T | | |
| BDD-SQ | A | I | E | P | R | S | F | S | Q | N | | | | | | | | | | | | | | | | | | | | | | | | P | P | V | L | K | R | H | Q | R | E | I | T | 0 | |
| VAR 1 | A | I | E | N | R | S | F | S | Q | N | | | | | | | | | | | | | | | | | | | | | | | | P | P | V | L | K | R | H | Q | R | E | I | T | 1 | 1 |
| VAR2 | A | I | E | P | R | N | F | S | Q | N | | | | | | | | | | | | | | | | | | | | | | | | P | P | V | L | K | R | H | Q | R | E | I | T | 1 | 1 |
| VAR3 | A | I | E | P | R | S | F | S | Q | N | | | | | | | | | | | | | | | | | | | | C | S | Q | N | P | P | V | L | K | R | H | Q | R | E | I | T | 1 | 0 |
| VAR4 | A | I | E | P | R | N | F | S | Q | N | | | | | | | | | | | | | | | | | | | | C | S | Q | N | P | P | V | L | K | R | H | Q | R | E | I | T | 2 | 1 |
| VAR5 | A | I | E | N | R | S | F | S | Q | N | | | | | | | | | | | | | | | | | | | | C | S | Q | N | P | P | V | L | K | R | H | Q | R | E | I | T | 2 | 1 |
| VAR6 | A | I | E | P | R | N | F | S | Q | N | | | | | | | | | | | | | | | | | | | | | | A | T | P | P | V | L | K | R | H | Q | R | E | I | T | 2 | 1 |
| VAR7 | A | I | E | N | R | S | N | F | S | Q | N | | | | | | | | | | | | | | | | | | | | | | | P | P | V | L | K | R | H | Q | R | E | I | T | 2 | 1 |
| VAR8 | A | I | E | N | R | S | N | F | S | Q | N | | | | | | | | | | | | | | | | | | | C | S | Q | N | P | P | V | L | K | R | H | Q | R | E | I | T | 3 | 1 |
| VAR9 | A | I | E | N | R | S | N | F | S | Q | N | | | | | | | | | | | | | | | | | | | | | A | T | P | P | V | L | K | R | H | Q | R | E | I | T | 3 | 1 |

Amino acid sequences of selected B-domain linker designs aligned

```
WT:    EPR SFSQNS-----//-----CSQNPPVLKRHQR
N6:    ENR SFSQNATNVSNNSNTSNASNVSPPVLKRHQR
VAR 2: EPR NFSQN ................PPVLKRHQR
VAR 3: EPR SFSQN ............CSQNPPVLKRHQR
VAR 4: EPR NFSQN ............CSQNPPVLKRHQR
VAR 8: ENRSNFSQN ............CSQNPPVLKRHQR
```

FIG. 22

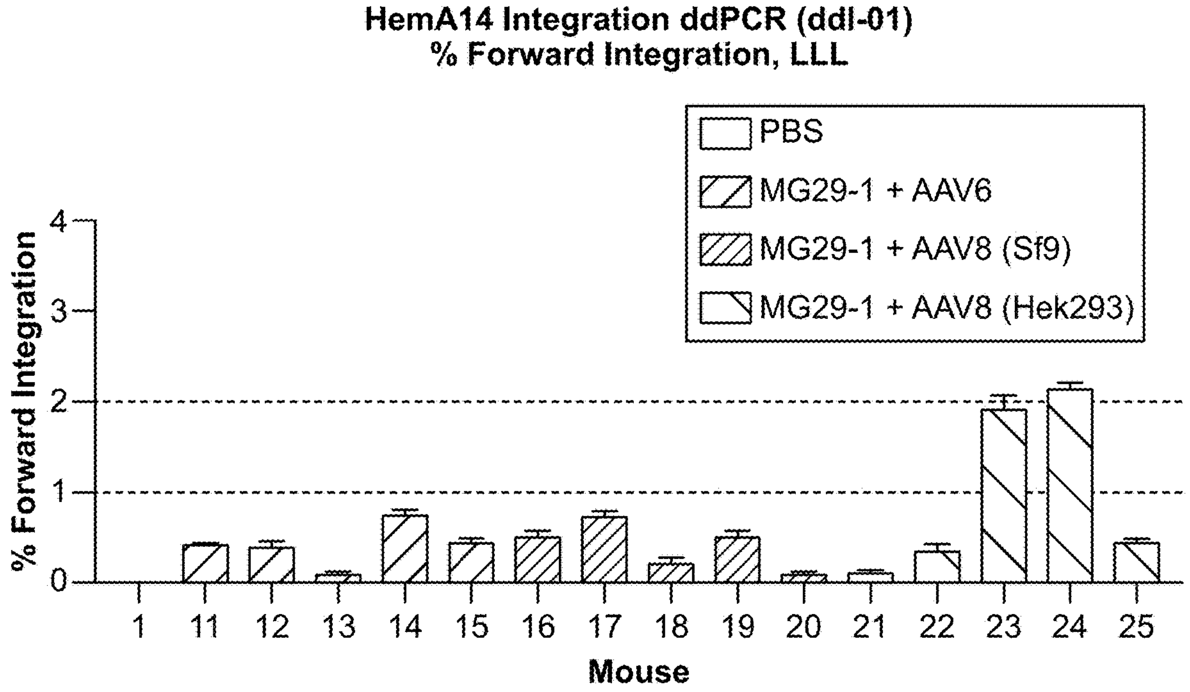
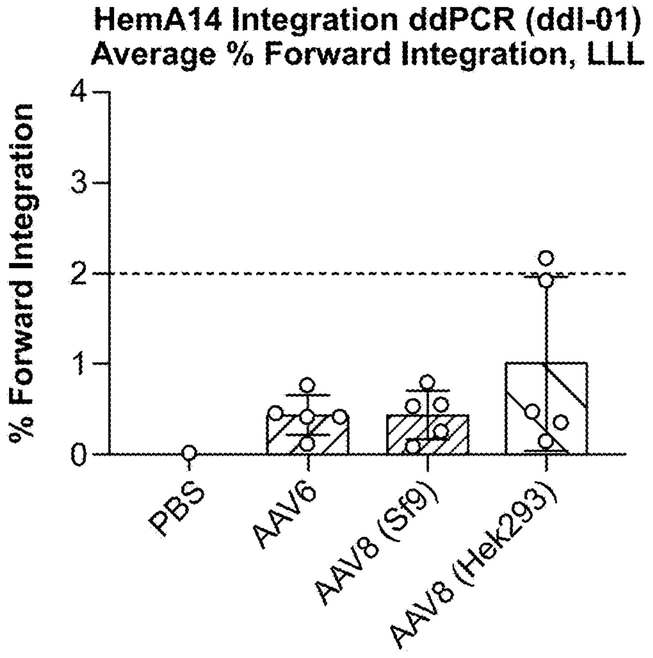
FIG. 28

SEQUENCE LISTING

```
Sequence total quantity: 160
SEQ ID NO: 1            moltype = DNA  length = 88
FEATURE                 Location/Qualifiers
source                  1..88
                        mol_type = genomic DNA
                        organism = Homo sapiens
SEQUENCE: 1
tgaattttgt aatcggttgg cagccaatga aatacaaaga tgagtctagt taataatcta  60
caattattgg ttaaagaagt atattagt                                     88

SEQ ID NO: 2            moltype = DNA  length = 69
FEATURE                 Location/Qualifiers
source                  1..69
                        mol_type = other DNA
                        organism = synthetic construct
SEQUENCE: 2
atgctttgca tacttctgcc tgctggggag cctggggact ttccacaccc taactgacac  60
acattccac                                                          69

SEQ ID NO: 3            moltype = DNA  length = 26
FEATURE                 Location/Qualifiers
source                  1..26
                        mol_type = genomic DNA
                        organism = Mus sp.
SEQUENCE: 3
tttcctgtaa cgatcgggaa ctggca                                       26

SEQ ID NO: 4            moltype = DNA  length = 26
FEATURE                 Location/Qualifiers
source                  1..26
                        mol_type = genomic DNA
                        organism = Mus sp.
SEQUENCE: 4
tgccagttcc cgatcgttac aggaaa                                       26

SEQ ID NO: 5            moltype = DNA  length = 26
FEATURE                 Location/Qualifiers
source                  1..26
                        mol_type = genomic DNA
                        organism = Mus sp.
SEQUENCE: 5
tttgagtgta gcagagagga accatt                                       26

SEQ ID NO: 6            moltype = DNA  length = 26
FEATURE                 Location/Qualifiers
source                  1..26
                        mol_type = genomic DNA
                        organism = Mus sp.
SEQUENCE: 6
aatggttcct ctctgctaca ctcaaa                                       26

SEQ ID NO: 7            moltype = DNA  length = 20
FEATURE                 Location/Qualifiers
source                  1..20
                        mol_type = other DNA
                        organism = synthetic construct
SEQUENCE: 7
agatatgcta tacctgatac                                              20

SEQ ID NO: 8            moltype = DNA  length = 157
FEATURE                 Location/Qualifiers
source                  1..157
```

```
                        mol_type = other DNA
                        organism = synthetic construct
SEQUENCE: 8
tgaattttgt aatcggttgg cagccaatga aatacaaaga tgagtctagt taataatcta  60
caattattgg ttaaagaagt atattagtat gctttgcata cttctgcctg ctggggagcc  120
tggggacttt ccacacccta actgacacac attccac                           157

SEQ ID NO: 9            moltype = DNA  length = 28
FEATURE                 Location/Qualifiers
source                  1..28
                        mol_type = other DNA
                        organism = synthetic construct
SEQUENCE: 9
actaaagaat tattctttta catttcag                                     28

SEQ ID NO: 10           moltype = DNA  length = 4365
FEATURE                 Location/Qualifiers
source                  1..4365
                        mol_type = other DNA
                        organism = synthetic construct
SEQUENCE: 10
gccaccagaa gatattacct gggagctgtg gaactgagct gggactacat gcagtctgac  60
ctgggagagc tgcctgtgga tgctagattt cctccaagag tgcccaagag cttccccttc  120
aacacctctg tggtgtacaa gaaaaccctg tttgtggaat tcacagacca cctgttcaat  180
attgccaagc ctagacctcc ttggatggga ctgctgggac ctacaattca ggctgaggtg  240
tatgacacag tggtcatcac cctgaagaac atggccagcc atcctgtgtc tctgcatgct  300
gtgggagtgt cttactggaa ggcttctgag ggagctgagt atgatgacca gacaagccag  360
agagagaaag aggatgacaa ggttttccct ggaggcagcc acacctatgt ctggcaggtc  420
ctgaaagaaa atggccctat ggcctctgat cctctgtgcc tgacatacag ctacctgagc  480
catgtggacc tggtcaagga cctgaattct ggcctgattg gagccctgct ggtgtgtaga  540
gaaggcagcc tggccaaaga gaaaacccag acactgcaca agttcatcct gctgtttgct  600
gtgtttgatg agggcaagag ctggcactct gagacaaaga acagcctgat gcaggacagg  660
gatgctgcct ctgctagagc ttggcctaag atgcacacag tgaatggcta tgtgaacaga  720
agcctgcctg gactgattgg ctgccacaga aagtctgtgt actggcatgt gattggcatg  780
ggcacaacac ctgaggtgca cagcatcttt ctggaaggac acaccttcct ggtgagaaac  840
catagacagg ccagcctgga aatcagccct atcaccttcc tgacagctca gaccctgctg  900
atggatctgg gccagtttct gctgttctgc cacatcagca gccaccagca tgatggcatg  960
gaagcctatg tgaaggtgga cagctgccct gaagaacccc agctgagaat gaagaacaat  1020
gaggaggctg aggactatga tgatgacctg acagactctg agatggatgt ggtcagattt  1080
gatgatgaca acagccccag cttcatccag atcagatctg tggccaagaa gcaccccaag  1140
acctgggtgc actatattgc tgctgaggaa gaggactggg attatgctcc tctggtgctg  1200
gcccctgatg acagaagcta caagagccag tacctgaaca atggccctca gagaattggc  1260
agaaagtata agaaagtgag attcatggcc tacacagatg agacattcaa gaccagagag  1320
gccattcagc atgagtctgg cattctgggc cctctgctgt atggagaagt gggagataca  1380
ctgctgatca tcttcaagaa ccaggccagc agaccctaca acatctaccc tcatggcatc  1440
acagatgtga gacccctgta ttccagaagg ctgcccaagg gagtgaagca cctgaaggac  1500
ttccctatcc tgcctggaga gatcttcaag tacaagtgga cagtgacagt ggaagatggc  1560
cccaccaagt ctgaccctag atgtctgaca agatactaca gcagctttgt gaacatggaa  1620
agagacctgg cctctggcct gattggacct ctgctgatct gctacaaaga atctgtggac  1680
cagagaggca accagatcat gtctgacaag agaaatgtga tcctgttttc tgtgtttgat  1740
gagaacagat cctggtatct gacagagaac atccagagat ttctgcccaa tcctgctgga  1800
gtgcagctgg aagatcctga gttccaggcc tccaacatca tgcactccat caatggctat  1860
gtgtttgaca gcctgcagct gtctgtgtgc ctgcatgaag tggcctactg gtacatcctg  1920
agcattggag cccagacaga cttcctgtct gtgttcttct ctggctacac cttcaagcac  1980
aagatggtgt atgaggatac cctgacactg ttcccattct ctggagagac agtgttcatg  2040
agcatggaaa accctggcct gtggatcctg ggctgtcaca actctgactt cagaaacaga  2100
ggcatgacag ccctgctgaa ggtgtccagc tgtgacaaga acacaggaga ctactatgag  2160
gacagctatg aggacatctc tgcctacctg ctgagcaaga acaatgccat tgagcccaga  2220
agcttcagcc agaatgccac caatgtgtcc aacaacagca acaccagcaa tgactccaat  2280
gtgtcccctc cagtgctgaa gagacaccag agagaaatca ccagaaccac actgcagtct  2340
gaccaagagg aaattgacta tgatgacacc atctctgtgg agatgaagaa agaagatttt  2400
gacatctatg atgaggatga gaatcagagc cccagatcct ttcagaaaaa gaccagacac  2460
tacttcattg ctgctgtgga gagactgtgg gactatggca tgtctagcag ccctcatgtg  2520
ctgagaaata gagcccagtc tggctctgtg ccccagttca agaaagtggt gttccaagag  2580
ttcacagatg gcagcttcac ccagccactg tatagaggag agctgaatga gcatctgggc  2640
ctgctgggcc cttatatcag agctgaagtg gaagataaca tcatggtcac cttcagaaat  2700
caggcctcta ggccctacag cttctacagc tccctgatca gctatgaaga ggaccagaga  2760
cagggagctg agcccagaaa gaactttgtg aagcccaatg agactaagac ctacttttgg  2820
aaggtgcagc accacatggc ccctacaaag gatgagtttg actgcaaggc ctgggcctac  2880
ttttctgatg tggatctgga aaaggatgtg cactctggac tcattggacc actgcttgtg  2940
tgccacacca acacactgaa ccctgctcat ggcagacaag tgacagtgca agagtttgcc  3000
ctgttcttca ccatctttga tgaaacaaag agctggtact tcacagagaa tatggagaga  3060
aactgcaggg ccccttgcaa catccagatg gaagatccca ccttcaaaga gaactacaga  3120
ttccatgcca tcaatggcta catcatggac acactgcctg gcctggttat ggctcaggat  3180
cagagaatca gatggtatct gctgtccatg ggctccaatg agaatatcca cagcatccac  3240
ttctctggcc atgtgttcac agtgagaaaa aaagaagagt acaaaatggc cctgtacaat  3300
ctgtaccctg ggtgtttga aacagtggaa atgctgcctt ccaaggctgg catttggaga  3360
gtggaatgtc tgattggaga gcacctccat gctggaatga gcaccctgtt tctggtgtac  3420
agcaacaagt gtcagacccc tctgggcatg gcctctggac acatcagaga cttccagatc  3480
```

```
acagcctctg gccagtatgg acagtgggct cctaaactgg ctagactgca ctactctggc  3540
agcatcaatg cctggtccac caaagagccc ttcagctgga tcaaggtgga cctgctggct  3600
cccatgatca tccatggaat caagacccag ggagccagac agaagttcag cagcctgtac  3660
atcagccagt tcatcatcat gtacagcctg gatggcaaga agtggcagac ctacagaggc  3720
aacagcacag gcacactcat ggtgttcttt ggcaatgtgg acagctctgg cattaagcac  3780
aacatcttca accctccaat cattgccaga tacatcagac tgcaccccac acactacagc  3840
atcagatcta ccctgagaat ggaactgatg ggctgtgacc tgaacagctg cagcatgccc  3900
ctgggaatgg aaagcaaggc catctctgat gcccagatca cagccagcag ctacttcacc  3960
aacatgtttg ccacttggag cccctccaag gctagactgc atctgcaggg cagaagcaat  4020
gcttggaggc cccaagtgaa caaccccaaa gagtggctgc aggtggactt tcaaaagacc  4080
atgaaagtga caggagtgac cacacaggga gtcaagtctc tgctgacctc tatgtatgtg  4140
aaagagttcc tgatctccag cagccaggat ggccaccagt ggaccctgtt tttccagaat  4200
ggcaaagtga aagtgttcca gggcaatcag gacagcttca cacctgtggt caactccctg  4260
gatcctccac tgctgaccag atacctgaga attcaccctc agtcttgggt gcaccagatt  4320
gctctgagaa tggaagtgct gggctgtgaa gctcaggacc tctac                 4365

SEQ ID NO: 11           moltype = DNA  length = 57
FEATURE                 Location/Qualifiers
source                  1..57
                        mol_type = other DNA
                        organism = synthetic construct
SEQUENCE: 11
tgatcctgaa taaaagatct ttattttcat tagatctgtg tgttggtttt ttgtgtg      57

SEQ ID NO: 12           moltype = DNA  length = 4936
FEATURE                 Location/Qualifiers
source                  1..4936
                        mol_type = other DNA
                        organism = synthetic construct
SEQUENCE: 12
atgctttgca tacttctgcc tgctggggag cctggggact ttccacaccc taactgacac  60
acattccact gaattttgta atcggttggc agccaatgaa atacaaagat gagtctagtt  120
aataatctac aattattggt taaagaagta tattagttca gattcagaat gtcaatattt  180
cctgtaacga tcgggaactg gcatttgagt gtagcagaga ggaaccattt ctcagtgtta  240
agcttactaa agaattattc ttttacattt cagtggccac cagaagatat tacctgggag  300
ctgtggaact gagctgggac tacatgcagt ctgacctggg agagctgcct gtggatgcta  360
gatttcctcc aagagtgccc aagagcttcc ccttcaacac ctctgtggtg tacaagaaaa  420
ccctgtttgt ggaattcaca gaccacctgt tcaatattgc caagcctaga cctccttgga  480
tgggactgct gggacctaca attcaggctg aggtgtatga cacagtggtc atcaccctga  540
agaacatggc cagccatcct gtgtctctgc atgctgtggg agtgtcttac tggaaggctt  600
ctgagggagc tgagtatgat gaccagacaa gccagagaga gaaagaggat gacaaggttt  660
tccctggagg cagccacacc tatgtctggc aggtcctgaa agaaaatggc cctatggcct  720
ctgatcctct gtgcctgaca tacagctacc tgagccatgt ggacctggtc aaggacctga  780
attctggcct gattggagcc ctgctggtgt gtagagaagg cagcctggcc aaagagaaaa  840
cccagacact gcacaagttc atcctgctgt ttgctgtgtt tgatgagggc aagagctggc  900
actctgagac aaagaacagc ctgatgcagg acagggatgc tgcctctgct agagcttggc  960
ctaagatgca cacagtgaat ggctatgtga acagaagcct gcctggactg attggctgcc  1020
acagaaagtc tgtgtactgg catgtgattg gcatgggcac aacacctgag gtgcacagca  1080
tctttctgga aggacacacc ttcctggtga gaaaccatag acaggccagc ctggaaatca  1140
gccctatcac cttcctgaca gctcagaccc tgctgatgga tctgggccag tttctgctgt  1200
tctgccacat cagcagccac cagcatgatg gcatggaagc ctatgtgaag gtggacagct  1260
gccctgaaga accccagctg agaatgaaga acaatgagga ggctgaggac tatgatgatg  1320
acctgacaga ctctgagatg gatgtggtca gatttgatga tgacaacagc cccagcttca  1380
tccagatcag atctgtggcc aagaagcacc ccaagacctg ggtgcactat attgctgctg  1440
aggaagagga ctgggattat gctcctctgg tgctggcccc tgatgacaga agctacaaga  1500
gccagtacct gaacaatggc cctcagagaa ttggcagaaa gtataagaaa gtgagattca  1560
tggcctacac agatgagaca ttcaagacca gagaggccat tcagcatgag tctggcattc  1620
tgggccctct gctgtatgga gaagtgggag atacactgct gatcatcttc aagaaccagg  1680
ccagcagacc ctacaacatc taccctcatg gcatcacaga tgtgagaccc ctgtattcca  1740
gaaggctgcc caagggagtg aagcacctga aggacttccc tatcctgcct ggagagatct  1800
tcaagtacaa gtggacagtg acagtggaag atggccccac caagtctgac cctagatgtc  1860
tgacaagata ctacagcagc tttgtgaaca tggaaagaga cctggcctct ggcctgattg  1920
gacctctgct gatctgctac aaagaatctg tggaccagag aggcaaccag atcatgtctg  1980
acaagagaaa tgtgatcctg ttttctgtgt ttgatgagaa cagatcctgg tatctgacag  2040
agaacatcca gagatttctg cccaatcctg ctggagtgca gctggaagat cctgagttcc  2100
aggcctccaa catcatgcac tccatcaatg gctatgtgtt tgacagcctg cagctgtctg  2160
tgtgcctgca tgaagtggcc tactggtaca tcctgagcat tggagcccag acagacttcc  2220
tgtctgtgtt cttctctggc tacaccttca agcacaagat ggtgtatgag gataccctga  2280
cactgttccc attctctgga gagacagtgt tcatgagcat ggaaaaccct ggcctgtgga  2340
tcctgggctg tcacaactct gacttcagaa acagaggcat gacagccctg ctgaaggtgt  2400
ccagctgtga caagaacaca ggagactact atgaggacag ctatgaggac atctctgcct  2460
acctgctgag caagaacaat gccattgagc ccagaagctt cagccagaat gccaccaatg  2520
tgtccaacaa cagcaacacc agcaatgact ccaatgtgtc ccctccagtg ctgaagagac  2580
accagagaga aatcaccaga accacactgc agtctgacca agaggaaatt gactatgatg  2640
acaccatctc tgtggagatg aagaaagaag attttgacat ctatgatgag gatgagaatc  2700
agagccccag atcctttcag aaaaagacca gacactactt cattgctgct gtggagagac  2760
tgtgggacta tggcatgtct agcagccctc atgtgctgag aaatagagcc cagtctggct  2820
ctgtgcccca gttcaagaaa gtggtgttcc aagagttcac agatggcagc ttcacccagc  2880
cactgtatag aggagagctg aatgagcatc tgggcctgct gggcccttat atcagagctg  2940
```

```
aagtggaaga taacatcatg gtcaccttca gaaatcaggc ctctaggccc tacagcttct  3000
acagctccct gatcagctat gaagaggacc agagacaggg agctgagccc agaaagaact  3060
ttgtgaagcc caatgagact aagacctact tttggaaggt gcagcaccac atggccccta  3120
caaaggatga gtttgactgc aaggcctggg cctacttttc tgatgtggat ctggaaaagg  3180
atgtgcactc tggactcatt ggaccactgc ttgtgtgcca caccaacaca ctgaaccctg  3240
ctcatggcag acaagtgaca gtgcaagagt ttgccctgtt cttcaccatc tttgatgaaa  3300
caaagagctg gtacttcaca gagaatatgg agagaaactg cagggcccct tgcaacatcc  3360
agatggaaga tcccaccttc aaagagaact acagattcca tgccatcaat ggctacatca  3420
tggacacact gcctggcctg gttatggctc aggatcagag aatcagatgg tatctgctgt  3480
ccatgggctc caatgagaat atccacagca tccacttctc tggccatgtg ttcacagtga  3540
gaaaaaaaga agagtacaaa atggccctgt acaatctgta ccctggggtg tttgaaacag  3600
tggaaatgct gccttccaag gctggcattt ggagagtgga atgtctgatt ggagagcacc  3660
tccatgctgg aatgagcacc ctgtttctgg tgtacagcaa caagtgtcag acccctctgg  3720
gcatggcctc tggacacatc agagacttcc agatcacagc ctctggccag tatggacagt  3780
gggctcctaa actggctaga ctgcactact ctggcagcat caatgcctgg tccaccaaag  3840
agcccttcag ctggatcaag gtggacctgc tggctcccat gatcatccat ggaatcaaga  3900
cccagggagc cagacagaag ttcagcagcc tgtacatcag ccagttcatc atcatgtaca  3960
gcctggatgg caagaagtgg cagacctaca gaggcaacag cacaggcaca ctcatggtgt  4020
tctttggcaa tgtggacagc tctggcatta agcacaacat cttcaaccct ccaatcattg  4080
ccagatacat cagactgcac ccccacacact acagcatcag atctaccctg agaatggaac  4140
tgatgggctg tgacctgaac agctgcagca tgcccctggg aatggaaagc aaggccatct  4200
ctgatgccca gatcacagcc agcagctact tcaccaacat gtttgccact tggagcccct  4260
ccaaggctag actgcatctg cagggcagaa gcaatgcttg gaggccccaa gtgaacaacc  4320
ccaaagagtg gctgcaggtg gactttcaaa agaccatgaa agtgacagga gtgaccacac  4380
agggagtcaa gtctctgctg acctctatgt atgtgaaaga gttcctgatc tccagcagcc  4440
aggatggcca ccagtggacc ctgtttttcc agaatggcaa agtgaaagtg ttccagggca  4500
atcaggacag cttcacacct gtggtcaact ccctggatcc tccactgctg accagatacc  4560
tgagaattca ccctcagtct tgggtgcacc agattgctct gagaatggaa gtgctgggct  4620
gtgaagctca ggacctctac tgatcctgaa taaaagatct ttattttcat tagatctgtg  4680
tgttggtttt ttgtgtgtat ttagctattt gagtgtagca gagaggaacc atttttcctg  4740
taacgatcgg gaactggcaa gatatgctat acctgatact gaattttgta atcggttggc  4800
agccaatgaa atacaaagat gagtctagtt aataatctac aattattggt taaagaagta  4860
tattagtatg ctttgcatac ttctgcctgc tggggagcct ggggactttc cacaccctaa  4920
ctgacacaca ttccac                                                  4936

SEQ ID NO: 13           moltype = DNA  length = 4931
FEATURE                 Location/Qualifiers
source                  1..4931
                        mol_type = other DNA
                        organism = synthetic construct
SEQUENCE: 13
atgctttgca tacttctgcc tgctggggag cctggggact ttccacaccc taactgacac  60
acattccact gaattttgta atcggttggc agccaatgaa atacaaagat gagtctagtt  120
aataatctac aattattggt taaagaagta tattagttca gattcagaat gtcaatatgc  180
cagttcccga tcgttacagg aaaaatggtt cctctctgct acactcaaat ctcaaagctt  240
actaaagaat tattctttta catttcagtg gccaccagaa gatattacct gggagctgtg  300
gaactgagct gggactacat gcagtctgac ctgggagagc tgcctgtgga tgctagattt  360
cctccaagag tgcccaagag cttccccttc aacacctctg tggtgtacaa gaaaaccctg  420
tttgtggaat tcacagacca cctgttcaat attgccaagc ctagacctcc ttggatggga  480
ctgctgggac ctacaattca ggctgaggtg tatgacacag tggtcatcac cctgaagaac  540
atggccagcc atcctgtgtc tctgcatgct gtgggagtgt cttactggaa ggcttctgag  600
ggagctgagt atgatgacca gacaagccag agagagaaag aggatgacaa ggttttccct  660
ggaggcagcc acacctatgt ctggcaggtc ctgaaagaaa atggccctat ggcctctgat  720
cctctgtgcc tgacatacag ctacctgagc catgtggacc tggtcaagga cctgaattct  780
ggcctgattg gagccctgct ggtgtgtaga gaaggcagcc tggccaaaga gaaaacccag  840
acactgcaca agttcatcct gctgtttgct gtgtttgatg agggcaagag ctggcactct  900
gagacaaaga acagcctgat gcaggacagg gatgctgcct ctgctagagc ttggcctaag  960
atgcacacag tgaatggcta tgtgaacaga agcctgcctg gactgattgg ctgccacaga  1020
aagtctgtgt actggcatgt gattggcatg ggcacaacac ctgaggtgca cagcatcttt  1080
ctggaaggac acaccttcct ggtgagaaac catagacagg ccagcctgga aatcagccct  1140
atcaccttcc tgacagctca gaccctgctg atggatctgg gccagtttct gctgttctgc  1200
cacatcagca gccaccagca tgatggcatg gaagcctatg tgaaggtgga cagctgccct  1260
gaagaacccc agctgagaat gaagaacaat gaggaggctg aggactatga tgatgacctg  1320
acagactctg agatggatgt ggtcagattt gatgatgaca acagccccag cttcatccag  1380
atcagatctg tggccaagaa gcaccccaag acctgggtgc actatattgc tgctgaggaa  1440
gaggactggg attatgctcc tctggtgctg gcccctgatg acagaagcta caagagccag  1500
tacctgaaca atggccctca gagaattggc agaaagtata agaaagtgag attcatggcc  1560
tacacagatg agacattcaa gaccagagag gccattcagc atgagtctgg cattctgggc  1620
cctctgctgt atggagaagt gggagataca ctgctgatca tcttcaagaa ccaggccagc  1680
agaccctaca acatctaccc tcatggcatc acagatgtga gacccctgta ttccagaagg  1740
ctgcccaagg gagtgaagca cctgaaggac ttccctatcc tgcctggaga gatcttcaag  1800
tacaagtgga cagtgacagt ggaagatggc cccaccaagt ctgaccctag atgtctgaca  1860
agatactaca gcagctttgt gaacatggaa agagacctgg cctctggcct gattggacct  1920
ctgctgatct gctacaaaga atctgtggac cagagaggca accagatcat gtctgacaag  1980
agaaatgtga tcctgttttc tgtgtttgat gagaacagat cctggtatct gacagagaac  2040
atccagagat ttctgcccaa tcctgctgga gtgcagctgg aagatcctga gttccaggcc  2100
tccaacatca tgcactccat caatggctat gtgtttgaca gcctgcagct gtctgtgtgc  2160
ctgcatgaag tggcctactg gtacatcctg agcattggag cccagacaga cttcctgtct  2220
gtgttcttct ctggctacac cttcaagcac aagatggtgt atgaggatac cctgacactg  2280
```

```
ttcccattct ctggagagac agtgttcatg agcatggaaa accctggcct gtggatcctg  2340
ggctgtcaca actctgactt cagaaacaga ggcatgacag ccctgctgaa ggtgtccagc  2400
tgtgacaaga acacaggaga ctactatgag gacagctatg aggacatctc tgcctacctg  2460
ctgagcaaga acaatgccat tgagcccaga agcttcagcc agaatgccac caatgtgtcc  2520
aacaacagca acaccagcaa tgactccaat gtgtcccctc cagtgctgaa gagacaccag  2580
agagaaatca ccagaaccac actgcagtct gaccaagagg aaattgacta tgatgacacc  2640
atctctgtgg agatgaagaa agaagatttt gacatctatg atgaggatga gaatcagagc  2700
cccagatcct ttcagaaaaa gaccagacac tacttcattg ctgctgtgga gagactgtgg  2760
gactatggca tgtctagcag ccctcatgtg ctgagaaata gagcccagtc tggctctgtg  2820
ccccagttca agaaagtggt gttccaagag ttcacagatg gcagcttcac ccagccactg  2880
tatagaggag agctgaatga gcatctgggc ctgctgggcc cttatatcag agctgaagtg  2940
gaagataaca tcatggtcac cttcagaaat caggcctcta ggccctacag cttctacagc  3000
tccctgatca gctatgaaga ggaccagaga cagggagctg agcccagaaa gaactttgtg  3060
aagcccaatg agactaagac ctacttttgg aaggtgcagc accacatggc ccctacaaag  3120
gatgagtttg actgcaaggc ctgggcctac ttttctgatg tggatctgga aaaggatgtg  3180
cactctggac tcattggacc actgcttgtg tgccacacca acacactgaa ccctgctcat  3240
ggcagacaag tgacagtgca agagtttgcc ctgttcttca ccatctttga tgaaacaaag  3300
agctggtact tcacagagaa tatggagaga aactgcaggg ccccttgcaa catccagatg  3360
gaagatccca ccttcaaaga gaactacaga ttccatgcca tcaatggcta catcatggac  3420
acactgcctg gcctggttat ggctcaggat cagagaatca gatggtatct gctgtccatg  3480
ggctccaatg agaatatcca cagcatccac ttctctggcc atgtgttcac agtgagaaaa  3540
aaagaagagt acaaaatggc cctgtacaat ctgtaccctg ggtgtttga aacagtggaa   3600
atgctgcctt ccaaggctgg catttggaga gtggaatgtc tgattggaga gcacctccat  3660
gctggaatga gcaccctgtt tctggtgtac agcaacaagt gtcagacccc tctgggcatg  3720
gcctctggac acatcagaga cttccagatc acagcctctg gccagtatgg acagtgggct  3780
cctaaactgg ctagactgca ctactctggc agcatcaatg cctggtccac caaagagccc  3840
ttcagctgga tcaaggtgga cctgctggct cccatgatca tccatggaat caagacccag  3900
ggagccagac agaagttcag cagcctgtac atcagccagt tcatcatcat gtacagcctg  3960
gatggcaaga agtggcagac ctacagaggc aacagcacag gcacactcat ggtgttcttt  4020
ggcaatgtgg acagctctgg cattaagcac aacatcttca accctccaat cattgccaga  4080
tacatcagac tgcaccccac acactacagc atcagatcta ccctgagaat ggaactgatg  4140
ggctgtgacc tgaacagctg cagcatgccc ctgggaatgg aaagcaaggc catctctgat  4200
gcccagatca cagccagcag ctacttcacc aacatgtttg ccacttggag cccctccaag  4260
gctagactgc atctgcaggg cagaagcaat gcttggaggc cccaagtgaa caaccccaaa  4320
gagtggctgc aggtggactt tcaaaagacc atgaaagtga caggagtgac cacacaggga  4380
gtcaagtctc tgctgacctc tatgtatgtg aaagagttcc tgatctccag cagccaggat  4440
ggccaccagt ggaccctgtt tttccagaat ggcaaagtga aagtgttcca gggcaatcag  4500
gacagcttca cacctgtggt caactccctg gatcctccac tgctgaccag atacctgaga  4560
attcaccctc agtcttgggt gcaccagatt gctctgagaa tggaagtgct gggctgtgaa  4620
gctcaggacc tctactgatc ctgaataaaa gatctttatt ttcattagat ctgtgtgttg  4680
gttttttgtg tgtatttagc taaatggttc ctctctgcta cactcaaatg ccagttcccg  4740
atcgttacag gaaaagatat gctatacctg atactgaatt ttgtaatcgg ttggcagcca  4800
atgaaataca aagatgagtc tagttaataa tctacaatta ttggttaaag aagtatatta  4860
gtatgctttg catacttctg cctgctgggg agcctgggga ctttccacac cctaactgac  4920
acacattcca c                                                       4931

SEQ ID NO: 14          moltype = RNA  length = 68
FEATURE                Location/Qualifiers
source                 1..68
                       mol_type = other RNA
                       organism = synthetic construct
modified_base          1..3
                       mod_base = OTHER
                       note = 2'-O-Methyl modified base
modified_base          11..14
                       mod_base = OTHER
                       note = 2'-O-Methyl modified base
modified_base          25..27
                       mod_base = OTHER
                       note = 2'-O-Methyl modified base
modified_base          34..37
                       mod_base = OTHER
                       note = 2'-O-Methyl modified base
modified_base          56..67
                       mod_base = OTHER
                       note = 2'-Fluoro modified base
modified_base          68
                       mod_base = OTHER
                       note = 2'-O-Methyl modified base
modified_base          1..4
                       mod_base = OTHER
                       note = phosphorothioate linkage
modified_base          10..14
                       mod_base = OTHER
                       note = phosphorothioate linkage
modified_base          24..29
                       mod_base = OTHER
                       note = phosphorothioate linkage
modified_base          39..43
```

```
                        mod_base = OTHER
                        note = phosphorothioate linkage
modified_base           65..68
                        mod_base = OTHER
                        note = phosphorothioate linkage
SEQUENCE: 14
gttgagaatc gaaagattct caacctttta atttctactg ttgtagatct gtaacgatcg  60
ggaactgg                                                           68

SEQ ID NO: 15           moltype = RNA  length = 68
FEATURE                 Location/Qualifiers
source                  1..68
                        mol_type = other RNA
                        organism = synthetic construct
modified_base           1..3
                        mod_base = OTHER
                        note = 2'-O-Methyl modified base
modified_base           11..14
                        mod_base = OTHER
                        note = 2'-O-Methyl modified base
modified_base           25..27
                        mod_base = OTHER
                        note = 2'-O-Methyl modified base
modified_base           34..37
                        mod_base = OTHER
                        note = 2'-O-Methyl modified base
modified_base           56..67
                        mod_base = OTHER
                        note = 2'-Fluoro modified base
modified_base           68
                        mod_base = OTHER
                        note = 2'-O-Methyl modified base
modified_base           1..4
                        mod_base = OTHER
                        note = phosphorothioate linkage
modified_base           10..14
                        mod_base = OTHER
                        note = phosphorothioate linkage
modified_base           24..29
                        mod_base = OTHER
                        note = phosphorothioate linkage
modified_base           39..43
                        mod_base = OTHER
                        note = phosphorothioate linkage
modified_base           65..68
                        mod_base = OTHER
                        note = phosphorothioate linkage
SEQUENCE: 15
gttgagaatc gaaagattct caacctttta atttctactg ttgtagatag tgtagcagag  60
aggaacca                                                           68

SEQ ID NO: 16           moltype = DNA  length = 4582
FEATURE                 Location/Qualifiers
source                  1..4582
                        mol_type = other DNA
                        organism = synthetic construct
SEQUENCE: 16
acgtttttcc tgtaacgatc gggaactggc atttgagtgt agcagagagg aaccatttct  60
caaagcttac taaagaatta ttcttttaca tttcagtggc caccagaaga tattacctgg  120
gagctgtgga actgagctgg gactacatgc agtctgacct gggagagctg cctgtggatg  180
ctagatttcc tccaagagtg cccaagagct tccccttcaa cacctctgtg gtgtacaaga  240
aaaccctgtt tgtggaattc acagaccacc tgttcaatat tgccaagcct agacctcctt  300
ggatgggact gctgggacct acaattcagg ctgaggtgta tgacacagtg gtcatcaccc  360
tgaagaacat ggccagccat cctgtgtctc tgcatgctgt gggagtgtct tactggaagg  420
cttctgaggg agctgagtat gatgaccaga caagccagag agagaaagag gatgacaagg  480
ttttccctgg aggcagccac acctatgtct ggcaggtcct gaaagaaaat ggccctatgg  540
cctctgatcc tctgtgcctg acatacagct acctgagcca tgtggacctg gtcaaggacc  600
tgaattctgg cctgattgga gccctgctgg tgtgtagaga aggcagcctg gccaaagaga  660
aaacccagac actgcacaag ttcatcctgc tgtttgctgt gtttgatgag ggcaagagct  720
ggcactctga gacaaagaac agcctgatgc aggacaggga tgctgcctct gctagagctt  780
ggcctaagat gcacacagtg aatggctatg tgaacagaag cctgcctgga ctgattggct  840
gccacagaaa gtctgtgtac tggcatgtga ttggcatggg cacaacacct gaggtgcaca  900
gcatctttct ggaaggacac accttcctgg tgagaaacca tagacaggcc agcctggaaa  960
tcagccctat caccttcctg acagctcaga ccctgctgat ggatctgggc cagtttctgc  1020
tgttctgcca catcagcagc caccagcatg atggcatgga agcctatgtg aaggtggaca  1080
gctgccctga agaaccccag ctgagaatga agaacaatga ggaggctgag gactatgatg  1140
atgacctgac agactctgag atggatgtgg tcagatttga tgatgacaac agccccagct  1200
tcatccagat cagatctgtg gccaagaagc accccaagac ctgggtgcac tatattgctg  1260
ctgaggaaga ggactgggat tatgctcctc tggtgctggc ccctgatgac agaagctaca  1320
```

-continued

```
agagccagta cctgaacaat ggccctcaga gaattggcag aaagtataag aaagtgagat  1380
tcatggccta cacagatgag acattcaaga ccagagaggc cattcagcat gagtctggca  1440
ttctgggccc tctgctgtat ggagaagtgg gagatacact gctgatcatc ttcaagaacc  1500
aggccagcag accctacaac atctaccctc atggcatcac agatgtgaga cccctgtatt  1560
ctagaaggct gcccaaggga gtgaagcacc tgaaggactt ccctatcctg cctggagaga  1620
tcttcaagta caagtggaca gtgacagtgg aagatggccc caccaagtct gaccctagat  1680
gtctgacaag atactacagc agctttgtga acatggaaag agacctggcc tctggcctga  1740
ttggacctct gctgatctgc tacaaagaat ctgtggacca gagaggcaac cagatcatgt  1800
ctgacaagag aaatgtgatc ctgttttctg tgtttgatga gaacagatcc tggtatctga  1860
cagagaacat ccagagattt ctgcccaatc ctgctggagt gcagctggaa gatcctgagt  1920
tccaggcctc caacatcatg cactccatca atggctatgt gtttgacagc ctgcagctgt  1980
ctgtgtgcct gcatgaagtg gcctactggt acatcctgag cattggagcc cagacagact  2040
tcctgtctgt gttcttctct ggctacacct tcaagcacaa gatggtgtat gaggataccc  2100
tgacactgtt cccattctct ggagagacag tgttcatgag catggaaaac cctggcctgt  2160
ggatcctggg ctgtcacaac tctgacttca gaaacagagg catgacagcc ctgctgaagg  2220
tgtccagctg tgacaagaac acaggagact actatgagga cagctatgag gacatctctg  2280
cctacctgct gagcaagaac aatgccattg agcccagaag cttcagccag aatgccacca  2340
atgtgtccaa caacagcaac accagcaatg actccaatgt gtcccctcca gtgctgaaga  2400
gacaccagag agaaatcacc agaaccacac tgcagtctga ccaagaggaa attgactatg  2460
atgacaccat ctctgtggag atgaagaaag aagattttga catctatgat gaggatgaga  2520
atcagagccc cagatccttt cagaaaaaga ccagacacta cttcattgct gctgtggaga  2580
gactgtggga ctatggcatg tctagcagcc ctcatgtgct gagaaataga gcccagtctg  2640
gctctgtgcc ccagttcaag aaagtggtgt tccaagagtt cacagatggc agcttcaccc  2700
agccactgta tagaggagag ctgaatgagc atctgggcct gctgggccct tatatcagag  2760
ctgaagtgga agataacatc atggtcacct tcagaaatca ggcctctaga ccctacagct  2820
tctacagctc cctgatcagc tatgaagagg accagagaca gggagctgag cccagaaaga  2880
actttgtgaa gcccaatgag actaagacct acttttggaa ggtgcagcac cacatggccc  2940
ctacaaagga tgagtttgac tgcaaggcct gggcctactt ttctgatgtg gatctggaaa  3000
aggatgtgca ctctggactc attggaccac tgcttgtgtg ccacaccaac acactgaacc  3060
ctgctcatgg cagacaagtg acagtgcaag agtttgccct gttcttcacc atctttgatg  3120
aaacaaagag ctggtacttc acagagaata tggagagaaa ctgcagggcc ccttgcaaca  3180
tccagatgga agatcccacc ttcaaagaga actacagatt ccatgccatc aatggctaca  3240
tcatggacac actgcctggc ctggttatgg ctcaggatca gagaatcaga tggtatctgc  3300
tgtccatggg ctccaatgag aatatccaca gcatccactt ctctggccat gtgttcacag  3360
tgagaaaaaa agaagagtac aaaatggccc tgtacaatct gtaccctggg gtgtttgaaa  3420
cagtggaaat gctgccttcc aaggctggca tttggagagt ggaatgtctg attggagagc  3480
acctccatgc tggaatgagc accctgtttc tggtgtacag caacaagtgt cagacccctc  3540
tgggcatggc ctctggacac atcagagact tccagatcac agcctctggc cagtatggac  3600
agtgggctcc taaactggct agactgcact actctggcag catcaatgcc tggtccacca  3660
aagagccctt cagctggatc aaggtggacc tgctggctcc catgatcatc catggaatca  3720
agacccaggg agccagacag aagttcagca gcctgtacat cagccagttc atcatcatgt  3780
acagcctgga tggcaagaag tggcagacct acagaggcaa cagcacaggc acactcatgg  3840
tgttctttgg caatgtggac agctctggca ttaagcacaa catcttcaac cctccaatca  3900
ttgccagata catcagactg caccccacac actacagcat cagatctacc ctgagaatgg  3960
aactgatggg ctgtgacctg aacagctgca gcatgcccct gggaatggaa agcaaggcca  4020
tctctgatgc ccagatcaca gccagcagct acttcaccaa catgtttgcc acttggagcc  4080
cctccaaggc tagactgcat ctgcagggca gaagcaatgc ttggaggccc caagtgaaca  4140
accccaaaga gtggctgcag gtggactttc aaaagaccat gaaagtgaca ggagtgacca  4200
cacagggagt caagtctctg ctgacctcta tgtatgtgaa agagttcctg atctccagca  4260
gccaggatgg ccaccagtgg accctgtttt tccagaatgg caaagtgaaa gtgttccagg  4320
gcaatcagga cagcttcaca cctgtggtca actccctgga tcctccactg ctgaccagat  4380
acctgagaat tcaccctcag tcttgggtgc accagattgc tctgagaatg gaagtgctgg  4440
gctgtgaagc tcaggacctc tactgatcgc gaataaaaga tctttatttt cattagatct  4500
gtgtgttggt tttttgtgtg tatttagcta tttgagtgta gcagagagga accatttttc  4560
ctgtaacgat cgggaactgg ca                                          4582

SEQ ID NO: 17          moltype = DNA  length = 4587
FEATURE                Location/Qualifiers
source                 1..4587
                       mol_type = other DNA
                       organism = synthetic construct
SEQUENCE: 17
acgttaatgg ttcctctctg ctacactcaa atgccagttc ccgatcgtta caggaaatct  60
caaagcttac taaagaatta ttcttttaca tttcagtggc caccagaaga tattacctgg  120
gagctgtgga actgagctgg gactacatgc agtctgacct gggagagctg cctgtggatg  180
ctagatttcc tccaagagtg cccaagagct tccccttcaa cacctctgtg gtgtacaaga  240
aaaccctgtt tgtggaattc acagaccacc tgttcaatat tgccaagcct agacctcctt  300
ggatgggact gctgggacct acaattcagg ctgaggtgta tgacacagtg gtcatcaccc  360
tgaagaacat ggccagccat cctgtgtctc tgcatgctgt gggagtgtct tactggaagg  420
cttctgaggg agctgagtat gatgaccaga caagccagag agagaaagag gatgacaagg  480
ttttccctgg aggcagccac acctatgtct ggcaggtcct gaaagaaaat ggccctatgg  540
cctctgatcc tctgtgcctg acatacagct acctgagcca tgtggacctg gtcaaggacc  600
tgaattctgg cctgattgga gccctgctgg tgtgtagaga aggcagcctg gccaaagaga  660
aaacccagac actgcacaag ttcatcctgc tgtttgctgt gtttgatgag ggcaagagct  720
ggcactctga gacaaagaac agcctgatgc aggacaggga tgctgcctct gctagagctt  780
ggcctaagat gcacacagtg aatggctatg tgaacagaag cctgcctgga ctgattggct  840
gccacagaaa gtctgtgtac tggcatgtga ttggcatggg cacaacacct gaggtgcaca  900
gcatctttct ggaaggacac accttcctgg tgagaaacca tagacaggcc agcctggaaa  960
tcagccctat caccttcctg acagctcaga ccctgctgat ggatctgggc cagtttctgc  1020
```

```
tgttctgcca catcagcagc caccagcatg atggcatgga agcctatgtg aaggtggaca  1080
gctgccctga agaaccccag ctgagaatga agaacaatga ggaggctgag gactatgatg  1140
atgacctgac agactctgag atggatgtgg tcagatttga tgatgacaac agccccagct  1200
tcatccagat cagatctgtg gccaagaagc accccaagac ctgggtgcac tatattgctg  1260
ctgaggaaga ggactgggat tatgctcctc tggtgctggc cctgatgac agaagctaca  1320
agagccagta cctgaacaat ggccctcaga gaattggcag aaagtataag aaagtgagat  1380
tcatggccta cacagatgag acattcaaga ccagagaggc cattcagcat gagtctggca  1440
ttctgggccc tctgctgtat ggagaagtgg gagatacact gctgatcatc ttcaagaacc  1500
aggccagcag accctacaac atctaccctc atggcatcac agatgtgaga cccctgtatt  1560
ctagaaggct gcccaaggga gtgaagcacc tgaaggactt ccctatcctg cctggagaga  1620
tcttcaagta caagtggaca gtgacagtgg aagatggccc caccaagtct gaccctagat  1680
gtctgacaag atactacagc agctttgtga acatggaaag agacctggcc tctggcctga  1740
ttggacctct gctgatctgc tacaaagaat ctgtggacca gagaggcaac cagatcatgt  1800
ctgacaagag aaatgtgatc ctgttttctg tgtttgatga gaacagatcc tggtatctga  1860
cagagaacat ccagagattt ctgcccaatc ctgctggagt gcagctggaa gatcctgagt  1920
tccaggcctc caacatcatg cactccatca atggctatgt gtttgacagc ctgcagctgt  1980
ctgtgtgcct gcatgaagtg gcctactggt acatcctgag cattggagcc cagacagact  2040
tcctgtctgt gttcttctct ggctacacct tcaagcacaa gatggtgtat gaggataccc  2100
tgacactgtt cccattctct ggagagacag tgttcatgag catggaaaac cctggcctgt  2160
ggatcctggg ctgtcacaac tctgacttca gaaacagagg catgacagcc ctgctgaagg  2220
tgtccagctg tgacaagaac acaggagact actatgagga cagctatgag gacatctctg  2280
cctacctgct gagcaagaac aatgccattg agcccagaag cttcagccag aatgccacca  2340
atgtgtccaa caacagcaac accagcaatg actccaatgt gtcccctcca gtgctgaaga  2400
gacaccagag agaaatcacc agaaccacac tgcagtctga ccaagaggaa attgactatg  2460
atgacaccat ctctgtggag atgaagaaag aagattttga catctatgat gaggatgaga  2520
atcagagccc cagatccttt cagaaaaaga ccagacacta cttcattgct gctgtggaga  2580
gactgtggga ctatggcatg tctagcagcc ctcatgtgct gagaaataga gcccagtctg  2640
gctctgtgcc ccagttcaag aaagtggtgt tccaagagtt cacagatggc agcttcaccc  2700
agccactgta tagaggagag ctgaatgagc atctgggcct gctgggccct tatatcagag  2760
ctgaagtgga agataacatc atggtcacct tcagaaatca ggcctctaga ccctacagct  2820
tctacagctc cctgatcagc tatgaagagg accagagaca gggagctgag cccagaaaga  2880
actttgtgaa gcccaatgag actaagacct acttttggaa ggtgcagcac cacatggccc  2940
ctacaaagga tgagtttgac tgcaaggcct gggcctactt ttctgatgtg gatctggaaa  3000
aggatgtgca ctctggactc attggaccac tgcttgtgtg ccacaccaac acactgaacc  3060
ctgctcatgg cagacaagtg acagtgcaag agtttgccct gttcttcacc atctttgatg  3120
aaacaaagag ctggtacttc acagagaata tggagagaaa ctgcagggcc ccttgcaaca  3180
tccagatgga agatcccacc ttcaaagaga actacagatt ccatgccatc aatggctaca  3240
tcatggacac actgcctggc ctggttatgg ctcaggatca gagaatcaga tggtatctgc  3300
tgtccatggg ctccaatgag aatatccaca gcatccactt ctctggccat gtgttcacag  3360
tgagaaaaaa agaagagtac aaaatggccc tgtacaatct gtaccctggg gtgtttgaaa  3420
cagtggaaat gctgccttcc aaggctggca tttggagagt ggaatgtctg attggagagc  3480
acctccatgc tggaatgagc accctgtttc tggtgtacag caacaagtgt cagacccctc  3540
tgggcatggc ctctggacac atcagagact tccagatcac agcctctggc cagtatggac  3600
agtgggctcc taaactggct agactgcact actctggcag catcaatgcc tggtccacca  3660
aagagccctt cagctggatc aaggtggacc tgctggctcc catgatcatc catggaatca  3720
agacccaggg agccagacag aagttcagca gcctgtacat cagccagttc atcatcatgt  3780
acagcctgga tggcaagaag tggcagacct acagaggcaa cagcacaggc acactcatgg  3840
tgttctttgg caatgtggac agctctggca ttaagcacaa catcttcaac cctccaatca  3900
ttgccagata catcagactg caccccacac actacagcat cagatctacc ctgagaatgg  3960
aactgatggg ctgtgacctg aacagctgca gcatgcccct gggaatggaa agcaaggcca  4020
tctctgatgc ccagatcaca gccagcagct acttcaccaa catgtttgcc acttggagcc  4080
cctccaaggc tagactgcat ctgcagggca gaagcaatgc ttggaggccc caagtgaaca  4140
accccaaaga gtggctgcag gtggactttc aaaagaccat gaaagtgaca ggagtgacca  4200
cacagggagt caagtctctg ctgacctcta tgtatgtgaa agagttcctg atctccagca  4260
gccaggatgg ccaccagtgg accctgtttt tccagaatgg caaagtgaaa gtgttccagg  4320
gcaatcagga cagcttcaca cctgtggtca actccctgga tcctccactg ctgaccagat  4380
acctgagaat tcaccctcag tcttgggtgc accagattgc tctgagaatg gaagtgctgg  4440
gctgtgaagc tcaggacctc tactgatcgc gaataaaaga tctttatttt cattagatct  4500
gtgtgttggt tttttgtgtg tatttagcta tgccagttcc cgatcgttac aggaaaaatg  4560
gttcctctct gctacactca aattcct                                4587
```

```
SEQ ID NO: 18          moltype = DNA  length = 4587
FEATURE                Location/Qualifiers
source                 1..4587
                       mol_type = other DNA
                       organism = synthetic construct
SEQUENCE: 18
acgtttttcc tgtaacgatc gggaactggc atttgagtgt agcagagagg aaccatttct  60
caaagcttac taaagaatta ttcttttaca tttcagtggc caccagaaga tattacctgg  120
gagctgtgga actgagctgg gactacatgc agtctgacct gggagagctg cctgtggatg  180
ctagatttcc tccaagagtg cccaagagct tccccttcaa cacctctgtg gtgtacaaga  240
aaaccctgtt tgtggaattc acagaccacc tgttcaatat tgccaagcct agacctcctt  300
ggatgggact gctgggacct acaattcagg ctgaggtgta tgacacagtg gtcatcaccc  360
tgaagaacat ggccagccat cctgtgtctc tgcatgctgt gggagtgtct tactggaagg  420
cttctgaggg agctgagtat gatgaccaga caagccagag agagaaagag gatgacaagg  480
ttttccctgg aggcagccac acctatgtct ggcaggtcct gaaagaaaat ggccctatgg  540
cctctgatcc tctgtgcctg acatacagct acctgagcca tgtggacctg gtcaaggacc  600
tgaattctgg cctgattgga gccctgctgg tgtgtagaga aggcagcctg gccaaagaga  660
aaacccagac actgcacaag ttcatcctgc tgtttgctgt gtttgatgag ggcaagagct  720
```

```
ggcactctga gacaaagaac agcctgatgc aggacaggga tgctgcctct gctagagctt  780
ggcctaagat gcacacagtg aatggctatg tgaacagaag cctgcctgga ctgattggct  840
gccacagaaa gtctgtgtac tggcatgtga ttggcatggg cacaacacct gaggtgcaca  900
gcatctttct ggaaggacac accttcctgg tgagaaacca tagacaggcc agcctggaaa  960
tcagccctat caccttcctg acagctcaga ccctgctgat ggatctgggc cagtttctgc  1020
tgttctgcca catcagcagc caccagcatg atggcatgga agcctatgtg aaggtggaca  1080
gctgccctga agaaccccag ctgagaatga agaacaatga ggaggctgag gactatgatg  1140
atgacctgac agactctgag atggatgtgg tcagatttga tgatgacaac agccccagct  1200
tcatccagat cagatctgtg gccaagaagc accccaagac ctgggtgcac tatattgctg  1260
ctgaggaaga ggactgggat tatgctcctc tggtgctggc cctgatgac agaagctaca  1320
agagccagta cctgaacaat ggccctcaga gaattggcag aaagtataag aaagtgagat  1380
tcatggccta cacagatgag acattcaaga ccagagaggc cattcagcat gagtctggca  1440
ttctgggccc tctgctgtat ggagaagtgg gagatacact gctgatcatc ttcaagaacc  1500
aggccagcag accctacaac atctaccctc atggcatcac agatgtgaga cccctgtatt  1560
ctagaaggct gcccaaggga gtgaagcacc tgaaggactt ccctatcctg cctggagaga  1620
tcttcaagta caagtggaca gtgacagtgg aagatggccc caccaagtct gaccctagat  1680
gtctgacaag atactacagc agctttgtga acatggaaag agacctggcc tctggcctga  1740
ttggacctct gctgatctgc tacaaagaat ctgtggacca gagaggcaac cagatcatgt  1800
ctgacaagag aaatgtgatc ctgttttctg tgtttgatga gaacagatcc tggtatctga  1860
cagagaacat ccagagattt ctgcccaatc ctgctggagt gcagctggaa gatcctgagt  1920
tccaggcctc caacatcatg cactccatca atggctatgt gtttgacagc ctgcagctgt  1980
ctgtgtgcct gcatgaagtg gcctactggt acatcctgag cattggagcc cagacagact  2040
tcctgtctgt gttcttctct ggctacacct tcaagcacaa gatggtgtat gaggataccc  2100
tgacactgtt cccattctct ggagagacag tgttcatgag catggaaaac cctggcctgt  2160
ggatcctggg ctgtcacaac tctgacttca gaaacagagg catgacagcc ctgctgaagg  2220
tgtccagctg tgacaagaac acaggagact actatgagga cagctatgag gacatctctg  2280
cctacctgct gagcaagaac aatgccattg agcccagaag cttcagccag aatgccacca  2340
atgtgtccaa caacagcaac accagcaatg actccaatgt gtcccctcca gtgctgaaga  2400
gacaccagag agaaatcacc agaaccacac tgcagtctga ccaagaggaa attgactatg  2460
atgacaccat ctctgtggag atgaagaaag aagattttga catctatgat gaggatgaga  2520
atcagagccc cagatccttt cagaaaaaga ccagacacta cttcattgct gctgtggaga  2580
gactgtggga ctatggcatg tctagcagcc ctcatgtgct gagaaataga gcccagtctg  2640
gctctgtgcc ccagttcaag aaagtggtgt tccaagagtt cacagatggc agcttcaccc  2700
agccactgta tagaggagag ctgaatgagc atctgggcct gctgggccct tatatcagag  2760
ctgaagtgga agataacatc atggtcacct tcagaaatca ggcctctaga ccctacagct  2820
tctacagctc cctgatcagc tatgaagagg accagagaca gggagctgag cccagaaaga  2880
actttgtgaa gcccaatgag actaagacct actttggaa ggtgcagcac cacatggccc  2940
ctacaaagga tgagtttgac tgcaaggcct gggcctactt ttctgatgtg gatctggaaa  3000
aggatgtgca ctctggactc attggaccac tgcttgtgtg ccacaccaac acactgaacc  3060
ctgctcatgg cagacaagtg acagtgcaag agtttgccct gttcttcacc atctttgatg  3120
aaacaaagag ctggtacttc acagagaata tggagagaaa ctgcagggcc ccttgcaaca  3180
tccagatgga agatcccacc ttcaaagaga actacagatt ccatgccatc aatggctaca  3240
tcatggacac actgcctggc ctggttatgg ctcaggatca gagaatcaga tggtatctgc  3300
tgtccatggg ctccaatgag aatatccaca gcatccactt ctctggccat gtgttcacag  3360
tgagaaaaaa agaagagtac aaaatggccc tgtacaatct gtaccctggg gtgtttgaaa  3420
cagtggaaat gctgccttcc aaggctggca tttggagagt ggaatgtctg attggagagc  3480
acctccatgc tggaatgagc accctgtttc tggtgtacag caacaagtgt cagacccctc  3540
tgggcatggc ctctggacac atcagagact tccagatcac agcctctggc cagtatggac  3600
agtgggctcc taaactggct agactgcact actctggcag catcaatgcc tggtccacca  3660
aagagccctt cagctggatc aaggtggacc tgctggctcc catgatcatc catggaatca  3720
agacccaggg agccagacag aagttcagca gcctgtacat cagccagttc atcatcatgt  3780
acagcctgga tggcaagaag tggcagacct acagaggcaa cagcacaggc acactcatgg  3840
tgttctttgg caatgtggac agctctggca ttaagcacaa catcttcaac cctccaatca  3900
ttgccagata catcagactg caccccacac actacagcat cagatctacc ctgagaatgg  3960
aactgatggg ctgtgacctg aacagctgca gcatgcccct gggaatggaa agcaaggcca  4020
tctctgatgc ccagatcaca gccagcagct acttcaccaa catgtttgcc acttggagcc  4080
cctccaaggc tagactgcat ctgcagggca gaagcaatgc ttggaggccc caagtgaaca  4140
accccaaaga gtggctgcag gtggactttc aaaagaccat gaaagtgaca ggagtgacca  4200
cacagggagt caagtctctg ctgacctcta tgtatgtgaa agagttcctg atctccagca  4260
gccaggatgg ccaccagtgg accctgtttt tccagaatgg caaagtgaaa gtgttccagg  4320
gcaatcagga cagcttcaca cctgtggtca actccctgga tcctccactg ctgaccagat  4380
acctgagaat tcaccctcag tcttgggtgc accagattgc tctgagaatg gaagtgctgg  4440
gctgtgaagc tcaggacctc tactgatcgc gaataaaaga tctttatttt cattagatct  4500
gtgtgttggt tttttgtgtg tatttagcta tgccagttcc cgatcgttac aggaaaaatg  4560
gttcctctct gctacactca aattcct                                     4587
```

```
SEQ ID NO: 19          moltype = DNA  length = 4587
FEATURE                Location/Qualifiers
source                 1..4587
                       mol_type = other DNA
                       organism = synthetic construct
SEQUENCE: 19
acgttaatgg ttcctctctg ctacactcaa atgccagttc ccgatcgtta caggaaatct  60
caaagcttac taaagaatta ttcttttaca tttcagtggc caccagaaga tattacctgg  120
gagctgtgga actgagctgg gactacatgc agtctgacct gggagagctg cctgtggatg  180
ctagatttcc tccaagagtg cccaagagct tcccctcaa cacctctgtg gtgtacaaga  240
aaaccctgtt tgtggaattc acagaccacc tgttcaatat tgccaagcct agacctcctt  300
ggatgggact gctgggacct acaattcagg ctgaggtgta tgacacagtg gtcatcaccc  360
tgaagaacat ggccagccat cctgtgtctc tgcatgctgt gggagtgtct tactggaagg  420
```

```
cttctgaggg agctgagtat gatgaccaga caagccagag agagaaagag gatgacaagg  480
ttttccctgg aggcagccac acctatgtct ggcaggtcct gaaagaaaat ggccctatgg  540
cctctgatcc tctgtgcctg acatacagct acctgagcca tgtggacctg gtcaaggacc  600
tgaattctgg cctgattgga gccctgctgg tgtgtagaga aggcagcctg gccaaagaga  660
aaacccagac actgcacaag ttcatcctgc tgtttgctgt gtttgatgag ggcaagagct  720
ggcactctga gacaaagaac agcctgatgc aggacaggga tgctgcctct gctagagctt  780
ggcctaagat gcacacagtg aatggctatg tgaacagaag cctgcctgga ctgattggct  840
gccacagaaa gtctgtgtac tggcatgtga ttggcatggg cacaacacct gaggtgcaca  900
gcatctttct ggaaggacac accttcctgg tgagaaacca tagacaggcc agcctggaaa  960
tcagccctat caccttcctg acagctcaga ccctgctgat ggatctgggc cagtttctgc  1020
tgttctgcca catcagcagc caccagcatg atggcatgga agcctatgtg aaggtggaca  1080
gctgccctga agaaccccag ctgagaatga agaacaatga ggaggctgag gactatgatg  1140
atgacctgac agactctgag atggatgtgg tcagatttga tgatgacaac agccccagct  1200
tcatccagat cagatctgtg gccaagaagc accccaagac ctgggtgcac tatattgctg  1260
ctgaggaaga ggactgggat tatgctcctc tggtgctggc cctgatgac agaagctaca  1320
agagccagta cctgaacaat ggccctcaga gaattggcag aaagtataag aaagtgagat  1380
tcatggccta cacagatgag acattcaaga ccagagaggc cattcagcat gagtctggca  1440
ttctgggccc tctgctgtat ggagaagtgg gagatacact gctgatcatc ttcaagaacc  1500
aggccagcag accctacaac atctaccctc atggcatcac agatgtgaga cccctgtatt  1560
ctagaaggct gcccaaggga gtgaagcacc tgaaggactt ccctatcctg cctggagaga  1620
tcttcaagta caagtggaca gtgacagtgg aagatggccc caccaagtct gaccctagat  1680
gtctgacaag atactacagc agctttgtga acatggaaag agacctggcc tctggcctga  1740
ttggacctct gctgatctgc tacaaagaat ctgtggacca gagaggcaac cagatcatgt  1800
ctgacaagag aaatgtgatc ctgttttctg tgtttgatga gaacagatcc tggtatctga  1860
cagagaacat ccagagattt ctgcccaatc ctgctggagt gcagctggaa gatcctgagt  1920
tccaggcctc caacatcatg cactccatca atggctatgt gtttgacagc ctgcagctgt  1980
ctgtgtgcct gcatgaagtg gcctactggt acatcctgag cattggagcc cagacagact  2040
tcctgtctgt gttcttctct ggctacacct tcaagcacaa gatggtgtat gaggataccc  2100
tgacactgtt cccattctct ggagagacag tgttcatgag catggaaaac cctggcctgt  2160
ggatcctggg ctgtcacaac tctgacttca gaaacagagg catgacagcc ctgctgaagg  2220
tgtccagctg tgacaagaac acaggagact actatgagga cagctatgag gacatctctg  2280
cctacctgct gagcaagaac aatgccattg agcccagaag cttcagccag aatgccacca  2340
atgtgtccaa caacagcaac accagcaatg actccaatgt gtcccctcca gtgctgaaga  2400
gacaccagag agaaatcacc agaaccacac tgcagtctga ccaagaggaa attgactatg  2460
atgacaccat ctctgtggag atgaagaaag aagattttga catctatgat gaggatgaga  2520
atcagagccc cagatccttt cagaaaaaga ccagacacta cttcattgct gctgtggaga  2580
gactgtggga ctatggcatg tctagcagcc ctcatgtgct gagaaataga gcccagtctg  2640
gctctgtgcc ccagttcaag aaagtggtgt tccaagagtt cacagatggc agcttcaccc  2700
agccactgta tagaggagag ctgaatgagc atctgggcct gctgggccct tatatcagag  2760
ctgaagtgga agataacatc atggtcacct tcagaaatca ggcctctaga ccctacagct  2820
tctacagctc cctgatcagc tatgaagagg accagagaca gggagctgag cccagaaaga  2880
actttgtgaa gcccaatgag actaagacct acttttggaa ggtgcagcac cacatggccc  2940
ctacaaagga tgagtttgac tgcaaggcct gggcctactt ttctgatgtg gatctggaaa  3000
aggatgtgca ctctggactc attggaccac tgcttgtgtg ccacaccaac acactgaacc  3060
ctgctcatgg cagacaagtg acagtgcaag agtttgccct gttcttcacc atctttgatg  3120
aaacaaagag ctggtacttc acagagaata tggagagaaa ctgcagggcc ccttgcaaca  3180
tccagatgga agatcccacc ttcaaagaga actacagatt ccatgccatc aatggctaca  3240
tcatggacac actgcctggc ctggttatgg ctcaggatca gagaatcaga tggtatctgc  3300
tgtccatggg ctccaatgag aatatccaca gcatccactt ctctggccat gtgttcacag  3360
tgagaaaaaa agaagagtac aaaatggccc tgtacaatct gtaccctggg gtgtttgaaa  3420
cagtggaaat gctgccttcc aaggctggca tttggagagt ggaatgtctg attggagagc  3480
acctccatgc tggaatgagc accctgtttc tggtgtacag caacaagtgt cagacccctc  3540
tgggcatggc ctctggacac atcagagact tccagatcac agcctctggc cagtatggac  3600
agtgggctcc taaactggct agactgcact actctggcag catcaatgcc tggtccacca  3660
aagagccctt cagctggatc aaggtggacc tgctggctcc catgatcatc catggaatca  3720
agacccaggg agccagacag aagttcagca gcctgtacat cagccagttc atcatcatgt  3780
acagcctgga tggcaagaag tggcagacct acagaggcaa cagcacaggc acactcatgg  3840
tgttctttgg caatgtggac agctctggca ttaagcacaa catcttcaac cctccaatca  3900
ttgccagata catcagactg caccccacac actacagcat cagatctacc ctgagaatgg  3960
aactgatggg ctgtgacctg aacagctgca gcatgcccct gggaatggaa agcaaggcca  4020
tctctgatgc ccagatcaca gccagcagct acttcaccaa catgtttgcc acttggagcc  4080
cctccaaggc tagactgcat ctgcagggca gaagcaatgc ttggaggccc caagtgaaca  4140
accccaaaga gtggctgcag gtggactttc aaaagaccat gaaagtgaca ggagtgacca  4200
cacagggagt caagtctctg ctgacctcta tgtatgtgaa agagttcctg atctccagca  4260
gccaggatgg ccaccagtgg accctgtttt tccagaatgg caaagtgaaa gtgttccagg  4320
gcaatcagga cagcttcaca cctgtggtca actccctgga tcctccactg ctgaccagat  4380
acctgagaat tcaccctcag tcttgggtgc accagattgc tctgagaatg gaagtgctgg  4440
gctgtgaagc tcaggacctc tactgatcgc gaataaaaga tctttatttt cattagatct  4500
gtgtgttggt tttttgtgtg tatttagcta tttgagtgta gcagagagga accatttttc  4560
ctgtaacgat cgggaactgg cattcct                                     4587

SEQ ID NO: 20           moltype = DNA  length = 4615
FEATURE                 Location/Qualifiers
source                  1..4615
                        mol_type = other DNA
                        organism = synthetic construct
SEQUENCE: 20
catagtacgc gtacgttctt aggtcagtga agagaagaac aaaatttatt acggtctcat  60
agggcctgcc ttctcaaagc ttactaaaga attattcttt tacatttcag tggccaccag  120
```

```
aagatattac ctgggagctg tggaactgag ctgggactac atgcagtctg acctgggaga  180
gctgcctgtg gatgctagat ttcctccaag agtgcccaag agcttcccct tcaacacctc  240
tgtggtgtac aagaaaaccc tgtttgtgga attcacagac cacctgttca atattgccaa  300
gcctagacct ccttggatgg gactgctggg acctacaatt caggctgagg tgtatgacac  360
agtggtcatc accctgaaga acatggccag ccatcctgtg tctctgcatg ctgtgggagt  420
gtcttactgg aaggcttctg agggagctga gtatgatgac cagacaagcc agagagagaa  480
agaggatgac aaggttttcc ctggaggcag ccacacctat gtctggcagg tcctgaaaga  540
aaatggccct atggcctctg atcctctgtg cctgacatac agctacctga gccatgtgga  600
cctggtcaag gacctgaatt ctggcctgat tggagccctg ctggtgtgta gagaaggcag  660
cctggccaaa gagaaaaccc agacactgca caagttcatc ctgctgtttg ctgtgtttga  720
tgagggcaag agctggcact ctgagacaaa gaacagcctg atgcaggaca gggatgctgc  780
ctctgctaga gcttggccta agatgcacac agtgaatggc tatgtgaaca gaagcctgcc  840
tggactgatt ggctgccaca gaaagtctgt gtactggcat gtgattggca tgggcacaac  900
acctgaggtg cacagcatct ttctggaagg acacaccttc ctggtgagaa accatagaca  960
ggccagcctg gaaatcagcc ctatcacctt cctgacagct cagaccctgc tgatggatct  1020
gggccagttt ctgctgttct gccacatcag cagccaccag catgatggca tggaagccta  1080
tgtgaaggtg gacagctgcc ctgaagaacc ccagctgaga atgaagaaca atgaggaggc  1140
tgaggactat gatgatgacc tgacagactc tgagatggat gtggtcagat ttgatgatga  1200
caacagcccc agcttcatcc agatcagatc tgtggccaag aagcacccca agacctgggt  1260
gcactatatt gctgctgagg aagaggactg ggattatgct cctctggtgc tggcccctga  1320
tgacagaagc tacaagagcc agtacctgaa caatggccct cagagaattg gcagaaagta  1380
taagaaagtg agattcatgg cctacacaga tgagacattc aagaccagag aggccattca  1440
gcatgagtct ggcattctgg gccctctgct gtatggagaa gtgggagata cactgctgat  1500
catcttcaag aaccaggcca gcagacccta caacatctac cctcatggca tcacagatgt  1560
gagacccctg tattctagaa ggctgcccaa gggagtgaag cacctgaagg acttccctat  1620
cctgcctgga gagatcttca agtacaagtg gacagtgaca gtggaagatg gccccaccaa  1680
gtctgaccct agatgtctga caagatacta cagcagcttt gtgaacatgg aaagagacct  1740
ggcctctggc ctgattggac ctctgctgat ctgctacaaa gaatctgtgg accagagagg  1800
caaccagatc atgtctgaca agagaaatgt gatcctgttt tctgtgtttg atgagaacag  1860
atcctggtat ctgacagaga acatccagag atttctgccc aatcctgctg gagtgcagct  1920
ggaagatcct gagttccagg cctccaacat catgcactcc atcaatggct atgtgtttga  1980
cagcctgcag ctgtctgtgt gcctgcatga agtggcctac tggtacatcc tgagcattgg  2040
agcccagaca gacttcctgt ctgtgttctt ctctggctac accttcaagc acaagatggt  2100
gtatgaggat accctgacac tgttcccatt ctctggagag acagtgttca tgagcatgga  2160
aaaccctggc ctgtggatcc tgggctgtca caactctgac ttcagaaaca gaggcatgac  2220
agccctgctg aaggtgtcca gctgtgacaa gaacacagga gactactatg aggacagcta  2280
tgaggacatc tctgcctacc tgctgagcaa gaacaatgcc attgagccca gaagcttcag  2340
ccagaatgcc accaatgtgt ccaacaacag caacaccagc aatgactcca atgtgtcccc  2400
tccagtgctg aagagacacc agagagaaat caccagaacc acactgcagt ctgaccaaga  2460
ggaaattgac tatgatgaca ccatctctgt ggagatgaag aaagaagatt ttgacatcta  2520
tgatgaggat gagaatcaga gccccagatc ctttcagaaa aagaccagac actacttcat  2580
tgctgctgtg gagagactgt gggactatgg catgtctagc agccctcatg tgctgagaaa  2640
tagagcccag tctggctctg tgccccagtt caagaaagtg gtgttccaag agttcacaga  2700
tggcagcttc acccagccac tgtatagagg agagctgaat gagcatctgg gcctgctggg  2760
cccttatatc agagctgaag tggaagataa catcatggtc accttcagaa atcaggcctc  2820
tagaccctac agcttctaca gctccctgat cagctatgaa gaggaccaga gacagggagc  2880
tgagcccaga aagaactttg tgaagcccaa tgagactaag acctactttt ggaaggtgca  2940
gcaccacatg gcccctacaa aggatgagtt tgactgcaag gcctgggcct actttttctga  3000
tgtggatctg gaaaaggatg tgcactctgg actcattgga ccactgcttg tgtgccacac  3060
caacacactg aaccctgctc atggcagaca agtgacagtg caagagtttg ccctgttctt  3120
caccatcttt gatgaaacaa agagctggta cttcacagag aatatggaga gaaactgcag  3180
ggccccttgc aacatccaga tggaagatcc caccttcaaa gagaactaca gattccatgc  3240
catcaatggc tacatcatgg acacactgcc tggcctggtt atggctcagg atcagagaat  3300
cagatggtat ctgctgtcca tgggctccaa tgagaatatc cacagcatcc acttctctgg  3360
ccatgtgttc acagtgagaa aaaaagaaga gtacaaaatg gccctgtaca atctgtaccc  3420
tggggtgttt gaaacagtgg aaatgctgcc ttccaaggct ggcatttgga gagtggaatg  3480
tctgattgga gagcacctcc atgctggaat gagcaccctg tttctggtgt acagcaacaa  3540
gtgtcagacc cctctgggca tggcctctgg acacatcaga gacttccaga tcacagcctc  3600
tggccagtat ggacagtggg ctcctaaact ggctagactg cactactctg gcagcatcaa  3660
tgcctggtcc accaaagagc ccttcagctg gatcaaggtg gacctgctgg ctcccatgat  3720
catccatgga atcaagaccc agggagccag acagaagttc agcagcctgt acatcagcca  3780
gttcatcatc atgtacagcc tggatggcaa gaagtggcag acctacagag gcaacagcac  3840
aggcacactc atggtgttct ttggcaatgt ggacagctct ggcattaagc acaacatctt  3900
caaccctcca atcattgcca gatacatcag actgcacccc acacactaca gcatcagatc  3960
taccctgaga atggaactga tgggctgtga cctgaacagc tgcagcatgc cctgggaat  4020
ggaaagcaag gccatctctg atgcccagat cacagccagc agctacttca ccaacatgtt  4080
tgccacttgg agcccctcca aggctagact gcatctgcag ggcagaagca atgcttggag  4140
gccccaagtg aacaacccca aagagtggct gcaggtggac tttcaaaaga ccatgaaagt  4200
gacaggagtg accacacagg gagtcaagtc tctgctgacc tctatgtatg tgaaagagtt  4260
cctgatctcc agcagccagg atggccacca gtggaccctg tttttccaga atggcaaagt  4320
gaaagtgttc cagggcaatc aggacagctt cacacctgtg gtcaactccc tggatcctcc  4380
actgctgacc agatacctga gaattcaccc tcagtcttgg gtgcaccaga ttgctctgag  4440
aatggaagtg ctgggctgtg aagctcagga cctctactga tcgcgaataa aagatcttta  4500
ttttcattag atctgtgtgt tggtttttttg tgtgtattta gctatttatt acggtctcat  4560
agggcctgcc tcttaggtca gtgaagagaa gaacaaaatt cctcacgtgc atagt       4615
```

```
SEQ ID NO: 21          moltype = DNA  length = 4613
FEATURE                Location/Qualifiers
source                 1..4613
```

mol_type = other DNA
organism = synthetic construct
SEQUENCE: 21
catagtacgc gtacgttttt gttcttctct tcactgacct aagaggcagg ccctatgaga 60
ccgtaataaa tctcaaagct tactaaagaa ttattctttt acatttcagt ggccaccaga 120
agatattacc tgggagctgt ggaactgagc tgggactaca tgcagtctga cctgggagag 180
ctgcctgtgg atgctagatt tcctccaaga gtgcccaaga gcttcccctt caacacctct 240
gtggtgtaca agaaaaccct gtttgtggaa ttcacagacc acctgttcaa tattgccaag 300
cctagacctc cttggatggg actgctggga cctacaattc aggctgaggt gtatgacaca 360
gtggtcatca ccctgaagaa catggccagc catcctgtgt ctctgcatgc tgtgggagtg 420
tcttactgga aggcttctga gggagctgag tatgatgacc agacaagcca gagagagaaa 480
gaggatgaca aggttttccc tggaggcagc cacacctatg tctggcaggt cctgaaagaa 540
aatggcccta tggcctctga tcctctgtgc ctgacataca gctacctgag ccatgtggac 600
ctggtcaagg acctgaattc tggcctgatt ggagccctgc tggtgtgtag agaaggcagc 660
ctggccaaag agaaaaccca gacactgcac aagttcatcc tgctgtttgc tgtgtttgat 720
gagggcaaga gctggcactc tgagacaaag aacagcctga tgcaggacag ggatgctgcc 780
tctgctagag cttggcctaa gatgcacaca gtgaatggct atgtgaacag aagcctgcct 840
ggactgattg gctgccacag aaagtctgtg tactggcatg tgattggcat gggcacaaca 900
cctgaggtgc acagcatctt tctggaagga cacaccttcc tggtgagaaa ccatagacag 960
gccagcctgg aaatcagccc tatcaccttc ctgacagctc agaccctgct gatggatctg 1020
ggccagtttc tgctgttctg ccacatcagc agccaccagc atgatggcat ggaagcctat 1080
gtgaaggtgg acagctgccc tgaagaaccc cagctgagaa tgaagaacaa tgaggaggct 1140
gaggactatg atgatgacct gacagactct gagatggatg tggtcagatt tgatgatgac 1200
aacagcccca gcttcatcca gatcagatct gtggccaaga agcaccccaa gacctgggtg 1260
cactatattg ctgctgagga agaggactgg gattatgctc ctctggtgct ggcccctgat 1320
gacagaagct acaagagcca gtacctgaac aatggccctc agagaattgg cagaaagtat 1380
aagaaagtga gattcatggc ctacacagat gagacattca agaccagaga ggccattcag 1440
catgagtctg gcattctggg ccctctgctg tatggagaag tgggagatac actgctgatc 1500
atcttcaaga accaggccag cagaccctac aacatctacc ctcatggcat cacagatgtg 1560
agacccctgt attctagaag gctgcccaag ggagtgaagc acctgaagga cttccctatc 1620
ctgcctggag agatcttcaa gtacaagtgg acagtgacag tggaagatgg ccccaccaag 1680
tctgacccta gatgtctgac aagatactac agcagctttg tgaacatgga aagagacctg 1740
gcctctggcc tgattggacc tctgctgatc tgctacaaag aatctgtgga ccagagaggc 1800
aaccagatca tgtctgacaa gagaaatgtg atcctgtttt ctgtgtttga tgagaacaga 1860
tcctggtatc tgacagagaa catccagaga tttctgccca atcctgctgg agtgcagctg 1920
gaagatcctg agttccaggc ctccaacatc atgcactcca tcaatggcta tgtgtttgac 1980
agcctgcagc tgtctgtgtg cctgcatgaa gtggcctact ggtacatcct gagcattgga 2040
gcccagacag acttcctgtc tgtgttcttc tctggctaca ccttcaagca caagatggtg 2100
tatgaggata ccctgacact gttcccattc tctggagaga cagtgttcat gagcatggaa 2160
aaccctggcc tgtggatcct gggctgtcac aactctgact tcagaaacag aggcatgaca 2220
gccctgctga aggtgtccag ctgtgacaag aacacaggag actactatga ggacagctat 2280
gaggacatct ctgcctacct gctgagcaag aacaatgcca ttgagcccag aagcttcagc 2340
cagaatgcca ccaatgtgtc caacaacagc aacaccagca atgactccaa tgtgtcccct 2400
ccagtgctga agagacacca gagagaaatc accagaacca cactgcagtc tgaccaagag 2460
gaaattgact atgatgacac catctctgtg gagatgaaga aagaagattt tgacatctat 2520
gatgaggatg agaatcagag ccccagatcc tttcagaaaa agaccagaca ctacttcatt 2580
gctgctgtgg agagactgtg ggactatggc atgtctagca gccctcatgt gctgagaaat 2640
agagcccagt ctggctctgt gccccagttc aagaaagtgg tgttccaaga gttcacagat 2700
ggcagcttca cccagccact gtatagagga gagctgaatg agcatctggg cctgctgggc 2760
ccttatatca gagctgaagt ggaagataac atcatggtca ccttcagaaa tcaggcctct 2820
agaccctaca gcttctacag ctccctgatc agctatgaag aggaccagag acagggagct 2880
gagcccagaa agaactttgt gaagcccaat gagactaaga cctacttttg gaaggtgcag 2940
caccacatgg cccctacaaa ggatgagttt gactgcaagg cctgggccta cttttctgat 3000
gtggatctgg aaaaggatgt gcactctgga ctcattggac cactgcttgt gtgccacacc 3060
aacacactga accctgctca tggcagacaa gtgacagtgc aagagtttgc cctgttcttc 3120
accatctttg atgaaacaaa gagctggtac ttcacagaga atatggagag aaactgcagg 3180
gccccttgca acatccagat ggaagatccc accttcaaag agaactacag attccatgcc 3240
atcaatggct acatcatgga cacactgcct ggcctggtta tggctcagga tcagagaatc 3300
agatggtatc tgctgtccat gggctccaat gagaatatcc acagcatcca cttctctggc 3360
catgtgttca cagtgagaaa aaaagaagag tacaaaatgg ccctgtacaa tctgtaccct 3420
ggggtgtttg aaacagtgga aatgctgcct tccaaggctg gcatttggag agtggaatgt 3480
ctgattggag agcacctcca tgctggaatg agcaccctgt ttctggtgta cagcaacaag 3540
tgtcagaccc ctctgggcat ggcctctgga cacatcagag acttccagat cacagcctct 3600
ggccagtatg gacagtgggc tcctaaactg gctagactgc actactctgg cagcatcaat 3660
gcctggtcca ccaaagagcc cttcagctgg atcaaggtgg acctgctggc tcccatgatc 3720
atccatggaa tcaagaccca gggagccaga cagaagttca gcagcctgta catcagccag 3780
ttcatcatca tgtacagcct ggatggcaag aagtggcaga cctacagagg caacagcaca 3840
ggcacactca tggtgttctt tggcaatgtg gacagctctg gcattaagca caacatcttc 3900
aaccctccaa tcattgccag atacatcaga ctgcacccca cacactacag catcagatct 3960
accctgagaa tggaactgat gggctgtgac ctgaacagct gcagcatgcc cctgggaatg 4020
gaaagcaagg ccatctctga tgcccagatc acagccagca gctacttcac caacatgttt 4080
gccacttgga gcccctccaa ggctagactg catctgcagg gcagaagcaa tgcttggagg 4140
ccccaagtga acaaccccaa agagtggctg caggtggact ttcaaaagac catgaaagtg 4200
acaggagtga ccacacaggg agtcaagtct ctgctgacct ctatgtatgt gaaagagttc 4260
ctgatctcca gcagccagga tggccaccag tggaccctgt tttccagaa tggcaaagtg 4320
aaagtgttcc agggcaatca ggacagcttc acacctgtgg tcaactccct ggatcctcca 4380
ctgctgacca gatacctgag aattcaccct cagtcttggg tgcaccagat tgctctgaga 4440
atggaagtgc tgggctgtga agctcaggac ctctactgat cgcgaataaa agatctttat 4500
tttcattaga tctgtgtgtt ggttttttgt gtgtatttag ctaaggcagg ccctatgaga 4560

```
ccgtaataaa tttgttcttc tcttcactga cctaagttcc tcacgtgcat agt         4613

SEQ ID NO: 22           moltype = DNA  length = 4613
FEATURE                 Location/Qualifiers
source                  1..4613
                        mol_type = other DNA
                        organism = synthetic construct
SEQUENCE: 22
catagtacgc gtacgttctt aggtcagtga agagaagaac aaatttatta cggtctcata  60
gggcctgcct tctcaaagct tactaaagaa ttattctttt acatttcagt ggccaccaga  120
agatattacc tgggagctgt ggaactgagc tgggactaca tgcagtctga cctgggagag  180
ctgcctgtgg atgctagatt tcctccaaga gtgcccaaga gcttcccctt caacacctct  240
gtggtgtaca agaaaaccct gtttgtggaa ttcacagacc acctgttcaa tattgccaag  300
cctagacctc cttggatggg actgctggga cctacaattc aggctgaggt gtatgacaca  360
gtggtcatca ccctgaagaa catggccagc catcctgtgt ctctgcatgc tgtgggagtg  420
tcttactgga aggcttctga gggagctgag tatgatgacc agacaagcca gagagagaaa  480
gaggatgaca aggttttccc tggaggcagc cacacctatg tctggcaggt cctgaaagaa  540
aatggcccta tggcctctga tcctctgtgc ctgacataca gctacctgag ccatgtggac  600
ctggtcaagg acctgaattc tggcctgatt ggagccctgc tggtgtgtag agaaggcagc  660
ctggccaaag agaaaaccca gacactgcac aagttcatcc tgctgtttgc tgtgtttgat  720
gagggcaaga gctggcactc tgagacaaag aacagcctga tgcaggacag ggatgctgcc  780
tctgctagag cttggcctaa gatgcacaca gtgaatggct atgtgaacag aagcctgcct  840
ggactgattg gctgccacag aaagtctgtg tactggcatg tgattggcat gggcacaaca  900
cctgaggtgc acagcatctt tctggaagga cacaccttcc tggtgagaaa ccatagacag  960
gccagcctgg aaatcagccc tatcaccttc ctgacagctc agaccctgct gatggatctg  1020
ggccagtttc tgctgttctg ccacatcagc agccaccagc atgatggcat ggaagcctat  1080
gtgaaggtgg acagctgccc tgaagaaccc cagctgagaa tgaagaacaa tgaggaggct  1140
gaggactatg atgatgacct gacagactct gagatggatg tggtcagatt tgatgatgac  1200
aacagcccca gcttcatcca gatcagatct gtggccaaga agcaccccaa gacctgggtg  1260
cactatattg ctgctgagga agaggactgg gattatgctc ctctggtgct ggcccctgat  1320
gacagaagct acaagagcca gtacctgaac aatggccctc agagaattgg cagaaagtat  1380
aagaaagtga gattcatggc ctacacagat gagacattca agaccagaga ggccattcag  1440
catgagtctg gcattctggg ccctctgctg tatggagaag tgggagatac actgctgatc  1500
atcttcaaga accaggccag cagaccctac aacatctacc ctcatggcat cacagatgtg  1560
agaccccctgt attctagaag gctgcccaag ggagtgaagc acctgaagga cttccctatc  1620
ctgcctggag agatcttcaa gtacaagtgg acagtgacag tggaagatgg ccccaccaag  1680
tctgacccta gatgtctgac aagatactac agcagctttg tgaacatgga aagagacctg  1740
gcctctggcc tgattggacc tctgctgatc tgctacaaag aatctgtgga ccagagaggc  1800
aaccagatca tgtctgacaa gagaaatgtg atcctgtttt ctgtgtttga tgagaacaga  1860
tcctggtatc tgacagagaa catccagaga tttctgccca atcctgctgg agtgcagctg  1920
gaagatcctg agttccaggc ctccaacatc atgcactcca tcaatggcta tgtgtttgac  1980
agcctgcagc tgtctgtgtg cctgcatgaa gtggcctact ggtacatcct gagcattgga  2040
gcccagacag acttcctgtc tgtgttcttc tctggctaca ccttcaagca caagatggtg  2100
tatgaggata ccctgacact gttcccattc tctggagaga cagtgttcat gagcatggaa  2160
aaccctggcc tgtggatcct gggctgtcac aactctgact tcagaaacag aggcatgaca  2220
gccctgctga aggtgtccag ctgtgacaag aacacaggag actactatga ggacagctat  2280
gaggacatct ctgcctacct gctgagcaag aacaatgcca ttgagcccag aagcttcagc  2340
cagaatgcca ccaatgtgtc caacaacagc aacaccagca atgactccaa tgtgtcccct  2400
ccagtgctga agagacacca gagagaaatc accagaacca cactgcagtc tgaccaagag  2460
gaaattgact atgatgacac catctctgtg gagatgaaga aagaagattt tgacatctat  2520
gatgaggatg agaatcagag ccccagatcc tttcagaaaa agaccagaca ctacttcatt  2580
gctgctgtgg agagactgtg ggactatggc atgtctagca gccctcatgt gctgagaaat  2640
agagcccagt ctggctctgt gccccagttc aagaaagtgg tgttccaaga gttcacagat  2700
ggcagcttca cccagccact gtatagagga gagctgaatg agcatctggg cctgctgggc  2760
ccttatatca gagctgaagt ggaagataac atcatggtca ccttcagaaa tcaggcctct  2820
agaccctaca gcttctacag ctccctgatc agctatgaag aggaccagag acagggagct  2880
gagcccagaa agaactttgt gaagcccaat gagactaaga cctacttttg gaaggtgcag  2940
caccacatgg cccctacaaa ggatgagttt gactgcaagg cctgggccta cttttctgat  3000
gtggatctgg aaaaggatgt gcactctgga ctcattggac cactgcttgt gtgccacacc  3060
aacacactga accctgctca tggcagacaa gtgacagtgc aagagtttgc cctgttcttc  3120
accatctttg atgaaacaaa gagctggtac ttcacagaga atatggagag aaactgcagg  3180
gccccttgca acatccagat ggaagatccc accttcaaag agaactacag attccatgcc  3240
atcaatggct acatcatgga cacactgcct ggcctggtta tggctcagga tcagagaatc  3300
agatggtatc tgctgtccat gggctccaat gagaatatcc acagcatcca cttctctggc  3360
catgtgttca cagtgagaaa aaaagaagag tacaaaatgg ccctgtacaa tctgtaccct  3420
ggggtgtttg aaacagtgga aatgctgcct tccaaggctg gcatttggag agtggaatgt  3480
ctgattggag agcacctcca tgctggaatg agcaccctgt ttctggtgta cagcaacaag  3540
tgtcagaccc ctctgggcat ggcctctgga cacatcagag acttccagat cacagcctct  3600
ggccagtatg gacagtgggc tcctaaactg gctagactgc actactctgg cagcatcaat  3660
gcctggtcca ccaaagagcc cttcagctgg atcaaggtgg acctgctggc tcccatgatc  3720
atccatggaa tcaagaccca gggagccaga cagaagttca gcagcctgta catcagccag  3780
ttcatcatca tgtacagcct ggatggcaag aagtggcaga cctacagagg caacagcaca  3840
ggcacactca tggtgttctt tggcaatgtg gacagctctg gcattaagca caacatcttc  3900
aaccctccaa tcattgccag atacatcaga ctgcacccca cacactacag catcagatct  3960
accctgagaa tggaactgat gggctgtgac ctgaacagct gcagcatgcc cctgggaatg  4020
gaaagcaagg ccatctctga tgcccagatc acagccagca gctacttcac caacatgttt  4080
gccacttgga gcccctccaa ggctagactg catctgcagg gcagaagcaa tgcttggagg  4140
ccccaagtga acaaccccaa agagtggctg caggtggact ttcaaaagac catgaaagtg  4200
acaggagtga ccacacaggg agtcaagtct ctgctgacct ctatgtatgt gaaagagttc  4260
```

```
ctgatctcca gcagccagga tggccaccag tggaccctgt ttttccagaa tggcaaagtg  4320
aaagtgttcc agggcaatca ggacagcttc acacctgtgg tcaactccct ggatcctcca  4380
ctgctgacca gatacctgag aattcaccct cagtcttggg tgcaccagat tgctctgaga  4440
atggaagtgc tgggctgtga agctcaggac ctctactgat cgcgaataaa agatctttat  4500
tttcattaga tctgtgtgtt ggttttttgt gtgtatttag ctaaggcagg ccctatgaga  4560
ccgtaataaa tttgttcttc tcttcactga cctaagttcc tcacgtgcat agt         4613

SEQ ID NO: 23           moltype = DNA  length = 4613
FEATURE                 Location/Qualifiers
source                  1..4613
                        mol_type = other DNA
                        organism = synthetic construct
SEQUENCE: 23
catagtacgc gtacgttttt gttcttctct tcactgacct aagaggcagg ccctatgaga  60
ccgtaataaa tctcaaagct tactaaagaa ttattctttt acatttcagt ggccaccaga  120
agatattacc tgggagctgt ggaactgagc tgggactaca tgcagtctga cctgggagag  180
ctgcctgtgg atgctagatt tcctccaaga gtgcccaaga gcttcccctt caacacctct  240
gtggtgtaca agaaaaccct gtttgtggaa ttcacagacc acctgttcaa tattgccaag  300
cctagacctc cttggatggg actgctggga cctacaattc aggctgaggt gtatgacaca  360
gtggtcatca ccctgaagaa catggccagc catcctgtgt ctctgcatgc tgtgggagtg  420
tcttactgga aggcttctga gggagctgag tatgatgacc agacaagcca gagagagaaa  480
gaggatgaca aggttttccc tggaggcagc cacacctatg tctggcaggt cctgaaagaa  540
aatggcccta tggcctctga tcctctgtgc ctgacataca gctacctgag ccatgtggac  600
ctggtcaagg acctgaattc tggcctgatt ggagccctgc tggtgtgtag agaaggcagc  660
ctggccaaag agaaaaccca gacactgcac aagttcatcc tgctgtttgc tgtgtttgat  720
gagggcaaga gctggcactc tgagacaaag aacagcctga tgcaggacag ggatgctgcc  780
tctgctagag cttggcctaa gatgcacaca gtgaatggct atgtgaacag aagcctgcct  840
ggactgattg gctgccacag aaagtctgtg tactggcatg tgattggcat gggcacaaca  900
cctgaggtgc acagcatctt tctggaagga cacaccttcc tggtgagaaa ccatagacag  960
gccagcctgg aaatcagccc tatcaccttc ctgacagctc agaccctgct gatggatctg  1020
ggccagtttc tgctgttctg ccacatcagc agccaccagc atgatggcat ggaagcctat  1080
gtgaaggtgg acagctgccc tgaagaaccc cagctgagaa tgaagaacaa tgaggaggct  1140
gaggactatg atgatgacct gacagactct gagatggatg tggtcagatt tgatgatgac  1200
aacagcccca gcttcatcca gatcagatct gtggccaaga agcaccccaa gacctgggtg  1260
cactatattg ctgctgagga agaggactgg gattatgctc ctctggtgct ggcccctgat  1320
gacagaagct acaagagcca gtacctgaac aatggccctc agagaattgg cagaaagtat  1380
aagaaagtga gattcatggc ctacacagat gagacattca agaccagaga ggccattcag  1440
catgagtctg gcattctggg ccctctgctg tatggagaag tgggagatac actgctgatc  1500
atcttcaaga accaggccag cagaccctac aacatctacc ctcatggcat cacagatgtg  1560
agacccctgt attctagaag gctgcccaag ggagtgaagc acctgaagga cttccctatc  1620
ctgcctggag agatcttcaa gtacaagtgg acagtgacag tggaagatgg ccccaccaag  1680
tctgacccta gatgtctgac aagatactac agcagctttg tgaacatgga aagagacctg  1740
gcctctggcc tgattggacc tctgctgatc tgctacaaag aatctgtgga ccagagaggc  1800
aaccagatca tgtctgacaa gagaaatgtg atcctgtttt ctgtgtttga tgagaacaga  1860
tcctggtatc tgacagagaa catccagaga tttctgccca atcctgctgg agtgcagctg  1920
gaagatcctg agttccaggc ctccaacatc atgcactcca tcaatggcta tgtgtttgac  1980
agcctgcagc tgtctgtgtg cctgcatgaa gtggcctact ggtacatcct gagcattgga  2040
gcccagacag acttcctgtc tgtgttcttc tctggctaca ccttcaagca caagatggtg  2100
tatgaggata ccctgacact gttcccattc tctggagaga cagtgttcat gagcatggaa  2160
aaccctggcc tgtggatcct gggctgtcac aactctgact tcagaaacag aggcatgaca  2220
gccctgctga aggtgtccag ctgtgacaag aacacaggag actactatga ggacagctat  2280
gaggacatct ctgcctacct gctgagcaag aacaatgcca ttgagcccag aagcttcagc  2340
cagaatgcca ccaatgtgtc caacaacagc aacaccagca atgactccaa tgtgtcccct  2400
ccagtgctga agagacacca gagagaaatc accagaacca cactgcagtc tgaccaagag  2460
gaaattgact atgatgacac catctctgtg gagatgaaga aagaagattt tgacatctat  2520
gatgaggatg agaatcagag ccccagatcc tttcagaaaa agaccagaca ctacttcatt  2580
gctgctgtgg agagactgtg ggactatggc atgtctagca gccctcatgt gctgagaaat  2640
agagcccagt ctggctctgt gccccagttc aagaaagtgg tgttccaaga gttcacagat  2700
ggcagcttca cccagccact gtatagagga gagctgaatg agcatctggg cctgctgggc  2760
ccttatatca gagctgaagt ggaagataac atcatggtca ccttcagaaa tcaggcctct  2820
agaccctaca gcttctacag ctccctgatc agctatgaag aggaccagag acagggagct  2880
gagcccagaa agaactttgt gaagcccaat gagactaaga cctacttttg gaaggtgcag  2940
caccacatgg cccctacaaa ggatgagttt gactgcaagg cctgggccta cttttctgat  3000
gtggatctgg aaaaggatgt gcactctgga ctcattggac cactgcttgt gtgccacacc  3060
aacacactga accctgctca tggcagacaa gtgacagtgc aagagtttgc cctgttcttc  3120
accatctttg atgaaacaaa gagctggtac ttcacagaga atatggagag aaactgcagg  3180
gccccttgca acatccagat ggaagatccc accttcaaag agaactacag attccatgcc  3240
atcaatggct acatcatgga cacactgcct ggcctggtta tggctcagga tcagagaatc  3300
agatggtatc tgctgtccat gggctccaat gagaatatcc acagcatcca cttctctggc  3360
catgtgttca cagtgagaaa aaaagaagag tacaaaatgg ccctgtacaa tctgtaccct  3420
ggggtgtttg aaacagtgga aatgctgcct tccaaggctg gcatttggag agtggaatgt  3480
ctgattggag agcacctcca tgctggaatg agcaccctgt ttctggtgta cagcaacaag  3540
tgtcagaccc ctctgggcat ggcctctgga cacatcagag acttccagat cacagcctct  3600
ggccagtatg gacagtgggc tcctaaactg gctagactgc actactctgg cagcatcaat  3660
gcctggtcca ccaaagagcc cttcagctgg atcaaggtgg acctgctggc tcccatgatc  3720
atccatggaa tcaagaccca gggagccaga cagaagttca gcagcctgta catcagccag  3780
ttcatcatca tgtacagcct ggatggcaag aagtggcaga cctacagagg caacagcaca  3840
ggcacactca tggtgttctt tggcaatgtg gacagctctg gcattaagca caacatcttc  3900
aaccctccaa tcattgccag atacatcaga ctgcacccca cacactacag catcagatct  3960
```

```
accctgagaa tggaactgat gggctgtgac ctgaacagct gcagcatgcc cctgggaatg  4020
gaaagcaagg ccatctctga tgcccagatc acagccagca gctacttcac caacatgttt  4080
gccacttgga gcccctccaa ggctagactg catctgcagg gcagaagcaa tgcttggagg  4140
ccccaagtga acaaccccaa agagtggctg caggtggact ttcaaaagac catgaaagtg  4200
acaggagtga ccacacaggg agtcaagtct ctgctgacct ctatgtatgt gaaagagttc  4260
ctgatctcca gcagccagga tggccaccag tggaccctgt tttccagaa tggcaaagtg  4320
aaagtgttcc agggcaatca ggacagcttc acacctgtgg tcaactccct ggatcctcca  4380
ctgctgacca gatacctgag aattcaccct cagtcttggg tgcaccagat tgctctgaga  4440
atggaagtgc tgggctgtga agctcaggac ctctactgat cgcgaataaa agatctttat  4500
tttcattaga tctgtgtgtt ggtttttgt gtgtatttag ctatttatta cggtctcata  4560
gggcctgcct cttaggtcag tgaagagaag aacaaattcc tcacgtgcat agt         4613

SEQ ID NO: 24          moltype = RNA  length = 68
FEATURE                Location/Qualifiers
source                 1..68
                       mol_type = other RNA
                       organism = synthetic construct
modified_base          1..3
                       mod_base = OTHER
                       note = 2'-O-Methyl modified base
modified_base          11..14
                       mod_base = OTHER
                       note = 2'-O-Methyl modified base
modified_base          25..27
                       mod_base = OTHER
                       note = 2'-O-Methyl modified base
modified_base          34..37
                       mod_base = OTHER
                       note = 2'-O-Methyl modified base
modified_base          56..67
                       mod_base = OTHER
                       note = 2'-Fluoro modified base
modified_base          68
                       mod_base = OTHER
                       note = 2'-O-Methyl modified base
modified_base          1..4
                       mod_base = OTHER
                       note = phosphorothioate linkage
modified_base          10..14
                       mod_base = OTHER
                       note = phosphorothioate linkage
modified_base          24..29
                       mod_base = OTHER
                       note = phosphorothioate linkage
modified_base          39..43
                       mod_base = OTHER
                       note = phosphorothioate linkage
modified_base          65..68
                       mod_base = OTHER
                       note = phosphorothioate linkage
SEQUENCE: 24
gttgagaatc gaaagattct caacctttta atttctactg ttgtagatct gtaacgatcg  60
ggaactgg                                                           68

SEQ ID NO: 25          moltype = RNA  length = 68
FEATURE                Location/Qualifiers
source                 1..68
                       mol_type = other RNA
                       organism = synthetic construct
modified_base          1..3
                       mod_base = OTHER
                       note = 2'-O-Methyl modified base
modified_base          11..14
                       mod_base = OTHER
                       note = 2'-O-Methyl modified base
modified_base          25..27
                       mod_base = OTHER
                       note = 2'-O-Methyl modified base
modified_base          34..37
                       mod_base = OTHER
                       note = 2'-O-Methyl modified base
modified_base          56..67
                       mod_base = OTHER
                       note = 2'-Fluoro modified base
modified_base          68
                       mod_base = OTHER
                       note = 2'-O-Methyl modified base
modified_base          1..4
                       mod_base = OTHER
```

```
                        note = phosphorothioate linkage
modified_base           10..14
                        mod_base = OTHER
                        note = phosphorothioate linkage
modified_base           24..29
                        mod_base = OTHER
                        note = phosphorothioate linkage
modified_base           39..43
                        mod_base = OTHER
                        note = phosphorothioate linkage
modified_base           65..68
                        mod_base = OTHER
                        note = phosphorothioate linkage
SEQUENCE: 25
gttgagaatc gaaagattct caacctttta atttctactg ttgtagatag tgtagcagag  60
aggaacca                                                           68

SEQ ID NO: 26           moltype = RNA  length = 110
FEATURE                 Location/Qualifiers
source                  1..110
                        mol_type = other RNA
                        organism = synthetic construct
modified_base           1..3
                        mod_base = OTHER
                        note = 2'-O-Methyl modified base
modified_base           108..110
                        mod_base = OTHER
                        note = 2'-O-Methyl modified base
modified_base           1..4
                        mod_base = OTHER
                        note = phosphorothioate linkage
modified_base           107..110
                        mod_base = OTHER
                        note = phosphorothioate linkage
SEQUENCE: 26
cttaggtcag tgaagagaag aagttgagaa tcgaaagatt cttaataagg catccttccg  60
atgctgactt ctcaccgtcc gttttccaat aggagcgggc ggtatgtttt             110

SEQ ID NO: 27           moltype = RNA  length = 110
FEATURE                 Location/Qualifiers
source                  1..110
                        mol_type = other RNA
                        organism = synthetic construct
modified_base           1..3
                        mod_base = OTHER
                        note = 2'-O-Methyl modified base
modified_base           108..110
                        mod_base = OTHER
                        note = 2'-O-Methyl modified base
modified_base           1..4
                        mod_base = OTHER
                        note = phosphorothioate linkage
modified_base           107..110
                        mod_base = OTHER
                        note = phosphorothioate linkage
SEQUENCE: 27
aggcaggccc tatgagaccg tagttgagaa tcgaaagatt cttaataagg catccttccg  60
atgctgactt ctcaccgtcc gttatccaat aggagcgggc ggtatgtttt             110

SEQ ID NO: 28           moltype = DNA  length = 18
FEATURE                 Location/Qualifiers
source                  1..18
                        mol_type = other DNA
                        organism = synthetic construct
SEQUENCE: 28
ctcctcttcg tctccggc                                                18

SEQ ID NO: 29           moltype = DNA  length = 19
FEATURE                 Location/Qualifiers
source                  1..19
                        mol_type = other DNA
                        organism = synthetic construct
SEQUENCE: 29
ctgccacatt gctcagcac                                               19

SEQ ID NO: 30           moltype = DNA  length = 3498
FEATURE                 Location/Qualifiers
source                  1..3498
                        mol_type = other DNA
```

```
                        organism = synthetic construct
SEQUENCE: 30
atggcccccca agaagaagcg gaaagttggc ggcggaggca gcagcaccga catgaagaac  60
taccggatcg gcgtggacgt gggcgataga tctgttggac tggccgccat cgagttcgac  120
gatgatggac tgcccatcca gaagctggcc ctggtcacct ttagacacga tggcggactg  180
gaccccacca agaacaagac ccctatgagc cggaaagaga cacggggaat cgccagacgg  240
accatgcgga tgaacagaga gcggaagcgg cggctgagaa acctggacaa cgtgctggaa  300
aacctgggct actctgtgcc tgagggccct gagcctgaga catatgaggc ctggacaagc  360
agagccctgc tggcctctat caaactggcc tctgccgacg agctgaacga acaccttgtc  420
agagccgtgc ggcacatggc cagacataga ggatgggcca atccttggtg gtccctggac  480
cagctggaaa aggccagcca agagcctagc gagacattcg agatcatcct ggccagagcc  540
agagagctgt tcggcgagaa ggtgcccgct aatcctacac tgggaatgct gggagccctg  600
gccgctaaca atgaggtgct gctgaggccc agggacgaga agaagagaaa gaccggatac  660
gtgcggggca cccctctgat gtttgctcaa gttcgacagg gcgatcagct ggccgagctg  720
cggagaattt gtgaagtgca gggcatcgag gaccagtacg aggctctgag actgggcgtg  780
ttcgaccaca agcacccccta cgtgcccaaa gaaagagtgg gcaaagaccc tctgaacccc  840
agcaccaaca gaaccatcag agccagcctg gaatttcaag agttccgcat cctggacagc  900
gtggccaatc tgagagtgcg gatcggcagc agagccaaga gggaactgac agaggccgag  960
tatgatgccg ccgtggaatt cctgatggac tacgccgaca aagagcagcc tagctgggcc  1020
gatgtggccg agaaaattgg cgtgcccggc aacagactgg tggcccctgt tctggaagat  1080
gtgcagcaga aaacagcccc ttacgacaga agcagcgccg cctttgagaa ggccatgggc  1140
aagaaaaccg aggccagaca gtggtgggag tccaccgatg atgaccagct gagaagcctg  1200
ctgattgcct tcctggtgga cgccaccaac gacacagaag aagccgctgc tgaagccggc  1260
ctgagcgagc tgtataagtc ttggcctgcc gaggaaagag aggccctgtc caacatcgac  1320
ttcgagaagg gcagagtggc ctacagccaa gaaaccctga gcaagctgag cgagtacatg  1380
cacgagtaca gagtgggact gcacgaggct agaaaggccg tgttcggagt ggatgatacc  1440
tggcggcctc ctctggataa gctggaagaa cctacaggac agcctgccgt ggacagagtg  1500
ctgaccatcc tgagaagatt cgtgctggac tgcgagcggc aatggggcag acctagagcc  1560
atcaccgtgg aacacacacg gacaggcctg atgggcccaa cacagagaca gaagatcctg  1620
aacgagcaga agaagaaccg ggccgacaac gagagaatcc gggatgagct gagagaatct  1680
ggcgtggaca acccctccag agccgaagtt cggagacacc tgatcgtgca agagcaagag  1740
tgccagtgcc tgtactgcgg caccatgatc accaccacca caagcgagct ggaccacatc  1800
gttcctagag ccggtggcgg cagcagcaga agggaaaatc tggccgctgt gtgcagagcc  1860
tgcaacgcca agaagaaacg cgagctgttc tacgcctggg ctggcccagt gaagtcccaa  1920
gagacaatcg agagagtcag acagctgaag gcctttaagg acagcaagaa agccaagatg  1980
ttcaagaacc agatccgccg gctgaaccag accgaggccg atgagcctat cgacgaaaga  2040
agcctggcca gcacatctta cgccgctgtg gccgttagag agcggctgga acagcacttc  2100
aacgaaggcc tggcactgga cgacaagtcc agagtggtgc tggatgtgta tgccggcgct  2160
gtgaccagag agtctcgtag agctggcggc atcgacgagc ggattctgct gagaggcgag  2220
cgggacaaga acagattcga tgtgcggcat cacgccgtgg acgctgctgt tatgaccctg  2280
ctgaacagat ccgtggctct gaccctggaa cagagatcac agctgaggcg ggccttctac  2340
gagctggaac tggacaaact ggaccgggac cagctcaagc ctggcgagga ttggagaaac  2400
ttcaccggcc tgtacgaggc ctctcagaac aagttcagcg agtggaagaa agccgccaca  2460
gtgctgggag atctgctggc tgaagccatc gaggatgacg ccattgccgt ggtgtctcca  2520
ctgagactga ggccccagaa tggcagcgtg cacgacgata ccatcaacgc cgtgaagaag  2580
ctgacactgg gctctgcctg gcctgcagac gctgtgaaga gaatcgtgga ccccgagatc  2640
tacctggcta tgaaggacgt gctgggcaag ctgaaagagc tgcccgagga ttctgccaga  2700
tctctggaac tgtccgacgg ccggtacatc gaagccgatg acgaggtgct gttcttccca  2760
aagaaggccg ctagcatcct gacacctaga ggcgccgctg agatcggcaa ctctatccac  2820
catgccagac tgtatagctg gctgaccaag aagggcgagc tgaagtttgg catgctgaga  2880
gtgtacggcg ccgagtttcc ctggctgatg agagagtctg gaagccgcga cgtgctgcat  2940
atgcctattc accctggcag ccagagcttc agaggcatgc aggatggcgt gcggaaagcc  3000
gtggaaagcg gagaggctgt ggaattcggc tggatcaccc aggacgatga gctggaattc  3060
gaccccgagg actacattgc ccacggcgga gatgacgaac tgaacagact gctgcgagtg  3120
atgcccgaga gaaggtggcg agtggacggc ttctataacg ccggcacact gagaatcaga  3180
cccgctctgc tgtctgctga gcagctgcct tctgagctgc agaaaaaggt ggccgacaag  3240
accctgagcg acgtggaact gatcctgctg agggctgttc agcggggact gttcgtggcc  3300
atcagcagct ttctgcccct ggaaagcctg aaagtgatcc ggcggaacaa tctgggcttc  3360
cccaggtggc gcggaaacgg aaatctgccc accagctttg aagtgcggag cagcgctctg  3420
agagccctgg gagttgaagg atctggcgga aaaagacctg ccgccacaaa gaaagccgga  3480
caggccaaga aaaagaag                                                3498

SEQ ID NO: 31           moltype = DNA  length = 4087
FEATURE                 Location/Qualifiers
source                  1..4087
                        mol_type = other DNA
                        organism = synthetic construct
SEQUENCE: 31
aaaagccagc tccagcaggc gctgctcact cctccccatc ctctccctct gtccctctgt  60
ccctctgacc ctgcactgtc ccagcaccat ggcccctaag aagaagagaa aagtcggcgg  120
aggcggcagc ttcaacaact tcatcaagaa gtacagcctg cagaaaaccc tgcgcttcga  180
gctgaagcct gtgggcgaga cagccgacta catcgaggac ttcaagagcg agtacctgaa  240
ggacaccgtg ctgaaggacg agcagagagc caaggactac caagagatca agaccctgat  300
cgacgattac caccgcgagt acatcgaaga gtgcctgaga gaacccgtgg acaagaaaac  360
cggcgagatc ctggacttca cccaggacct ggaagatgcc ttcagctact accagaagct  420
gaaagagaac cccaccgaga acagagtcgg ctgggagaaa gagcaagaga gcctgaggaa  480
gaagctggtc acctccttcg tgggcaacga cggcctgttc aagaaaagagt tcatcaccag  540
ggacctgcct gagtggctgc agaagaaagg actctggggc gagtacaagg acacagtgga  600
aaacttcaag aagttcacca cctacttcag cggcttccac gagaaccgga agaacatgta  660
```

```
caccgccgag gctcagagca ccgctatcgc caacagactg atgaacgaca acctgcctaa  720
gttctttaac aactacctgg cctaccagac catcaaagag aagcaccccg acctggtgtt  780
cagactggat gatgctctgc tgcaggccgc tggcgtggaa catctggatg aggctttcca  840
gcctagatac ttcagcagac tgttcgccca gagcggcatc accgctttca acgagctgat  900
cggcggcaga accacagaga acggcgagaa gatccagggc ctgaacgagc agatcaacct  960
gtacagacag cagaaccccg agaaggccaa gggcttcccc agattcatgc ctctgttcaa  1020
gcagatcctg agcgacagag agacacacag ctttctgccc gacgccttcg agaacgacaa  1080
agagctgctc caggctctga gagactacgt ggacgccgcc acatctgagg aaggcatgat  1140
cagccagctg aacaaggcca tgaaccagtt cgtgaccgcc gacctgaaga gagtgtacat  1200
caagagcgcc gctctgacca gcctgagcca agagctgttc cacttcttcg gcgtgatcag  1260
cgacgctatc gcttggtacg ccgagaagag actgagcccc aagaaggccc aagagtcttt  1320
cctgaagcaa gaggtgtacg ccatcgagga actgaaccag gctgtcgtgg gctacatcga  1380
ccagctggaa gatcagagcg agctgcagca actgctggtg gacctgccag atcctcagaa  1440
acccgtgtcc agcttcatcc tgacacactg gcagaagtct caagagcccc tgcaggcagt  1500
gatcgccaag gtggaacctc tgttcgaact ggaagaactg agcaagaaca agagggcccc  1560
aaagcacgac aaggaccaag gcggcgaggg atttcagcag gtcgacgcca tcaagaacat  1620
gctggacgcc ttcatggaag tgtcccacgc tatcaagccc ctgtacctgg tcaagggaag  1680
aaaggccatc gacatgcccg acgtggacac cggcttctac gctgatttcg ccgaggccta  1740
cagcgcctac gagcaagtga cagtgtccct gtacaacaag accagaaacc acctgtccaa  1800
gaagcccttc agcaaggaca agatcaagat caacttcgac gcccctacac tgctgaacgg  1860
ctgggacctg aacaaagaga gcgacaacaa gtccatcatc ctgcggaagg acggcaactt  1920
ctacctggca atcatgcacc ccaagcacac caaggtgttc gactgctact ctgcctctga  1980
ggctgccggc aagtgctacg agaagatgaa ctacaagctg ctgagcggcg ccaacaagat  2040
gctgcctaag gtgttcttta gcaagaaggg catcgagaca ttcagccctc cacaagaaat  2100
cctggacctg tacaagaaca acgagcataa gaagggcgcc accttcaagc tggaatcctg  2160
ccacaagctg atcgatttct tcaagcggaa catccccaag tacaaggtgc accctaccga  2220
caactttggc tgggacgtgt tcggctttca cttcagccct accagcagct acggcgacct  2280
gtctggcttc tacagagagg tggaagccca gggatacaag ctgtggttca gcgacgtgtc  2340
cgaggcttac atcaacaaat gcgtggaaga gggcaagctg ttcctgttcc aaatctacaa  2400
caaggacttc tcccctaact ccaccggcaa gcccaacctg cacaccctgt attggaaggg  2460
cctgttcgag cccgagaacc tgaaagacgt ggtgctgaag ctgaatggcg aggccgagat  2520
cttctaccgg aagcacagca tcaagcacga ggacaagacc atccacagag ctaaggaccc  2580
tatcgctaac aagaacgctg acaaccccaa gaaacagagc gtgttcgatt acgacatcat  2640
caaggataag cggtataccc aggacaagtt cttcttccac gtgccaatca gcctgaactt  2700
caaaagccag ggcgtcgtgc ggttcaacga taagatcaac ggcctgctgg ccgctcagga  2760
cgatgtgcat ggtgatcggca tcgacagagg cgagagacat ctgctgtact acaccgtggt  2820
caacggcaag ggcgaagtgg tggaacaggg cagcctgaat caggtggcca cagatcaggg  2880
ctacgtggtg gattaccagc agaagctgca cgccaaagag aaagaacgcg accaggccag  2940
aaagaactgg tccaccatcg agaacatcaa agaactgaag gccggctacc tgagccaggt  3000
ggtgcataag ctggctcagc tgatcgtgaa gcacaacgcc atcgtgtgcc tcgaggacct  3060
gaatttcggc ttcaagaggg gcagattcaa ggtcgagaaa caggtgtacc agaagttcga  3120
gaaggctctg atcgacaagc tgaactacct cgtgttcaaa gagagaggcg ccacacaggc  3180
tggcggatac ctgaatgctt accagctggc cgcacctttc gagagctttg agaagctggg  3240
caagcagacc ggcatcctgt actacgtgcg gagcgactac accagcaaga tcgaccctgc  3300
taccggcttc gtggactttc tgaagcctaa gtacgagagc atggccaaga gcaaagtgtt  3360
cttcgagtcc ttcgagcgca tccagtggaa ccaggccaaa ggctacttcg agttcgagtt  3420
tgactacaag aagatgtgcc ccagcagaaa gttcggcgac tacagaacca gatgggtcgt  3480
gtgcaccttc ggcgacaccc gctaccagaa cagaagaaac aagagcagcg gccagtggga  3540
gacagagaca atcgatgtga cagcccagct gaaagccctg ttcgccgctt acggcatcac  3600
atacaatcaa gaggataaca tcaaggacgc cattgccgcc gtgaagtaca ccaagttcta  3660
caagcagctg tactggctgc tgagactgac cctgagcctg agacacagcg tgacaggcac  3720
cgacgaggat ttcatcctgt ctccagtggc cgacgagaat ggcgtgttct ttgactctag  3780
gaaggccacc gacaagcagc ctaaggacgc tgatgctaac ggcgcctacc atatcgccct  3840
gaaaggcctg tggaatctcc agcagatcag acagcacgac tggaacgtgg aaaagcccaa  3900
aaagctgaac ctcgccatga agaacgaaga gtggttcggc ttcgctcaga agaagaagtt  3960
tagagccagc ggcggcaaga ggcctgccgc tacaaaaaaa gccggccagg ccaagaaaaa  4020
gaagtgacca cacccccatt cccccactcc agatagaact tcagttatat ctcacgtgtc  4080
tggagtt                                                            4087
```

```
SEQ ID NO: 32          moltype = DNA  length = 4956
FEATURE                Location/Qualifiers
source                 1..4956
                       mol_type = other DNA
                       organism = synthetic construct
SEQUENCE: 32
atgctttgca tacttctgcc tgctggggag cctggggact ttccacaccc taactgacac  60
acattccact gaattttgta atcggttggc agccaatgaa atacaaagat gagtctagtt  120
aataatctac aattattggt taaagaagta tattagttca gattcagaat gtcaatattt  180
cctgtaacga tcgggaactg gcatttgagt gtagcagaga ggaaccattt ctcagtgtta  240
agcttactaa agaattattc ttttacattt cagtggccac cagaagatat tacctgggag  300
ctgtggaact gagctgggac tacatgcagt ctgacctggg agagctgcct gtggatgcta  360
gatttcctcc aagagtgccc aagagcttcc ccttcaacac ctctgtggtg tacaagaaaa  420
ccctgtttgt ggaattcaca gaccacctgt tcaatattgc caagcctaga cctccttgga  480
tgggactgct gggacctaca attcaggctg aggtgtatga cacagtggtc atcaccctga  540
agaacatggc cagccatcct gtgtctctgc atgctgtggg agtgtcttac tggaaggctt  600
ctgagggagc tgagtatgat gaccagacaa gccagagaga gaaagaggat gacaaggttt  660
tccctggagg cagccacacc tatgtctggc aggtcctgaa agaaaatggc cctatggcct  720
ctgatcctct gtgcctgaca tacagctacc tgagccatgt ggacctggtc aaggacctga  780
attctggcct gattggagcc ctgctggtgt gtagagaagg cagcctggcc aaagagaaaa  840
```

```
cccagacact gcacaagttc atcctgctgt ttgctgtgtt tgatgagggc aagagctggc  900
actctgagac aaagaacagc ctgatgcagg acagggatgc tgcctctgct agagcttggc  960
ctaagatgca cacagtgaat ggctatgtga acagaagcct gcctggactg attggctgcc  1020
acagaaagtc tgtgtactgg catgtgattg gcatgggcac aacacctgag gtgcacagca  1080
tctttctgga aggacacacc ttcctggtga gaaaccatag acaggccagc ctggaaatca  1140
gccctatcac cttcctgaca gctcagaccc tgctgatgga tctgggccag tttctgctgt  1200
tctgccacat cagcagccac cagcatgatg gcatggaagc ctatgtgaag gtggacagct  1260
gccctgaaga accccagctg agaatgaaga acaatgagga ggctgaggac tatgatgatg  1320
acctgacaga ctctgagatg gatgtggtca gatttgatga tgacaacagc cccagcttca  1380
tccagatcag atctgtggcc aagaagcacc ccaagacctg ggtgcactat attgctgctg  1440
aggaagagga ctgggattat gctcctctgg tgctggcccc tgatgacaga agctacaaga  1500
gccagtacct gaacaatggc cctcagagaa ttggcagaaa gtataagaaa gtgagattca  1560
tggcctacac agatgagaca ttcaagacca gagaggccat tcagcatgag tctggcattc  1620
tgggccctct gctgtatgga gaagtgggag atacactgct gatcatcttc aagaaccagg  1680
ccagcagacc ctacaacatc taccctcatg gcatcacaga tgtgagaccc ctgtattcca  1740
gaaggctgcc caagggagtg aagcacctga aggacttccc tatcctgcct ggagagatct  1800
tcaagtacaa gtggacagtg acagtggaag atggccccac caagtctgac cctagatgtc  1860
tgacaagata ctacagcagc tttgtgaaca tggaaagaga cctggcctct ggcctgattg  1920
gacctctgct gatctgctac aaagaatctg tggaccagag aggcaaccag atcatgtctg  1980
acaagagaaa tgtgatcctg ttttctgtgt ttgatgagaa cagatcctgg tatctgacag  2040
agaacatcca gagatttctg cccaatcctg ctggagtgca gctggaagat cctgagttcc  2100
aggcctccaa catcatgcac tccatcaatg gctatgtgtt tgacagcctg cagctgtctg  2160
tgtgcctgca tgaagtggcc tactggtaca tcctgagcat tggagcccag acagacttcc  2220
tgtctgtgtt cttctctggc tacaccttca agcacaagat ggtgtatgag gataccctga  2280
cactgttccc attctctgga gagacagtgt tcatgagcat ggaaaaccct ggcctgtgga  2340
tcctgggctg tcacaactct gacttcagaa acagaggcat gacagccctg ctgaaggtgt  2400
ccagctgtga caagaacaca ggagactact atgaggacag ctatgaggac atctctgcct  2460
acctgctgag caagaacaat gccattgagc ccagaagctt cagccagaat gccaccaatg  2520
tgtccaacaa cagcaacacc agcaatgact ccaatgtgtc cctccagtg ctgaagagac  2580
accagagaga aatcaccaga accacactgc agtctgacca agaggaaatt gactatgatg  2640
acaccatctc tgtggagatg aagaaagaag attttgacat ctatgatgag gatgagaatc  2700
agagccccag atcctttcag aaaaagacca gacactactt cattgctgct gtggagagac  2760
tgtgggacta tggcatgtct agcagccctc atgtgctgag aaatagagcc cagtctggct  2820
ctgtgcccca gttcaagaaa gtggtgttcc aagagttcac agatggcagc ttcacccagc  2880
cactgtatag aggagagctg aatgagcatc tgggcctgct gggcccttat atcagagctg  2940
aagtggaaga taacatcatg gtcaccttca gaaatcaggc ctctaggccc tacagcttct  3000
acagctccct gatcagctat gaagaggacc agagacaggg agctgagccc agaaagaact  3060
ttgtgaagcc caatgagact aagacctact tttggaaggt gcagcaccac atggccccta  3120
caaaggatga gtttgactgc aaggcctggg cctacttttc tgatgtggat ctggaaaagg  3180
atgtgcactc tggactcatt ggaccactgc ttgtgtgcca caccaacaca ctgaaccctg  3240
ctcatggcag acaagtgaca gtgcaagagt ttgccctgtt cttcaccatc tttgatgaaa  3300
caaagagctg gtacttcaca gagaatatgg agagaaactg cagggcccct tgcaacatcc  3360
agatggaaga tcccaccttc aaagagaact acagattcca tgccatcaat ggctacatca  3420
tggacacact gcctggcctg gttatggctc aggatcagag aatcagatgg tatctgctgt  3480
ccatgggctc caatgagaat atccacagca tccacttctc tggccatgtg ttcacagtga  3540
gaaaaaaaga agagtacaaa atggccctgt acaatctgta ccctggggtg tttgaaacag  3600
tggaaatgct gccttccaag gctggcattt ggagagtgga atgtctgatt ggagagcacc  3660
tccatgctgg aatgagcacc ctgtttctgg tgtacagcaa caagtgtcag acccctctgg  3720
gcatggcctc tggacacatc agagacttcc agatcacagc ctctggccag tatggacagt  3780
gggctcctaa actggctaga ctgcactact ctggcagcat caatgcctgg tccaccaaag  3840
agcccttcag ctggatcaag gtggacctgc tggctcccat gatcatccat ggaatcaaga  3900
cccagggagc cagacagaag ttcagcagcc tgtacatcag ccagttcatc atcatgtaca  3960
gcctggatgg caagaagtgg cagacctaca gaggcaacag cacaggcaca ctcatggtgt  4020
tctttggcaa tgtggacagc tctggcatta agcacaacat cttcaaccct ccaatcattg  4080
ccagatacat cagactgcac cccacacact acagcatcag atctaccctg agaatggaac  4140
tgatgggctg tgacctgaac agctgcagca tgcccctggg aatggaaagc aaggccatct  4200
ctgatgccca gatcacagcc agcagctact tcaccaacat gtttgccact tggagcccct  4260
ccaaggctag actgcatctg cagggcagaa gcaatgcttg gaggccccaa gtgaacaacc  4320
ccaaagagtg gctgcaggtg gactttcaaa agaccatgaa agtgacagga gtgaccacac  4380
agggagtcaa gtctctgctg acctctatgt atgtgaaaga gttcctgatc tccagcagcc  4440
aggatggcca ccagtggacc ctgtttttcc agaatggcaa agtgaaagtg ttccagggca  4500
atcaggacag cttcacacct gtggtcaact ccctggatcc tccactgctg accagatacc  4560
tgagaattca ccctcagtct tgggtgcacc agattgctct gagaatggaa gtgctgggct  4620
gtgaagctca ggacctctac tgatcctgaa taaaagatct ttattttcat tagatctgtg  4680
tgttggtttt ttgtgtgtat ttagctaaca gtatgattaa gtggataaat ggttcctctc  4740
tgctacactc aaatgccagt tcccgatcgt tacaggaaaa gatatgctat acctgatact  4800
gaattttgta atcggttggc agccaatgaa atacaaagat gagtctagtt aataatctac  4860
aattattggt taaagaagta tattagtatg ctttgcatac ttctgcctgc tggggagcct  4920
ggggactttc cacaccctaa ctgacacaca ttccac                            4956
```

```
SEQ ID NO: 33          moltype = DNA  length = 4935
FEATURE                Location/Qualifiers
source                 1..4935
                       mol_type = other DNA
                       organism = synthetic construct
SEQUENCE: 33
atgctttgca tacttctgcc tgctggggag cctggggact ttccacaccc taactgacac  60
acattccact gaattttgta atcggttggc agccaatgaa atacaaagat gagtctagtt  120
aataatctac aattattggt taaagaagta tattagttca gattcagaat gtcaatatgc  180
```

-continued

```
cagttcccga tcgttacagg aaaaatggtt cctctctgct acactcaaat ctcatattaa  240
gcttactaaa gaattattct tttacatttc agtggccacc agaagatatt acctgggagc  300
tgtggaactg agctgggact acatgcagtc tgacctggga gagctgcctg tggatgctag  360
atttcctcca agagtgccca agagcttccc cttcaacacc tctgtggtgt acaagaaaac  420
cctgtttgtg gaattcacag accacctgtt caatattgcc aagcctagac ctccttggat  480
gggactgctg ggacctacaa ttcaggctga ggtgtatgac acagtggtca tcaccctgaa  540
gaacatggcc agccatcctg tgtctctgca tgctgtggga gtgtcttact ggaaggcttc  600
tgagggagct gagtatgatg accagacaag ccagagagag aaagaggatg acaaggtttt  660
ccctggaggc agccacacct atgtctggca ggtcctgaaa gaaaatggcc ctatggcctc  720
tgatcctctg tgcctgacat acagctacct gagccatgtg gacctggtca aggacctgaa  780
ttctggcctg attggagccc tgctggtgtg tagagaaggc agcctggcca aagagaaaac  840
ccagacactg cacaagttca tcctgctgtt tgctgtgttt gatgagggca agagctggca  900
ctctgagaca aagaacagcc tgatgcagga cagggatgct gcctctgcta gagcttggcc  960
taagatgcac acagtgaatg gctatgtgaa cagaagcctg cctggactga ttggctgcca  1020
cagaaagtct gtgtactggc atgtgattgg catgggcaca acacctgagg tgcacagcat  1080
ctttctggaa ggacacacct tcctggtgag aaaccataga caggccagcc tggaaatcag  1140
ccctatcacc ttcctgacag ctcagaccct gctgatggat ctgggccagt ttctgctgtt  1200
ctgccacatc agcagccacc agcatgatgg catggaagcc tatgtgaagg tggacagctg  1260
ccctgaagaa ccccagctga gaatgaagaa caatgaggag gctgaggact atgatgatga  1320
cctgacagac tctgagatgg atgtggtcag atttgatgat gacaacagcc ccagcttcat  1380
ccagatcaga tctgtggcca agaagcaccc caagacctgg gtgcactata ttgctgctga  1440
ggaagaggac tgggattatg ctcctctggt gctggcccct gatgacagaa gctacaagag  1500
ccagtacctg aacaatggcc ctcagagaat tggcagaaag tataagaaag tgagattcat  1560
ggcctacaca gatgagacat tcaagaccag agaggccatt cagcatgagt ctggcattct  1620
gggccctctg ctgtatggag aagtgggaga tacactgctg atcatcttca agaaccaggc  1680
cagcagaccc tacaacatct accctcatgg catcacagat gtgagacccc tgtattccag  1740
aaggctgccc aagggagtga agcacctgaa ggacttccct atcctgcctg gagagatctt  1800
caagtacaag tggacagtga cagtggaaga tggccccacc aagtctgacc ctagatgtct  1860
gacaagatac tacagcagct ttgtgaacat ggaaagagac ctggcctctg gcctgattgg  1920
acctctgctg atctgctaca aagaatctgt ggaccagaga ggcaaccaga tcatgtctga  1980
caagagaaat gtgatcctgt tttctgtgtt tgatgagaac agatcctggt atctgacaga  2040
gaacatccag agatttctgc ccaatcctgc tggagtgcag ctggaagatc ctgagttcca  2100
ggcctccaac atcatgcact ccatcaatgg ctatgtgttt gacagcctgc agctgtctgt  2160
gtgcctgcat gaagtggcct actggtacat cctgagcatt ggagcccaga cagacttcct  2220
gtctgtgttc ttctctggct acaccttcaa gcacaagatg gtgtatgagg ataccctgac  2280
actgttccca ttctctggag agacagtgtt catgagcatg gaaaaccctg gcctgtggat  2340
cctgggctgt cacaactctg acttcagaaa cagaggcatg acagccctgc tgaaggtgtc  2400
cagctgtgac aagaacacag gagactacta tgaggacagc tatgaggaca tctctgccta  2460
cctgctgagc aagaacaatg ccattgagcc cagaagcttc agccagaatg ccaccaatgt  2520
gtccaacaac agcaacacca gcaatgactc caatgtgtcc cctccagtgc tgaagagaca  2580
ccagagagaa atcaccagaa ccacactgca gtctgaccaa gaggaaattg actatgatga  2640
caccatctct gtggagatga agaaagaaga ttttgacatc tatgatgagg atgagaatca  2700
gagccccaga tcctttcaga aaaagaccag acactacttc attgctgctg tggagagact  2760
gtgggactat ggcatgtcta gcagccctca tgtgctgaga aatagagccc agtctggctc  2820
tgtgccccag ttcaagaaag tggtgttcca agagttcaca gatggcagct tcacccagcc  2880
actgtataga ggagagctga atgagcatct gggcctgctg ggcccttata tcagagctga  2940
agtggaagat aacatcatgg tcaccttcag aaatcaggcc tctaggccct acagcttcta  3000
cagctccctg atcagctatg aagaggacca gagacaggga gctgagccca gaaagaactt  3060
tgtgaagccc aatgagacta agacctactt ttggaaggtg cagcaccaca tggcccctac  3120
aaaggatgag tttgactgca aggcctgggc ctacttttct gatgtggatc tggaaaagga  3180
tgtgcactct ggactcattg gaccactgct tgtgtgccac accaacacac tgaaccctgc  3240
tcatggcaga caagtgacag tgcaagagtt tgccctgttc ttcaccatct ttgatgaaac  3300
aaagagctgg tacttcacag agaatatgga gagaaactgc agggcccctt gcaacatcca  3360
gatggaagat cccaccttca aagagaacta cagattccat gccatcaatg gctacatcat  3420
ggacacactg cctggcctgg ttatggctca ggatcagaga atcagatggt atctgctgtc  3480
catgggctcc aatgagaata tccacagcat ccacttctct ggccatgtgt tcacagtgag  3540
aaaaaaagaa gagtacaaaa tggccctgta caatctgtac cctggggtgt ttgaaacagt  3600
ggaaatgctg ccttccaagg ctggcatttg gagagtggaa tgtctgattg gagagcacct  3660
ccatgctgga atgagcaccc tgtttctggt gtacagcaac aagtgtcaga cccctctggg  3720
catggcctct ggacacatca gagacttcca gatcacagcc tctggccagt atggacagtg  3780
ggctcctaaa ctggctagac tgcactactc tggcagcatc aatgcctggt ccaccaaaga  3840
gcccttcagc tggatcaagg tggacctgct ggctcccatg atcatccatg gaatcaagac  3900
ccagggagcc agacagaagt tcagcagcct gtacatcagc cagttcatca tcatgtacag  3960
cctggatggc aagaagtggc agacctacag aggcaacagc acaggcacac tcatggtgtt  4020
ctttggcaat gtggacagct ctggcattaa gcacaacatc ttcaaccctc caatcattgc  4080
cagatacatc agactgcacc ccacacacta cagcatcaga tctaccctga gaatggaact  4140
gatgggctgt gacctgaaca gctgcagcat gcccctggga atggaaagca aggccatctc  4200
tgatgcccag atcacagcca gcagctactt caccaacatg tttgccactt ggagcccctc  4260
caaggctaga ctgcatctgc agggcagaag caatgcttgg aggccccaag tgaacaaccc  4320
caaagagtgg ctgcaggtgg actttcaaaa gaccatgaaa gtgacaggag tgaccacaca  4380
gggagtcaag tctctgctga cctctatgta tgtgaaagag ttcctgatct ccagcagcca  4440
ggatggccac cagtggaccc tgtttttcca gaatggcaaa gtgaaagtgt tccagggcaa  4500
tcaggacagc ttcacacctg tggtcaactc cctggatcct ccactgctga ccagatacct  4560
gagaattcac cctcagtctt gggtgcacca gattgctctg agaatggaag tgctgggctg  4620
tgaagctcag gacctctact gatcctgaat aaaagatctt tattttcatt agatctgtgt  4680
gttggttttt tgtgtgtatt tagctatttg agtgtagcag agaggaacca tttttcctgt  4740
aacgatcggg aactggcaag atatgctata cctgatactg aattttgtaa tcggttggca  4800
gccaatgaaa tacaaagatg agtctagtta ataatctaca attattggtt aaagaagtat  4860
attagtatgc tttgcatact tctgcctgct ggggagcctg ggactttcc acaccctaac  4920
```

```
tgacacacat tccac                                        4935

SEQ ID NO: 34          moltype =   length =
SEQUENCE: 34
000

SEQ ID NO: 35          moltype =   length =
SEQUENCE: 35
000

SEQ ID NO: 36          moltype =   length =
SEQUENCE: 36
000

SEQ ID NO: 37          moltype = DNA  length = 12
FEATURE                Location/Qualifiers
source                 1..12
                       mol_type = other DNA
                       organism = synthetic construct
SEQUENCE: 37
ttaatnntta ac                                           12

SEQ ID NO: 38          moltype =   length =
SEQUENCE: 38
000

SEQ ID NO: 39          moltype = DNA  length = 10
FEATURE                Location/Qualifiers
source                 1..10
                       mol_type = other DNA
                       organism = synthetic construct
SEQUENCE: 39
aagatcaaag                                              10

SEQ ID NO: 40          moltype =   length =
SEQUENCE: 40
000

SEQ ID NO: 41          moltype = DNA  length = 11
FEATURE                Location/Qualifiers
source                 1..11
                       mol_type = other DNA
                       organism = synthetic construct
SEQUENCE: 41
aaarygaaac c                                            11

SEQ ID NO: 42          moltype =   length =
SEQUENCE: 42
000

SEQ ID NO: 43          moltype = RNA  length = 100
FEATURE                Location/Qualifiers
source                 1..100
                       mol_type = other RNA
                       organism = synthetic construct
modified_base          1..3
                       mod_base = OTHER
                       note = 2'-O-Methyl modified base
modified_base          97..99
                       mod_base = OTHER
                       note = 2'-O-Methyl modified base
modified_base          1..4
                       mod_base = OTHER
                       note = phosphorothioate linkage
modified_base          97..100
                       mod_base = OTHER
                       note = phosphorothioate linkage
SEQUENCE: 43
ttagtatagc atggtcgagc gttttagagc tagaaatagc aagttaaaat aaggctagtc  60
cgttatcaac ttgaaaaagt ggcaccgagt cggtgctttt                        100

SEQ ID NO: 44          moltype = RNA  length = 100
FEATURE                Location/Qualifiers
source                 1..100
                       mol_type = other RNA
                       organism = synthetic construct
modified_base          1..3
                       mod_base = OTHER
                       note = 2'-O-Methyl modified base
```

```
modified_base          97..99
                       mod_base = OTHER
                       note = 2'-O-Methyl modified base
modified_base          1..4
                       mod_base = OTHER
                       note = phosphorothioate linkage
modified_base          97..100
                       mod_base = OTHER
                       note = phosphorothioate linkage
SEQUENCE: 44
ttcctgtaac gatcgggaac gttttagagc tagaaatagc aagttaaaat aaggctagtc  60
cgttatcaac ttgaaaaagt ggcaccgagt cggtgctttt                        100

SEQ ID NO: 45          moltype = RNA  length = 100
FEATURE                Location/Qualifiers
source                 1..100
                       mol_type = other RNA
                       organism = synthetic construct
modified_base          1..3
                       mod_base = OTHER
                       note = 2'-O-Methyl modified base
modified_base          97..99
                       mod_base = OTHER
                       note = 2'-O-Methyl modified base
modified_base          1..4
                       mod_base = OTHER
                       note = phosphorothioate linkage
modified_base          97..100
                       mod_base = OTHER
                       note = phosphorothioate linkage
SEQUENCE: 45
tgccagttcc cgatcgttac gttttagagc tagaaatagc aagttaaaat aaggctagtc  60
cgttatcaac ttgaaaaagt ggcaccgagt cggtgctttt                        100

SEQ ID NO: 46          moltype = DNA  length = 18
FEATURE                Location/Qualifiers
source                 1..18
                       mol_type = other DNA
                       organism = synthetic construct
SEQUENCE: 46
ctcctcttcg tctccggc                                                18

SEQ ID NO: 47          moltype = DNA  length = 19
FEATURE                Location/Qualifiers
source                 1..19
                       mol_type = other DNA
                       organism = synthetic construct
SEQUENCE: 47
ctgccacatt gctcagcac                                               19

SEQ ID NO: 48          moltype = DNA  length = 21
FEATURE                Location/Qualifiers
source                 1..21
                       mol_type = other DNA
                       organism = synthetic construct
SEQUENCE: 48
ttgcatctga gaacccttag g                                            21

SEQ ID NO: 49          moltype = DNA  length = 20
FEATURE                Location/Qualifiers
source                 1..20
                       mol_type = other DNA
                       organism = synthetic construct
SEQUENCE: 49
gcctgctcga ccatgctata                                              20

SEQ ID NO: 50          moltype = RNA  length = 100
FEATURE                Location/Qualifiers
source                 1..100
                       mol_type = other RNA
                       organism = synthetic construct
modified_base          1..3
                       mod_base = OTHER
                       note = 2'-O-Methyl modified base
modified_base          29..32
                       mod_base = OTHER
                       note = 2'-O-Methyl modified base
modified_base          37..40
                       mod_base = OTHER
```

```
                        note = 2'-O-Methyl modified base
modified_base           68..72
                        mod_base = OTHER
                        note = 2'-O-Methyl modified base
modified_base           77..99
                        mod_base = OTHER
                        note = 2'-O-Methyl modified base
modified_base           1..4
                        mod_base = OTHER
                        note = phosphorothioate linkage
modified_base           97..100
                        mod_base = OTHER
                        note = phosphorothioate linkage
SEQUENCE: 50
ttcctgtaac gatcgggaac gttttagagc tagaaatagc aagttaaaat aaggctagtc  60
cgttatcaac ttgaaaaagt ggcaccgagt cggtgctttt                        100

SEQ ID NO: 51           moltype = DNA  length = 4493
FEATURE                 Location/Qualifiers
source                  1..4493
                        mol_type = other DNA
                        organism = synthetic construct
SEQUENCE: 51
gcggccgcta atacgactca ctataagaaa agccagctcc agcaggcgct gctcactcct  60
ccccatcctc tccctctgtc cctctgtccc tctgaccctg cactgtccca gcaccatggc  120
cccaagaag aagcggaaag ttggcggcgg aggcagcgac aagaagtact ctatcggcct  180
ggacatcggc accaactctg ttggatgggc cgtgatcacc gacgagtaca aggtgcccag  240
caagaaattc aaggtgctgg gcaacaccga ccggcacagc atcaagaaga atctgatcgg  300
cgccctgctg ttcgactctg gcgaaacagc cgaagccacc agactgaaga gaaccgccag  360
acggcggtac accagaagaa agaaccggat ctgctacctg caagagatct tcagcaacga  420
gatggccaag gtggacgaca gcttcttcca cagactggaa gagtccttcc tggtggaaga  480
ggacaagaag cacgagcggc accccatctt cggcaacatc gtggatgagg tggcctacca  540
cgagaagtac cccaccatct accacctgag aaagaaactg gtggacagca ccgacaaggc  600
cgacctgaga ctgatctatc tggccctggc tcacatgatc aagttccggg gccacttcct  660
gatcgagggc gacctgaatc ctgacaacag cgacgtggac aagctgttca tccagctggt  720
gcagacctac aaccagctgt tcgaggaaaa ccccatcaac gccagcggag tggatgccaa  780
ggccatcctg tctgccagac tgagcaagag cagacggctg gaaaacctga tcgctcagct  840
gcccggcgag aagaagaatg gcctgttcgg caacctgatt gccctgagcc tgggcctgac  900
acctaacttc aagagcaact tcgacctggc cgaggacgcc aaactgcagc tgtccaagga  960
cacctacgac gacgacctgg acaatctgct ggcccagatc ggcgatcagt acgccgactt  1020
gtttctggcc gccaagaacc tgtccgacgc catcctgctg agcgacatcc tgagagtgaa  1080
caccgagatc acaaaggccc ctctgagcgc ctctatgatc aagagatacg acgagcacca  1140
ccaggatctg accctgctga aggccctcgt tagacagcag ctgcctgaga agtacaaaga  1200
gattttcttc gaccagagca agaacggcta cgccggctac attgatggcg gagccagcca  1260
agaggaattc tacaagttca tcaagcccat cctcgagaag atggacggca ccgaggaact  1320
gctggtcaag ctgaacagag aggacctgct gcggaagcag cggaccttcg acaatggctc  1380
tatccctcac cagatccacc tgggagagct gcacgccatt ctgcggagac aagaggactt  1440
ttacccattc ctgaaggaca accgggaaaa gattgagaag atcctgacct tcaggatccc  1500
ctactacgtg ggaccactgg ccagaggcaa tagcagattc gcctggatga ccagaaagag  1560
cgaggaaacc atcacaccct ggaacttcga ggaagtggtg gacaagggcg ccagcgctca  1620
gtccttcatc gagcggatga ccaacttcga taagaacctg cctaacgaga aggtgctgcc  1680
caagcacagc ctgctgtacg agtacttcac cgtgtacaac gagctgacca aagtgaaata  1740
cgtgaccgag ggaatgagaa agcccgcctt tctgagcggc gagcagaaaa aggccattgt  1800
ggatctgctg ttcaagacca accggaaagt gaccgtgaag cagctgaaag aggactactt  1860
caagaaaatc gagtgcttcg acagcgtgga aatcagcggc gtggaagatc ggttcaatgc  1920
cagcctgggc acataccacg acctgctgaa aattatcaag gacaaggact tcctggacaa  1980
cgaagagaac gaggacatcc tggaagatat cgtgctgacc ctgacactgt ttgaggacag  2040
agagatgatc gaggaacggc tgaaaacata cgcccacctg ttcgacgaca aagtgatgaa  2100
gcaactgaag cggcggagat acaccggctg gggcagactg tctcggaagc tgatcaacgg  2160
catccgggat aagcagtccg gcaagaccat cctggacttt ctgaagtccg acggcttcgc  2220
caacagaaac ttcatgcagc tgatccacga cgacagcctg acctttaaag aggatatcca  2280
gaaagcccag gtgtccggcc agggcgattc tctgcatgag cacattgcca acctggccgg  2340
ctctcccgcc attaagaagg gcattctgca gacagtgaag gtggtggacg agctggtcaa  2400
agtcatgggc agacacaagc ccgagaacat cgtgatcgaa atggccagag agaaccagac  2460
cacacagaag ggccagaaga acagccgcga gagaatgaag cggatcgaag agggcatcaa  2520
agagctgggc agccagatcc tgaaagaaca ccccgtggaa aacacccagc tgcagaacga  2580
gaagctgtac ctgtactacc tccagaacgg ccgggatatg tacgtggacc aagagctgga  2640
catcaaccgg ctgtccgact acgatgtgga ccatatcgtg ccccagtctt ttctgaagga  2700
cgactccatc gacaacaagg tcctgaccag atccgacaag aatcggggca agagcgacaa  2760
cgtgccctcc gaagaggtgg tcaagaagat gaagaactac tggcgacagc tgctgaacgc  2820
caagctgatt acccagcgga agttcgataa cctgaccaag gccgagagag gcggcctgtc  2880
tgaactggat aaggccggct tcatcaagag acagctggtg gaaacccggc agatcaccaa  2940
acacgtggca cagattctgg actcccggat gaacactaag tacgacgaga atgacaagct  3000
gatccgggaa gtgaaagtga tcaccctgaa gtccaagctg gtgtccgatt tccggaagga  3060
tttccagttc tacaaagtgc gcgagatcaa caactaccat cacgcccacg acgcctacct  3120
gaatgccgtt gttggaacag ccctgatcaa gaagtatccc aagctggaaa gcgagttcgt  3180
gtacggcgac tacaaggtgt acgacgtgcg gaagatgatc gccaagagcg agcaagagat  3240
tggcaaggct accgccaagt actttttcta cagcaacatc atgaactttt tcaagaccga  3300
gattaccctg gccaacggcg agatcagaaa gcggcctctg atcgagacaa acggcgaaac  3360
```

```
cggcgagatt gtgtgggata agggcagaga ctttgccaca gtgcggaaag tgctgagcat  3420
gccccaagtg aatatcgtga agaaaaccga ggtgcagaca ggcggcttca gcaaagagtc  3480
cattctgccc aagagaaaca gcgataagct gatcgcccgg aagaaggact gggaccctaa  3540
gaagtacggc ggcttcgata gccctaccgt ggcctattct gtgctggtgg tggccaaagt  3600
ggaaaagggc aagtccaaga aactcaagag cgtgaaagag ctgctgggga tcaccatcat  3660
ggaaagaagc agcttcgaga agaatcctat cgatttcctc gaggccaagg gctacaaaga  3720
agtgaaaaag gacctgatca tcaagctccc caagtactcc ctgttcgagc tggaaaatgg  3780
ccggaagcgg atgctggctt ctgctggcga actgcagaag ggaaacgaac tggccctgcc  3840
tagcaaatat gtgaacttcc tgtacctggc cagccactat gagaagctga agggcagccc  3900
cgaggacaat gagcaaaagc agctgtttgt ggaacagcac aagcactacc tggacgagat  3960
catcgagcag atcagcgagt tctccaagag agtgatcctg gccgacgcta atctggacaa  4020
agtgctgtcc gcctacaaca agcaccggga caagcctatc agagagcagg ccgagaatat  4080
catccacctg tttaccctga ccaatctggg agcccctgcc gccttcaagt acttcgacac  4140
caccatcgac cggaagcgct acaccagcac caaagaggtg ctggacgcca cactgatcca  4200
ccagtctatc accggcctgt acgagacacg gatcgacctg tctcagctcg gaggcgattc  4260
tggcggaaaa agacctgccg ccacaaagaa agccggacag gccaagaaaa agaagtgacc  4320
acacccccat tcccccactc cagataaagc ttcagttata tctcacgtgt ctggagttaa  4380
aaaaaaaaaa aaaaaaaaaa aaaaaaaaaa aaaaaaaaaa aaaaaaaaaa aaaaaaaaaa  4440
aaaaaaaaaa aaaaaaaaaa aaaaaaaaaa aaaaaaaaga agagccctgc agg         4493

SEQ ID NO: 52          moltype = AA  length = 1400
FEATURE                Location/Qualifiers
source                 1..1400
                       mol_type = protein
                       organism = synthetic construct
SEQUENCE: 52
MAPKKKRKVG GGGSDKKYSI GLDIGTNSVG WAVITDEYKV PSKKFKVLGN TDRHSIKKNL  60
IGALLFDSGE TAEATRLKRT ARRRYTRRKN RICYLQEIFS NEMAKVDDSF FHRLEESFLV  120
EEDKKHERHP IFGNIVDEVA YHEKYPTIYH LRKKLVDSTD KADLRLIYLA LAHMIKFRGH  180
FLIEGDLNPD NSDVDKLFIQ LVQTYNQLFE ENPINASGVD AKAILSARLS KSRRLENLIA  240
QLPGEKKNGL FGNLIALSLG LTPNFKSNFD LAEDAKLQLS KDTYDDDLDN LLAQIGDQYA  300
DLFLAAKNLS DAILLSDILR VNTEITKAPL SASMIKRYDE HHQDLTLLKA LVRQQLPEKY  360
KEIFFDQSKN GYAGYIDGGA SQEEFYKFIK PILEKMDGTE ELLVKLNRED LLRKQRTFDN  420
GSIPHQIHLG ELHAILRRQE DFYPFLKDNR EKIEKILTFR IPYYVGPLAR GNSRFAWMTR  480
KSEETITPWN FEEVVDKGAS AQSFIERMTN FDKNLPNEKV LPKHSLLYEY FTVYNELTKV  540
KYVTEGMRKP AFLSGEQKKA IVDLLFKTNR KVTVKQLKED YFKKIECFDS VEISGVEDRF  600
NASLGTYHDL LKIIKDKDFL DNEENEDILE DIVLTLTLFE DREMIEERLK TYAHLFDDKV  660
MKQLKRRRYT GWGRLSRKLI NGIRDKQSGK TILDFLKSDG FANRNFMQLI HDDSLTFKED  720
IQKAQVSGQG DSLHEHIANL AGSPAIKKGI LQTVKVVDEL VKVMGRHKPE NIVIEMAREN  780
QTTQKGQKNS RERMKRIEEG IKELGSQILK EHPVENTQLQ NEKLYLYYLQ NGRDMYVDQE  840
LDINRLSDYD VDHIVPQSFL KDDSIDNKVL TRSDKNRGKS DNVPSEEVVK KMKNYWRQLL  900
NAKLITQRKF DNLTKAERGG LSELDKAGFI KRQLVETRQI TKHVAQILDS RMNTKYDEND  960
KLIREVKVIT LKSKLVSDFR KDFQFYKVRE INNYHHAHDA YLNAVVGTAL IKKYPKLESE  1020
FVYGDYKVYD VRKMIAKSEQ EIGKATAKYF FYSNIMNFFK TEITLANGEI RKRPLIETNG  1080
ETGEIVWDKG RDFATVRKVL SMPQVNIVKK TEVQTGGFSK ESILPKRNSD KLIARKKDWD  1140
PKKYGGFDSP TVAYSVLVVA KVEKGKSKKL KSVKELLGIT IMERSSFEKN PIDFLEAKGY  1200
KEVKKDLIIK LPKYSLFELE NGRKRMLASA GELQKGNELA LPSKYVNFLY LASHYEKLKG  1260
SPEDNEQKQL FVEQHKHYLD EIIEQISEFS KRVILADANL DKVLSAYNKH RDKPIREQAE  1320
NIIHLFTLTN LGAPAAFKYF DTTIDRKRYT STKEVLDATL IHQSITGLYE TRIDLSQLGG  1380
DSGGKRPAAT KKAGQAKKKK                                             1400

SEQ ID NO: 53          moltype = DNA  length = 4220
FEATURE                Location/Qualifiers
source                 1..4220
                       mol_type = other DNA
                       organism = synthetic construct
SEQUENCE: 53
taatacgact cactataagg aaaagccagc tccagcaggc gctgctcact cctccccatc  60
ctctccctct gtccctctgt ccctctgacc ctgcactgtc ccagcaccat ggcccctaag  120
aagaagagaa aagtcggcgg aggcggcagc ttcaacaact tcatcaagaa gtacagcctg  180
cagaaaaccc tgcgcttcga gctgaagcct gtgggcgaga cagccgacta catcgaggac  240
ttcaagagcg agtacctgaa ggacaccgtg ctgaaggacg agcagagagc caaggactac  300
caagagatca agaccctgat cgacgattac caccgcgagt acatcgaaga gtgcctgaga  360
gaacccgtgg acaagaaaac cggcgagatc ctggacttca cccaggacct ggaagatgcc  420
ttcagctact accagaagct gaaagagaac cccaccgaga acagagtcgg ctgggagaaa  480
gagcaagaga gcctgaggaa gaagctggtc acctccttcg tgggcaacga cggcctgttc  540
aagaaagagt tcatcaccag ggacctgcct gagtggctgc agaagaaagg actctggggc  600
gagtacaagg acacagtgga aaacttcaag aagttcacca cctacttcag cggcttccac  660
gagaaccgga agaacatgta caccgccgag gctcagagca ccgctatcgc caacagactg  720
atgaacgaca acctgcctaa gttctttaac aactacctgg cctaccagac catcaaagag  780
aagcaccccg acctggtgtt cagactggat gatgctctgc tgcaggccgc tggcgtggaa  840
catctggatg aggctttcca gcctagatac ttcagcagac tgttcgccca gagcggcatc  900
accgctttca acgagctgat cggcggcaga accacagaga acggcgagaa gatccagggc  960
ctgaacgagc agatcaacct gtacagacag cagaaccccg agaaggccaa gggcttcccc  1020
agattcatgc ctctgttcaa gcagatcctg agcgacagag agacacacag ctttctgccc  1080
gacgccttcg agaacgacaa agagctgctc caggctctga gagactacgt ggacgccgcc  1140
acatctgagg aaggcatgat cagccagctg aacaaggcca tgaaccagtt cgtgaccgcc  1200
gacctgaaga gagtgtacat caagagcgcc gctctgacca gcctgagcca agagctgttc  1260
cacttcttcg gcgtgatcag cgacgctatc gcttggtacg ccgagaagag actgagcccc  1320
```

```
aagaaggccc aagagtcttt cctgaagcaa gaggtgtacg ccatcgagga actgaaccag  1380
gctgtcgtgg gctacatcga ccagctggaa gatcagagcg agctgcagca actgctggtg  1440
gacctgccag atcctcagaa acccgtgtcc agcttcatcc tgacacactg gcagaagtct  1500
caagagcccc tgcaggcagt gatcgccaag gtggaacctc tgttcgaact ggaagaactg  1560
agcaagaaca agagggcccc aaagcacgac aaggaccaag gcggcgaggg atttcagcag  1620
gtcgacgcca tcaagaacat gctggacgcc ttcatggaag tgtcccacgc tatcaagccc  1680
ctgtacctgg tcaagggaag aaaggccatc gacatgcccg acgtggacac cggcttctac  1740
gctgatttcg ccgaggccta cagcgcctac gagcaagtga cagtgtccct gtacaacaag  1800
accagaaacc acctgtccaa gaagcccttc agcaaggaca agatcaagat caacttcgac  1860
gcccctacac tgctgaacgg ctgggacctg aacaaagaga gcgacaacaa gtccatcatc  1920
ctgcggaagg acggcaactt ctacctggca atcatgcacc ccaagcacac caaggtgttc  1980
gactgctact ctgcctctga ggctgccggc aagtgctacg agaagatgaa ctacaagctg  2040
ctgagcggcg ccaacaagat gctgcctaag gtgttcttta gcaagaaggg catcgagaca  2100
ttcagccctc cacaagaaat cctggacctg tacaagaaca acgagcataa gaagggcgcc  2160
accttcaagc tggaatcctg ccacaagctg atcgatttct tcaagcggaa catccccaag  2220
tacaaggtgc accctaccga caactttggc tgggacgtgt tcggctttca cttcagccct  2280
accagcagct acggcgacct gtctggcttc tacagagagg tggaagccca gggatacaag  2340
ctgtggttca gcgacgtgtc cgaggcttac atcaacaaat gcgtggaaga gggcaagctg  2400
ttcctgttcc aaatctacaa caaggacttc tcccctaact ccaccggcaa gcccaacctg  2460
cacaccctgt attggaaggg cctgttcgag cccgagaacc tgaaagacgt ggtgctgaag  2520
ctgaatggcg aggccgagat cttctaccgg aagcacagca tcaagcacga ggacaagacc  2580
atccacagag ctaaggaccc tatcgctaac aagaacgctg acaaccccaa gaaacagagc  2640
gtgttcgatt acgacatcat caaggataag cggtataccc aggacaagtt cttcttccac  2700
gtgccaatca gcctgaactt caaaagccag ggcgtcgtgc ggttcaacga taagatcaac  2760
ggcctgctgg ccgctcagga cgatgtgcat gtgatcggca tcgacagagg cgagagacat  2820
ctgctgtact acaccgtggt caacggcaag ggcgaagtgg tggaacaggg cagcctgaat  2880
caggtggcca cagatcaggg ctacgtggtg gattaccagc agaagctgca cgccaaagag  2940
aaagaacgcg accaggccag aaagaactgg tccaccatcg agaacatcaa agaactgaag  3000
gccggctacc tgagccaggt ggtgcataag ctggctcagc tgatcgtgaa gcacaacgcc  3060
atcgtgtgcc tcgaggacct gaatttcggc ttcaagaggg gcagattcaa ggtcgagaaa  3120
caggtgtacc agaagttcga gaaggctctg atcgacaagc tgaactacct cgtgttcaaa  3180
gagagaggcg ccacacaggc tggcggatac ctgaatgctt accagctggc cgcacctttc  3240
gagagctttg agaagctggg caagcagacc ggcatcctgt actacgtgcg gagcgactac  3300
accagcaaga tcgaccctgc taccggcttc gtggactttc tgaagcctaa gtacgagagc  3360
atggccaaga gcaaagtgtt cttcgagtcc ttcgagcgca tccagtggaa ccaggccaaa  3420
ggctacttcg agttcgagtt tgactacaag aagatgtgcc ccagcagaaa gttcggcgac  3480
tacagaacca gatgggtcgt gtgcaccttc ggcgacaccc gctaccagaa cagaagaaac  3540
aagagcagcg gccagtggga gacagagaca atcgatgtga cagcccagct gaaagccctg  3600
ttcgccgctt acggcatcac atacaatcaa gaggataaca tcaaggacgc cattgccgcc  3660
gtgaagtaca ccaagttcta caagcagctg tactggctgc tgagactgac cctgagcctg  3720
agacacagcg tgacaggcac cgacgaggat ttcatcctgt ctccagtggc cgacgagaat  3780
ggcgtgttct ttgactctag gaaggccacc gacaagcagc ctaaggacgc tgatgctaac  3840
ggcgcctacc atatcgccct gaaaggcctg tggaatctcc agcagatcag acagcacgac  3900
tggaacgtgg aaaagcccaa aaagctgaac ctcgccatga agaacgaaga gtggttcggc  3960
ttcgctcaga agaagaagtt tagagccagc ggcggcaaga ggcctgccgc tacaaaaaaa  4020
gccggccagg ccaagaaaaa gaagtgacca cacccccatt cccccactcc agatagaact  4080
tcagttatat ctcacgtgtc tggagttaaa aaaaaaaaaa aaaaaaaaaa aaaaaaaaaa  4140
aaaaaaaaaa aaaaaaaaaa aaaaaaaaaa aaaaaaaaaa aaaaaaaaaa aaaaaaaaaa  4200
aaaaagaaga gccctgcagg                                              4220
```

```
SEQ ID NO: 54          moltype = AA  length = 1312
FEATURE                Location/Qualifiers
source                 1..1312
                       mol_type = protein
                       organism = synthetic construct
SEQUENCE: 54
MAPKKKRKVG GGGSFNNFIK KYSLQKTLRF ELKPVGETAD YIEDFKSEYL KDTVLKDEQR  60
AKDYQEIKTL IDDYHREYIE ECLREPVDKK TGEILDFTQD LEDAFSYYQK LKENPTENRV  120
GWEKEQESLR KKLVTSFVGN DGLFKKEFIT RDLPEWLQKK GLWGEYKDTV ENFKKFTTYF  180
SGFHENRKNM YTAEAQSTAI ANRLMNDNLP KFFNNYLAYQ TIKEKHPDLV FRLDDALLQA  240
AGVEHLDEAF QPRYFSRLFA QSGITAFNEL IGGRTTENGE KIQGLNEQIN LYRQQNPEKA  300
KGFPRFMPLF KQILSDRETH SFLPDAFEND KELLQALRDY VDAATSEEGM ISQLNKAMNQ  360
FVTADLKRVY IKSAALTSLS QELFHFFGVI SDAIAWYAEK RLSPKKAQES FLKQEVYAIE  420
ELNQAVVGYI DQLEDQSELQ QLLVDLPDPQ KPVSSFILTH WQKSQEPLQA VIAKVEPLFE  480
LEELSKNKRA PKHDKDQGGE GFQQVDAIKN MLDAFMEVSH AIKPLYLVKG RKAIDMPDVD  540
TGFYADFAEA YSAYEQVTVS LYNKTRNHLS KKPFSKDKIK INFDAPTLLN GWDLNKESDN  600
KSIILRKDGN FYLAIMHPKH TKVFDCYSAS EAAGKCYEKM NYKLLSGANK MLPKVFFSKK  660
GIETFSPPQE ILDLYKNNEH KKGATFKLES CHKLIDFFKR NIPKYKVHPT DNFGWDVFGF  720
HFSPTSSYGD LSGFYREVEA QGYKLWFSDV SEAYINKCVE EGKLFLFQIY NKDFSPNSTG  780
KPNLHTLYWK GLFEPENLKD VVLKLNGEAE IFYRKHSIKH EDKTIHRAKD PIANKNADNP  840
KKQSVFDYDI IKDKRYTQDK FFFHVPISLN FKSQGVVRFN DKINGLLAAQ DDVHVIGIDR  900
GERHLLYYTV VNGKGEVVEQ GSLNQVATDQ GYVVDYQQKL HAKEKERDQA RKNWSTIENI  960
KELKAGYLSQ VVHKLAQLIV KHNAIVCLED LNFGFKRGRF KVEKQVYQKF EKALIDKLNY  1020
LVFKERGATQ AGGYLNAYQL AAPFESFEKL GKQTGILYYV RSDYTSKIDP ATGFVDFLKP  1080
KYESMAKSKV FFESFERIQW NQAKGYFEFE FDYKKMCPSR KFGDYRTRWV VCTFGDTRYQ  1140
NRRNKSSGQW ETETIDVTAQ LKALFAAYGI TYNQEDNIKD AIAAVKYTKF YKQLYWLLRL  1200
TLSLRHSVTG TDEDFILSPV ADENGVFFDS RKATDKQPKD ADANGAYHIA LKGLWNLQQI  1260
RQHDWNVEKP KKLNLAMKNE EWFGFAQKKK FRASGGKRPA ATKKAGQAKK KK          1312
```

```
SEQ ID NO: 55          moltype = RNA  length = 70
FEATURE                Location/Qualifiers
source                 1..70
                       mol_type = other RNA
                       organism = synthetic construct
modified_base          1..3
                       mod_base = OTHER
                       note = 2'-O-Methyl modified base
modified_base          11..14
                       mod_base = OTHER
                       note = 2'-O-Methyl modified base
modified_base          25..27
                       mod_base = OTHER
                       note = 2'-O-Methyl modified base
modified_base          34..37
                       mod_base = OTHER
                       note = 2'-O-Methyl modified base
modified_base          56..69
                       mod_base = OTHER
                       note = 2'-Fluoro modified base
modified_base          70
                       mod_base = OTHER
                       note = 2'-O-Methyl modified base
modified_base          1..4
                       mod_base = OTHER
                       note = phosphorothioate linkage
modified_base          10..14
                       mod_base = OTHER
                       note = phosphorothioate linkage
modified_base          24..29
                       mod_base = OTHER
                       note = phosphorothioate linkage
modified_base          39..43
                       mod_base = OTHER
                       note = phosphorothioate linkage
modified_base          65..67
                       mod_base = OTHER
                       note = phosphorothioate linkage
modified_base          68..70
                       mod_base = OTHER
                       note = phosphorothioate linkage
SEQUENCE: 55
gttgagaatc gaaagattct caacctttta atttctactg ttgtagatct gtaacgatcg  60
ggaactggca                                                         70

SEQ ID NO: 56          moltype = DNA  length = 4582
FEATURE                Location/Qualifiers
source                 1..4582
                       mol_type = other DNA
                       organism = synthetic construct
SEQUENCE: 56
acgtttttcc tgtaacgatc gggaactggc atttgagtgt agcagagagg aaccatttct  60
caaagcttac taaagaatta ttcttttaca tttcagtggc caccagaaga tattacctgg  120
gagctgtgga actgagctgg gactacatgc agtctgacct gggagagctg cctgtggatg  180
ctagatttcc tccaagagtg cccaagagct tccccttcaa cacctctgtg gtgtacaaga  240
aaaccctgtt tgtggaattc acagaccacc tgttcaatat tgccaagcct agacctcctt  300
ggatgggact gctgggacct acaattcagg ctgaggtgta tgacacagtg gtcatcaccc  360
tgaagaacat ggccagccat cctgtgtctc tgcatgctgt gggagtgtct tactggaagg  420
cttctgaggg agctgagtat gatgaccaga caagccagag agagaaagag gatgacaagg  480
ttttccctgg aggcagccac acctatgtct ggcaggtcct gaaagaaaat ggccctatgg  540
cctctgatcc tctgtgcctg acatacagct acctgagcca tgtggacctg gtcaaggacc  600
tgaattctgg cctgattgga gccctgctgg tgtgtagaga aggcagcctg gccaaagaga  660
aaacccagac actgcacaag ttcatcctgc tgtttgctgt gtttgatgag ggcaagagct  720
ggcactctga gacaaagaac agcctgatgc aggacaggga tgctgcctct gctagagctt  780
ggcctaagat gcacacagtg aatggctatg tgaacagaag cctgcctgga ctgattggct  840
gccacagaaa gtctgtgtac tggcatgtga ttggcatggg cacaacacct gaggtgcaca  900
gcatctttct ggaaggacac accttcctgg tgagaaacca tagacaggcc agcctggaaa  960
tcagccctat caccttcctg acagctcaga ccctgctgat ggatctgggc cagtttctgc  1020
tgttctgcca catcagcagc caccagcatg atggcatgga agcctatgtg aaggtggaca  1080
gctgccctga agaaccccag ctgagaatga agaacaatga ggaggctgag gactatgatg  1140
atgacctgac agactctgag atggatgtgg tcagatttga tgatgacaac agccccagct  1200
tcatccagat cagatctgtg gccaagaagc accccaagac ctgggtgcac tatattgctg  1260
ctgaggaaga ggactgggat tatgctcctc tggtgctggc ccctgatgac agaagctaca  1320
agagccagta cctgaacaat ggccctcaga gaattggcag aaagtataag aaagtgagat  1380
tcatggccta cacagatgag acattcaaga ccagagaggc cattcagcat gagtctggca  1440
ttctgggccc tctgctgtat ggagaagtgg gagatacact gctgatcatc ttcaagaacc  1500
aggccagcag accctacaac atctaccctc atggcatcac agatgtgaga cccctgtatt  1560
ctagaaggct gcccaaggga gtgaagcacc tgaaggactt ccctatcctg cctggagaga  1620
tcttcaagta caagtggaca gtgacagtgg aagatggccc caccaagtct gaccctagat  1680
```

```
gtctgacaag atactacagc agctttgtga acatggaaag agacctggcc tctggcctga  1740
ttggacctct gctgatctgc tacaaagaat ctgtggacca gagaggcaac cagatcatgt  1800
ctgacaagag aaatgtgatc ctgttttctg tgtttgatga gaacagatcc tggtatctga  1860
cagagaacat ccagagattt ctgcccaatc ctgctggagt gcagctggaa gatcctgagt  1920
tccaggcctc caacatcatg cactccatca atggctatgt gtttgacagc ctgcagctgt  1980
ctgtgtgcct gcatgaagtg gcctactggt acatcctgag cattggagcc cagacagact  2040
tcctgtctgt gttcttctct ggctacacct tcaagcacaa gatggtgtat gaggataccc  2100
tgacactgtt cccattctct ggagagacag tgttcatgag catggaaaac cctggcctgt  2160
ggatcctggg ctgtcacaac tctgacttca gaaacagagg catgacagcc ctgctgaagg  2220
tgtccagctg tgacaagaac acaggagact actatgagga cagctatgag gacatctctg  2280
cctacctgct gagcaagaac aatgccattg agcccagaag cttcagccag aatgccacca  2340
atgtgtccaa caacagcaac accagcaatg actccaatgt gtcccctcca gtgctgaaga  2400
gacaccagag agaaatcacc agaaccacac tgcagtctga ccaagaggaa attgactatg  2460
atgacaccat ctctgtggag atgaagaaag aagattttga catctatgat gaggatgaga  2520
atcagagccc cagatccttt cagaaaaaga ccagacacta cttcattgct gctgtggaga  2580
gactgtggga ctatggcatg tctagcagcc ctcatgtgct gagaaataga gcccagtctg  2640
gctctgtgcc ccagttcaag aaagtggtgt tccaagagtt cacagatggc agcttcaccc  2700
agccactgta tagaggagag ctgaatgagc atctgggcct gctgggccct tatatcagag  2760
ctgaagtgga agataacatc atggtcacct tcagaaatca ggcctctaga ccctacagct  2820
tctacagctc cctgatcagc tatgaagagg accagagaca gggagctgag cccagaaaga  2880
actttgtgaa gcccaatgag actaagacct acttttggaa ggtgcagcac cacatggccc  2940
ctacaaagga tgagtttgac tgcaaggcct gggcctactt ttctgatgtg gatctggaaa  3000
aggatgtgca ctctggactc attggaccac tgcttgtgtg ccacaccaac acactgaacc  3060
ctgctcatgg cagacaagtg acagtgcaag agtttgccct gttcttcacc atctttgatg  3120
aaacaaagag ctggtacttc acagagaata tggagagaaa ctgcagggcc ccttgcaaca  3180
tccagatgga agatcccacc ttcaaagaga actacagatt ccatgccatc aatggctaca  3240
tcatggacac actgcctggc ctggttatgg ctcaggatca gagaatcaga tggtatctgc  3300
tgtccatggg ctccaatgag aatatccaca gcatccactt ctctggccat gtgttcacag  3360
tgagaaaaaa agaagagtac aaaatggccc tgtacaatct gtaccctggg gtgtttgaaa  3420
cagtggaaat gctgccttcc aaggctggca tttggagagt ggaatgtctg attggagagc  3480
acctccatgc tggaatgagc accctgtttc tggtgtacag caacaagtgt cagacccctc  3540
tgggcatggc ctctggacac atcagagact tccagatcac agcctctggc cagtatggac  3600
agtgggctcc taaactggct agactgcact actctggcag catcaatgcc tggtccacca  3660
aagagccctt cagctggatc aaggtggacc tgctggctcc catgatcatc catggaatca  3720
agacccaggg agccagacag aagttcagca gcctgtacat cagccagttc atcatcatgt  3780
acagcctgga tggcaagaag tggcagacct acagaggcaa cagcacaggc acactcatgg  3840
tgttctttgg caatgtggac agctctggca ttaagcacaa catcttcaac cctccaatca  3900
ttgccagata catcagactg caccccacac actacagcat cagatctacc ctgagaatgg  3960
aactgatggg ctgtgacctg aacagctgca gcatgcccct gggaatggaa agcaaggcca  4020
tctctgatgc ccagatcaca gccagcagct acttcaccaa catgtttgcc acttggagcc  4080
cctccaaggc tagactgcat ctgcagggca gaagcaatgc ttggaggccc caagtgaaca  4140
accccaaaga gtggctgcag gtggactttc aaaagaccat gaaagtgaca ggagtgacca  4200
cacagggagt caagtctctg ctgacctcta tgtatgtgaa agagttcctg atctccagca  4260
gccaggatgg ccaccagtgg accctgtttt tccagaatgg caaagtgaaa gtgttccagg  4320
gcaatcagga cagcttcaca cctgtggtca actccctgga tcctccactg ctgaccagat  4380
acctgagaat tcaccctcag tcttgggtgc accagattgc tctgagaatg gaagtgctgg  4440
gctgtgaagc tcaggacctc tactgatcgc gaataaaaga tctttatttt cattagatct  4500
gtgtgttggt tttttgtgtg tatttagcta tttgagtgta gcagagagga accatttttc  4560
ctgtaacgat cgggaactgg ca                                           4582
```

```
SEQ ID NO: 57          moltype = DNA  length = 4587
FEATURE                Location/Qualifiers
source                 1..4587
                       mol_type = other DNA
                       organism = synthetic construct
SEQUENCE: 57
acgttaatgg ttcctctctg ctacactcaa atgccagttc ccgatcgtta caggaaatct  60
caaagcttac taaagaatta ttcttttaca tttcagtggc caccagaaga tattacctgg  120
gagctgtgga actgagctgg gactacatgc agtctgacct gggagagctg cctgtggatg  180
ctagatttcc tccaagagtg cccaagagct tccccttcaa cacctctgtg gtgtacaaga  240
aaaccctgtt tgtggaattc acagaccacc tgttcaatat tgccaagcct agacctcctt  300
ggatgggact gctgggacct acaattcagg ctgaggtgta tgacacagtg gtcatcaccc  360
tgaagaacat ggccagccat cctgtgtctc tgcatgctgt gggagtgtct tactggaagg  420
cttctgaggg agctgagtat gatgaccaga caagccagag agagaaagag gatgacaagg  480
ttttccctgg aggcagccac acctatgtct ggcaggtcct gaaagaaaat ggccctatgg  540
cctctgatcc tctgtgcctg acatacagct acctgagcca tgtggacctg gtcaaggacc  600
tgaattctgg cctgattgga gccctgctgg tgtgtagaga aggcagcctg gccaaagaga  660
aaacccagac actgcacaag ttcatcctgc tgtttgctgt gtttgatgag ggcaagagct  720
ggcactctga gacaaagaac agcctgatgc aggacaggga tgctgcctct gctagagctt  780
ggcctaagat gcacacagtg aatggctatg tgaacagaag cctgcctgga ctgattggct  840
gccacagaaa gtctgtgtac tggcatgtga ttggcatggg cacaacacct gaggtgcaca  900
gcatctttct ggaaggacac accttcctgg tgagaaacca tagacaggcc agcctggaaa  960
tcagccctat caccttcctg acagctcaga ccctgctgat ggatctgggc cagtttctgc  1020
tgttctgcca catcagcagc caccagcatg atggcatgga agcctatgtg aaggtggaca  1080
gctgccctga agaaccccag ctgagaatga agaacaatga ggaggctgag gactatgatg  1140
atgacctgac agactctgag atggatgtgg tcagatttga tgatgacaac agccccagct  1200
tcatccagat cagatctgtg gccaagaagc accccaagac ctgggtgcac tatattgctg  1260
ctgaggaaga ggactgggat tatgctcctc tggtgctggc ccctgatgac agaagctaca  1320
agagccagta cctgaacaat ggccctcaga gaattggcag aaagtataag aaagtgagat  1380
```

```
tcatggccta cacagatgag acattcaaga ccagagaggc cattcagcat gagtctggca  1440
ttctgggccc tctgctgtat ggagaagtgg gagatacact gctgatcatc ttcaagaacc  1500
aggccagcag accctacaac atctaccctc atggcatcac agatgtgaga cccctgtatt  1560
ctagaaggct gcccaaggga gtgaagcacc tgaaggactt ccctatcctg cctggagaga  1620
tcttcaagta caagtggaca gtgacagtgg aagatggccc caccaagtct gaccctagat  1680
gtctgacaag atactacagc agctttgtga acatggaaag agacctggcc tctggcctga  1740
ttggacctct gctgatctgc tacaaagaat ctgtggacca gagaggcaac cagatcatgt  1800
ctgacaagag aaatgtgatc ctgttttctg tgtttgatga gaacagatcc tggtatctga  1860
cagagaacat ccagagattt ctgcccaatc ctgctggagt gcagctggaa gatcctgagt  1920
tccaggcctc caacatcatg cactccatca atggctatgt gtttgacagc ctgcagctgt  1980
ctgtgtgcct gcatgaagtg gcctactggt acatcctgag cattggagcc cagacagact  2040
tcctgtctgt gttcttctct ggctacacct tcaagcacaa gatggtgtat gaggataccc  2100
tgacactgtt cccattctct ggagagacag tgttcatgag catggaaaac cctggcctgt  2160
ggatcctggg ctgtcacaac tctgacttca gaaacagagg catgacagcc ctgctgaagg  2220
tgtccagctg tgacaagaac acaggagact actatgagga cagctatgag gacatctctg  2280
cctacctgct gagcaagaac aatgccattg agcccagaag cttcagccag aatgccacca  2340
atgtgtccaa caacagcaac accagcaatg actccaatgt gtcccctcca gtgctgaaga  2400
gacaccagag agaaatcacc agaaccacac tgcagtctga ccaagaggaa attgactatg  2460
atgacaccat ctctgtggag atgaagaaag aagattttga catctatgat gaggatgaga  2520
atcagagccc cagatccttt cagaaaaaga ccagacacta cttcattgct gctgtggaga  2580
gactgtggga ctatggcatg tctagcagcc ctcatgtgct gagaaataga gcccagtctg  2640
gctctgtgcc ccagttcaag aaagtggtgt tccaagagtt cacagatggc agcttcaccc  2700
agccactgta tagaggagag ctgaatgagc atctgggcct gctgggccct tatatcagag  2760
ctgaagtgga agataacatc atggtcacct tcagaaatca ggcctctaga ccctacagct  2820
tctacagctc cctgatcagc tatgaagagg accagagaca gggagctgag cccagaaaga  2880
actttgtgaa gcccaatgag actaagacct acttttggaa ggtgcagcac cacatggccc  2940
ctacaaagga tgagtttgac tgcaaggcct gggcctactt ttctgatgtg gatctggaaa  3000
aggatgtgca ctctggactc attggaccac tgcttgtgtg ccacaccaac acactgaacc  3060
ctgctcatgg cagacaagtg acagtgcaag agtttgccct gttcttcacc atctttgatg  3120
aaacaaagag ctggtacttc acagagaata tggagagaaa ctgcagggcc ccttgcaaca  3180
tccagatgga agatcccacc ttcaaagaga actacagatt ccatgccatc aatggctaca  3240
tcatggacac actgcctggc ctggttatgg ctcaggatca gagaatcaga tggtatctgc  3300
tgtccatggg ctccaatgag aatatccaca gcatccactt ctctggccat gtgttcacag  3360
tgagaaaaaa agaagagtac aaaatggccc tgtacaatct gtaccctggg gtgtttgaaa  3420
cagtggaaat gctgccttcc aaggctggca tttggagagt ggaatgtctg attggagagc  3480
acctccatgc tggaatgagc accctgtttc tggtgtacag caacaagtgt cagacccctc  3540
tgggcatggc ctctggacac atcagagact tccagatcac agcctctggc cagtatggac  3600
agtgggctcc taaactggct agactgcact actctggcag catcaatgcc tggtccacca  3660
aagagccctt cagctggatc aaggtggacc tgctggctcc catgatcatc catggaatca  3720
agacccaggg agccagacag aagttcagca gcctgtacat cagccagttc atcatcatgt  3780
acagcctgga tggcaagaag tggcagacct acagaggcaa cagcacaggc acactcatgg  3840
tgttctttgg caatgtggac agctctggca ttaagcacaa catcttcaac cctccaatca  3900
ttgccagata catcagactg caccccacac actacagcat cagatctacc ctgagaatgg  3960
aactgatggg ctgtgacctg aacagctgca gcatgcccct gggaatggaa agcaaggcca  4020
tctctgatgc ccagatcaca gccagcagct acttcaccaa catgtttgcc acttggagcc  4080
cctccaaggc tagactgcat ctgcagggca gaagcaatgc ttggaggccc caagtgaaca  4140
accccaaaga gtggctgcag gtggactttc aaaagaccat gaaagtgaca ggagtgacca  4200
cacagggagt caagtctctg ctgacctcta tgtatgtgaa agagttcctg atctccagca  4260
gccaggatgg ccaccagtgg accctgtttt tccagaatgg caaagtgaaa gtgttccagg  4320
gcaatcagga cagcttcaca cctgtggtca actccctgga tcctccactg ctgaccagat  4380
acctgagaat tcaccctcag tcttgggtgc accagattgc tctgagaatg gaagtgctgg  4440
gctgtgaagc tcaggacctc tactgatcgc gaataaaaga tctttatttt cattagatct  4500
gtgtgttggt tttttgtgtg tatttagcta tgccagttcc cgatcgttac aggaaaaatg  4560
gttcctctct gctacactca aattcct                                      4587

SEQ ID NO: 58           moltype = DNA  length = 4587
FEATURE                 Location/Qualifiers
source                  1..4587
                        mol_type = other DNA
                        organism = synthetic construct
SEQUENCE: 58
acgtttttcc tgtaacgatc gggaactggc atttgagtgt agcagagagg aaccatttct  60
caaagcttac taaagaatta ttcttttaca tttcagtggc caccagaaga tattacctgg  120
gagctgtgga actgagctgg gactacatgc agtctgacct gggagagctg cctgtggatg  180
ctagatttcc tccaagagtg cccaagagct tccccttcaa cacctctgtg gtgtacaaga  240
aaaccctgtt tgtggaattc acagaccacc tgttcaatat tgccaagcct agacctcctt  300
ggatgggact gctgggacct acaattcagg ctgaggtgta tgacacagtg gtcatcaccc  360
tgaagaacat ggccagccat cctgtgtctc tgcatgctgt gggagtgtct tactggaagg  420
cttctgaggg agctgagtat gatgaccaga caagccagag agagaaagag gatgacaagg  480
ttttccctgg aggcagccac acctatgtct ggcaggtcct gaaagaaaat ggccctatgg  540
cctctgatcc tctgtgcctg acatacagct acctgagcca tgtggacctg gtcaaggacc  600
tgaattctgg cctgattgga gccctgctgg tgtgtagaga aggcagcctg gccaaagaga  660
aaacccagac actgcacaag ttcatcctgc tgtttgctgt gtttgatgag ggcaagagct  720
ggcactctga gacaaagaac agcctgatgc aggacaggga tgctgcctct gctagagctt  780
ggcctaagat gcacacagtg aatggctatg tgaacagaag cctgcctgga ctgattggct  840
gccacagaaa gtctgtgtac tggcatgtga ttggcatggg cacaacacct gaggtgcaca  900
gcatctttct ggaaggacac accttcctgg tgagaaacca tagacaggcc agcctggaaa  960
tcagccctat caccttcctg acagctcaga ccctgctgat ggatctgggc cagtttctgc  1020
tgttctgcca catcagcagc caccagcatg atggcatgga agcctatgtg aaggtggaca  1080
```

-continued

```
gctgccctga agaaccccag ctgagaatga agaacaatga ggaggctgag gactatgatg  1140
atgacctgac agactctgag atggatgtgg tcagatttga tgatgacaac agccccagct  1200
tcatccagat cagatctgtg gccaagaagc accccaagac ctgggtgcac tatattgctg  1260
ctgaggaaga ggactgggat tatgctcctc tggtgctggc ccctgatgac agaagctaca  1320
agagccagta cctgaacaat ggccctcaga gaattggcag aaagtataag aaagtgagat  1380
tcatggccta cacagatgag acattcaaga ccagagaggc cattcagcat gagtctggca  1440
ttctgggccc tctgctgtat ggagaagtgg gagatacact gctgatcatc ttcaagaacc  1500
aggccagcag accctacaac atctaccctc atggcatcac agatgtgaga cccctgtatt  1560
ctagaaggct gcccaaggga gtgaagcacc tgaaggactt ccctatcctg cctggagaga  1620
tcttcaagta caagtggaca gtgacagtgg aagatggccc caccaagtct gaccctagat  1680
gtctgacaag atactacagc agctttgtga acatggaaag agacctggcc tctggcctga  1740
ttggacctct gctgatctgc tacaaagaat ctgtggacca gagaggcaac cagatcatgt  1800
ctgacaagag aaatgtgatc ctgttttctg tgtttgatga gaacagatcc tggtatctga  1860
cagagaacat ccagagattt ctgcccaatc ctgctggagt gcagctggaa gatcctgagt  1920
tccaggcctc caacatcatg cactccatca atggctatgt gtttgacagc ctgcagctgt  1980
ctgtgtgcct gcatgaagtg gcctactggt acatcctgag cattggagcc cagacagact  2040
tcctgtctgt gttcttctct ggctacacct tcaagcacaa gatggtgtat gaggataccc  2100
tgacactgtt cccattctct ggagagacag tgttcatgag catggaaaac cctggcctgt  2160
ggatcctggg ctgtcacaac tctgacttca gaaacagagg catgacagcc ctgctgaagg  2220
tgtccagctg tgacaagaac acaggagact actatgagga cagctatgag gacatctctg  2280
cctacctgct gagcaagaac aatgccattg agcccagaag cttcagccag aatgccacca  2340
atgtgtccaa caacagcaac accagcaatg actccaatgt gtcccctcca gtgctgaaga  2400
gacaccagag agaaatcacc agaaccacac tgcagtctga ccaagaggaa attgactatg  2460
atgacaccat ctctgtggag atgaagaaag aagattttga catctatgat gaggatgaga  2520
atcagagccc cagatccttt cagaaaaaga ccagacacta cttcattgct gctgtggaga  2580
gactgtggga ctatggcatg tctagcagcc ctcatgtgct gagaaataga gcccagtctg  2640
gctctgtgcc ccagttcaag aaagtggtgt tccaagagtt cacagatggc agcttcaccc  2700
agccactgta tagaggagag ctgaatgagc atctgggcct gctgggccct tatatcagag  2760
ctgaagtgga agataacatc atggtcacct tcagaaatca ggcctctaga ccctacagct  2820
tctacagctc cctgatcagc tatgaagagg accagagaca gggagctgag cccagaaaga  2880
actttgtgaa gcccaatgag actaagacct acttttggaa ggtgcagcac cacatggccc  2940
ctacaaagga tgagtttgac tgcaaggcct gggcctactt ttctgatgtg gatctggaaa  3000
aggatgtgca ctctggactc attggaccac tgcttgtgtg ccacaccaac acactgaacc  3060
ctgctcatgg cagacaagtg acagtgcaag agtttgccct gttcttcacc atctttgatg  3120
aaacaaagag ctggtacttc acagagaata tggagagaaa ctgcagggcc ccttgcaaca  3180
tccagatgga agatcccacc ttcaaagaga actacagatt ccatgccatc aatggctaca  3240
tcatggacac actgcctggc ctggttatgg ctcaggatca gagaatcaga tggtatctgc  3300
tgtccatggg ctccaatgag aatatccaca gcatccactt ctctggccat gtgttcacag  3360
tgagaaaaaa agaagagtac aaaatggccc tgtacaatct gtaccctggg gtgtttgaaa  3420
cagtggaaat gctgccttcc aaggctggca tttggagagt ggaatgtctg attggagagc  3480
acctccatgc tggaatgagc accctgtttc tggtgtacag caacaagtgt cagacccctc  3540
tgggcatggc ctctggacac atcagagact tccagatcac agcctctggc cagtatggac  3600
agtgggctcc taaactggct agactgcact actctggcag catcaatgcc tggtccacca  3660
aagagccctt cagctggatc aaggtggacc tgctggctcc catgatcatc catggaatca  3720
agacccaggg agccagacag aagttcagca gcctgtacat cagccagttc atcatcatgt  3780
acagcctgga tggcaagaag tggcagacct acagaggcaa cagcacaggc acactcatgg  3840
tgttctttgg caatgtggac agctctggca ttaagcacaa catcttcaac cctccaatca  3900
ttgccagata catcagactg caccccacac actacagcat cagatctacc ctgagaatgg  3960
aactgatggg ctgtgacctg aacagctgca gcatgcccct gggaatggaa agcaaggcca  4020
tctctgatgc ccagatcaca gccagcagct acttcaccaa catgtttgcc acttggagcc  4080
cctccaaggc tagactgcat ctgcagggca gaagcaatgc ttggaggccc caagtgaaca  4140
accccaaaga gtggctgcag gtggactttc aaaagaccat gaaagtgaca ggagtgacca  4200
cacagggagt caagtctctg ctgacctcta tgtatgtgaa agagttcctg atctccagca  4260
gccaggatgg ccaccagtgg accctgtttt tccagaatgg caaagtgaaa gtgttccagg  4320
gcaatcagga cagcttcaca cctgtggtca actccctgga tcctccactg ctgaccagat  4380
acctgagaat tcaccctcag tcttgggtgc accagattgc tctgagaatg gaagtgctgg  4440
gctgtgaagc tcaggacctc tactgatcgc gaataaaaga tctttatttt cattagatct  4500
gtgtgttggt tttttgtgtg tatttagcta tgccagttcc cgatcgttac aggaaaaatg  4560
gttcctctct gctacactca aattcct                                      4587
```

```
SEQ ID NO: 59          moltype = DNA  length = 4587
FEATURE                Location/Qualifiers
source                 1..4587
                       mol_type = other DNA
                       organism = synthetic construct
SEQUENCE: 59
acgttaatgg ttcctctctg ctacactcaa atgccagttc ccgatcgtta caggaaatct  60
caaagcttac taaagaatta ttcttttaca tttcagtggc caccagaaga tattacctgg  120
gagctgtgga actgagctgg gactacatgc agtctgacct gggagagctg cctgtggatg  180
ctagatttcc tccaagagtg cccaagagct tccccttcaa cacctctgtg gtgtacaaga  240
aaaccctgtt tgtggaattc acagaccacc tgttcaatat tgccaagcct agacctcctt  300
ggatgggact gctgggacct acaattcagg ctgaggtgta tgacacagtg gtcatcaccc  360
tgaagaacat ggccagccat cctgtgtctc tgcatgctgt gggagtgtct tactggaagg  420
cttctgaggg agctgagtat gatgaccaga caagccagag agagaaagag gatgacaagg  480
ttttccctgg aggcagccac acctatgtct ggcaggtcct gaaagaaaat ggccctatgg  540
cctctgatcc tctgtgcctg acatacagct acctgagcca tgtggacctg gtcaaggacc  600
tgaattctgg cctgattgga gccctgctgg tgtgtagaga aggcagcctg gccaaagaga  660
aaacccagac actgcacaag ttcatcctgc tgtttgctgt gtttgatgag ggcaagagct  720
ggcactctga gacaaagaac agcctgatgc aggacaggga tgctgcctct gctagagctt  780
```

```
ggcctaagat gcacacagtg aatggctatg tgaacagaag cctgcctgga ctgattggct  840
gccacagaaa gtctgtgtac tggcatgtga ttggcatggg cacaacacct gaggtgcaca  900
gcatctttct ggaaggacac accttcctgg tgagaaacca tagacaggcc agcctggaaa  960
tcagccctat caccttcctg acagctcaga ccctgctgat ggatctgggc cagtttctgc  1020
tgttctgcca catcagcagc caccagcatg atggcatgga agcctatgtg aaggtggaca  1080
gctgccctga agaaccccag ctgagaatga agaacaatga ggaggctgag gactatgatg  1140
atgacctgac agactctgag atggatgtgg tcagatttga tgatgacaac agccccagct  1200
tcatccagat cagatctgtg gccaagaagc accccaagac ctgggtgcac tatattgctg  1260
ctgaggaaga ggactgggat tatgctcctc tggtgctggc cctgatgac agaagctaca  1320
agagccagta cctgaacaat ggccctcaga gaattggcag aaagtataag aaagtgagat  1380
tcatggccta cacagatgag acattcaaga ccagagaggc cattcagcat gagtctggca  1440
ttctgggccc tctgctgtat ggagaagtgg gagatacact gctgatcatc ttcaagaacc  1500
aggccagcag accctacaac atctaccctc atggcatcac agatgtgaga cccctgtatt  1560
ctagaaggct gcccaaggga gtgaagcacc tgaaggactt ccctatcctg cctggagaga  1620
tcttcaagta caagtggaca gtgacagtgg aagatggccc caccaagtct gaccctagat  1680
gtctgacaag atactacagc agctttgtga acatggaaag agacctggcc tctggcctga  1740
ttggacctct gctgatctgc tacaaagaat ctgtggacca gagaggcaac cagatcatgt  1800
ctgacaagag aaatgtgatc ctgttttctg tgtttgatga gaacagatcc tggtatctga  1860
cagagaacat ccagagattt ctgcccaatc ctgctggagt gcagctggaa gatcctgagt  1920
tccaggcctc caacatcatg cactccatca atggctatgt gtttgacagc ctgcagctgt  1980
ctgtgtgcct gcatgaagtg gcctactggt acatcctgag cattggagcc cagacagact  2040
tcctgtctgt gttcttctct ggctacacct tcaagcacaa gatggtgtat gaggataccc  2100
tgacactgtt cccattctct ggagagacag tgttcatgag catggaaaac cctggcctgt  2160
ggatcctggg ctgtcacaac tctgacttca gaaacagagg catgacagcc ctgctgaagg  2220
tgtccagctg tgacaagaac acaggagact actatgagga cagctatgag gacatctctg  2280
cctacctgct gagcaagaac aatgccattg agcccagaag cttcagccag aatgccacca  2340
atgtgtccaa caacagcaac accagcaatg actccaatgt gtcccctcca gtgctgaaga  2400
gacaccagag agaaatcacc agaaccacac tgcagtctga ccaagaggaa attgactatg  2460
atgacaccat ctctgtggag atgaagaaag aagattttga catctatgat gaggatgaga  2520
atcagagccc cagatccttt cagaaaaaga ccagacacta cttcattgct gctgtggaga  2580
gactgtggga ctatggcatg tctagcagcc ctcatgtgct gagaaataga gcccagtctg  2640
gctctgtgcc ccagttcaag aaagtggtgt tccaagagtt cacagatggc agcttcaccc  2700
agccactgta tagaggagag ctgaatgagc atctgggcct gctgggccct tatatcagag  2760
ctgaagtgga agataacatc atggtcacct tcagaaatca ggcctctaga ccctacagct  2820
tctacagctc cctgatcagc tatgaagagg accagagaca gggagctgag cccagaaaga  2880
actttgtgaa gcccaatgag actaagacct acttttggaa ggtgcagcac cacatggccc  2940
ctacaaagga tgagtttgac tgcaaggcct gggcctactt ttctgatgtg gatctggaaa  3000
aggatgtgca ctctggactc attggaccac tgcttgtgtg ccacaccaac acactgaacc  3060
ctgctcatgg cagacaagtg acagtgcaag agtttgccct gttcttcacc atctttgatg  3120
aaacaaagag ctggtacttc acagagaata tggagagaaa ctgcagggcc ccttgcaaca  3180
tccagatgga agatcccacc ttcaaagaga actacagatt ccatgccatc aatggctaca  3240
tcatggacac actgcctggc ctggttatgg ctcaggatca gagaatcaga tggtatctgc  3300
tgtccatggg ctccaatgag aatatccaca gcatccactt ctctggccat gtgttcacag  3360
tgagaaaaaa agaagagtac aaaatggccc tgtacaatct gtaccctggg gtgtttgaaa  3420
cagtggaaat gctgccttcc aaggctggca tttggagagt ggaatgtctg attggagagc  3480
acctccatgc tggaatgagc accctgtttc tggtgtacag caacaagtgt cagacccctc  3540
tgggcatggc ctctggacac atcagagact tccagatcac agcctctggc cagtatggac  3600
agtgggctcc taaactggct agactgcact actctggcag catcaatgcc tggtccacca  3660
aagagccctt cagctggatc aaggtggacc tgctggctcc catgatcatc catggaatca  3720
agacccaggg agccagacag aagttcagca gcctgtacat cagccagttc atcatcatgt  3780
acagcctgga tggcaagaag tggcagacct acagaggcaa cagcacaggc acactcatgg  3840
tgttctttgg caatgtggac agctctggca ttaagcacaa catcttcaac cctccaatca  3900
ttgccagata catcagactg caccccacac actacagcat cagatctacc ctgagaatgg  3960
aactgatggg ctgtgacctg aacagctgca gcatgcccct gggaatggaa agcaaggcca  4020
tctctgatgc ccagatcaca gccagcagct acttcaccaa catgtttgcc acttggagcc  4080
cctccaaggc tagactgcat ctgcagggca gaagcaatgc ttggaggccc caagtgaaca  4140
accccaaaga gtggctgcag gtggactttc aaaagaccat gaaagtgaca ggagtgacca  4200
cacagggagt caagtctctg ctgacctcta tgtatgtgaa agagttcctg atctccagca  4260
gccaggatgg ccaccagtgg accctgtttt tccagaatgg caaagtgaaa gtgttccagg  4320
gcaatcagga cagcttcaca cctgtggtca actccctgga tcctccactg ctgaccagat  4380
acctgagaat tcaccctcag tcttgggtgc accagattgc tctgagaatg gaagtgctgg  4440
gctgtgaagc tcaggacctc tactgatcgc gaataaaaga tctttatttt cattagatct  4500
gtgtgttggt tttttgtgtg tatttagcta tttgagtgta gcagagagga accatttttc  4560
ctgtaacgat cgggaactgg cattcct                                     4587
```

```
SEQ ID NO: 60           moltype = RNA  length = 68
FEATURE                 Location/Qualifiers
source                  1..68
                        mol_type = other RNA
                        organism = synthetic construct
modified_base           1..3
                        mod_base = OTHER
                        note = 2'-O-Methyl modified base
modified_base           11..14
                        mod_base = OTHER
                        note = 2'-O-Methyl modified base
modified_base           25..27
                        mod_base = OTHER
                        note = 2'-O-Methyl modified base
```

```
modified_base          34..37
                       mod_base = OTHER
                       note = 2'-O-Methyl modified base
modified_base          56..67
                       mod_base = OTHER
                       note = 2'-Fluoro modified base
modified_base          68
                       mod_base = OTHER
                       note = 2'-O-Methyl modified base
modified_base          1..4
                       mod_base = OTHER
                       note = phosphorothioate linkage
modified_base          10..14
                       mod_base = OTHER
                       note = phosphorothioate linkage
modified_base          24..29
                       mod_base = OTHER
                       note = phosphorothioate linkage
modified_base          39..43
                       mod_base = OTHER
                       note = phosphorothioate linkage
modified_base          65..68
                       mod_base = OTHER
                       note = phosphorothioate linkage
SEQUENCE: 60
gttgagaatc gaaagattct caacctttta atttctactg ttgtagatct gtaacgatcg  60
ggaactgg                                                           68

SEQ ID NO: 61          moltype = RNA  length = 68
FEATURE                Location/Qualifiers
source                 1..68
                       mol_type = other RNA
                       organism = synthetic construct
modified_base          1..3
                       mod_base = OTHER
                       note = 2'-O-Methyl modified base
modified_base          11..14
                       mod_base = OTHER
                       note = 2'-O-Methyl modified base
modified_base          25..27
                       mod_base = OTHER
                       note = 2'-O-Methyl modified base
modified_base          34..37
                       mod_base = OTHER
                       note = 2'-O-Methyl modified base
modified_base          56..67
                       mod_base = OTHER
                       note = 2'-Fluoro modified base
modified_base          68
                       mod_base = OTHER
                       note = 2'-O-Methyl modified base
modified_base          1..4
                       mod_base = OTHER
                       note = phosphorothioate linkage
modified_base          10..14
                       mod_base = OTHER
                       note = phosphorothioate linkage
modified_base          24..29
                       mod_base = OTHER
                       note = phosphorothioate linkage
modified_base          39..43
                       mod_base = OTHER
                       note = phosphorothioate linkage
modified_base          65..68
                       mod_base = OTHER
                       note = phosphorothioate linkage
SEQUENCE: 61
gttgagaatc gaaagattct caacctttta atttctactg ttgtagatag tgtagcagag  60
aggaacca                                                           68

SEQ ID NO: 62          moltype = RNA  length = 46
FEATURE                Location/Qualifiers
source                 1..46
                       mol_type = other RNA
                       organism = synthetic construct
modified_base          1..3
                       mod_base = OTHER
                       note = 2'-O-Methyl modified base
modified_base          10..13
```

```
                         mod_base = OTHER
                         note = 2'-O-Methyl modified base
modified_base            32..45
                         mod_base = OTHER
                         note = 2'-Fluoro modified base
modified_base            46
                         mod_base = OTHER
                         note = 2'-O-Methyl modified base
modified_base            1..5
                         mod_base = OTHER
                         note = phosphorothioate linkage
modified_base            15..19
                         mod_base = OTHER
                         note = phosphorothioate linkage
modified_base            41..43
                         mod_base = OTHER
                         note = phosphorothioate linkage
modified_base            44..46
                         mod_base = OTHER
                         note = phosphorothioate linkage
SEQUENCE: 62
cttttaattt ctactgttgt agatctgtaa cgatcgggaa ctggca                  46

SEQ ID NO: 63            moltype = RNA  length = 46
FEATURE                  Location/Qualifiers
source                   1..46
                         mol_type = other RNA
                         organism = synthetic construct
modified_base            1..3
                         mod_base = OTHER
                         note = 2'-O-Methyl modified base
modified_base            10..13
                         mod_base = OTHER
                         note = 2'-O-Methyl modified base
modified_base            32..45
                         mod_base = OTHER
                         note = 2'-Fluoro modified base
modified_base            46
                         mod_base = OTHER
                         note = 2'-O-Methyl modified base
modified_base            1..5
                         mod_base = OTHER
                         note = phosphorothioate linkage
modified_base            15..19
                         mod_base = OTHER
                         note = phosphorothioate linkage
modified_base            41..43
                         mod_base = OTHER
                         note = phosphorothioate linkage
modified_base            44..46
                         mod_base = OTHER
                         note = phosphorothioate linkage
SEQUENCE: 63
cttttaattt ctactgttgt agatagtgta gcagagagga accatt                  46

SEQ ID NO: 64            moltype = RNA  length = 68
FEATURE                  Location/Qualifiers
source                   1..68
                         mol_type = other RNA
                         organism = synthetic construct
modified_base            1..3
                         mod_base = OTHER
                         note = 2'-O-Methyl modified base
modified_base            11..14
                         mod_base = OTHER
                         note = 2'-O-Methyl modified base
modified_base            25..27
                         mod_base = OTHER
                         note = 2'-O-Methyl modified base
modified_base            34..37
                         mod_base = OTHER
                         note = 2'-O-Methyl modified base
modified_base            56..67
                         mod_base = OTHER
                         note = 2'-Fluoro modified base
modified_base            68
                         mod_base = OTHER
                         note = 2'-O-Methyl modified base
modified_base            1..4
```

```
                        mod_base = OTHER
                        note = phosphorothioate linkage
modified_base           10..14
                        mod_base = OTHER
                        note = phosphorothioate linkage
modified_base           24..29
                        mod_base = OTHER
                        note = phosphorothioate linkage
modified_base           39..43
                        mod_base = OTHER
                        note = phosphorothioate linkage
modified_base           65..68
                        mod_base = OTHER
                        note = phosphorothioate linkage
SEQUENCE: 64
gttgagaatc gaaagattct caacctttta atttctactg ttgtagataa taaagcatag  60
tgcaatgg                                                           68

SEQ ID NO: 65           moltype = RNA  length = 68
FEATURE                 Location/Qualifiers
source                  1..68
                        mol_type = other RNA
                        organism = synthetic construct
modified_base           1..3
                        mod_base = OTHER
                        note = 2'-O-Methyl modified base
modified_base           11..14
                        mod_base = OTHER
                        note = 2'-O-Methyl modified base
modified_base           25..27
                        mod_base = OTHER
                        note = 2'-O-Methyl modified base
modified_base           34..37
                        mod_base = OTHER
                        note = 2'-O-Methyl modified base
modified_base           56..67
                        mod_base = OTHER
                        note = 2'-Fluoro modified base
modified_base           68
                        mod_base = OTHER
                        note = 2'-O-Methyl modified base
modified_base           1..4
                        mod_base = OTHER
                        note = phosphorothioate linkage
modified_base           10..14
                        mod_base = OTHER
                        note = phosphorothioate linkage
modified_base           24..29
                        mod_base = OTHER
                        note = phosphorothioate linkage
modified_base           39..43
                        mod_base = OTHER
                        note = phosphorothioate linkage
modified_base           65..68
                        mod_base = OTHER
                        note = phosphorothioate linkage
SEQUENCE: 65
gttgagaatc gaaagattct caacctttta atttctactg ttgtagattt ttgcccacta  60
aggaaagt                                                           68

SEQ ID NO: 66           moltype = RNA  length = 68
FEATURE                 Location/Qualifiers
source                  1..68
                        mol_type = other RNA
                        organism = synthetic construct
modified_base           1..3
                        mod_base = OTHER
                        note = 2'-O-Methyl modified base
modified_base           11..14
                        mod_base = OTHER
                        note = 2'-O-Methyl modified base
modified_base           25..27
                        mod_base = OTHER
                        note = 2'-O-Methyl modified base
modified_base           34..37
                        mod_base = OTHER
                        note = 2'-O-Methyl modified base
modified_base           56..67
                        mod_base = OTHER
```

```
                        note = 2'-Fluoro modified base
modified_base           68
                        mod_base = OTHER
                        note = 2'-O-Methyl modified base
modified_base           1..4
                        mod_base = OTHER
                        note = phosphorothioate linkage
modified_base           10..14
                        mod_base = OTHER
                        note = phosphorothioate linkage
modified_base           24..29
                        mod_base = OTHER
                        note = phosphorothioate linkage
modified_base           39..43
                        mod_base = OTHER
                        note = phosphorothioate linkage
modified_base           65..68
                        mod_base = OTHER
                        note = phosphorothioate linkage
SEQUENCE: 66
gttgagaatc gaaagattct caacctttta atttctactg ttgtagattg agatcaacag  60
cacaggtt                                                           68

SEQ ID NO: 67           moltype = RNA  length = 68
FEATURE                 Location/Qualifiers
source                  1..68
                        mol_type = other RNA
                        organism = synthetic construct
modified_base           1..3
                        mod_base = OTHER
                        note = 2'-O-Methyl modified base
modified_base           11..14
                        mod_base = OTHER
                        note = 2'-O-Methyl modified base
modified_base           25..27
                        mod_base = OTHER
                        note = 2'-O-Methyl modified base
modified_base           34..37
                        mod_base = OTHER
                        note = 2'-O-Methyl modified base
modified_base           56..67
                        mod_base = OTHER
                        note = 2'-Fluoro modified base
modified_base           68
                        mod_base = OTHER
                        note = 2'-O-Methyl modified base
modified_base           1..4
                        mod_base = OTHER
                        note = phosphorothioate linkage
modified_base           10..14
                        mod_base = OTHER
                        note = phosphorothioate linkage
modified_base           24..29
                        mod_base = OTHER
                        note = phosphorothioate linkage
modified_base           39..43
                        mod_base = OTHER
                        note = phosphorothioate linkage
modified_base           65..68
                        mod_base = OTHER
                        note = phosphorothioate linkage
SEQUENCE: 67
gttgagaatc gaaagattct caacctttta atttctactg ttgtagatca ctttccttag  60
tgggcaaa                                                           68

SEQ ID NO: 68           moltype = RNA  length = 68
FEATURE                 Location/Qualifiers
source                  1..68
                        mol_type = other RNA
                        organism = synthetic construct
modified_base           1..3
                        mod_base = OTHER
                        note = 2'-O-Methyl modified base
modified_base           11..14
                        mod_base = OTHER
                        note = 2'-O-Methyl modified base
modified_base           25..27
                        mod_base = OTHER
                        note = 2'-O-Methyl modified base
```

```
modified_base          34..37
                       mod_base = OTHER
                       note = 2'-O-Methyl modified base
modified_base          56..67
                       mod_base = OTHER
                       note = 2'-Fluoro modified base
modified_base          68
                       mod_base = OTHER
                       note = 2'-O-Methyl modified base
modified_base          1..4
                       mod_base = OTHER
                       note = phosphorothioate linkage
modified_base          10..14
                       mod_base = OTHER
                       note = phosphorothioate linkage
modified_base          24..29
                       mod_base = OTHER
                       note = phosphorothioate linkage
modified_base          39..43
                       mod_base = OTHER
                       note = phosphorothioate linkage
modified_base          65..68
                       mod_base = OTHER
                       note = phosphorothioate linkage
SEQUENCE: 68
gttgagaatc gaaagattct caacctttta atttctactg ttgtagatcc cactaaggaa  60
agtgcaaa                                                           68

SEQ ID NO: 69          moltype = AA  length = 4
FEATURE                Location/Qualifiers
source                 1..4
                       mol_type = protein
                       note = furin cleavage site
                       organism = unidentified
SEQUENCE: 69
RHQR                                                               4

SEQ ID NO: 70          moltype = AA  length = 31
FEATURE                Location/Qualifiers
source                 1..31
                       mol_type = protein
                       organism = synthetic construct
SEQUENCE: 70
SFSQNATNVS NNSNTSNDSN VSPPVLKRHQ R                                 31

SEQ ID NO: 71          moltype = AA  length = 17
FEATURE                Location/Qualifiers
source                 1..17
                       mol_type = protein
                       organism = synthetic construct
SEQUENCE: 71
ENRSFSQNPP VLKRHQR                                                 17

SEQ ID NO: 72          moltype = AA  length = 17
FEATURE                Location/Qualifiers
source                 1..17
                       mol_type = protein
                       organism = synthetic construct
SEQUENCE: 72
ENRSFSQNPP VLKRHQR                                                 17

SEQ ID NO: 73          moltype = AA  length = 21
FEATURE                Location/Qualifiers
source                 1..21
                       mol_type = protein
                       organism = synthetic construct
SEQUENCE: 73
EPRSFSQNCS QNPPVLKRHQ R                                            21

SEQ ID NO: 74          moltype = AA  length = 21
FEATURE                Location/Qualifiers
source                 1..21
                       mol_type = protein
                       organism = synthetic construct
SEQUENCE: 74
EPRNFSQNCS QNPPVLKRHQ R                                            21

SEQ ID NO: 75          moltype = AA  length = 21
FEATURE                Location/Qualifiers
```

```
source                 1..21
                       mol_type = protein
                       organism = synthetic construct
SEQUENCE: 75
ENRSFSQNCS QNPPVLKRHQ R                                        21

SEQ ID NO: 76          moltype = AA  length = 19
FEATURE                Location/Qualifiers
source                 1..19
                       mol_type = protein
                       organism = synthetic construct
SEQUENCE: 76
EPRNFSQNAT PPVLKRHQR                                           19

SEQ ID NO: 77          moltype = AA  length = 18
FEATURE                Location/Qualifiers
source                 1..18
                       mol_type = protein
                       organism = synthetic construct
SEQUENCE: 77
ENRSNFSQNP PVLKRHQR                                            18

SEQ ID NO: 78          moltype = AA  length = 22
FEATURE                Location/Qualifiers
source                 1..22
                       mol_type = protein
                       organism = synthetic construct
SEQUENCE: 78
ENRSNFSQNC SQNPPVLKRH QR                                       22

SEQ ID NO: 79          moltype = AA  length = 20
FEATURE                Location/Qualifiers
source                 1..20
                       mol_type = protein
                       organism = synthetic construct
SEQUENCE: 79
ENRSNFSQNA TPPVLKRHQR                                          20

SEQ ID NO: 80          moltype = AA  length = 17
FEATURE                Location/Qualifiers
source                 1..17
                       mol_type = protein
                       organism = synthetic construct
SEQUENCE: 80
EPRSFSQNPP VLKRHQR                                             17

SEQ ID NO: 81          moltype = DNA  length = 4573
FEATURE                Location/Qualifiers
source                 1..4573
                       mol_type = other DNA
                       organism = synthetic construct
SEQUENCE: 81
acgcgtacgt ttttcctgta acgatcggga actggcattt gagtgtagca gagaggaacc  60
atttctcagt gttaagctta ctaaagaatt attcttttac atttcagtgg ccaccagaag  120
atattacctg ggagctgtgg aactgagctg ggactacatg cagtctgacc tgggagagct  180
gcctgtggat gctagatttc ctccaagagt gcccaagagc ttccccttca acacctctgt  240
ggtgtacaag aaaaccctgt ttgtggaatt cacagaccac ctgttcaata ttgccaagcc  300
tagacctcct tggatgggac tgctgggacc tacaattcag gctgaggtgt atgacacagt  360
ggtcatcacc ctgaagaaca tggccagcca tcctgtgtct ctgcatgctg tgggagtgtc  420
ttactggaag gcttctgagg gagctgagta tgatgaccag acaagccaga gagagaaaga  480
ggatgacaag gttttccctg gaggcagcca cacctatgtc tggcaggtcc tgaaagaaaa  540
tggccctatg gcctctgatc ctctgtgcct gacatacagc tacctgagcc atgtggacct  600
ggtcaaggac ctgaattctg gcctgattgg agccctgctg gtgtgtagag aaggcagcct  660
ggccaaagag aaaacccaga cactgcacaa gttcatcctg ctgtttgctg tgtttgatga  720
gggcaagagc tggcactctg agacaaagaa cagcctgatg caggacaggg atgctgcctc  780
tgctagagct tggcctaaga tgcacacagt gaatggctat gtgaacagaa gcctgcctgg  840
actgattggc tgccacagaa agtctgtgta ctggcatgtg attggcatgg gcacaacacc  900
tgaggtgcac agcatctttc tggaaggaca caccttcctg gtgagaaacc atagacaggc  960
cagcctggaa atcagcccta tcaccttcct gacagctcag accctgctga tggatctggg  1020
ccagtttctg ctgttctgcc acatcagcag ccaccagcat gatggcatgg aagcctatgt  1080
gaaggtggac agctgccctg aagaacccca gctgagaatg aagaacaatg aggaggctga  1140
ggactatgat gatgacctga cagactctga gatggatgtg gtcagatttg atgatgacaa  1200
cagccccagc ttcatccaga tcagatctgt ggccaagaag caccccaaga cctgggtgca  1260
ctatattgct gctgaggaag aggactggga ttatgctcct ctggtgctgg cccctgatga  1320
cagaagctac aagagccagt acctgaacaa tggccctcag agaattggca gaaagtataa  1380
gaaagtgaga ttcatggcct acacagatga gacattcaag accagagagg ccattcagca  1440
tgagtctggc attctgggcc ctctgctgta tggagaagtg ggagatacac tgctgatcat  1500
cttcaagaac caggccagca gaccctacaa catctaccct catggcatca cagatgtgag  1560
acccctgtat tctagaaggc tgcccaaggg agtgaagcac ctgaaggact tccctatcct  1620
```

```
gcctggagag atcttcaagt acaagtggac agtgacagtg gaagatggcc ccaccaagtc  1680
tgaccctaga tgtctgacaa gatactacag cagctttgtg aacatggaaa gagacctggc  1740
ctctggcctg attggacctc tgctgatctg ctacaaagaa tctgtggacc agagaggcaa  1800
ccagatcatg tctgacaaga gaaatgtgat cctgtttttct gtgtttgatg agaacagatc  1860
ctggtatctg acagagaaca tccagagatt tctgcccaat cctgctggag tgcagctgga  1920
agatcctgag ttccaggcct ccaacatcat gcactccatc aatggctatg tgtttgacag  1980
cctgcagctg tctgtgtgcc tgcatgaagt ggcctactgg tacatcctga gcattggagc  2040
ccagacagac ttcctgtctg tgttcttctc tggctacacc ttcaagcaca agatggtgta  2100
tgaggatacc ctgacactgt tcccattctc tggagagaca gtgttcatga gcatggaaaa  2160
ccctggcctg tggatcctgg gctgtcacaa ctctgacttc agaaacagag gcatgacagc  2220
cctgctgaag gtgtccagct gtgacaagaa cacaggagac tactatgagg acagctatga  2280
ggacatctct gcctacctgc tgagcaagaa caatgccatt gagcccagaa gcttcagcca  2340
gaatcctcca gtgctgaaga gacaccagag agaaatcacc agaaccacac tgcagtctga  2400
ccaagaggaa attgactatg atgacaccat ctctgtggag atgaagaaag aagattttga  2460
catctatgat gaggatgaga atcagagccc cagatccttt cagaaaaaga ccagacacta  2520
cttcattgct gctgtggaga gactgtggga ctatggcatg tctagcagcc ctcatgtgct  2580
gagaaataga gcccagtctg gctctgtgcc ccagttcaag aaagtggtgt tccaagagtt  2640
cacagatggc agcttcaccc agccactgta tagaggagag ctgaatgagc atctgggcct  2700
gctgggccct tatatcagag ctgaagtgga agataacatc atggtcacct tcagaaatca  2760
ggcctctaga ccctacagct tctacagctc cctgatcagc tatgaagagg accagagaca  2820
gggagctgag cccagaaaga actttgtgaa gcccaatgag actaagacct acttttggaa  2880
ggtgcagcac cacatggccc ctacaaagga tgagtttgac tgcaaggcct gggcctactt  2940
ttctgatgtg gatctggaaa aggatgtgca ctctggactc attggaccac tgcttgtgtg  3000
ccacaccaac acactgaacc ctgctcatgg cagacaagtg acagtgcaag agtttgccct  3060
gttcttcacc atctttgatg aaacaaagag ctggtacttc acagagaata tggagagaaa  3120
ctgcagggcc ccttgcaaca tccagatgga agatcccacc ttcaaagaga actacagatt  3180
ccatgccatc aatggctaca tcatggacac actgcctggc ctggttatgg ctcaggatca  3240
gagaatcaga tggtatctgc tgtccatggg ctccaatgag aatatccaca gcatccactt  3300
ctctggccat gtgttcacag tgagaaaaaa agaagagtac aaaatggccc tgtacaatct  3360
gtaccctggg gtgtttgaaa cagtggaaat gctgccttcc aaggctggca tttggagagt  3420
ggaatgtctg attggagagc acctccatgc tggaatgagc accctgtttc tggtgtacag  3480
caacaagtgt cagacccctc tgggcatggc ctctggacac atcagagact tccagatcac  3540
agcctctggc cagtatggac agtgggctcc taaactggct agactgcact actctggcag  3600
catcaatgcc tggtccacca aagagccctt cagctggatc aaggtggacc tgctggctcc  3660
catgatcatc catggaatca agacccaggg agccagacag aagttcagca gcctgtacat  3720
cagccagttc atcatcatgt acagcctgga tggcaagaag tggcagacct acagaggcaa  3780
cagcacaggc acactcatgg tgttctttgg caatgtggac agctctggca ttaagcacaa  3840
catcttcaac cctccaatca ttgccagata catcagactg caccccacac actacagcat  3900
cagatctacc ctgagaatgg aactgatggg ctgtgacctg aacagctgca gcatgcccct  3960
gggaatggaa agcaaggcca tctctgatgc ccagatcaca gccagcagct acttcaccaa  4020
catgtttgcc acttggagcc cctccaaggc tagactgcat ctgcagggca gaagcaatgc  4080
ttggaggccc caagtgaaca accccaaaga gtggctgcag gtggactttc aaaagaccat  4140
gaaagtgaca ggagtgacca cacagggagt caagtctctg ctgacctcta tgtatgtgaa  4200
agagttcctg atctccagca gccaggatgg ccaccagtgg accctgtttt tccagaatgg  4260
caaagtgaaa gtgttccagg gcaatcagga cagcttcaca cctgtggtca actccctgga  4320
tcctccactg ctgaccagat acctgagaat tcaccctcag tcttgggtgc accagattgc  4380
tctgagaatg gaagtgctgg gctgtgaagc tcaggacctc tactgatcgc gaataaaaga  4440
tctttatttt cattagatct gtgtgttggt tttttgtgtg tatttagcta acagtatgat  4500
taagtggata aatggttcct ctctgctaca ctcaaatgcc agttcccgat cgttacagga  4560
aattcctcac gtg                                                    4573
```

```
SEQ ID NO: 82          moltype = DNA  length = 4573
FEATURE                Location/Qualifiers
source                 1..4573
                       mol_type = other DNA
                       organism = synthetic construct
SEQUENCE: 82
acgcgtacgt ttttcctgta acgatcggga actggcattt gagtgtagca gagaggaacc  60
atttctcagt gttaagctta ctaaagaatt attcttttac atttcagtgg ccaccagaag  120
atattacctg ggagctgtgg aactgagctg ggactacatg cagtctgacc tgggagagct  180
gcctgtggat gctagatttc ctccaagagt gcccaagagc ttccccttca acacctctgt  240
ggtgtacaag aaaaccctgt ttgtggaatt cacagaccac ctgttcaata ttgccaagcc  300
tagacctcct tggatgggac tgctgggacc tacaattcag gctgaggtgt atgacacagt  360
ggtcatcacc ctgaagaaca tggccagcca tcctgtgtct ctgcatgctg tgggagtgtc  420
ttactggaag gcttctgagg gagctgagta tgatgaccag acaagccaga gagagaaaga  480
ggatgacaag gttttccctg gaggcagcca cacctatgtc tggcaggtcc tgaaagaaaa  540
tggccctatg gcctctgatc ctctgtgcct gacatacagc tacctgagcc atgtggacct  600
ggtcaaggac ctgaattctg gcctgattgg agccctgctg gtgtgtagag aaggcagcct  660
ggccaaagag aaaacccaga cactgcacaa gttcatcctg ctgtttgctg tgtttgatga  720
gggcaagagc tggcactctg agacaaagaa cagcctgatg caggacaggg atgctgcctc  780
tgctagagct tggcctaaga tgcacacagt gaatggctat gtgaacagaa gcctgcctgg  840
actgattggc tgccacagaa agtctgtgta ctggcatgtg attggcatgg gcacaacacc  900
tgaggtgcac agcatctttc tggaaggaca caccttcctg gtgagaaacc atagacaggc  960
cagcctggaa atcagcccta tcaccttcct gacagctcag accctgctga tggatctggg  1020
ccagtttctg ctgttctgcc acatcagcag ccaccagcat gatggcatgg aagcctatgt  1080
gaaggtggac agctgccctg aagaacccca gctgagaatg aagaacaatg aggaggctga  1140
ggactatgat gatgacctga cagactctga gatggatgtg gtcagatttg atgatgacaa  1200
cagccccagc ttcatccaga tcagatctgt ggccaagaag caccccaaga cctgggtgca  1260
ctatattgct gctgaggaag aggactggga ttatgctcct ctggtgctgg cccctgatga  1320
```

```
cagaagctac aagagccagt acctgaacaa tggccctcag agaattggca gaaagtataa  1380
gaaagtgaga ttcatggcct acacagatga gacattcaag accagagagg ccattcagca  1440
tgagtctggc attctgggcc ctctgctgta tggagaagtg ggagatacac tgctgatcat  1500
cttcaagaac caggccagca gaccctacaa catctaccct catggcatca cagatgtgag  1560
acccctgtat tctagaaggc tgcccaaggg agtgaagcac ctgaaggact tccctatcct  1620
gcctggagag atcttcaagt acaagtggac agtgacagtg gaagatggcc ccaccaagtc  1680
tgaccctaga tgtctgacaa gatactacag cagctttgtg aacatggaaa gagacctggc  1740
ctctggcctg attggacctc tgctgatctg ctacaaagaa tctgtggacc agagaggcaa  1800
ccagatcatg tctgacaaga gaaatgtgat cctgttttct gtgtttgatg agaacagatc  1860
ctggtatctg acagagaaca tccagagatt tctgcccaat cctgctggag tgcagctgga  1920
agatcctgag ttccaggcct ccaacatcat gcactccatc aatggctatg tgtttgacag  1980
cctgcagctg tctgtgtgcc tgcatgaagt ggcctactgg tacatcctga gcattggagc  2040
ccagacagac ttcctgtctg tgttcttctc tggctacacc ttcaagcaca agatggtgta  2100
tgaggatacc ctgacactgt tcccattctc tggagagaca gtgttcatga gcatggaaaa  2160
ccctggcctg tggatcctgg gctgtcacaa ctctgacttc agaaacagag gcatgacagc  2220
cctgctgaag gtgtccagct gtgacaagaa cacaggagac tactatgagg acagctatga  2280
ggacatctct gcctacctgc tgagcaagaa caatgccatt gagcccagaa acttcagcca  2340
gaatcctcca gtgctgaaga gacaccagag agaaatcacc agaaccacac tgcagtctga  2400
ccaagaggaa attgactatg atgacaccat ctctgtggag atgaagaaag aagattttga  2460
catctatgat gaggatgaga atcagagccc cagatccttt cagaaaaaga ccagacacta  2520
cttcattgct gctgtggaga gactgtggga ctatggcatg tctagcagcc ctcatgtgct  2580
gagaaataga gcccagtctg gctctgtgcc ccagttcaag aaagtggtgt tccaagagtt  2640
cacagatggc agcttcaccc agccactgta tagaggagag ctgaatgagc atctgggcct  2700
gctgggccct tatatcagag ctgaagtgga agataacatc atggtcacct tcagaaatca  2760
ggcctctaga ccctacagct tctacagctc cctgatcagc tatgaagagg accagagaca  2820
gggagctgag cccagaaaga actttgtgaa gcccaatgag actaagacct acttttggaa  2880
ggtgcagcac cacatggccc ctacaaagga tgagtttgac tgcaaggcct gggcctactt  2940
ttctgatgtg gatctggaaa aggatgtgca ctctggactc attggaccac tgcttgtgtg  3000
ccacaccaac acactgaacc ctgctcatgg cagacaagtg acagtgcaag agtttgccct  3060
gttcttcacc atctttgatg aaacaaagag ctggtacttc acagagaata tggagagaaa  3120
ctgcagggcc ccttgcaaca tccagatgga agatcccacc ttcaaagaga actacagatt  3180
ccatgccatc aatggctaca tcatggacac actgcctggc ctggttatgg ctcaggatca  3240
gagaatcaga tggtatctgc tgtccatggg ctccaatgag aatatccaca gcatccactt  3300
ctctggccat gtgttcacag tgagaaaaaa agaagagtac aaaatggccc tgtacaatct  3360
gtaccctggg gtgtttgaaa cagtggaaat gctgccttcc aaggctggca tttggagagt  3420
ggaatgtctg attggagagc acctccatgc tggaatgagc accctgtttc tggtgtacag  3480
caacaagtgt cagacccctc tgggcatggc ctctggacac atcagagact tccagatcac  3540
agcctctggc cagtatggac agtgggctcc taaactggct agactgcact actctggcag  3600
catcaatgcc tggtccacca aagagccctt cagctggatc aaggtggacc tgctggctcc  3660
catgatcatc catggaatca agacccaggg agccagacag aagttcagca gcctgtacat  3720
cagccagttc atcatcatgt acagcctgga tggcaagaag tggcagacct acagaggcaa  3780
cagcacaggc acactcatgg tgttctttgg caatgtggac agctctggca ttaagcacaa  3840
catcttcaac cctccaatca ttgccagata catcagactg caccccacac actacagcat  3900
cagatctacc ctgagaatgg aactgatggg ctgtgacctg aacagctgca gcatgcccct  3960
gggaatggaa agcaaggcca tctctgatgc ccagatcaca gccagcagct acttcaccaa  4020
catgtttgcc acttggagcc cctccaaggc tagactgcat ctgcagggca gaagcaatgc  4080
ttggaggccc caagtgaaca accccaaaga gtggctgcag gtggactttc aaaagaccat  4140
gaaagtgaca ggagtgacca cacagggagt caagtctctg ctgacctcta tgtatgtgaa  4200
agagttcctg atctccagca gccaggatgg ccaccagtgg accctgtttt tccagaatgg  4260
caaagtgaaa gtgttccagg gcaatcagga cagcttcaca cctgtggtca actccctgga  4320
tcctccactg ctgaccagat acctgagaat tcaccctcag tcttgggtgc accagattgc  4380
tctgagaatg gaagtgctgg gctgtgaagc tcaggacctc tactgatcgc gaataaaaga  4440
tctttatttt cattagatct gtgtgttggt tttttgtgtg tatttagcta acagtatgat  4500
taagtggata aatggttcct ctctgctaca ctcaaatgcc agttcccgat cgttacagga  4560
aattcctcac gtg                                                       4573

SEQ ID NO: 83          moltype = DNA  length = 4585
FEATURE                Location/Qualifiers
source                 1..4585
                       mol_type = other DNA
                       organism = synthetic construct
SEQUENCE: 83
acgcgtacgt tttcctgta acgatcggga actggcattt gagtgtagca gagaggaacc  60
atttctcagt gttaagctta ctaaagaatt attcttttac atttcagtgg ccaccagaag  120
atattacctg ggagctgtgg aactgagctg ggactacatg cagtctgacc tgggagagct  180
gcctgtggat gctagatttc ctccaagagt gcccaagagc ttccccttca acacctctgt  240
ggtgtacaag aaaaccctgt ttgtggaatt cacagaccac ctgttcaata ttgccaagcc  300
tagacctcct tggatgggac tgctgggacc tacaattcag gctgaggtgt atgacacagt  360
ggtcatcacc ctgaagaaca tggccagcca tcctgtgtct ctgcatgctg tgggagtgtc  420
ttactggaag gcttctgagg gagctgagta tgatgaccag acaagccaga gagagaaaga  480
ggatgacaag gttttccctg gaggcagcca cacctatgtc tggcaggtcc tgaaagaaaa  540
tggccctatg gcctctgatc ctctgtgcct gacatacagc tacctgagcc atgtggacct  600
ggtcaaggac ctgaattctg gcctgattgg agccctgctg gtgtgtagag aaggcagcct  660
ggccaaagag aaaacccaga cactgcacaa gttcatcctg ctgtttgctg tgtttgatga  720
gggcaagagc tggcactctg agacaaagaa cagcctgatg caggacaggg atgctgcctc  780
tgctagagct tggcctaaga tgcacacagt gaatggctat gtgaacagaa gcctgcctgg  840
actgattggc tgccacagaa agtctgtgta ctggcatgtg attggcatgg gcacaacacc  900
tgaggtgcac agcatctttc tggaaggaca caccttcctg gtgagaaacc atagacaggc  960
cagcctggaa atcagcccta tcaccttcct gacagctcag accctgctga tggatctggg  1020
```

-continued

```
ccagtttctg ctgttctgcc acatcagcag ccaccagcat gatggcatgg aagcctatgt  1080
gaaggtggac agctgccctg aagaacccca gctgagaatg aagaacaatg aggaggctga  1140
ggactatgat gatgacctga cagactctga gatggatgtg gtcagatttg atgatgacaa  1200
cagccccagc ttcatccaga tcagatctgt ggccaagaag caccccaaga cctgggtgca  1260
ctatattgct gctgaggaag aggactggga ttatgctcct ctggtgctgg cccctgatga  1320
cagaagctac aagagccagt acctgaacaa tggccctcag agaattggca gaaagtataa  1380
gaaagtgaga ttcatggcct acacagatga gacattcaag accagagagg ccattcagca  1440
tgagtctggc attctgggcc ctctgctgta tggagaagtg ggagatacac tgctgatcat  1500
cttcaagaac caggccagca gaccctacaa catctaccct catggcatca cagatgtgag  1560
acccctgtat tctagaaggc tgcccaaggg agtgaagcac ctgaaggact tccctatcct  1620
gcctggagag atcttcaagt acaagtggac agtgacagtg gaagatggcc ccaccaagtc  1680
tgaccctaga tgtctgacaa gatactacag cagctttgtg aacatggaaa gagacctggc  1740
ctctggcctg attggacctc tgctgatctg ctacaaagaa tctgtggacc agagaggcaa  1800
ccagatcatg tctgacaaga gaaatgtgat cctgtttict gtgtttgatg agaacagatc  1860
ctggtatctg acagagaaca tccagagatt tctgcccaat cctgctggag tgcagctgga  1920
agatcctgag ttccaggcct ccaacatcat gcactccatc aatggctatg tgtttgacag  1980
cctgcagctg tctgtgtgcc tgcatgaagt ggcctactgg tacatcctga gcattggagc  2040
ccagacagac ttcctgtctg tgttcttctc tggctacacc ttcaagcaca agatggtgta  2100
tgaggatacc ctgacactgt tcccattctc tggagagaca gtgttcatga gcatggaaaa  2160
ccctggcctg tggatcctgg gctgtcacaa ctctgacttc agaaacagag gcatgacagc  2220
cctgctgaag gtgtccagct gtgacaagaa cacaggagac tactatgagg acagctatga  2280
ggacatctct gcctacctgc tgagcaagaa caatgccatt gagcccagaa gcttcagcca  2340
gaattgcagc cagaaccctc cagtgctgaa gagacaccag agagaaatca ccagaaccac  2400
actgcagtct gaccaagagg aaattgacta tgatgacacc atctctgtgg agatgaagaa  2460
agaagatttt gacatctatg atgaggatga gaatcagagc cccagatcct ttcagaaaaa  2520
gaccagacac tacttcattg ctgctgtgga gagactgtgg gactatggca tgtctagcag  2580
ccctcatgtg ctgagaaata gagcccagtc tggctctgtg ccccagttca agaaagtggt  2640
gttccaagag ttcacagatg gcagcttcac ccagccactg tatagaggag agctgaatga  2700
gcatctgggc ctgctgggcc cttatatcag agctgaagtg gaagataaca tcatggtcac  2760
cttcagaaat caggcctcta gaccctacag cttctacagc tccctgatca gctatgaaga  2820
ggaccagaga cagggagctg agcccagaaa gaactttgtg aagcccaatg agactaagac  2880
ctacttttgg aaggtgcagc accacatggc cctacaaag gatgagtttg actgcaaggc  2940
ctgggcctac ttttctgatg tggatctgga aaaggatgtg cactctggac tcattggacc  3000
actgcttgtg tgccacacca acacactgaa ccctgctcat ggcagacaag tgacagtgca  3060
agagtttgcc ctgttcttca ccatctttga tgaaacaaag agctggtact tcacagagaa  3120
tatggagaga aactgcaggg ccccttgcaa catccagatg gaagatccca ccttcaaaga  3180
gaactacaga ttccatgcca tcaatggcta catcatggac acactgcctg gcctggttat  3240
ggctcaggat cagagaatca gatggtatct gctgtccatg ggctccaatg agaatatcca  3300
cagcatccac ttctctggcc atgtgttcac agtgagaaaa aaagaagagt acaaaatggc  3360
cctgtacaat ctgtaccctg ggtgtttga aacagtggaa atgctgcctt ccaaggctgg  3420
catttggaga gtggaatgtc tgattggaga gcacctccat gctggaatga gcaccctgtt  3480
tctggtgtac agcaacaagt gtcagacccc tctgggcatg gcctctggac acatcagaga  3540
cttccagatc acagcctctg gccagtatgg acagtgggct cctaaactgg ctagactgca  3600
ctactctggc agcatcaatg cctggtccac caaagagccc ttcagctgga tcaaggtgga  3660
cctgctggct cccatgatca tccatggaat caagacccag ggagccagac agaagttcag  3720
cagcctgtac atcagccagt tcatcatcat gtacagcctg gatggcaaga agtggcagac  3780
ctacagaggc aacagcacag gcacactcat ggtgttcttt ggcaatgtgg acagctctgg  3840
cattaagcac aacatcttca accctccaat cattgccaga tacatcagac tgcaccccac  3900
acactacagc atcagatcta ccctgagaat ggaactgatg ggctgtgacc tgaacagctg  3960
cagcatgccc ctgggaatgg aaagcaaggc catctctgat gcccagatca cagccagcag  4020
ctacttcacc aacatgtttg ccacttggag cccctccaag gctagactgc atctgcaggg  4080
cagaagcaat gcttggaggc cccaagtgaa caaccccaaa gagtggctgc aggtggactt  4140
tcaaaagacc atgaaagtga caggagtgac cacacaggga gtcaagtctc tgctgacctc  4200
tatgtatgtg aaagagttcc tgatctccag cagccaggat ggccaccagt ggaccctgtt  4260
tttccagaat ggcaaagtga aagtgttcca gggcaatcag gacagcttca cacctgtggt  4320
caactccctg gatcctccac tgctgaccag atacctgaga attcaccctc agtcttgggt  4380
gcaccagatt gctctgagaa tggaagtgct gggctgtgaa gctcaggacc tctactgatc  4440
gcgaataaaa gatctttatt ttcattagat ctgtgtgttg gtttttgtg tgtatttagc  4500
taacagtatg attaagtgga taaatggttc ctctctgcta cactcaaatg ccagttcccg  4560
atcgttacag gaaattcctc acgtg                                       4585
```

```
SEQ ID NO: 84          moltype = DNA  length = 4585
FEATURE                Location/Qualifiers
source                 1..4585
                       mol_type = other DNA
                       organism = synthetic construct
SEQUENCE: 84
acgcgtacgt ttttcctgta acgatcggga actggcattt gagtgtagca gagaggaacc  60
atttctcagt gttaagctta ctaaagaatt attcttttac atttcagtgg ccaccagaag  120
atattacctg ggagctgtgg aactgagctg ggactacatg cagtctgacc tgggagagct  180
gcctgtggat gctagatttc ctccaagagt gcccaagagc ttccccttca acacctctgt  240
ggtgtacaag aaaaccctgt ttgtggaatt cacagaccac ctgttcaata ttgccaagcc  300
tagacctcct tggatgggac tgctgggacc tacaattcag gctgaggtgt atgacacagt  360
ggtcatcacc ctgaagaaca tggccagcca tcctgtgtct ctgcatgctg tgggagtgtc  420
ttactggaag gcttctgagg gagctgagta tgatgaccag acaagccaga gagagaaaga  480
ggatgacaag gttttccctg gaggcagcca cacctatgtc tggcaggtcc tgaaagaaaa  540
tggccctatg gcctctgatc ctctgtgcct gacatacagc tacctgagcc atgtggacct  600
ggtcaaggac ctgaattctg gcctgattgg agccctgctg gtgtgtagag aaggcagcct  660
ggccaaagag aaaacccaga cactgcacaa gttcatcctg ctgtttgctg tgtttgatga  720
```

```
gggcaagagc tggcactctg agacaaagaa cagcctgatg caggacaggg atgctgcctc  780
tgctagagct tggcctaaga tgcacacagt gaatggctat gtgaacagaa gcctgcctgg  840
actgattggc tgccacagaa agtctgtgta ctggcatgtg attggcatgg gcacaacacc  900
tgaggtgcac agcatctttc tggaaggaca caccttcctg gtgagaaacc atagacaggc  960
cagcctggaa atcagcccta tcaccttcct gacagctcag accctgctga tggatctggg  1020
ccagtttctg ctgttctgcc acatcagcag ccaccagcat gatggcatgg aagcctatgt  1080
gaaggtggac agctgccctg aagaacccca gctgagaatg aagaacaatg aggaggctga  1140
ggactatgat gatgacctga cagactctga gatggatgtg gtcagatttg atgatgacaa  1200
cagccccagc ttcatccaga tcagatctgt ggccaagaag caccccaaga cctgggtgca  1260
ctatattgct gctgaggaag aggactggga ttatgctcct ctggtgctgg cccctgatga  1320
cagaagctac aagagccagt acctgaacaa tggccctcag agaattggca gaaagtataa  1380
gaaagtgaga ttcatggcct acacagatga gacattcaag accagagagg ccattcagca  1440
tgagtctggc attctgggcc ctctgctgta tggagaagtg ggagatacac tgctgatcat  1500
cttcaagaac caggccagca gaccctacaa catctaccct catggcatca cagatgtgag  1560
acccctgtat tctagaaggc tgcccaaggg agtgaagcac ctgaaggact tccctatcct  1620
gcctggagag atcttcaagt acaagtggac agtgacagtg gaagatggcc ccaccaagtc  1680
tgaccctaga tgtctgacaa gatactacag cagctttgtg aacatggaaa gagacctggc  1740
ctctggcctg attggacctc tgctgatctg ctacaaagaa tctgtggacc agagaggcaa  1800
ccagatcatg tctgacaaga gaaatgtgat cctgtttttct gtgtttgatg agaacagatc  1860
ctggtatctg acagagaaca tccagagatt tctgcccaat cctgctggag tgcagctgga  1920
agatcctgag ttccaggcct ccaacatcat gcactccatc aatggctatg tgtttgacag  1980
cctgcagctg tctgtgtgcc tgcatgaagt ggcctactgg tacatcctga gcattggagc  2040
ccagacagac ttcctgtctg tgttcttctc tggctacacc ttcaagcaca agatggtgta  2100
tgaggatacc ctgacactgt tcccattctc tggagagaca gtgttcatga gcatggaaaa  2160
ccctggcctg tggatcctgg gctgtcacaa ctctgacttc agaaacagag gcatgacagc  2220
cctgctgaag gtgtccagct gtgacaagaa cacaggagac tactatgagg acagctatga  2280
ggacatctct gcctacctgc tgagcaagaa caatgccatt gagcccagaa acttcagcca  2340
gaattgcagc cagaaccctc cagtgctgaa gagacaccag agagaaatca ccagaaccac  2400
actgcagtct gaccaagagg aaattgacta tgatgacacc atctctgtgg agatgaagaa  2460
agaagatttt gacatctatg atgaggatga gaatcagagc cccagatcct ttcagaaaaa  2520
gaccagacac tacttcattg ctgctgtgga gagactgtgg gactatggca tgtctagcag  2580
ccctcatgtg ctgagaaata gagcccagtc tggctctgtg ccccagttca agaaagtggt  2640
gttccaagag ttcacagatg gcagcttcac ccagccactg tatagaggag agctgaatga  2700
gcatctgggc ctgctgggcc cttatatcag agctgaagtg gaagataaca tcatggtcac  2760
cttcagaaat caggcctcta gaccctacag cttctacagc tccctgatca gctatgaaga  2820
ggaccagaga cagggagctg agcccagaaa gaactttgtg aagcccaatg agactaagac  2880
ctacttttgg aaggtgcagc accacatggc cctacaaag gatgagtttg actgcaaggc  2940
ctgggcctac ttttctgatg tggatctgga aaaggatgtg cactctggac tcattggacc  3000
actgcttgtg tgccacacca acacactgaa ccctgctcat ggcagacaag tgacagtgca  3060
agagtttgcc ctgttcttca ccatctttga tgaaacaaag agctggtact tcacagagaa  3120
tatggagaga aactgcaggg ccccttgcaa catccagatg gaagatccca ccttcaaaga  3180
gaactacaga ttccatgcca tcaatggcta catcatggac acactgcctg gcctggttat  3240
ggctcaggat cagagaatca gatggtatct gctgtccatg ggctccaatg agaatatcca  3300
cagcatccac ttctctggcc atgtgttcac agtgagaaaa aaagaagagt acaaaatggc  3360
cctgtacaat ctgtaccctg gggtgtttga aacagtggaa atgctgcctt ccaaggctgg  3420
catttggaga gtggaatgtc tgattggaga gcacctccat gctggaatga gcaccctgtt  3480
tctggtgtac agcaacaagt gtcagacccc tctgggcatg gcctctggac acatcagaga  3540
cttccagatc acagcctctg gccagtatgg acagtgggct cctaaactgg ctagactgca  3600
ctactctggc agcatcaatg cctggtccac caaagagccc ttcagctgga tcaaggtgga  3660
cctgctggct cccatgatca tccatggaat caagacccag ggagccagac agaagttcag  3720
cagcctgtac atcagccagt tcatcatcat gtacagcctg gatggcaaga agtggcagac  3780
ctacagaggc aacagcacag gcacactcat ggtgttcttt ggcaatgtgg acagctctgg  3840
cattaagcac aacatcttca accctccaat cattgccaga tacatcagac tgcaccccac  3900
acactacagc atcagatcta ccctgagaat ggaactgatg ggctgtgacc tgaacagctg  3960
cagcatgccc ctgggaatgg aaagcaaggc catctctgat gcccagatca cagccagcag  4020
ctacttcacc aacatgtttg ccacttggag cccctccaag gctagactgc atctgcaggg  4080
cagaagcaat gcttggaggc cccaagtgaa caaccccaaa gagtggctgc aggtggactt  4140
tcaaaagacc atgaaagtga caggagtgac cacacaggga gtcaagtctc tgctgacctc  4200
tatgtatgtg aaagagttcc tgatctccag cagccaggat ggccaccagt ggaccctgtt  4260
tttccagaat ggcaaagtga aagtgttcca gggcaatcag gacagcttca cacctgtggt  4320
caactccctg gatcctccac tgctgaccag atacctgaga attcaccctc agtcttgggt  4380
gcaccagatt gctctgagaa tggaagtgct gggctgtgaa gctcaggacc tctactgatc  4440
gcgaataaaa gatctttatt ttcattagat ctgtgtgttg gttttttgtg tgtatttagc  4500
taacagtatg attaagtgga taaatggttc ctctctgcta cactcaaatg ccagttcccg  4560
atcgttacag gaaattcctc acgtg                                       4585
```

```
SEQ ID NO: 85           moltype = DNA  length = 4588
FEATURE                 Location/Qualifiers
source                  1..4588
                        mol_type = other DNA
                        organism = synthetic construct
SEQUENCE: 85
acgcgtacgt ttttcctgta acgatcggga actggcattt gagtgtagca gagaggaacc  60
atttctcagt gttaagctta ctaaagaatt attcttttac atttcagtgg ccaccagaag  120
atattacctg ggagctgtgg aactgagctg ggactacatg cagtctgacc tgggagagct  180
gcctgtggat gctagatttc ctccaagagt gcccaagagc ttccccttca acacctctgt  240
ggtgtacaag aaaaccctgt ttgtggaatt cacagaccac ctgttcaata ttgccaagcc  300
tagacctcct tggatgggac tgctgggacc tacaattcag gctgaggtgt atgacacagt  360
ggtcatcacc ctgaagaaca tggccagcca tcctgtgtct ctgcatgctg tgggagtgtc  420
```

```
ttactggaag gcttctgagg gagctgagta tgatgaccag acaagccaga gagagaaaga  480
ggatgacaag gttttccctg gaggcagcca cacctatgtc tggcaggtcc tgaaagaaaa  540
tggccctatg gcctctgatc ctctgtgcct gacatacagc tacctgagcc atgtggacct  600
ggtcaaggac ctgaattctg gcctgattgg agccctgctg gtgtgtagag aaggcagcct  660
ggccaaagag aaaacccaga cactgcacaa gttcatcctg ctgtttgctg tgtttgatga  720
gggcaagagc tggcactctg agacaaagaa cagcctgatg caggacaggg atgctgcctc  780
tgctagagct tggcctaaga tgcacacagt gaatggctat gtgaacagaa gcctgcctgg  840
actgattggc tgccacagaa agtctgtgta ctggcatgtg attggcatgg gcacaacacc  900
tgaggtgcac agcatctttc tggaaggaca caccttcctg gtgagaaacc atagacaggc  960
cagcctggaa atcagcccta tcaccttcct gacagctcag accctgctga tggatctggg  1020
ccagtttctg ctgttctgcc acatcagcag ccaccagcat gatggcatgg aagcctatgt  1080
gaaggtggac agctgccctg aagaacccca gctgagaatg aagaacaatg aggaggctga  1140
ggactatgat gatgacctga cagactctga gatggatgtg gtcagatttg atgatgacaa  1200
cagccccagc ttcatccaga tcagatctgt ggccaagaag caccccaaga cctgggtgca  1260
ctatattgct gctgaggaag aggactggga ttatgctcct ctggtgctgg cccctgatga  1320
cagaagctac aagagccagt acctgaacaa tggccctcag agaattggca gaaagtataa  1380
gaaagtgaga ttcatggcct acacagatga gacattcaag accagagagg ccattcagca  1440
tgagtctggc attctgggcc ctctgctgta tggagaagtg ggagatacac tgctgatcat  1500
cttcaagaac caggccagca gaccctacaa catctaccct catggcatca cagatgtgag  1560
acccctgtat tctagaaggc tgcccaaggg agtgaagcac ctgaaggact tccctatcct  1620
gcctggagag atcttcaagt acaagtggac agtgacagtg gaagatggcc ccaccaagtc  1680
tgaccctaga tgtctgacaa gatactacag cagctttgtg aacatggaaa gagacctggc  1740
ctctggcctg attggacctc tgctgatctg ctacaaagaa tctgtggacc agagaggcaa  1800
ccagatcatg tctgacaaga gaaatgtgat cctgtttttct gtgtttgatg agaacagatc  1860
ctggtatctg acagagaaca tccagagatt tctgcccaat cctgctggag tgcagctgga  1920
agatcctgag ttccaggcct ccaacatcat gcactccatc aatggctatg tgtttgacag  1980
cctgcagctg tctgtgtgcc tgcatgaagt ggcctactgg tacatcctga gcattggagc  2040
ccagacagac ttcctgtctg tgttcttctc tggctacacc ttcaagcaca agatggtgta  2100
tgaggatacc ctgacactgt tcccattctc tggagagaca gtgttcatga gcatggaaaa  2160
ccctggcctg tggatcctgg gctgtcacaa ctctgacttc agaaacagag gcatgacagc  2220
cctgctgaag gtgtccagct gtgacaagaa cacaggagac tactatgagg acagctatga  2280
ggacatctct gcctacctgc tgagcaagaa caatgccatt gagaacagaa gcaacttcag  2340
ccagaattgc agccagaacc ctccagtgct gaagagacac cagagagaaa tcaccagaac  2400
cacactgcag tctgaccaag aggaaattga ctatgatgac accatctctg tggagatgaa  2460
gaaagaagat tttgacatct atgatgagga tgagaatcag agccccagat cctttcagaa  2520
aaagaccaga cactacttca ttgctgctgt ggagagactg tgggactatg gcatgtctag  2580
cagccctcat gtgctgagaa atagagccca gtctggctct gtgccccagt tcaagaaagt  2640
ggtgttccaa gagttcacag atggcagctt cacccagcca ctgtatagag gagagctgaa  2700
tgagcatctg ggcctgctgg gcccttatat cagagctgaa gtggaagata acatcatggt  2760
caccttcaga aatcaggcct ctagacccta cagcttctac agctccctga tcagctatga  2820
agaggaccag agacagggag ctgagcccag aaagaacttt gtgaagccca atgagactaa  2880
gacctacttt tggaaggtgc agcaccacat ggcccctaca aaggatgagt ttgactgcaa  2940
ggcctgggcc tacttttctg atgtggatct ggaaaaggat gtgcactctg gactcattgg  3000
accactgctt gtgtgccaca ccaacacact gaaccctgct catggcagac aagtgacagt  3060
gcaagagttt gccctgttct tcaccatctt tgatgaaaca aagagctggt acttcacaga  3120
gaatatggag agaaactgca gggccccttg caacatccag atggaagatc ccaccttcaa  3180
agagaactac agattccatg ccatcaatgg ctacatcatg gacacactgc ctggcctggt  3240
tatggctcag gatcagagaa tcagatggta tctgctgtcc atgggctcca atgagaatat  3300
ccacagcatc cacttctctg gccatgtgtt cacagtgaga aaaaaagaag agtacaaaat  3360
ggccctgtac aatctgtacc ctggggtgtt tgaaacagtg gaaatgctgc cttccaaggc  3420
tggcatttgg agagtggaat gtctgattgg agagcacctc catgctggaa tgagcaccct  3480
gtttctggtg tacagcaaca agtgtcagac ccctctgggc atggcctctg gacacatcag  3540
agacttccag atcacagcct ctggccagta tggacagtgg gctcctaaac tggctagact  3600
gcactactct ggcagcatca atgcctggtc caccaaagag cccttcagct ggatcaaggt  3660
ggacctgctg gctcccatga tcatccatgg aatcaagacc cagggagcca gacagaagtt  3720
cagcagcctg tacatcagcc agttcatcat catgtacagc ctggatggca agaagtggca  3780
gacctacaga ggcaacagca caggcacact catggtgttc tttggcaatg tggacagctc  3840
tggcattaag cacaacatct tcaaccctcc aatcattgcc agatacatca gactgcaccc  3900
cacacactac agcatcagat ctaccctgag aatggaactg atgggctgtg acctgaacag  3960
ctgcagcatg cccctgggaa tggaaagcaa ggccatctct gatgcccaga tcacagccag  4020
cagctacttc accaacatgt ttgccacttg gagcccctcc aaggctagac tgcatctgca  4080
gggcagaagc aatgcttgga ggccccaagt gaacaacccc aaagagtggc tgcaggtgga  4140
ctttcaaaag accatgaaag tgacaggagt gaccacacag ggagtcaagt ctctgctgac  4200
ctctatgtat gtgaaagagt tcctgatctc cagcagccag gatggccacc agtggaccct  4260
gtttttccag aatggcaaag tgaaagtgtt ccagggcaat caggacagct tcacacctgt  4320
ggtcaactcc ctggatcctc cactgctgac cagatacctg agaattcacc ctcagtcttg  4380
ggtgcaccag attgctctga gaatggaagt gctgggctgt gaagctcagg acctctactg  4440
atcgcgaata aaagatcttt attttcatta gatctgtgtg ttggtttttt gtgtgtattt  4500
agctaacagt atgattaagt ggataaatgg ttcctctctg ctacactcaa atgccagttc  4560
ccgatcgtta caggaaattc ctcacgtg                                    4588
```

```
SEQ ID NO: 86          moltype = AA  length = 1457
FEATURE                Location/Qualifiers
source                 1..1457
                       mol_type = protein
                       organism = synthetic construct
SEQUENCE: 86
MQIELSTYFF LCLLRFCFSA TRRYYLGAVE LSWDYMQSDL GELPVDTRFP PRVPRSFPFN  60
TSVMYKKTVF VEFTDHLFNI AKPRPPWMGL LGPTIQAEVY DTVVITLKNM ASHPVSLHAV  120
```

```
GVSYWKASEG AEYDDQTSQR EKEDDKVFPG GSHTYVWQVL KENGPMASDP LCLTYSYLSH  180
VDLVKDLNSG LIGALLVCRE GSLAKEKTQT LHKFVLLFAV FDEGKSWHSE TKNSLMQDRD  240
DASARAWPKM HTVNGYVNRS LPGLIGCHRK SVYWHVIGMG TTPEVHSIFL EGHTFLVRNH  300
RQASLEISPI TFLTAQTLLM DLGQFLLFCH ISSHQHDGME AYVKVDSCPE EPQLRMKNNE  360
EAEDYDDDLA DSEMDVVRFD DDNSPSFIQI RSVAKKHPKT WVHYIAAEEE VWDYAPSVLA  420
PDDRSYKSQY LNNGSQRIGR KYKKVRFMAY TDETFKTREA IQYESGILGP LLYGEVGDTL  480
LIIFKNQASR PYNIYPHGIT DVRPLYSRRL PKGVKHLKDF PILPGEIFKY KWTVTVEDGP  540
TKSDPRCLTR YYSSFINMER DLASGLIGPL LICYKESVDQ RGNQIMSDKR NVILFSVFDE  600
NQSWYLTENI QRFLPNPVGV QLEDPEFQAS NIMHSINGYV FDSLQLSVCL HEVAYWYILS  660
IGAQTDFLSV FFSGYTFKHK MVYEDTLTLF PFSGETVFMS MENPGLWILG CHNSDFRNRG  720
MTALLKVSSC DKNTGDYYED SYEDISTYLL SKNNAIEPRS FSQNPPVLKR HQREITLNTL  780
QSDQEEIDYD DTISVEMKKE DFDIYGEDEN QSPRSFQKKT RHYFIAAVER LWDYGMSSSP  840
HVLRNRAQSG SVPQFKKVVF QEFTDGSFTQ PLYRGELNEH LGLLGPYIRA EVEDNIMVTF  900
KNQASRPYSF YSSLISYEED QRQGAEPRKN FVKPNETKTY FWKVQHHMAP TKDEFDCKAW  960
AYFSDVDLEK DVHSGLIGPL LVCHTNTLNP AHGRQVTVQE FALFFTIFDE TKSWYFTENT  1020
ERNCRAPCNI QMEDPTFKEN YRFHAINGYI MDTLPGLVMA QDQRIRWYLL SMGSNENIHS  1080
IHFSGHVFTV RKKEEYKMAV YNLYPGVFET VEMLPSKAGI WRVECLIGEH LHAGMSTLFL  1140
VYSNKCQTPL GMASGRIRDF QITASGQYGQ WAPKLARLHY SGSINAWSTK EPFSWIKVDL  1200
LAPMIIHGIK TQGARQKFSS LYISQFIIMY SLDGKKWQTY RGNSTGTLMV FFGNVDSSGI  1260
KHNIFNPPII ARYIRLHPTH YSIRSTLRME LMGCDLNSCS MPLGMESKAI SDAQITASSY  1320
KTNMFATWSP SKARLNLQGR SNAWRPQVNN PKEWLQVDFQ KTMKVTGITT QGVKSLLTSM  1380
YVKEFLISSS QDGHHWTLFF QNGKVKVFQG NQDSFTPVVN SLDSPLLTRY LRIHPQSWVH  1440
QIALRIEVLG CEAQELY                                                1457

SEQ ID NO: 87          moltype = AA  length = 1442
FEATURE                Location/Qualifiers
source                 1..1442
                       mol_type = protein
                       organism = synthetic construct
SEQUENCE: 87
ATRRYYLGAV ELSWDYMQSD LGELPVDTRF PPRVPRSFPF NTSVMYKKTV FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFVLLFA VFDEGKSWHS ETKNSLMQDR DDASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL ADSEMDVVRF  360
DDDNSPSFIQ IRSVAKKHPK TWVHYIAAEE EVWDYAPSVL APDDRSYKSQ YLNNGSQRIG  420
RKYKKVRFMA YTDETFKTRE AIQYESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFINME  540
RDLASGLIGP LLICYKESVD QRGNQIMSDK RNVILFSVFD ENQSWYLTEN IQRFLPNPVG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISTYL LSKNNAIEPR NFSQNCSQNP PVLKRHQREI TLNTLQSDQE EIDYDDTISV  780
EMKKEDFDIY GEDENQSPRS FQKKTRHYFI AAVERLWDYG MSSSPHVLRN RAQSGSVPQF  840
KKVVFQEFTD GSFTQPLYRG ELNEHLGLLG PYIRAEVEDN IMVTFKNQAS RPYSFYSSLI  900
SYEEDQRQGA EPRKNFVKPN ETKTYFWKVQ HHMAPTKDEF DCKAWAYFSD VDLEKDVHSG  960
LIGPLLVCHT NTLNPAHGRQ VTVQEFALFF TIFDETKSWY FTENTERNCR APCNIQMEDP  1020
TFKENYRFHA INGYIMDTLP GLVMAQDQRI RWYLLSMGSN ENIHSIHFSG HVFTVRKKEE  1080
YKMAVYNLYP GVFETVEMLP SKAGIWRVEC LIGEHLHAGM STLFLVYSNK CQTPLGMASG  1140
RIRDFQITAS GQYGQWAPKL ARLHYSGSIN AWSTKEPFSW IKVDLLAPMI IHGIKTQGAR  1200
QKFSSLYISQ FIIMYSLDGK KWQTYRGNST GTLMVFFGNV DSSGIKHNIF NPPIIARYIR  1260
LHPTHYSIRS TLRMELMGCD LNSCSMPLGM ESKAISDAQI TASSYKTNMF ATWSPSKARL  1320
NLQGRSNAWR PQVNNPKEWL QVDFQKTMKV TGITTQGVKS LLTSMYVKEF LISSSQDGHH  1380
WTLFFQNGKV KVFQGNQDSF TPVVNSLDSP LLTRYLRIHP QSWVHQIALR IEVLGCEAQE  1440
LY                                                                1442

SEQ ID NO: 88          moltype = DNA  length = 4589
FEATURE                Location/Qualifiers
source                 1..4589
                       mol_type = other DNA
                       organism = synthetic construct
SEQUENCE: 88
catagtacgc gtacgttttt tcttttgccc actaaggaaa gtgcaaaata ttgggctctg  60
attcctacag aaaaatctca gcatcaagct tactaaagaa ttattctttt acatttcagt  120
ggccaccaga agatattacc tgggagctgt ggaactgagc tgggactaca tgcagtctga  180
cctgggagag ctgcctgtgg ataccagatt tcctccaaga gtgcccagaa gcttcccctt  240
caacacctct gtgatgtaca agaaaacagt gtttgtggaa ttcacagacc acctgttcaa  300
tattgccaag cctagacctc cttggatggg actgctggga cctacaattc aggctgaggt  360
gtatgacaca gtggtcatca ccctgaagaa catggccagc catcctgtgt ctctgcatgc  420
tgtgggagtg tcttactgga aggcttctga gggagctgag tatgatgacc agacaagcca  480
gagagagaaa gaggatgaca aggttttccc tggaggcagc cacacctatg tctggcaggt  540
cctgaaagaa aatggcccta tggcctctga tcctctgtgc ctgacataca gctacctgag  600
ccatgtggac ctggtcaagg acctgaattc tggcctgatt ggagccctgc tggtgtgtag  660
agaaggcagc ctggccaaag agaaaaccca gacactgcac aagtttgtgc tgctgtttgc  720
tgtgtttgat gagggcaaga gctggcactc tgagacaaag aacagcctga tgcaggacag  780
ggatgatgcc tctgctagag cttggcctaa gatgcacaca gtgaatggct atgtgaacag  840
aagcctgcct ggactgattg gctgccacag aaagtctgtg tactggcatg tgattggcat  900
gggcacaaca cctgaggtgc acagcatctt tctggaagga cacaccttcc tggtgagaaa  960
ccatagacag gccagcctgg aaatcagccc tatcaccttc ctgacagctc agaccctgct  1020
```

```
gatggatctg ggccagtttc tgctgttctg ccacatcagc agccaccagc atgatggcat  1080
ggaagcctat gtgaaggtgg acagctgccc tgaagaaccc cagctgagaa tgaagaacaa  1140
tgaggaggct gaggactatg atgatgacct ggctgactct gagatggatg tggtcagatt  1200
tgatgatgac aacagcccca gcttcatcca gatcagatct gtggccaaga agcaccccaa  1260
gacctgggtg cactatattg ctgctgagga agaggtgtgg gattatgctc ctagtgtgct  1320
ggcccctgat gacagaagct acaagagcca gtacctgaac aatggcagcc agagaattgg  1380
cagaaagtat aagaaagtga gattcatggc ctacacagat gagacattca agaccagaga  1440
ggccattcag tatgagtctg gcattctggg ccctctgctg tatggagaag tgggagatac  1500
actgctgatc atcttcaaga accaggccag cagaccctac aacatctacc ctcatggcat  1560
cacagatgtg agacccctgt attctagaag gctgcccaag ggagtgaagc acctgaagga  1620
cttccctatc ctgcctggag agatcttcaa gtacaagtgg acagtgacag tggaagatgg  1680
ccccaccaag tctgacccta gatgtctgac aagatactac agcagcttta tcaacatgga  1740
aagagacctg gcctctggcc tgattggacc tctgctgatc tgctacaaag aatctgtgga  1800
ccagagaggc aaccagatca tgtctgacaa gagaaatgtg atcctgtttt ctgtgtttga  1860
tgagaaccag tcctggtatc tgacagagaa catccagaga tttctgccca atcctgtggg  1920
agtgcagctg gaagatcctg agttccaggc ctccaacatc atgcactcca tcaatggcta  1980
tgtgtttgac agcctgcagc tgtctgtgtg cctgcatgaa gtggcctact ggtacatcct  2040
gagcattgga gcccagacag acttcctgtc tgtgttcttc tctggctaca ccttcaagca  2100
caagatggtg tatgaggata ccctgacact gttcccattc tctggagaga cagtgttcat  2160
gagcatggaa aaccctggcc tgtggatcct gggctgtcac aactctgact tcagaaacag  2220
aggcatgaca gccctgctga aggtgtccag ctgtgacaag aacacaggag actactatga  2280
ggacagctat gaggacatct ctacctacct gctgagcaag aacaatgcca ttgagcccag  2340
aaacttcagc cagaattgct cccagaaccc tccagtgctg aagagacacc agagagaaat  2400
caccctgaac acactgcagt ctgaccaaga ggaaattgac tatgatgaca ccatctctgt  2460
ggagatgaag aaagaagatt ttgacatcta tggagaggat gagaatcaga gccccagatc  2520
ctttcagaaa aagaccagac actacttcat tgctgctgtg gagagactgt gggactatgg  2580
catgtctagc agccctcatg tgctgagaaa tagagcccag tctggctctg tgccccagtt  2640
caagaaagtg gtgttccaag agttcacaga tggcagcttc acccagccac tgtatagagg  2700
agagctgaat gagcatctgg gcctgctggg cccttatatc agagctgaag tggaagataa  2760
catcatggtc accttcaaga atcaggcctc tagaccctac agcttctaca gctccctgat  2820
cagctatgaa gaggaccaga gacagggagc tgagcccaga aagaactttg tgaagcccaa  2880
tgagactaag acctactttt ggaaggtgca gcaccacatg gcccctacaa aggatgagtt  2940
tgactgcaag gcctgggcct actttctga tgtggatctg gaaaaggatg tgcactctgg  3000
actcattgga ccactgcttg tgtgccacac caacacactg aaccctgctc atggcagaca  3060
agtgacagtg caagagtttg ccctgttctt caccatcttt gatgaaacaa agagctggta  3120
cttcacagag aatacagaga gaaactgcag ggccccttgc aacatccaga tggaagatcc  3180
caccttcaaa gagaactaca gattccatgc catcaatggc tacatcatgg acacactgcc  3240
tggcctggtt atggctcagg atcagagaat cagatggtat ctgctgtcca tgggctccaa  3300
tgagaatatc cacagcatcc acttctctgg ccatgtgttc acagtgagaa aaaaagaaga  3360
gtacaaaatg gctgtgtaca atctgtaccc tggggtgttt gaaacagtgg aaatgctgcc  3420
ttccaaggct ggcatttgga gagtggaatg tctgattgga gagcacctcc atgctggaat  3480
gagcaccctg tttctggtgt acagcaacaa gtgtcagacc cctctgggca tggcctctgg  3540
aagaatcaga gacttccaga tcacagcctc tggccagtat ggacagtggg ctcctaaact  3600
ggctagactg cactactctg gcagcatcaa tgcctggtcc accaaagagc ccttcagctg  3660
gatcaaggtg gacctgctgg ctcccatgat catccatgga atcaagaccc agggagccag  3720
acagaagttc agcagcctgt acatcagcca gttcatcatc atgtacagcc tggatggcaa  3780
gaagtggcag acctacagag gcaacagcac aggcacactc atggtgttct ttggcaatgt  3840
ggacagctct ggcattaagc acaacatctt caaccctcca atcattgcca gatacatcag  3900
actgcacccc acacactaca gcatcagatc taccctgaga atggaactga tgggctgtga  3960
cctgaacagc tgcagcatgc ccctgggaat ggaaagcaag gccatctctg atgcccagat  4020
cacagccagc agctacaaga ccaacatgtt tgccacttgg agcccctcca aggctagact  4080
gaacctgcag ggcagaagca atgcttggag gccccaagtg aacaacccca aagagtggct  4140
gcaggtggac tttcaaaaga ccatgaaagt gacaggaatc accacacagg gagtcaagtc  4200
tctgctgacc tctatgtatg tgaaagagtt cctgatctcc agcagccagg atggccacca  4260
ctggaccctg tttttccaga atggcaaagt gaaagtgttc cagggcaatc aggacagctt  4320
cacacctgtg gtcaactccc tggatagccc actgctgacc agatacctga gaattcaccc  4380
tcagtcttgg gtgcaccaga ttgctctgag aattgaagtg ctgggctgtg aagctcagga  4440
gctctactga tcgcgaataa aagatcttta ttttcattag atctgtgtgt tggttttttg  4500
tgtgtattta gctaatattg ggctctgatt cctacagaaa aatttgcact ttccttagtg  4560
ggcaaaagaa aattcctcac gtgcatagt                                    4589
```

```
SEQ ID NO: 89           moltype = AA  length = 15
FEATURE                 Location/Qualifiers
source                  1..15
                        mol_type = protein
                        organism = synthetic construct
SEQUENCE: 89
NFSQNCSQNP PVLKR                                                   15
```

```
SEQ ID NO: 90           moltype = AA  length = 1439
FEATURE                 Location/Qualifiers
source                  1..1439
                        mol_type = protein
                        organism = synthetic construct
SEQUENCE: 90
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
```

```
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR NFSQNCSQNP PVLKREITRT TLQSDQEEID YDDTISVEMK  780
KEDFDIYDED ENQSPRSFQK KTRHYFIAAV ERLWDYGMSS SPHVLRNRAQ SGSVPQFKKV  840
VFQEFTDGSF TQPLYRGELN EHLGLLGPYI RAEVEDNIMV TFRNQASRPY SFYSSLISYE  900
EDQRQGAEPR KNFVKPNETK TYFWKVQHHM APTKDEFDCK AWAYFSDVDL EKDVHSGLIG  960
PLLVCHTNTL NPAHGRQVTV QEFALFFTIF DETKSWYFTE NMERNCRAPC NIQMEDPTFK  1020
ENYRFHAING YIMDTLPGLV MAQDQRIRWY LLSMGSNENI HSIHFSGHVF TVRKKEEYKM  1080
ALYNLYPGVF ETVEMLPSKA GIWRVECLIG EHLHAGMSTL FLVYSNKCQT PLGMASGHIR  1140
DFQITASGQY GQWAPKLARL HYSGSINAWS TKEPFSWIKV DLLAPMIIHG IKTQGARQKF  1200
SSLYISQFII MYSLDGKKWQ TYRGNSTGTL MVFFGNVDSS GIKHNIFNPP IIARYIRLHP  1260
THYSIRSTLR MELMGCDLNS CSMPLGMESK AISDAQITAS SYFTNMFATW SPSKARLHLQ  1320
GRSNAWRPQV NNPKEWLQVD FQKTMKVTGV TTQGVKSLLT SMYVKEFLIS SSQDGHQWTL  1380
FFQNGKVKVF QGNQDSFTPV VNSLDPPLLT RYLRIHPQSW VHQIALRMEV LGCEAQDLY   1439

SEQ ID NO: 91          moltype = DNA  length = 4604
FEATURE                Location/Qualifiers
source                 1..4604
                       mol_type = other DNA
                       organism = synthetic construct
SEQUENCE: 91
acgcgtacgt taaagcttac gtttttcctg taacgatcgg gaactggcac ttaggtcagt  60
gaagagaaga acaaaaatat ttagctactc aaagcttact aaagaattat tcttttacat  120
ttcagtggcc accagaagat attacctggg agctgtggaa ctgagctggg actacatgca  180
gtctgacctg ggagagctgc ctgtggatgc tagatttcct ccaagagtgc ccaagagctt  240
ccccttcaac acctctgtgg tgtacaagaa aaccctgttt gtggaattca cagaccacct  300
gttcaatatt gccaagccta gacctccttg gatgggactg ctgggaccta caattcaggc  360
tgaggtgtat gacacagtgg tcatcaccct gaagaacatg gccagccatc ctgtgtctct  420
gcatgctgtg ggagtgtctt actggaaggc ttctgaggga gctgagtatg atgaccagac  480
aagccagaga gagaaagagg atgacaaggt tttccctgga ggcagccaca cctatgtctg  540
gcaggtcctg aaagaaaatg gccctatggc ctctgatcct ctgtgcctga catacagcta  600
cctgagccat gtggacctgg tcaaggacct gaattctggc ctgattggag ccctgctggt  660
gtgtagagaa ggcagcctgg ccaaagagaa aacccagaca ctgcacaagt tcatcctgct  720
gtttgctgtg tttgatgagg gcaagagctg gcactctgag acaaagaaca gcctgatgca  780
ggacagggat gctgcctctg ctagagcttg gcctaagatg cacacagtga atggctatgt  840
gaacagaagc ctgcctggac tgattggctg ccacagaaag tctgtgtact ggcatgtgat  900
tggcatgggc acaacacctg aggtgcacag catctttctg gaaggacaca ccttcctggt  960
gagaaaccat agacaggcca gcctggaaat cagccctatc accttcctga cagctcagac  1020
cctgctgatg gatctgggcc agtttctgct gttctgccac atcagcagcc accagcatga  1080
tggcatggaa gcctatgtga aggtggacag ctgccctgaa gaaccccagc tgagaatgaa  1140
gaacaatgag gaggctgagg actatgatga tgacctgaca gactctgaga tggatgtggt  1200
cagatttgat gatgacaaca gccccagctt catccagatc agatctgtgg ccaagaagca  1260
ccccaagacc tgggtgcact atattgctgc tgaggaagag gactgggatt atgctcctct  1320
ggtgctggcc cctgatgaca gaagctacaa gagccagtac ctgaacaatg gccctcagag  1380
aattggcaga aagtataaga aagtgagatt catggcctac acagatgaga cattcaagac  1440
cagagaggcc attcagcatg agtctggcat tctgggccct ctgctgtatg gagaagtggg  1500
agatacactg ctgatcatct tcaagaacca ggccagcaga ccctacaaca tctaccctca  1560
tggcatcaca gatgtgagac ccctgtattc tagaaggctg cccaagggag tgaagcacct  1620
gaaggacttc cctatcctgc ctggagagat cttcaagtac aagtggacag tgacagtgga  1680
agatggcccc accaagtctg accctagatg tctgacaaga tactacagca gctttgtgaa  1740
catggaaaga gacctggcct ctggcctgat tggacctctg ctgatctgct acaaagaatc  1800
tgtggaccag agaggcaacc agatcatgtc tgacaagaga aatgtgatcc tgttttctgt  1860
gtttgatgag aacagatcct ggtatctgac agagaacatc cagagatttc tgcccaatcc  1920
tgctggagtg cagctggaag atcctgagtt ccaggcctcc aacatcatgc actccatcaa  1980
tggctatgtg tttgacagcc tgcagctgtc tgtgtgcctg catgaagtgg cctactggta  2040
catcctgagc attggagccc agacagactt cctgtctgtg ttcttctctg gctacacctt  2100
caagcacaag atggtgtatg aggataccct gacactgttc ccattctctg gagagacagt  2160
gttcatgagc atggaaaacc ctggcctgtg gatcctgggc tgtcacaact ctgacttcag  2220
aaacagaggc atgacagccc tgctgaaggt gtccagctgt gacaagaaca caggagacta  2280
ctatgaggac agctatgagg acatctctgc ctacctgctg agcaagaaca atgccattga  2340
gcccagaaac ttcagccaga attgctccca gaaccctcca gtgctgaaga gagaaatcac  2400
cagaaccaca ctgcagtctg accaagagga aattgactat gatgacacca tctctgtgga  2460
gatgaagaaa gaagattttg acatctatga tgaggatgag aatcagagcc ccagatcctt  2520
tcagaaaaag accagacact acttcattgc tgctgtggag agactgtggg actatggcat  2580
gtctagcagc cctcatgtgc tgagaaatag agcccagtct ggctctgtgc cccagttcaa  2640
gaaagtggtg ttccaagagt tcacagatgg cagcttcacc cagccactgt atagaggaga  2700
gctgaatgag catctgggcc tgctgggccc ttatatcaga gctgaagtgg aagataacat  2760
catggtcacc ttcagaaatc aggcctctag accctacagc ttctacagct ccctgatcag  2820
ctatgaagag gaccagagac agggagctga gcccagaaag aactttgtga agcccaatga  2880
gactaagacc tacttttgga aggtgcagca ccacatggcc cctacaaagg atgagtttga  2940
ctgcaaggcc tgggcctact tttctgatgt ggatctggaa aaggatgtgc actctggact  3000
cattggacca ctgcttgtgt gccacaccaa cacactgaac cctgctcatg gcagacaagt  3060
gacagtgcaa gagtttgccc tgttcttcac catctttgat gaaacaaaga gctggtactt  3120
```

```
cacagagaat atggagagaa actgcagggc cccttgcaac atccagatgg aagatcccac  3180
cttcaaagag aactacagat tccatgccat caatggctac atcatggaca cactgcctgg  3240
cctggttatg gctcaggatc agagaatcag atggtatctg ctgtccatgg gctccaatga  3300
gaatatccac agcatccact tctctggcca tgtgttcaca gtgagaaaaa aagaagagta  3360
caaaatggcc ctgtacaatc tgtaccctgg ggtgtttgaa acagtggaaa tgctgccttc  3420
caaggctggc atttggagag tggaatgtct gattggagag cacctccatg ctggaatgag  3480
caccctgttt ctggtgtaca gcaacaagtg tcagacccct ctgggcatgg cctctggaca  3540
catcagagac ttccagatca cagcctctgg ccagtatgga cagtgggctc ctaaactggc  3600
tagactgcac tactctggca gcatcaatgc ctggtccacc aaagagccct tcagctggat  3660
caaggtggac ctgctggctc ccatgatcat ccatggaatc aagacccagg gagccagaca  3720
gaagttcagc agcctgtaca tcagccagtt catcatcatg tacagcctgg atggcaagaa  3780
gtggcagacc tacagaggca acagcacagg cacactcatg gtgttctttg gcaatgtgga  3840
cagctctggc attaagcaca acatcttcaa ccctccaatc attgccagat acatcagact  3900
gcaccccaca cactacagca tcagatctac cctgagaatg gaactgatgg gctgtgacct  3960
gaacagctgc agcatgcccc tgggaatgga aagcaaggcc atctctgatg cccagatcac  4020
agccagcagc tacttcacca acatgtttgc cacttggagc cctccaaggg ctagactgca  4080
tctgcagggc agaagcaatg cttggaggcc ccaagtgaac aaccccaaag agtggctgca  4140
ggtggacttt caaaagacca tgaaagtgac aggagtgacc acacagggag tcaagtctct  4200
gctgacctct atgtatgtga aagagttcct gatctccagc agccaggatg gccaccagtg  4260
gaccctgttt ttccagaatg gcaaagtgaa agtgttccag ggcaatcagg acagcttcac  4320
acctgtggtc aactccctgg atcctccact gctgaccaga tacctgagaa ttcaccctca  4380
gtcttgggtg caccagattg ctctgagaat ggaagtgctg ggctgtgaag ctcaggacct  4440
ctactgatcg cgaataaaag atctttattt tcattagatc tgtgtgttgg ttttttgtgt  4500
gtattacagt atgatagcta ctcaaagcac tttttgttct tctcttcact gacctaagtg  4560
ccagttcccg atcgttacag gaaattcaac tatagctaca cgtg                  4604

SEQ ID NO: 92          moltype = DNA  length = 4604
FEATURE                Location/Qualifiers
source                 1..4604
                       mol_type = other DNA
                       organism = synthetic construct
SEQUENCE: 92
acgcgtacgt taaagcttac gtttttcctg taacgatcgg gaactggcac ttaggtcagt  60
gaagagaaga acaaaaatat ttagctactc aaagcttact aaagaattat tcttttacat  120
ttcagtggcc accaggagat actacctggg ggctgtggag cttagctggg actacatgca  180
gtctgacctg ggggagctgc ctgtggatgc cagattccca cccagagtgc ccaaatcctt  240
cccattcaac accagcgtgg tctacaagaa gaccctcttt gtggagttca ctgaccacct  300
gttcaacatt gccaaaccca ggccaccctg gatgggactc ctgggaccca ccattcaggc  360
tgaggtctat gacactgtgg tcatcaccct caagaacatg gcctcccacc ctgtgagcct  420
gcatgctgtg ggggtcagct actggaaggc ctctgagggg gctgagtatg atgaccagac  480
ctcccagagg gagaaggagg atgacaaagt gttccctggg ggcagccaca cctatgtgtg  540
gcaggtcctc aaggagaatg gccccatggc ctctgaccca ctctgcctga cctactccta  600
cctttctcat gtggacctgg tcaaggacct caactctgga ctgattgggg ccctgctggt  660
gtgcagagag ggctccctgg ccaaagagaa gacccagacc ctgcacaagt tcattctcct  720
gtttgctgtc tttgatgagg gcaagagctg gcactctgaa accaagaact ccctgatgca  780
ggacagggat gctgcctctg ccagagcctg gcccaagatg cacactgtga atggctatgt  840
caacaggagc ctgcctggac tcattggctg ccacaggaaa agcgtctact ggcatgtgat  900
tggcatgggg acaacccctg aggtgcactc cattttcctg gagggccaca ccttcctggt  960
cagaaaccac agacaggcca gcctggagat cagccccatc accttcctca ctgcccagac  1020
cctgctgatg gacctcggac agttcctgct gttctgccac atcagctccc accagcatga  1080
tggcatggag gcctatgtca aggtggacag ctgccctgag gagccacagc tcagaatgaa  1140
gaacaatgag gaggctgagg actatgatga tgacctgact gactctgaga tggatgtggt  1200
ccgctttgat gatgacaaca gcccatcctt cattcagatc aggtctgtgg ccaagaaaca  1260
ccccaagacc tgggtgcact acattgctgc tgaggaggag gactgggact atgcccccact  1320
ggtcctggcc cctgatgaca gaagctacaa gagccagtac ctcaacaatg gcccacagag  1380
gattggacgg aagtacaaga aagtcaggtt catggcctac actgatgaaa ccttcaagac  1440
cagagaggcc attcagcatg agtctggcat cctgggccca ctcctgtatg ggaggtggg  1500
ggacaccctg ctcatcatct tcaagaacca ggcctccagg ccctacaaca tctacccaca  1560
tggcatcact gatgtcagac ccctgtacag ccgcaggctg ccaaaggggg tcaaacacct  1620
caaggacttc cccattctgc ctggggagat cttcaagtac aagtggactg tcactgtgga  1680
ggatggacca accaaatctg accccagatg cctcaccaga tactactcca gctttgtgaa  1740
catggagagg gacctggcct ctggcctgat tggcccactg ctcatctgct acaaggagag  1800
cgtggaccag aggggaaacc agatcatgtc tgacaagagg aatgtgattc tgttctctgt  1860
ctttgatgag aacaggagct ggtacctgac tgagaacatt cagcgcttcc tgcccaaccc  1920
tgctggggtg cagctggagg accctgagtt ccaggccagc aacatcatgc actccatcaa  1980
tggctatgtc tttgacagcc tccagctttc tgtctgcctg catgaggtgg cctactggta  2040
cattctttcc attggggccc agactgactt cctttctgtc ttcttcagcg gctacacctt  2100
caaacacaag atggtgtatg aggacaccct gaccctcttc ccattctctg ggagactgt  2160
gttcatgagc atggagaacc ctggcctgtg gattctggga tgccacaact ctgacttccg  2220
gaacagaggc atgactgccc tgctcaaagt ctcctcctgt gacaagaaca ctggggacta  2280
ctatgaggac agctatgagg acatctctgc ctacctgctc agcaagaaca atgccattga  2340
gcccaggaac ttcagccaga attgctccca gaaccctcca gtcctgaaga gagagatcac  2400
cagaaccacc ctccagtctg accaggagga gattgactat gatgacacca tttctgtgga  2460
gatgaagaaa gaggactttg acatctatga cgaggacgag aaccagagcc caaggagctt  2520
ccagaagaag accaggcact acttcattgc tgctgtggag cgcctgtggg actatggcat  2580
gagctccagc cccatgtcc tcagaaacag ggcccagtct ggctctgtcc cacagttcaa  2640
gaaagtggtc ttccaagagt tcactgatgg cagcttcacc cagcccctgt acagagggga  2700
gctgaatgag cacctgggac tcctgggccc atacatcagg gctgaggtgg aggacaacat  2760
catggtcacc ttccgcaacc aggcctccag accctacagc ttctacagct ccctcatcag  2820
```

```
ctatgaggag gaccagaggc agggggctga gccacggaag aactttgtca aacccaatga  2880
aaccaagacc tacttctgga aagtccagca ccacatggcc ccccaccaagg atgagtttga  2940
ctgcaaggcc tgggcctact tcagcgatgt ggacctggag aaggatgtcc actctggcct  3000
gattggccca ctcctggtct gccacaccaa caccctgaac cctgcccatg gaagacaagt  3060
cactgtgcag gagtttgccc tcttcttcac catctttgat gaaaccaaga gctggtactt  3120
cactgagaac atggagcgca actgcagagc cccatgcaac attcagatgg aggaccccac  3180
cttcaaagag aactaccggt tccatgccat caatggctac atcatggaca ccctgcctgg  3240
gcttgtcatg gcccaggacc agaggatcag atggtacctg cttagcatgg gctccaatga  3300
gaacattcac tccatccact tcagcgggca tgtcttcact gtgcgcaaga aggaggagta  3360
caagatggcc ctgtacaacc tctaccctgg ggtctttgag actgtggaga tgctgccctc  3420
caaagctggc atctggaggg tggagtgcct cattggggag cacctgcatg ctggcatgag  3480
caccctgttc ctggtctaca gcaacaagtg ccagaccccc ctgggaatgg cctctggcca  3540
catcagggac ttccagatca ctgcctctgg ccagtatggc cagtgggccc ccaagctggc  3600
cagactccac tactctggat ccatcaatgc ctggagcacc aaggagccat tcagctggat  3660
caaagtggac ctgctggccc ccatgatcat ccatggcatc aagacccagg gggccaggca  3720
gaagttctcc agcctgtaca tcagccagtt catcatcatg tacagcctgg atggcaagaa  3780
atggcagacc tacagaggca actccactgg aacactcatg gtcttctttg gcaatgtgga  3840
cagctctggc atcaagcaca acatcttcaa ccccccaatc atcgccagat acatcaggct  3900
gcaccccacc cactacagca tccggagcac cctcagaatg gagctgatgg gctgtgacct  3960
gaactcctgc agcatgcccc tgggcatgga gagcaaggcc atttctgatg cccagatcac  4020
tgcctccagc tacttcacca acatgtttgc cacctggagc ccaagcaagg ccaggctgca  4080
cctccaggga aggagcaatg cctggagacc ccaggtcaac aacccaaagg agtggctgca  4140
ggtggacttc cagaagacca tgaaggtcac tggggtcacc acccaggggg tcaagagcct  4200
gctcaccagc atgtatgtga aggagttcct gatcagctcc agccaggatg gccaccagtg  4260
gaccctcttc ttccagaatg gcaaggtcaa ggtgttccag ggcaaccagg acagcttcac  4320
ccctgtggtg aacagcctgg accccccccct cctgaccaga tacctgagga ttcacccccca  4380
gagctgggtc caccagattg ccctgagaat ggaggtcctg ggatgtgagg cccaggacct  4440
gtactgatcg cgaataaaag atctttattt tcattagatc tgtgtgttgg tttttttgtgt  4500
gtattacagt atgatagcta ctcaaagcac tttttgttct tctcttcact gacctaagtg  4560
ccagttcccg atcgttacag gaaattcaac tatagctaca cgtg                  4604

SEQ ID NO: 93          moltype = DNA  length = 4604
FEATURE                Location/Qualifiers
source                 1..4604
                       mol_type = other DNA
                       organism = synthetic construct
SEQUENCE: 93
acgcgtacgt taaagcttac gtttttcctg taacgatcgg gaactggcac ttaggtcagt  60
gaagagaaga acaaaaatat ttagctactc aaagcttact aaagaattat tcttttacat  120
ttcagtggcc accaggagat actacctggg ggctgtggag ctgagctggg actacatgca  180
gtctgacctg gggggagctgc ctgtggatgc caggttcccc cccagagtgc ccaagagctt  240
ccccttcaac acctctgtgg tgtacaagaa gaccctgttt gtggagttca ctgaccacct  300
gttcaacatt gccaagccca ggccccccctg gatgggcctg ctgggcccca ccatccaggc  360
tgaggtgtat gacactgtgg tgatcaccct gaagaacatg gccagccacc ctgtgagcct  420
gcatgctgtg gggtgagct actggaaggc ctctgagggg gctgagtatg atgaccagac  480
cagccagagg gagaaggagg atgacaaggt gttccctggg ggcagccaca cctatgtgtg  540
gcaggtgctg aaggagaatg gccccatggc ctctgacccc ctgtgcctga cctacagcta  600
cctgagccat gtggacctgg tgaaggacct gaactctggc ctgattgggg ccctgctggt  660
gtgcagggag ggcagcctgg ccaaggagaa gacccagacc ctgcacaagt tcatcctgct  720
gtttgctgtg tttgatgagg gcaagagctg gcactctgaa accaagaaca gcctgatgca  780
ggacagggat gctgcctctg ccagggcctg gcccaagatg cacactgtga atggctatgt  840
gaacaggagc ctgcctggcc tgattggctg ccacaggaag tctgtgtact ggcatgtgat  900
tggcatgggc accacccctg aggtgcacag catcttcctg gagggccaca ccttcctggt  960
caggaaccac aggcaggcca gcctggagat cagccccatc accttcctga ctgcccagac  1020
cctgctgatg gacctgggcc agttcctgct gtcttgccac atcagcagcc accagcatga  1080
tggcatggag gcctatgtga aggtggacag ctgccctgag gagccccagc tgaggatgaa  1140
gaacaatgag gaggctgagg actatgatga tgacctgact gactctgaga tggatgtggt  1200
gaggtttgat gatgacaaca gccccagctt catccagatc aggtctgtgg ccaagaagca  1260
ccccaagacc tgggtgcact acattgctgc tgaggaggag gactgggact atgccccccct  1320
ggtgctggcc cctgatgaca ggagctacaa gagccagtac ctgaacaatg gcccccagag  1380
gattggcagg aagtacaaga aggtcaggtt catggcctac actgatgaaa ccttcaagac  1440
cagggaggcc atccagcatg agtctggcat cctgggcccc ctgctgtatg gggaggtggg  1500
ggacaccctg ctgatcatct tcaagaacca ggccagcagg ccctacaaca tctaccccca  1560
tggcatcact gatgtgaggc ccctgtacag caggaggctg cccaaggggg tgaagcacct  1620
gaaggacttc cccatcctgc ctggggagat cttcaagtac aagtggactg tgactgtgga  1680
ggatggcccc accaagtctg accccaggtg cctgaccaga tactacagca gctttgtgaa  1740
catggagagg gacctggcct ctggcctgat tggcccccctg ctgatctgct acaaggagtc  1800
tgtggaccag aggggcaacc agatcatgtc tgacaagagg aatgtgatcc tgttctctgt  1860
gtttgatgag aacaggagct ggtacctgac tgagaacatc cagaggttcc tgcccaaccc  1920
tgctggggtg cagctggagg accctgagtt ccaggccagc aacatcatgc acagcatcaa  1980
tggctatgtg tttgacagcc tgcagctgtc tgtgtgcctg catgaggtgg cctactggta  2040
catcctgagc attggggccc agactgactt cctgtctgtg ttcttctctg gctacacctt  2100
caagcacaag atggtgtatg aggacaccct gaccctgttc cccttctctg ggagactgt  2160
gttcatgagc atggagaacc ctggcctgtg gattctgggc tgccacaact ctgacttcag  2220
gaacaggggc atgactgccc tgctgaaagt ctccagctgt gacaagaaca ctggggacta  2280
ctatgaggac agctatgagg acatctctgc ctacctgctg agcaagaaca atgccattga  2340
gcccaggaac ttcagccaga attgctccca gaaccctcca gtgctgaaga gagagatcac  2400
caggaccacc ctgcagtctg accaggagga gattgactat gatgacacca tctctgtgga  2460
gatgaagaag gaggactttg acatctacga cgaggacgag aaccagagcc ccaggagctt  2520
```

```
ccagaagaag accaggcact acttcattgc tgctgtggag aggctgtggg actatggcat  2580
gagcagcagc ccccatgtgc tgaggaacag ggcccagtct ggctctgtgc cccagttcaa  2640
gaaggtggtg ttccaggagt tcactgatgg cagcttcacc cagcccctgt acagagggga  2700
gctgaatgag cacctgggcc tgctgggccc ctacatcagg gctgaggtgg aggacaacat  2760
catggtgacc ttcaggaacc aggccagcag gccctacagc ttctacagca gcctgatcag  2820
ctatgaggag gaccagaggc agggggctga gcccaggaag aactttgtga agcccaatga  2880
aaccaagacc tacttctgga aggtgcagca ccacatggcc ccaccaagg atgagtttga  2940
ctgcaaggcc tgggcctact tctctgatgt ggacctggag aaggatgtgc actctggcct  3000
gattggcccc ctgctggtgt gccacaccaa caccctgaac cctgcccatg gcaggcaggt  3060
gactgtgcag gagtttgccc tgttcttcac catctttgat gaaaccaaga gctggtactt  3120
cactgagaac atggagagga actgcagggc cccctgcaac atccagatgg aggaccccac  3180
cttcaaggag aactacaggt tccatgccat caatggctac atcatggaca ccctgcctgg  3240
cctggtgatg gcccaggacc agaggatcag gtggtacctg ctgagcatgg gcagcaatga  3300
gaacatccac agcatccact tctctggcca tgtgttcact gtgaggaaga aggaggagta  3360
caagatggcc ctgtacaacc tgtaccctgg ggtgtttgag actgtggaga tgctgcccag  3420
caaggctggc atctggaggg tggagtgcct gattggggag cacctgcatg ctggcatgag  3480
caccctgttc ctggtgtaca gcaacaagtg ccagaccccc ctgggcatgg cctctggcca  3540
catcagggac ttccagatca ctgcctctgg ccagtatggc cagtgggccc ccaagctggc  3600
caggctgcac tactctggca gcatcaatgc ctggagcacc aaggagccct tcagctggat  3660
caaggtggac ctgctggccc ccatgatcat ccatggcatc aagacccagg gggccaggca  3720
gaagttcagc agcctgtaca tcagccagtt catcatcatg tacagcctgg atggcaagaa  3780
gtggcagacc tacaggggca acagcactgg caccctgatg gtgttctttg gcaatgtgga  3840
cagctctggc atcaagcaca acatcttcaa cccccccatc attgccagat acatcaggct  3900
gcacccccacc cactacagca tcaggagcac cctgaggatg gagctgatgg gctgtgacct  3960
gaacagctgc agcatgcccc tgggcatgga gagcaaggcc atctctgatg cccagatcac  4020
tgccagcagc tacttcacca acatgtttgc cacctggagc cccagcaagg ccaggctgca  4080
cctgcagggc aggagcaatg cctggaggcc ccaggtcaac aaccccaagg agtggctgca  4140
ggtggacttc cagaagacca tgaaggtgac tggggtgacc acccaggggg tgaagagcct  4200
gctgaccagc atgtatgtga aggagttcct gatcagcagc agccaggatg gccaccagtg  4260
gaccctgttc ttccagaatg gcaaggtgaa ggtgttccag ggcaaccagg acagcttcac  4320
ccctgtggtg aacagcctgg accccccct gctgaccaga tacctgagga ttcaccccca  4380
gagctgggtg caccagattg ccctgaggat ggaggtgctg ggctgtgagg cccaggacct  4440
gtactgatcg cgaataaaag atctttattt tcattagatc tgtgtgttgg tttttttgtgt  4500
gtattacagt atgatagcta ctcaaagcac tttttgttct tctcttcact gacctaagtg  4560
ccagttcccg atcgttacag gaaattcaac tatagctaca cgtg                    4604

SEQ ID NO: 94          moltype = DNA  length = 4604
FEATURE                Location/Qualifiers
source                 1..4604
                       mol_type = other DNA
                       organism = synthetic construct
SEQUENCE: 94
acgcgtacgt taaagcttac gtttttcctg taacgatcgg gaactggcac ttaggtcagt  60
gaagagaaga acaaaaatat ttagctactc aaagcttact aaagaattat tcttttacat  120
ttcagtggcc accaggagat actacctggg ggctgtggag cttagctggg actacatgca  180
gtctgacctg gggggagctgc ctgtggatgc cagattccca cccagagtgc ccaaatcctt  240
cccattcaac accagcgtgg tctacaagaa gaccctcttt gtggagttca ctgaccacct  300
gttcaacatt gccaaaccca ggccaccctg gatgggactc ctgggaccca ccattcaggc  360
tgaggtctat gacactgtgg tcatcaccct caagaacatg gcctccccacc ctgtgagcct  420
gcatgctgtg gggtcagct actggaaggc ctctgagggg gctgagtatg atgaccagac  480
ctcccagagg gagaaggagg atgacaaagt gttccctggg ggcagccaca cctatgtgtg  540
gcaggtcctc aaggagaatg gccccatggc ctctgaccca ctctgcctga cctactccta  600
cctttctcat gtggacctgg tcaaggacct caactctgga ctgattgggg ccctgctggt  660
gtgcagagag ggctccctgg ccaaagagaa gacccagacc ctgcacaagt tcattctcct  720
gtttgctgtc tttgatgagg gcaagagctg gcactctgaa accaagaact ccctgatgca  780
ggacagggat gctgcctctg ccagagcctg gcccaagatg cacactgtga atggctatgt  840
caacaggagc ctgcctggac tcattggctg ccacaggaaa agcgtctact ggcatgtgat  900
tggcatgggg acaaccccctg aggtgcactc cattttcctg gagggccaca ccttcctggt  960
cagaaaccac agacaggcca gcctggagat cagccccatc accttcctca ctgcccagac  1020
cctgctgatg gacctcggac agttcctgct gtcttgccac atcagctccc accagcatga  1080
tggcatggag gcctatgtca aggtggacag ctgccctgag gagccacagc tcagaatgaa  1140
gaacaatgag gaggctgagg actatgatga tgacctgact gactctgaga tggatgtggt  1200
ccgctttgat gatgacaaca gcccatcctt cattcagatc aggtctgtgg ccaagaaaca  1260
ccccaagacc tgggtgcact acattgctgc tgaggaggag gactgggact atgccccact  1320
ggtcctggcc cctgatgaca gaagctacaa gagccagtac ctcaacaatg gcccacagag  1380
gattggacgg aagtacaaga aagtcaggtt catggcctac actgatgaaa ccttcaagac  1440
cagagaggcc attcagcatg agtctggcat cctgggccca ctcctgtatg gggaggtggg  1500
ggacaccctg ctcatcatct tcaagaacca ggcctccagg ccctacaaca tctacccaca  1560
tggcatcact gatgtcagac ccctgtacag ccgcaggctg ccaaaggggg tcaaacacct  1620
caaggacttc cccattctgc ctggggagat cttcaagtac aagtggactg tcactgtgga  1680
ggatggacca accaaatctg accccagatg cctcaccaga tactactcca gctttgtgaa  1740
catggagagg gacctggcct ctggcctgat tggcccactg ctcatctgct acaaggagag  1800
cgtggaccag aggggaaacc agatcatgtc tgacaagagg aatgtgattc tgttctctgt  1860
ctttgatgag aacaggagct ggtacctgac tgagaacatt cagcgcttcc tgcccaaccc  1920
tgctggggtg cagctggagg accctgagtt ccaggccagc aacatcatgc actccatcaa  1980
tggctatgtc tttgacagcc tccagctttc tgtctgcctg catgaggtgg cctactggta  2040
cattctttcc attggggccc agactgactt cctttctgtc ttcttcagcg gctacacctt  2100
caaacacaag atggtgtatg aggacaccct gaccctcttc ccattctctg ggagactgt  2160
gttcatgagc atggagaacc ctggcctgtg gattctggga tgccacaact ctgacttccg  2220
```

```
gaacagaggc atgactgccc tgctcaaagt ctcctcctgt gacaagaaca ctggggacta  2280
ctatgaggac agctatgagg acatctctgc ctacctgctc agcaagaaca atgccattga  2340
gcccaggaac ttcagccaga attgctccca gaaccctcca gtcctgaaga gagagatcac  2400
cagaaccacc ctccagtctg accaggagga gattgactat gatgacacca tttctgtgga  2460
gatgaagaaa gaggactttg acatctatga cgaggacgag aaccagagcc caaggagctt  2520
ccagaagaag accaggcact acttcattgc tgctgtggag cgcctgtggg actatggcat  2580
gagctccagc cccatgtcc tcagaaacag ggcccagtct ggctctgtcc cacagttcaa  2640
gaaagtggtc ttccaagagt tcactgatgg cagcttcacc cagcccctgt acagagggga  2700
gctgaatgag cacctgggac tcctgggccc atacatcagg gctgaggtgg aggacaacat  2760
catggtcacc ttccgcaacc aggcctccag accctacagc ttctacagct ccctcatcag  2820
ctatgaggag gaccagaggc agggggctga gccacggaag aactttgtca aacccaatga  2880
aaccaagacc tacttctgga aagtccagca ccacatggcc cccaccaagg atgagtttga  2940
ctgcaaggcc tgggcctact tcagcgatgt ggacctggag aaggatgtcc actctggcct  3000
gattggccca ctcctggtct gccacaccaa caccctgaac cctgcccatg gaagacaagt  3060
cactgtgcag gagtttgccc tcttcttcac catctttgat gaaaccaaga gctggtactt  3120
cactgagaac atggagcgca actgcagagc cccatgcaac attcagatgg aggaccccac  3180
cttcaaagag aactaccggt tccatgccat caatggctac atcatggaca ccctgcctgg  3240
gcttgtcatg gcccaggacc agaggatcag atggtacctg cttagcatgg gctccaatga  3300
gaacattcac tccatccact tcagcgggca tgtcttcact gtgcgcaaga aggaggagta  3360
caagatggcc ctgtacaacc tctaccctgg ggtctttgag actgtggaga tgctgccctc  3420
caaagctggc atctggaggg tggagtgcct cattggggag cacctgcatg ctggcatgag  3480
caccctgttc ctggtctaca gcaacaagtg ccagaccccc ctgggaatgg cctctggcca  3540
catcagggac ttccagatca ctgcctctgg ccagtatggc cagtgggccc ccaagctggc  3600
cagactccac tactctggat ccatcaatgc ctggagcacc aaggagccat tcagctggat  3660
caaagtggac ctgctggccc ccatgatcat ccatggcatc aagacccagg gggccaggca  3720
gaagttctcc agcctgtaca tcagccagtt catcatcatg tacagcctgg atggcaagaa  3780
atggcagacc tacagaggca actccactgg aacactcatg gtcttctttg gcaatgtgga  3840
cagctctggc atcaagcaca acatcttcaa ccccccaatc atcgccagat acatcaggct  3900
gcaccccacc cactacagca tccggagcac cctcagaatg gagctgatgg gctgtgacct  3960
gaactcctgc agcatgcccc tgggcatgga gagcaaggcc atttctgatg cccagatcac  4020
tgcctccagc tacttcacca acatgtttgc cacctggagc ccaagcaagg ccaggctgca  4080
cctccaggga aggagcaatg cctggagacc ccaggtcaac aacccaaagg agtggctgca  4140
ggtggacttc cagaagacca tgaaggtcac tggggtcacc acccaggggg tcaagagcct  4200
gctcaccagc atgtatgtga aggagttcct gatcagctcc agccaggatg gccaccagtg  4260
gaccctcttc ttccagaatg gcaaggtcaa ggtgttccag ggcaaccagg acagcttcac  4320
ccctgtggtg aacagcctgg acccccccct cctgaccaga tacctgagga ttcaccccca  4380
gagctgggtc caccagattg ccctgagaat ggaggtcctg ggatgtgagg cccaggacct  4440
gtactgatcg cgaataaaag atctttattt tcattagatc tgtgtgttgg tttttgtgt  4500
gtattacagt atgatagcta ctcaaagcac tttttgttct tctcttcact gacctaagtg  4560
ccagttcccg atcgttacag gaaattcaac tatagctaca cgtg                4604
```

```
SEQ ID NO: 95           moltype = RNA  length = 3705
FEATURE                 Location/Qualifiers
source                  1..3705
                        mol_type = other RNA
                        organism = synthetic construct
SEQUENCE: 95
atgcatgcgc ggccgcaagc tttaatacga ctcactataa ggaaaagcca gctccagcag  60
gcgctgctca ctcctcccca tcctctccct ctgtccctct gtccctctga ccctgcactg  120
tcccagcacc atggccccca agaagaagcg gaaagttggc ggcggaggca gcagcaccga  180
catgaagaac taccggatcg gcgtggacgt gggcgataga tctgttggac tggccgccat  240
cgagttcgac gatgatggac tgcccatcca gaagctggcc ctggtcacct ttagacacga  300
tggcggactg gaccccacca agaacaagac ccctatgagc cggaaagaga cacggggaat  360
cgccagacgg accatgcgga tgaacagaga gcggaagcgg cggctgagaa acctggacaa  420
cgtgctggaa aacctgggct actctgtgcc tgagggccct gagcctgaga catatgaggc  480
ctggacaagc agagccctgc tggcctctat caaactggcc tctgccgacg agctgaacga  540
acaccttgtc agagccgtgc ggcacatggc cagacataga ggatgggcca atccttggtg  600
gtccctggac cagctggaaa aggccagcca agagcctagc gagacattcg agatcatcct  660
ggccagagcc agagagctgt tcggcgagaa ggtgcccgct aatcctacac tgggaatgct  720
gggagccctg gccgctaaca atgaggtgct gctgaggccc agggacgaga agaagagaaa  780
gaccggatac gtgcggggca cccctctgat gtttgctcaa gttcgacagg gcgatcagct  840
ggccgagctg cggagaattt gtgaagtgca gggcatcgag gaccagtacg aggctctgag  900
actgggcgtg ttcgaccaca agcacccccta cgtgcccaaa gaaagagtgg gcaaagaccc  960
tctgaacccc agcaccaaca gaaccatcag agccagcctg gaatttcaag agttccgcat  1020
cctggacagc gtggccaatc tgagagtgcg gatcggcagc agagccaaga gggaactgac  1080
agaggccgag tatgatgccg ccgtggaatt cctgatggac tacgccgaca aagagcagcc  1140
tagctgggcc gatgtggccg agaaaattgg cgtgcccggc aacagactgg tggcccctgt  1200
tctggaagat gtgcagcaga aaacagcccc ttacgacaga agcagcgccg cctttgagaa  1260
ggccatgggc aagaaaaccg aggccagaca gtggtgggag tccaccgatg atgaccagct  1320
gagaagcctg ctgattgcct tcctggtgga cgccaccaac gacacagaag aagccgctgc  1380
tgaagccggc ctgagcgagc tgtataagtc ttggcctgcc gaggaaagag aggccctgtc  1440
caacatcgac ttcgagaagg gcagagtggc ctacagccaa gaaaccctga gcaagctgag  1500
cgagtacatg cacgagtaca gagtgggact gcacgaggct agaaaggccg tgttcggagt  1560
ggatgatacc tggcggcctc ctctggataa gctggaagaa cctacaggac agcctgccgt  1620
ggacagagtg ctgaccatcc tgagaagatt cgtgctggac tgcgagcggc aatggggcag  1680
acctagagcc atcaccgtgg aacacacacg gacaggcctg atgggcccaa cacagagaca  1740
gaagatcctg aacgagcaga agaagaaccg ggccgacaac gagagaatcc gggatgagct  1800
gagagaatct ggcgtggaca acccctccag agccgaagtt cggagacacc tgatcgtgca  1860
agagcaagag tgccagtgcc tgtactgcgg caccatgatc accaccacca caagcgagct  1920
```

```
ggaccacatc gttcctagag ccggtggcgg cagcagcaga agggaaaatc tggccgctgt  1980
gtgcagagcc tgcaacgcca agaagaaacg cgagctgttc tacgcctggg ctggcccagt  2040
gaagtcccaa gagacaatcg agagagtcag acagctgaag gcctttaagg acagcaagaa  2100
agccaagatg ttcaagaacc agatccgccg gctgaaccag accgaggccg atgagcctat  2160
cgacgaaaga agcctggcca gcacatctta cgccgctgtg gccgttagag agcggctgga  2220
acagcacttc aacgaaggcc tggcactgga cgacaagtcc agagtggtgc tggatgtgta  2280
tgccggcgct gtgaccagag agtctcgtag agctggcggc atcgacgagc ggattctgct  2340
gagaggcgag cgggacaaga acagattcga tgtgcggcat cacgccgtgg acgctgctgt  2400
tatgaccctg ctgaacagat ccgtggctct gaccctggaa cagagatcac agctgaggcg  2460
ggccttctac gagctggaac tggacaaact ggaccgggac cagctcaagc ctggcgagga  2520
ttggagaaac ttcaccggcc tgtacgaggc ctctcagaac aagttcagcg agtggaagaa  2580
agccgccaca gtgctgggag atctgctggc tgaagccatc gaggatgacg ccattgccgt  2640
ggtgtctcca ctgagactga ggccccagaa tggcagcgtg cacgacgata ccatcaacgc  2700
cgtgaagaag ctgacactgg gctctgcctg gcctgcagac gctgtgaaga gaatcgtgga  2760
ccccgagatc tacctggcta tgaaggacgt gctgggcaag ctgaaagagc tgcccgagga  2820
ttctgccaga tctctggaac tgtccgacgg ccggtacatc gaagccgatg acgaggtgct  2880
gttcttccca aagaaggccg ctagcatcct gacacctaga ggcgccgctg agatcggcaa  2940
ctctatccac catgccagac tgtatagctg gctgaccaag aagggcgagc tgaagtttgg  3000
catgctgaga gtgtacggcg ccgagtttcc ctggctgatg agagagtctg gaagccgcga  3060
cgtgctgcat atgcctattc accctggcag ccagagcttc agaggcatgc aggatggcgt  3120
gcggaaagcc gtggaaagcg gagaggctgt ggaattcggc tggatcaccc aggacgatga  3180
gctggaattc gaccccgagg actacattgc ccacggcgga gatgacgaac tgaacagact  3240
gctgcgagtg atgcccgaga gaaggtggcg agtggacggc ttctataacg ccggcacact  3300
gagaatcaga cccgctctgc tgtctgctga gcagctgcct tctgagctgc agaaaaaggt  3360
ggccgacaag accctgagcg acgtggaact gatcctgctg agggctgttc agcggggact  3420
gttcgtggcc atcagcagct ttctgcccct ggaaagcctg aaagtgatcc ggcggaacaa  3480
tctgggcttc cccaggtggc gcggaaacgg aaatctgccc accagctttg aagtgcggag  3540
cagcgctctg agagccctgg gagttgaagg atctggcgga aaaagacctg ccgccacaaa  3600
gaaagccgga caggccaaga aaaagaagtg accacacccc cattccccca ctccagatag  3660
aacttcagtt atatctcacg tgtctggagt tggatccatg catgc                  3705
```

```
SEQ ID NO: 96           moltype = AA  length = 1166
FEATURE                 Location/Qualifiers
source                  1..1166
                        mol_type = protein
                        organism = synthetic construct
SEQUENCE: 96
MAPKKKRKVG GGGSSTDMKN YRIGVDVGDR SVGLAAIEFD DDGLPIQKLA LVTFRHDGGL  60
DPTKNKTPMS RKETRGIARR TMRMNRERKR RLRNLDNVLE NLGYSVPEGP EPETYEAWTS  120
RALLASIKLA SADELNEHLV RAVRHMARHR GWANPWWSLD QLEKASQEPS ETFEIILARA  180
RELFGEKVPA NPTLGMLGAL AANNEVLLRP RDEKKRKTGY VRGTPLMFAQ VRQGDQLAEL  240
RRICEVQGIE DQYEALRLGV FDHKHPYVPK ERVGKDPLNP STNRTIRASL EFQEFRILDS  300
VANLRVRIGS RAKRELTEAE YDAAVEFLMD YADKEQPSWA DVAEKIGVPG NRLVAPVLED  360
VQQKTAPYDR SSAAFEKAMG KKTEARQWWE STDDDQLRSL LIAFLVDATN DTEEAAAEAG  420
LSELYKSWPA EEREALSNID FEKGRVAYSQ ETLSKLSEYM HEYRVGLHEA RKAVFGVDDT  480
WRPPLDKLEE PTGQPAVDRV LTILRRFVLD CERQWGRPRA ITVEHTRTGL MGPTQRQKIL  540
NEQKKNRADN ERIRDELRES GVDNPSRAEV RRHLIVQEQE CQCLYCGTMI TTTTSELDHI  600
VPRAGGGSSR RENLAAVCRA CNAKKKRELF YAWAGPVKSQ ETIERVRQLK AFKDSKKAKM  660
FKNQIRRLNQ TEADEPIDER SLASTSYAAV AVRERLEQHF NEGLALDDKS RVVLDVYAGA  720
VTRESRRAGG IDERILLRGE RDKNRFDVRH HAVDAAVMTL LNRSVALTLE QRSQLRRAFY  780
ELELDKLDRD QLKPGEDWRN FTGLYEASQN KFSEWKKAAT VLGDLLAEAI EDDAIAVVSP  840
LRLRPQNGSV HDDTINAVKK LTLGSAWPAD AVKRIVDPEI YLAMKDVLGK LKELPEDSAR  900
SLELSDGRYI EADDEVLFFP KKAASILTPR GAAEIGNSIH HARLYSWLTK KGELKFGMLR  960
VYGAEFPWLM RESGSRDVLH MPIHPGSQSF RGMQDGVRKA VESGEAVEFG WITQDDELEF  1020
DPEDYIAHGG DDELNRLLRV MPERRWRVDG FYNAGTLRIR PALLSAEQLP SELQKKVADK  1080
TLSDVELILL RAVQRGLFVA ISSFLPLESL KVIRRNNLGF PRWRGNGNLP TSFEVRSSAL  1140
RALGVEGSGG KRPAATKKAG QAKKKK                                       1166
```

```
SEQ ID NO: 97           moltype = RNA  length = 110
FEATURE                 Location/Qualifiers
source                  1..110
                        mol_type = other RNA
                        organism = synthetic construct
modified_base           1..3
                        mod_base = OTHER
                        note = 2'-O-Methyl modified base
modified_base           108..110
                        mod_base = OTHER
                        note = 2'-O-Methyl modified base
modified_base           1..4
                        mod_base = OTHER
                        note = phosphorothioate linkage
modified_base           107..110
                        mod_base = OTHER
                        note = phosphorothioate linkage
SEQUENCE: 97
cttaggtcag tgaagagaag aagttgagaa tcgaaagatt cttaataagg catccttccg  60
atgctgactt ctcaccgtcc gttatccaat aggagcgggc ggtatgtttt             110
```

```
SEQ ID NO: 98          moltype = RNA  length = 110
FEATURE                Location/Qualifiers
source                 1..110
                       mol_type = other RNA
                       organism = synthetic construct
modified_base          1..3
                       mod_base = OTHER
                       note = 2'-O-Methyl modified base
modified_base          108..110
                       mod_base = OTHER
                       note = 2'-O-Methyl modified base
modified_base          1..4
                       mod_base = OTHER
                       note = phosphorothioate linkage
modified_base          107..110
                       mod_base = OTHER
                       note = phosphorothioate linkage
SEQUENCE: 98
aggcaggccc tatgagaccg tagttgagaa tcgaaagatt cttaataagg catccttccg  60
atgctgactt ctcaccgtcc gttatccaat aggagcgggc ggtatgtttt             110

SEQ ID NO: 99          moltype = AA  length = 34
FEATURE                Location/Qualifiers
source                 1..34
                       mol_type = protein
                       organism = synthetic construct
SEQUENCE: 99
ENRSFSQNAT NVSNNSNTSN ASNVSPPVLK RHQR                              34

SEQ ID NO: 100         moltype = AA  length = 18
FEATURE                Location/Qualifiers
source                 1..18
                       mol_type = protein
                       organism = synthetic construct
SEQUENCE: 100
NFSQNCSQNP PVLKRHQR                                                18

SEQ ID NO: 101         moltype = AA  length = 34
FEATURE                Location/Qualifiers
source                 1..34
                       mol_type = protein
                       organism = synthetic construct
SEQUENCE: 101
ENRSFSQNAT NVSNNSNTSN DSNVSPPVLK RHQR                              34

SEQ ID NO: 102         moltype = AA  length = 18
FEATURE                Location/Qualifiers
source                 1..18
                       mol_type = protein
                       organism = synthetic construct
SEQUENCE: 102
EPRNFSQNCS QNPPVLKR                                                18

SEQ ID NO: 103         moltype = AA  length = 12
FEATURE                Location/Qualifiers
source                 1..12
                       mol_type = protein
                       organism = synthetic construct
SEQUENCE: 103
PKKKRKVGGG GS                                                      12

SEQ ID NO: 104         moltype = AA  length = 19
FEATURE                Location/Qualifiers
source                 1..19
                       mol_type = protein
                       organism = synthetic construct
SEQUENCE: 104
SGGKRPAATK KAGQAKKKK                                               19

SEQ ID NO: 105         moltype = DNA  length = 25
FEATURE                Location/Qualifiers
source                 1..25
                       mol_type = other DNA
                       organism = synthetic construct
SEQUENCE: 105
gcacagatat aaacacttaa cgggt                                        25

SEQ ID NO: 106         moltype = DNA  length = 22
FEATURE                Location/Qualifiers
```

```
source                  1..22
                        mol_type = other DNA
                        organism = synthetic construct
SEQUENCE: 106
ggaggaaatc tagcatccac ag                                            22

SEQ ID NO: 107          moltype = DNA  length = 20
FEATURE                 Location/Qualifiers
source                  1..20
                        mol_type = other DNA
                        organism = synthetic construct
modified_base           1..2
                        mod_base = OTHER
                        note = locked nucleic acid base
modified_base           12
                        mod_base = OTHER
                        note = locked nucleic acid base
modified_base           15..16
                        mod_base = OTHER
                        note = locked nucleic acid base
SEQUENCE: 107
ccaccagaag atattacctg                                               20

SEQ ID NO: 108          moltype = DNA  length = 24
FEATURE                 Location/Qualifiers
source                  1..24
                        mol_type = other DNA
                        organism = synthetic construct
SEQUENCE: 108
gcacagatat aaacacttaa cggg                                          24

SEQ ID NO: 109          moltype = DNA  length = 20
FEATURE                 Location/Qualifiers
source                  1..20
                        mol_type = other DNA
                        organism = synthetic construct
SEQUENCE: 109
tgctctgaga atggaagtgc                                               20

SEQ ID NO: 110          moltype = DNA  length = 21
FEATURE                 Location/Qualifiers
source                  1..21
                        mol_type = other DNA
                        organism = synthetic construct
modified_base           1..2
                        mod_base = OTHER
                        note = locked nucleic acid base
modified_base           9
                        mod_base = OTHER
                        note = locked nucleic acid base
SEQUENCE: 110
cgatcagtag aggtcctgag c                                             21

SEQ ID NO: 111          moltype = DNA  length = 22
FEATURE                 Location/Qualifiers
source                  1..22
                        mol_type = other DNA
                        organism = synthetic construct
SEQUENCE: 111
taacctttct cctcctcctc tt                                            22

SEQ ID NO: 112          moltype = DNA  length = 20
FEATURE                 Location/Qualifiers
source                  1..20
                        mol_type = other DNA
                        organism = synthetic construct
SEQUENCE: 112
tccacagctc ccaggtaata                                               20

SEQ ID NO: 113          moltype = DNA  length = 23
FEATURE                 Location/Qualifiers
source                  1..23
                        mol_type = other DNA
                        organism = synthetic construct
SEQUENCE: 113
tcttctggtg gccagtgctt ctc                                           23

SEQ ID NO: 114          moltype = AA  length = 5
FEATURE                 Location/Qualifiers
```

```
source                  1..5
                        mol_type = protein
                        organism = synthetic construct
SEQUENCE: 114
SFSQN                                                                   5

SEQ ID NO: 115          moltype = AA  length = 9
FEATURE                 Location/Qualifiers
source                  1..9
                        mol_type = protein
                        organism = synthetic construct
SEQUENCE: 115
PPVLKRHQR                                                               9

SEQ ID NO: 116          moltype = AA  length = 14
FEATURE                 Location/Qualifiers
source                  1..14
                        mol_type = protein
                        organism = synthetic construct
SEQUENCE: 116
SFSQNPPVLK RHQR                                                         14

SEQ ID NO: 117          moltype = AA  length = 8
FEATURE                 Location/Qualifiers
source                  1..8
                        mol_type = protein
                        organism = synthetic construct
SEQUENCE: 117
ASSYKTNM                                                                8

SEQ ID NO: 118          moltype = DNA  length = 22
FEATURE                 Location/Qualifiers
source                  1..22
                        mol_type = other DNA
                        organism = synthetic construct
SEQUENCE: 118
tcttgagttt gaatgcacag at                                                22

SEQ ID NO: 119          moltype = DNA  length = 19
FEATURE                 Location/Qualifiers
source                  1..19
                        mol_type = other DNA
                        organism = synthetic construct
SEQUENCE: 119
tagtcccagc tcagttcca                                                    19

SEQ ID NO: 120          moltype = DNA  length = 26
FEATURE                 Location/Qualifiers
source                  1..26
                        mol_type = other DNA
                        organism = synthetic construct
SEQUENCE: 120
tggccaccag aagatattac ctggga                                            26

SEQ ID NO: 121          moltype = DNA  length = 18
FEATURE                 Location/Qualifiers
source                  1..18
                        mol_type = other DNA
                        organism = synthetic construct
SEQUENCE: 121
ctcttcgtct ccggctct                                                     18

SEQ ID NO: 122          moltype = AA  length = 4
FEATURE                 Location/Qualifiers
source                  1..4
                        mol_type = protein
                        organism = synthetic construct
SEQUENCE: 122
SQNC                                                                    4

SEQ ID NO: 123          moltype = DNA  length = 73
FEATURE                 Location/Qualifiers
source                  1..73
                        mol_type = unassigned DNA
                        note = non-target strand sequence
                        organism = unidentified
SEQUENCE: 123
cgacaggttt cccgactgga aaaggtttgg tcgaggcttg cgacgtggtg gctaatttaa  60
gccagccccg aca                                                          73
```

```
SEQ ID NO: 124          moltype = DNA  length = 69
FEATURE                 Location/Qualifiers
source                  1..69
                        mol_type = unassigned DNA
                        note = non-target strand sequence
                        organism = unidentified
SEQUENCE: 124
aaaggtttgg tcgaggcttg cgacgtggtg gctaatttaa gccagccccg acacccgcca  60
acacccgct                                                          69

SEQ ID NO: 125          moltype = DNA  length = 68
FEATURE                 Location/Qualifiers
source                  1..68
                        mol_type = other DNA
                        organism = synthetic construct
SEQUENCE: 125
cgacaggttt cccgactgga aaaggtttgg tcgaggcttg cgacgtggtg gcancngnan  60
ngggccnn                                                           68

SEQ ID NO: 126          moltype = DNA  length = 56
FEATURE                 Location/Qualifiers
source                  1..56
                        mol_type = other DNA
                        organism = synthetic construct
SEQUENCE: 126
aggcttgcga cgtttttntt aatttaagcc agccccgaca cccgccaaca cccgct      56

SEQ ID NO: 127          moltype = DNA  length = 31
FEATURE                 Location/Qualifiers
source                  1..31
                        mol_type = unassigned DNA
                        note = non-target strand sequence
                        organism = unidentified
SEQUENCE: 127
aggtttggtc gaggcttgcg acgtggtggc t                                 31

SEQ ID NO: 128          moltype = RNA  length = 20
FEATURE                 Location/Qualifiers
source                  1..20
                        mol_type = other RNA
                        organism = synthetic construct
SEQUENCE: 128
gtcgaggctt gcgacgtggt                                              20

SEQ ID NO: 129          moltype = RNA  length = 131
FEATURE                 Location/Qualifiers
source                  1..131
                        mol_type = other RNA
                        organism = synthetic construct
SEQUENCE: 129
atgaagtggg taacctttct cctcctcctc ttcgtctccg gctctgcttt ttccaggggt  60
gtgtttcgcc gagaagcact ggccaccaga agatattacc tgggagctgt ggaactgagc  120
tgggactaca t                                                       131

SEQ ID NO: 130          moltype = AA  length = 19
FEATURE                 Location/Qualifiers
source                  1..19
                        mol_type = protein
                        organism = Homo sapiens
SEQUENCE: 130
AIEPRSFSQN SRHPSTRQK                                               19

SEQ ID NO: 131          moltype = AA  length = 25
FEATURE                 Location/Qualifiers
source                  1..25
                        mol_type = protein
                        organism = Homo sapiens
SEQUENCE: 131
AKQGRTERLC SQNPPVLKRH QREIT                                        25

SEQ ID NO: 132          moltype = AA  length = 22
FEATURE                 Location/Qualifiers
source                  1..22
                        mol_type = protein
                        organism = synthetic construct
SEQUENCE: 132
AIEPRSFSQN PPVLKRHQRE IT                                           22
```

```
SEQ ID NO: 133          moltype = AA  length = 22
FEATURE                 Location/Qualifiers
source                  1..22
                        mol_type = protein
                        organism = synthetic construct
SEQUENCE: 133
AIENRSFSQN PPVLKRHQRE IT                                              22

SEQ ID NO: 134          moltype = AA  length = 22
FEATURE                 Location/Qualifiers
source                  1..22
                        mol_type = protein
                        organism = synthetic construct
SEQUENCE: 134
AIEPRNFSQN PPVLKRHQRE IT                                              22

SEQ ID NO: 135          moltype = AA  length = 26
FEATURE                 Location/Qualifiers
source                  1..26
                        mol_type = protein
                        organism = synthetic construct
SEQUENCE: 135
AIEPRSFSQN CSQNPPVLKR HQREIT                                          26

SEQ ID NO: 136          moltype = AA  length = 26
FEATURE                 Location/Qualifiers
source                  1..26
                        mol_type = protein
                        organism = synthetic construct
SEQUENCE: 136
AIEPRNFSQN CSQNPPVLKR HQREIT                                          26

SEQ ID NO: 137          moltype = AA  length = 26
FEATURE                 Location/Qualifiers
source                  1..26
                        mol_type = protein
                        organism = synthetic construct
SEQUENCE: 137
AIENRSFSQN CSQNPPVLKR HQREIT                                          26

SEQ ID NO: 138          moltype = AA  length = 24
FEATURE                 Location/Qualifiers
source                  1..24
                        mol_type = protein
                        organism = synthetic construct
SEQUENCE: 138
AIEPRNFSQN ATPPVLKRHQ REIT                                            24

SEQ ID NO: 139          moltype = AA  length = 23
FEATURE                 Location/Qualifiers
source                  1..23
                        mol_type = protein
                        organism = synthetic construct
SEQUENCE: 139
AIENRSNFSQ NPPVLKRHQR EIT                                             23

SEQ ID NO: 140          moltype = AA  length = 27
FEATURE                 Location/Qualifiers
source                  1..27
                        mol_type = protein
                        organism = synthetic construct
SEQUENCE: 140
AIENRSNFSQ NCSQNPPVLK RHQREIT                                         27

SEQ ID NO: 141          moltype = AA  length = 25
FEATURE                 Location/Qualifiers
source                  1..25
                        mol_type = protein
                        organism = synthetic construct
SEQUENCE: 141
AIENRSNFSQ NATPPVLKRH QREIT                                           25

SEQ ID NO: 142          moltype = AA  length = 14
FEATURE                 Location/Qualifiers
source                  1..14
                        mol_type = protein
                        organism = Homo sapiens
SEQUENCE: 142
EPRSFSQNSX XXXX                                                       14
```

```
SEQ ID NO: 143          moltype = AA  length = 18
FEATURE                 Location/Qualifiers
source                  1..18
                        mol_type = protein
                        organism = Homo sapiens
SEQUENCE: 143
XXXXXCSQNP PVLKRHQR                                                18

SEQ ID NO: 144          moltype = AA  length = 7
FEATURE                 Location/Qualifiers
source                  1..7
                        mol_type = protein
                        organism = synthetic construct
SEQUENCE: 144
PKKKRKV                                                            7

SEQ ID NO: 145          moltype = AA  length = 16
FEATURE                 Location/Qualifiers
source                  1..16
                        mol_type = protein
                        organism = synthetic construct
SEQUENCE: 145
KRPAATKKAG QAKKKK                                                  16

SEQ ID NO: 146          moltype = AA  length = 9
FEATURE                 Location/Qualifiers
source                  1..9
                        mol_type = protein
                        organism = synthetic construct
SEQUENCE: 146
PAAKRVKLD                                                          9

SEQ ID NO: 147          moltype = AA  length = 11
FEATURE                 Location/Qualifiers
source                  1..11
                        mol_type = protein
                        organism = synthetic construct
SEQUENCE: 147
RQRRNELKRS P                                                       11

SEQ ID NO: 148          moltype = AA  length = 38
FEATURE                 Location/Qualifiers
source                  1..38
                        mol_type = protein
                        organism = synthetic construct
SEQUENCE: 148
NQSSNFGPMK GGNFGGRSSG PYGGGGQYFA KPRNQGGY                          38

SEQ ID NO: 149          moltype = AA  length = 42
FEATURE                 Location/Qualifiers
source                  1..42
                        mol_type = protein
                        organism = synthetic construct
SEQUENCE: 149
RMRIZFKNKG KDTAELRRRR VEVSVELRKA KKDEQILKRR NV                     42

SEQ ID NO: 150          moltype = AA  length = 8
FEATURE                 Location/Qualifiers
source                  1..8
                        mol_type = protein
                        organism = synthetic construct
SEQUENCE: 150
VSRKRPRP                                                           8

SEQ ID NO: 151          moltype = AA  length = 8
FEATURE                 Location/Qualifiers
source                  1..8
                        mol_type = protein
                        organism = synthetic construct
SEQUENCE: 151
PPKKARED                                                           8

SEQ ID NO: 152          moltype = AA  length = 8
FEATURE                 Location/Qualifiers
source                  1..8
                        mol_type = protein
                        organism = synthetic construct
SEQUENCE: 152
```

```
PQPKKKPL                                                           8

SEQ ID NO: 153          moltype = AA  length = 12
FEATURE                 Location/Qualifiers
source                  1..12
                        mol_type = protein
                        organism = synthetic construct
SEQUENCE: 153
SALIKKKKKM AP                                                      12

SEQ ID NO: 154          moltype = AA  length = 5
FEATURE                 Location/Qualifiers
source                  1..5
                        mol_type = protein
                        organism = synthetic construct
SEQUENCE: 154
DRLRR                                                              5

SEQ ID NO: 155          moltype = AA  length = 7
FEATURE                 Location/Qualifiers
source                  1..7
                        mol_type = protein
                        organism = synthetic construct
SEQUENCE: 155
PKQKKRK                                                            7

SEQ ID NO: 156          moltype = AA  length = 10
FEATURE                 Location/Qualifiers
source                  1..10
                        mol_type = protein
                        organism = synthetic construct
SEQUENCE: 156
RKLKKKIKKL                                                         10

SEQ ID NO: 157          moltype = AA  length = 10
FEATURE                 Location/Qualifiers
source                  1..10
                        mol_type = protein
                        organism = synthetic construct
SEQUENCE: 157
REKKKFLKRR                                                         10

SEQ ID NO: 158          moltype = AA  length = 20
FEATURE                 Location/Qualifiers
source                  1..20
                        mol_type = protein
                        organism = synthetic construct
SEQUENCE: 158
KRKGDEVDGV DEVAKKKSKK                                              20

SEQ ID NO: 159          moltype = AA  length = 17
FEATURE                 Location/Qualifiers
source                  1..17
                        mol_type = protein
                        organism = synthetic construct
SEQUENCE: 159
RKCLQAGMNL EARKTKK                                                 17

SEQ ID NO: 160          moltype = AA  length = 17
FEATURE                 Location/Qualifiers
source                  1..17
                        mol_type = protein
                        organism = synthetic construct
SEQUENCE: 160
EPRNFSQNPP VLKRHQR                                                 17
```

SUPPLEMENTATION OF LIVER ENZYME EXPRESSION

CROSS-REFERENCE

This application is a continuation of International Application No. PCT/US2023/067509, filed May 25, 2023, which claims the benefit of and priority to U.S. Provisional Patent Application No. 63/345,526, filed May 25, 2022, U.S. Provisional Patent Application No. 63/359,288, filed Jul. 8, 2022, and U.S. Provisional Patent Application No. 63/396,421, filed Aug. 9, 2022, each of which is incorporated by reference in its entirety herein.

SEQUENCE LISTING

The contents of the electronic sequence listing (MTG-017WOC1_SL.xml; Size: 397,946 bytes; and Date of Creation: May 17, 2023) is herein incorporated by reference in its entirety.

SUMMARY

A variety of disorders are caused by deficiencies in liver-produced factors (e.g., liver enzymes), the deficiencies themselves resulting from genetically inherited mutations. For example, hemophilia A and hemophilia B are genetic disorders caused by mutations in genes encoding coagulation factors such as Factor VIII that are produced by the liver. Individuals with hemophilia have lower levels of these coagulation factors, resulting in their blood being unable to clot properly. Treating these disorders with gene therapy approaches that integrate liver genes encoding functional liver enzymes (e.g., Factor VIII) into the genome in vivo in patients enables continuous expression of the functional liver enzymes. Accordingly, described herein are methods, compositions, and systems for supplementation of liver enzymes via gene therapy methods.

Disclosed herein, in certain embodiments, are engineered nuclease systems, comprising: a) an endonuclease comprising an amino acid sequence having at least 80% sequence identity to SEQ ID NO: 54 or SEQ ID NO: 96; b) an engineered guide polynucleotide configured to form a complex with the endonuclease and to hybridize to a target nucleic acid sequence within an albumin gene or within an intron of the albumin gene; and c) a donor template comprising a nucleic acid sequence encoding a Factor VIII (FVIII) gene or a functional fragment thereof. In some embodiments, the target nucleic acid sequence within the albumin gene is within intron 1 of the albumin gene. In some embodiments, the sequence encoding a Factor VIII (FVIII) gene or a functional fragment thereof is linked to a splice acceptor sequence targeting exon 1 of the albumin gene. In some embodiments, the endonuclease comprises a sequence having at least 90% sequence identity to SEQ ID NO: 54 or SEQ ID NO: 96. In some embodiments, the endonuclease comprises a sequence having 100% sequence identity to SEQ ID NO: 54 or SEQ ID NO: 96. In some embodiments, the endonuclease is encoded by a nucleic acid sequence having at least 80% sequence identity to any one of SEQ ID NOs: 30, 31, 53, and 95. In some embodiments, the endonuclease is encoded by a nucleic acid sequence having at least 90% sequence identity to any one of SEQ ID NOs: 30, 31, 53, and 95. In some embodiments, the endonuclease is encoded by a nucleic acid sequence having 100% sequence identity to any one of SEQ ID NOs: 30, 31, 53, and 95. In some embodiments, the engineered guide polynucleotide comprises a sequence having at least 90% sequence identity to any one of SEQ ID NOs: 14-15, 24-27, 43-45, 50, 55, 60-68, 97-98. In some embodiments, the engineered guide polynucleotide comprises a sequence having 100% sequence identity to any one of SEQ ID NOs: 14-15, 24-27, 43-45, 50, 55, 60-68, 97-98. In some embodiments, the target nucleic acid sequence comprises a sequence having at least 80% sequence identity to any one of SEQ ID NOs: 1, 2, and 8. In some embodiments, the target nucleic acid sequence comprises a sequence having at least 90% sequence identity to any one of SEQ ID NOs: 1, 2, and 8. In some embodiments, the target nucleic acid sequence comprises a sequence having 100% sequence identity to any one of SEQ ID NOs: 1, 2, and 8. In some embodiments, the target nucleic acid sequence comprises a sequence having at least 80% sequence identity to any one of SEQ ID NOs: 3-6. In some embodiments, the target nucleic acid sequence comprises a sequence having at least 90% sequence identity to any one of SEQ ID NOs: 3-6. In some embodiments, the target nucleic acid sequence comprises a sequence having 100% sequence identity to any one of SEQ ID NOs: 3-6. In some embodiments, the donor template further comprises a polyadenylation signal. In some embodiments, the donor template further comprises a nucleus-targeting sequence. In some embodiments, the nucleus-targeting sequence comprises a plurality of transcription factor binding sites. In some embodiments, the transcription factor is TCF1, HNF1, NFY, CEBP, OCT1, AP1, HNF1-α, HNF1-β, CEBPA, LEF-1, FOX D1, IRF1, HNF3, HNF4, HNF5, Tal1β/E47, or MyoD. In some embodiments, the nucleus-targeting sequence is on a 5' end and a 3' end of the donor template. In some embodiments, the donor template further comprises a recognition site sequence for the endonuclease on a 5' end or a 3' end. In some embodiments, the nucleus-targeting sequence is 5' to the recognition site sequence when the donor template is flanked on a 5' end. In some embodiments, the nucleus-targeting sequence is 3' to the recognition site sequence when the donor template is flanked on a 3' end. In some embodiments, the donor template comprises, from 5' to 3':NTS(1)-NRS(1)-SA-FVIII-NRS(2)-NTS(2), wherein NTS(1) denotes a first nucleus-targeting sequence; NTS(2) denotes a second nucleus-targeting sequence; NRS(1) denotes a first nuclease recognition site sequence; NRS(2) denotes a second nuclease recognition site sequence; SA denotes the splice acceptor sequence targeting exon 1 of said albumin gene; and FVIII denotes the Factor VIII gene or fragment thereof. In some embodiments, a 5' to 3' orientation of NRS(1) and NRS(2) is according to: (a) forward, forward; (b) reverse, reverse; (c) forward, reverse; (d) reverse, forward; wherein forward denotes a same 5' to 3' orientation as the target nucleic acid sequence, and reverse denotes an opposite 5' to 3' orientation as the target nucleic acid sequence. In some embodiments, the donor template comprises a sequence having at least 80% sequence identity to any one of SEQ ID NOs: 12-13, 16-23, 32-33, 56-59, 81-88, and 90-94. In some embodiments, the donor template comprises a sequence having at least 90% sequence identity to any one of SEQ ID NOs: 12-13, 16-23, 32-33, 56-59, 81-88, and 90-94. In some embodiments, the donor template comprises a sequence having at least 100% sequence identity to any one of SEQ ID NOs: 12-13, 16-23, 32-33, 56-59, 81-88, and 90-94. In some embodiments, the FVIII gene or functional fragment thereof is codon-optimized to remove at least one cytosine-guanine (CG or CpG) motif. In some embodiments, the FVIII gene or functional fragment thereof comprises a sequence having at least 80% identity to any one of SEQ ID NOs: 10, 71-79, and 89. In some embodiments, the FVIII gene or functional fragment thereof comprises a sequence having at least 90% identity to any one of SEQ ID NOs: 10, 71-79, and 89. In some embodiments, the FVIII gene or functional fragment thereof comprises a sequence having 100% identity to any one of SEQ ID NOs: 10, 71-79, and 89. In some embodiments, the FVIII gene or functional fragment thereof comprises a sequence having at least 80% identity to SEQ ID NO: 10. In some embodiments, the FVIII gene or functional fragment thereof comprises a sequence having at least 90% identity to SEQ ID NO: 10. In some embodiments, the FVIII gene or functional fragment thereof comprises a sequence having 100% identity to SEQ ID NO: 10. In some embodiments, the FVIII gene or functional fragment thereof is modified to comprise a B-domain comprising a sequence having at least 90% identity to any one of SEQ ID NOs: 71-79 and 89. In some embodiments, the FVIII gene or functional fragment thereof is modified to comprise a B-domain comprising a sequence having 100% identity to any one of SEQ ID NOs: 71-79 and 89. In some embodiments, the FVIII gene or functional fragment thereof comprising a modified B-domain comprises a sequence having at least about 90% identity to any one of SEQ ID NOs: 86-87 and 90. In some embodiments, the FVIII gene or functional fragment thereof comprising a modified B-domain comprises a sequence having 100% identity to any one of SEQ ID NOs: 86-87 and 90.

Disclosed herein, in certain embodiments, are methods for supplementing liver enzyme expression in a subject in need thereof, comprising administering to the subject: a) an endonuclease comprising an amino acid sequence having at least 80% sequence identity to SEQ ID NO: 54 or SEQ ID NO: 96; b) an engineered guide polynucleotide configured to form a complex with the endonuclease and to hybridize to a target nucleic acid sequence within an albumin gene or within an intron of the albumin gene; and c) a donor template comprising a nucleic acid sequence encoding a Factor VIII (FVIII) gene or a functional fragment thereof, thereby supplementing liver enzyme expression in said subject. In some embodiments, the target nucleic acid sequence within the albumin gene is within intron 1 of the albumin gene. In some embodiments, the sequence encoding a Factor VIII (FVIII) gene or a functional fragment thereof is operably linked to a splice acceptor sequence targeting exon 1 of the albumin gene. In some embodiments, the endonuclease comprises a sequence having at least 90% sequence identity to SEQ ID NO: 54 or SEQ ID NO: 96. In some embodiments, the endonuclease comprises a sequence having 100% sequence identity to SEQ ID NO: 54 or SEQ ID NO: 96. In some embodiments, the endonuclease is encoded by a nucleic acid sequence having at least 80% sequence identity to any one of SEQ ID NOs: 30, 31, 53, and 95. In some embodiments, the endonuclease is encoded by a nucleic acid sequence having at least 90% sequence identity to any one of SEQ ID NOs: 30, 31, 53, and 95. In some embodiments, the endonuclease is encoded by a nucleic acid sequence having 100% sequence identity to any one of SEQ ID NOs: 30, 31, 53, and 95. In some embodiments, the engineered guide polynucleotide comprises a sequence having at least 90% sequence identity to any one of SEQ ID NOs: 14-15, 24-27, 43-45, 50, 55, 60-68, 97-98. In some embodiments, the engineered guide polynucleotide comprises a sequence having 100% sequence identity to any one of SEQ ID NOs: 14-15, 24-27, 43-45, 50, 55, 60-68, 97-98. In some embodiments, the target nucleic acid sequence comprises a sequence having at least 80% sequence identity to any one of SEQ ID NOs: 1, 2, and 8. In some embodiments, the target nucleic acid sequence comprises a sequence having at least 90% sequence identity to any one of SEQ ID NOs: 1, 2, and 8. In some embodiments, the target nucleic acid sequence comprises a sequence having 100% sequence identity to any one of SEQ ID NOs: 1, 2, and 8. In some embodiments, the target nucleic acid sequence comprises a sequence having at least 80% sequence identity to any one of SEQ ID NOs: 3-6. In some embodiments, the target nucleic acid sequence comprises a sequence having at least 90% sequence identity to any one of SEQ ID NOs: 3-6. In some embodiments, the target nucleic acid sequence comprises a sequence having 100% sequence identity to any one of SEQ ID NOs: 3-6. In some embodiments, the donor template further comprises a polyadenylation signal. In some embodiments, the donor template further comprises a nucleus-targeting sequence. In some embodiments, the nucleus-targeting sequence comprises a plurality of transcription factor binding sites. In some embodiments, the transcription factor is TCF1, HNF1, NFY, CEBP, OCT1, AP1, HNF1-α, HNF1-β, CEBPA, LEF-1, FOX D1, IRF1, HNF3, HNF4, HNF5, Tallo/E47, or MyoD. In some embodiments, the nucleus-targeting sequence is on a 5' end and a 3' end of the donor template. In some embodiments, the donor template further comprises a recognition site sequence for the endonuclease on a 5' end or a 3' end. In some embodiments, the nucleus-targeting sequence is 5' to the recognition site sequence when the donor template is flanked on a 5' end. In some embodiments, the nucleus-targeting sequence is 3' to the recognition site sequence when the donor template is flanked on a 3' end. In some embodiments, the donor template comprises, from 5' to 3':NTS(1)-NRS(1)-SA-FVIII-NRS(2)-NTS(2), wherein NTS(1) denotes a first nucleus-targeting sequence; NTS(2) denotes a second nucleus-targeting sequence; NRS(1) denotes a first nuclease recognition site sequence; NRS(2) denotes a second nuclease recognition site sequence; SA denotes the splice acceptor sequence targeting exon 1 of said albumin gene; and FVIII denotes the Factor VIII gene or fragment thereof. In some embodiments, a 5' to 3' orientation of NRS(1) and NRS(2) is according to: (a) forward, forward; (b) reverse, reverse; (c) forward, reverse; (d) reverse, forward; wherein forward denotes a same 5' to 3' orientation as the target nucleic acid sequence, and reverse denotes an opposite 5' to 3' orientation as the target nucleic acid sequence. In some embodiments, the donor template comprises a sequence having at least 80% sequence identity to any one of SEQ ID NOs: 12-13, 16-23, 32-33, 56-59, 81-88, and 90-94. In some embodiments, the donor template comprises a sequence having at least 90% sequence identity to any one of SEQ ID NOs: 12-13, 16-23, 32-33, 56-59, 81-88, and 90-94. In some embodiments, the donor template comprises a sequence having at least 100% sequence identity to any one of SEQ ID NOs: 12-13, 16-23, 32-33, 56-59, 81-88, and 90-94. In some embodiments, the FVIII gene or functional fragment thereof is codon-optimized to remove at least one cytosine-guanine (CG or CpG) motif. In some embodiments, the FVIII gene or functional fragment thereof comprises a sequence having at least 80% identity to any one of SEQ ID NOs: 10, 71-79, and 89. In some embodiments, the FVIII gene or functional fragment thereof comprises a sequence having at least 90% identity to any one of SEQ ID NOs: 10, 71-79, and 89. In some embodiments, the FVIII gene or functional fragment thereof comprises a sequence having 100% identity to any one of SEQ ID NOs: 10, 71-79, and 89. In some embodiments, the FVIII gene or functional fragment thereof comprises a sequence having at least 80% identity to SEQ ID NO: 10. In some embodiments, the FVIII gene or functional fragment thereof comprises a sequence having at least 90% identity to SEQ ID NO: 10. In some embodiments, the FVIII gene or functional fragment thereof comprises a sequence having 100% identity to SEQ ID NO: 10. In some embodiments, the FVIII gene or functional fragment thereof is modified to comprise a B-domain comprising a sequence having at least 90% identity to any one of SEQ ID NOs: 71-79 and 89. In some embodiments, the FVIII gene or functional fragment thereof is modified to comprise a B-domain comprising a sequence having 100% identity to any one of SEQ ID NOs: 71-79 and 89. In some embodiments, the FVIII gene or functional fragment thereof comprising a modified B-domain comprises a sequence having at least about 90% identity to any one of SEQ ID NOs: 86-87 and 90. In some embodiments, the FVIII gene or functional fragment thereof comprising a modified B-domain comprises a sequence having 100% identity to any one of SEQ ID NOs: 86-87 and 90.

Disclosed herein, in certain embodiments, are cells comprising the engineered nuclease system disclosed herein. In some embodiments, the cell is a liver cell. In some embodiments, the cell is a eukaryotic cell. In some embodiments, the cell is a mammalian cell. In some embodiments, the cell is an immortalized cell. In some embodiments, the cell is an insect cell. In some embodiments, the cell is a yeast cell. In some embodiments, the cell is a plant cell. In some embodiments, the cell is a fungal cell. In some embodiments, the cell is a prokaryotic cell. In some embodiments, the cell is an A549, HEK-293, HEK-293T, BHK, CHO, HeLa, MRC5, Sf9, Cos-1, Cos-7, Vero, BSC 1, BSC 40, BMT 10, W138, HeLa, Saos, C2C12, L cell, HT1080, HepG2, Huh7, K562, primary cell, or a derivative thereof. In some embodiments, the cell is an engineered cell. In some embodiments, the cell is a stable cell.

Disclosed herein, in certain embodiments, are lipid nanoparticles (LNPs) comprising components (a) and (b) or components (a), (b), and (c) of the engineered nuclease system disclosed herein. In some embodiments, the LNP comprises a cationic lipid, a neutral lipid, cholesterol or a cholesterol analog, and a PEG-linked lipid. In some embodiments, the cationic lipid comprises C12-200 (1,1'-((2-(4-(2-((2-(bis(2-hydroxydodecyl)amino)ethyl)(2-hydroxydodecyl)amino)ethyl)piperazin-1-yl)ethyl)azanediyl)bis (dodecan-2-ol)), said neutral lipid comprises 1,2-dioleoyl-sn-glycero-3-phosphoethanolamine (DOPE), or said PEG-linked lipid comprises 1,2-dimyristoyl-rac-glycero-3-methoxypolyethylene glycol-2000 (DMG-PEG-2000).

Disclosed herein, in certain embodiments, are viral vectors comprising the engineered nuclease system disclosed herein. In some embodiments, the viral vector is an adeno-associated viral (AAV) vector. In some embodiments, the AAV is AAV1, AAV2, AAV3, AAV4, AAV5, AAV6, AAV7, AAV8, AAV9, AAV10, AAV11, AAV12, AAV13, AAV14, AAV15, AAV16, AAV-rh8, AAV-rh10, AAV-rh20, AAV-rh39, AAV-rh74, AAV-rhM4-1, AAV-hu37, AAV-Anc80, AAV-Anc80L65, AAV-7m8, AAV-PHP-B, AAV-PHP-EB, AAV-2.5, AAV-2tYF, AAV-3B, AAV-LK03, AAV-HSC1, AAV-HSC2, AAV-HSC3, AAV-HSC4, AAV-HSC5, AAV-HSC6, AAV-HSC7, AAV-HSC8, AAV-HSC9, AAV-HSC10, AAV-HSC11, AAV-HSC12, AAV-HSC13, AAV-HSC14, AAV-HSC15, AAV-TT, AAV-DJ/8, AAV-Myo, AAV-NP40, AAV-NP59, AAV-NP22, AAV-NP66, AAV-HSC16, or a derivative thereof. In some embodiments, the AAV is AAV6. In some embodiments, the AAV is AAV8.

Disclosed herein, in certain embodiments, are methods for supplementing liver enzyme expression in an individual in need thereof, comprising administering to the individual: (a) an endonuclease comprising a RuvC domain or a nucleic acid encoding the endonuclease, the endonuclease having at least 80% sequence identity to the nucleic acid sequence of SEQ ID NO: 30; (b) an engineered guide RNA (i) configured to form a complex with the endonuclease and (ii) comprising a spacer sequence configured to hybridize to at least a portion of a target nucleic acid sequence within an albumin gene or within an intron of the albumin gene; and (c) a donor template comprising a nucleic acid sequence encoding a therapeutic gene encoding a functional liver enzyme (e.g., Factor VIII), thereby supplementing liver enzyme (e.g., Factor VIII) expression in the individual. In some embodiments, the spacer sequence is configured to hybridize to an intron 1 of the albumin gene. In some embodiments, the nucleic acid sequence encoding the therapeutic gene is linked to a splice acceptor sequence targeting exon 1 of the albumin gene.

Disclosed herein, in certain embodiments, are methods for supplementing liver enzyme expression in an individual in need thereof, comprising administering to the individual: (a) an endonuclease comprising a RuvC domain or a nucleic acid encoding the endonuclease, wherein the endonuclease has at least 80% sequence identity to the nucleic acid sequence of SEQ ID NO: 31; (b) an engineered guide RNA (i) configured to form a complex with the endonuclease and (ii) comprising a spacer sequence configured to hybridize to a target nucleic acid sequence within an albumin gene; and (c) a donor template comprising a nucleic acid sequence encoding a functional liver enzyme (e.g., Factor VIII), linked to a splice acceptor sequence targeting exon 1 of an albumin gene, thereby supplementing liver enzyme expression in the subject.

In some embodiments, the endonuclease induces a single-stranded break or a double-stranded break at or proximal to the target nucleic acid sequence. In some embodiments, the endonuclease induces a double-stranded break at or proximal to the target nucleic acid sequence. In some embodiments, the donor template is integrated into the target nucleic acid sequence at the double-stranded break. In some embodiments, the donor template is integrated into the target nucleic acid sequence at the double-stranded break via non-homologous end joining (NHEJ). In some embodiments, the donor template is integrated into the target nucleic acid sequence at the double-stranded break via homology-directed repair (HDR).

In some embodiments, the engineered guide RNA is configured to hybridize to a sequence having at least 80% identity to any one of SEQ ID NOs: 3-6. In some embodiments, the engineered guide RNA comprises a sequence according to any one of SEQ ID NOs: 24-27.

In some embodiments, the donor template further comprises a polyadenylation signal. In some embodiments, the donor template is a closed-end linear duplex. In some embodiments, the donor template further comprises a recognition site sequence for the endonuclease on a 5' end or a 3' end of the donor template. In some embodiments, the donor template further comprises a nucleus-targeting sequence that is: (a) 5' to the recognition site sequence when the coding sequence is flanked on a 5' end of the donor template, or (b) 3' to the recognition site sequence when the coding sequence is flanked on a 3' end of the donor template. In some embodiments, the donor template comprises a nucleus-targeting sequence on a 5' end and a 3' end of the donor template. In some embodiments, the donor template comprises, from 5' to 3':NTS(1)-NRS(1)-SA-TG-NRS(2)-NTS(2), wherein NTS(1) denotes a first nucleus-targeting sequence; NTS(2) denotes a second nucleus-targeting sequence; NRS(1) denotes a first nuclease recognition site sequence; NRS(2) denotes a second nuclease recognition site sequence; SA denotes a splice acceptor sequence targeting exon 1 of the albumin gene; and TG denotes the therapeutic gene. In some embodiments, a 5' to 3' orientation of the NRS(1) and NRS(2) is according to: (a) forward, forward; (b) reverse, reverse; (c) forward, reverse; (d) reverse, forward; wherein forward denotes a same 5' to 3' orientation as the target nucleic acid sequence, and reverse denotes an opposite 5' to 3' orientation as the target nucleic acid sequence. In some embodiments, the first nucleus-targeting sequence or second nucleus-targeting sequence comprises a plurality of binding sites for LEF/TCF1, HNF1, NFY, CEBP, OCT1, AP1, HNF1-A, HNF1-B, CEBPA, LEF-1, FOX D1, or IRF1. In some embodiments, the first nucleus-targeting sequence or second nucleus-targeting sequence comprises a sequence having at least 80% identity to SEQ ID NO: 1 or SEQ ID NO: 1 with SEQ ID NO: 2 appended to a 5' or a 3' end of the nucleus-targeting sequence.

In some embodiments, the donor template comprises a sequence having at least 80% identity to any one of SEQ ID NOs: 12-13, 16-23, and 32-33. In some embodiments, the donor template comprises a sequence having at least 80% identity to any one of SEQ ID NOs: 16-23. In some embodiments, the donor template comprises a sequence having at least 75% identity to any one of SEQ ID NOs: 16-19. In some embodiments, the donor template comprises a sequence having at least 80% identity to any one of SEQ ID NOs: 20-23.

In some embodiments, the therapeutic gene is a Factor VIII (FVIII) gene or a functional fragment thereof. In some embodiments, the FVIII gene or functional fragment thereof is codon-optimized to remove at least one cytosine-guanine (CG or CpG) motif. In some embodiments, the codon-optimized FVIII gene or functional fragment thereof comprises a sequence having at least 80% identity to SEQ ID NO: 10.

Disclosed herein, in certain embodiments, are vectors comprising the endonuclease systems disclosed herein. In some embodiments, the vector is a viral vector. In some embodiments, the viral vector is an adeno-associated viral (AAV) vector. In some embodiments, the vector is a lipid nanoparticle (LNP). In some embodiments, the LNP comprises a cationic lipid, a neutral lipid, cholesterol or a cholesterol analog, or a PEG-linked lipid. In some embodiments, the cationic lipid comprises C12-200 (1,1'-((2-(4-(2-((2-(bis(2-hydroxydodecyl)amino)ethyl)(2-hydroxydodecyl)amino)ethyl)piperazin-1-yl)ethyl)azanediyl)bis(dodecan-2-ol)), the neutral lipid comprises 1,2-dioleoyl-sn-glycero-3-phosphoethanolamine (DOPE), or the PEG-linked lipid comprises 1,2-dimyristoyl-rac-glycero-3-methoxypolyethylene glycol-2000 (DMG-PEG-2000).

Disclosed herein, in certain embodiments, are systems comprising: (a) an endonuclease capable of cleaving at least one strand of a target nucleic acid within a first nuclease recognition site sequence or a second nuclease recognition site sequence and (b) a nucleic acid comprising from 5' to 3': (i) a first nucleus-targeting sequence; and (ii) a coding sequence for a therapeutic gene encoding a functional liver enzyme (e.g., Factor VIII), wherein the coding sequence is flanked on a 5' end by the first nuclease recognition sequence and/or a 3' end by the second nuclease recognition sequence. In some embodiments, the nucleic acid is double-stranded DNA. In some embodiments, the double-stranded DNA is a closed-end linear duplex. In some embodiments, the coding sequence of the coding sequence for the therapeutic gene is flanked on a 5' end by the first nuclease recognition sequence, and the first recognition site sequence is 3' to the first nucleus-targeting sequence. In some embodiments, the coding sequence for the therapeutic gene is flanked on a 3' end by the second nuclease recognition site sequence. In some embodiments, the nucleic acid further comprises a second nucleus-targeting sequence. In some embodiments, the nucleic acid comprises a first nucleus-targeting sequence on a 5' end of the nucleic acid and a second nucleus-targeting sequence on a 3' end. In some embodiments, the nucleic acid comprises, from 5' to 3':NTS(1)-NRS(1)-SA-TG-NRS(2)-NTS(2), wherein NTS(1) denotes a first nucleus-targeting sequence; NTS(2) denotes a second nucleus-targeting sequence; NRS(1) denotes a first nuclease recognition site sequence; NRS(2) denotes a second nuclease recognition site sequence; SA denotes a splice acceptor sequence targeting exon 1 of the albumin gene; and TG denotes the therapeutic gene. In some embodiments, a 5' to 3' orientation of the NRS(1) and NRS(2) is according to: (a) forward, forward; (b) reverse, reverse; (c) forward, reverse; (d) reverse, forward; wherein forward denotes a same 5' to 3' orientation as the target nucleic acid sequence, and reverse denotes an opposite 5' to 3' orientation as the target nucleic acid sequence. In some embodiments, the nucleic acid comprises a sequence having at least 80% identity to any one of SEQ ID NOs: 12-13, 16-23, or 32-33. In some embodiments, the first nucleus-targeting sequence or the second nucleus-targeting sequence comprises binding sites for LEF/TCF1, HNF1, NFY, CEBP, OCT1, AP1, HNF1-A, HNF1-B, CEBPA, LEF-1, FOX D1, or IRF1. In some embodiments, the first nucleus-targeting sequence or the second nucleus-targeting sequence comprises a sequence having at least 80% identity to SEQ ID NO: 1 or SEQ ID NO: 1 with SEQ ID NO: 2 appended to a 5' or a 3' end to a 5' or a 3' end of the nucleus-targeting sequence. In some embodiments, the therapeutic gene is a Factor VIII (FVIII) gene or a functional fragment thereof. In some embodiments, the FVIII gene or functional fragment thereof is codon-optimized to remove at least one cytosine-guanine (CG or CpG) motif. In some embodiments, the codon-optimized FVIII gene or functional fragment thereof comprises a sequence having at least 80% identity to SEQ ID NO: 10.

Disclosed herein, in certain embodiments, are viral vectors comprising from 5' to 3': (a) a nucleic acid comprising a nucleic acid sequence having at least 80% identity to a first intron 1 sequence of an albumin gene and comprising a KTTN (K=G or T, N=any base) or AAANNN sequence (N=any base); (b) a splice acceptor sequence targeting exon 1 of the albumin gene; (c) a coding sequence for a therapeutic gene encoding a functional liver enzyme (e.g., Factor VIII) linked to a polyadenylation signal and to the splice acceptor sequence; and (d) a sequence comprising a nucleic acid sequence having at least 80% identity to a second intron 1 sequence of an albumin gene and comprising a KTTN (K=G or T, N=any base) or AAANNN (N=any base), wherein the second intron 1 sequence is 3' to the first intron 1 sequence of the albumin gene. In some embodiments, the nucleic acid further comprises a first nucleus-targeting sequence (NTS) 5' to the recognition site sequence when the coding sequence is flanked on a 5' end of the nucleic acid, or 3' to the recognition site sequence when the coding sequence is flanked on a 3' end of the nucleic acid. In some embodiments, the nucleic acid further comprises a second nucleus-targeting sequence (NTS). In some embodiments, the nucleic acid comprises a first nucleus-targeting sequence on 5' end of the nucleic acid and a second nucleus-targeting sequence on a 3' end of the nucleic acid. In some embodiments, the nucleic acid comprises, from 5' to 3':NTS (1)-

NRS(1)-SA-TG-NRS(2)-NTS(2), wherein NTS(1) denotes a first nucleus-targeting sequence; NTS(2) denotes a second nucleus-targeting sequence; NRS(1) denotes a first nuclease recognition site sequence; NRS(2) denotes a second nuclease recognition site sequence; SA denotes a splice acceptor sequence targeting exon 1 of the albumin gene; and TG denotes the coding sequence for the therapeutic gene. In some embodiments, a 5' to 3' orientation of NRS(1) and NRS(2) is according to: (a) forward, forward; (b) reverse, reverse; (c) forward, reverse; (d) reverse, forward; wherein forward denotes a same 5' to 3' orientation as the target nucleic acid sequence, and reverse denotes an opposite 5' to 3' orientation as the target nucleic acid sequence. In some embodiments, the nucleic acid comprises a sequence having at least 80% identity to any one of SEQ ID NOs: 12-13, 16-23, or 32-33. In some embodiments, the first nucleus-targeting sequence or the second nucleus-targeting sequence comprises binding sites for LEF/TCF1, HNF1, NFY, CEBP, OCT1, AP1, HNF1-A, HNF1-B, CEBPA, LEF-1, FOX D1, or IRF1. In some embodiments, the first nucleus-targeting sequence or second nucleus-targeting sequence comprises a sequence having at least 80% identity to SEQ ID NO: 1, SEQ ID NO: 1 with SEQ ID NO: 2 appended to a 5' or a 3' end. In some embodiments, the therapeutic gene is a Factor VIII (FVIII) gene or a functional fragment thereof. In some embodiments, the FVIII gene or functional fragment thereof is codon-optimized to remove at least one cytosine-guanine (CG or CpG) motif. In some embodiments, the codon-optimized FVIII gene or functional fragment thereof comprises a sequence having at least 80% identity to SEQ ID NO: 10.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 discloses SEQ ID NOS 123-124, 126, 125 and 127-128, respectively, in order of appearance.

FIG. 13 depicts the predicted mRNA sequence of the junction between mouse albumin exon 1 and human FVIII after correct splicing. FIG. 13 discloses SEQ ID NOS 129 and 111-113, respectively, in order of appearance.

FIG. 22 depicts sequences of human FVIII around the B-domain junctions aligned to different designs of a B-domain replacement sequence. FIG. 22 discloses SEQ ID NOS 130-143, 99, 160, 73-74 and 78, respectively, in order of appearance.

FIG. 28 depicts quantitation of integration of the cyno-FVIII gene cassette into albumin intron 1 in mice dosed with $1\times10^{13}$ vg/kg of AAV6(sf)-pMG4016, AAV8(sf)-pMG4016, or AAV8(HK)-pMG4016 followed by a mixture of LNP A and LNP B.

BRIEF DESCRIPTION OF THE SEQUENCE LISTING

Figure 1:
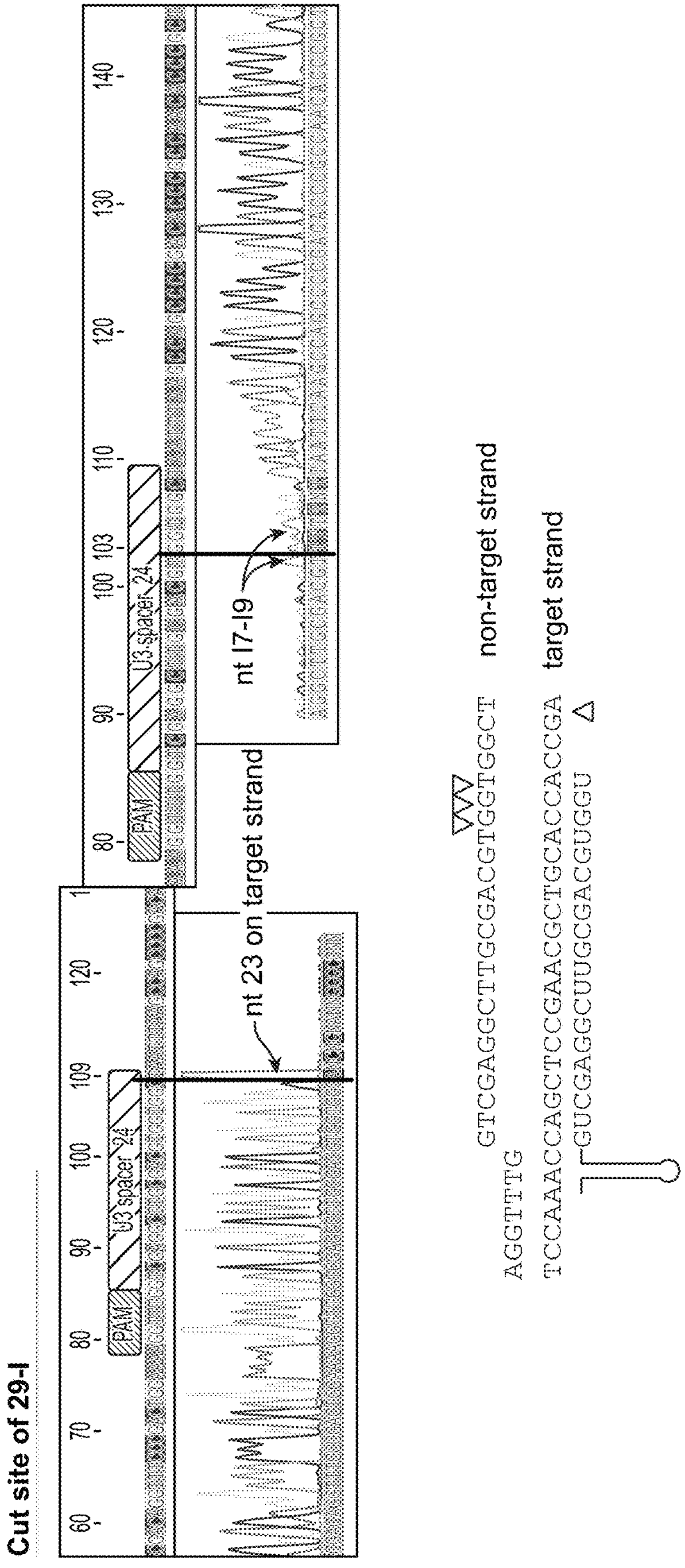
FIG. 1 depicts the location of MG29-1 cut sites on the target and non-target strand as determined from an in vitro editing assay.

The Sequence Listing filed herewith provides exemplary polynucleotide and polypeptide sequences for use in methods, compositions, and systems according to the disclosure. Below are exemplary descriptions of sequences therein.

SEQ ID NO: 1 shows the DNA sequence of the human albumin target site.

SEQ ID NO: 2 shows the DNA sequence of a transcriptional enhancer.

SEQ ID NOs: 3-6 show the DNA sequences of mouse albumin target sites.

SEQ ID NO: 7 shows the nucleotide sequence of a 20 bp spacer.

SEQ ID NO: 8 shows the DNA sequence of the human albumin target site and the transcriptional enhancer.

SEQ ID NO: 9 shows the DNA sequence of a splice acceptor.

SEQ ID NO: 10 shows the DNA sequence of a human Factor VIII coding sequence.

SEQ ID NO: 11 shows the DNA sequence of a stop codon, spacer, and polyadenylation signal.

SEQ ID NOs: 12-13, 16-23, and 32-33 show the DNA sequences of Factor VIII donor templates.

SEQ ID NOs: 14-15 and 24-25 show the nucleotide sequences of MG29-1 sgRNAs targeting mouse albumin.

SEQ ID NOs: 26-27 show the nucleotide sequences of MG3-6/3-4 sgRNAs targeting mouse albumin.

SEQ ID NOs: 28-29 show the nucleotide sequences of PCR primers.

SEQ ID NO: 30 shows the DNA sequence encoding the MG3-6/3-4 mRNA.

SEQ ID NO: 31 shows the DNA sequence encoding the MG29-1 mRNA.

SEQ ID NOs: 37, 39, and 41 show the nucleotide sequences of transcription factor binding sequences.

SEQ ID NOs: 43-45 show the nucleotide sequences of MG29-1 sgRNAs targeting mouse albumin.

SEQ ID NOs: 46-49 show the nucleotide sequences of PCR primers.

SEQ ID NO: 50 shows the nucleotide sequence of an MG29-1 sgRNA targeting mouse albumin.

SEQ ID NO: 51 shows the DNA sequence encoding the spCas9 mRNA.

SEQ ID NO: 52 shows the spCas9 amino acid sequence.

SEQ ID NO: 53 shows the DNA sequence encoding the MG29-1 mRNA.

SEQ ID NO: 54 shows the MG29-1 amino acid sequence.

SEQ ID NO: 55 shows the nucleotide sequence of an MG29-1 sgRNA targeting mouse albumin.

SEQ ID NOs: 56-59 show the DNA sequences of Factor VIII donor templates.

SEQ ID NOs: 60-63 show the nucleotide sequences of MG29-1 sgRNAs targeting mouse albumin.

SEQ ID NOs: 64-68 show the nucleotide sequences of MG29-1 sgRNAs targeting human albumin intron 1.

SEQ ID NO: 69 shows the protein sequence of a protease recognition site.

SEQ ID NOs: 71-79 show protein sequences intended to replace the B-domain of FVIII.

SEQ ID NO: 80 shows the protein sequence of an SQ linker.

SEQ ID NOs: 81-85 show the nucleotide sequences of human FVIII donor cassettes.

SEQ ID NOs: 86-87 show the protein sequences of Cynomolgus macaque FVIII sequences in which the B-domain has been replaced.

SEQ ID NO: 88 shows the nucleotide sequences of a Cynomolgus macaque FVIII donor cassette.

SEQ ID NO: 89 shows a protein sequence intended to replace the B-domain of FVIII.

SEQ ID NO: 90 shows the protein sequence of a human FVIII sequence in which the B-domain has been replaced.

SEQ ID NOs: 91-94 show the nucleotide sequences of human FVIII donor cassettes.

SEQ ID NO: 95 shows the nucleotide sequence of a messenger RNA encoding the MG3-6/3-4 nuclease with nuclear localization signals added at both the N- and C-termini.

SEQ ID NO: 96 shows the protein sequence of the MG3-6/3-4 nuclease with nuclear localization signals added at both the N- and C-termini.

SEQ ID NOs: 97-98 show the nucleotide sequences of MG3-6/3-4 sgRNAs targeting mouse albumin intron 1.

DETAILED DESCRIPTION

While various embodiments of the disclosure have been shown and described herein, it will be obvious to those skilled in the art that such embodiments are provided by way of example only. Numerous variations, changes, and substitutions may occur to those skilled in the art without departing from the disclosure. It should be understood that various alternatives to the embodiments of the disclosure described herein may be employed.

The practice of some methods disclosed herein employ, unless otherwise indicated, techniques of immunology, biochemistry, chemistry, molecular biology, microbiology, cell biology, genomics, and recombinant DNA. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R.I. Freshney, ed. (2010)).

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within one or more than one standard deviation, per the practice in the art. Alternatively, "about" can mean a range of up to 20%, up to 15%, up to 10%, up to 5%, or up to 1% of a given value.

The term "nucleotide," as used herein, refers to a base-sugar-phosphate combination. Contemplated nucleotides include naturally occurring nucleotides and synthetic nucleotides. Nucleotides are monomeric units of a nucleic acid sequence (e.g., deoxyribonucleic acid (DNA) and ribonucleic acid (RNA)). The term nucleotide includes ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP, and nucleotide derivatives that confer nuclease resistance on the nucleic acid molecule containing them. The term nucleotide as used herein encompasses dideoxyribonucleoside triphosphates (ddNTPs) and their derivatives. Illustrative examples of ddNTPs include, but are not limited to, ddATP, ddCTP, ddGTP, ddITP, and ddTTP. A nucleotide may be unlabeled or detectably labeled, such as using moieties comprising optically detectable moieties (e.g., fluorophores) or quantum dots. Detectable labels include, for example, radioactive isotopes, fluorescent labels, chemiluminescent labels, bioluminescent labels, and enzyme labels. Fluorescent labels of nucleotides include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo)benzoic acid (DABCYL), Cascade Blue, Oregon Green, Texas Red, Cyanine and 5-(2'-aminoethyl) aminonaphthalene-1-sulfonic acid (EDANS). Specific examples of fluorescently labeled nucleotides include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAMRA]ddGTP, [ROX]ddTTP, [dR6G]ddATP, [dR110]ddCTP, [dTAMRA]ddGTP, and [dROX]ddTTP available from Perkin Elmer, Foster City, Calif; FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, IL; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. The term nucleotide encompasses chemically modified nucleotides. An exemplary chemically-modified nucleotide is biotin-dNTP. Non-limiting examples of biotinylated dNTPs include, biotin-dATP (e.g., bio-N6-ddATP, biotin-14-dATP), biotin-dCTP (e.g., biotin-11-dCTP, biotin-14-dCTP), and biotin-dUTP (e.g., biotin-11-dUTP, biotin-16-dUTP, biotin-20-dUTP).

The terms "polynucleotide," "oligonucleotide," and "nucleic acid" are used interchangeably to refer to a polymeric form of nucleotides of any length, either deoxyribonucleotides or ribonucleotides, or analogs thereof, either in single-, double-, or multi-stranded form. Contemplated polynucleotides include a gene or fragment thereof. Exemplary polynucleotides include, but are not limited to, DNA, RNA, coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, cell-free polynucleotides including cell-free DNA (cfDNA) and cell-free RNA (cfRNA), nucleic acid probes, and primers. In a polynucleotide when referring to a T, a T means U (Uracil) in RNA and T (Thymine) in DNA. A polynucleotide can be exogenous or endogenous to a cell and/or exist in a cell-free environment. The term polynucleotide encompasses modified polynucleotides (e.g., altered backbone, sugar, or nucleobase). If present, modifications to the nucleotide structure are imparted before or after assembly of the polymer. Non-limiting examples of modifications include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol-containing nucleotides, biotin-linked nucleotides, fluorescent base analogs, CpG islands, methyl-7-guanosine, methylated nucleotides, inosine, thiouridine, pseudouridine, dihydrouridine, queuosine, and wyosine. The sequence of nucleotides may be interrupted by non-nucleotide components.

The terms "transfection" or "transfected" refer to introduction of a polynucleotide into a cell by non-viral or viral-based methods. The polynucleotides may be gene sequences encoding complete proteins or functional portions thereof. See, e.g., Sambrook et al., 1989, Molecular Cloning: A Laboratory Manual, 18.1-18.88.

The terms "peptide," "polypeptide," and "protein" are used interchangeably herein to refer to a polymer of at least two amino acid residues joined by peptide bond(s). This term does not connote a specific length of polymer, nor is it intended to imply or distinguish whether the peptide is produced using recombinant techniques, chemical or enzymatic synthesis, or is naturally occurring. The terms apply to naturally occurring amino acid polymers as well as amino acid polymers comprising at least one modified amino acid. In some cases, the polymer is interrupted by non-amino acids. The terms include amino acid chains of any length, including full length proteins, and proteins with or without secondary or tertiary structure (e.g., domains). The terms also encompass an amino acid polymer that has been modified, for example, by disulfide bond formation, glycosylation, lipidation, acetylation, phosphorylation, oxidation, and any other manipulation such as conjugation with a labeling component. The terms "amino acid" and "amino acids," as used herein, refer to natural and non-natural amino acids, including, but not limited to, modified amino acids. Modified amino acids include amino acids that have been chemically modified to include a group or a chemical moiety not naturally present on the amino acid. The term "amino acid" includes both D-amino acids and L-amino acids.

As used herein, the "non-native" refers to a nucleic acid or polypeptide sequence that is non-naturally occurring. Non-native refers to a non-naturally occurring nucleic acid or polypeptide sequence that comprises modifications such as mutations, insertions, or deletions. The term non-native encompasses fusion nucleic acids or polypeptides that encodes or exhibits an activity (e.g., enzymatic activity, methyltransferase activity, acetyltransferase activity, kinase activity, ubiquitinating activity, etc.) of the nucleic acid or polypeptide sequence to which the non-native sequence is fused. A non-native nucleic acid or polypeptide sequence includes those linked to a naturally-occurring nucleic acid or polypeptide sequence (or a variant thereof) by genetic engineering to generate a chimeric nucleic acid or polypeptide sequence encoding a chimeric nucleic acid or polypeptide.

The term "promoter", as used herein, refers to the regulatory DNA region which controls transcription or expression of a polynucleotide (e.g., a gene) and which may be located adjacent to or overlapping a nucleotide or region of nucleotides at which RNA transcription is initiated. A promoter may contain specific DNA sequences which bind protein factors, often referred to as transcription factors, which facilitate binding of RNA polymerase to the DNA leading to gene transcription. Eukaryotic basal promoters typically, though not necessarily, contain a TATA-box and/or a CAAT box.

The term "expression", as used herein, refers to the process by which a nucleic acid sequence or a polynucleotide is transcribed from a DNA template (such as into mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, the term expression includes splicing of the mRNA in a eukaryotic cell.

As used herein, "operably linked", "operable linkage", "operatively linked", or grammatical equivalents thereof refer to an arrangement of genetic elements, e.g., a promoter, an enhancer, a polyadenylation sequence, etc., wherein an operation (e.g., movement or activation) of a first genetic element has some effect on the second genetic element. The effect on the second genetic element can be, but need not be, of the same type as operation of the first genetic element. For example, two genetic elements are operably linked if movement of the first element causes an activation of the second element. For instance, a regulatory element, which may comprise promoter and/or enhancer sequences, is operatively linked to a coding region if the regulatory element helps initiate transcription of the coding sequence. There may be intervening residues between the regulatory element and coding region so long as this functional relationship is maintained.

A "vector" as used herein, refers to a macromolecule or association of macromolecules that comprises or associates with a polynucleotide and which mediates delivery of the polynucleotide to a cell. Examples of vectors include nucleic-based vectors (e.g., plasmids and viral vectors) and liposomes. An exemplary nucleic-acid based vector comprises genetic elements, e.g., regulatory elements, operatively linked to a gene to facilitate expression of the gene in a target.

As used herein, "expression cassette" and "nucleic acid cassette" are used interchangeably to refer to a component of a vector comprising a combination of nucleic acid sequences or elements (e.g., therapeutic gene, promoter, and a terminator) that are expressed together or are operably linked for expression. The terms encompass an expression cassette including a combination of regulatory elements and a gene or genes to which they are operably linked for expression.

A "functional fragment" of a DNA or protein sequence refers to a fragment that retains a biological activity (either functional or structural) that is substantially similar to a biological activity of the full-length DNA or protein sequence. A biological activity of a DNA sequence includes its ability to influence expression in a manner attributed to the full-length sequence.

The terms "engineered," "synthetic," and "artificial" are used interchangeably herein to refer to an object that has been modified by human intervention. For example, the terms refer to a polynucleotide or polypeptide that is non-naturally occurring. An engineered peptide has, but does not require, low sequence identity (e.g., less than 50% sequence identity, less than 25% sequence identity, less than 10% sequence identity, less than 5% sequence identity, less than 1% sequence identity) to a naturally occurring human protein. For example, VPR and VP64 domains are synthetic transactivation domains. Non-limiting examples include the following: a nucleic acid modified by changing its sequence to a sequence that does not occur in nature; a nucleic acid modified by ligating it to a nucleic acid that it does not associate with in nature such that the ligated product possesses a function not present in the original nucleic acid; an engineered nucleic acid synthesized in vitro with a sequence that does not exist in nature; a protein modified by changing its amino acid sequence to a sequence that does not exist in nature; an engineered protein acquiring a new function or property. An "engineered" system comprises at least one engineered component.

The term "tracrRNA" or "tracr sequence" means trans-activating CRISPR RNA. tracrRNA interacts with the CRISPR (cr) RNA to form guide (g) RNA in type II and subtype V-B CRISPR-Cas systems. If the tracrRNA is engineered, it may have about 5%, 10%, 20%, 30%, 40%, 50%, 60%, 70%, 80%, 90%, 95%, or 100% sequence identity and/or sequence similarity to a wild type exemplary tracrRNA sequence (e.g., a tracrRNA from *S. pyogenes, S. aureus*). tracrRNA may refer to a modified form of a tracrRNA that can comprise a nucleotide change such as a deletion, insertion, or substitution, variant, mutation, or chimera. The term tracrRNA encompasses a nucleic acid that can be at least about 60% identical to a wild type exemplary tracrRNA (e.g., a tracrRNA from *S. pyogenes, S. aureus*, etc) sequence over a stretch of at least 6 contiguous nucleotides. For example, a tracrRNA sequence has at least about 60% identical, at least about 65% identical, at least about 70% identical, at least about 75% identical, at least about 80% identical, at least about 85% identical, at least about 90% identical, at least about 95% identical, at least about 98% identical, at least about 99% identical, or 100% identical to a wild type exemplary tracrRNA (e.g., a tracrRNA from *S. pyogenes, S. aureus*, etc) sequence over a stretch of at least 6 contiguous nucleotides. Type II tracrRNA sequences can be predicted on a genome sequence by identifying regions with complementarity to part of the repeat sequence in an adjacent CRISPR array.

As used herein, a "guide nucleic acid" or "guide polynucleotide" refers to a nucleic acid that may hybridize to a target nucleic acid and thereby directs an associated nuclease to the target nucleic acid. A guide nucleic acid is, but is not limited to, RNA (guide RNA or gRNA), DNA, or a mixture of RNA and DNA. A guide nucleic acid can include a crRNA or a tracrRNA or a combination of both. The term guide nucleic acid encompasses an engineered guide nucleic acid and a programmable guide nucleic acid to specifically bind to the target nucleic acid. A portion of the target nucleic acid may be complementary to a portion of the guide nucleic acid. The strand of a double-stranded target polynucleotide that is complementary to and hybridizes with the guide nucleic acid is the complementary strand. The strand of the double-stranded target polynucleotide that is complementary to the complementary strand, and therefore is not complementary to the guide nucleic acid is called non-complementary strand. A guide nucleic acid having a polynucleotide chain is a "single guide nucleic acid." A guide nucleic acid having two polynucleotide chains is a "double guide nucleic acid." If not otherwise specified, the term "guide nucleic acid" is inclusive, referring to both single guide nucleic acids and double guide nucleic acids. A guide nucleic acid may comprise a segment referred to as a "nucleic acid-targeting segment" or a "nucleic acid-targeting sequence," or a "spacer." A nucleic acid-targeting segment can include a sub-segment referred to as a "protein binding segment" or "protein binding sequence" or "Cas protein binding segment."

As used herein, the term "Cas12a" refers to a family of Cas endonucleases that are class 2, Type V-A Cas endonucleases and that (a) use a relatively small guide RNA (about 42-44 nucleotides) that is processed by the nuclease itself following transcription from the CRISPR array, and (b) cleave DNA to leave staggered cut sites.

As used herein, the term "RuvC_III domain" refers to a third discontinuous segment of a RuvC endonuclease domain (the RuvC nuclease domain being comprised of three discontiguous segments, RuvC_I, RuvC_II, and RuvC_III). A RuvC domain or segments thereof can generally be identified by alignment to documented domain sequences, structural alignment to proteins with annotated domains, or by comparison to Hidden Markov Models (HMMs) built based on documented domain sequences (e.g., Pfam HMM PF18541 for RuvC_III).

As used herein, the term "Wedge" (WED) domain refers to a domain (e.g., present in a Cas protein) interacting primarily with repeat:anti-repeat duplex of the sgRNA and PAM duplex. A WED domain can generally be identified by alignment to documented domain sequences, structural alignment to proteins with annotated domains, or by comparison to Hidden Markov Models (HMMs) built based on documented domain sequences.

As used herein, the term "PAM interacting domain" or "PI domain" refers to a domain interacting with the protospacer-adjacent motif (PAM) external to the seed sequence in a region targeted by a Cas protein. Examples of PAM-interacting domains include, but are not limited to, Topoisomerase-homology (TOPO) domains and C-terminal domains (CTD) present in Cas proteins. A PAM interacting domain or segments thereof can generally be identified by alignment to documented domain sequences, structural alignment to proteins with annotated domains, or by comparison to Hidden Markov Models (HMMs) built based on documented domain sequences.

As used herein, the term "REC domain" refers to a domain (e.g., present in a Cas protein) comprising at least one of two segments (REC1 or REC2) that are alpha helical domains thought to contact the guide RNA. A REC domain or segments thereof can generally be identified by alignment to documented domain sequences, structural alignment to proteins with annotated domains, or by comparison to Hidden Markov Models (HMMs) built based on documented domain sequences (e.g., Pfam PF19501 for domain REC1).

As used herein, the term "BH domain" refers to a domain (e.g., present in a Cas protein) that is a bridge helix between NUC and REC lobes of a Type II Cas enzyme. A BH domain or segments thereof can generally be identified by alignment to documented domain sequences, structural alignment to proteins with annotated domains, or by comparison to Hidden Markov Models (HMMs) built based on documented domain sequences (e.g., Pfam PF16593 for domain BH).

As used herein, the term "HNH domain" refers to an endonuclease domain having characteristic histidine and asparagine residues. An HNH domain can generally be identified by alignment to documented domain sequences, structural alignment to proteins with annotated domains, or by comparison to Hidden Markov Models (HMMs) built based on documented domain sequences (e.g., Pfam HMM PF01844 for domain HNH).

"Factor VIII" or "FVIII" refers to an anti-hemophilic factor (i.e. blood clotting or coagulation protein) encoded by the FVIII gene. In its inactive form, Factor VIII is bound to von Willebrand factor. In response to an injury, the two factors separate, and FVIII activates and interacts with FIX to initiate the chain of chemical reactions that lead to a blood clot. Genetic deficiency in Factor VIII result in hemophilia A.

The term "donor template" refers to a polynucleotide that includes an exogenous polynucleotide sequence (e.g., a nucleic acid sequence for a therapeutic gene) and one or more polynucleotide sequences for mediating recombination such as by non-homologous end joining (NHEJ) or homology directed repair (HDR).

As used herein, the term "complex" refers to a joining of at least two components. The two components may each retain the properties/activities they had prior to forming the complex or gain properties as a result of forming the complex. The joining includes, but is not limited to, covalent bonding, non-covalent bonding (i.e., hydrogen bonding, ionic interactions, Van der Waals interactions, and hydrophobic bond), use of a linker, fusion, or any other suitable method. Contemplated components of the complex include polynucleotides, polypeptides, or combinations thereof. For example, a complex comprises an endonuclease and a guide polynucleotide.

The term "sequence identity" or "percent identity" in the context of two or more nucleic acids or polypeptide sequences, refers to two (e.g., in a pairwise alignment) or more (e.g., in a multiple sequence alignment) sequences that are the same or have a specified percentage of amino acid residues or nucleotides that are the same, when compared and aligned for maximum correspondence over a local or global comparison window, as measured using a sequence comparison algorithm. Suitable sequence comparison algorithms for polypeptide sequences include, e.g., BLASTP using parameters of a wordlength (W) of 3, an expectation (E) of 10, and the BLOSUM62 scoring matrix setting gap costs at existence of 11, extension of 1, and using a conditional compositional score matrix adjustment for polypeptide sequences longer than 30 residues; BLASTP using parameters of a wordlength (W) of 2, an expectation (E) of 1000000, and the PAM30 scoring matrix setting gap costs at 9 to open gaps and 1 to extend gaps for sequences of less than 30 residues (these are the default parameters for BLASTP in the BLAST suite available at blast.ncbi.nlm.nih.gov); CLUSTALW with the Smith-Waterman homology search algorithm parameters with a match of 2, a mismatch of −1, and a gap of −1; MUSCLE with default parameters; MAFFT with parameters of a retree of 2 and max iterations of 1000; Novafold with default parameters; HMMER hmmalign with default parameters.

The term "optimally aligned" in the context of two or more nucleic acids or polypeptide sequences, refers to two (e.g., in a pairwise alignment) or more (e.g., in a multiple sequence alignment) sequences that have been aligned to maximal correspondence of amino acids residues or nucleotides, for example, as determined by the alignment producing a highest or "optimized" percent identity score.

Included in the current disclosure are variants of any of the enzymes described herein with one or more conservative amino acid substitutions. Such conservative substitutions can be made in the amino acid sequence of a polypeptide without disrupting the three-dimensional structure or function of the polypeptide. Conservative substitutions can be accomplished by substituting amino acids with similar hydrophobicity, polarity, and R chain length for one another. Additionally, or alternatively, by comparing aligned sequences of homologous proteins from different species, conservative substitutions can be identified by locating amino acid residues that have been mutated between species (e.g., non-conserved residues) without altering the basic functions of the encoded proteins. Such conservatively substituted variants may include variants with at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% identity to any one of the endonuclease protein sequences described herein (e.g. MG3 or MG29 family endonucleases described herein, or any other family nuclease described herein). In some embodiments, such conservatively substituted variants are functional variants. Such functional variants can encompass sequences with substitutions such that the activity of one or more critical active site residues or guide RNA binding residues of the endonuclease are not disrupted. In some embodiments, a functional variant of any of the proteins described herein lacks substitution of at least one conserved or functional residue.

Also included in the current disclosure are variants of any of the enzymes described herein with substitution of one or more catalytic residues to decrease or eliminate activity of the enzyme (e.g. decreased-activity variants). In some embodiments, a decreased activity variant as a protein described herein comprises a disrupting substitution of at least one, at least two, or all three catalytic residues.

Conservative substitution tables providing functionally similar amino acids are available from a variety of references (see, for e.g., Creighton, Proteins: Structures and Molecular Properties (W H Freeman & Co.; 2nd edition (December 1993)). The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

Overview

Treatment of diseases and disorders caused by a genetic defect can include correcting the genetic defect using gene editing systems. This can be done by integrating a copy of the gene into the genome at an appropriate site and in the appropriate cells or tissue such that the gene is expressed and produces functional protein.

Hemophilia A is caused by mutations in the Factor VIII (FVIII) gene that reduce the expression of FVIII or inactivate the function of the FVIII protein. Because many different mutations in FVIII are responsible for hemophilia A, gene therapy approaches that are not specific for individual mutations are preferred. A promising approach is complementation of the defective genomic copy of FVIII with a functional transgenic copy of the gene. In one embodiment of this approach, a functional copy of the FVIII gene is delivered to the hepatocytes of the liver by systemic (e.g. intravenous) administration of a vector comprising a nuclease and a guide polynucleotide that targets a target nucleic acid at a safe harbor locus, such as the albumin locus. The FVIII gene is then integrated at the break created by the nuclease into the target nucleic acid via non-homologous end joining (NHEJ) or homology directed repair (HDR), a combination of the two DNA repair mechanisms, or by other DNA repair mechanisms.

CRISPR/Cas Enzymes

The discovery of new Cas enzymes with unique functionality and structure offers the potential to further gene editing technologies, improving speed, specificity, functionality, and ease of use. Relative to the predicted prevalence of Clustered Regularly Interspaced Short Palindromic Repeats (CRISPR) systems in microbes and the sheer diversity of microbial species, relatively few functionally characterized CRISPR/Cas enzymes exist in the literature. This is partly because a huge number of microbial species may not be readily cultivated in laboratory conditions. Metagenomic sequencing from natural environmental niches containing large numbers of microbial species may offer the potential to drastically increase the number of new CRISPR/Cas systems characterized and speed the discovery of new oligonucleotide editing functionalities. A recent example of the fruitfulness of such an approach is demonstrated by the 2016 discovery of CasX/CasY CRISPR systems from metagenomic analysis of natural microbial communities.

CRISPR/Cas systems are RNA-directed nuclease complexes that function as an adaptive immune system in microbes. In their natural context, CRISPR/Cas systems occur in CRISPR (clustered regularly interspaced short palindromic repeats) operons or loci, which generally are made up of two parts: (i) an array of short repetitive sequences (30-40 bp) separated by short spacer sequences, which encode the RNA-based targeting element; and (ii) ORFs encoding the Cas nuclease. Efficient nuclease targeting of a particular target nucleic acid sequence generally requires both (i) complementary hybridization between the first 6-8 nucleic acids of the target nucleic acid and a crRNA guide; and (ii) presence of a protospacer-adjacent motif (PAM) sequence within a certain vicinity of the target nucleic acid sequence depending on the specific Cas nuclease (the PAM usually being a sequence not commonly represented within the host genome). Depending on the exact function and organization of the system, CRISPR-Cas systems are commonly organized into 2 classes, 5 types and 16 subtypes based on shared functional characteristics and evolutionary similarity.

Class 1 CRISPR-Cas systems have large, multi-subunit effector complexes, and include Types I, III, and IV Cas nucleases. Class 2 CRISPR-Cas systems generally have single-polypeptide multidomain nuclease effectors, and include Types II, V and VI Cas nucleases.

Type I CRISPR-Cas systems are considered of moderate complexity in terms of components. In Type I CRISPR-Cas systems, the array of RNA-targeting elements is transcribed as a long precursor crRNA (pre-crRNA) that is processed at repeat elements to liberate short, mature crRNAs that direct the nuclease complex to nucleic acid targets when they are followed by a suitable short consensus sequence called a protospacer-adjacent motif (PAM). This processing occurs via an endoribonuclease subunit (Cas6) of a large endonuclease complex called Cascade, which also includes a nuclease (Cas3) protein component of the crRNA-directed nuclease complex. Cas I nucleases function primarily as DNA nucleases.

Type III CRISPR systems are characterized by the presence of a central nuclease, known as Cas10, alongside a repeat-associated mysterious protein (RAMP) that includes Csm or Cmr protein subunits. Like in Type I systems, the mature crRNA is processed from a pre-crRNA using a Cas6-like enzyme. Unlike Type I and II systems, type III systems appear to target and cleave DNA-RNA duplexes (such as DNA strands being used as templates for an RNA polymerase).

Type IV CRISPR-Cas systems possess an effector complex that consists of a highly reduced large subunit nuclease (csf1), two genes for RAMP proteins of the Cas5 (csf3) and Cas7 (csf2) groups, and, in some cases, a gene for a predicted small subunit; such systems are commonly found on endogenous plasmids.

Class 2 CRISPR-Cas systems generally have single-polypeptide multidomain nuclease effectors, and include Types II, V, and VI.

Type II CRISPR-Cas systems are considered the simplest in terms of components. In Type II CRISPR-Cas systems, the processing of the CRISPR array into mature crRNAs does not require the presence of a special endonuclease subunit, but rather a small trans-encoded crRNA (tracrRNA) with a region complementary to the array repeat sequence; the tracrRNA interacts with both its corresponding effector nuclease (e.g. Cas9) and the repeat sequence to form a precursor dsRNA structure, which is cleaved by endogenous RNAse III to generate a mature effector enzyme loaded with both tracrRNA and crRNA. Cas II nucleases are identified as DNA nucleases. Type 2 effectors generally exhibit a structure comprising a RuvC-like endonuclease domain that adopts the RNase H fold with an unrelated HNH nuclease domain inserted within the folds of the RuvC-like nuclease domain. The RuvC-like domain is responsible for the cleavage of the target (e.g., crRNA complementary) DNA strand, while the HNH domain is responsible for cleavage of the displaced DNA strand.

Type V CRISPR-Cas systems are characterized by a nuclease effector (e.g. Cas12) structure similar to that of Type II effectors, comprising a RuvC-like domain. Similar to Type II, most (but not all) Type V CRISPR systems use a tracrRNA to process pre-crRNAs into mature crRNAs. However, unlike Type II systems which requires RNAse III to cleave the pre-crRNA into multiple crRNAs. Type V systems are capable of using the effector nuclease itself to cleave pre-crRNAs. Like Type-II CRISPR-Cas systems, Type V CRISPR-Cas systems are again identified as DNA nucleases. Unlike Type II CRISPR-Cas systems, some Type V enzymes (e.g., Cas12a) appear to have a robust single-stranded nonspecific deoxyribonuclease activity that is activated by the first crRNA directed cleavage of a double-stranded target sequence.

Type VI CRISPR-Cas systems have RNA-guided RNA endonucleases. Instead of RuvC-like domains, the single polypeptide effector of Type VI systems (e.g. Cas13) include two HEPN ribonuclease domains. Differing from both Type II and V systems, Type VI systems also appear to not require a tracrRNA for processing of pre-crRNA into crRNA. Similar to Type V systems, however, some Type VI systems (e.g., C2C2) appear to possess robust single-stranded nonspecific nuclease (ribonuclease) activity activated by the first crRNA directed cleavage of a target RNA.

Gene Editing Systems

Described herein, in certain embodiments, are engineered nuclease systems, comprising: a) an endonuclease; b) an engineered guide polynucleotide configured to form a complex with the endonuclease and to hybridize to a target nucleic acid sequence within an albumin gene or within an intron of the albumin gene; and c) a donor template comprising a nucleic acid sequence encoding a Factor VIII (FVIII) gene or a functional fragment thereof.

MG Endonucleases

Disclosed herein are systems and methods for supplementation of liver enzymes. In some embodiments, the systems and methods comprise an endonuclease. In some embodiments, the endonucleases are functional in prokaryotic or eukaryotic cells for in vitro, in vivo, or ex vivo applications. In some embodiments, the endonucleases are nucleic acid guided nucleases, chimeric nucleases, or fusion nucleases.

In some embodiments, the endonuclease is MG29-1 (i.e., SEQ ID NO: 54). In some embodiments, the endonuclease is MG3-6/3-4 (i.e., SEQ ID NO: 96). MG29-1 is a type V CRISPR nuclease, and MG3-6/3-4 is a type II CRISPR nuclease that was created by exchanging the PAM-interacting domain (PID) of MG3-6 with the PID of MG3-4 to alter the PAM recognition specificity. In some embodiments, the PAM for MG29-1 is functionally defined in mammalian cells as KTTN (K=G or T, N=any base). In some embodiments, the PAM for MG3-6 or MG3-4 is functionally defined in mammalian cells as AAANN (N=any base).

In some embodiments, the endonuclease comprises a sequence having at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity sequence identity to SEQ ID NO: 54 or SEQ ID NO: 96. In some embodiments, the endonuclease comprises a sequence having at least about 70% identity to any one of SEQ ID NOs: 54 and 96. In some embodiments, the endonuclease comprises a sequence having at least about 75% identity to SEQ ID NO: 54 or SEQ ID NO: 96. In some embodiments, the endonuclease comprises a sequence having at least about 80% identity to SEQ ID NO: 54 or SEQ ID NO: 96. In some embodiments, the endonuclease comprises a sequence having at least about 85% identity to SEQ ID NO: 54 or SEQ ID NO: 96. In some embodiments, the endonuclease comprises a sequence having at least about 90% identity to SEQ ID NO: 54 or SEQ ID NO: 96. In some embodiments, the endonuclease comprises a sequence having at least about 95% identity to SEQ ID NO: 54 or SEQ ID NO: 96. In some embodiments, the endonuclease comprises a sequence having at least about 96% identity to SEQ ID NO: 54 or SEQ ID NO: 96. In some embodiments, the endonuclease comprises a sequence having at least about 97% identity to SEQ ID NO: 54 or SEQ ID NO: 96. In some embodiments, the endonuclease comprises a sequence having at least about 98% identity to SEQ ID NO: 54 or SEQ ID NO: 96. In some embodiments, the endonuclease comprises a sequence having at least about 99% identity to SEQ ID NO: 54 or SEQ ID NO: 96. In some embodiments, the endonuclease comprises a sequence having 100% identity to SEQ ID NO: 54 or SEQ ID NO: 96.

In some embodiments, the endonuclease is encoded by a nucleic acid sequence having at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity sequence identity to any one of SEQ ID NOs: 30, 31, 53, and 95. In some embodiments, the endonuclease is encoded by a nucleic acid sequence having at least about 70% identity to any one of SEQ ID NOs: 30, 31, 53, and 95. In some embodiments, the endonuclease is encoded by a nucleic acid sequence having at least about 75% identity to any one of SEQ ID NOs: 30, 31, 53, and 95. In some embodiments, the endonuclease is encoded by a nucleic acid sequence having at least about 80% identity to any one of SEQ ID NOs: 30, 31, 53, and 95. In some embodiments, the endonuclease is encoded by a nucleic acid sequence having at least about 85% identity to any one of SEQ ID NOs: 30, 31, 53, and 95. In some embodiments, the endonuclease is encoded by a nucleic acid sequence having at least about 90% identity to any one of SEQ ID NOs: 30, 31, 53, and 95. In some embodiments, the endonuclease is encoded by a nucleic acid sequence having at least about 95% identity to any one of SEQ ID NOs: 30, 31, 53, and 95. In some embodiments, the endonuclease is encoded by a nucleic acid sequence having at least about 96% identity to any one of SEQ ID NOs: 30, 31, 53, and 95. In some embodiments, the endonuclease is encoded by a nucleic acid sequence having at least about 97% identity to any one of SEQ ID NOs: 30, 31, 53, and 95. In some embodiments, the endonuclease is encoded by a nucleic acid sequence having at least about 98% identity to any one of SEQ ID NOs: 30, 31, 53, and 95. In some embodiments, the endonuclease is encoded by a nucleic acid sequence having at least about 99% identity to any one of SEQ ID NOs: 30, 31, 53, and 95. In some embodiments, the endonuclease is encoded by a nucleic acid sequence having 100% identity to any one of SEQ ID NOs: 30, 31, 53, and 95.

In some embodiments, the endonuclease comprises one or more fragments or domains of a nuclease, such as nucleic acid-guided nuclease. In some embodiments, the endonuclease comprises one or more fragments or domains of a nuclease from orthologs of organisms, genus, species, or other phylogenetic groups described herein. In some embodiments, the endonuclease comprises one or more fragments or domains from nuclease orthologs of different species.

In some embodiments, the endonuclease comprises one or more fragments or domains of a nuclease, such as nucleic acid-guided nuclease. In some embodiments, the endonuclease comprises one or more fragments or domains of a nuclease from orthologs of organisms, genus, species, or other phylogenetic groups described herein. In some embodiments, the endonuclease comprises one or more fragments or domains from nuclease orthologs of different species.

In some embodiments, the endonuclease comprises one or more fragments or domains from at least two different nucleases. In some embodiments, the endonuclease comprises one or more fragments or domains from at least 2, 3, 4, 5, 6, 7, 8, 9, 10, or more different nucleases. In some embodiments, the endonuclease comprises one or more fragments or domains from at least 2, 3, 4, 5, 6, 7, 8, 9, 10, or more nucleases from different species. In some embodiments, the endonuclease comprises 2 fragments or domains, each from a different nuclease. In some embodiments, the endonuclease comprises 3 fragments or domains, each from a different nuclease. In some embodiments, the endonuclease comprises 4 fragments or domains, each from a different nuclease. In some embodiments, the endonuclease comprises 5 fragments or domains, each from a different nuclease. In some embodiments, the endonuclease comprises 3 fragments or domains, wherein at least one fragment or domain is from a different nuclease. In some embodiments, the endonuclease comprises 4 fragments or domains, wherein at least one fragment or domain is from a different nuclease. In some embodiments, the endonuclease comprises 5 fragments or domains, wherein at least one fragment or domain is from a different nuclease.

In some embodiments, junctions between fragments or domains from different nucleases or species occur in stretches of unstructured regions. Unstructured regions in polynucleotides include, for example, regions that have no predicted secondary structure elements such as alpha helices or beta strands. Unstructured regions may include for example, regions which are exposed within a protein structure, loop regions, or regions that are not conserved within various protein orthologs as predicted by sequence or structural alignments.

In some embodiments, the endonuclease comprises one or more nuclear localization sequences (NLSs) proximal to an N- or C-terminus of the endonuclease. In some embodiments, the NLS comprises a sequence of any one of SEQ ID NOs: 144-159. In some embodiments, the NLS comprises a sequence of any one of SEQ ID NOs: 144-159, or a sequence having at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identity to any one of SEQ ID NOs: 144-159. In some embodiments, the NLS comprises a sequence having at least about 80% identity to SEQ ID NOs: 144-159. In some embodiments, the NLS comprises a sequence having at least about 85% identity to SEQ ID NOs: 144-159. In some embodiments, the NLS comprises a sequence having at least about 90% identity to SEQ ID NOs: 144-159. In some embodiments, the NLS comprises a sequence having at least about 91% identity to SEQ ID NOs: 144-159. In some embodiments, the NLS comprises a sequence having at least about 92% identity to SEQ ID NOs: 144-159. In some embodiments, the NLS comprises a sequence having at least about 93% identity to SEQ ID NOs: 144-159. In some embodiments, the NLS comprises a sequence having at least about 94% identity to SEQ ID NOs: 144-159. In some embodiments, the NLS comprises a sequence having at least about 95% identity to SEQ ID NOs: 144-159. In some embodiments, the NLS comprises a sequence having at least about 96% identity to SEQ ID NOs: 144-159. In some embodiments, the NLS comprises a sequence having at least about 97% identity to SEQ ID NOs: 144-159. In some embodiments, the NLS comprises a sequence having at least about 98% identity to SEQ ID NOs: 144-159. In some embodiments, the NLS comprises a sequence having at least about 99% identity to SEQ ID NOs: 144-159. In some embodiments, the NLS comprises a sequence having 10000 identity to SEQ ID NOs: 144-159.

TABLE 1A

Examples NLS Sequences that are used with Cas effectors according to the present disclosure.

| Source | NLS amino acid sequence | SEQ ID NO: |
|---|---|---|
| SV40 NLS | PKKKRKV | 144 |
| nucleoplasmin bipartite | KRPAATKKAGQAKKKK | 145 |
| c-myc | PAAKRVKLD | 146 |
| c-myc | RQRRNELKRSP | 147 |
| hnRNPA1 M9 | NQSSNFGPMKGGNFGGRSSG PYGGGGQYFAKPRNQGGY | 148 |
| Importin-alpha IBB domain | RMRIZFKNKGKDTAELRRRRV EVSVELRKAKKDEQILKRRNV | 149 |

TABLE 1A-continued

Examples NLS Sequences that are used with Cas effectors according to the present disclosure.

| Source | NLS amino acid sequence | SEQ ID NO: |
|---|---|---|
| Myoma T protein | VSRKRPRP | 150 |
| Myoma T protein | PPKKARED | 151 |
| p53 | PQPKKKPL | 152 |
| mouse c-abl IV | SALIKKKKKMAP | 153 |
| influenza virus NS1 | DRLRR | 154 |
| influenza virus NS1 | PKQKKRK | 155 |
| Hepatitis virus delta antigen | RKLKKKIKKL | 156 |
| mouse Mx1 protein | REKKKFLKRR | 157 |
| human poly(ADP-ribose) polymerase | KRKGDEVDGVDEVAKKKSKK | 158 |
| steroid hormone receptors glucocorticoid | RKCLQAGMNLEARKTKK | 159 |

Guide Polynucleotides

The systems and methods for supplementing liver enzymes, described herein, may comprise guide polynucleotides e.g., a guide ribonucleic acid (gRNA), a single gRNA, or a dual guide RNA for supplementing liver enzymes. In a polynucleotide when referring to a T, a T means U (Uracil) in RNA and T (Thymine) in DNA.

In some embodiments, the target gene or locus is albumin. In some embodiments, the guide polynucleotide targets or hybridizes to a target nucleic acid sequence in albumin. In some embodiments, the guide polynucleotide targets or hybridizes to a target nucleic acid sequence in intron 1 in albumin. In some embodiments, the guide polynucleotide targets or hybridizes to a target nucleic acid sequence in exon 1 in albumin.

In some embodiments, the target gene or locus is albumin. In some embodiments, the guide polynucleotide targeting albumin is encoded by any one of SEQ ID NOs: 14-15, 24-27, 43-45, 50, 55, 60-68, and 97-98 or a sequence having at least 90%, 95%, 97%, 98%, or 99% sequence identity to any one of SEQ ID NOs: 14-15, 24-27, 43-45, 50, 55, 60-68, and 97-98. In some embodiments, the guide polynucleotide comprises a sequence comprising at least about 46-80 consecutive nucleotides having at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identity to any one of SEQ ID NOs: 14-15, 24-27, 43-45, 50, 55, 60-68, and 97-98. In some embodiments, the guide polynucleotide is encoded by a sequence having at least about 80% identity to any one of SEQ ID NOs: 14-15, 24-27, 43-45, 50, 55, 60-68, and 97-98. In some embodiments, the guide polynucleotide is encoded by a sequence having at least about 85% identity to any one of SEQ ID NOs: 14-15, 24-27, 43-45, 50, 55, 60-68, and 97-98. In some embodiments, the guide polynucleotide is encoded by a sequence having at least about 90% identity to any one of SEQ ID NOs: 14-15, 24-27, 43-45, 50, 55, 60-68, and 97-98. In some embodiments, the guide polynucleotide is encoded by a sequence having at least about 95% identity to any one of SEQ ID NOs: 14-15, 24-27, 43-45, 50, 55, 60-68, and 97-98. In some embodiments, the guide polynucleotide is encoded by a sequence having at least about 96% identity to any one of SEQ ID NOs: 14-15, 24-27, 43-45, 50, 55, 60-68, and 97-98. In some embodiments, the guide polynucleotide is encoded by a sequence having at least about 97% identity to any one of SEQ ID NOs: 14-15, 24-27, 43-45, 50, 55, 60-68, and 97-98. In some embodiments, the guide polynucleotide is encoded by a sequence having at least about 98% identity to any one of SEQ ID NOs: 14-15, 24-27, 43-45, 50, 55, 60-68, and 97-98. In some embodiments, the guide polynucleotide is encoded by a sequence having at least about 99% identity to any one of SEQ ID NOs: 14-15, 24-27, 43-45, 50, 55, 60-68, and 97-98. In some embodiments, the guide polynucleotide is encoded by a sequence having 100% identity to any one of SEQ ID NOs: 14-15, 24-27, 43-45, 50, 55, 60-68, and 97-98.

In some embodiments, the guide polynucleotide hybridizes or targets a sequence complementary to a target nucleic acid sequence within the albumin gene or within an intron of the albumin gene (e.g., SEQ ID NOs: 14-15, 24-27, 43-45, 50, 55, 60-68, and 97-98). In some embodiments, the guide polynucleotide hybridizes or targets a sequence complementary to any one of SEQ ID NOs: 14-15, 24-27, 43-45, 50, 55, 60-68, and 97-98 or a sequence having at least 90%, 95%, 97%, 98%, or 99% sequence identity to any one of SEQ ID NOs: 14-15, 24-27, 43-45, 50, 55, 60-68, and 97-98. In some embodiments, the guide polynucleotide hybridizes or targets a sequence complementary to a sequence having at least about 80% identity to any one of SEQ ID NOs: 14-15, 24-27, 43-45, 50, 55, 60-68, and 97-98. In some embodiments, the guide polynucleotide hybridizes or targets a sequence complementary to a sequence having at least about 85% identity to any one of SEQ ID NOs: 14-15, 24-27, 43-45, 50, 55, 60-68, and 97-98. In some embodiments, the guide polynucleotide hybridizes or targets a sequence complementary to a sequence having at least about 90% identity to any one of SEQ ID NOs: 14-15, 24-27, 43-45, 50, 55, 60-68, and 97-98. In some embodiments, the guide polynucleotide hybridizes or targets a sequence complementary to a sequence having at least about 95% identity to any one of SEQ ID NOs: 14-15, 24-27, 43-45, 50, 55, 60-68, and 97-98. In some embodiments, the guide polynucleotide hybridizes or targets a sequence complementary to a sequence having at least about 96% identity to any one of SEQ ID NOs: 14-15, 24-27, 43-45, 50, 55, 60-68, and 97-98. In some embodiments, the guide polynucleotide hybridizes or targets a sequence complementary to a sequence having at least about 97% identity to any one of SEQ ID NOs: 14-15, 24-27, 43-45, 50, 55, 60-68, and 97-98. In some embodiments, the guide polynucleotide hybridizes or targets a sequence complementary to a sequence having at least about 98% identity to any one of SEQ ID NOs: 14-15, 24-27, 43-45, 50, 55, 60-68, and 97-98. In some embodiments, the guide polynucleotide hybridizes or targets a sequence complementary to a sequence having at least about 99% identity to any one of SEQ ID NOs: 14-15, 24-27, 43-45, 50, 55, 60-68, and 97-98. In some embodiments, the guide polynucleotide hybridizes or targets a sequence complementary to a sequence having 100% identity to any one of SEQ ID NOs: 14-15, 24-27, 43-45, 50, 55, 60-68, and 97-98.

In some embodiments, the guide polynucleotide hybridizes or targets a sequence complementary to a target nucleic acid sequence within the albumin gene or within an intron of the albumin gene (e.g., SEQ ID NOs: 3-6). In some embodiments, the guide polynucleotide hybridizes or targets a sequence according to any one of SEQ ID NOs: 3-6 or a sequence having at least 90%, 95%, 97%, 98%, or 99% sequence identity to any one of SEQ ID NOs: 3-6. In some embodiments, the guide polynucleotide hybridizes or targets a sequence having at least about 80% identity to any one of SEQ ID NOs: 3-6. In some embodiments, the guide polynucleotide hybridizes or targets a sequence having at least about 85% identity to any one of SEQ ID NOs: 3-6. In some embodiments, the guide polynucleotide hybridizes or targets a sequence having at least about 90% identity to any one of SEQ ID NOs: 3-6. In some embodiments, the guide polynucleotide hybridizes or targets a sequence having at least about 95% identity to any one of SEQ ID NOs: 3-6. In some embodiments, the guide polynucleotide hybridizes or targets a sequence having at least about 96% identity to any one of SEQ ID NOs: 3-6. In some embodiments, the guide polynucleotide hybridizes or targets a sequence having at least about 97% identity to any one of SEQ ID NOs: 3-6. In some embodiments, the guide polynucleotide hybridizes or targets a sequence having at least about 98% identity to any one of SEQ ID NOs: 3-6. In some embodiments, the guide polynucleotide hybridizes or targets a sequence having at least about 99% identity to any one of SEQ ID NOs: 3-6. In some embodiments, the guide polynucleotide hybridizes or targets a sequence having 100% identity to any one of SEQ ID NOs: 3-6.

In some embodiments, the guide polynucleotide hybridizes or targets a sequence complementary to a target nucleic acid sequence within the albumin gene or within an intron of the albumin gene (e.g., SEQ ID NOs: 1, 2, and 8). In some embodiments, the guide polynucleotide hybridizes or targets a sequence according to any one of SEQ ID NOs: 1, 2, and 8 or a sequence having at least 90%, 95%, 97%, 98%, or 99% sequence identity to any one of SEQ ID NOs: 1, 2, and 8. In some embodiments, the guide polynucleotide hybridizes or targets a sequence having at least about 80% identity to any one of SEQ ID NOs: 1, 2, and 8. In some embodiments, the guide polynucleotide hybridizes or targets a sequence having at least about 85% identity to any one of SEQ ID NOs: 1, 2, and 8. In some embodiments, the guide polynucleotide hybridizes or targets a sequence having at least about 90% identity to any one of SEQ ID NOs: 1, 2, and 8. In some embodiments, the guide polynucleotide hybridizes or targets a sequence having at least about 95% identity to any one of SEQ ID NOs: 1, 2, and 8. In some embodiments, the guide polynucleotide hybridizes or targets a sequence having at least about 96% identity to any one of SEQ ID NOs: 1, 2, and 8. In some embodiments, the guide polynucleotide hybridizes or targets a sequence having at least about 97% identity to any one of SEQ ID NOs: 1, 2, and 8. In some embodiments, the guide polynucleotide hybridizes or targets a sequence having at least about 98% identity to any one of SEQ ID NOs: 1, 2, and 8. In some embodiments, the guide polynucleotide hybridizes or targets a sequence having at least about 99% identity to any one of SEQ ID NOs: 1, 2, and 8. In some embodiments, the guide polynucleotide hybridizes or targets a sequence having 100% identity to any one of SEQ ID NOs: 1, 2, and 8.

In some embodiments, the guide polynucleotide is configured to form a complex with the endonuclease. In some embodiments, the guide polynucleotide binds to the endonuclease to form a complex. In some embodiments, the guide polynucleotide binds (e.g., non-covalently through electrostatic interactions or hydrogen bonds) to the endonuclease to form a complex. In some embodiments, the guide polynucleotide is fused to the endonuclease to form a complex.

In some embodiments, the guide polynucleotide comprises a spacer sequence. In some embodiments, the spacer sequence is configured to hybridize to a target nucleic acid sequence. In some embodiments, the endonuclease is configured to bind to a protospacer adjacent motif (PAM) sequence.

In some embodiments, the guide polynucleotide (e.g., gRNA) targets a gene or locus in a cell. In some embodiments, the guide polynucleotide targets a gene or locus in a mammalian cell. In some embodiments, the mammalian cell is a pig, a cow, a goat, a sheep, a rodent, a rat, a mouse, a non-human primate, or a human cell.

In some embodiments, the guide polynucleotides (e.g., guide RNAs) comprise various structural elements including but not limited to: a spacer sequence which binds to the protospacer sequence (target sequence), a crRNA, and an optional tracrRNA. In some embodiments, the genome editing system comprises a CRISPR guide RNA. In some embodiments, the guide RNA comprises a crRNA comprising a spacer sequence. In some embodiments, the guide RNA additionally comprises a tracrRNA or a modified tracrRNA.

In some embodiments, the systems provided herein comprise one or more guide polynucleotides. In some embodiments, the guide polynucleotide comprises a sense sequence. In some embodiments, the guide polynucleotide comprises an anti-sense sequence. In some embodiments, the guide polynucleotide comprises nucleotide sequences other than the region complementary to or substantially complementary to a region of a target sequence. For example, a crRNA is part or considered part of a guide polynucleotide, or is comprised in a guide polynucleotide, e.g., a crRNA: tracrRNA chimera.

In some embodiments, the guide polynucleotide comprises synthetic nucleotides or modified nucleotides. In some embodiments, the guide polynucleotide comprises one or more inter-nucleoside linkers modified from the natural phosphodiester. In some embodiments, all of the inter-nucleoside linkers of the guide polynucleotide, or contiguous nucleotide sequence thereof, are modified. For example, in some embodiments, the inter nucleoside linkage comprises Sulphur (S), such as a phosphorothioate inter-nucleoside linkage. In some embodiments, the guide polynucleotide comprises greater than about 10%, 25%, 50%, 75%, or 90% modified inter-nucleoside linkers. In some embodiments, the guide polynucleotide comprises 1, 2, 3, 4, 5, 6, 7, 8, 9, 10, or more than 10 modified inter-nucleoside linkers (e.g., phosphorothioate inter-nucleoside linkage).

In some embodiments, the guide polynucleotide comprises modifications to a ribose sugar or nucleobase. In some embodiments, the guide polynucleotide comprises one or more nucleosides comprising a modified sugar moiety, wherein the modified sugar moiety is a modification of the sugar moiety when compared to the ribose sugar moiety found in deoxyribose nucleic acid (DNA) and RNA. In some embodiments, the modification is within the ribose ring structure. Exemplary modifications include, but are not limited to, replacement with a hexose ring (HNA), a bicyclic ring having a biradical bridge between the C2 and C4 carbons on the ribose ring (e.g., locked nucleic acids (LNA)), or an unlinked ribose ring which typically lacks a bond between the C2 and C3 carbons (e.g., UNA). In some embodiments, the sugar-modified nucleosides comprise bicyclohexose nucleic acids or tricyclic nucleic acids. In some embodiments, the modified nucleosides comprise nucleosides where the sugar moiety is replaced with a non-sugar moiety, for example peptide nucleic acids (PNA) or morpholino nucleic acids.

In some embodiments, the guide polynucleotide comprises one or more modified sugars. In some embodiments, the sugar modifications comprise modifications made by altering the substituent groups on the ribose ring to groups other than hydrogen, or the 2'—OH group naturally found in DNA and RNA nucleosides. In some embodiments, substituents are introduced at the 2', 3', 4', 5' positions, or combinations thereof. In some embodiments, nucleosides with modified sugar moieties comprise 2' modified nucleosides, e.g., 2' substituted nucleosides. A 2' sugar modified nucleoside, in some embodiments, is a nucleoside that has a substituent other than H or —OH at the 2' position (2' substituted nucleoside) or comprises a 2' linked biradical, and comprises 2' substituted nucleosides and LNA (2'-4' biradical bridged) nucleosides. Examples of 2'-substituted modified nucleosides comprise, but are not limited to, 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. In some embodiments, the modification in the ribose group comprises a modification at the 2' position of the ribose group. In some embodiments, the modification at the 2' position of the ribose group is selected from the group consisting of 2'-O-methyl, 2'-fluoro, 2'-deoxy, and 2'-O-(2-methoxyethyl).

In some embodiments, the guide polynucleotide comprises one or more modified sugars. In some embodiments, the guide polynucleotide comprises only modified sugars. In some embodiments, the guide polynucleotide comprises greater than about 10%, 25%, 50%, 75%, or 90% modified sugars. In some embodiments, the modified sugar is a bicyclic sugar. In some embodiments, the modified sugar comprises a 2'-O-methyl. In some embodiments, the modified sugar comprises a 2'-fluoro. In some embodiments, the modified sugar comprises a 2'-O-methoxyethyl group. In some embodiments, the guide polynucleotide comprises 1, 2, 3, 4, 5, 6, 7, 8, 9, 10, or more than 10 modified sugars (e.g., comprising a 2'-O-methyl or 2'-fluoro).

In some embodiments, the guide polynucleotide comprises both inter-nucleoside linker modifications and nucleoside modifications. In some embodiments, the guide polynucleotide comprises greater than about 10%, 25%, 50%, 75%, or 90% modified inter-nucleoside linkers and greater than about 10%, 25%, 50%, 75%, or 90% modified sugars. In some embodiments, the guide polynucleotide comprises 1, 2, 3, 4, 5, 6, 7, 8, 9, 10, or more than 10 modified inter-nucleoside linkers (e.g., phosphorothioate inter-nucleoside linkage) and 1, 2, 3, 4, 5, 6, 7, 8, 9, 10, or more than 10 modified sugars (e.g., comprising a 2'-O-methyl or 2'-fluoro).

In some embodiments, the guide polynucleotide comprises a sequence complementary to a eukaryotic, fungal, plant, mammalian, or human genomic polynucleotide sequence. In some embodiments, the guide polynucleotide comprises a sequence complementary to a eukaryotic genomic polynucleotide sequence. In some embodiments, the guide polynucleotide comprises a sequence complementary to a fungal genomic polynucleotide sequence. In some embodiments, the guide polynucleotide comprises a sequence complementary to a plant genomic polynucleotide sequence. In some embodiments, the guide polynucleotide comprises a sequence complementary to a mammalian genomic polynucleotide sequence. In some embodiments, the guide polynucleotide comprises a sequence complementary to a human genomic polynucleotide sequence.

In some embodiments, the guide polynucleotide is 30-250 nucleotides in length. In some embodiments, the guide polynucleotide is more than 90 nucleotides in length. In some embodiments, the guide polynucleotide is less than 245 nucleotides in length. In some embodiments, the guide polynucleotide is 30, 40, 50, 60, 70, 80, 90, 100, 120, 140, 160, 180, 200, 220, 240, or more than 240 nucleotides in length. In some embodiments, the guide polynucleotide is about 30 to about 40, about 30 to about 50, about 30 to about 60, about 30 to about 70, about 30 to about 80, about 30 to about 90, about 30 to about 100, about 30 to about 120, about 30 to about 140, about 30 to about 160, about 30 to about 180, about 30 to about 200, about 30 to about 220, about 30 to about 240, about 50 to about 60, about 50 to about 70, about 50 to about 80, about 50 to about 90, about 50 to about 100, about 50 to about 120, about 50 to about 140, about 50 to about 160, about 50 to about 180, about 50 to about 200, about 50 to about 220, about 50 to about 240, about 100 to about 120, about 100 to about 140, about 100 to about 160, about 100 to about 180, about 100 to about 200, about 100 to about 220, about 100 to about 240, about 160 to about 180, about 160 to about 200, about 160 to about 220, or about 160 to about 240 nucleotides in length.

MG Gene Editing Systems

Described herein, in certain embodiments, are engineered nuclease systems, comprising: a) an endonuclease; b) an engineered guide polynucleotide configured to form a complex with the endonuclease and to hybridize to a target nucleic acid sequence within an albumin gene or within an intron of the albumin gene; and c) a donor template comprising a nucleic acid sequence encoding a Factor VIII (FVIII) gene or a functional fragment thereof.

In some embodiments, the endonuclease induces a single-stranded break at or proximal to the target nucleic acid sequence. In some embodiments, the endonuclease induces a double-stranded break at or proximal to the target nucleic acid sequence. In some embodiments, the donor template is integrated into the target nucleic acid sequence at the double-stranded break. In some embodiments, the donor template is integrated into the target nucleic acid sequence at the double-stranded break via non-homologous end joining (NHEJ). In some embodiments, the donor template is integrated into the target nucleic acid sequence at the double-stranded break via homology-directed repair (HDR).

In some embodiments, the engineered nuclease system comprises a) an endonuclease comprising a sequence having at least about 70% identity to SEQ ID NO: 54 or SEQ ID NO: 96; b) an engineered guide polynucleotide; and c) a donor template comprising a nucleic acid sequence encoding a FVIII gene or a functional fragment thereof. In some embodiments, the engineered nuclease system comprises a) an endonuclease comprising a sequence having at least about 75% identity to SEQ ID NO: 54 or SEQ ID NO: 96; b) an engineered guide polynucleotide; and c) a donor template comprising a nucleic acid sequence encoding a FVIII gene or a functional fragment thereof. In some embodiments, the engineered nuclease system comprises a) an endonuclease comprising a sequence having at least about 80% identity to SEQ ID NO: 54 or SEQ ID NO: 96; b) an engineered guide polynucleotide; and c) a donor template comprising a nucleic acid sequence encoding a FVIII gene or a functional fragment thereof. In some embodiments, the engineered nuclease system comprises a) an endonuclease comprising a sequence having at least about 85% identity to SEQ ID NO: 54 or SEQ ID NO: 96; b) an engineered guide polynucleotide; and c) a donor template comprising a nucleic acid sequence encoding a FVIII gene or a functional fragment thereof. In some embodiments, the engineered nuclease system comprises a) an endonuclease comprising a sequence having at least about 90% identity to SEQ ID NO: 54 or SEQ ID NO: 96; b) an engineered guide polynucleotide; and c) a donor template comprising a nucleic acid sequence encoding a FVIII gene or a functional fragment thereof. In some embodiments, the engineered nuclease system comprises a) an endonuclease comprising a sequence having at least about 95% identity to SEQ ID NO: 54 or SEQ ID NO: 96; b) an engineered guide polynucleotide; and c) a donor template comprising a sequence encoding a FVIII gene or a functional fragment thereof. In some embodiments, the engineered nuclease system comprises a) an endonuclease comprising a sequence having at least about 96% identity to SEQ ID NO: 54 or SEQ ID NO: 96; b) an engineered guide polynucleotide; and c) a donor template comprising a nucleic acid sequence encoding a FVIII gene or a functional fragment thereof. In some embodiments, the engineered nuclease system comprises a) an endonuclease comprising a sequence having at least about 97% identity to SEQ ID NO: 54 or SEQ ID NO: 96; b) an engineered guide polynucleotide; and c) a donor template comprising a nucleic acid sequence encoding a FVIII gene or a functional fragment thereof. In some embodiments, the engineered nuclease system comprises a) an endonuclease comprising a sequence having at least about 98% identity to SEQ ID NO: 54 or SEQ ID NO: 96; b) an engineered guide polynucleotide; and c) a donor template comprising a nucleic acid sequence encoding a FVIII gene or a functional fragment thereof. In some embodiments, the engineered nuclease system comprises a) an endonuclease comprising a sequence having at least about 99% identity to SEQ ID NO: 54 or SEQ ID NO: 96; b) an engineered guide polynucleotide; and c) a donor template comprising a nucleic acid sequence encoding a FVIII gene or a functional fragment thereof. In some embodiments, the engineered nuclease system comprises a) an endonuclease comprising 100% identity to SEQ ID NO: 54 or SEQ ID NO: 96; b) an engineered guide polynucleotide; and c) a donor template comprising a nucleic acid sequence encoding a FVIII gene or a functional fragment thereof.

In some embodiments, the engineered guide polynucleotide is a single guide nucleic acid. In some embodiments, the engineered guide polynucleotide is a dual guide nucleic acid. In some embodiments, the engineered guide polynucleotide is RNA. In some embodiments, the endonuclease is in a complex with the engineered guide polynucleotide. In some embodiments, the endonuclease is linked to the engineered guide polynucleotide.

In some embodiments, the engineered nuclease system comprises a) an endonuclease comprising a sequence having at least about 70% identity to SEQ ID NO: 54 or SEQ ID NO: 96; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide comprising a sequence having at least about 70% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease comprising a sequence having at least about 75% identity to SEQ ID NO: 54 or SEQ ID NO: 96; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide comprising a sequence having at least about 75% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease comprising a sequence having at least about 80% identity to SEQ ID NO: 54 or SEQ ID NO: 96; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide comprising a sequence having at least about 80% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease comprising a sequence having at least about 85% identity to SEQ ID NO: 54 or SEQ ID NO: 96; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide comprising a sequence having at least about 85% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease comprising a sequence having at least about 90% identity to SEQ ID NO: 54 or SEQ ID NO: 96; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide comprising a sequence having at least about 90% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease comprising a sequence having at least about 95% identity to SEQ ID NO: 54 or SEQ ID NO: 96; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide comprising a sequence having at least about 95% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease comprising a sequence having at least about 96% identity to SEQ ID NO: 54 or SEQ ID NO: 96; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide comprising a sequence having at least about 96% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease comprising a sequence having at least about 97% identity to SEQ ID NO: 54 or SEQ ID NO: 96; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide comprising a sequence having at least about 97% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease comprising a sequence having at least about 98% identity to SEQ ID NO: 54 or SEQ ID NO: 96; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide comprising a sequence having at least about 98% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease comprising a sequence having at least about 99% identity to SEQ ID NO: 54 or SEQ ID NO: 96; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide comprising a sequence having at least about 99% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease comprising 100% identity to SEQ ID NO: 54 or SEQ ID NO: 96; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide comprising 100% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the guide polynucleotide hybridizes or targets a sequence complementary to any one of SEQ ID NOs: 14-15, 24-27, 43-45, 50, 55, 60-68, and 97-98 or a sequence having at least 90%, 95%, 97%, 98%, or 99% sequence identity to any one of SEQ ID NOs: 14-15, 24-27, 43-45, 50, 55, 60-68, and 97-98; and c) a donor template comprising a nucleic acid sequence encoding a FVIII gene or a functional fragment thereof.

In some embodiments, the engineered nuclease system comprises a) an endonuclease encoded by a nucleic acid sequence having at least about 70% identity to any one of SEQ ID NOs: 30, 31, 53, and 95; b) an engineered guide polynucleotide; and c) a donor template comprising a nucleic acid sequence encoding a FVIII gene or a functional fragment thereof. In some embodiments, the engineered nuclease system comprises a) an endonuclease encoded by a nucleic acid sequence having at least about 75% identity to any one of SEQ ID NOs: 30, 31, 53, and 95; b) an engineered guide polynucleotide; and c) a donor template comprising a nucleic acid sequence encoding a FVIII gene or a functional fragment thereof. In some embodiments, the engineered nuclease system comprises a) an endonuclease encoded by a nucleic acid sequence having at least about 80% identity to any one of SEQ ID NOs: 30, 31, 53, and 95; b) an engineered guide polynucleotide; and c) a donor template comprising a nucleic acid sequence encoding a FVIII gene or a functional fragment thereof. In some embodiments, the engineered nuclease system comprises a) an endonuclease encoded by a nucleic acid sequence having at least about 85% identity to any one of SEQ ID NOs: 30, 31, 53, and 95; b) an engineered guide polynucleotide; and c) a donor template comprising a nucleic acid sequence encoding a FVIII gene or a functional fragment thereof. In some embodiments, the engineered nuclease system comprises a) an endonuclease encoded by a nucleic acid sequence having at least about 90% identity to any one of SEQ ID NOs: 30, 31, 53, and 95; b) an engineered guide polynucleotide; and c) a donor template comprising a nucleic acid sequence encoding a FVIII gene or a functional fragment thereof. In some embodiments, the engineered nuclease system comprises a) an endonuclease encoded by a nucleic acid sequence having at least about 95% identity to any one of SEQ ID NOs: 30, 31, 53, and 95; b) an engineered guide polynucleotide; and c) a donor template comprising a nucleic acid sequence encoding a FVIII gene or a functional fragment thereof. In some embodiments, the engineered nuclease system comprises a) an endonuclease encoded by a nucleic acid sequence having at least about 96% identity to any one of SEQ ID NOs: 30, 31, 53, and 95; b) an engineered guide polynucleotide; and c) a donor template comprising a nucleic acid sequence encoding a FVIII gene or a functional fragment thereof. In some embodiments, the engineered nuclease system comprises a) an endonuclease encoded by a nucleic acid sequence having at least about 97% identity to any one of SEQ ID NOs: 30, 31, 53, and 95; b) an engineered guide polynucleotide; and c) a donor template comprising a nucleic acid sequence encoding a FVIII gene or a functional fragment thereof. In some embodiments, the engineered nuclease system comprises a) an endonuclease encoded by a nucleic acid sequence having at least about 98% identity to any one of SEQ ID NOs: 30, 31, 53, and 95; b) an engineered guide polynucleotide; and c) a donor template comprising a nucleic acid sequence encoding a FVIII gene or a functional fragment thereof. In some embodiments, the engineered nuclease system comprises a) an endonuclease encoded by a nucleic acid sequence having at least about 99% identity to any one of SEQ ID NOs: 30, 31, 53, and 95; b) an engineered guide polynucleotide; and c) a donor template comprising a nucleic acid sequence encoding a FVIII gene or a functional fragment thereof. In some embodiments, the engineered nuclease system comprises a) an endonuclease comprising 100% identity to any one of SEQ ID NOs: 30, 31, 53, and 95; b) an engineered guide polynucleotide; and c) a donor template comprising a nucleic acid sequence encoding a FVIII gene or a functional fragment thereof.

In some embodiments, the engineered nuclease system comprises a) an endonuclease encoded by a nucleic acid sequence having at least about 70% identity to any one of SEQ ID NOs: 30, 31, 53, and 95; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide encoded by a nucleic acid sequence having at least about 70% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease encoded by a nucleic acid sequence having at least about 75% identity to any one of SEQ ID NOs: 30, 31, 53, and 95; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide encoded by a nucleic acid sequence having at least about 75% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease encoded by a nucleic acid sequence having at least about 80% identity to any one of SEQ ID NOs: 30, 31, 53, and 95; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide encoded by a nucleic acid sequence having at least about 80% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease encoded by a nucleic acid sequence having at least about 85% identity to any one of SEQ ID NOs: 30, 31, 53, and 95; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide encoded by a nucleic acid sequence having at least about 85% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease encoded by a nucleic acid sequence having at least about 90% identity to any one of SEQ ID NOs: 30, 31, 53, and 95; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide encoded by a nucleic acid sequence having at least about 90% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease encoded by a nucleic acid sequence having at least about 95% identity to any one of SEQ ID NOs: 30, 31, 53, and 95; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide encoded by a nucleic acid sequence having at least about 95% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease encoded by a nucleic acid sequence having at least about 96% identity to any one of SEQ ID NOs: 30, 31, 53, and 95; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide encoded by a nucleic acid sequence having at least about 96% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease encoded by a nucleic acid sequence having at least about 97% identity to any one of SEQ ID NOs: 30, 31, 53, and 95; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide encoded by a nucleic acid sequence having at least about 97% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease encoded by a nucleic acid sequence having at least about 98% identity to any one of SEQ ID NOs: 30, 31, 53, and 95; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide encoded by a nucleic acid sequence having at least about 98% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease encoded by a nucleic acid sequence having at least about 99% identity to any one of SEQ ID NOs: 30, 31, 53, and 95; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide encoded by a nucleic acid sequence having at least about 99% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the engineered nuclease system comprises a) an endonuclease comprising 100% identity to any one of SEQ ID NOs: 30, 31, 53, and 95; b) an engineered guide polynucleotide configured to form a complex with the endonuclease and comprising a spacer sequence configured to hybridize to at least a portion of a target nucleic acid sequence within an albumin gene or within an intron of the albumin gene, the engineered guide polynucleotide comprising 100% identity to any one of SEQ ID NOs: 14-15, 24-27, 43-45, 50, 55, 60-68, and 97-98; and c) a donor template comprising a nucleic acid sequence encoding a FVIII gene or a functional fragment thereof. In some embodiments, the guide polynucleotide hybridizes or targets a sequence complementary to any one of SEQ ID NOs: 14-15, 24-27, 43-45, 50, 55, 60-68, and 97-98 or a sequence having at least 90%, 95%, 97%, 98%, or 99% sequence identity to any one of SEQ ID NOs: 14-15, 24-27, 43-45, 50, 55, 60-68, and 97-98; and c) a donor template comprising a nucleic acid sequence encoding a FVIII gene or a functional fragment thereof.

In some embodiments, the donor template comprises a polyadenylation signal. In some embodiments, the polyadenylation signal is at a C-terminus of the Factor VIII gene or fragment thereof. In some embodiments, the polyadenylation signal is linked to the Factor VIII gene or fragment thereof. In some embodiments, the polyadenylation signal is fused to the Factor VIII gene or fragment thereof.

In some embodiments, the donor template comprises a nucleus-targeting sequence (NTS). In some embodiments, the nucleus-targeting sequence comprises a plurality of transcription factor binding sites. In some embodiments, the transcription factor (TF) binding site is a SV40 enhancer region. In some embodiments, the transcription factor is TCF1, HNF1, NFY, CEBP, OCT1, AP1, HNF1-α, HNF1-β, CEBPA, LEF-1, FOX D1, IRF1, HNF3, HNF4, HNF5, Tal1β/E47, or MyoD. Table 1B includes examples of TF that are found in the promoters and enhancers of genes that are highly expressed in the liver. Common liver specific transcription factors include: HNF3, HNF4, HNF5, C/EBP, HNF1α, LEF1, FOX, IRF, and TCF.

TABLE 1B

Binding sites for TF that are known to be expressed at high levels in the liver

| TF | Consensus binding site |
|---|---|
| OCT1 (POU2F1) | TATGCAAAT |
| AP1 | TGACTCA |
| HNF1-A | (G/T)TTAAT(A/T)TT |
| HNF1-B | TTAATNNTTAAC (SEQ ID NO: 37) |
| CEBPA | TT(G/T)CA(C/T)AA(T/C) |
| LEF-1 | AAGATCAAAG (SEQ ID NO: 39) |
| FOX D1 | GTAAACA |
| IRF1 | AAA(G/A)(C/T)GAAACC (SEQ ID NO: 41) or cTTTCnnTTTC |

In some embodiments, functional fragments of the albumin promoter are used with the donor template. In some embodiments, the functional fragments comprise a sequence of about 100 bp located 5' of the transcription start site and containing binding sites for several TF including HNF1, CEBP, LEF-1, FOX, IRF1, and LEF1.

In some embodiments, the transcription factor binding sequence comprises a sequence having at least about 90% identity to any one of SEQ ID NOs: 37, 39, and 41 or any sequence listed in Table 1B. In some embodiments, the transcription factor binding sequence comprises a sequence having at least about 95% identity to any one of SEQ ID NOs: 37, 39, and 41 or any sequence listed in Table 1B. In some embodiments, the transcription factor binding sequence comprises a sequence having at least about 96% identity to any one of SEQ ID NOs: 37, 39, and 41 or any sequence listed in Table 1B. In some embodiments, the transcription factor binding sequence comprises a sequence having at least about 97% identity to any one of SEQ ID NOs: 37, 39, and 41 or any sequence listed in Table 1B. In some embodiments, the transcription factor binding sequence comprises a sequence having at least about 98% identity to any one of SEQ ID NOs: 37, 39, and 41 or any sequence listed in Table 1B. In some embodiments, the transcription factor binding sequence comprises a sequence having at least about 99% identity to any one of SEQ ID NOs: 37, 39, and 41 or any sequence listed in Table 1B. In some embodiments, the transcription factor binding sequence comprises a sequence having 100% identity to any one of SEQ ID NOs: 37, 39, and 41 or any sequence listed in Table 1B.

In some embodiments, the nucleus-targeting sequence is on a 5' end of the donor template. In some embodiments, the nucleus-targeting sequence is on a 3' end of the donor template. In some embodiments, the nucleus-targeting sequence is on a 5' end and a 3' end of the donor template.

In some embodiments, the donor template further comprises a recognition site sequence for the endonuclease on a 5' end or a 3' end of the donor template. In some embodiments, the nucleus-targeting sequence is 5' to the recognition site sequence when the donor template is flanked on a 5' end by the nucleus-targeting sequence. In some embodiments, the nucleus-targeting sequence is 3' to the recognition site sequence when the donor template is flanked on a 3' end by the nucleus targeting sequence.

In some embodiments, the donor template comprises a splice acceptor sequence. In some embodiments, the splice acceptor sequence targets the albumin gene. In some embodiments, the splice acceptor sequence targets exon 1 of the albumin gene. In some embodiments, the splice acceptor sequence targets intron 1 of the albumin gene. In some embodiments, the splice acceptor sequence is linked to the Factor VIII gene or fragment thereof. In some embodiments, the splice acceptor sequence is an intronic sequence linked to the Factor VIII gene or fragment thereof exonic sequence. In some embodiments, the splice acceptor sequence is linked to the Factor VIII gene or fragment thereof at a 5' end of the Factor VIII gene or fragment. In some embodiments, the splice acceptor sequence is linked to the Factor VIII gene or fragment thereof at a 3' end of the Factor VIII gene or fragment. In some embodiments, the splice acceptor sequence is linked to the Factor VIII gene or fragment thereof using a linker. In some embodiments, the linker comprises a sequence having at least 80% sequence identity to SEQ ID NO: 80. In some embodiments, the linker comprises a sequence having at least 90% sequence identity to SEQ ID NO: 80. In some embodiments, the linker comprises a sequence having at least 95% sequence identity to SEQ ID NO: 80. In some embodiments, the linker comprises a sequence having at least 96% sequence identity to SEQ ID NO: 80. In some embodiments, the linker comprises a sequence having at least 97% sequence identity to SEQ ID NO: 80. In some embodiments, the linker comprises a sequence having at least 98% sequence identity to SEQ ID NO: 80. In some embodiments, the linker comprises a sequence having at least 99% sequence identity to SEQ ID NO: 80. In some embodiments, the linker comprises a sequence having 100% sequence identity to SEQ ID NO: 80. In some embodiments, the splice acceptor sequence is fused to the Factor VIII gene or fragment thereof.

In some embodiments, the donor template comprises, from 5' to 3':NTS(1)-NRS(1)-SA-FVIII-NRS(2)-NTS(2), wherein NTS(1) denotes a first nucleus-targeting sequence; NTS(2) denotes a second nucleus-targeting sequence; NRS (1) denotes a first nuclease recognition site sequence; NRS (2) denotes a second nuclease recognition site sequence; SA denotes the splice acceptor sequence targeting exon 1 of said albumin gene; and FVIII denotes the Factor VIII gene or fragment thereof. In some embodiments, a 5' to 3' orientation of NRS(1) and NRS(2) is according to: (a) forward, forward; (b) reverse, reverse; (c) forward, reverse; (d) reverse, forward; wherein forward denotes a same 5' to 3' orientation as the target nucleic acid sequence, and reverse denotes an opposite 5' to 3' orientation as the target nucleic acid sequence. In some embodiments, the donor template comprises a KTTN (K=G or T, N=any base) or AAANNN (N=any base) sequence.

In some embodiments, the donor template comprises a sequence having at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity sequence identity to any one of SEQ ID NOs: 12-13, 16-23, 32-33, 56-59, 81-88, and 90-94. In some embodiments, the donor template comprises a sequence having at least about 70% identity to any one of SEQ ID NOs: 12-13, 16-23, 32-33, 56-59, 81-88, and 90-94. In some embodiments, the donor template comprises a sequence having at least about 75% identity to any one of SEQ ID NOs: 12-13, 16-23, 32-33, 56-59, 81-88, and 90-94. In some embodiments, the donor template comprises a sequence having at least about 80% identity to any one of SEQ ID NOs: 12-13, 16-23, 32-33, 56-59, 81-88, and 90-94. In some embodiments, the donor template comprises a sequence having at least about 85% identity to any one of SEQ ID NOs: 12-13, 16-23, 32-33, 56-59, 81-88, and 90-94. In some embodiments, the donor template comprises a sequence having at least about 90% identity to any one of SEQ ID NOs: 12-13, 16-23, 32-33, 56-59, 81-88, and 90-94. In some embodiments, the donor template comprises a sequence having at least about 95% identity to any one of SEQ ID NOs: 12-13, 16-23, 32-33, 56-59, 81-88, and 90-94. In some embodiments, the donor template comprises a sequence having at least about 96% identity to any one of SEQ ID NOs: 12-13, 16-23, 32-33, 56-59, 81-88, and 90-94. In some embodiments, the donor template comprises a sequence having at least about 97% identity to any one of SEQ ID NOs: 12-13, 16-23, 32-33, 56-59, 81-88, and 90-94. In some embodiments, the donor template comprises a sequence having at least about 98% identity to any one of SEQ ID NOs: 12-13, 16-23, 32-33, 56-59, 81-88, and 90-94. In some embodiments, the donor template comprises a sequence having at least about 99% identity to any one of SEQ ID NOs: 12-13, 16-23, 32-33, 56-59, 81-88, and 90-94. In some embodiments, the donor template comprises a sequence having 100% identity to any one of SEQ ID NOs: 12-13, 16-23, 32-33, 56-59, 81-88, and 90-94.

In some embodiments, the FVIII gene or functional fragment thereof is codon-optimized to remove at least one cytosine-guanine (CG or CpG) motif.

In some embodiments, the FVIII gene or functional fragment thereof comprises a sequence having at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity sequence identity to any one of SEQ ID NOs: 10, 71-79, and 89. In some embodiments, the FVIII gene or functional fragment thereof comprises a sequence having at least about 70% identity to any one of SEQ ID NOs: 10, 71-79, and 89. In some embodiments, the FVIII gene or functional fragment thereof comprises a sequence having at least about 75% identity to any one of SEQ ID NOs: 10, 71-79, and 89. In some embodiments, the FVIII gene or functional fragment thereof comprises a sequence having at least about 80% identity to any one of SEQ ID NOs: 10, 71-79, and 89. In some embodiments, the FVIII gene or functional fragment thereof comprises a sequence having at least about 85% identity to any one of SEQ ID NOs: 10, 71-79, and 89. In some embodiments, the FVIII gene or functional fragment thereof comprises a sequence having at least about 90% identity to any one of SEQ ID NOs: 10, 71-79, and 89. In some embodiments, the FVIII gene or functional fragment thereof comprises a sequence having at least about 95% identity to any one of SEQ ID NOs: 10, 71-79, and 89. In some embodiments, the FVIII gene or functional fragment thereof comprises a sequence having at least about 96% identity to any one of SEQ ID NOs: 10, 71-79, and 89. In some embodiments, the FVIII gene or functional fragment thereof comprises a sequence having at least about 97% identity to any one of SEQ ID NOs: 10, 71-79, and 89. In some embodiments, the FVIII gene or functional fragment thereof comprises a sequence having at least about 98% identity to any one of SEQ ID NOs: 10, 71-79, and 89. In some embodiments, the FVIII gene or functional fragment thereof comprises a sequence having at least about 99% identity to any one of SEQ ID NOs: 10, 71-79, and 89. In some embodiments, the FVIII gene or functional fragment thereof comprises a sequence having 100% identity to any one of SEQ ID NOs: 10, 71-79, and 89.

In some embodiments, the FVIII gene or functional fragment thereof comprises a sequence having at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity sequence identity to SEQ ID NO: 10. In some embodiments, the FVIII gene or functional fragment thereof comprises a sequence having at least about 70% identity to SEQ ID NO: 10. In some embodiments, the FVIII gene or functional fragment thereof comprises a sequence having at least about 75% identity to SEQ ID NO: 10. In some embodiments, the FVIII gene or functional fragment thereof comprises a sequence having at least about 80% identity to SEQ ID NO: 10. In some embodiments, the FVIII gene or functional fragment thereof comprises a sequence having at least about 85% identity to SEQ ID NO: 10. In some embodiments, the FVIII gene or functional fragment thereof comprises a sequence having at least about 90% identity to SEQ ID NO: 10. In some embodiments, the FVIII gene or functional fragment thereof comprises a sequence having at least about 95% identity to SEQ ID NO: 10. In some embodiments, the FVIII gene or functional fragment thereof comprises a sequence having at least about 96% identity to SEQ ID NO: 10. In some embodiments, the FVIII gene or functional fragment thereof comprises a sequence having at least about 97% identity to SEQ ID NO: 10. In some embodiments, the FVIII gene or functional fragment thereof comprises a sequence having at least about 98% identity to SEQ ID NO: 10. In some embodiments, the FVIII gene or functional fragment thereof comprises a sequence having at least about 99% identity to SEQ ID NO: 10. In some embodiments, the FVIII gene or functional fragment thereof comprises a sequence having 100% identity to SEQ ID NO: 10.

In some embodiments, the FVIII gene or functional fragment thereof is modified to comprise a B-domain comprising a sequence having at least about 90% identity to any one of SEQ ID NOs: 71-79 and 89. In some embodiments, the FVIII gene or functional fragment thereof is modified to comprise a B-domain comprising a sequence having at least about 95% identity to any one of SEQ ID NOs: 71-79 and 89. In some embodiments, the FVIII gene or functional fragment thereof is modified to comprise a B-domain comprising a sequence having at least about 96% identity to any one of SEQ ID NOs: 71-79 and 89. In some embodiments, the FVIII gene or functional fragment thereof is modified to comprise a B-domain comprising a sequence having at least about 97% identity to any one of SEQ ID NOs: 71-79 and 89. In some embodiments, the FVIII gene or functional fragment thereof is modified to comprise a B-domain comprising a sequence having at least about 98% identity to any one of SEQ ID NOs: 71-79 and 89. In some embodiments, the FVIII gene or functional fragment thereof is modified to comprise a B-domain comprising a sequence having at least about 99% identity to any one of SEQ ID NOs: 71-79 and 89. In some embodiments, the FVIII gene or functional fragment thereof is modified to comprise a B-domain comprising a sequence having 100% identity to any one of SEQ ID NOs: 71-79 and 89.

In some embodiments, the FVIII gene or functional fragment thereof comprising a modified B-domain comprises a sequence having at least about 90% identity to any one of SEQ ID NOs: 86-87 and 90. In some embodiments, the FVIII gene or functional fragment thereof comprising a modified B-domain comprises a sequence having at least about 95% identity to any one of SEQ ID NOs: 86-87 and 90. In some embodiments, the FVIII gene or functional fragment thereof comprising a modified B-domain comprises a sequence having at least about 96% identity to any one of SEQ ID NOs: 86-87 and 90. In some embodiments, the FVIII gene or functional fragment thereof comprising a modified B-domain comprises a sequence having at least about 97% identity to any one of SEQ ID NOs: 86-87 and 90. In some embodiments, the FVIII gene or functional fragment thereof comprising a modified B-domain comprises a sequence having at least about 98% identity to any one of SEQ ID NOs: 86-87 and 90. In some embodiments, the FVIII gene or functional fragment thereof comprising a modified B-domain comprises a sequence having at least about 99% identity to any one of SEQ ID NOs: 86-87 and 90. In some embodiments, the FVIII gene or functional fragment thereof comprising a modified B-domain comprises a sequence having 100% identity to any one of SEQ ID NOs: 86-87 and 90.

Methods of Use

Provided herein are methods for supplementing liver enzymes using the engineered nuclease systems described herein. Methods for supplementing liver enzymes comprise integrating a liver gene into the genome at an appropriate site and in the appropriate cells or tissue such that the gene is expressed and produces functional protein (e.g., functional FVIII) and thus supplements the deficiency.

In some embodiments, the engineered nuclease systems described herein are used to integrate Factor VIII genes into a genome of an individual in need thereof. In some embodiments, the engineered nuclease systems described herein are used to integrate Factor VIII genes into the genome of an individual in need thereof, thereby treating hemophilia A. In some embodiments, the engineered nuclease systems described herein are used to treat hemophilia A in an individual in need thereof.

In some embodiments, the FVIII gene or functional fragment thereof is delivered to the hepatocytes of the liver by systemic (e.g. intravenous) administration of a vector comprising an endonuclease and a guide polynucleotide that targets a target nucleic acid sequence in a safe harbor locus, such as the albumin locus.

In some embodiments, the site of integration for the FVIII gene is in the albumin gene. In some embodiments, the site of integration for the FVIII gene is intron 1 of the albumin gene. As the albumin gene is expressed at high levels in hepatocytes, the promoter of the albumin gene is expected to drive efficient expression of the integrated FVIII gene. This methodology of integration into an intron has the advantage that double-strand breaks that are subsequently repaired by error-prone NHEJ will not deleteriously impact the function of the albumin gene. In some embodiments, in order to capture transcription initiating from the albumin promoter, a splice acceptor site is included at the 5' end of the donor template immediately before the N-terminus of the FVIII protein coding sequence. This splice acceptor can capture some of the splicing events from exon 1 of albumin, resulting in an mRNA that comprises the 5' UTR and exon 1 of albumin fused in frame to the coding sequence for FVIII.

Delivery and Vectors

Disclosed herein, in some embodiments, are nucleic acid sequences encoding an engineered nuclease system described herein or components thereof (e.g., endonuclease, engineered guide polynucleotide, or donor template).

In some embodiments, the nucleic acid encoding the engineered nuclease system described herein or components thereof is a DNA, for example a linear DNA, a plasmid DNA, or a minicircle DNA. In some embodiments, the nucleic acid encoding the engineered nuclease system described herein or components thereof is an RNA, for example a mRNA.

In some embodiments, the nucleic acid encoding the engineered nuclease system described herein or components thereof is delivered by a nucleic acid-based vector. In some embodiments, the nucleic acid-based vector is a plasmid (e.g., circular DNA molecules that can autonomously replicate inside a cell), cosmid (e.g., pWE or sCos vectors), artificial chromosome, human artificial chromosome (HAC), yeast artificial chromosomes (YAC), bacterial artificial chromosome (BAC), P1-derived artificial chromosomes (PAC), phagemid, phage derivative, bacmid, or virus. In some embodiments, the nucleic acid-based vector is selected from the list consisting of: pSF-CMV-NEO-NH2-PPT-3XFLAG, pSF-CMV-NEO—COOH-3XFLAG, pSF-CMV—PURO-NH2-GST-TEV, pSF-OXB20-COOH-TEV-FLAG(R)-6His, pCEP4 pDEST27, pSF-CMV-Ub-KrYFP, pSF-CMV-FMDV-daGFP, pEFla-mCherry-N1 vector, pEFla-tdTomato vector, pSF-CMV-FMDV-Hygro, pSF-CMV-PGK-Puro, pMCP-tag(m), pSF-CMV—PURO-NH2-CMYC, pSF-OXB20-BetaGal, pSF-OXB20-Fluc, pSF-OXB20, pSF-Tac, pRI 101-AN DNA, pCambia2301, pTYB21, pKLAC2, pAc5.1/V5-His A, and pDEST8.

In some embodiments, the nucleic acid-based vector comprises a promoter. In some embodiments, the promoter is selected from the group consisting of a mini promoter, an inducible promoter, a constitutive promoter, and derivatives thereof. In some embodiments, the promoter is selected from the group consisting of CMV, CBA, EF1a, CAG, PGK, TRE, U6, UAS, T7, Sp6, lac, araBad, trp, Ptac, p5, p19, p40, Synapsin, CaMKII, GRK1, and derivatives thereof. In some embodiments the promoter is a U6 promoter. In some embodiments, the promoter is a CAG promoter.

In some embodiments, the nucleic acid-based vector is a virus. In some embodiments, the virus is an alphavirus, a parvovirus, an adenovirus, an AAV, a baculovirus, a Dengue virus, a lentivirus, a herpesvirus, a poxvirus, an anellovirus, a bocavirus, a vaccinia virus, or a retrovirus. In some embodiments, the virus is an alphavirus. In some embodiments, the virus is a parvovirus. In some embodiments, the virus is an adenovirus. In some embodiments, the virus is an AAV. In some embodiments, the virus is a baculovirus. In some embodiments, the virus is a Dengue virus. In some embodiments, the virus is a lentivirus. In some embodiments, the virus is a herpesvirus. In some embodiments, the virus is a poxvirus. In some embodiments, the virus is an anellovirus. In some embodiments, the virus is a bocavirus. In some embodiments, the virus is a vaccinia virus. In some embodiments, the virus is or a retrovirus.

In some embodiments, the AAV is AAV1, AAV2, AAV3, AAV4, AAV5, AAV6, AAV7, AAV8, AAV9, AAV10, AAV11, AAV12, AAV13, AAV14, AAV15, AAV16, AAV-rh8, AAV-rh10, AAV-rh20, AAV-rh39, AAV-rh74, AAV-rhM4-1, AAV-hu37, AAV-Anc80, AAV-Anc80L65, AAV-7m8, AAV—PHP—B, AAV-PHP-EB, AAV-2.5, AAV-2tYF, AAV-3B, AAV-LK03, AAV-HSC1, AAV-HSC2, AAV-HSC3, AAV-HSC4, AAV-HSC5, AAV-HSC6, AAV-HSC7, AAV-HSC8, AAV-HSC9, AAV-HSC10, AAV-HSC11, AAV-HSC12, AAV-HSC13, AAV-HSC14, AAV-HSC15, AAV-TT, AAV-DJ/8, AAV-Myo, AAV-NP40, AAV-NP59, AAV-NP22, AAV-NP66, AAV-HSC16, or a derivative thereof. In some embodiments, the herpesvirus is HSV type 1, HSV-2, VZV, EBV, CMV, HHV-6, HHV-7, or HHV-8.

In some embodiments, the virus is AAV1 or a derivative thereof. In some embodiments, the virus is AAV2 or a derivative thereof. In some embodiments, the virus is AAV3 or a derivative thereof. In some embodiments, the virus is AAV4 or a derivative thereof. In some embodiments, the virus is AAV5 or a derivative thereof. In some embodiments, the virus is AAV6 or a derivative thereof. In some embodiments, the virus is AAV7 or a derivative thereof. In some embodiments, the virus is AAV8 or a derivative thereof. In some embodiments, the virus is AAV9 or a derivative thereof. In some embodiments, the virus is AAV10 or a derivative thereof. In some embodiments, the virus is AAV11 or a derivative thereof. In some embodiments, the virus is AAV12 or a derivative thereof. In some embodiments, the virus is AAV13 or a derivative thereof. In some embodiments, the virus is AAV14 or a derivative thereof. In some embodiments, the virus is AAV15 or a derivative thereof. In some embodiments, the virus is AAV16 or a derivative thereof. In some embodiments, the virus is AAV-rh8 or a derivative thereof. In some embodiments, the virus is AAV-rh10 or a derivative thereof. In some embodiments, the virus is AAV-rh20 or a derivative thereof. In some embodiments, the virus is AAV-rh39 or a derivative thereof. In some embodiments, the virus is AAV-rh74 or a derivative thereof. In some embodiments, the virus is AAV-rhM4-1 or a derivative thereof. In some embodiments, the virus is AAV-hu37 or a derivative thereof. In some embodiments, the virus is AAV-Anc80 or a derivative thereof. In some embodiments, the virus is AAV-Anc80L65 or a derivative thereof. In some embodiments, the virus is AAV-7m8 or a derivative thereof. In some embodiments, the virus is AAV—PHP—B or a derivative thereof. In some embodiments, the virus is AAV-PHP-EB or a derivative thereof. In some embodiments, the virus is AAV-2.5 or a derivative thereof. In some embodiments, the virus is AAV-2tYF or a derivative thereof. In some embodiments, the virus is AAV-3B or a derivative thereof. In some embodiments, the virus is AAV-LK03 or a derivative thereof. In some embodiments, the virus is AAV-HSC1 or a derivative thereof. In some embodiments, the virus is AAV-HSC2 or a derivative thereof. In some embodiments, the virus is AAV-HSC3 or a derivative thereof. In some embodiments, the virus is AAV-HSC4 or a derivative thereof. In some embodiments, the virus is AAV-HSC5 or a derivative thereof. In some embodiments, the virus is AAV-HSC6 or a derivative thereof. In some embodiments, the virus is AAV-HSC7 or a derivative thereof. In some embodiments, the virus is AAV-HSC8 or a derivative thereof. In some embodiments, the virus is AAV-HSC9 or a derivative thereof. In some embodiments, the virus is AAV-HSC10 or a derivative thereof. In some embodiments, the virus is AAV-HSCT 1 or a derivative thereof. In some embodiments, the virus is AAV-HSC12 or a derivative thereof. In some embodiments, the virus is AAV-HSC13 or a derivative thereof. In some embodiments, the virus is AAV-HSC14 or a derivative thereof. In some embodiments, the virus is AAV-HSC15 or a derivative thereof. In some embodiments, the virus is AAV-TT or a derivative thereof. In some embodiments, the virus is AAV-DJ/8 or a derivative thereof. In some embodiments, the virus is AAV-Myo or a derivative thereof. In some embodiments, the virus is AAV-NP40 or a derivative thereof. In some embodiments, the virus is AAV-NP59 or a derivative thereof. In some embodiments, the virus is AAV-NP22 or a derivative thereof. In some embodiments, the virus is AAV-NP66 or a derivative thereof. In some embodiments, the virus is AAV-HSC16 or a derivative thereof.

In some embodiments, the virus is HSV-1 or a derivative thereof. In some embodiments, the virus is HSV-2 or a derivative thereof. In some embodiments, the virus is VZV or a derivative thereof. In some embodiments, the virus is EBV or a derivative thereof. In some embodiments, the virus is CMV or a derivative thereof. In some embodiments, the virus is HHV-6 or a derivative thereof. In some embodiments, the virus is HHV-7 or a derivative thereof. In some embodiments, the virus is HHV-8 or a derivative thereof.

In some embodiments, the nucleic acid encoding the engineered nuclease system described herein or components thereof is delivered by a non-nucleic acid-based delivery system (e.g., a non-viral delivery system). In some embodiments, the non-viral delivery system is a liposome. In some embodiments, the nucleic acid is associated with a lipid. The nucleic acid associated with a lipid, in some embodiments, is encapsulated in the aqueous interior of a liposome, interspersed within the lipid bilayer of a liposome, attached to a liposome via a linking molecule that is associated with both the liposome and the nucleic acid, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. In some embodiments, the nucleic acid is comprised in a lipid nanoparticle (LNP).

In some embodiments, the engineered nuclease system described herein or components thereof is introduced into the cell in any suitable way, either stably or transiently. In some embodiments, the engineered nuclease system described herein or components thereof is transfected into the cell. In some embodiments, the cell is transduced or transfected with a nucleic acid construct that encodes the engineered nuclease system described herein or components thereof. For example, a cell is transduced (e.g., with a virus encoding the engineered nuclease system described herein or components thereof), or transfected (e.g., with a plasmid encoding the engineered nuclease system described herein or components thereof) with a nucleic acid that encodes the engineered nuclease system described herein or components thereof, or the translated the engineered nuclease system described herein or components thereof. In some embodiments, the transduction is a stable or transient transduction. In some embodiments, cells expressing the engineered nuclease system described herein or components thereof or containing the engineered nuclease system described herein or components thereof are transduced or transfected with one or more gRNA molecules, for example, when the engineered nuclease system described herein or components thereof comprises a CRISPR nuclease. In some embodiments, a plasmid expressing the engineered nuclease system described herein or components thereof is introduced into cells through electroporation, transient (e.g., lipofection) and stable genome integration (e.g., piggybac) and viral transduction (for example lentivirus or AAV) or other methods known to those of skill in the art. In some embodiments, the gene editing system is introduced into the cell as one or more polypeptides. In some embodiments, delivery is achieved through the use of RNP complexes. Delivery methods to cells for polypeptides and/or RNPs are known in the art, for example by electroporation or by cell squeezing.

Exemplary methods of delivery of nucleic acids include lipofection, nucleofection, electroporation, stable genome integration (e.g., piggybac), microinjection, biolistics, virosomes, liposomes, immunoliposomes, polycation or lipid nucleic acid conjugates, naked DNA, artificial virions, and agent-enhanced uptake of DNA. Lipofection is described in e.g., U.S. Pat. Nos. 5,049,386; 4,946,787; and 4,897,355) and lipofection reagents are sold commercially (e.g., Transfectam™, Lipofectin™ and SF Cell Line 4D-Nucleofector X Kit™ (Lonza)). Cationic and neutral lipids that are suitable for efficient receptor-recognition lipofection of polynucleotides include those of WO 91/17424 and WO 91/16024. In some embodiments, the delivery is to cells (e.g., in vitro or ex vivo administration) or target tissues (e.g., in vivo administration). In some embodiments, the nucleic acid is comprised in a liposome or a nanoparticle that specifically targets a host cell.

Additional methods for the delivery of nucleic acids to cells are known to those skilled in the art. See, for example, US 2003/0087817.

In some embodiments, the present disclosure provides a cell comprising a vector or a nucleic acid described herein. In some embodiments, the cell expresses a gene editing system or parts thereof. In some embodiments, the cell is a human cell. In some embodiments, the cell is genome edited ex vivo. In some embodiments, the cell is genome edited in vivo.

Lipid Nanoparticles

Disclosed herein, in certain embodiments, are lipid nanoparticles comprising an engineered nuclease system of the disclosure for delivery of the engineered nuclease system into a cell.

In some embodiments, the lipid nanoparticle comprises the engineered nuclease system or a nucleic acid encoding the engineered nuclease system. In some embodiments, the lipid nanoparticle comprises the one or more components of the engineered nuclease system. In some embodiments, the lipid nanoparticle comprises the endonuclease or a nucleic acid encoding the endonuclease. In some embodiments, the lipid nanoparticle comprises the engineered guide polynucleotide. In some embodiments, the lipid nanoparticle comprises the donor template.

In some embodiments, the lipid nanoparticle is tethered to the engineered nuclease system.

Lipid nanoparticles as described herein can be 4-component lipid nanoparticles. Such nanoparticles can be configured for delivery of RNA or other nucleic acids (e.g., synthetic RNA, mRNA, or in vitro-synthesized mRNA) and can be generally formulated as described in WO2012135805A2. Such nanoparticles can generally comprise: (a) a cationic lipid, (b) a neutral lipid (e.g., DSPC or DOPE), (c) a sterol (e.g., cholesterol or a cholesterol analog), or (d) a PEG-modified lipid (e.g., PEG-DMG).

The cationic lipid referred to herein as "C12-200" is disclosed by Love et al., Proc Natl Acad Sci USA. 2010 107:1864-1869 and Liu and Huang, Molecular Therapy. 2010 669-670. Cationic lipid formulations can include particles comprising either 3 or 4 or more components in addition to polynucleotide, primary construct, or RNA (e.g., mRNA). As an example, formulations with certain cationic lipids, include, but are not limited to, 98N12-5 and may contain 42% lipidoid, 48% cholesterol and 10% PEG (C14 or greater alkyl chain length). As another example, formulations with certain lipidoids include, but are not limited to, C12-200 and may contain 50% cationic lipid, 10% disteroylphosphatidyl choline, 38.5% cholesterol, and 1.5% PEG-DMG.

In some embodiments, the cationic lipid nanoparticle comprises a cationic lipid, a PEG-modified lipid, a sterol, and a non-cationic lipid. In some embodiments, the cationic lipid nanoparticle has a molar ratio of about 20-60% cationic lipid: about 5-25% non-cationic lipid: about 25-55% sterol; and about 0.5-15% PEG-modified lipid. In some embodiments, the cationic lipid nanoparticle comprises a molar ratio of about 50% cationic lipid, about 1.5% PEG-modified lipid, about 38.5% cholesterol, and about 10% non-cationic lipid. In some embodiments, the cationic lipid nanoparticle comprises a molar ratio of about 55% cationic lipid, about 2.5% PEG-modified lipid, about 32.5% cholesterol, and about 10% non-cationic lipid. In some embodiments, the cationic lipid is an ionizable cationic lipid, the non-cationic lipid is a neutral lipid, and the sterol is a cholesterol. In some embodiments, the cationic lipid nanoparticle has a molar ratio of 50:38.5:10:1.5 of cationic lipid:cholesterol: PEG2000-DMG:DSPC or DMG:DOPE. In some embodiments, lipid nanoparticles as described herein can comprise cholesterol, 1,2-dioleoyl-sn-glycero-3-phosphoethanolamine (DOPE), 1,1'-((2-(4-(2-((2-(bis(2-hydroxydodecyl)amino)ethyl)(2-hydroxydodecyl)amino)ethyl)piperazin-1-yl)ethyl)azanediyl)bis(dodecan-2-ol) (C12-200), and DMG-PEG-2000 at molar ratios of 47.5:16:35:1.5.

Cells

Described herein, in certain embodiments, is a cell comprising the engineered nuclease system described herein.

In some embodiments, the cell is a eukaryotic cell (e.g., a plant cell, an animal cell, a protist cell, or a fungi cell), a mammalian cell (a Chinese hamster ovary (CHO) cell, baby hamster kidney (BHK), human embryo kidney (HEK), mouse myeloma (NSO), or human retinal cells), an immortalized cell (e.g., a HeLa cell, a COS cell, a HEK-293T cell, a MDCK cell, a 3T3 cell, a PC12 cell, a Huh7 cell, a HepG2 cell, a K562 cell, a N2a cell, or a SY5Y cell), an insect cell (e.g., a *Spodoptera frugiperda* cell, a *Trichoplusia ni* cell, a *Drosophila melanogaster* cell, a S2 cell, or a *Helhothis virescens* cell), a yeast cell (e.g., a *Saccharomyces cerevisiae* cell, a *Cryptococcus* cell, or a *Candida* cell), a plant cell (e.g., a parenchyma cell, a collenchyma cell, or a sclerenchyma cell), a fungal cell (e.g., a *Saccharomyces cerevisiae* cell, a *Cryptococcus* cell, or a *Candida* cell), or a prokaryotic cell (e.g., a *E. coli* cell, a *streptococcus* bacterium cell, a *streptomyces* soil bacteria cell, or an archaea cell). In some embodiments, the cell is a eukaryotic cell. In some embodiments, the cell is a mammalian cell. In some embodiments, the cell is an immortalized cell. In some embodiments, the cell is an insect cell. In some embodiments, the cell is a yeast cell. In some embodiments, the cell is a plant cell. In some embodiments, the cell is a fungal cell. In some embodiments, the cell is a prokaryotic cell.

In some embodiments, the cell is an A549, HEK-293, HEK-293T, BHK, CHO, HeLa, MRC5, Sf9, Cos-1, Cos-7, Vero, BSC 1, BSC 40, BMT 10, W138, HeLa, Saos, C2C12, L cell, HT1080, HepG2, Huh7, K562, a primary cell, or derivative thereof.

In some embodiments, the cell is a liver cell.

Kits

In some embodiments, this disclosure provides kits comprising one or more nucleic acid constructs encoding the various components of the engineered nuclease system described herein. In some embodiments, the nucleotide sequence comprises a heterologous promoter that drives expression of the engineered nuclease system components.

In some embodiments, the engineered nuclease system or components thereof disclosed herein is assembled into a pharmaceutical, diagnostic, or research kit to facilitate its use in therapeutic, diagnostic, or research applications. A kit may include one or more containers housing any of the vectors disclosed herein and instructions for use.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions, in some embodiments, are in a form prescribed by a governmental agency regulating the manufacture, use, or sale of pharmaceuticals or biological products, which instructions can also reflect approval by the agency of manufacture, use, or sale for animal administration.

EXAMPLES

Example 1—Design of a DNA Donor Template Optimized for Non-Viral Delivery for the Purpose of Integrating a FVIII into the Genome and Producing Functional FVIII Protein A sequence of 88 bp from the human albumin promoter that encompasses several transcription factor (TF) binding sites was selected as part of the donor template. This 88 bp sequence spans from 111 bp 5' of the transcription start site to just 8 bp 3' of the transcription start site, and contains binding sites for transcription factors LEF/TCF1, HNF1, NFY and CEBP. This sequence was designated as the human albumin nucleus-targeting sequence (hANTS) and comprises the sequence: 5'-TGAATTTTGTAATCG-GTTGGCAGCCAATGAAATACAAAGATGAGTCTAGT-TAATAAT CTACAATTATTGGTTAAAGAAGTATATT-AGT-3' (SEQ ID NO: 1). In addition, the 72 bp SV40 enhancer: ATGCTTTGCATACTTCTGCCTGCTGGG-GAGCCTGGGGACTTTCCACACCCTAACTGA CACA-CATTCCAC (SEQ ID NO: 2) was optionally included in the template.

A donor DNA template to be used for non-viral delivery was designed with the following general structure: 5' Closed end (CE)-nucleus-targeting DNA sequence (NTDS)-spacer-target site for CRISPR nuclease or other sequence-specific nuclease-therapeutic gene (TG)-polyA signal-spacer-target site for CRISPR nuclease or other sequence-specific nuclease-spacer-nucleus-targeting DNA sequence (NTDS)-closed end (CE). The target sites for the CRISPR nuclease or other sequence-specific nuclease in the donor DNA are the same as the target site in the genomic locus that is selected as the site of integration in the genome. The closed end (CE) indicates that the DNA sequence is synthesized such that the 5' and 3' ends of the duplex are covalently joined, which increases the stability against degradation by nucleases.

As the specific sequence of the NTDS can potentially affect the integration efficiency of the donor template, donor DNAs with different NTDSes were designed. In one example, the NTDS comprised a single copy of the hANTS (SEQ ID NO: 1) present at one or both ends of the DNA donor. In another example, the NTDS comprised a single copy of the SV40e (SEQ ID NO: 2) present at one or both ends of the DNA donor. In still another example, the NTDS comprised a single copy of the hANTS (SEQ ID NO: 1) and a single copy of the SV40e (SEQ ID NO: 2) present at one or both ends of the DNA donor.

In the case of the Factor VIII gene, in which the target locus in the genome is the albumin locus (specifically intron 1 of the albumin gene), a donor DNA template was designed with the following components in order: 5' closed end (CE)-nucleus-targeting sequence (NTS) –20 bp spacer-target sites for guide 8 and 12 for nuclease MG29-1 in mouse albumin intron 1-spacer (37 bp)-Splice acceptor-FVIII CDS-polyA-spacer (36 nt)-target sites for guide 8 and 12 for CRISPR nuclease MG29-1 in mouse albumin intron 1-20 bp spacer-nucleus-targeting sequence (NTS)-closed end (CE)-3'. A total of 12 possible combinations of guide polynucleotide target site orientations and NTDS sequences were designed comprising each of the 4 guide orientations combined with either the hANTS alone, the SV40e alone, or the combination of the nANTS and SV40e at both ends of the donor. The individual sequence components are listed in SEQ ID NOs: 3 to 11.

As the relative orientations of the cut sites within the donor relative to the genomic site were considered to be a factor that affects integration efficiency, examples with all combinations of cut site orientations within the donor DNA were designed. Four possible orientations were envisioned: (1) Forward-Forward, (2) Reverse-Reverse, (3) Forward-Reverse, and (4) Reverse-Forward, where forward means the target site is in the same orientation as in the genome and reverse means the target site is the reverse complement of the sequence in the genome. Two examples of the full sequence of the donor template for FVIII are the F-F orientation of the guide cut sites with the NTDS comprising both hANTS and CMVe (pMG4010, SEQ ID NO: 12) and the R-R orientation of the guide cut sites with the NTDS comprising both hANTS and CMVe (pMG4011, SEQ ID NO: 13). The 2 other possible orientations of the guide cut sites are created by inverting the orientation of the cut sites on the appropriate ends to make the F-R (pMG4022, SEQ ID NO: 32) and R-F (pMG4023, SEQ ID NO: 33) variants with all other sequence elements unchanged. pMG4010 and pMG4011 are 4931 bp in length. In one embodiment, the FVIII coding sequence was codon optimized to improve expression of the FVIII gene after it is integrated into the target locus in the genome. The innate immune system can recognize and eliminate DNA via recognition of un-methylated CG dinucleotides (CpG motifs). Codon optimization typically involves the selection of the most frequently used codons for each amino acid. In the case of the FVIII coding sequence in SEQ ID NO: 10, all of the CpG motifs were eliminated by careful selection of alternate codons following codon optimization. In addition, spacer sequences were designed without CpG residues. There are a total of 6 CpG residues in each of pMG4010 and pMG4011.

Example 2—In Vivo Testing of Non-Viral Delivery of DNA Donor Templates Containing the FVIII Gene Cassette Flanked by NTDS and Guide RNA Target Sites (Prophetic)

To evaluate whether or not the DNA donor templates designed in Example 1 (e.g. SEQ ID NO: 12, 13, 32, and 33) are able to function in vivo after non-viral delivery, the donor DNA templates are synthesized with closed ends. This DNA is encapsulated in lipid nanoparticles. Lipids are dissolved in ethanol. The donor DNA is prepared in water then diluted in 100 mM sodium acetate (pH4.0) to make the DNA working stock. The four lipid components are combined in ethanol at the desired ratios to make the lipid working stock. A typical lipid mixture comprises cholesterol, 1,2-dioleoyl-sn-glycero-3-phosphoethanolamine (DOPE), 1,1'-((2-(4-(2-((2-(bis(2-hydroxydodecyl)amino)ethyl)(2-hydroxydodecyl)amino)ethyl)piperazin-1-yl)ethyl)azanediyl)bis(dodecan-2-ol) (C12-200), and 1,2-dimyristoyl-rac-glycero-3-methoxypolyethylene glycol-2000 (DMG-PEG-2000) at molar ratios of 47.5:16:35:1.5. The lipid working stock and the DNA working stock are combined in a microfluidics mixing device (Precision Nanosystems) at a flow rate of 12 mL/min and a ratio of 1 volume of lipid working stock to 3 volumes of DNA working stock. The mass ratio of C12-200 to DNA in the formulation is between 5 to 1 to 20 to 1. The formulated LNP is diluted 1:1 with 1×PBS then dialyzed twice in 1×PBS for 1 hour each followed by concentration in Amicon spin concentrators. The final LNP is formulated into 1×PBS buffer, filter sterilized through a 0.2 μM filter, and stored at 4° C. The concentration of the DNA inside and outside of the LNP is measured. The average diameter and polydispersity of the LNP is measured in the final concentrated LNP by dynamic light scattering. The expected size range of LNP is from 80 to 100 nanometers with a PDI<0.15 and a DNA encapsulation ratio of greater than 90%.

Separate LNP are formulated with mRNA encoding the MG29-1 nuclease and guide RNA 8 or guide RNA 12, both of which target sites within mouse albumin intron 1. The guide RNAs contained a specific set of chemical modifications that have been optimized to improve stability and in vivo potency (SEQ ID NOs: 14 and 15). The guide RNA and the mRNA are separately packaged. Lipids are dissolved in ethanol. The mRNA or guide RNA are prepared in water then diluted in 100 mM sodium acetate (pH 4.0) to make the RNA working stock. The four lipid components are combined in ethanol at the desired ratios to make the lipid working stock. A typical lipid mixture comprises cholesterol, DOPE, C12-200, and DMG-PEG-2000 at molar ratios of 47.5:16:35:1.5. The lipid working stock and the RNA working stock are combined in a microfluidics mixing device at a flow rate of 12 mL/min and a ratio of 1 volume of lipid working stock to 3 volumes of RNA working stock. The mass ratio of C12-200 to RNA in the formulation is 10 to 1. The formulated LNP is diluted 1:1 with 1×PBS then dialyzed twice in 1×PBS for 1 hour each followed by concentration in spin concentrators. The final LNP is formulated into 1×PBS buffer, filter sterilized through a 0.2 μM filter, and stored at 4° C. The concentration of the RNA inside and outside of the LNP is measured. The average diameter and polydispersity of the LNP is measured in the final concentrated LNP by dynamic light scattering. Typically, the LNP range in size from 80 to 100 nanometers with a PDI<0.15 and an RNA encapsulation ratio of greater than 90%. LNP encapsulating the guide RNA mAlb29-8-50 or mAlb29-12-50 are mixed with LNP encapsulating the MG29-1 mRNA at an RNA mass ratio of 1:1 (Guide RNA:mRNA).

To initiate the gene therapy, wild-type C57B16 mice are injected intravenously (0.1 mL via the tail vein) with LNP encapsulated donor DNA pMG4010 or pMG4011 (or other variations of the donor as described in Example 1) at doses between 0.1 mg/kg and 2 mg/kg. The timing of dosing of the LNP encapsulating the MG29-1 mRNA and guide RNA relative to the DNA-donor LNP is evaluated. In one dosing regimen, the DNA donor-LNP and the MG29-1 mRNA/guide RNA LNP are pre-mixed and dosed in a single injection. In another dosing regimen, the DNA donor-LNP is dosed into mice between 1 h and 48 h prior to dosing of the MG29-1 mRNA/guide RNA LNP. In still another dosing regimen, the MG29-1 mRNA/guide RNA LNP is dosed into mice between 1 h and 48 h prior to dosing of the DNA donor-LNP. The doses of DNA-donor LNP range from 0.1 mg/kg to 2 mg/kg of DNA in a total volume of 0.1 mL per mouse and the dose of the MG29-1 mRNA/guide RNA LNP is initially set at 0.25 mg/kg with the goal of achieving editing (cleavage) of the target site in the range of 20% to 40%. Plasma is collected from the mice at 7 days and 14 days post-dosing and assayed for human FVIII levels using a capture-CoA test assay that detects the activity of human FVIII in a background of mouse FVIII. At 14 days, the mice are sacrificed and the whole liver flash frozen and stored at −80° C. The entire left lateral lobe of the liver is homogenized using 0.4 mL of buffer per 100 mg of tissue weight in a Bead Mill. Genomic DNA is purified from an aliquot of the homogenate. The genomic DNA is analyzed for integration at the predicted target site in albumin intron 1 by in-out PCR using one primer complementary to a sequence in the genome next to the target site and one primer in the DNA donor template. The frequency of integration in the correct orientation or the reverse orientation is measured using either quantitative real time PCR or droplet digital PCR versions of the in-out PCR assay. The percentage of cells that express the integrated human FVIII mRNA is measured on liver sections by in situ hybridization with fluorescent probes designed to detect the hybrid mRNA transcript at the junction between albumin mRNA and FVIII mRNA.

Example 3—Design of a DNA Donor Template Optimized for Viral Delivery by AAV for the Purpose of Integrating a Functional FVIII Gene into the Genome that Produces Functional FVIII Protein (Prophetic)

A donor DNA template cassette is designed with the following sequence elements in order from 5' to 3': Target site for a CRISPR nuclease-Spacer-Splice acceptor-therapeutic gene-polyA signal-Spacer-Target site for a CRISPR nuclease. This donor template cassette is flanked by the AAV inverted terminal repeats (ITR) to enable packaging into any AAV virus serotype of interest. In the case of studies in mice, the AAV8 serotype or the AAV6 serotype is selected. In this example, the target site for the CRISPR nuclease or other sequence-specific nuclease is selected from target sites for the nucleases MG29-1 or MG3-6/3-4. The specific guide RNA target sites for MG29-1 or MG3-6/3-4 are selected from guide target sites at the genomic target locus that were identified by screening for active guides that promote efficient DSB formation. In this specific example, the target locus in the genome is albumin and the specific region of the albumin that is targeted is intron 1. It is envisaged that other genomic target sites may be selected in order to integrate the FVIII gene at different genomic loci. A screen for active guides that target albumin intron 1 of the mouse and human for both MG29-1 and MG3-6/3-4 identified a number of highly active guide RNA.

The orientation of the guide RNA target sites in the donor template can be designed to be the same as that of the target site in albumin intron 1 or another target site (forward orientation, F) or the reverse complement of the target site in albumin intron 1 or another target site (reverse orientation, R). Thus, there are 4 possible combinations of guide target site orientations designated as FF, RR, FR, RF. The FVIII donor cassette can be integrated into albumin intron 1 in either orientation and only the "forward" orientation in which the splice acceptor in the donor is located proximal to the albumin promoter is expected to result in production of functional FVIII protein. The orientations of the guide RNA target sites in the donor template can impact the efficiency by which the donor template cassette is integrated into albumin intron 1 in the forward orientation that can result in the production of functional FVIII protein. The MG29-1 and MG3-6/3-4 nucleases have not been tested in this context for integration of a DNA donor template in hepatocytes in vivo. MG29-1 is a type V CRISPR nuclease, and it makes a staggered cut at the target site, which is in contrast to the blunt end cut generated by Cas9 nucleases and by MG3-6/3-4. The end result of the repair of DSB generated by MG29-1 and MG3-6/3-4 in mammalian cells in the absence of a donor DNA is primarily deletions with very few alleles having inserted bases. In the case of MG29-1, deletions in the size range of 1 to 15 bases are the most frequent, while MG3-6/3-4 tends to generate on average smaller deletions in the range of 1 to 6 bases. The profile of insertions and deletions (INDELS) resulting from a DSB (the INDEL profile) reflects the DNA repair process that the cell uses to repair the DSB. Larger deletions are generally indicative of the alternative NHEJ repair pathway, while short deletions are indicative of the canonical NHEJ repair pathway. MG29-1 creates staggered cuts in the genome and leaves a 5' overhang covering bases ~18 to 22 3' of the PAM end in the target site, and the DNA donor template as shown in FIG. 1. The size of the single-stranded 5' overhang is predicted to be 3 to 6 nucleotides based on in vitro assays as shown in FIG. 1. A single-stranded overhang can be more efficiently joined to a complementary single-stranded overhang due to base pairing interactions in the same way that "sticky end" ligations are more efficient than blunt end ligations in traditional cloning methodologies. Therefore, including the guide target site at each side of the donor cassette not only can generate a linear double-stranded template in vivo inside the nucleus of the hepatocytes, but the resultant product can have single-stranded overhangs compatible with the overhangs at the double-strand break in the genome. In some cases, one of the 4 possible orientations of guide RNA target sites in the donor will result in a superior frequency of integration in the forward orientation, which can therefore be empirically determined.

It should be noted that in the situation when both of the guide target sites in the donor DNA template are in the same orientation as the same target site in the genome and the staggered cuts created by MG29-1 are joined to the donor via complementarity of the single-stranded 5' overhangs, then the guide target site can be re-created perfectly at both junctions and the DNA can be re-cut, thereby releasing the donor DNA (Tables 2 and 3).

TABLE 2

Predicted complementarity and annealing outcomes for DNA Donors with different guide target site orientations for MG29-1 guide 8 target site containing donors and assuming a 6 5' overhang created at each site

| Donor DNA guide target site orientations | Donor 5' overhang | Donor 3' overhang | Genomic target site 5' overhang | Genomic target site 3' overhang |
|---|---|---|---|---|
| FF (pMG4006) | 5'-CTGGCA | GACCGT-5' | GACCGT-5' | 5'-CTGGCA |
| RR (pMG4007) | 5'-TGCCAG | ACGGTC-5' | GACCGT-5' | 5'-CTGGCA |
| FR (pMG4008) | 5'-CTGGCA | ACGGTC-5' | GACCGT-5' | 5'-CTGGCA |
| RF (pMG4009) | 5'-TGCCAG | GACCGT-5' | GACCGT-5' | 5'-CTGGCA |

In the case where the 5' overhangs in the donor DNA and the target anneal and promote integration, the impacts on integration can be hypothesized as follows. For the donor with the FF orientation of the guide target sites, integration in the forward orientation only (not in the reverse orientation) is expected to occur via annealing of complementary ends, however this is expected to re-create the guide target site which can then be re-cut, thereby excising the donor template. Alignment of the cleaved donor template in the reverse orientation into the cleaved genome does not result in complementary 5' overhangs at either Junction.

For the donor with the RR orientation of the guide target sites, integration in the reverse orientation can occur via annealing of complementary ends, while integration in the forward orientation is disfavored due to lack of annealing of complementary ends. For the donor with the FR orientation of the guide target sites, integration in both orientations can occur via annealing of complementary ends at the 5' junction only. For the donor with the RF orientation of the guide target sites, integration in both orientations can occur via annealing of complementary ends at the 3' junction only. For each junction that is formed by perfect annealing of complementary overhangs, the guide target site can be re-created, which presumably will then be re-cut, thereby excising the donor template, which can disfavor integration efficiency. However, as NHEJ repair process is error-prone and introduces insertions and deletions at the sites of DSB during the repair process, these integration events may not occur simply without insertions or deletions of DNA as described above. This is clearly seen in the case of MG29-1 and MG3-6/3-4 by the observed INDEL profiles.

One possible mechanism for donor DNA integration is a repetitive process of end joining and re-cleavage by the nuclease until insertions/deletions (indels) occur at the junction which prevent cleavage by the nuclease. If complementary 5' overhangs at the ends of the donor template and the DSB in the genome promote annealing as an integral part of the NHEJ driven repair process, the junctions formed by annealing of complementary ends can become fixed and stable once sufficient indels are introduced at the junction to block re-cleavage. Given the complexity of the DNA repair processes, it may be necessary to determine the optimal design of the donor template empirically, especially in the case of novel nucleases.

TABLE 3

Impact of different guide target site orientations for MG29-1 guide 8 target site containing donors on integration outcomes assuming a 6 base 5' overhang is created at each site which then joins by annealing of complementary single-stranded overhangs without any deletions of sequences at either end

| | Donor integrates in Forward orientation | | | | Donor integrates in Reverse orientation | | | |
|---|---|---|---|---|---|---|---|---|
| | Donor DNA guide target site orientations | | | | | | | |
| | Ends complementary? | | Guide target site recreated? * | | Ends complementary? | | Guide target site recreated? * | |
| Junction: | 5' | 3' | 5' | 3' | 5' | 3' | 5' | 3' |
| FF (pMG4006) | Y | Y | Y | Y | N | N | N | N |
| RR (pMG4007) | N | N | N | N | Y | Y | Y | Y |
| FR (pMG4008) | Y | N | Y | N | Y | N | Y | N |
| RF (pMG4009) | N | Y | N | Y | N | Y | N | Y |

* In the event that the ends that do not exhibit sequence complementarity at the two overhangs were joined by a mechanism in which the ends were resected, the target site will not be re-created because the locations of the PAM are not compatible For MG29-1 two guides called mAlb29-8-50b (SEQ ID NO: 24) and mAlb29-12-50b (SEQ ID NO: 25) were selected based on their editing activity in the mouse liver cell line Hepal-6 and in vivo in mouse liver. These guides contain 20 nucleotide spacers and a variety of chemical modifications as well as an additional stem loop at the 5' end that together significantly improve guide RNA stability and potency in vivo. The target sites for both mAlb29-8-50b and mAlb29-12-50b are present in albumin intron 1 of mouse in the forward orientation (defined as the PAM sequence being at the 5' side of the guide target site, or closest to exon 1).

For MG3-6/3-4, two guides called mAlb3634-34 (SEQ ID NO: 26) and mAlb3634-59 (SEQ ID NO: 27) were selected based on their editing activity in the mouse liver cell line Hepal-6 and in vivo in mouse liver. These guides contain chemical modifications that improve guide stability and potency in vivo. The target site for guide mAlb3634-34 is present in albumin intron 1 of mouse in the reverse orientation (defined as the PAM sequence being at the 3' side of the guide target site, or closest to exon 2). The target site for guide mAlb3634-59 is present in albumin intron 1 of mouse in the forward orientation (defined as the PAM sequence being at the 5' side of the guide target site, or closest to exon 1). Four FVIII donor DNA template cassettes comprising the 4 guide RNA target site orientations were designed for each of the nucleases MG29-1 and MG3-6/3-4. For MG29-1, the donor DNA templates with the orientations FF, RR, FR, and RF were designated as pMG4006 (SEQ ID NO: 16), pMG4007 (SEQ ID NO: 17), pMG4008 (SEQ ID NO: 18) and pMG4009 (SEQ ID NO: 19), respectively. The 4 MG29-1 donors contain the target sites for both guides mAlb29-8 and mAlb29-12 on both sides of the donor cassette.

For use with the MG3-6/3-4 nuclease, the donor DNA templates with the orientations FF, RR, FR, and RF of the guide target sites were designated as pMG4012 (SEQ ID NO: 20), pMG4013 (SEQ ID NO: 21), pMG4014 (SEQ ID NO: 22) and pMG4015 (SEQ ID NO: 23), respectively. The 4 MG3-6/3-4 donors contain the target sites for both guides mAlb3634-34 and mAlb3634-59 on both sides of the donor cassette. Because the "F" designation means the same orientation as the target site in the genome, the F orientation of mAlb3634-34 means the PAM site on the 3' side of the target site and the F orientation of mAlb3634-59 means the PAM site on the 5' side of the target site.

A summary of the relative orientations of the different guide target sites in the donors and the genomic target with respect to the location of the PAM are shown in Table 4 and Table 5 below.

TABLE 4

Relative orientations of the different guide target sites in MG29-1 based DNA donors and the genomic target with respect to the location of the PAM

| Donor Template Name | Guide Target in Albumin Intron 1/PAM location relative to target site | Donor template guide orientation |
|---|---|---|
| MG29-1/FF | mAlb29-8/5' | 5' PAM-target site -FVIII- PAM-target site 3' |
| (pMG4006) | mAlb29-12/5' | 5' PAM-target site -FVIII- PAM-target site 3' |
| MG29-1/RR | mAlb29-8/5' | 5' target site-PAM -FVIII- target site-PAM 3' |
| (pMG4007) | mAlb29-12/5' | 5' target site-PAM -FVIII- target site-PAM 3' |
| MG29-1/FR | mAlb29-8/5' | 5' PAM-target site -FVIII- target site-PAM 3' |
| (pMG4008) | mAlb29-12/5' | 5' PAM-target site -FVIII- target site-PAM 3' |
| MG29-1/RF | mAlb29-8/5' | 5' target site-PAM -FVIII- PAM-target site 3' |
| (pMG4009) | mAlb29-12/5' | 5' target site-PAM -FVIII- PAM-target site 3' |

TABLE 5

Relative orientations of the different guide target sites in MG3-6/3-4 based DNA donors and the genomic target with respect to the location of the PAM

| Donor Template Name | Guide Target in Albumin Intron 1/ PAM location relative to target site | Donor template guide orientation |
|---|---|---|
| MG3-6/3-4/FF (pMG4012) | mAlb3634-34/3' | 5' target site-PAM -FVIII- target site-PAM 3' |
| | mAlb3634-59/5' | 5' PAM-target site -FVIII- PAM-target site 3' |
| MG3-6/3-4/RR (pMG4013) | mAlb3634-34/3' | 5' PAM-target site -FVIII- PAM-target site 3' |
| | mAlb3634-59/5' | 5' target site-PAM -FVIII- target site-PAM 3' |
| MG3-6/3-4/FR (pMG4014) | mAlb3634-34/3' | 5' target site-PAM -FVIII- PAM-target site 3' |
| | mAlb3634-59/5' | 5' PAM-target site -FVIII- target site-PAM 3' |
| MG3-6/3-4/RF (pMG4015) | mAlb3634-34/3' | 5' PAM-target site -FVIII- target site-PAM 3' |
| | mAlb3634-59/5' | 5' target site-PAM -FVIII- PAM-target site 3' |

Example 4—Testing FVIII Donor Templates Delivered by AAV for Integration into Albumin Intron 1 in Mice (Prophetic)

The human FVIII donor templates pMG4006 to pMG4009 (MG29-1 targeted) and pMG4012 to pMG4015 (MG3-6/3-4 targeted) are packaged into AAV8 viral capsids using molecular biology techniques. The AAV virus is purified using CsCl gradients and analyzed for purity by protein gel electrophoresis to visualize the viral capsid proteins. The titer of each virus is determined by quantitative PCR with primers directed to the inverted terminal repeat sequences (ITR) and expressed in vector genome copies per mL (vg/mL).

Messenger RNA encoding the MG29-1 nuclease and the MG3-6/3-4 nuclease is generated by in vitro transcription of a linearized plasmid template using T7 RNA polymerase, a mixture of ribonucleotides rATP, rCTP, and rGTP, Ni-methyl pseudouridine, and the capping reagent. The SV40-derived nuclear localization sequence (PKKK(RKVGGGGS (SEQ ID NO: 103)) followed by a short linker is included at the N terminus of the coding sequence of both MG3-6/3-4 and MG29-1. The nuclear localization signal from nucleoplasmin preceded by a short linker (SGGKRPAATKK- AGQAKKKK (SEQ ID NO: 104)) is added to the C-terminus of the coding sequence for both MG3-6/3-4 and MG29-1. Thus, the same nuclear localization signals are used for both MG29-1 and MG3-6/3-4. The plasmids also encode an approximately 100 nt polyA tail at the 3' end of both MG3-6/3-4 and MG29-1 coding sequences, which generates a polyA tail in the mRNA. The coding sequences for both MG3-6/3-4 and MG29-1 are codon optimized. The DNA sequence encoding the MG3-6/3-4 mRNA is shown in SEQ ID NO: 30 and the DNA sequence encoding the MG29-1 mRNA is shown in SEQ ID NO: 31. The mRNA is purified on spin columns, the concentration is determined by absorbance at 260 nM, and the purity is determined and is equivalent for both MG3-6/3-4 mRNA and MG29-1 mRNA. For in vivo delivery to mice, the MG3-6/3-4 mRNA or the MG29-1 mRNA and their corresponding guide RNA are separately packaged inside lipid nanoparticles (LNP). The guide RNA and the mRNA are separately packaged for both MG3-6/3-4 and for MG29-1. Lipids are dissolved in ethanol. The mRNA or guide RNA is prepared in water, then diluted in 100 mM sodium acetate (pH 4.0) to make the RNA working stock. The four lipid components are combined in ethanol at the desired ratios to make the lipid working stock. A typical lipid mixture comprises cholesterol, DOPE, C12-200 and DMG-PEG-2000 at molar ratios of 47.5:16:35:1.5. The lipid working stock and the RNA working stock are combined in a microfluidics mixing device at a flow rate of 12 m/min and a ratio of 1 volume of lipid working stock to 3 volumes of RNA working stock. The mass ratio of C12-200 to RNA in the formulation is 10 to 1. The formulated LNP are diluted 1:1 with 1×PBS, then dialyzed twice in 1×PBS for 1 hour each, followed by concentration in spin concentrators. The final LNP are formulated into 1×PBS buffer, filter sterilized through a 0.2 μM filter, and stored at 4° C. The concentration of the RNA inside and outside of the LNP is measured. The average diameter and polydispersity of the LNP are measured in the final concentrated LNP by dynamic light scattering. Typically, the LNP range in size from 80 to 100 nanometers with a PDI<0.15 and an RNA encapsulation ratio of greater than 90%.

LNP encapsulating the guide RNA mAlb29-8-50b (SEQ ID NO: 24) or mAlb29-12-50b (SEQ ID NO: 25) and the MG29-1 mRNA are mixed at an RNA mass ratio of 1:1 (guide RNA: mRNA). LNP encapsulating the guide RNA mAlb3634-34 (SEQ ID NO: 26) or mAlb3634-59 (SEQ ID NO: 27) and the MG3-6/3-4 mRNA are mixed at an RNA mass ratio of 1:1 (guide RNA mRNA). The mixture of guide RNA LNP and matching mRNA LNP are injected intravenously into wild-type C57Bl/6 mice via the tail vein at total RNA doses of between 1 mg/kg and 0.25 mg/kg of RNA in a total volume of 0.1 mL per mouse (N=5 mice per LNP dose).

The optimal order and timing of dosing of the AAV encapsulated donor template and the LNP encapsulated nuclease mRNA and guide RNA are determined empirically. Following AAV transduction of mammalian cells, the single-stranded DNA packaged inside the AAV (referred to as the AAV genome) is converted to double-stranded DNA inside the nucleus of the mammalian cells either by annealing of complementary (positive and negative single strands) that are packaged in equal proportions in the bulk AAV preparation, or by de novo synthesis of new complementary strands, or by a combination of these two mechanisms. Once converted to double-stranded DNA, the AAV genomes undergo concatemerization, whereby multiple copies of the AAV genome are joined to form circular concatemers that are able to persist episomally for years in non-dividing cells in vivo. Double-stranded DNA is a substrate for NHEJ-mediated integration at DSB, while single-stranded DNA is not a substrate for this mechanism of integration. Given that conversion of single-stranded AAV genomes to double-stranded DNA takes time, and that the double-stranded AAV genome persists in vivo for months to years, it is logical to administer the AAV virus before the editing nuclease and guide RNA. This is especially important when the editing nuclease is encoded in an mRNA and delivered together with the guide RNA in an LNP, because this results in transient expression of the nuclease by translation of the limited amount of mRNA into nuclease protein. The nuclease protein has a limited life-span inside the cell. Thus, it can be beneficial to dose the AAV-encapsulated donor template first, followed at some later time by the LNP encapsulating the nuclease mRNA and guide RNA. The optimal time between AAV dosing and LNP dosing is empirically determined and may vary between mammalian species. In the case of mice, dosing the LNP between 24 h and 21 days after the AAV is evaluated. In one potential study design, wild-type C57B16 mice or Hemophilia A mice (deficient in mouse FVIII) are dosed with the AAV encapsulating the different FVIII donor cassettes at doses of between $5\times10^{11}$ vg/kg to $1\times10^{13}$ vg/kg by intravenous injection. At 1 day, 7 days, 14 days, or 21 days post AAV dosing, the same mice are injected with the appropriate LNP encapsulating the nuclease mRNA and guide RNA that matches the guide target sites in the donor template that was previously administered. Plasma is collected from the mice at day 7 and day 14 after LNP dosing and assayed for human FVIII protein or human FVIII activity using an appropriate assay. For detection of human FVIII protein, a human FVIII specific ELISA assay can be used. For detection of human FVIII activity, a capture-Coatest assay can be used in which the human FVIII in the mouse plasma samples is first captured on the surface of a 96 well plate by human FVIII specific antibodies that do not bind to mouse FVIII. After washing away the unbound mouse FVIII in the plasma, the bound human FVIII can be quantified using a human FVIII activity assay. A human FVIII standard curve is created in each assay run using purified human FVIII protein that is diluted into naive mouse plasma such that the level of mouse plasma is the same as that in the samples during the capture step. Alternatively, if a strain of Hemophilia A mice which lack mouse FVIII are used, then the FVIII activity can be directly measured in the plasma. At 14 days post LNP dosing, the mice are sacrificed and the whole liver flash frozen and stored at −80° C. An entire lobe of the liver is homogenized in genomic digestion buffer using 0.4 mL of buffer per 100 mg of tissue weight in a Bead Mill. Genomic DNA is purified from an aliquot of the homogenate. To measure total editing efficiency at the target site in albumin intron 1, the albumin intron 1 region is PCR amplified from 50 ng of the genomic DNA in a reaction containing 0.5 micro molar each of the primers mAlb90F (SEQ ID NO: 28, CTCCTCTTCGTCTCCGGC) and mAlb1073R (SEQ ID NO: 29, CTGCCACATTGCTCAGCAC) and 1× high fidelity PCR Master Mix. The resulting 984 bp PCR product, which spans the entire intron 1 of mouse albumin, is purified using a column-based purification kit. The PCR product is sequenced by next generation sequencing (NGS). When a nuclease creates a double-strand break (DSB) in DNA inside a living cell, the DSB can be repaired by the cellular DNA repair machinery. In actively dividing cells, such as transformed mammalian cells in culture, and in the absence of a repair template, this repair can occur by the NHEJ pathway. The NHEJ pathway can be an error-prone process that introduces insertions or deletions of bases at the site of the double-strand break. These insertions and deletions (INDELS) are therefore a hallmark of a double-strand break that occurred and will be subsequently repaired, and is widely used as a readout of the editing or cutting efficiency of the nuclease. The sequencing reads are analyzed that aligns each sequence read to the wild-type target sequence (in this case, Albumin intron 1) and calculates the number of reads that contain at least one INDEL irrespective of the INDEL size within a window that spans 10 base pairs either side of the predicted on-target cut site for the nuclease. The same liver genomic DNA is analyzed for integration at the predicted target site in albumin intron 1 by in-out PCR using one primer complementary to a sequence in the genome next to the target site and one primer in the DNA donor template. The frequency of integration in the correct orientation or the reverse orientation is measured using either quantitative real time PCR or droplet digital PCR versions of the in-out PCR assay. The percentage of cells that express the integrated human FVIII mRNA is measured on liver sections by in situ hybridization with fluorescent probes designed to detect the hybrid mRNA transcript at the junction between albumin mRNA and FVIII mRNA.

Example 5—Comparison of the In Vivo Editing Efficiency of MG29-1 to spCas9

To compare the in vivo editing efficiency of the MG29-1 nuclease to that of spCas9, a dose response was performed in wild type C57B16 mice. Albumin intron 1 was selected as a genomic target locus for both spCas9 and MG29-1. An in silico search for spCas9 guide target sites in mouse intron 1 using the Chop-Chop algorithm identified a total of 39 potential guides, which were ranked according to their efficiency score and off-target prediction. In addition, guide target sites located within 50 bp of exon 1 or exon 2 were excluded. The top 3 guides from this ranking were designated mAlbR1 (SEQ ID NO: 43), mAlbR2 (SEQ ID NO: 44), and mAlbR3 (SEQ ID NO: 45) and were chemically synthesized with chemical modifications at both the 5' and 3' ends comprising methylated bases (represented by the nomenclature mA, mC, mG, and mU) and phosphorothioate backbone linkages (represented by the nomenclature A*, C*, G*, and U*). The editing efficiencies of these 3 guides were evaluated in the mouse liver cell line Hepal-6 by nucleofection of ribonucleoprotein complexes formed by mixing the guide RNA and spCas9 protein at a molar ratio of 1:2.5 (protein to guide RNA). 20 moles of spCas9 protein was mixed with 50 moles of guide RNA and subsequently nucleofected into $2\times10^5$ Hepal-6 cells using an electroporation device with program setting EH100. The nucleofected cells were each transferred to a well of a 48 well plate in fresh growth media and cultured for 48 h in a 5% $CO_2$/37° C. humidified incubator. Genomic DNA was purified from the cells and analyzed for editing at the target site in albumin intron 1 by PCR amplification of the target locus using primers mAlb90F and mAlb1073R (SEQ ID NOs: 46 and 47) and a high fidelity PCR enzyme mix. The PCR product was subjected to Sanger sequencing using primers mAlb282F or mAlb460F (SEQ ID NOs: 48 and 49). The Sanger sequencing chromatograms were analyzed for insertions and deletions ("indels"). The presence of indels at the target site is the consequence of the generation of double strand breaks in the DNA, which are then repaired by the error prone cellular repair machinery which introduces insertions and deletions. The results of the TIDE analysis are shown in Table 6. All three guides generated indel frequencies of greater than 90%, demonstrating that all three guides are highly active.

TABLE 6

INDEL frequencies in Hepa1-6 cells nucleofected with guide RNA for spCas9 targeting mouse albumin intron 1 and spCas9 protein as an RNP

| Sample ID | Guide | INDEL % | R2 |
|---|---|---|---|
| 1 | mAlbR1 | 92 | 0.95 |
| 2 | mAlbR2 | 91 | 0.91 |
| 3 | mAlbR3 | 96 | 0.96 |

Guide mALbR2 was synthesized with extensive chemical modifications. The chemical modifications include modifications of the 3 bases at the 5' end and 3 bases at the 3' end with 2'-O-methyl bases and phosphorothioate linkages between the 3 bases at the 5' end and the 3 bases at the 3' end. In addition, 33 of the internal bases are modified with 2'-O-methyl (SEQ ID NO: 50). These chemical modifications of the guide RNA for spCas9 were reported to enable efficient editing in vivo in mouse liver after delivery of the mRNA for spCas9 and the guide RNA in a lipid nanoparticle.

A guide screen for guides that target the MG29-1 nuclease to mouse albumin intron 1 and promote cleavage and indel formation was performed. The two guides with the highest editing activity in Hepal-6 cells when the nuclease was delivered as a mRNA were mALb29-8 and mAlb29-12. Guide mALb29-8 was selected for comparison to spCas9 guide mAlbR2 in vivo in mice. Chemical and structural modifications to the guide RNA for MG29-1 were optimized by evaluating the impact of different chemical modifications including 2'O-methyl and 2'-fluoro modified bases, phosphorothioate linkages, as well as an additional stem loop upon the stability and editing activity of the guide.

Experiments on guide chemistry optimization indicated that guide chemistry #50 was the most active guide chemistry among those tested. When delivered in vivo to mice using a LNP encapsulating MG29-1 mRNA and the same guide RNA sequence targeting mouse albumin intron 1, but with two different guide chemistries (#37 and #50), chemistry #50 was about 4-fold more potent than chemistry #37 at a dose of 0.5 mg/kg. Therefore, MG29-1 guide chemistry #50 was selected to test in vivo in comparison to spCas9 with its cognate guide mALbR2 (SEQ ID NO: 50).

Messenger RNA encoding the MG29-1 nuclease or the spCas9 nuclease was generated by in vitro transcription of a linearized plasmid template using T7 RNA polymerase and a mixture of ribonucleotides rATP, rCTP, and rGTP, N1-methyl pseudouridine, and the CleanCAP capping reagent. The SV40-derived nuclear localization sequence (PKKKRKVGGGGS (SEQ ID NO: 103)) followed by a short linker was included at the N terminus of the coding sequence of both spCas9 and MG29-1. The nuclear localization signal from nucleoplasmin preceded by a short linker (SGGKRPAATKKAGQAKKKK (SEQ ID NO: 104)) was added to the C-terminus of the coding sequence for both spCas9 and MG29-1. Thus, the same nuclear localization signals were used for both MG29-1 and spCas9. The plasmids also encoded an approximately 100 nt polyA tail at the 3' end of both spCas9 and MG29-1 coding sequences, which generates a polyA tail in the mRNA. The coding sequences for both spCas9 and MG29-1 were codon optimized using the same algorithm. The DNA sequence encoding the spCas9 mRNA is in SEQ ID NO: 51 and the amino acid sequence encoded by the spCas9 mRNA is in SEQ ID NO: 52. The mRNA was purified on commercial spin columns, the concentration was determined by absorbance at 260 nM, and the purity was determined and the purity was found to be equivalent for both spCas9 mRNA and MG29-1 mRNA. For in vivo delivery to mice, the spCas9 mRNA/mAlbR2 guide or the MG29-1 mRNA/mAlb29-8-50 guide were packaged inside lipid nanoparticles (LNP). The guide RNA and the mRNA were separately packaged for both spCas9 and for MG29-1. Lipids were dissolved in ethanol. The mRNA or guide RNA was prepared in water, then diluted in 100 mM sodium acetate (pH 4.0) to make the RNA working stock. The four lipid components were combined in ethanol at the specified ratios to make the lipid working stock. An example lipid mixture comprised cholesterol, a neutral lipid such as 1,2-dioleoyl-sn-glycero-3-phosphoethanolamine (DOPE), a cationic lipid such as 1,1'-((2-(4-(2-((2-(bis(2-hydroxydodecyl)amino)ethyl)(2-hydroxydodecyl)amino) ethyl)piperazin-1-yl)ethyl)azanediyl)bis(dodecan-2-ol) (C12-200), and a PEG-linked lipid such as 1,2-dimyristoyl-rac-gly cero-3-methoxypolyethylene glycol-2000 (DMG-PEG-2000) at molar ratios of 47.5:16:35:1.5. The lipid working stock and the RNA working stock were combined in a microfluidics mixing device at a flow rate of 12 mL/min and a ratio of 1 volume of lipid working stock to 3 volumes of RNA working stock. The mass ratio of C12-200 to RNA in the formulation was 10 to 1. The formulated LNP were diluted 1:1 with 1×PBS then dialyzed twice in 1×PBS for 1 hour each, followed by concentration in spin concentrators. The resultant LNP were formulated into 1×PBS buffer, filter sterilized through a 0.2 μM filter and stored at 4° C. The concentration of the RNA inside and outside of the LNP was measured. The average diameter and polydispersity of the LNP were measured in the resultant concentrated LNP by dynamic light scattering. Representative LNP ranged in size from 80 to 100 nanometers with a PDI<0.15 and an RNA encapsulation ratio of greater than 90%. The average diameter, polydispersity, and RNA encapsulation efficiency is shown below in Table 7.

TABLE 7

Summary of LNP characteristics

| LNP | RNA | Average Diameter (nm) | Polydispersity | Percent encapsulation of RNA |
|---|---|---|---|---|
| LNP-A | MG29-1 mRNA | 57 | 0.082 | 94.9 |
| LNP-B | mAlb29-8-50 guide (SEQ ID NO: 55) | 47 | 0.082 | 93.7 |
| LNP-C | Cas9 mRNA | 60 | 0.114 | 94.5 |
| LNP-D | mAlbR2 guide (SEQ ID NO: 50) | 50 | 0.059 | 94.5 |

LNP encapsulating the guide RNA mAlb29-8-50 and the MG29-1 mRNA were mixed at an RNA mass ratio of 1:1. LNP encapsulating the guide RNA mAlbR1 and the spCas9 mRNA were mixed at an RNA mass ratio of 1:1. Both LNP mixtures were injected intravenously into wild type C57Bl/6 mice via the tail vein with total RNA doses of 1 mg/kg, 0.5 mg/kg, or 0.25 mg/kg of RNA in a total volume of 0.1 mL per mouse (N=5 mice per LNP dose). Mice were sacrificed at 5 days post-dosing and the whole liver was flash frozen and stored at −80° C. The entire left lateral lobe of the liver was homogenized using 0.4 mL of buffer per 100 mg of tissue weight in a Bead Mill. Genomic DNA was purified from an aliquot of the homogenate. The albumin intron 1 region was PCR amplified from 50 ng of the genomic DNA in a reaction containing 0.5 micromolar each of the primers mAlb90F (SEQ ID NO: 46, CTCCTCTTCGTCTCCGGC) and mAlb1073R (SEQ ID NO: 47, CTGCCACATTGCTCAGCAC) and 1× high fidelity PCR Master Mix. The resulting 984 bp PCR product, which spans the entire intron 1 of mouse albumin, was purified using a column-based purification kit. The PCR product was sequenced by next generation sequencing (NGS), analyzing for creation of indels in the target sequence, which were used as indicators of creation of double-strand breaks by the Cas enzymes and engagement of the NHEJ pathway.

Figure 2:
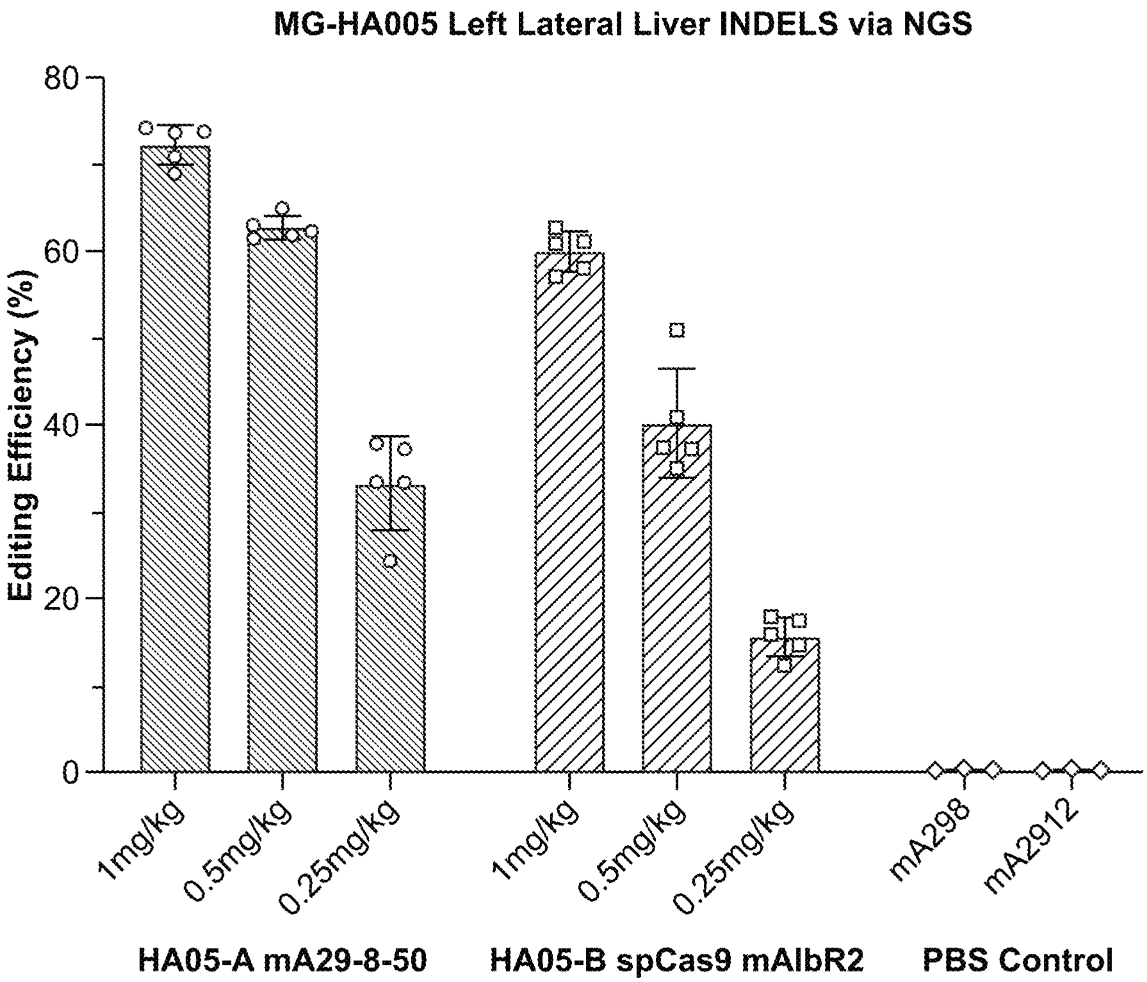
FIG. 2 depicts editing efficiency in the whole liver of mice at 5 days after intravenous injection of LNP encapsulating MG29-1 mRNA and guide mAlb29-8-50 (mA29-8-50), spCas9 mRNA and guide mAlbR2 at three doses, or PBS buffer (Control). Each circle represents a single mouse and the bars indicate the mean and standard deviation.

The sequencing reads were analyzed that aligns each sequence read to the wild-type target sequence (in this case Albumin intron 1) and calculates the number of reads that contain at least one indel irrespective of the indel size within a window that spans 10 base pairs either side of the predicted on-target cut site for the nuclease. The editing efficiency (indel frequency) in each of the 5 mice in each group, as well as the mean and standard deviation for the group, are summarized in FIG. 2. No editing was detected in the control mice injected with PBS buffer. Both spCas9 mRNA/mAlbR2 LNP and the MG29-1 mRNA/mAlb29-8-50 LNP resulted in dose-dependent editing. At all 3 doses, the editing efficiency was higher for the MG29-1 mRNA/mAlb29-8-50 LNP than for the spCas9 mRNA/mAlbR2 LNP. The mean editing efficiencies at the 3 doses are summarized in Table 8. At a dose of 1 mg/kg (0.5 mg/kg mRNA and 0.5 mg/kg guide RNA), MG29-1 was slightly more potent than spCas9, resulting in about 15% more indels. At a dose of 0.5 mg/kg (0.25 mg/kg mRNA and 0.25 mg/kg guide RNA), MG29-1 resulted in about 50% more indels. At a dose of 0.25 mg/kg (0.125 mg/kg mRNA and 0.125 mg/kg guide RNA), MG29-1 resulted in 100% more indels. These data demonstrate that using the same LNP for delivery and mRNA produced using an identical process, the MG29-1 nuclease combined with an appropriately optimized guide RNA is more potent than the spCas9 nuclease and an appropriately modified guide RNA. The superior in vivo editing efficiency of MG29-1 was especially evident at the lowest dose tested, where MG29-1 was 2-fold more potent than spCas9 at the same dose. These results suggest that the MG29-1 nuclease and an appropriately modified guide RNA exemplified by chemistry #50 may have an advantage for in vivo gene editing using LNP delivery.

TABLE 8

Mean editing efficiency in the whole liver of mice at 5 days after intravenous injection of LNP encapsulating either MG29-1 mRNA and guide mAlb29-8-50 (mA29-8-50) or spCas9 mRNA and guide mAlbR2 at three doses, or PBS buffer (Control).

| mRNA | Guide RNA | Dose (mg/kg) | Mean editing (%) | Standard deviation |
|---|---|---|---|---|
| MG29-1 | mAlb29-8-50 | 1 | 72.3 | 2.3 |
| MG29-1 | mAlb29-8-50 | 0.5 | 62.7 | 1.4 |
| MG29-1 | mAlb29-8-50 | 0.25 | 33.2 | 5.4 |
| spCas9 | mAlbR2 | 1 | 60.0 | 2.3 |
| spCas9 | mAlbR2 | 0.5 | 40.3 | 6.3 |
| spCas9 | mAlbR2 | 0.25 | 15.6 | 2.3 |
| PBS control | | — | 0.18 | 0.1 |

Example 6—Integration of a FVIII Gene Cassette at Albumin Intron 1 in the Liver of Mice Mediated by the Sequence Specific Double Strand DNA Cleavage by the MG29-1 RNA Guided Nuclease To evaluate if a human FVIII gene can be integrated into albumin intron 1 in the liver of mice and generate human FVIII protein in the blood of the mice, a dual vector approach was utilized in which the FVIII cassette was delivered in an AAV8 virus and the mRNA encoding the MG29-1 nuclease and an albumin intron 1-targeting sgRNA were delivered using a lipid nanoparticle. The human FVIII gene cassette was designed as described in Example 3.

The FVIII gene cassettes pMG4006 (SEQ ID NO: 56), pMG4007 (SEQ ID NO: 57), pMG4008 (SEQ ID NO: 58) and pMG4009 (SEQ ID NO: 59) were packaged into Adeno Associated Virus serotype 8 (AAV8) using molecular biology techniques. These viruses were titered by quantitative PCR measurement of the encapsulated DNA and expressed as genome copies per mL. Synthetic mRNA encoding the MG29-1 nuclease flanked by nuclear localization signals (NLS) was produced as described above in example 1. This MG29-1 mRNA (SEQ ID NO: 53) which encodes the amino acid sequence of SEQ ID NO: 54 and the sgRNA mA29-8b-50 (SEQ ID NO: 60) or mA29-12b-50 (SEQ ID NO: 61) were co-formulated into LNP at an RNA mass ratio of 1:1 (mRNA:sgRNA) using the methodology described above in Example 5. After AAV8 virus is dosed systemically by intravenous injection, it is taken up primarily by the liver but also by other tissues. After AAV transduces hepatocytes, the single-stranded AAV genome is converted to a double-stranded form, and this subsequently concatemerizes to form circular head-to-tail and head-to-head multimers which are believed to represent the main episomal forms of the AAV genome that persist long-term in the nucleus. The process of cellular transduction and conversion to stable concatemeric AAV genomes occurs over a period of days to weeks and may explain at least in part why expression of transgenes encoded in the AAV genome can take several weeks to reach maximal levels. By contrast, LNP delivery of mRNA is a rapid process with maximal gene expression occurring within 24 hr of systemic IV dosing in mice as evidenced with an mRNA encoding the reporter protein luciferase. Therefore, the AAV8-FVIII viruses were injected 21 days before the administration of the LNP-encapsulated MG29-1 mRNA/sgRNA in order to allow time for efficient AAV transduction of the hepatocytes in the liver and conversion of the single-stranded AAV genomes to stable double-stranded forms. Groups of five wild type C57Bl/6 mice were given intravenous (IV) injections via the tail vein of each of the four AAV8 viruses encapsulating the FVIII gene cassettes pMG4006, pMG4007, pMG4008, and pMG4009 at a dose of $1\times10^{13}$ vector genomes (vg) per kg of body weight. 21 days later, the same mice were given IV injections of LNP encapsulating either MG29-1 mRNA and the sgRNA mA29-12b-50 or MG29-1 mRNA and the sgRNA mA29-8b-50 at a dose of 0.5 mg of total RNA per kg body weight (formulated at 1:1 mass ratio of mRNA:sgRNA). At day 7 post LNP dose, plasma was collected from each mouse for analysis of human FVIII levels. At day 12 post LNP dose, the mice were sacrificed, and plasma was collected from all the mice by cardiac puncture and samples of the livers were collected for genomic DNA extraction.

Liver samples were homogenized using 0.4 mL of buffer per 100 mg of tissue weight in a Bead Mill. Genomic DNA was purified from an aliquot of the homogenate. The albumin intron 1 region was PCR amplified from 50 ng of the genomic DNA in a reaction containing 0.5 micro molar each of the primers mAlb90F (SEQ ID NO: 46, CTCCTCTTCGTCTCCGGC) and mAlb1073R (SEQ ID NO: 47, CTGCCACATTGCTCAGCAC) and 1× high fidelity PCR Master Mix. The resulting 984 bp PCR product, which spans the entire intron 1 of mouse albumin, was purified using a column-based purification kit. The PCR product was sequenced by next generation sequencing (NGS).

Figure 3:
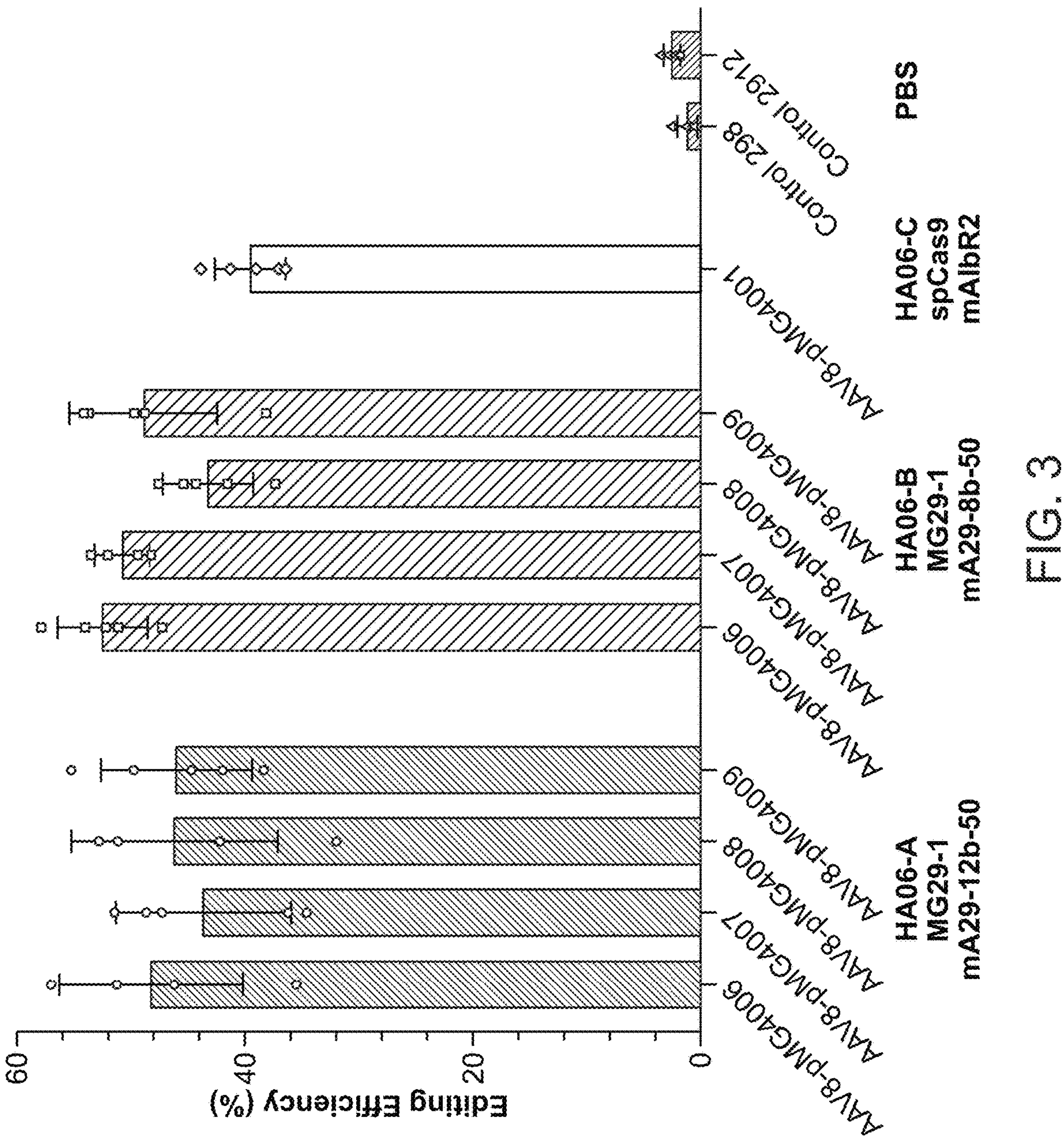
FIG. 3 depicts editing efficiency in the whole liver of mice at 12 days after intravenous injection of LNP encapsulating MG29-1 mRNA and the sgRNA mA29-12b-50, MG29-1 mRNA and the sgRNA mA29-8b-50 at a dose of 0.5 mg/kg, or PBS buffer (Control). Each circle represents a single mouse and the bars indicate the mean and standard deviation.

The sequencing reads were analyzed with a custom Python script that aligns each sequence read to the wild-type target sequence (in this case Albumin intron 1) and calculates the number of reads that contain at least one INDEL irrespective of the INDEL size within a window that spans 10 base pairs either side of the predicted on-target cut site for the nuclease. The data are summarized in FIG. 3 that plots the editing efficiency (INDEL frequency) in each of the 5 mice in each group as well as the mean and standard deviation for the group. The editing data are also summarized in Table 9 below. The mean INDEL frequency in the 8 groups treated with LNP encapsulating MG29-1 mRNA and the albumin-targeting sgRNA ranged from 43% to 53%. There was no significant difference in the INDEL frequency between individual groups or between groups 1 to 4 that were edited with guide mA29-12b-50 and groups 5 to 8 that were edited with guide mA29-8b-50.

TABLE 9

Editing efficiency in the whole liver of mice at 12 days after intravenous injection of LNP encapsulating either MG29-1 mRNA and the sgRNA mA29-12b-50 or MG29-1 mRNA and the sgRNA mA29-8b-50 at a dose of 0.5 mg/kg or PBS buffer (Control).

| | | | | INDEL % in liver tissue | |
|---|---|---|---|---|---|
| Group number | Mouse ID NOs | AAV virus | sgRNA | Group mean | Group standard deviation |
| 2 | 6-10 | AAV8-pMG4006 | mA29-12b-50 | 48.2 | 8.06 |
| 3 | 11-15 | AAV8-pMG4007 | mA29-12b-50 | 43.64 | 7.66 |
| 4 | 16-20 | AAV8-pMG4008 | mA29-12b-50 | 46.17 | 9.06 |
| 5 | 21-25 | AAV8-pMG4009 | mA29-12b-50 | 45.98 | 6.64 |
| 7 | 31-35 | AAV8-pMG4006 | mA29-8b-50 | 52.48 | 3.91 |
| 8 | 36-40 | AAV8-pMG4007 | mA29-8b-50 | 50.76 | 2.42 |
| 9 | 41-45 | AAV8-pMG4008 | mA29-8b-50 | 43.2 | 3.95 |
| 10 | 46-50 | AAV8-pMG4009 | mA29-8b-50 | 48.89 | 6.46 |
| 1 | 1-5 | None | PBS Control | 1.22 | 0.82 |

Human FVIII in the plasma from the mice in groups 1 to 8 was measured using a human FVIII-specific ELISA kit (that is documented to have no cross-reactivity to mouse FVIII. Plasma from the control untreated mice (group 9) was included in each assay and the value subtracted from the experimental samples. The background signal from untreated mouse plasma was low. A standard curve comprised of a plasma-derived full-length human FVIII drug product diluted in a matrix of 25% naive C57BL/6 mouse plasma was run in duplicate on each assay plate over a range of 10 mIU/mL to 200 mIU/mL. Plasma samples from treated mice were also diluted to 25% plasma before being added in duplicate to the well of the ELISA plate. After binding to the capture antibody and washing with PBS/0.05% Tween, the bound human FVIII was detected using the biotin-labeled detection antibody in the kit followed by addition of streptavidin-HRP and TMB substrate and measurement of absorbance at 450 nM in a plate reader. The concentration of human FVIII in the plasma samples of the treated mice (mIU FVIII per mL of plasma) was interpolated from the standard curve. At day 7 post LNP administration, human FVIII levels in the treated mice ranged from 13 mIU/mL to 46 mIU/mL, which represents 1.3% to 4.6% of normal FVIII levels in humans (Tables 10 and 11). At day 12 post LNP administration, human FVIII levels in the treated mice ranged from 39 mIU/mL to 120 mIU/mL, which represents 3.9% to 12% of normal FVIII levels (Tables 10 and 11).

TABLE 10

Human FVIII antigen levels in the plasma from mice at day 7 and day 12 post LNP. Normal human plasma was assayed in parallel as a positive control

| Time point | AAV: | Human FVIII antigen (mIU/mL) sgRNA: mA29-12b-50 pMG4006 | pMG4007 | pMG4008 | pMG4009 | Human Plasma |
|---|---|---|---|---|---|---|
| Day 7 | average | 19.42 | 46.37 | 30.98 | 19.45 | 825 |
| | stdev | 12.96 | 21.09 | 8.42 | 6.7 | 18 |
| Day 12 | average | 50.18 | 70.04 | 58.66 | 39.52 | 915 |
| | stdev | 8.01 | 36.41 | 9.05 | 22.98 | 260 |

TABLE 11

Human FVIII antigen levels in the plasma from mice at day 7 and day 12 post LNP. Normal human plasma was assayed in parallel as a positive control

| Time point | AAV: | Human FVIII antigen (mIU/mL) sgRNA: mA29-8b-50 pMG4006 | pMG4007 | pMG4008 | pMG4009 |
|---|---|---|---|---|---|
| Day 7 | average | 22.03 | 13.06 | 37.78 | 28.28 |
| | stdev | 15.04 | 6.93 | 26 | 21.81 |
| Day 12 | average | 74.4 | 84.12 | 121.14 | 109.54 |
| | stdev | 18.82 | 23.4 | 42.18 | 36.71 |

The day 7 plasma samples from mice in groups 5 to 8 (treated with LNP containing the guide mA29-8b-50) were re-assayed with the same human FVIII-specific ELISA kit but using a recombinant human B-domain deleted FVIII drug product (Xyntha). The mean human FVIII levels determined using Xyntha as the standard were 67±36 mIU/mL, 33±18 mIU/mL, 104±62 mIU/mL, and 78±53 mIU/mL in groups 5, 6, 7, and 8, respectively. The FVIII levels determined using Xyntha as the standard were on average 2.8-fold higher than measured when using Octanate as the standard. The FVIII gene that was delivered to the mice encodes a B3-domain deleted FVIII protein and is the identical protein sequence in all 4 viruses (pMG4006, pMG4007, pMG4008, pMG4009). The B-domain of FVIII comprises 908 amino acids (38% of the full length FVIII protein) and thus makes up a significant proportion of the FVIII protein in Octanate. In summary, these data demonstrate that delivery of a human FVIII donor cassette to mice followed by a LNP encapsulating MG29-1 mRNA and an sgRNA targeting albumin intron 1 results in measurable human FVIII protein expression that is detectable in the blood of the mice at day 7 and day 12 post LNP dosing.

The FVIII gene cassette that was packaged in the AAV lacks a promoter to drive expression of the FVIII gene from episomal AAV genomes. However, because the AAV ITR possesses weak promoter activity, it is possible that RNA encoding the FVIII coding sequence might be transcribed from episomal genomes. However, it is unlikely that episome-derived RNA could be translated into FVIII protein that is secreted into the blood for two reasons. Firstly, the FVIII gene cassette does not contain an in-frame translation initiation codon (ATG) and also lacks a translation initiation consensus sequence (KOZAK sequence) at the 5' end of the cassette. Therefore, it is highly unlikely that any FVIII protein would be translated from any putative RNA produced from episomal AAV genomes. Secondly, any FVIII protein that was produced from episomal AAV genomes will not contain a signal peptide at the N-terminus. Because a signal peptide is required to direct secretion of protein from the cell, any FVIII protein that might be expressed from episomal AAV genomes would not be secreted into the blood. The FVIII gene cassette was designed to express a FVIII protein after integration into albumin intron 1. After integration into albumin intron 1 in the forward orientation, transcription from the endogenous albumin promoter will produce a pre-mRNA that encodes albumin exon 1 followed by part of intron 1 and the human FVIII coding sequence. Splicing of the pre-mRNA from the albumin exon 1 splice donor to the splice acceptor that was included in the FVIII gene cassette will result in a hybrid mRNA transcript in which albumin exon is fused in frame to the mature B-domain deleted human FVIII coding sequence. Because albumin exon 1 encodes the signal peptide of albumin, this will provide the signal peptide necessary for secretion of FVIII into the blood.

The frequency of FVIII gene integration in albumin intron 1 in the liver of the mice was measured using quantitative assays designed to measure forward integration and reverse integration. These assays used the digital droplet PCR (dd-PCR) technology in which the sample genomic DNA was encapsulated in individual droplets such that a droplet contained either a single molecule of DNA or no DNA.

Droplets that contained DNA that was positive for the integration junction (as detected by PCR-based amplification that incorporated fluorescent probes) were scored as positive and droplets that lacked the integration junction were scored as negative. The dd-PCR instrumentation counted the number of positive droplets and used an algorithm to determine the absolute number of copies of the target amplicon (in this case the integration junction) in the original genomic DNA sample. The PCR primers and probes were optimized to ensure that the assay was specific and quantitative. An internal control assay against the cytochrome C1 gene was used to normalize to the copies of genomic DNA in each sample. The results are expressed as percent integration calculated as the copies of the FVIII gene integration junction per 100 copies of cytochrome C1. Two assays for FVIII integration were used, one which detects the 5' Junction of the forward integration product, and the other which detects the 5' Junction of the reverse integration product. The sequences of primers and probes to quantify the forward integration product are KAS_401_F1-Fwd: 5'GCACAGATATAAACACTTAACGGGT3' (SEQ ID NO: 105); KAS_401_F1-Rev: 5'GGAGGAAATCTAGCATCCACAG3' (SEQ ID NO: 106); KAS_401_F1-Probe: 5'+C+CACCAGAAGA+TAT+T+ACCTG3' 6-FAM/3'IBFQ (SEQ ID NO: 107). The sequences of primers and probes to quantify the reverse integration product are: KAS_501_R2-Fwd: 5'GCACAGATATAAACACTTAACGGG3' (SEQ ID NO: 108); KAS_501_R2-Rev: 5'TGCTCTGAGAATGGAAGTGC3' (SEQ ID NO: 109); KAS_501_R2-Probe: 5'+C+GATCAGT+AGAGGTCCTGAGC3' 6-FAM/3'IBFQ (SEQ ID NO: 110) (+ indicates a locked nucleic acid base). These results for individual mice are summarized in Table 12.

TABLE 12

Frequency of integration of the FVIII cassette in the forward orientation and quantitation of albumin-FVIII fusion mRNA in the livers of individual mice

| Group | Guide RNA | AAV8-FVIII | Mouse # | Forward Integration (% of Cyt C1) | Albumin-FVIII fusion mRNA(% of Cyt C1) |
|---|---|---|---|---|---|
| 1 | | — | 1 | 0.00% | 0.00% |
| | | | 2 | Not Analyzed | 0.00% |
| | | | 3 | Not Analyzed | Not Analyzed |
| | | | 4 | 0.00% | 0.00% |
| | | | 5 | 0.00% | 0.00% |
| 2 | 12 | pMG4006 | 6 | 1.33% | 4.68% |
| | | | 7 | 2.00% | 4.34% |
| | | | 8 | 1.07% | 1.86% |
| | | | 9 | 0.83% | 1.28% |
| | | | 10 | 1.90% | 3.75% |
| 3 | 12 | pMG4007 | 11 | 1.39% | 8.92% |
| | | | 12 | 2.30% | 9.08% |
| | | | 13 | 0.85% | 15.52% |
| | | | 14 | 1.72% | 4.98% |
| | | | 15 | 0.32% | 0.41% |
| 4 | 12 | pMG4008 | 16 | 1.63% | 5.08% |
| | | | 17 | 2.25% | 19.14% |
| | | | 18 | 2.09% | 4.20% |
| | | | 19 | 2.03% | 13.42% |
| | | | 20 | 2.03% | 5.91% |
| 5 | 12 | pMG4009 | 21 | Droplet Error | 1.82% |
| | | | 22 | 0.86% | 5.07% |
| | | | 23 | 2.43% | 9.59% |
| | | | 24 | 1.30% | 8.31% |
| | | | 25 | 1.46% | 9.40% |

TABLE 12-continued

Frequency of integration of the FVIII cassette in the forward orientation and quantitation of albumin-FVIII fusion mRNA in the livers of individual mice

| Group | Guide RNA | AAV8-FVIII | Mouse # | Forward Integration (% of Cyt C1) | Albumin-FVIII fusion mRNA(% of Cyt C1) |
|---|---|---|---|---|---|
| 7 | 8 | pMG4006 | 31 | 1.88% | 17.77% |
| | | | 32 | 1.16% | 24.01% |
| | | | 33 | 1.49% | 16.50% |
| | | | 34 | 1.04% | 10.46% |
| | | | 35 | 1.47% | 37.99% |
| 8 | 8 | pMG4007 | 36 | 0.32% | 12.50% |
| | | | 37 | 1.38% | 48.33% |
| | | | 38 | 1.02% | 20.05% |
| | | | 39 | 1.93% | 23.22% |
| | | | 40 | 1.60% | 25.81% |
| 9 | 8 | pMG4008 | 41 | 0.98% | 39.26% |
| | | | 42 | 1.53% | 34.40% |
| | | | 43 | 1.77% | 55.36% |
| | | | 44 | 1.14% | 26.41% |
| | | | 45 | 1.02% | 9.41% |
| 10 | 8 | pMG4009 | 46 | 0.89% | 23.07% |
| | | | 47 | 2.42% | 56.36% |
| | | | 48 | 1.72% | 38.36% |
| | | | 49 | 0.39% | 11.42% |
| | | | 50 | 1.25% | 34.83% |

Figure 7:
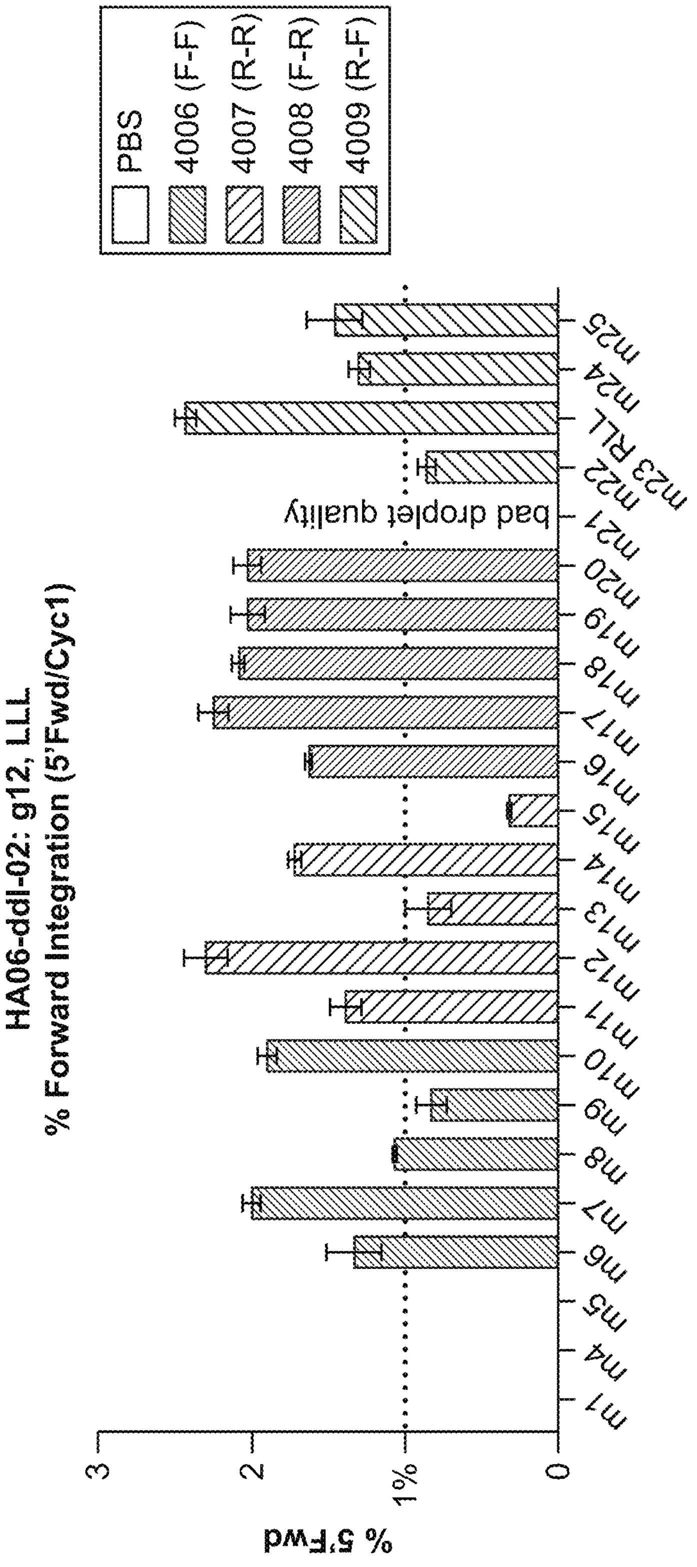
FIG. 7 depicts the frequency of forward integration of the FVIII gene cassette into the albumin intron site mediated by MG29-1 and guide 12 measured in the liver by dd-PCR and normalized to cytochrome C1.
Figure 8:
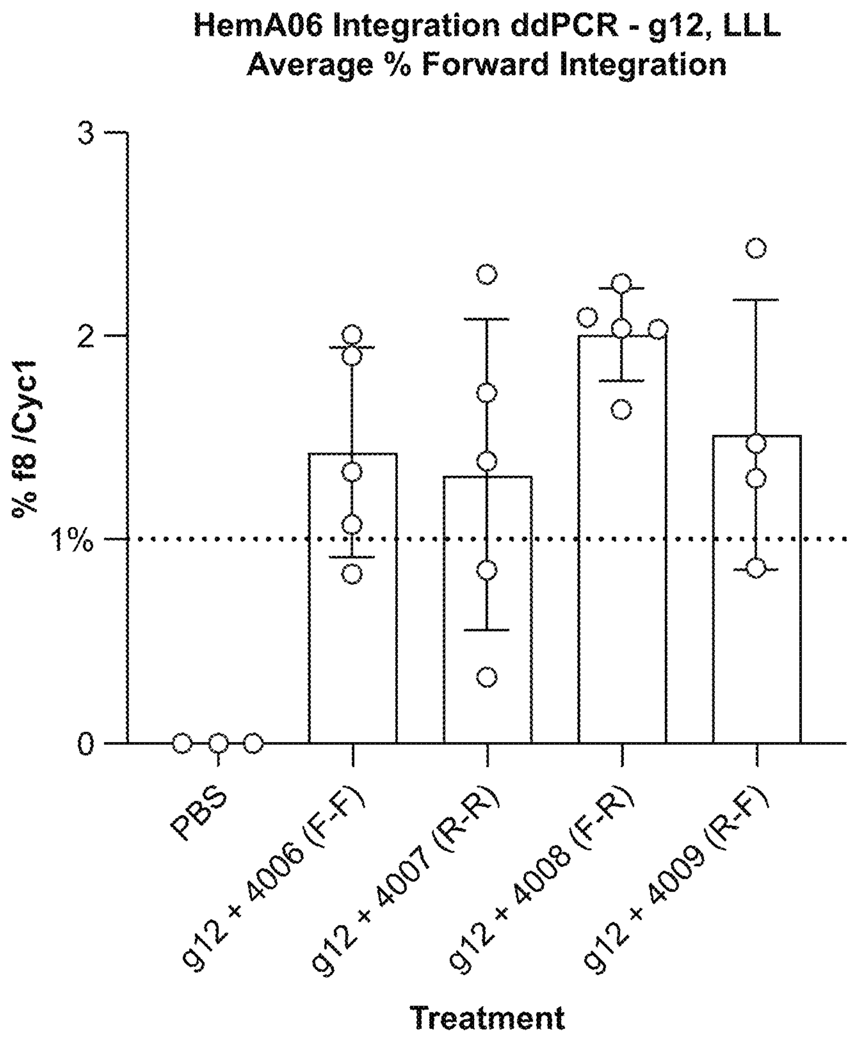
FIG. 8 depicts the average frequency of forward integration of the FVIII gene cassette into the albumin intron site mediated by MG29-1 and guide 12 measured in the liver by dd-PCR and normalized to cytochrome C1.
Figure 9:
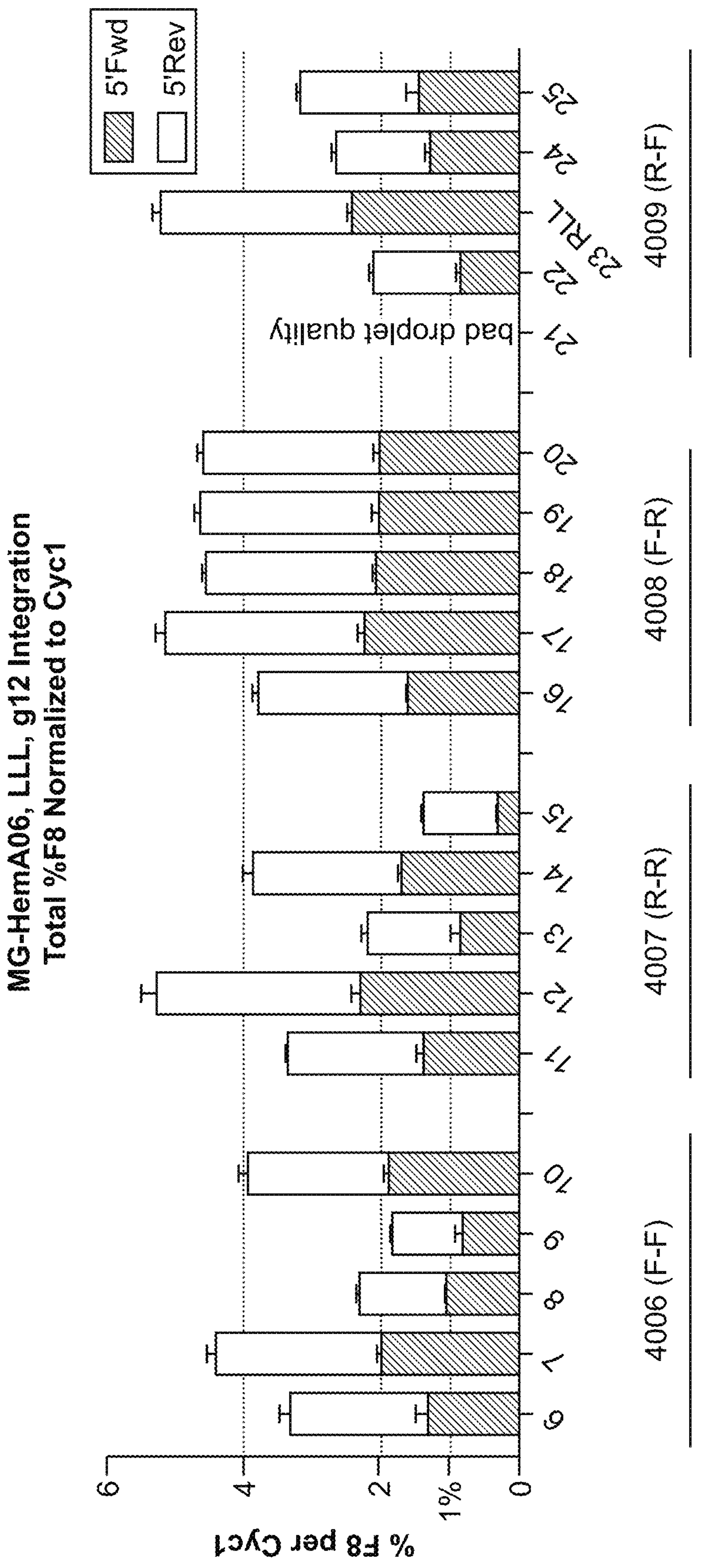
FIG. 9 depicts the frequency of forward and reverse integration of the FVIII gene cassette into the albumin intron site mediated by MG29-1 and guide 12 measured in the liver by dd-PCR and normalized to cytochrome C1.

FIG. 7 shows the forward integration frequency in individual mice from each group. Animals ml, m4, m5 are control mice that were injected with PBS buffer only, and no integration was detected, demonstrating that the assay had no background signal. All mice that received AAV8-pMG4006, AAV8-pMG4007, AAV8-pMG4008, or AAV8-pMG4009, followed by LNP encapsulating the MG29-1 mRNA and guide RNA 12 (mA29-12b-50), had measurable integration in the forward orientation that ranged from 0.25% to 2% (0.25 to 2 copies per 100 copies of cytochrome C1). The data for mouse m21 was not reported due to a technical issue with the dd-PCR assay on that sample. The mean forward integration frequency per group is shown in FIG. 8. There was no significant difference between the 4 groups that received the 4 AAV donors (AAV8-pMG4006, AAV8-pMG4007, AAV8-pMG4008, AAV8-pMG4009) that differ in the orientation of the guide RNA target sites flanking the donor, although pMG4008 exhibited the most consistent frequency among mice and the highest mean forward integration of 2%. The frequency of integration of the FVIII cassette into albumin intron 1 in the reverse orientation was measured and plotted in FIG. 9, together with the forward integration frequency. Reverse integration frequencies ranged from 1% to 2% and were not statistically significantly different between the groups the received the 4 AAV donors (AAV8-pMG4006, AAV8-pMG4007, AAV8-pMG4008, AAV8-pMG4009). Overall, the reverse integration frequency was similar to the forward integration frequency in each mouse, demonstrating that there was no preferential integration of the FVIII cassette in either the forward or reverse orientations.

Figure 10:
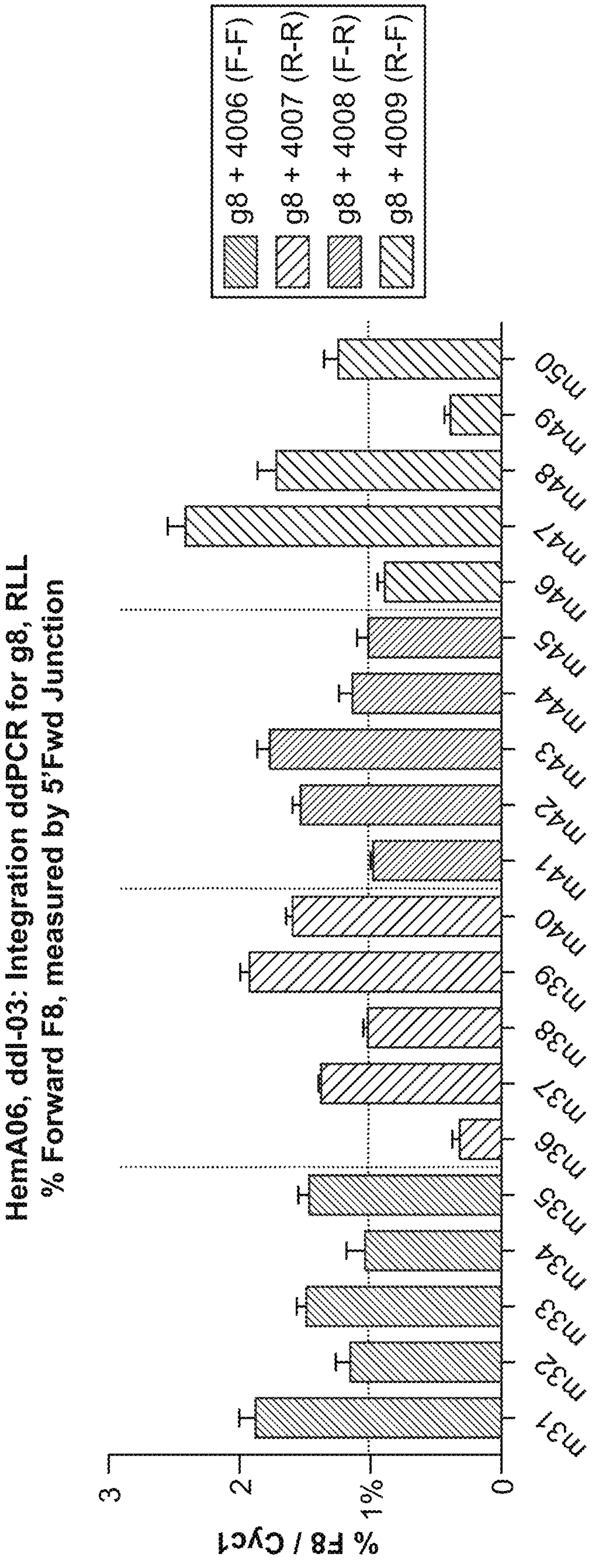
FIG. 10 depicts the frequency of forward and reverse integration of the FVIII gene cassette into the albumin intron site mediated by MG29-1 and guide 8 measured in the liver by dd-PCR and normalized to cytochrome C1.
Figure 11:
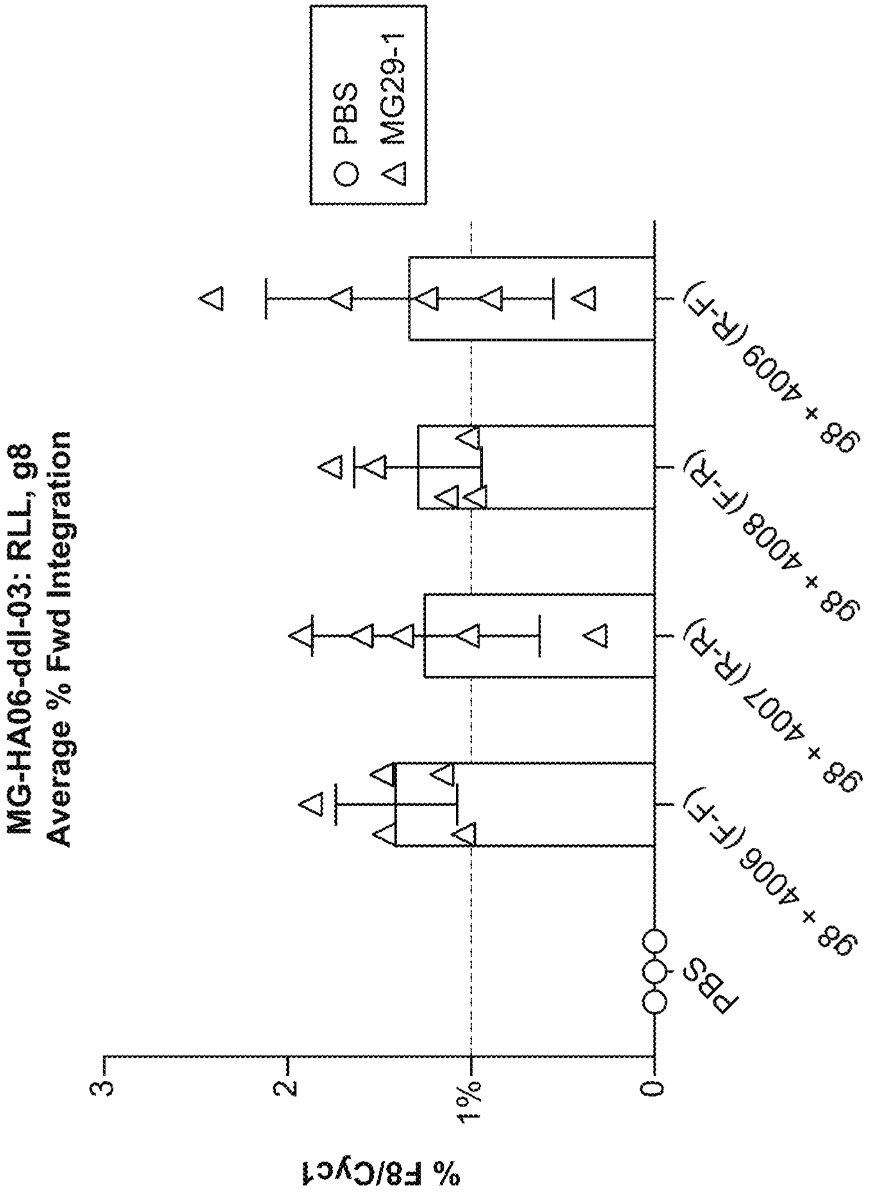
FIG. 11 depicts the average frequency of forward integration of the FVIII gene cassette into the albumin intron site mediated by MG29-1 and guide 8 measured in the liver by dd-PCR and normalized to cytochrome C1.
Figure 12:
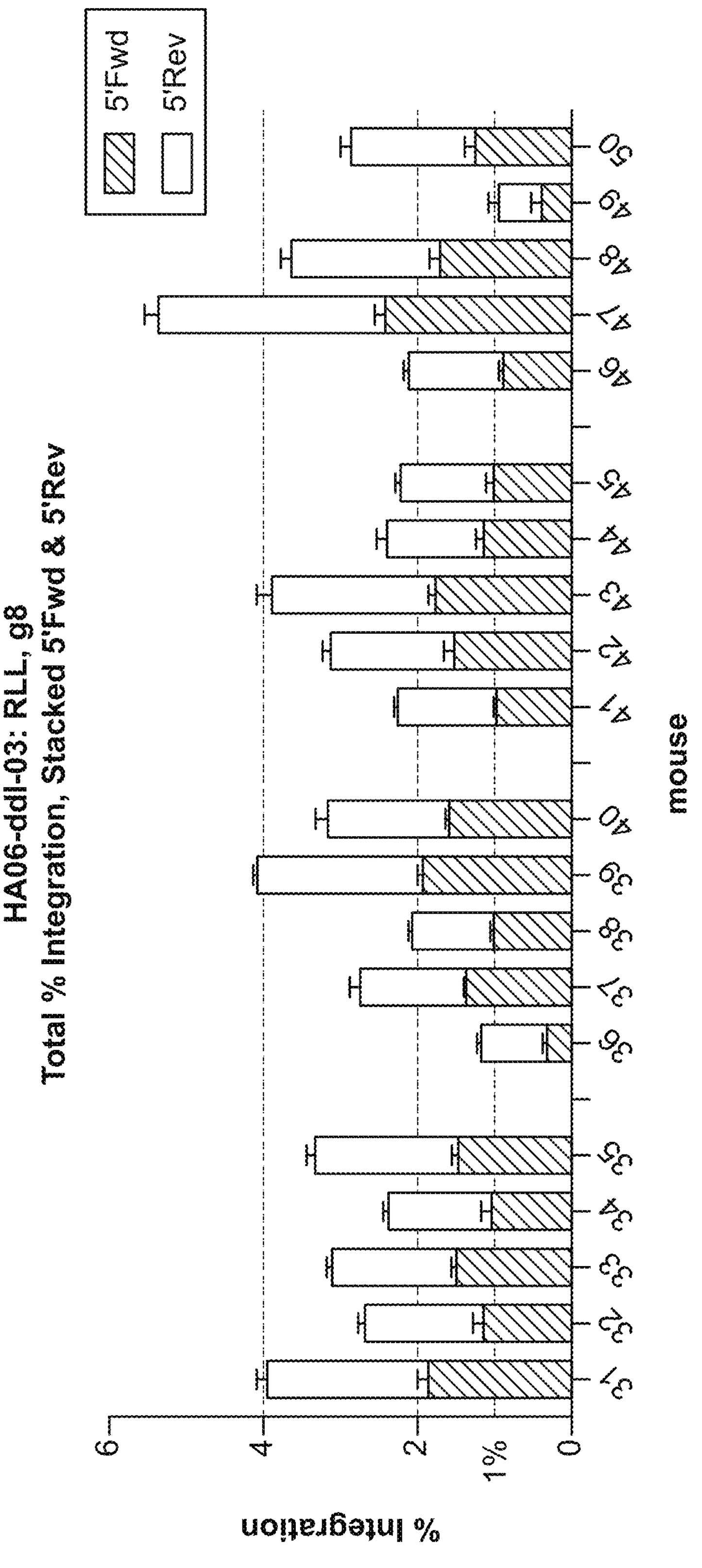
FIG. 12 depicts the frequency of forward and reverse integration of the FVIII gene cassette into the albumin intron site mediated by MG29-1 and guide 8 measured in the liver by dd-PCR and normalized to cytochrome C1.

FIG. 10 shows the forward integration frequency in individual mice from each group that received AAV8-pMG4006, AAV8-pMG4007, AAV8-pMG4008, or AAV8-pMG4009, followed by LNP encapsulating the MG29-1 mRNA and guide RNA 8 (mA29-8b-50). All mice had measurable integration in the forward orientation that ranged from 0.25% to 2% (0.25 to 2 copies per 100 copies of cytochrome C1). The mean forward integration frequency per group is shown in FIG. 11. There was no significant difference between the 4 groups that received the 4 AAV donors (AAV8-pMG4006, AAV8-pMG4007, AAV8-pMG4008, AAV8-pMG4009) that differ in the orientation of the guide RNA target sites flanking the donor. The frequency of integration of the FVIII cassette into albumin intron 1 in the reverse orientation was measured and plotted in FIG. 12, together with the forward integration frequency. Reverse integration frequencies ranged from 0.5% to 3% and were not statistically significantly different between the groups that received the 4 AAV donors (AAV8-pMG4006, AAV8-pMG4007, AAV8-pMG4008, AAV8-pMG4009). Overall, the reverse integration frequency was similar to the forward integration frequency in each mouse, demonstrating that there was no preferential integration of the FVIII cassette in either the forward or reverse orientations.

The expression of the expected FVIII-encoding mRNA from the integrated FVIII cassette in the liver of the same mice was quantified using a dd-PCR assay. Integration of the FVIII cassette in the forward orientation (defined as the 5' end of the FVIII cassette being adjacent to the albumin exon 1) at the double strand break created by the MG29-1 nuclease and guide RNA is predicted to produce a hybrid mRNA resulting from RNA splicing between the albumin exon 1 splice donor and the splice acceptor at the 5' end of the FVIII cassette. This hybrid mRNA will therefore contain a novel sequence junction between albumin exon 1 and the 5' end of the coding sequence for mature FVIII as shown in FIG. 13. A dd-PCR assay was designed in which the forward primer is complementary to a sequence within albumin exon 1, the reverse primer is complementary to a sequence within the 5' end of human FVIII, and the probe spans the predicted junction between albumin exon 1 and the 5' end of human FVIII after correct splicing. The sequences of the primers and probe are:

```
MG101-set1-FWD:
                                        (SEQ ID NO: 111)
5'TAACCTTTCTCCTCCTCCTCTT3';

MG101-set1-REV:
                                        (SEQ ID NO: 112)
5'TCCACAGCTCCCAGGTAATA3';

MG101-set1-Probe:
                                        (SEQ ID NO: 113)
5'TCTTCTGGTGGCCAGTGCTTCTC3' FAM, ZEN/3' IBFQ.
```

Figure 14:
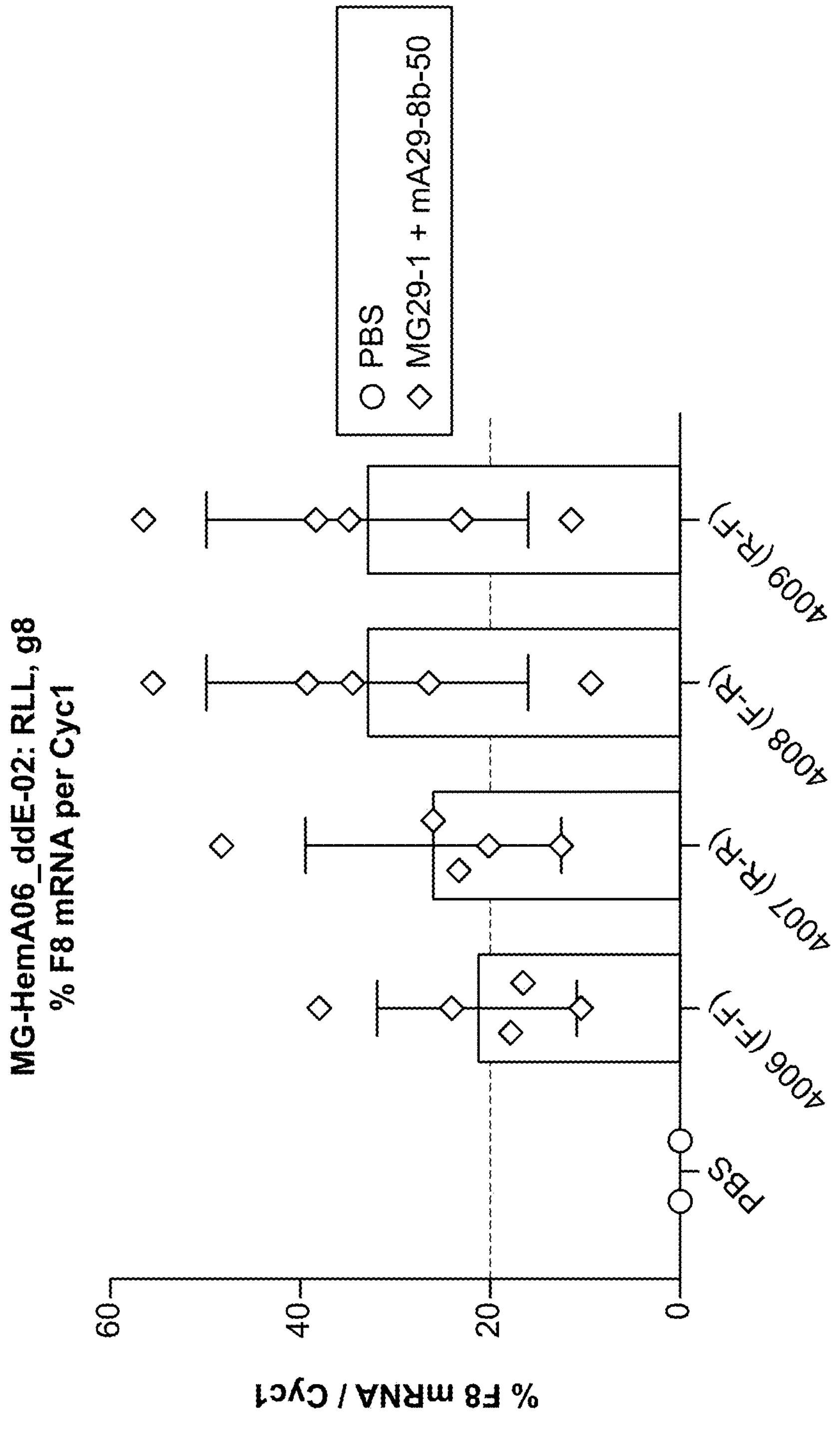
FIG. 14 depicts quantitation of the Albumin-FVIII fusion mRNA in the liver of mice dosed with either of 4 AAV8-FVIII donors ($1\times10^{13}$ vg/kg) and LNP encapsulating MG29-1 mRNA and guide RNA 8 (mA29-8b-50, 0.5 mpk dose).

Total RNA was purified from the left lateral lobe of the liver from each mouse. After DNase digestion to eliminate any remaining genomic DNA, cDNA was prepared from 500 ng of total RNA. The cDNA was assayed for the albumin-FVIII fusion mRNA and for cytochrome C1 mRNA. The level of cytochrome C1 mRNA was used to normalize for the quality and quantity of mRNA assayed by dividing the absolute copies of the albumin-FVIII hybrid mRNA by the absolute copies of the cytochrome C1 mRNA and expressing this as a percentage. The results for mice that received either of the 4 AAV8-FVIII donors (AAV8-pMG4006, AAV8-pMG4007, AAV8-pMG4008, AAV8-pMG4009) and LNP encapsulating MG29-1 mRNA and guide RNA mA29-8b-50 (guide 8) are shown in FIG. 14. No signal was detected in PBS-injected control mice, demonstrating that the assay is specific. The level of the albumin-FVIII fusion mRNA ranged from 20% of cytochrome C1 to 30% of cytochrome C1 in the 4 groups. While the differences between the groups was not statistically significant, there was a trend to higher levels of the albumin-FVIII fusion mRNA in mice that received AAV8-pMG4008 or AAV8-pMG4009.

Figure 15:
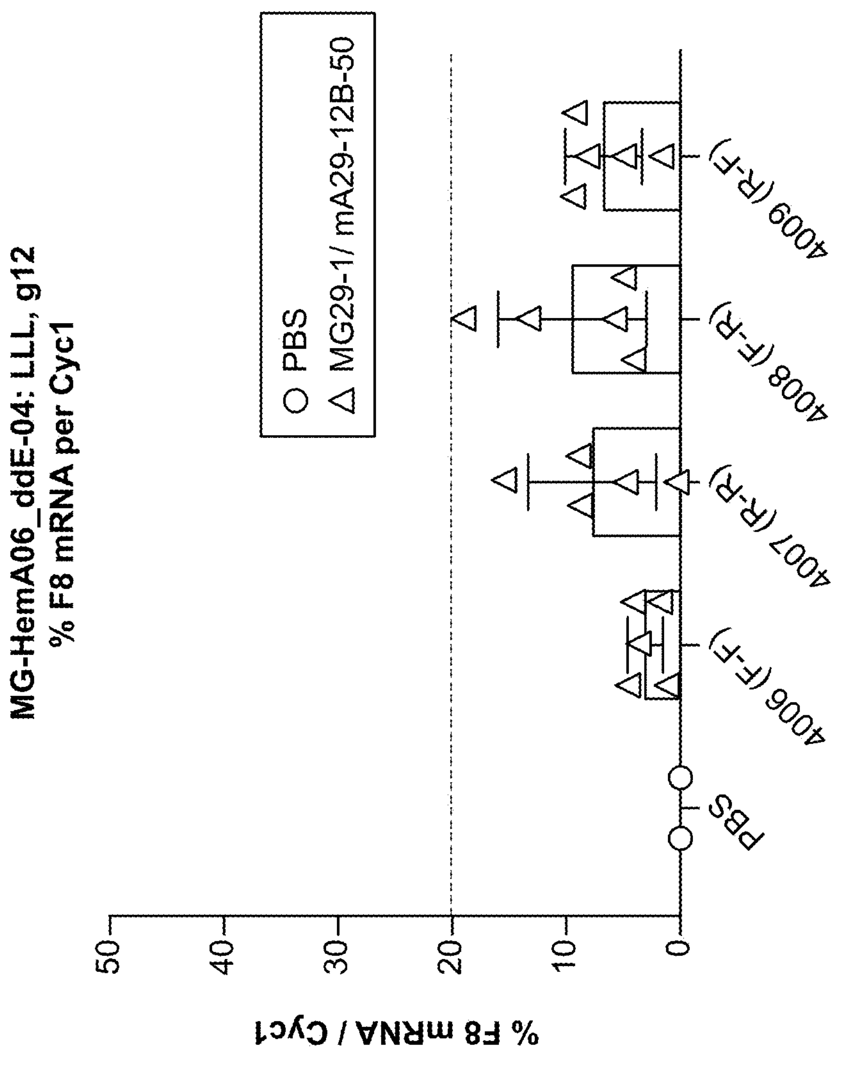
FIG. 15 depicts quantitation of the Albumin-FVIII fusion mRNA in the liver of mice dosed with either of 4 AAV8-FVIII donors and LNP encapsulating MG29-1 mRNA and guide RNA 12 (mA29-12b-50).

The results for mice that received any of the 4 AAV8-FVIII donors (AAV8-pMG4006, AAV8-pMG4007, AAV8-pMG4008, AAV8-pMG4009) and LNP encapsulating MG29-1 mRNA and guide RNA mA29-12b-50 (guide 12) are shown in FIG. 15. No signal was detected in PBS-injected control mice, demonstrating that the assay is specific. The level of the albumin-FVIII fusion mRNA ranged from 5% of cytochrome C1 to 10% of cytochrome C1 in the 4 groups. While the differences between the groups was not statistically significant, there was a trend to higher levels of the albumin-FVIII fusion mRNA in mice that received AAV8-pMG4007, AAV8-pMG4008, or AAV8-pMG4009. Overall, the levels of the albumin-FVIII fusion mRNA were lower in the set of mice that received guide 12 (mA29-12b-50) compared to those that received guide 8 (mA29-8b-50). The higher level of albumin-FVIII fusion mRNA observed in mice in which the FVIII gene was integrated at the guide 8 target site was not correlated with higher frequencies of FVIII gene integration in the forward orientation. The highest frequency of FVIII integration in the forward orientation was observed in mice that received pMG4008 and guide 12, where the albumin-FVIII fusion mRNA frequency was 10%, lower than the 30% measured in mice that received pMG4008 and pMG4008 and guide 8.

Example 7—Demonstration of Integration of a Human FVIII Gene Cassette into Albumin Intron 1 of Mice A cohort of 15 adult C57BL/6 mice (8 week old) were given IV injections of $5\times10^{12}$ vg/kg of pMG4006 packaged in AAV8 (groups 2, 3, 4). A group of 5 mice were not injected with AAV (group 1). 21 days later, the 5 mice in group 3 were given IV injections of a LNP encapsulating MG29-1 mRNA and the sgRNA mA29-8-37 (SEQ ID NO: 62), and the 5 mice in group 4 were given IV injections of an LNP encapsulating MG29-1 mRNA and the sgRNA mA29-12-37 (SEQ ID NO: 63). The sgRNA mA29-12-37 targets the same genomic sequence in albumin intron 1 as mA29-12b-50 (SEQ ID NO: 61) does, and the sgRNA mA29-8-37 targets the same genomic sequence in albumin intron 1 as mA29-8b-50 (SEQ ID NO: 60) does. The mice in groups 1 and 2 were given IV injections of PBS buffer as a control. At day 12 after LNP dosing, plasma was collected from all the mice by cardiac puncture, and liver tissue was collected for genomic DNA analysis.

The frequency of editing at the target site in albumin intron in genomic DNA purified from the livers of the mice was measured by NGS as described in earlier examples (Table 13).

TABLE 13

INDEL frequency in the liver and FVIII protein levels in the blood of mice

| Group | AAV | LNP or PBS (control) | Mouse # | Avg % FVIII | INDELS by NGS |
|---|---|---|---|---|---|
| 1 | None | PBS | 1 | 0.18 | 0.18 |
| | | | 2 | 0 | 0.13 |
| | | | 3 | 0 | 0.26 |
| | | | 4 | 0.05 | 0 |
| | | | 5 | 0 | 0 |

TABLE 13-continued

INDEL frequency in the liver and FVIII protein levels in the blood of mice

| Group | AAV | LNP or PBS (control) | Mouse # | Avg % FVIII | INDELS by NGS |
|---|---|---|---|---|---|
| 2 | Yes | PBS | 6 | 0.26 | 0.33 |
| | | | 7 | 0 | 0.47 |
| | | | 8 | 0.07 | 0.3 |
| | | | 9 | 0 | 0.16 |
| | | | 10 | 0 | 0.17 |
| 3 | Yes | MG29-1 mRNA and mA29-8-37 | 11 | 4.78 | 43.9 |
| | | | 12 | 3.8 | 50.85 |
| | | | 13 | 3.69 | 49.21 |
| | | | 14 | 0 | 42.94 |
| | | | 15 | 0.17 | 48.88 |
| 4 | Yes | MG29-1 mRNA and mA29-12-37 | 16 | 13.3 | 48.98 |
| | | | 17 | 1.6 | 0.15 |
| | | | 18 | 2.58 | 18.91 |
| | | | 19 | 0 | 44.6 |
| | | | 20 | 0.17 | 1.14 |

Groups 1 and 2 that did not receive LNP had background levels of editing as expected. Mice in group 3 that were injected with LNP encapsulating MG29-1 mRNA and sgRNA mA29-8-37 had INDEL frequencies that ranged from 43% to 51%. Two of the mice in group 4 (mice #16 and #19) that were injected with LNP encapsulating MG29-1 mRNA and sgRNA mA29-12-37 had high INDEL frequencies of 45% and 49%, similar to those observed in group 3. One mouse in group 4 (mouse #18) had a medium INDEL frequency of 19%. Two mice in group 4 (mouse #17 and #20) had low or undetectable INDEL frequencies similar to that of un-injected mice, indicating that the administration of the LNP was probably not successful in these 2 mice.

The human FVIII levels in the plasma samples were measured using a capture-chromogenic activity assay that measures FVIII activity after the human FVIII in the plasma is captured on the surface of a plate using human FVIII-specific antibodies that do not bind to mouse FVIII. 96 wells plates were first coated with a mixture of two human specific anti-FVIII antibodies. After blocking the plate surface with milk powder in PBS buffer and washing with PBS plus 0.05% tween, appropriately diluted mouse plasma samples and standards were added to the wells and incubated at 37° C. for 2 hours. The standards were prepared by diluting the human plasma derived European Pharmacopoeia (EP) Reference Standard in naive C57BL/6 mouse plasma. The wells were washed 3 times with PBS containing 0.05% Tween, and the FVIII activity that was bound to each well was assayed using the commercial FVIII chromogenic assay kit according to the manufacturer's protocol. The results were back calculated to the percent of FVIII levels in normal human plasma that were present in the mouse plasma. The results (Table 13) demonstrate that no human FVIII activity was measured in the plasma of mice from group 1 that received no AAV and no LNP. Group 2 mice that received the AAV encoding the human FVIII gene cassette but did not receive LNP (and so was not edited at the albumin locus) also had no detectable human FVIII activity in their blood. This demonstrates that the AAV virus alone that delivers the FVIII gene cassette and is expected to result in episomal AAV genomes was not capable of producing active human FVIII protein. Three of the five mice in Group 3 that received both the AAV and the LNP (with guide mA29-8-37) had detectable human FVIII activity in their blood of around 4% of normal human levels. Two of the five mice in Group 4 that received both the AAV and the LNP (with guide mA29-12-37) had detectable human FVIII activity in their blood of 2.6% and 13% of normal human levels. The two mice in group 4 that had no INDELS had no detectable FVIII. Taken together, the data from groups 3 and 4 demonstrate that 5 of the 8 mice that were edited at the albumin locus expressed detectable human FVIII activity in their blood at day 12 after LNP dosing.

Figure 4:
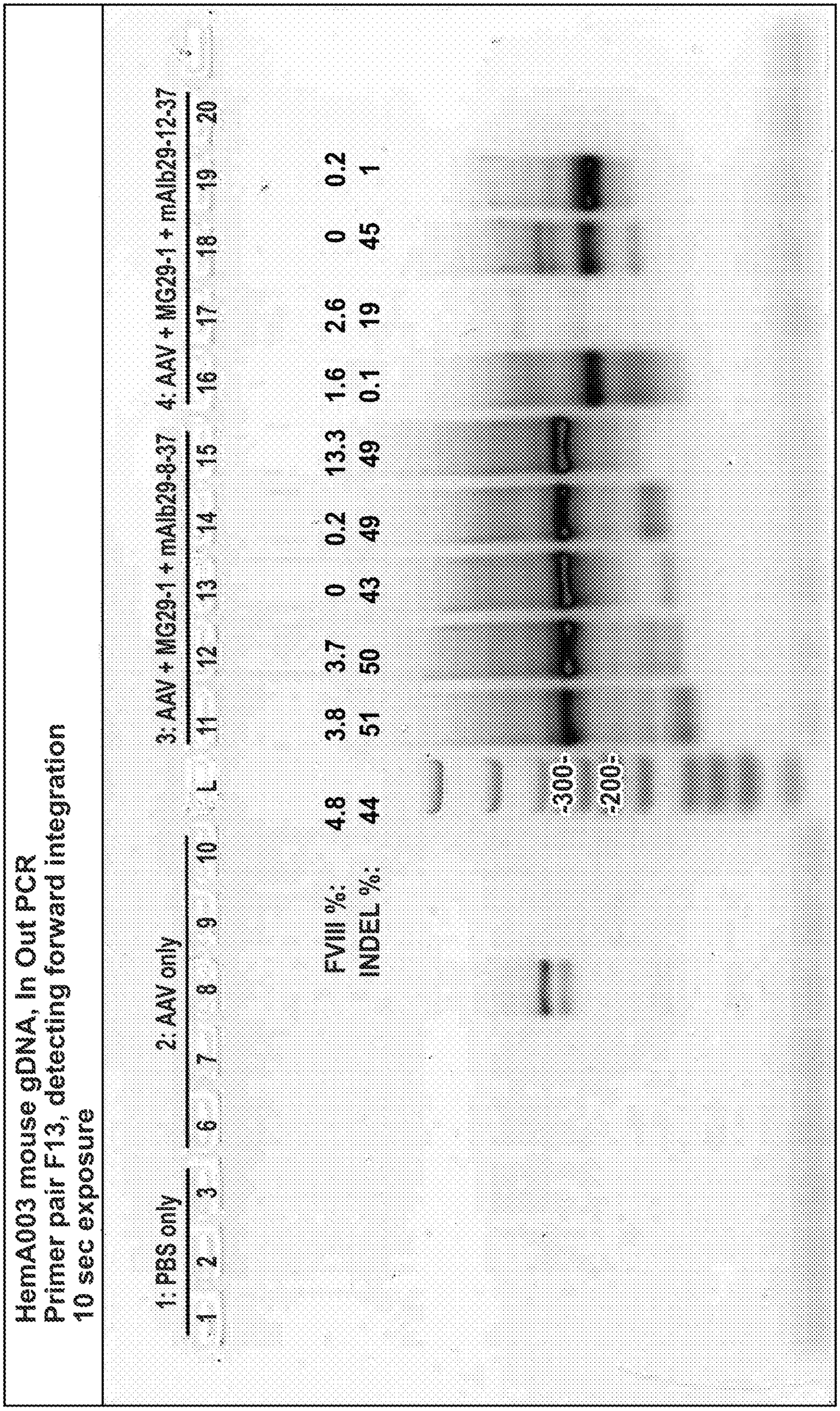
FIG. 4 depicts a gel demonstrating integration of the FVIII gene cassette in the forward orientation by In-Out PCR.

To confirm that the expression of human FVIII in the blood of these mice was associated with integration of the FVIII gene cassette into the sgRNA target site in albumin intron 1, an in-out PCR assay was performed. A pair of PCR primers was designed that are complementary to DNA sequences that flank the predicted junction between albumin intron 1 and the 5' end of the human FVIII gene cassette that was packaged in the AAV virus. The primer that binds to albumin intron 1 was located 5' of the target site of the sgRNA. In the event that the FVIII gene cassette was integrated at the target site of the sgRNA in albumin intron 1, a PCR product of 286 bp would be generated for group 3 (integration into the mA29-8-37 target site) and 221 bp for group 4 (integration into the mA29-12-37 target site) using genomic DNA purified from the liver of the mice as a template. The products of the PCR reactions were fractionated on agarose gels and imaged by staining. As shown in FIG. 4, in-out PCR analysis of genomic DNA from mice in group 1 (lanes 1 to 3) gave no bands, indicating the absence of background PCR amplification. Four of the five mice from group 2 (mice 6, 7, 9, 10) that were injected with AAV only (no LNP) also failed to generate a PCR product, while mouse 8 from group 2 gave a faint band that is not the correct size for an integrated FVIII gene. This demonstrates that the FVIII gene cassette did not become integrated at the guide RNA target site in mice injected with the AAV that carries the FVIII gene cassette but were not edited by LNP delivery of MG29-1 and the cognate sgRNA. Liver genomic DNA from all five mice in group 3 (mice #11 to #15) produced a PCR product whose size matches the predicted size of 286 bp for a FVIII cassette integrated in the forward (expression competent) orientation at the mA29-8-37 target site. This PCR assay is not quantitative, so the PCR band intensity does not represent the relative integration frequency between the different mice. Liver genomic DNA from 3 of the 5 mice in group 4 (mice #16, #18, #19) produced a PCR product that matches the expected 221 bp size for a FVIII cassette integrated in the forward (expression competent) orientation at the mA29-12-37 target site. Mice #17 and #20 from group 4 did not generate a PCR product, indicating that in these two mice, no integration of the FVIII cassette integrated in the forward (expression competent) was detectable using this assay. This is consistent with the fact that mice #17 and #20 had no INDELS at the guide target site in albumin intron 1 (probably because of unsuccessful LNP dosing) and provides further evidence that integration is dependent on editing by MG29-1.

In summary, these data demonstrate that the MG29-1 nuclease combined with an appropriately designed guide RNA can induce integration of an appropriately designed human FVIII gene cassette into the genome in the liver of mice at albumin intron 1. Furthermore, this integration results in the expression of functional human FVIII protein in the blood.

Example 8—Efficient Editing by the MG29-1 Nuclease in the Liver of Non-Human Primates Following Systemic Administration of MRG29-1 mRNA and a Suitable Guide RNA Packaged in a Lipid Nanoparticle Five guide RNA for MG29-1 targeting human albumin intron 1 were selected based upon testing 23 guides in the liver cell line Hep3B. These 5 guide RNA designated chA29-74B-50 (SEQ ID NO: 64), cA29-78B-50 (SEQ ID NO: 65), chA29-83B-50 (SEQ ID NO: 66), cA29-84B-50 (SEQ ID NO: 67), and cA29-87B-50 (SEQ ID NO: 68) were synthesized with specific chemical modifications to the RNA to improve the in vitro stability and in vivo potency of gene editing for MG29-1 (chemistry 50). The nomenclature for modifications to the RNA are as follows; m indicates the base has a 2'-O-methyl group (for example mG), f indicates the base has a 2'-fluoro group (for example fG), and * indicates that the backbone comprises a phosphorothioate linkage (for example G*G).

Messenger RNA encoding the MG29-1 nuclease was generated by in vitro transcription of a linearized plasmid template using T7 RNA polymerase and a mixture of ribonucleotides rATP, rCTP, and rGTP, N1-methyl pseudouridine, and the CleanCAP capping reagent. The SV40-derived nuclear localization sequence (PKKKRKVGGGGS (SEQ ID NO: 103)) followed by a short linker was included at the N terminus of the coding sequence. The nuclear localization signal from nucleoplasmin preceded by a short linker (SGGKRPAATKKAGQAKKKK (SEQ ID NO: 104)) was added to the C-terminus of the coding sequence. The plasmid also encoded an approximately 100 nt polyA tail at the 3' end which generates a polyA tail in the mRNA. The coding sequence for MG29-1 was codon optimized. The DNA sequence encoding the MG29-1 mRNA was as in SEQ ID NO: 53 and the amino acid sequence encoded by the MG29-1 mRNA was as in SEQ ID NO: 54. The mRNA was column purified, the concentration was determined by absorbance at 260 nm, and the purity was determined.

Figure 5:
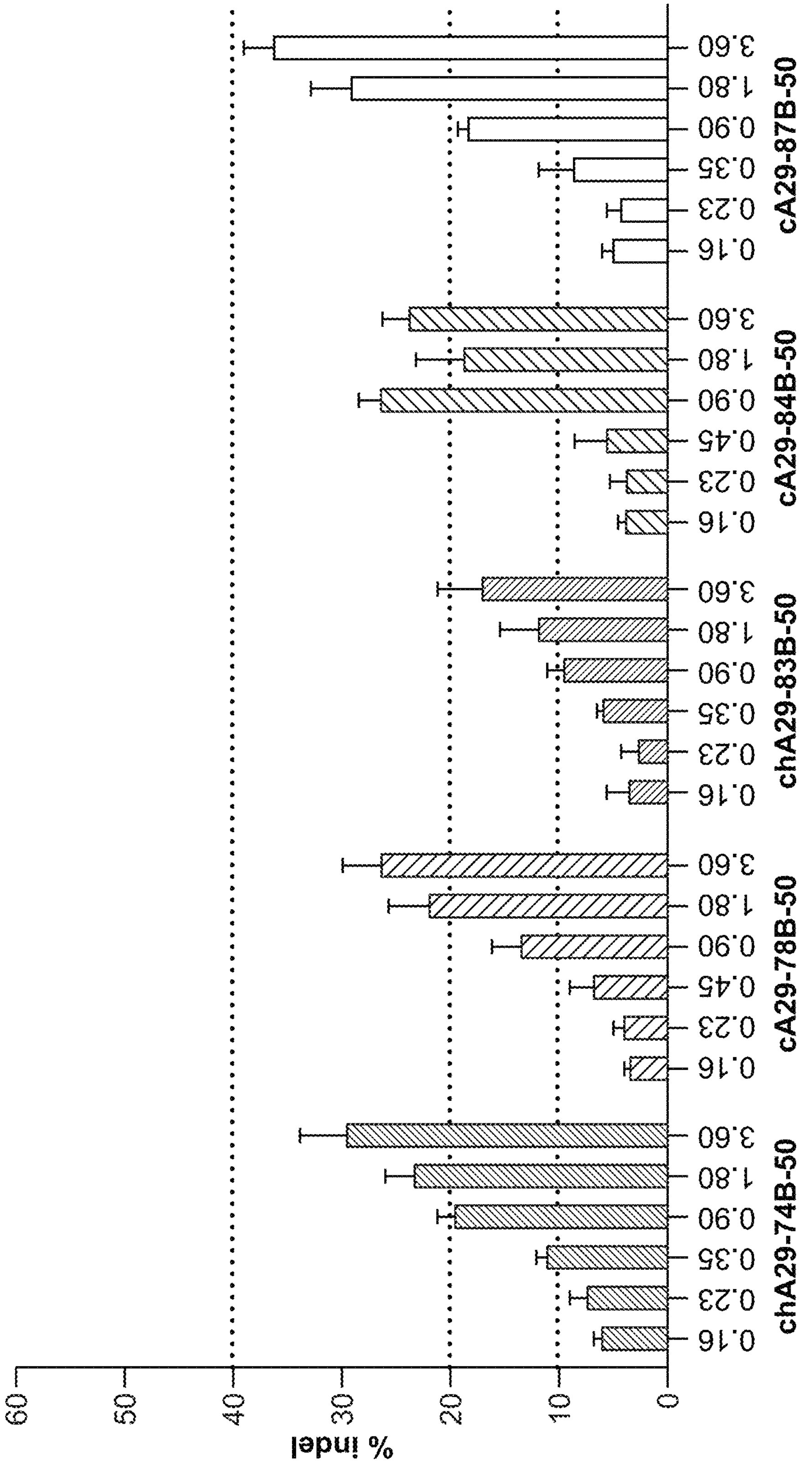
FIG. 5 depicts editing by MG29-1 and 5 guides targeting Albumin intron 1 in primary hepatocytes from cynomolgus monkeys.

The relative potencies of the five lead guide RNAs were evaluated in primary hepatocytes from cynomolgus monkeys (PCH). Cyropreserved PCH cells were plated in 24 well plates according to the supplier's instructions. The MG29-1 mRNA and each of the guides were mixed at a 1:20 mRNA:guide molar ratio, mixed with transfection reagent according to the manufacturer's protocol, and then applied to the PCH. The media on the cells was changed every 24 h post transfection, and after 48 h genomic DNA was purified from the cells. The target region in albumin intron 1 was PCR amplified using pairs of primers and a high fidelity PCR Master Mix. The purified PCR product of the right size was sequenced by next generation sequencing. The sequence reads were aligned to the reference sequence for the albumin gene from cynomolgus macaque, and a custom script was used to count the number of reads that contained insertions or deletions (indels) at the target site for the specific guide RNA. The editing frequency was defined as the percentage of the total of sequence reads that contained indels. The results (FIG. 5) demonstrate that all 5 guides resulted in editing at the expected target site in a dose-dependent manner. The ranking of the guide potency from most to least potent was cA29-87B-50>chA29-74B-50>cA29-78B-50>cA29-84B-50>chA29-83B-50. The editing efficiency of these guides and MG29-1 mRNA in primary human hepatocytes at a single dose was 38%, 43%, 55%, 40%, and 40.5% for guides chA29-74B-50, cA29-78B-50, chA29-83B-50, cA29-84B-50, and cA29-87B-50, respectively. Thus, in primary human hepatocytes, guide chA29-83B-50 appeared to be the most potent. Based on these data on PCH and PHH, the two guides cA29-87B-50 and chA29-83B-50 were selected to be tested in non-human primates.

The MG29-1 mRNA and either guide chA29-83B-50 (SEQ ID NO: 66) or guide cA29-87B-50 (SEQ ID NO: 68) were co-formulated in two lipid nanoparticle formulations called L1 and L2 at a mass ratio of 1:1 (mRNA: guide RNA). The lipid nanoparticles (LNPs) had an average diameter of less than 100 nm, a polydispersity index of less than 0.12 as measured by dynamic light scattering, and encapsulation greater than 85% as measured by the ribogreen assay. After formulation, the LNPs were buffer exchanged into phosphate buffered saline containing sucrose, frozen, and stored at −80° C. for several weeks prior to dosing.

Purpose-bred naive cynomolgus monkeys (*Macaca fascicularis*) with an average body weight of 1.8 kg±0.16 kg were acclimated for 2 weeks prior to dosing. LNP formulations were thawed and diluted to 0.3 mg total RNA per mL by dilution with sterile 0.9% sodium chloride. Groups of 3 monkeys were dosed with each of the 4 LNP preparations by infusion into the tail vein (5 mL/kg of body weight) over a period of 60 minutes. All animals were monitored by veterinary staff, and no serious adverse events were observed. The retains of the dosing solution were assayed for the concentration of RNA using the ribogreen assay with standards comprising the guide and mRNA used to produce the LNP. Baked on this analysis, the actual dose of RNA given to each group was 1.4, 1.3, 1.25, and 1.25 mg per kg for groups 1, 2, 3, and 4 respectively as shown in Table 14.

TABLE 14

NHP Study Groups and Doses

| Grp | N | LNP name | Dose (mg/kg) | Route | Guide RNA | mRNA | Actual Dose |
|---|---|---|---|---|---|---|---|
| 1 | 3 | MG-A2-L1 | 1.5 | IV | chA2983B-50 | MG29-1 | 1.4 |
| 2 | 3 | MG-A4-L1 | 1.5 | IV | cA29-87B-50 | MG29-1 | 1.25 |
| 3 | 3 | MG-A2-L2 | 1.5 | IV | chA2983B-50 | MG29-1 | 1.3 |
| 4 | 3 | MG-A4-L2 | 1.5 | IV | cA29-87B-50 | MG29-1 | 1.25 |

Figure 6:
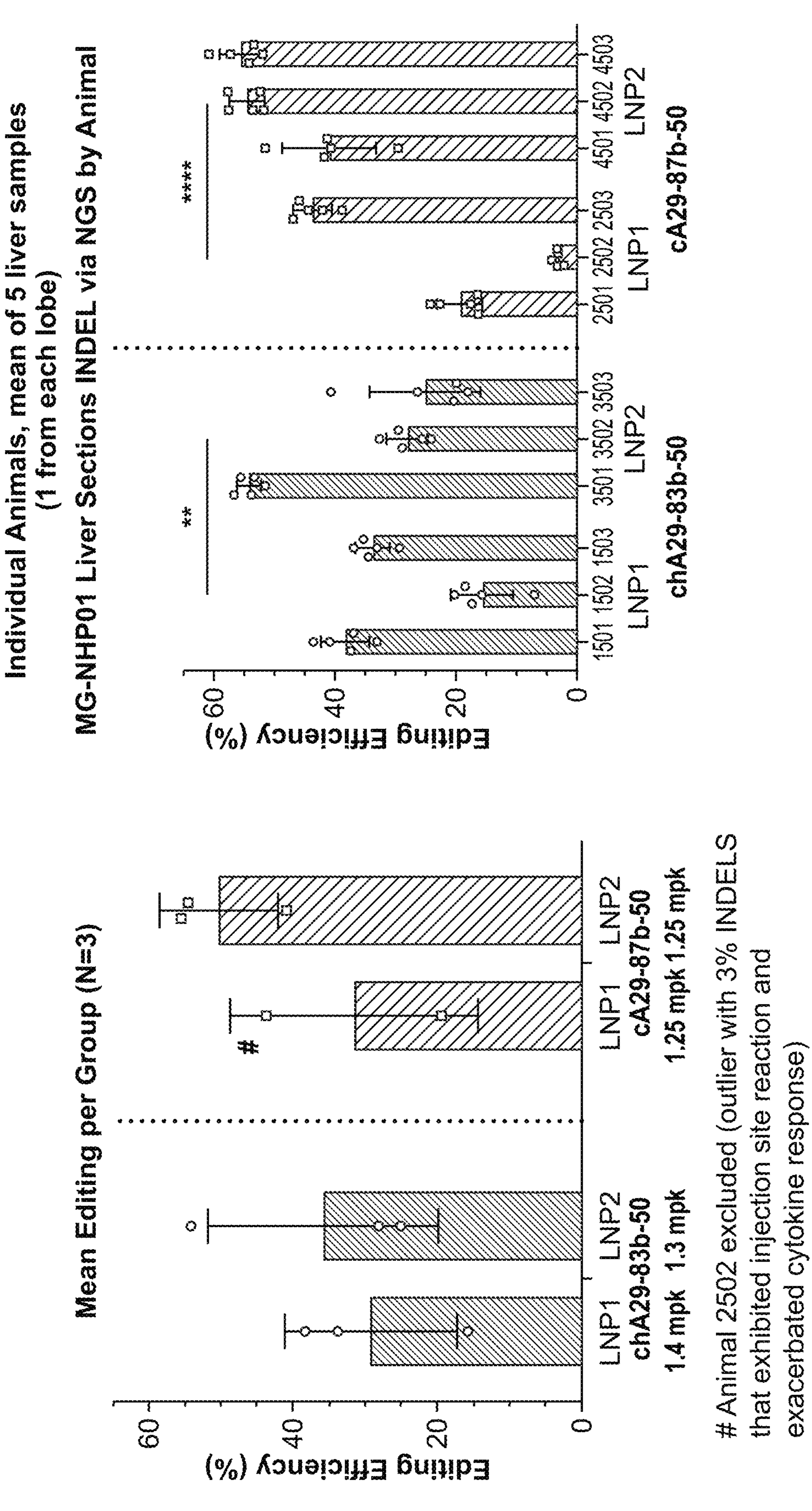
FIG. 6 depicts editing in the liver of NHP 8 days after administration of LNP-encapsulated MG29-1 mRNA and guide RNA.

At 8 days post dose, all groups underwent necropsy and samples of different tissues were collected for analysis. Samples of each of the 5 lobes of the liver were collected separately from each animal and stored frozen prior to extraction and purification of genomic DNA. The target region in albumin intron 1 was PCR amplified from the genomic DNA purified from each of the 5 liver lobes of each animal using pairs of primers and a high fidelity PCR Master Mix. The purified PCR product of the right size was sequenced by next generation sequencing on an Illumina MiSeq instrument. The sequence reads were aligned to the reference sequence for the albumin gene from cynomolgus macaque and a custom script was used to count the number of reads that contained insertions or deletions (indels) at the target site for the specific guide RNA. The editing frequency was defined as the percentage of the total of sequence reads that contains indels. Editing at the expected target site for each guide was detected in the liver of all 12 animals (FIG. 6). The mean editing percentage from the 5 liver lobes of each animal is tabulated in Table 15 along with the average of the editing for each group. The mean editing in the groups ranged from 29% to 50%. Group 4 (treated with LNP L2 encapsulating MG29-1 mRNA and guide cA29-87B-50) exhibited the highest mean editing (50%) and also the most consistent editing among the 3 animals per group. Animal 2502 exhibited scaly skin at the injection site and elevated cytokines at days 1 to 3 post dose, indicating that this animal experienced an acute but self-resolving inflammatory response to the test article. This suggests that the low levels of editing (3%) in this animal were caused by an inflammatory response that prevented efficient delivery to the liver. None of the animals received anti-inflammatory drugs prior to or during the course of the study.

Overall, these data demonstrated that the MG29-1 nuclease, when combined with an appropriate guide RNA, can mediate efficient editing in the liver of non-human primates when delivered systemically as RNA packaged in an LNP.

TABLE 15

Editing percentage in the liver of Cynomolgus monkeys (average of 5 liver lobes per animal) 8 days after systemic dosing of LNP encapsulating MG29-1 mRNA and 2 different guide RNA

| Guide/LNP | Cyno ID | % editing (mean of 5 lobes) | Stdev |
|---|---|---|---|
| chA2983B-50/L1 | 1501 | 38.66 | 3.99 |
| | 1502 | 15.91 | 5.21 |
| | 1503 | 34.06 | 2.84 |
| Group 1 mean and stdev: | | 29.54 | 9.82 |
| chA2983B-50/L2 | 3501 | 54.55 | 2.05 |
| | 3502 | 28.43 | 3.38 |
| | 3503 | 25.32 | 9.26 |
| Group 2 mean and stdev: | | 36.10 | 13.11 |
| cA29-87B-50/L1 | 2501 | 19.37 | 3.55 |
| | 2502 | 3.21 | 0.69 |
| | 2503 | 43.39 | 3.22 |
| Group 3 mean and stdev: | | 31.38 | 12.01 |
| cA29-87B-50/L2 | 4501 | 40.52 | 7.67 |
| | 4502 | 54.20 | 2.96 |
| | 4503 | 55.31 | 3.62 |
| Group 4 mean and stdev: | | 50.01 | 6.72 |

Example 9—Integration of a FVIII Gene Cassette at Albumin Intron 1 in the Liver of Mice Mediated by the Sequence Specific Double Strand DNA Cleavage by the MG3-6/3-4 RNA Guided Nuclease To evaluate if the Type II CRISPR system MG3-6/3-4 can mediate integration of a human FVIII gene into albumin intron 1 in the liver of mice and generate human FVIII protein in the blood of the mice, a dual vector approach was utilized. The FVIII cassette was delivered in an AAV8 virus, and the mRNA encoding the MG3-6/3-4 nuclease and an albumin intron 1 targeting sgRNA were delivered using a lipid nanoparticle. The human FVIII gene cassettes comprised the identical human FVIII coding sequence as in pMG4006 (SEQ ID NO: 16), pMG4007 (SEQ ID NO: 17), pMG4008 (SEQ ID NO: 18) and pMG4009 (SEQ ID NO: 19), but the flanking sequences were modified to contain the target sites for two MG3-6/3-4 guide RNAs called mA364-34 and mA364-59 that target intron 1 of mouse albumin. These guide RNAs were selected based on editing (INDEL) efficiency from a screen of guides for mG3-6/3-4 in the mouse liver cell line Hepal-6. The FVIII cassettes in pMG4012 (SEQ ID NO: 20), pMG4013 (SEQ ID NO: 21), pMG4014 (SEQ ID NO: 22), and pMG4015 (SEQ ID NO: 23) differ in the orientation of the flanking guide RNA target sites: pMG4012 (Forward-Forward orientation), pMG4013 (Reverse-Reverse orientation), pMG4014 (Forward-Reverse orientation), and pMG4015 (Reverse-Forward orientation).

The FVIII cassettes in pMG4012 (SEQ ID NO: 20), pMG4013 (SEQ ID NO: 21), pMG4014 (SEQ ID NO: 22) and pMG4015 (SEQ ID NO: 23) were packaged into Adeno Associated Virus serotype 8 (AAV8) using standard methodologies. These viruses were titered by quantitative PCR measurement of the encapsulated DNA and expressed as genome copies per mL. Synthetic mRNA encoding the MG3-6/3-4 nuclease flanked by nuclear localization signals (NLS) was produced as described above in Example 1. This MG3-6/3-4 mRNA (SEQ ID NO: 95), which encodes the amino acid sequence of SEQ ID NO: 96, and the sgRNA mA364-34-1 (SEQ ID NO: 97) or mA364-59-1 (SEQ ID NO: 98) were co-formulated into LNP at an RNA mass ratio of 1:1 (mRNA:sgRNA) using the methodology described above in Example 5.

Groups of five immune-deficient mice were given intravenous (iv) injections via the tail vein of each of the four AAV8 viruses encapsulating the FVIII gene cassettes pMG4012, pMG4013, pMG4014, and pMG4015 at a dose of $1\times10^{13}$ vector genomes (vg) per kg of body weight. 21 days later, the same mice were given iv injections of LNP encapsulating either MG3-6/3-4 mRNA and the sgRNA mA364-34-1 or MG3-6/3-4 mRNA and the sgRNA mA364-59-1 at a dose of either 0.5 mg or 0.7 mg of total RNA per kg body weight (formulated at 1:1 mass ratio of mRNA: sgRNA). Additional mice were dosed with the 4 AAV viruses but not given LNP.

Figure 16:
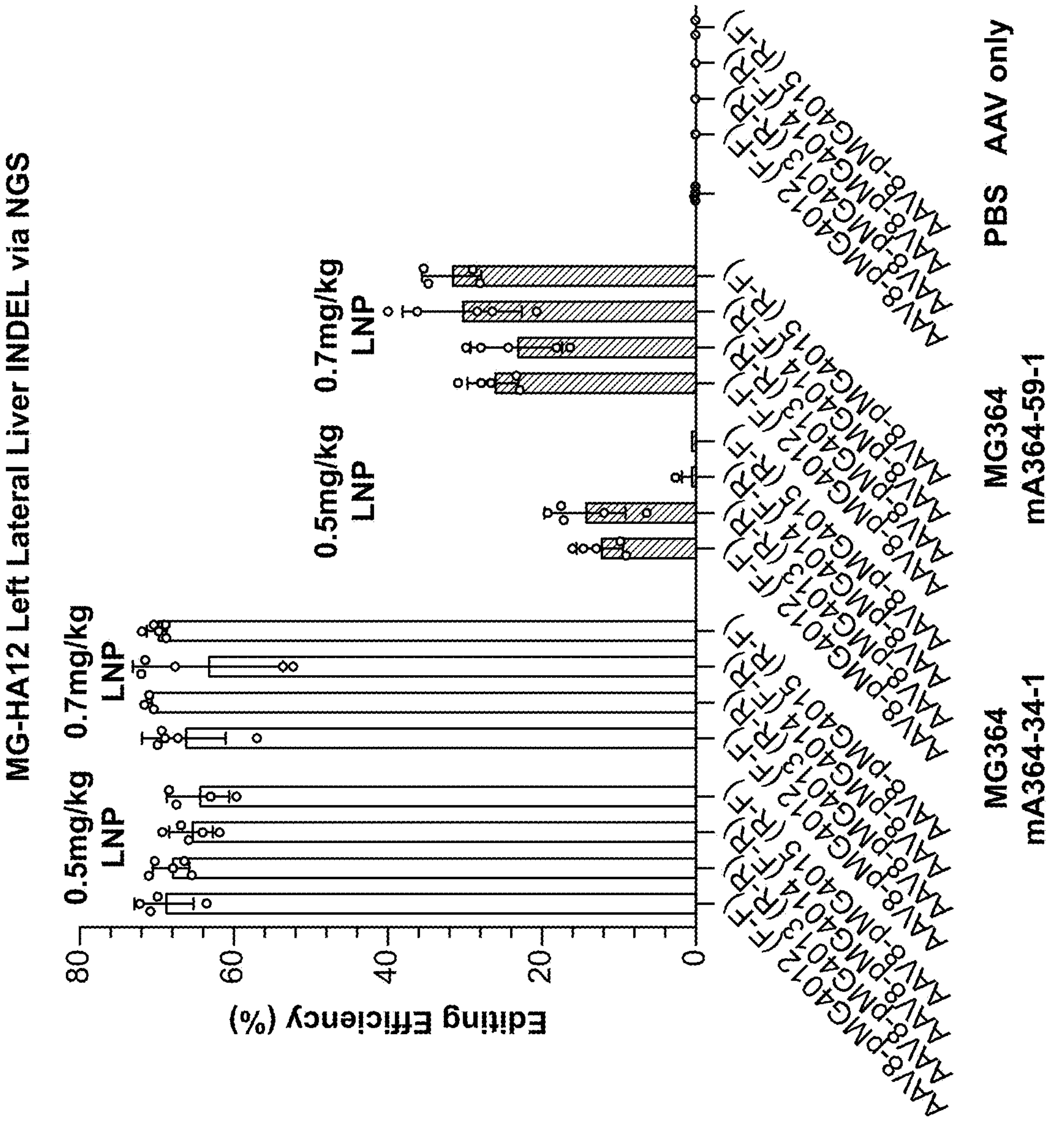
FIG. 16 depicts editing (Indels) in the liver of mice dosed with various AAV8-FVIII donors or PBS and either LNP encapsulating MG3-6/3-4 mRNA and one of guides mA364-34-1 or mA364-59-1. From left to right: the first 4 columns are mice dosed with AAV8-pMG4012 to AAV8-pMG4015 followed by LNP encapsulating MG3-6/3-4 mRNA and guide mA364-34-1 at 0.5 mpk dose. The next 4 columns are mice dosed with AAV8-pMG4012 to AAV8-pMG4015 followed by LNP encapsulating MG3-6/3-4 mRNA and guide mA364-34-1 at 0.7 mpk dose. The next 4 columns are mice dosed with AAV8-pMG4012 to AAV8-pMG4015 followed by LNP encapsulating MG3-6/3-4 mRNA and guide mA364-59-1 at 0.5 mpk dose. The next 4 columns are mice dosed with AAV8-pMG4012 to AAV8-pMG4015 followed by LNP encapsulating MG3-6/3-4 mRNA and guide mA364-59-1 at 0.7 mpk dose. The next column is mice dosed with PBS only (controls). The final 4 columns are mice dosed with AAV8-pMG4012 to AAV8-pMG4015 only.

At the end of the study when the mice were sacrificed (about 5 months post LNP dosing), genomic DNA was purified from the liver tissues of each mouse and analyzed for editing at the target site for the guide RNA by NGS. The results are shown in FIG. 16. Mice dosed with LNP encapsulating MG3-6/3-4 mRNA and guide RNA mA364-34-1 at either 0.5 or 0.7 mg per kg body weight had INDELS between 63% and 70% in the whole liver. Because hepatocytes make up about 60-70% of the cells in the liver and the LNP used delivers primarily to hepatocytes, 70% Indels in the whole liver represents saturating editing of the hepatocytes. In contrast, mice dosed with LNP encapsulating MG3-6/3-4 mRNA and guide RNA mA364-59-1 at either 0.5 or 0.7 mg per kg body weight had INDELS between 0% and 35% in the whole liver. The two groups that received AAV8-pMG4014 and AAV8-pMG4015 and LNP encapsulating MG3-6/3-4 mRNA and guide RNA mA364-59-lat 0.5 mpk exhibited almost no editing, which was attributed to a dosing failure. Overall, the editing efficiency of guide mA364-34-1 was at least 2-fold higher than that of guide mA364-59-1.

A dd-PCR assay was used to measure integration of the FVIII gene cassette into the target site in albumin intron 1 in either the forward or reverse orientations. Genomic DNA purified from the livers of the mice was digested with EcoRI. For quantitation of the forward orientation, the primers used to amplify the 5' forward junction were KAS_401_F1-Fwd: 5'GCACAGATATAAACACTTAACGGGT3' (SEQ ID NO: 105); KAS_401_F1-Rev: 5'GGAGGAAATCTAGCATCCACAG3' (SEQ ID NO: 106); KAS_401_F1-Probe: 5'+C+CACCAGAAGA+TAT+T+ACCTG3' 6-FAM/3'IBFQ (SEQ ID NO: 107). For quantitation of the reverse orientation, the primers used to amplify the 5' reverse junction were KAS_501_R2-Fwd: 5'GCACAGATATAAACACTTAACGGG3' (SEQ ID NO: 108); KAS_501_R2-Rev: 5'TGCTCTGAGAATGGAAGTGC3' (SEQ ID NO: 109);

KAS_501_R2-Probe: 5'+C+GATCAGT+AGAGGTCCT-GAGC3' 6-FAM/3'IBFQ (SEQ ID NO: 110) (+ indicates a locked nucleic acid base).

Figure 17:
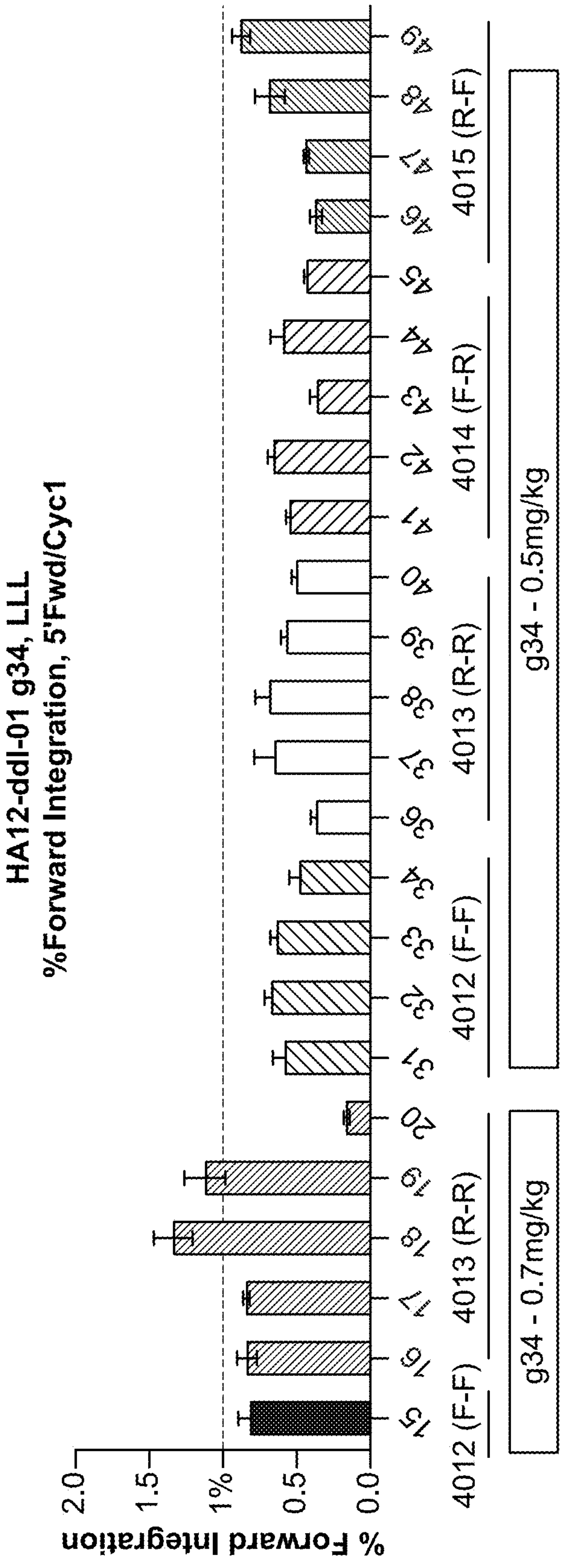
FIG. 17 depicts the frequency of integration of a FVIII gene cassette in the forward orientation into albumin intron 1 mediated by MG3-6/3-4 and guide mA364-34-1 (guide 34).
Figure 18:
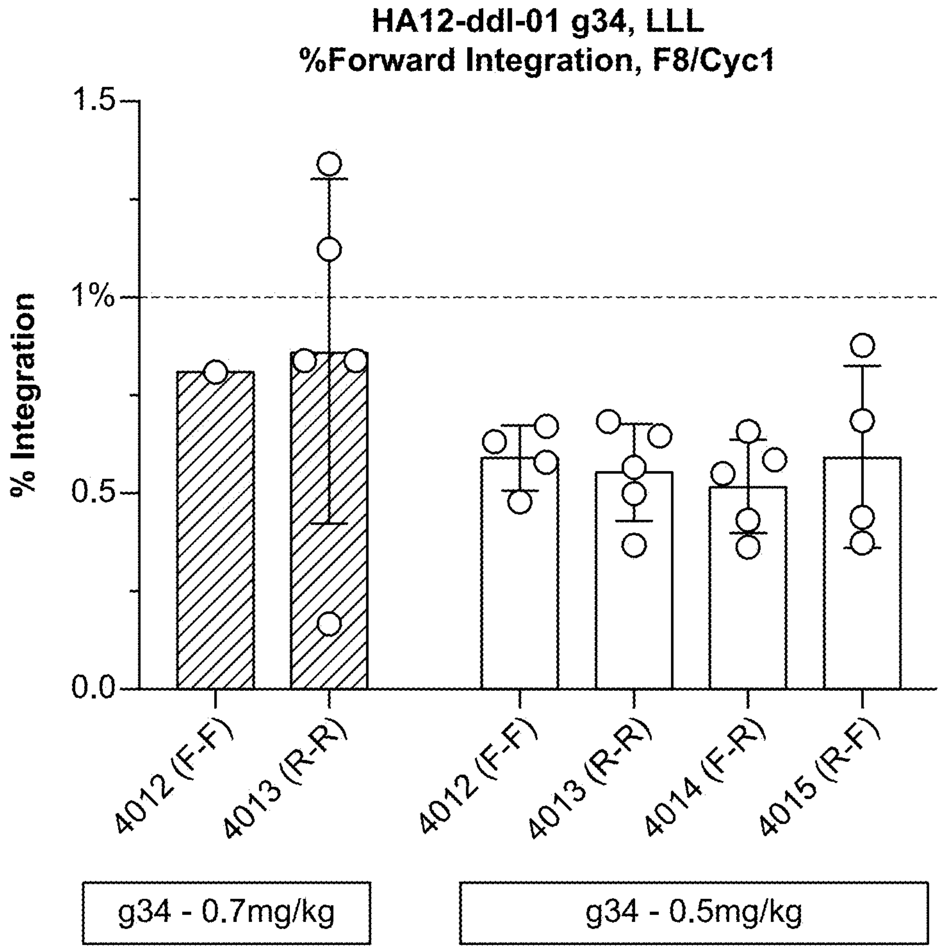
FIG. 18 depicts the mean frequency of integration of a FVIII gene cassette in the forward orientation into albumin intron 1 mediated by MG3-6/3-4 and guide mA364-34-1 (guide 34).
Figure 19:
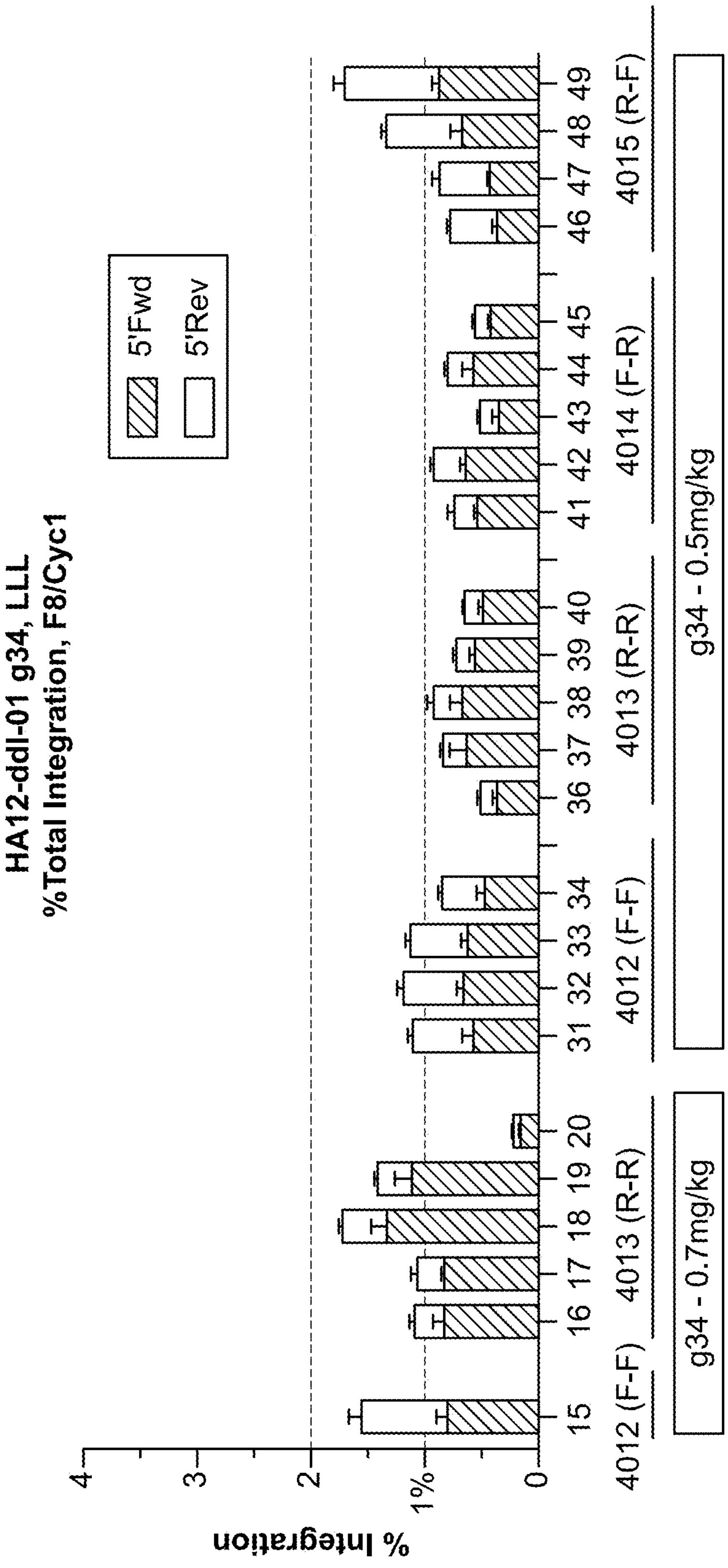
FIG. 19 depicts the frequency of integration of a FVIII gene cassette in the forward and reverse orientations into albumin intron 1 mediated by MG3-6/3-4 and guide mA364-34-1 (guide 34).

A dd-PCR assay for Cytochrome C1 was used to correct for the copies of genomic DNA in each sample. The results were calculated as the percentage forward integration (copies of the forward integration junction per 100 copies of cytochrome C1). Mice that were dosed with either of the 4 AAV8 FVIII donors (pMG4012, pMG4013, pMG4014, or pMG4015) followed by LNP encapsulating MG3-6/3-4 mRNA and the sgRNA mA364-34-1 were analyzed at the end of the study for integration of the FVIII gene cassette. Mice from the groups treated with AAV followed by LNP encapsulating MG3-6/3-4 mRNA and the sgRNA mA364-59-1 were not assayed for integration due to the low levels of editing that was achieved. The results demonstrated that forward integration occurred at a frequency of between 0.2% and 1.3% amongst the 24 mice analyzed (FIG. 17). The average forward integration frequency in the groups was about 0.5% (FIG. 18), and no significant differences were seen between groups. The reverse integration frequency ranged between 0.05% to 0.8% amongst the 24 mice analyzed (FIG. 19). In each of the individual mice that received pMG4013 (total of 10 mice, 5 that received 0.7 mpk LNP and 5 that received 0.5 mpk LNP) and pMG4014 (total of 5 mice), the reverse integration frequency was lower than the forward integration frequency (FIG. 19). In contrast, the forward and reverse integration frequencies were similar in each individual mouse in the groups that received AAV8-pMG4012 and AAV8-pMG4015. In AAV8-pMG4012 and AAV8-pMG4015, the guide 34 (mA364-34-1) target sites flanking the FVIII cassette are in the orientations Forward-Forward and Reverse-Forward, respectively. In AAV8-pMG4013 and AAV8-pMG4014, which resulted in preferential integration in the desired forward orientation, the guide 34 (mA364-34-1) target sites flanking the FVIII cassette are in the orientations Reverse-Reverse and Forward-Reverse, respectively. These data demonstrate that including guide target sites for MG3-6/3-4 flanking the FVIII cassette in the Reverse-Reverse or Forward-Reverse orientations results in favorable preferential integration of the FVIII cassette in the forward orientation in albumin intron 1. The forward orientation of integration is favorable because it is capable of being expressed from the albumin promoter to produce mRNA encoding FVIII.

To evaluate the expression of the FVIII transgene as driven by the endogenous albumin promoter, a dd-PCR assay was used. Integration of the FVIII cassette in the forward orientation (defined as the 5' end of the FVIII cassette being adjacent to the albumin exon 1) at the double strand break created by the MG3-6/3-4 nuclease and guide RNA is predicted to produce a hybrid mRNA resulting from RNA splicing between the albumin exon 1 splice donor and the splice acceptor at the 5' end of the FVIII cassette. This hybrid mRNA will therefore contain a novel sequence junction between albumin exon 1 and the 5' end of the coding sequence for mature FVIII as shown in FIG. 13. A dd-PCR assay was designed in which the forward primer is complementary to a sequence within albumin exon 1, the reverse primer is complementary to a sequence within the 5' end of human FVIII, and the probe spans the predicted junction between albumin exon 1 and the 5' end of human FVIII after correct splicing. The sequences of the primers are probe are: MG101-set1-FWD: 5'TAACCTTTC-TCCTCCTCCTCTT3' (SEQ ID NO: 111); MG101-set1-REV: 5'TCCACAGCTCCCAGGTAATA3' (SEQ ID NO: 112); MG101-set1-Probe: 5'TCTTCTGGTGGCCA-GTGCTTCTC3' FAM, ZEN/3' IBFQ (SEQ ID NO: 113).

Figure 20:
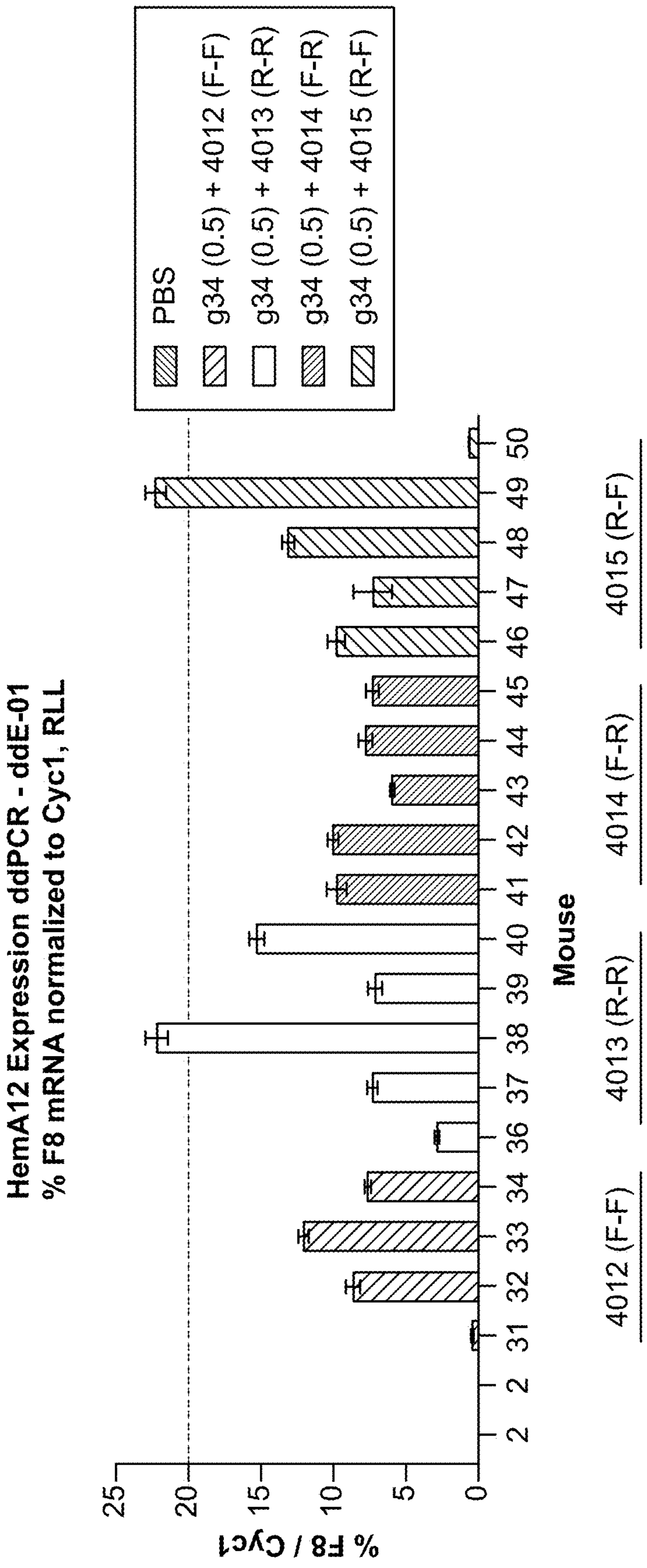
FIG. 20 depicts quantitation of the Albumin-FVIII fusion mRNA in the liver of mice dosed with either of 4 AAV8-FVIII donors and LNP encapsulating MG3-6/3-4 mRNA and guide RNA 34 (mA364-34-1).
Figure 21:
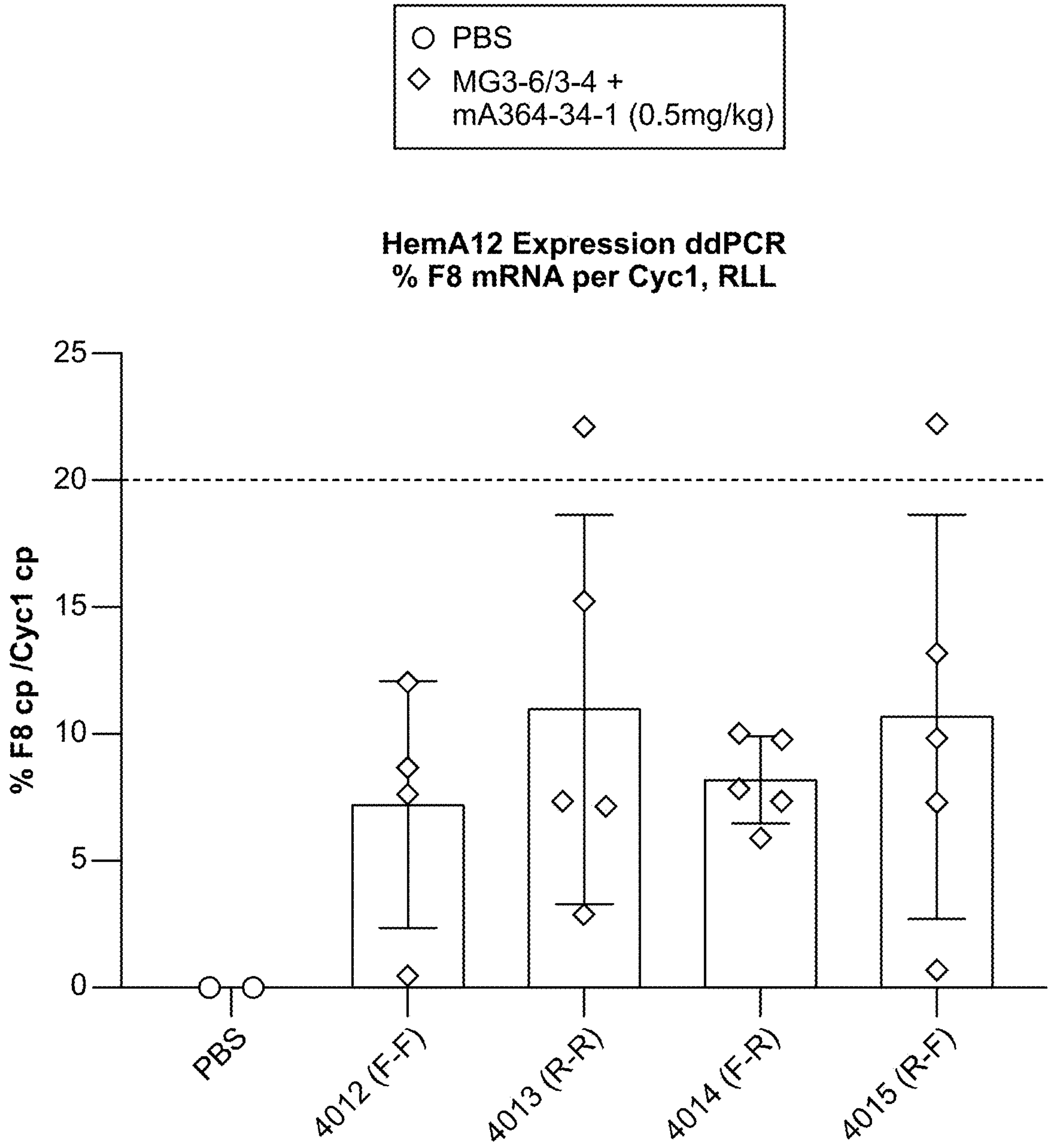
FIG. 21 depicts the mean Albumin-FVIII fusion mRNA levels in the liver of mice dosed with either of 4 AAV8-FVIII donors and LNP encapsulating MG3-6/3-4 mRNA and guide RNA 34 (mA364-34-1).

Total RNA was purified from the left lateral lobe of the liver from each mouse using the QIAGEN RNeasy Plus Mini kit with genomic DNA eliminator column. After ezD-Nase digestion to eliminate any remaining genomic DNA, cDNA was prepared from 500 ng of total RNA. The cDNA was assayed for the albumin-FVIII fusion mRNA and for cytochrome C1 mRNA. The level of cytochrome C1 mRNA was used to normalize for the quality and quantity of mRNA assayed by dividing the absolute copies of the albumin-FVIII hybrid mRNA by the absolute copies of the cytochrome C1 mRNA and expressing this as a percentage. In mice that received one of the AAV8-FVIII donor viruses (AAV8-pMG4012, AAV8-pMG4013, AAV8-pMG4014, or AV8-pMG4015) and LNP encapsulating MG3-6/3-4 mRNA and guide RNA mA364-34-1, the albumin-FVIII fusion mRNA levels ranged from 1% to 20% of the endogenous cytochrome C1 mRNA level (FIG. 20). Two mice had very low levels of albumin-FVIII fusion mRNA while the remaining mice exhibited levels of between 3% and 20% of the endogenous cytochrome C1 mRNA level. The mean albumin-FVIII fusion mRNA level were between 7% and 11% and were not significantly different between groups (FIG. 21).

Example 10—Evaluation of FVIII B-Domain Replacement Sequences Incorporating Different Numbers of N-Linked Glycosylation Sites and a Furin Cleavage Site The un-processed full-length wild-type FVIII protein contains 6 domains termed (in order from N-terminus to C-terminus): A1-A2-B-A3-C1-C2. During post-translational processing, the full-length FVIII protein is cleaved by furin protease that results in the removal of a large portion of the B-domain and generates the mature 2 chain form of FVIII in which the heavy chain and the light chain are held together by a metal bridge. The B-domain of FVIII contains the majority of the N-linked glycosylation sites in FVIII but is not required for the biologic activity of the protein and is commonly absent in recombinantly produced FVIII (commonly referred to as B-domain deleted FVIII) that is marketed as a drug to treat hemophilia A patients. In these B-domain deleted FVIII proteins, the B-domain is commonly replaced with a short linker sequence called the "SQ linker" that is derived from the N- and C-terminal ends of the B-domain and retains the natural furin cleavage site (RHQR, SEQ ID NO: 69), thereby ensuring that the protein is processed into the natural 2 chain FVIII protein during expression.

The consensus sequence for an N-linked glycosylation site is the triplet amino acid sequence N—X-S/T, where X represents any amino acid, N is asparagine, and S/T represents either a serine or a threonine residue in the 3rd position. The glycan chain is attached to the asparagine. Not all N—X-S/T sequences in a protein will be glycosylated, and which specific sequences are glycosylated cannot be accurately predicted from the surrounding sequence. The N6 amino acid sequence (SFSQNATNVSNNS- NTSNDSN-VSPPVLKRHQR, SEQ ID NO: 70) was shown to function in mice.

Nine possible designs for a B-domain replacement sequence that fulfill these criteria were created as shown in FIG. 22. These designs termed VAR1 to VAR9 (SEQ ID NOs: 71-79) contain between 1 and 3 N-linked glycosylation sites and between 0 and 1 amino acid changes to wild-type human FVIII. Four of these designs, VAR2 (ENRSFSQNPPVLKRHQR; SEQ ID NO: 72), VAR3 (EPRSFSQNCSQNPPVLKRHQR; SEQ ID NO: 73), VAR4 (EPRNFSQNCSQNPPVLKRHQR; SEQ ID NO: 74), and VAR8 (ENRSNFSQNCSQNPPVLKRHQR; SEQ ID NO: 78) were selected for experimental evaluation. VAR 2 and VAR 3 contain 1 N-linked glycan site and 1 amino acid difference from wild-type FVIII. VAR 4 contains 2 N-linked glycan sites and 1 amino acid difference from wild-type FVIII. VAR8 contains 3 N-linked glycan sites and 3 amino acid differences from wild-type FVIII. All 4 of these B-domain replacement designs as well as the SQ linker (EPRSFSQNPPVLKRHQR; SEQ ID NO: 80) and the N6 glycan B-domain replacement comprising the sequence ENRSFSQNATNVSNNSNTSNASNVSPPVLKRHQR (SEQ ID NO: 99) were inserted in place of the B-domain in a human FVIII coding sequence to create constructs called pMG4017 (SQ linker; SEQ ID NO: 81), pMG4018 (VAR2; SEQ ID NO: 82), pMG4019 (VAR3; SEQ ID NO: 83), pMG4020 (VAR4; SEQ ID NO: 84), and pMG4021 (VAR8; SEQ ID NO: 85). It should be noted that for each of these B-domain replacements (SEQ ID NOs: 71-79), only the sequence between SFSQN (SEQ ID NO: 114) and PPVLKRHQR (SEQ ID NO: 115) is part of what was previously defined as the linker that replaces the B-domain in B-domain deleted FVIII. The sequence listings include 3 or 4 residues prior to "SFSQN (SEQ ID NO: 114)" because some of the novel variants contain amino acid changes or additions within this sequence before the "SFSQN (SEQ ID NO: 114)". Because each of these B-domain replacements contains the native furin cleavage site (RHQR (SEQ ID NO: 69)), the FVIII proteins expressed from all these constructs are predicted to be cleaved by furin to generate 2-chain FVIII. The human FVIII coding sequence was identical in these constructs except for the differences in the B-domain replacement sequences, and consisted of the co1 codon optimized DNA sequence as described below.

The human FVIII coding sequence used here lacks the signal peptide and was codon optimized that is designed to improve the expression by a species of choice by selecting more frequently used codons, as well as eliminating cryptic splice sites and other undesirable sequence features. When applied to the FVIII coding sequence for use in human cells, this sequence optimization increased the number of CpG dinucleotides in the FVIII coding sequence from 53 in native human FVIII to 210. Because CpG dinucleotides are recognized by the innate immune response, all the CpG dinucleotides were eliminated by altering either of the adjacent codons to the next most frequent codon that removed the CpG dinucleotide. This codon optimization was designated as copt1. The overall G/C content for the copt1 codon optimized B-domain deleted FVIII sequence with the SQ linker is 51%, which is similar to native human FVIII. The DNA sequence identity between FVIII-BDD after copt1 codon optimization and native human FVIII was about 80%. Because most DNA base changes are in the last position of a codon, the 80% identity represents changes to about 3×20%=60% of the codons in native FVIII.

Each of the constructs pMG4017, pMG4018, pMG4019 pMG4020, and pMG4021 contained identical sequences flanking the FVIII gene cassette. The target site for the MG29-1 guide RNA 8 (mAlb29-8-50) and MG29-1 guide RNA 12 (mAlb29-12b-50) in the forward orientation followed by a spacer sequence, a splice acceptor sequence, and the dinucleotide TG (required to maintain the correct reading frame after RNA splicing between albumin exon 1 and the splice acceptor site) were added at the 5' end of the FVIII coding sequence. A polyadenylation signal, a short spacer sequence, the target site for MG29-1 guide RNA 12 (mAlb29-12b-50) followed by the target site for MG29-1 guide RNA 8 (mAlb29-8-50) in the reverse orientation were added after the stop codon at the 3' end of the FVIII coding sequence.

Figure 23:
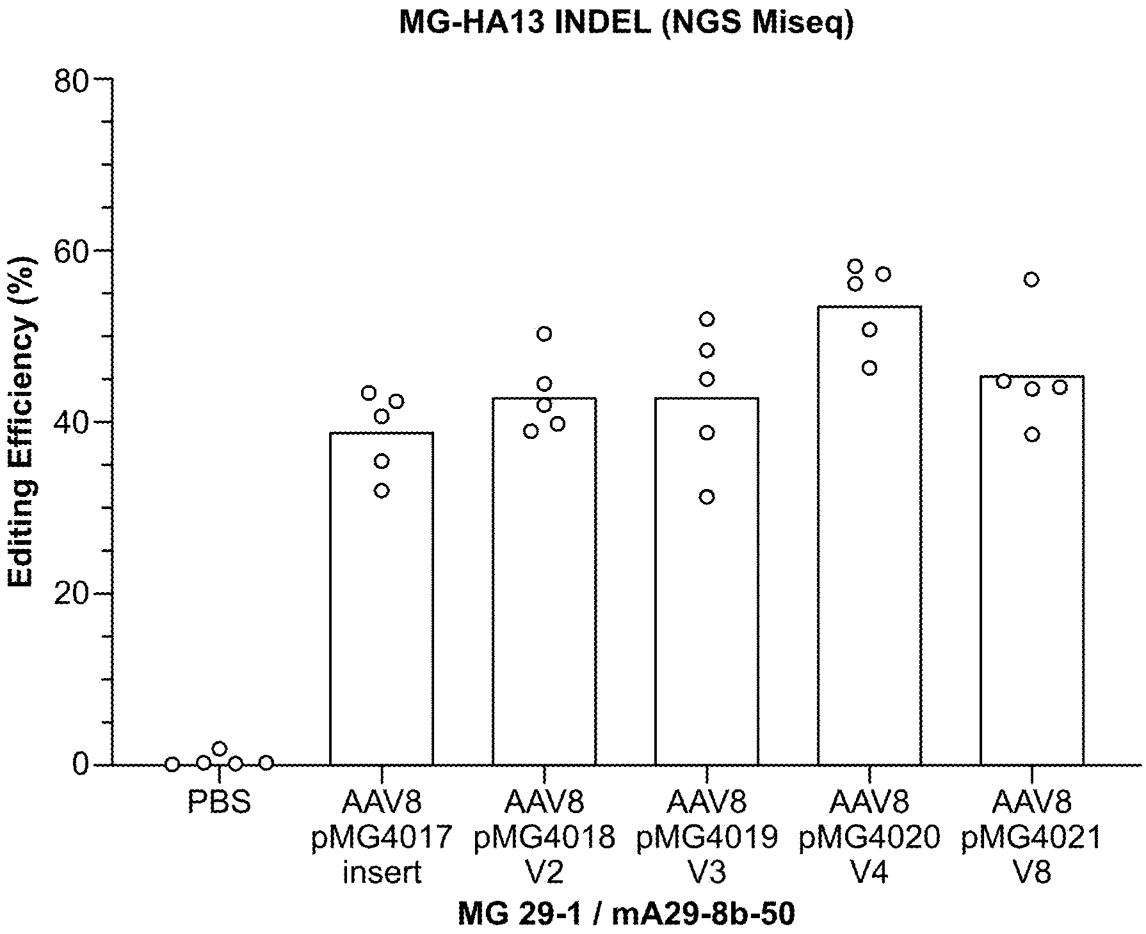
FIG. 23 depicts editing in the liver of mice dosed with AAV8-pMG4017, AAV8-pMG4018, AAV8-pMG4019, AAV8-pMG40120, AAV8-pMG4021 ($1\times10^{13}$ vg/kg) followed by LNP encapsulating MG29-1 mRNA and guide RNA mAlb28-8b-50 (0.5 mpk dose). The assay was performed at the end of the study.

AAV8 viruses were produced from constructs pMG4017, pMG4018, pMG4019, pMG4020, and pMG4021 using standard methodologies, and the viral genome copy number was measured by PCR. Wild-type adult C57BL/6 mice were given IV injections of each of the AAV8 viruses (AAV8-pMG4017, AAV8-pMG4018, AAV8-pMG4019, AAV8-pMG4020, AAV8-pMG4021) at a dose of $1\times10^{13}$ vg/kg. Three weeks later, all mice were given IV injections of a liver trophic LNP encapsulating the mRNA for MG29-1 and the guide RNA mA29-8b-50 at a dose of 0.5 mg/kg (total RNA dose per kg body weight). The LNP was prepared as described in earlier examples. All mice were sacrificed at 16 days post LNP dose, plasma was collected by cardiac puncture, and liver tissue was collected for purification of genomic DNA or total RNA. Editing in the whole liver ranged from 40% to 50% in the 5 groups (FIG. 23) with no editing detected in the PBS-injected control mice.

Total RNA was purified from the left lateral lobe of the liver from each mouse using the QIAGEN RNeasy Plus Mini kit with genomic DNA eliminator column. After ezDNase digestion to eliminate any remaining genomic DNA, cDNA was prepared from 500 ng of total RNA. The cDNA was assayed for the albumin-FVIII fusion mRNA using primers MG101-set1-FWD (5'TAACCTTTCTCCTCCTCCTCTT3' (SEQ ID NO: 111)) and MG101-set1-REV (5'TCCACAGCTCCCAGGTAATA3' (SEQ ID NO: 112)), and MG101-set1-Probe: (5'TCTTCTGGTGGCCAGTGCTTCTC3' FAM, ZEN/3' IBFQ (SEQ ID NO: 113)) and for cytochrome C1 mRNA. The level of cytochrome C1 mRNA was used to normalize for the quality and quantity of mRNA assayed by dividing the absolute copies of the albumin-FVIII hybrid mRNA by the absolute copies of the cytochrome C1 mRNA and expressing this as a percentage. The results (FIG. 24) demonstrated that mice dosed with AAV8-pMG4020 had the highest level of albumin-FVIII fusion mRNA expressed from the integrated FVIII gene cassette. The level of the albumin-FVIII fusion mRNA was higher for all 4 of the constructs containing B-domain replacements containing 1 or more N-linked glycosylation sites as compared to AAV8-pMG4017 in which the B-domain is replaced by the SQ linker that lacks an N-linked glycosylation site. These data demonstrate that inclusion of 1, 2, or 3 N-linked glycosylation sites in place of the B-domain of FVIII improved the level of mRNA expressed. While AAV8-pMG4020 (which contains 2 N-linked glycan sites) had higher levels of mRNA expression that AAV8-pMG4018 and AAV8-pMG4019 (which both contain 1 N-linked glycan), AAV8-pMG4021 (which contains 3 N-linked glycans) had similar levels of mRNA expression as the constructs with a single N-linked glycan. Therefore, more N-linked glycans are not necessarily associated with higher mRNA expression. Based on these results, the B-domain var4 replacement design present in pMG4020 (which contains 2 N-linked glycans and only 1 amino acid change compared to wild-type FVIII) produces the highest level of the albumin-FVIII fusion mRNA that encodes the integrated FVIII protein.

Figure 24:
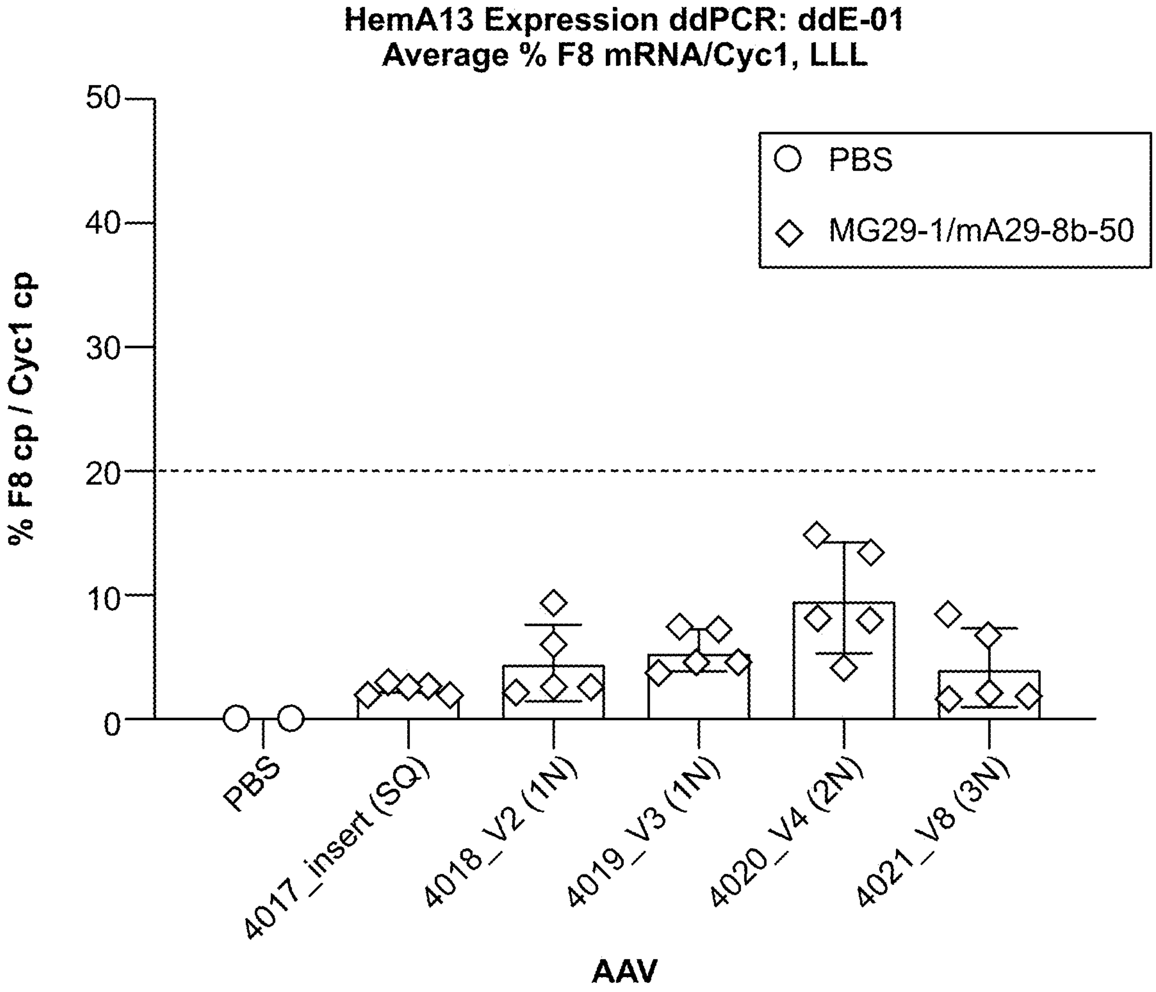
FIG. 24 depicts quantitation of the albumin-FVIII fusion mRNA in the liver of mice dosed with AAV8-pMG4017, AAV8-pMG4018, AAV8-pMG4019, AAV8-pMG4020, AAV8-pMG4021 at $1\times10^{13}$ vg/kg followed by LNP delivery of MG29-1 mRNA and guide RNA mA29-8b50 (0.5 mpk).
Figure 25:
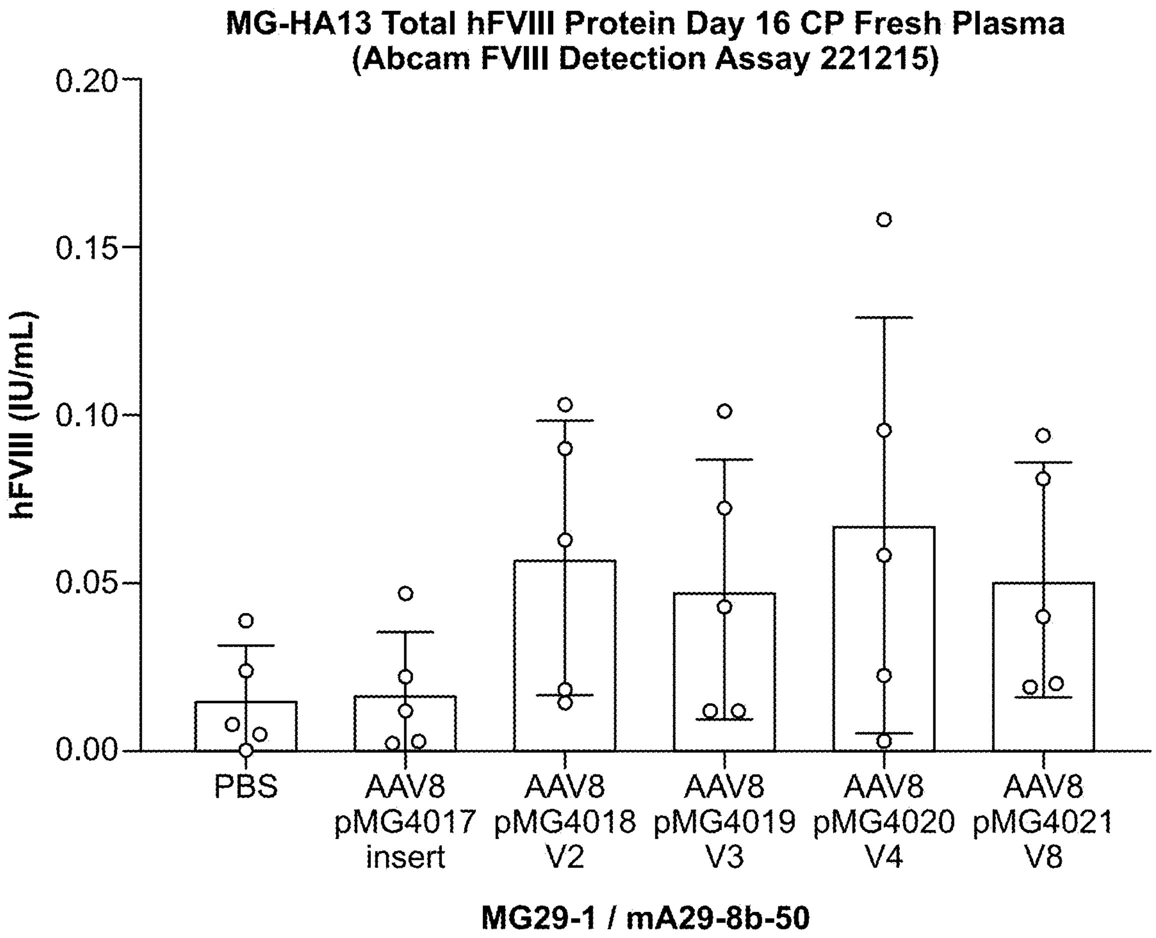
FIG. 25 depicts FVIII protein levels in the blood of mice dosed with AAV8-pMG4017, AAV8-pMG4018, AAV8-pMG4019, AAV8-pMG4020, AAV8-pMG4021 at $1\times10^{13}$ vg/kg followed by LNP delivery of MG29-1 mRNA and guide RNA mA29-8b50 (0.5 mpk).

Plasma from the same mice collected 16 days after LNP dosing was assayed for human FVIII protein using a human FVIII specific ELISA assay. Recombinant human FVIII (Xyntha) spiked into the same percentage of naive mouse plasma was used for the standard curve. FVIII above the background in PBS-injected control mice was detectable in the mice that were dosed with AAV8-pMG4018, AAV8-pMG4019, AAV8-pMG4020, and AAV8-pMG4021, but not in the plasma from mice dosed with AAV8-pMG4017 (which contains the SQ linker in place of the B-domain). Thus, the inclusion of the B-domain replacement sequences var2, var3, var4 and var8 (which contain either 1, 2 or 3 N-linked glycosylation sites) enabled the expression of detectable levels of human FVIII after integration into albumin intron 1 (FIG. 25). The highest levels of FVIII were seen in mice that received AAV8-pMG4020 (var4) which correlates with the higher levels of albumin-FVIII fusion mRNA (FIG. 24). AAV8-pMG4020 (var4) contains the B-domain replacement with 2 N-glycans sites.

Example 11—Design and Evaluation in Mice of a Cynomolgus FVIII Gene Donor Cassette Cynomolgus macaques (cyno) are an accepted pre-clinical model that more closely predicts the behavior of drugs in humans. The human FVIII protein is immunogenic when expressed or administered to non-human primates, such as cynomolgus macaques, due to amino acid sequence differences between the human and cynomolgus FVIII proteins resulting in the generation of neutralizing antibodies within the first 1 to 2 months post-dose. The genome editing approach contemplated here for the treatment of Hemophilia A integrates a FVIII gene into the genome with the goal of providing a durable curative therapy from a single administration. In order to evaluate the durability of this approach in NHP, a FVIII gene encoding cynomolgus FVIII protein is used. A B-domain deleted form of the Macca Fasicularis FVIII protein sequence was generated by alignment to human FVIII BDD-SQ in which the B-domain is replaced with the so called "SQ" linker that comprises the sequence "SFSQNPPVLKRHQR (SEQ ID NO: 116)". The cyno FVIII has the identical sequence to human FVIII around the B-domain junctions such that deletion of the B-domain from cyno FVIII yields a junction that is identical to the SQ linker. Upon alignment of the B-domain deleted versions of human and cyno FVIII (both with the SQ linker), it was apparent that the cyno FVIII protein sequence has 28 amino acid differences to human FVIII. To enable detection of the cyno FVIII protein derived from the integrated transgene, a single amino acid change F2196K (Lysine is underlined bold in the sequence: ASSYKTNM (SEQ ID NO: 117)) was introduced into the B3-domain deleted (SQ linker) cyno FVIII protein sequence (SEQ ID NO: 86). The inclusion of Lysine instead ofphenylalanine at residue 2196 (numbering according to full-length human FVIII) blocks binding of the neutralizing anti-FVIII monoclonal antibody BO2C11. This enables the activity of the cynoFVIII-F2196K protein to be measured in plasma after neutralizing the endogenous cynoFVIII protein with the BO2C11 antibody. To generate the DNA sequence encoding cyno-FVIII-F2196K, the DNA sequence encoding human B-domain deleted FVIII with the var 4 B domain replacement (present in pMG4020) that was identified in Example 10 was modified to change the codons for the 28 amino acids that differ to cynoFVIII by selecting the most frequent codon that encodes the cynoFVIII amino acid but did not create a CG dinucleotide in the DNA sequence. In 3 instances, the previous codon was changed to avoid the creation of a CG dinucleotide (CpG). In addition, residue F2196 was changed to lysine, selecting the most frequent codon for lysine resulting in protein SEQ ID NO: 87. The sequence changes made to create protein SEQ ID NO: 87 are shown in Table 16.

TABLE 16

DNA sequence changes made to the FVIII coding sequence in pMG4020 to convert it to encode cyno FVIII with F2196K.

| Amino acid to change | Position # | Human FVIII residue/ codon | Cyno FVIII residue | New codon | Change to previous codon |
|---|---|---|---|---|---|
| 1 | 28 | A/GCT | T | ACC | |
| 2 | 36 | K/AAG | R | AGA | |
| 3 | 45 | V/GTG | M | ATG | |
| 4 | 50 | L/CTG | V | GTG | ACC (T) to ACA |
| 5 | 196 | I/ATC | V | GTG | TTC (F) to TTT |
| 6 | 222 | A/GCT | D | GAT | |
| 7 | 351 | T/ACA | A | GCT | |
| 8 | 392 | D/GAC | V | GTG | |
| 9 | 398 | L/CTG | S | AGT | |
| 10 | 416 | P/CCT | S | AGC | |
| 11 | 444 | H/CAT | Y | TAT | |
| 12 | 537 | V/GTG | I | ATC | |
| 13 | 583 | R/AGA | Q | CAG | |
| 14 | 599 | A/GCT | V | GTG | |
| 15 | 728 | A/GCC | T | ACC | |
| Numbering shifts by +4 aa due to var4 B-domain replacement | | | | | |
| 16 | 758/762 | R/AGA | L | CTG | |
| 17 | 759/763 | T/ACC | N | AAC | |
| 18 | 787/791 | D/GAT | G | GGA | |
| 19 | 882/886 | R/AGA | K | AAG | |
| 20 | 1001/1005 | M/ATG | T | ACA | |
| 21 | 1081/1085 | L/CTG | V | GTG | GCC(A) to GCT |
| 22 | 1137/1141 | H/CAC | R | AGA | |
| 23 | 1317/1321 | H/CAT | N | AAC | |
| 24 | 1349/1353 | V/GTG | I | ATC | |
| 25 | 1376/1380 | Q/CAG | H | CAC | |
| 26 | 1405/1409 | P/CCT | S | AGC | |

TABLE 16-continued

DNA sequence changes made to the FVIII coding sequence in pMG4020 to convert it to encode cyno FVIII with F2196K.

| Amino acid to change | Position # | Human FVIII residue/ codon | Cyno FVIII residue | New codon | Change to previous codon |
|---|---|---|---|---|---|
| 27 | 1427/1431 | M/ATG | I | ATT | |
| 28 | 1436/1440 | D/GAC | E | GAG | |
| — | 2196 | F/TTC | K | AAG | |

# the numbering (position) is based on mature (no signal peptide) human FVIII-BDD numbering, but after position 728, this is shifted by 4 amino acids because of the inclusion of the var4 B-domain replacement To enable integration and expression of FVIII from albumin intron 1 in cyno monkeys, guide cA29-87b (guide 87) was selected for nuclease MG29-1 and guide ch364-58 (guide 58) was selected for nuclease MG3-6/3-4. Target sites for both guides were included in the donor DNA sequence flanking the FVIII donor cassette. When describing the orientation of the guide target sites in the FVIII donor cassette, the orientation is relative to the orientation of the target site in the genome, so forward orientation means the same orientation as the target site for that guide in the genome, in this case within albumin intron 1. For MG29-1, the orientation of the flanking guides did not significantly impact integration efficiency based on studies described in Example 6, and the forward-FVIII gene-reverse orientation was selected. For the MG29-1 guide cA29-87b, the orientation of the two guide target sites in the donor was forward (PAM to the 5' side) at the 5' end of the FVIII cassette and reverse (PAM to the 3' side) at the 3' end of the FVIII cassette.

In the case of the MG3-6/3-4 nuclease, including guide cut sites flanking the FVIII donor in the reverse-FVII gene-reverse or forward-FVIII gene-reverse orientations resulted in a higher frequency of integration of the FVIII gene cassette into albumin 1 in the preferred forward orientation (See Example 9, FIG. 19). Based on this data, the reverse-FVIII gene-reverse orientation of the MG3-6/3-4 guide was selected for use in the cyno FVIII construct. For the MG3-6/3-4 guide ch364-58, the orientation of the two guide target sites in the donor was reverse (PAM to the 3' side) at the 5' end of the FVIII cassette and reverse (PAM to the 3' side) at the 3' end of the FVIII cassette.

In addition to guide RNA cut sites, the same splice acceptor sequence used in pMG4008 was inserted at the 5' end of the FVIII coding sequence followed by the dinucleotide TG, which maintains the correct reading frame in the mRNA after splicing from albumin exon 1. The same polyadenylation signal was inserted 3' of the stop codon in the FVIII coding sequence. In addition, short spacer sequences were inserted between the guide target sites (TS) and the splice acceptor and between the polyA signal and the guide target sites. These spacer sequences are designed to insulate the FVIII gene cassette from small deletions at the guide cut site that might occur as part of the NHEJ-driven repair process prior to integration.

Figure 26:
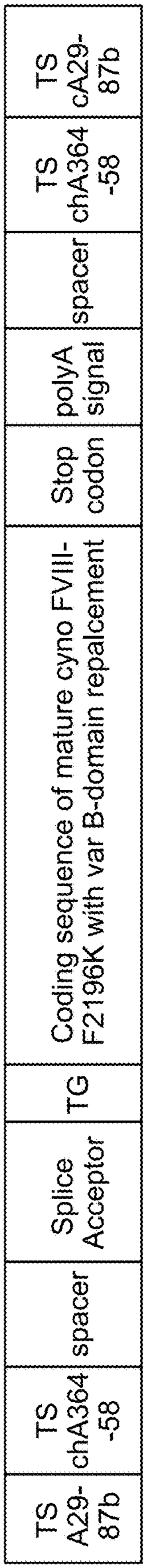
FIG. 26 depicts sequence elements present in the cyno FVIII donor cassette pMG4016 (not to scale). TS=target site for designated guide.

The DNA sequence elements present in the full cyno FVIII donor cassette that was designated as pMG4016 (SEQ ID NO: 88) are as follows: 5' TS for cA29-87b-TS for chA364-58-spacer (16 bp)-splice acceptor-TG-mature cynoFVIII-F2196K coding sequence with var4 B-domain replacement-stop codon-polyadenylation signal-spacer (10 bp)-TS for chA364-58-TS for cA29-87b-3' (FIG. 26).

To evaluate the cynoFVIII donor cassette in mice, pMG4016 was packaged into AAV6 or AAV8 virus using either the HEK293 (HK) based packaging system or the sf9 insect cell packaging system (sf) using standard methodologies. Wild-type C57Bl/6 mice were given IV injections of $1\times10^{13}$ vg/kg of AAV6(sf)-pMG4016, AAV8(sf)-pMG4016, or AAV8(HK)-pMG4016. 21 days later, the same mice were given IV injections of 0.5 mg/kg of LNP A and 0.5 mg/kg of LNP B. LNP A contained the MG29-1 mRNA and the mA29-8b-50 guide RNA co-formulated at a 1:1 mass ratio. LNP B contained the MG29-1 mRNA and the cAlb29-87b-50 guide RNA co-formulated at a 1:1 mass ratio. The guide RNA in LNP A targets mouse albumin intron 1 in the genome of the mouse. The guide RNA in LNP B targets the MG29-1 guide RNA target sites flanking the FVIII gene cassette in pMG4016. 2 weeks later, the mice were sacrificed, and liver tissue was collected for genomic DNA purification and total RNA purification.

Figure 27:
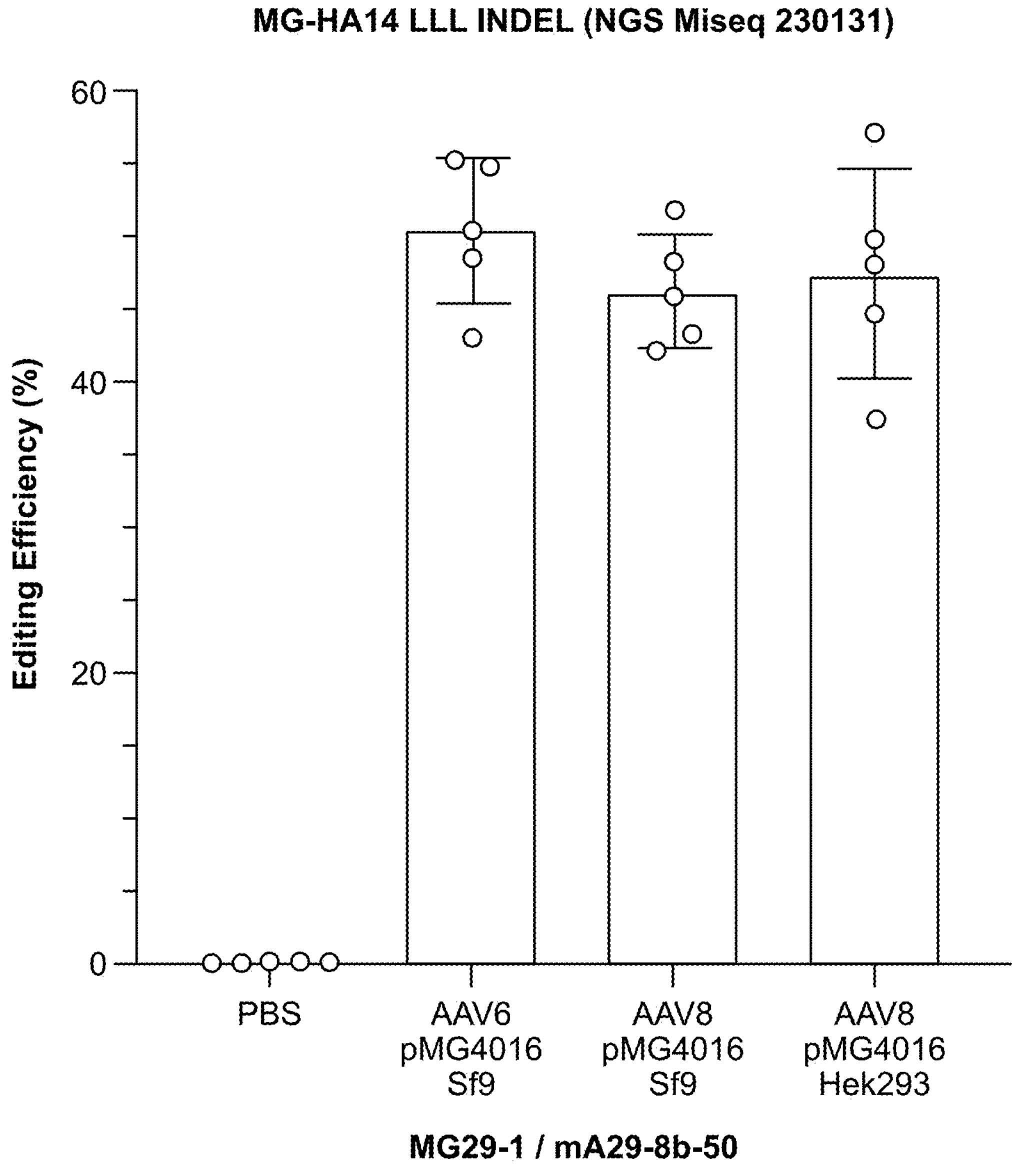
FIG. 27 depicts editing in the liver of mice dosed with $1\times10^{13}$ vg/kg of AAV6(sf)-pMG4016, AAV8(sf)-pMG4016, or AAV8(HK)-pMG4016.

Editing of the albumin intron 1 target site (targeted by guide mA29-8b-50) in the liver of the mice ranged from 45% to 50% in the whole liver, demonstrating efficient delivery of the MG29-1 editing system and the expected editing of the genomic target (FIG. 27).

Integration of the cyno_FVIII gene cassette into the target site in mouse albumin intron 1 was quantified using a dd-PCR assay. Genomic DNA purified from the livers of the mice was digested with EcoRI. For quantification of integration in the forward orientation, the primer and probe set called MG401_set3, which detects the 5' integration junction, was used. The sequences of the primers are probe are: MG401-set3-FWD: 5'TCTTGAGTTTGAATGCACAGAT3' (SEQ ID NO: 118); MG401-set3-REV: 5'TAGTCCCAGCTCAGTTCCA3' (SEQ ID NO: 119); MG401-set3-Probe: 5'TGGCCACCAGAAGATATTACCTGGGA3' FAM, ZEN/3' IBFQ (SEQ ID NO: 120).

A dd-PCR assay for Cytochrome C1 was used to correct for the copies of genomic DNA in each sample. The results were calculated as the percentage forward integration (copies of the forward integration junction per 100 copies of cytochrome C1). Integration of the cynoFVIII gene in the forward orientation was detected in all mice, albeit at different levels ranging from about 0.1% to about 2% (FIG. 28). Comparing the average forward integration in the groups of 5 mice that received the 3 different AAV viruses, the forward integration was highest in the group that received AAV8(HK)-pMG4016 (mice #22 to #25), with a mean of 1% integration (FIG. 28). The average integration frequency for AAV8(sf)-pMG4016 and AAV6(sf)-pMG4016 was about 0.5%.

The expression of the predicted cyno FVIII encoding mRNA from the integrated cyno FVIII cassette in the liver of the same mice was quantified using a dd-PCR assay. Integration of the cyno FVIII cassette in the forward orientation (defined as the 5' end of the cyno FVIII cassette being adjacent to the albumin exon 1) at the double strand break created by the MG29-1 nuclease and guide RNA is predicted to produce a hybrid mRNA resulting from RNA splicing between the albumin exon 1 splice donor and the splice acceptor at the 5' end of the cyno FVIII cassette. This hybrid mRNA will therefore contain a novel sequence junction between albumin exon 1 and the 5' end of the coding sequence for mature FVIII as shown in FIG. 13. A dd-PCR assay was designed in which the forward primer is complementary to a sequence within albumin exon 1, the reverse primer is complementary to a sequence within the 5' end of cyno FVIII, and the probe spans the predicted junction between albumin exon 1 and the 5' end of cyno FVIII after correct splicing. The sequences of the primers are probe are: MG113-set1: MG113-set1-FWD: 5'CTCTTCGTCTCCGGCTCT3' (SEQ ID NO: 121); MG113-set1-REV: 5'TCCACAGCTCCCAGGTAATA3' (SEQ ID NO: 112); MG113-set1-Probe: 5'TCTTCTGGTGGCCAGTGCTTCTC3' FAM, ZEN/3' IBFQ (SEQ ID NO: 113).

Figure 29:
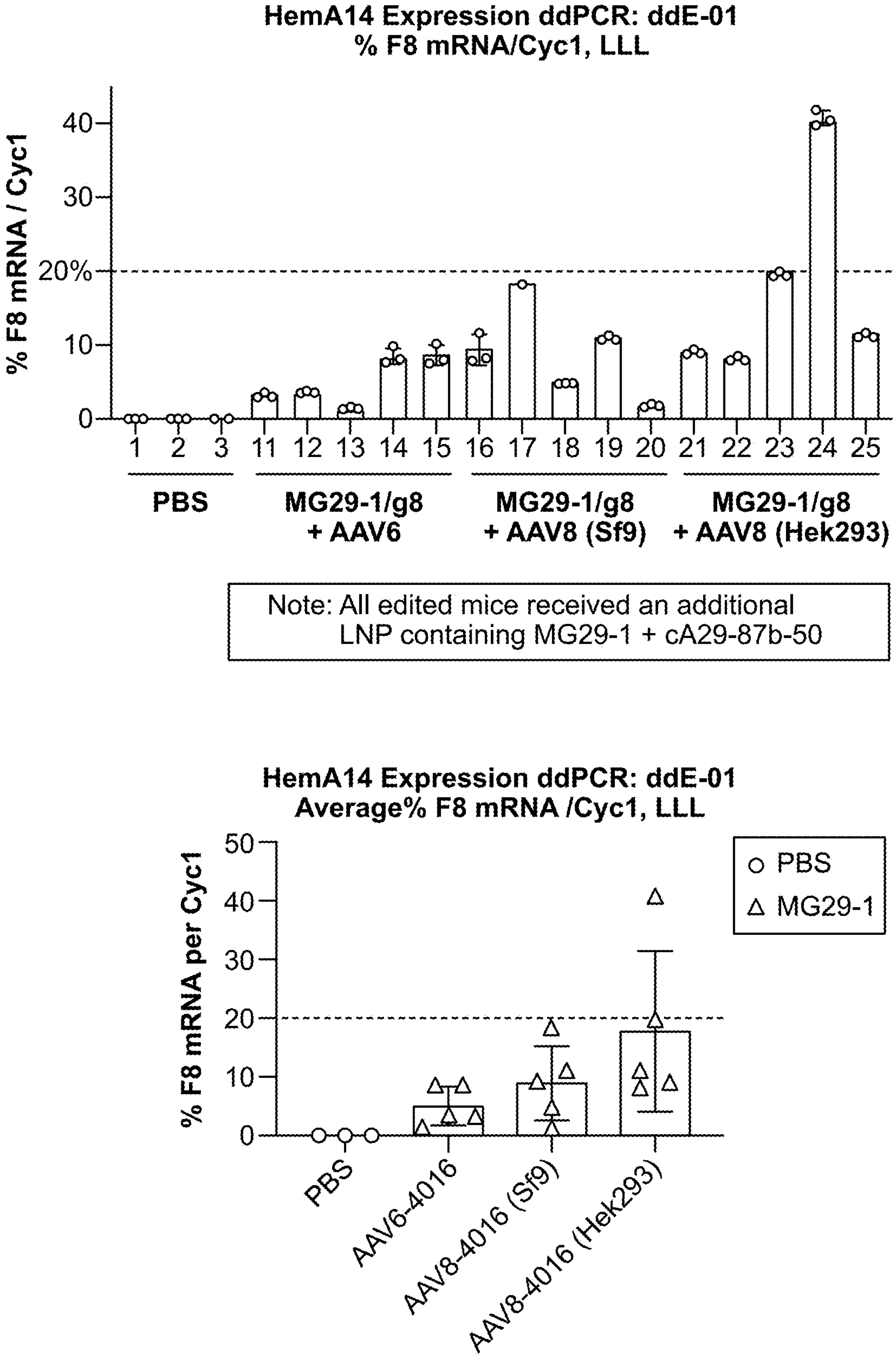
FIG. 29 depicts quantitation of the level of albumin-cynoFVIII fusion mRNA in the liver of mice dosed with $1\times10^{13}$ vg/kg of AAV6(sf)-pMG4016, AAV8(sf)-pMG4016, or AAV8(HK)-pMG4016 followed by a mixture of LNP A and LNP B.

Total RNA was purified from the left lateral lobe of the liver from each mouse. After DNase digestion to eliminate any remaining genomic DNA, cDNA was prepared from 500 ng of total RNA. The cDNA was assayed for the albumin-FVIII fusion mRNA and for cytochrome C1 mRNA. The level of cytochrome C1 mRNA was used to normalize for the quality and quantity of mRNA assayed by dividing the absolute copies of the albumin-FVIII hybrid mRNA by the absolute copies of the cytochrome C1 mRNA and expressing this as a percentage. The albumin-cynoFVIII fusion mRNA was detected in all mice, and the levels ranged from 2% to 40% of cytochrome C1 (FIG. 29). The average albumin-cynoFVIII fusion mRNA level in each group of 5 mice that were dosed with the 3 different AAV viruses was 5% for AAV6(sf)-pMG4016, 10% for AAV8(sf)-pMG4016, and 18% for AAV8(HK)-pMG4016. These mRNA levels correlated with the forward integration frequencies measured in the liver of the same mice. The observation that AAV8-pMG4016, which was packaged in HEK293 production system, resulted in higher frequencies of forward integration and higher levels of albumin-cyno FVIII fusion mRNA suggests that differences in the quality of the AAV virus are an important factor in optimizing integration using this gene editing approach. Overall, these results validated the pMG4016 cynoFVIII cassette design.

Example 12—Design of Additional FVIII Donor Sequences Comprised of Human FVIII Coding Sequences Encoding a Single Chain FVIII Protein Native FVIII protein in circulation is comprised of two separate protein chains called the heavy chain and the light chain, which are generated from a single FVIII protein by post-translational cleavage by the protease called furin. To generate a single chain version of B-domain deleted human FVIII containing the var4 B-domain replacement, the furin cleavage site at the C-terminal end of the B-domain replacement sequence was inactivated. The sequence of the var4 B domain replacement sequence containing 2 N-linked glycosylation sites is: NFSQNCSQNPPVLKRHOR (SEQ ID NO: 100), in which the furin cleavage site is underlined. Three of the four amino acids that make up the furin cleavage site were deleted, resulting in a sequence called var4sc (NFSQNCSQNPPVLKR, SEQ ID NO: 89). When incorporated into human B-domain deleted FVIII, this creates the protein with SEQ ID NO: 90, in which, relative to native FVIII, there is a 1 aa substitution (S to N that creates one of the 2 N glycan sites), an insertion of 4 amino acids (SQNC (SEQ ID NO: 122)) that is normal sequence within the B-domain of FVIII, and the deletion of 3 residues (RHQ). This sequence was selected partly because it minimizes the sequence differences to native human FVIII or recombinant B-domain deleted FVIII proteins.

Example 13—Design of DNA Sequences Encoding Single Chain FVIII with 2 N-Linked Glycans in Place of the B-Domain Comprised of Alternate Codon Optimizations To evaluate the functionality of the single chain B-domain deleted human FVIII containing the var4sc B-domain replacement (SEQ ID NO: 90), two DNA sequences encoding this protein were generated with the goal of optimizing expression. A given protein amino acid sequence can be encoded by a large number of unique DNA sequences because of the redundancy in the genetic code, in which there are several codons that encode each amino acid. On average, there are about 4 codons for each amino acid, with some amino acids encoded by 2 codons and some amino acids encoded by 5 or 6 codons, while one amino acid (methionine) is encoded by a single codon. The number of DNA sequences that can encode a given protein sequence is calculated by multiplying together the number of codons for each amino acid. For example, a protein with only 10 amino acids in which each amino acid can be encoded by 4 possible codons can be encoded by $4^{10}$, which is 1,048,576, DNA molecules. The number of possible DNA molecules that can encode even a short protein composed of 100 amino acids is extremely large at approximately $2\times10^{60}$ ($4^{100}$). A large protein, such as B-domain deleted FVIII (1438 amino acids), can be encoded by approximately $4^{1438}$ DNA molecules. Therefore, there are a large number of possible DNA sequences that can be used to encode a FVIII protein.

The frequency at which each codon is used in naturally produced proteins in living organisms tends to correlate to the cellular abundance of the transfer RNA (tRNA) for that codon, and it is generally accepted that codons that occur at lower frequencies can limit translation efficiencies in mammalian cells due to limiting concentrations of the corresponding tRNA. Codon usage frequencies are known to differ significantly between prokaryotes and eukaryotes, and adjustment of codon usage to match that of the organism in which a heterologous gene is being expressed can improve the level of protein produced, especially when a gene identified in a prokaryote is expressed in a eukaryotic system, and vice versa. There are also reports that codon usage is different for genes that are highly expressed in specific tissues, such as the liver, as compared to the average codon usage for a large set of genes for the same organism, again suggesting that the codon usage was selected during evolution to enable high levels of expression. Codons that are utilized at especially low frequencies in expressed human genes were hereby defined as those with codon usage frequencies of less than 10 according to the published human codon usage tables. Codon frequency in this case is defined as the number of times that codon is used per 1,000 amino acids.

This list ofFrare codons consists of the following 12 codons where the amino acid and frequency is shown in brackets after each codon: GCG (A, 7.6), TGT (C, 9.6), CAT (H, 9.9), ATA (I, 5.5), CTA (L, 5.9), TTA (L, 5.7), CCG (P, 6.2), CGA (R, 6.1), CGT (R, 4.5), TCG (S, 4.9), ACG (T, 6.4), and GTA (V2 6.9). Alternatively, one may consider the rarest codons for each amino acid which adds an additional 8 codons: GAA (E, 27.5), TTT (F, 17.1), GGT (G, 11/.), AAA (K, 24.8), CAA (Q, 10.4), TAT (Y, 13.1). GAT (D, 22), and AAT (N, 17.5).

The native human FVIII DNA sequence in the human genome (with the B-domain artificially removed) contains 18 of these rare codons. Comparing the codon usage frequency within the native human FVIII DNA sequence to that of liver expressed human genes (Table 17) reveals the codons that are used at higher or lower frequencies in FVIII as compared to genes expressed in the liver.

TABLE 17

Rare codons in native human FVIII DNA sequence with B-domain removed resulting in sequence that encodes a 1443 amino acid protein.

| Codon | Amino acid | Freq ^ | Number * | FVIII codon usage # | Liver Human codon usage # | FVIII codon usage % difference to liver |
|---|---|---|---|---|---|---|
| GCA | A | 25.7% | 18 | 12.5 | 15.8 | 79% |
| GCC | A | 27.1% | 19 | 13.2 | 27.7 | **48%** |
| GCG | A | 2.9% | 2 | 1.4 | 7.40 | **19%** |
| GCT | A | 44.3% | 31 | 21.5 | 18.4 | 117% |
| TGC | C | 68.2% | 15 | 10.4 | 12.6 | 83% |
| TGT | C | 31.8% | 7 | 4.9 | **10.6** | 46% |
| GAC | D | 32.9% | 27 | 18.7 | 25.1 | 75% |
| GAT | D | 67.1% | 55 | 38.1 | 21.8 | *175%* |
| GAA | E | 60.0% | 51 | 35.3 | 29.0 | 122% |
| GAG | E | 40.0% | 34 | 23.6 | 39.6 | 60% |
| TTC | F | 41.8% | 33 | 22.9 | 20.3 | 113% |
| TTT | F | 58.2% | 46 | 31.9 | 17.6 | *181%* |
| GGA | G | 41.5% | 34 | 23.6 | 16.5 | 143% |
| GGC | G | 24.4% | 20 | 13.9 | 22.2 | 62% |
| GGG | G | 14.6% | 12 | 8.3 | 16.5 | 50% |
| GGT | G | 19.5% | 16 | 11.1 | 10.8 | 103% |
| CAC | H | 44.9% | 22 | 15.2 | 15.1 | 101% |
| CAT | H | 55.1% | 27 | 18.7 | **10.9** | *172%* |
| ATA | I | 18.7% | 14 | 9.7 | **7.5** | 129% |
| ATC | I | 33.3% | 25 | 17.3 | 20.8 | 83% |
| ATT | I | 48.0% | 36 | 24.9 | 16.0 | *156%* |
| AAA | K | 60.3% | 47 | 32.6 | 24.4 | 133% |
| AAG | K | 39.7% | 31 | 21.5 | 31.9 | 67% |
| CTA | L | 11.7% | 15 | 10.4 | **7.2** | 144% |
| CTC | L | 16.4% | 21 | 14.6 | 19.60 | 74% |
| CTG | L | 28.9% | 37 | 25.6 | 39.60 | 65% |
| CTT | L | 19.5% | 25 | 17.3 | 13.20 | 131% |
| TTA | L | 7.8% | 10 | 6.9 | **7.7** | 90% |
| TTG | L | 15.6% | 20 | 13.9 | 12.90 | 107% |
| ATG | M | 100.0% | 44 | 30.5 | 22.00 | 139% |
| AAC | N | 41.0% | 25 | 17.3 | 19.10 | 91% |
| AAT | N | 59.0% | 36 | 24.9 | 17.00 | 147% |
| CCA | P | 42.3% | 30 | 20.8 | 16.90 | 123% |
| CCC | P | 21.1% | 15 | 10.4 | 19.80 | 53% |
| CCG | P | 1.4% | 1 | 0.7 | **6.9** | **10%** |
| CCT | P | 35.2% | 25 | 17.3 | 17.50 | 99% |
| CAA | Q | 35.9% | 23 | 15.9 | 12.30 | 130% |
| CAG | Q | 64.1% | 41 | 28.4 | 34.20 | 83% |
| AGA | R | 30.0% | 21 | 14.6 | 12.20 | 119% |
| AGG | R | 24.3% | 17 | 11.8 | 12.00 | 98% |
| CGA | R | 15.7% | 11 | 7.6 | **6.2** | 123% |
| CGC | R | 12.9% | 9 | 6.2 | 10.40 | 60% |
| CGG | R | 7.1% | 5 | 3.5 | 11.40 | 30% |
| CGT | R | 10.0% | 7 | 4.9 | **4.5** | 108% |
| AGC | S | 18.6% | 22 | 15.2 | 19.50 | 78% |
| AGT | S | 19.5% | 23 | 15.9 | **12.1** | 132% |
| TCA | S | 22.0% | 26 | 18.0 | **12.2** | 148% |
| TCC | S | 15.3% | 18 | 12.5 | 17.70 | 70% |
| TCG | S | 1.7% | 2 | 1.4 | **4.4** | **32%** |
| TCT | S | 22.9% | 27 | 18.7 | 15.20 | 123% |
| ACA | T | 28.0% | 23 | 15.9 | 15.10 | 106% |
| ACC | T | 28.0% | 23 | 15.9 | 18.90 | 84% |
| ACG | T | 1.2% | 1 | 0.7 | **6.1** | **11%** |
| ACT | T | 42.7% | 35 | 24.3 | 13.10 | *185%* |
| GTA | V | 21.8% | 19 | 13.2 | **7.1** | *185%* |
| GTC | V | 25.3% | 22 | 15.2 | 14.50 | 105% |

TABLE 17-continued

Rare codons in native human FVIII DNA sequence with B-domain removed resulting in sequence that encodes a 1443 amino acid protein.

| Codon | Amino acid | Freq ^ | Number * | FVIII codon usage # | Liver Human codon usage # | FVIII codon usage % difference to liver |
|---|---|---|---|---|---|---|
| GTG | V | 33.3% | 29 | 20.1 | 28.10 | 72% |
| GTT | V | 19.5% | 17 | 11.8 | 11.00 | 107% |
| TGG | W | 100.0% | 28 | 19.4 | 13.20 | 147% |
| TAC | Y | 39.7% | 27 | 18.7 | 15.30 | 122% |
| TAT | Y | 60.3% | 41 | 28.4 | 12.20 | *233%* |

The Frequency in native FVIII was calculated as the number of occurrences of that codon in native FVIII divided by the total amino acid size of FVIII (1443 residues).

Codon usage frequencies are occurrences per 1000 amino acids.

* Number is the number of times that codon appears in native FVIII without the B-domain.

^ Freq is the percentage at which that codon is used for that amino acid within native human FVIII without the B-domain. Codon usage in FVIII that are at 50% or less than that of the codon usage in liver expressed human genes are shown in bold while those that are higher than 150% are in italics.

In particular, GCT (A), GCG (A), CCG (P), CGG (R), TCG (S), and ACG (T) are used at less than 50% of the frequency that they are used on average in liver expressed genes. In contrast, GAT (D), TTT (F), CAT (H), ATT (I), ACT (T), and GTA (V) are used in FVIII at a frequency greater than 150% of the frequency that they are used on average in liver-expressed genes. This indicates that the native FVIII contains a significant number of codons that are present at frequencies different from that in the average gene expressed in the liver. This codon usage difference may negatively impact the ability of liver cells to express human FVIII. This provides a rationale for modifying the codon usage of an artificially generated FVIII DNA sequence to improve expression without altering the encoded amino acid sequence.

The mature B-domain deleted FVIII amino acid sequence containing the var4 B-domain replacement was codon optimized followed by removal of all CG dinucleotides using a custom designed algorithm that selected the next most frequent codon for either of the codons that may span a given CG sequence. The rationale for eliminating the CG dinucleotides is that CpG can be recognized by the innate immune system as part of the cellular response against foreign viral and bacterial DNA and thus may negatively impact DNA delivery in vivo or potentially expression. This algorithm removed a total of 210 CG sequences and in the process altered about 210 codons while retaining the identical encoded amino acid sequence. The resulting DNA sequence was designed as codon optimization 1 (copt 1) and is contained in the construct pMG4026 (SEQ ID NO: 91). Analysis of the codon usage in the copt1 DNA sequence revealed that compared to the native human FVIII DNA sequence, the copt1 sequence had altered the frequencies of specific codons. Amongst the 12 codons defined as rare in liver-expressed human genes (<10 codons per 1000 amino acids), six were reduced in their frequency in copt1 as compared to native FVIII while the CAT codon frequency was reduced by 50%, the TGT codon frequency was unchanged, and the frequencies of 4 codons were already present at low frequencies (1 or 2 occurrences in the entire sequence) in native FVIII. The codons that are utilized at the lowest frequency for that amino acid in liver-expressed genes but are not rare in liver-expressed genes (i.e. have a frequency>10 per 1000 amino acids) were all reduced in frequency in copt1 compared to native FVIII, but only by about 50% on average. These differences are summarized in Table 18.

TABLE 18

Comparison of codon usage between the native DNA sequence for human B-domain deleted FVIII and B-domain deleted FVIII after codon optimization 1 (copt1)

| Native FVIII | copt1 (pMG4026) |
|---|---|
| Codon, amino acid, % of AA Freq, Number of occurrences | |
| GCA A 25.7% 18 | GCA A 0.0% 0 |
| GCC A 27.1% 19 | GCC A 55.7% 39 |
| GCG A 2.9% 2 | GCG A 0.0% 0 |
| GCT A 44.3% 31 | GCT A 44.3% 31 |
| TGC C 68.2% 15 | TGC C 60.0% 12 |
| TGT C 31.8% 7 | TGT C 40.0% 8 |
| GAC D 32.9% 27 | GAC D 52.4% 43 |
| GAT D 67.1% 55 | GAT D 47.6% 39 |
| GAA E 60.0% 51 | GAA E 40.5% 34 |
| GAG E 40.0% 34 | GAG E 59.5% 50 |
| TTC F 41.8% 33 | TTC F 65.8% 50 |
| TTT F 58.2% 46 | TTT F 34.2% 26 |
| GGA G 41.5% 34 | GGA G 39.0% 32 |
| GGC G 24.4% 20 | GGC G 59.8% 49 |
| GGG G 14.6% 12 | GGG G 1.2% 1 |
| GGT G 19.5% 16 | GGT G 0.0% 0 |
| CAC H 44.9% 22 | CAC H 65.3% 32 |
| CAT H 55.1% 27 | CAT H 34.7% 17 |
| ATA I 18.7% 14 | ATA I 0.0% 0 |
| ATC I 33.3% 25 | ATC I 71.6% 53 |
| ATT I 48.0% 36 | ATT I 28.4% 21 |
| AAA K 60.3% 47 | AAA K 26.6% 21 |
| AAG K 39.7% 31 | AAG K 73.4% 58 |
| CTA L 11.7% 15 | CTA L 0.0% 0 |
| CTC L 16.4% 21 | CTC L 3.2% 4 |
| CTG L 28.9% 37 | CTG L 96.0% 120 |
| CTT L 19.5% 25 | CTT L 0.8% 1 |
| TTA L 7.8% 10 | TTA L 0.0% 0 |
| TTG L 15.6% 20 | TTG L 0.0% 0 |
| ATG M 100% 44 | ATG M 100% 43 |
| AAC N 41.0% 25 | AAC N 59.4% 38 |
| AAT N 59.0% 36 | AAT N 40.6% 26 |
| CCA P 42.3% 30 | CCA P 9.6% 7 |
| CCC P 21.1% 15 | CCC P 32.9% 24 |
| CCG P 1.4% 1 | CCG P 0.0% 0 |
| CCT P 35.2% 25 | CCT P 57.5% 42 |
| CAA Q 35.9% 23 | CAA Q 9.2% 6 |
| CAG Q 64.1% 41 | CAG Q 90.8% 59 |
| AGA R 30.0% 21 | AGA R 94.3% 66 |
| AGG R 24.3% 17 | AGG R 5.7% 4 |
| CGA R 15.7% 11 | CGA R 0.0% 0 |
| CGC R 12.9% 9 | CGC R 0.0% 0 |
| CGG R 7.1% 5 | CGG R 0.0% 0 |
| CGT R 10.0% 7 | CGT R 0.0% 0 |
| AGC S 18.6% 22 | AGC S 51.7% 61 |
| AGT S 19.5% 23 | AGT S 0.0% 0 |
| TCA S 22.0% 26 | TCA S 0.0% 0 |
| TCC S 15.3% 18 | TCC S 11.9% 14 |
| TCG S 1.7% 2 | TCG S 0.0% 0 |
| TCT S 22.9% 27 | TCT S 36.4% 43 |
| ACA T 28.0% 23 | ACA T 53.1% 43 |
| ACC T 28.0% 23 | ACC T 44.4% 36 |
| ACG T 1.2% 1 | ACG T 0.0% 0 |
| ACT T 42.7% 35 | ACT T 2.5% 2 |
| GTA V 21.8% 19 | GTA V 0.0% 0 |
| GTC V 25.3% 22 | GTC V 9.1% 8 |
| GTG V 33.3% 29 | GTG V 88.6% 78 |
| GTT V 19.5% 17 | GTT V 2.3% 2 |
| TGG W 100% 28 | TGG W 100% 28 |
| TAC Y 39.7% 27 | TAC Y 61.8% 42 |
| TAT Y 60.3% 41 | TAT Y 38.2% 26 |

As shown in Table 19, the copt1 sequence still contains a number of rare codons that make up between 27% and 48% of the codons that encode that specific amino acid. This is unlikely to be optimal for the protein expression from this FVIII DNA sequence. Further reducing or eliminating these rare codons was therefore included in a second codon optimization design called copt4.

TABLE 19

Rare codons present in the copt1 DNA sequence of B-domain deleted FVIII

| Codon | Amino acid | Occurrence in copt1 | Number of that amino acid in FVIII | % of that amino acid in encoded by this rare codon in FVIII |
|---|---|---|---|---|
| TGT | C | 8 | 20 | 40% |
| CAT | H | 17 | 49 | 35% |
| GAT | D | 39 | 82 | 48% |
| TTT | F | 26 | 76 | 34% |
| AAA | K | 21 | 79 | 27% |
| AAT | N | 26 | 64 | 41% |
| TAT | Y | 26 | 68 | 38% |

The removal of all of the CpG dinucleotides from a sequence that has been codon optimized by using the most frequent codons is particularly impactful on the distribution of arginine codons, because 4 of the 6 Arg codons contain CG sequences, and 2 of these are among the most frequently used Arg codons. There are 70 Arginine codons in the mature FVIII-BDD sequence that contains the var 4 B-domain replacement. CpG can be recognized by the innate immune system as part of the cellular response against foreign viral and bacterial DNA. However, CpG are also naturally present in mammalian genomic DNA, albeit with different distributions than in foreign DNA and with different methylation patterns (e.g. bacterial CpG are not methylated, while in eukaryotes CpG tend to be methylated). Therefore, the removal of all CpG may not be required to minimize innate immune response. Sequence elements in the genomes of mammals called CpG islands (defined as being a 200-bp region of DNA with a G+C content greater than 50%) or a high density of CpG are more likely to be problematic.

The usage of arginine codons in cop1 is summarized in Table 20.

TABLE 20

Usage of arginine codons in copt optimized FVIII-BDD

| Codon | Occurrences in FVIII-BDD: Native | Occurrences in FVIII-BDD: copt1 | Codon frequency in liver expressed genes |
|---|---|---|---|
| AGA | 21 | 66 | 11.11 |
| AGG | 17 | 4 | 10.44 |
| CGA | 11 | 0 | 6.13 |
| CGC | 9 | 0 | 10.48 |
| CGG | 5 | 0 | 10.44 |
| CGT | 7 | 0 | 4.55 |

Analysis of the arginine (R) codons in copt1 reveals almost exclusive use of the codon AGA (66 occurrences), with the only other codon being used 4 times (AGG). This contrasts to that of native FVIII, where all 6 codons are used with a bias towards AGA and AGG codons. Given that the frequency of codon usage for arginine in liver-expressed genes varies over only a 3-fold range (4.55 to 11.11), with 4 of the 6 codons having similar frequencies, a more even distribution of R codons among the 4 most frequently used codons (AGA, AGG, CGC, CGG) is likely to provide improved expression. Adjusting the usage of R codons was therefore included in a second codon optimization design called copt4 which necessarily increases the CG dinucleotide content. While CpG can be immunogenic, they are also naturally present in mammalian genomic DNA, albeit with different distributions than in foreign DNA, and with different methylation patterns (e.g. bacterial CpG are not methylated, while in eukaryotes CpG tend to be methylated). Therefore, the removal of all CpG may not be required to minimize innate immune response. Sequence elements in the genomes of mammals called CpG islands (defined as being a 200-bp region of DNA with a G+C content greater than 50%) or a high density of CpG are more likely to be problematic and were avoided. Other considerations when codon optimizing a coding sequence are that some codon pairs are used more frequently in coding regions of genes while other codon pairs are avoided. In addition, out-frame TAA or TAG stop codons should be avoided if possible.

A stochastic design approach was used to modify the copt1 sequence to eventually create codon optimization copt 4 encoding B-domain deleted FVIII containing the var4 B-domain replacement via several iterative steps. After each step, the impact on CpG content and codon usage was evaluated. The resulting DNA sequence, which encodes B-domain deleted FVIII containing the var4 B-domain replacement, was designated copt4 and is contained in the construct pMG4029 (SEQ ID NO: 92). The codon usage in copt4 compared to native B-domain deleted FVIII is shown in Table 21.

TABLE 21

Comparison of the codon usage in copt4 and native FVIII.

| Native FVIII Codon AA % of AA Freq | co4 (pMG4029) Codon AA % of AA Freq | Fold reduction vs native |
|---|---|---|
| GCA A 25.7% 18 | GCA A 0.0% 0 | |
| GCC A 27.1% 19 | GCC A 77.1% 54 | |
| **GCG A 2.9% 2** | **GCG A 0.0% 0** | **Eliminated** |
| GCT A 44.3% 31 | GCT A 22.9% 16 | |
| TGC C 68.2% 15 | TGC C 85.0% 17 | |
| **TGT C 31.8% 7** | **TGT C 15.0% 3** | **2.3** |
| GAC D 32.9% 27 | GAC D 69.5% 57 | |
| ***GAT D 67.1% 55*** | ***GAT D 30.5%*** 25 | ***2.2*** |
| GAA E 60.0% 51 | GAA E 4.8% 4 | |
| GAG E 40.0% 34 | GAG E 95.2% 80 | |
| TTC F 41.8% 33 | TTC F 80.3% 61 | |
| ***TTT F 58.2% 46*** | ***TTT F 19.7% 15*** | ***3.0*** |
| GGA G 41.5% 34 | GGA G 19.5% 16 | |
| GGC G 24.4% 20 | GGC G 51.2% 42 | |
| GGG G 14.6% 12 | GGG G 29.3% 24 | |
| ***GGT G 19.5% 16*** | ***GGT G 0.0% 0*** | ***Eliminated*** |
| CAC H 44.9% 22 | CAC H 73.5% 36 | |
| **CAT H 55.1% 27** | **CAT H 26.5% 13** | **2.1** |
| **ATA I 18.7% 14** | **ATA I 0.0% 0** | **Eliminated** |
| ATC I 33.3% 25 | ATC I 60.8% 45 | |
| ATT I 48.0% 36 | ATT I 39.2% 29 | |
| ***AAA K 60.3% 47*** | ***AAA K 24.1% 19*** | ***2.5*** |
| AAG K 39.7% 31 | AAG K 75.9% 60 | |
| **CTA L 11.7% 15** | **CTA L 0.0% 0** | **Eliminated** |
| CTC L 16.4% 21 | CTC L 28.8% 36 | |
| CTG L 28.9% 37 | CTG L 65.6% 82 | |
| CTT L 19.5% 25 | CTT L 5.6% 7 | |
| **TTA L 7.8% 10** | **TTA L 0.0% 0** | **Eliminated** |
| TTG L 15.6% 20 | TTG L 0.0% 0 | |
| ATG M 100% 44 | ATG M 100% 43 | |
| AAC N 41.0% 25 | AAC N 75.0% 48 | |
| ***AAT N 59.0% 36*** | ***AAT N 25.0% 16*** | ***2.3*** |
| CCA P 42.3% 30 | CCA P 34.2% 25 | |
| CCC P 21.1% 15 | CCC P 43.8% 32 | |
| **CCG P 1.4% 1** | **CCG P 0.0% 0** | **Eliminated** |
| CCT P 35.2% 25 | CCT P 21.9% 16 | |
| CAA Q 35.9% 23 | CAA Q 3.1% 2 | |
| CAG Q 64.1% 41 | CAG Q 96.9% 63 | |
| AGA R 30.0% 21 | AGA R 41.4% 29 | 0.7 |
| AGG R 24.3% 17 | AGG R 41.4% 29 | 0.6 |
| **CGA R 15.7% 11** | **CGA R 0.0% 0** | **Eliminated** |
| CGC R 12.9% 9 | CGC R 10.0% 7 | 1.3 |
| CGG R 7.1% 5 | CGG R 7.1% 5 | 1.0 |
| **CGT R 10.0% 7** | **CGT R 0.0% 0** | **Eliminated** |
| AGC S 18.6% 22 | AGC S 51.7% 61 | |
| AGT S 19.5% 23 | AGT S 0.0% 0 | |
| TCA S 22.0% 26 | TCA S 0.0% 0 | |
| TCC S 15.3% 18 | TCC S 23.7% 28 | |
| **TCG S 1.7% 2** | **TCG S 0.0% 0** | **Eliminated** |
| TCT S 22.9% 27 | TCT S 24.6% 29 | |
| ACA T 28.0% 23 | ACA T 2.5% 2 | |
| ACC T 28.0% 23 | ACC T 69.1% 56 | |
| **ACG T 1.2% 1** | **ACG T 0.0% 0** | **Eliminated** |
| ACT T 42.7% 35 | ACT T 28.4% 23 | |
| **GTA V 21.8% 19** | **GTA V 0.0% 0** | **Eliminated** |
| GTC V 25.3% 22 | GTC V 50.0% 44 | |
| GTG V 33.3% 29 | GTG V 50.0% 44 | |
| GTT V 19.5% 17 | GTT V 0.0% 0 | |
| TGG W 100% 28 | TGG W 100% 28 | |
| TAC Y 39.7% 27 | TAC Y 73.5% 50 | |
| ***TAT Y 60.3% 41*** | ***TAT Y 26.5% 18*** | ***2.3*** |

Highlighted codons are rare codons (present at <10 per 1,000 amino acids in liver expressed genes). Codons in bold italic are those that are used least frequently in liver expressed genes but are used at >10 per 1,000 codons.

Compared to native FVIII, the frequency of all 12 rare codons was reduced with only TGT and CAT being retained, while the other 10 were eliminated entirely. Among the 6 codons that are the least frequent for that amino acid but not otherwise rare (i.e. are present at >10 per 1,000 codons in liver-expressed genes), all were significantly reduced (by 2- to 3-fold) in occurrence compared to native FVIII.

The codon usage for arginine is similar to that of native FVIII except that the rare codon CGT, present in 7 of the 70 R codons in native FVIII, was eliminated. The total CG dinucleotide content of copt4 is 22, compared to 53 in native B-domain deleted FVIII. Thus, a mixture of arginine codons more representative of their usage in liver-expressed genes was included, eliminating the one rare arginine codon and maintaining a CpG content less than native FVIII.

Another notable change in the copt4 sequence as compared to the copt1 sequence was in the valine codons. In copt1, 78 of the 88 valine amino acids are encoded by the GTG codon, which is not the most frequently used codon for valine. The most frequently used codon for valine in liver-expressed genes (codons per 1,000 amino acids listed in brackets) is GTC (29.9), followed by GTG (15), GTT (11.3), and GTA (6.8). In copt4, 44 of the valine residues are encoded by GTC and 44 are encoded by GTG. There are 6 codons for serine, with 3 codons (AGC, TCC, TCT) being the most frequently used in liver-expressed genes. While copt1 only utilized these 3 most frequent codons (in contrast to native FVIII, which contains 23 AGT codons and 26 TCA codons), the distribution of these codons was heavily skewed to 2 codons: AGC with 61 occurrences and TCT with 43 occurrences. This was adjusted in copt 4 to be distributed amongst codons AGC, TCC, and TCT with 61, 28, and 29 occurrences, respectively.

These two DNA sequences encoding the same B-domain deleted human FVIII protein containing the var4sc B-domain replacement were synthesized with the appropriate flanking sequences to enable expression after integration into albumin intron 1 via RNA splicing from albumin exon 1. Specifically, a splice acceptor site followed by the dinucleotide TG was included 5' of the N-terminus of the FVIII coding sequence. The TG dinucleotide is required to maintain the correct reading frame after splicing from albumin exon one to the splice acceptor. In addition, guide target sites for MG29-1 guide 8 (mAb29-8) and MG3-6/3-4 guide 12 (mA364-12) and appropriate spacer sequences were placed 5' of the splice acceptor. A stop codon and polyadenylation signal was added at the C-terminus of the FVIII coding sequence, followed by a spacer and the target sites for MG29-1 guide 8 (mAb29-8) and MG3-6/3-4 guide 12 (mA364-12). The resulting constructs were designated as pMG4026 (SEQ ID NO: 91) and pMG4029 (SEQ ID NO: 92), in which the codon optimization of the FVIII coding sequence used was copt1 or copt4, respectively (Table 22).

TABLE 22

Construct ID's and description for single chain B-domain deleted human FVIII designs with var4 B-domain replacements

| Construct name | FVIII design | Codon optimization | SEQ ID NO |
|---|---|---|---|
| pMG4026 | BDD with 2 N-glycan and no furin site | copt1 | 91 |
| pMG4029 | BDD with 2 N-glycan and no furin site | copt4 | 92 |

AAV8 viruses encapsulating the DNA sequences of pMG4026 and pMG4029m were produced in HEK293 cells using standard protocols. These AAV viruses can be tested in mice for their integration efficiency and levels of albumin-FVIII fusion protein and FVIII protein in circulation using the methods described herein.

Example 14—Design of Additional FVIII Donor Sequences Comprised of Human FVIII Coding Sequences Encoding a Single Chain FVIII Protein Containing a B-Domain Replacement with 2 N-Linked Glycosylation Sites with Amino Acid Change F309S Passage of the FVIII protein through the ER-Golgi apparatus is known to be a limiting factor for FVIII protein secretion. The two DNA sequences encoding single chain FVIII protein containing the var4sc B-domain replacement were modified to include serine in place of phenylalanine at position 309 (amino acid numbering as per full-length FVIII). The resulting DNA sequences were designated as pMG4027_co1_F309S, which utilizes an alternative codon optimization called copt2 (SEQ ID NO: 93) and pMG4029_co4_F309S which utilizes copt4 codon optimization (SEQ ID NO: 94). Both sequences encode the same amino acid sequence. Both pMG4027_co2_F309S and pMG4029_co4_F309S include the same sequences flanking the FVIII coding sequence as is present in pMG4026 and pMG4029, which are required for splicing from albumin exon 1 after integration at the target sites for guides.

TABLE 23

Listing of additional protein and nucleic acid sequences referred to herein not included in the sequence listing

| Category | SEQ ID NO: | Description | Type | Sequence |
|---|---|---|---|---|
| DNA sequence of human albumin nucleus-targeting sequence | 1 | hANTS | Nucleotide | TGAATTTTGTAATCGGTTGGCAGCCAATGAAATACAAAGATGAG TCTAGTTAATAATCTACAATTATTGGTTAAAGAAGTATATTAGT |
| Transcriptional enhancer | 2 | SV40e | Nucleotide | ATGCTTTGCATACTTCTGCCTGCTGGGGAGCCTGGGGACTTTCC ACACCCTAACTGACACACATTCCAC |
| DNA sequence of mouse albumin target site | 3 | target site for mA29-8 guide RNA in forward orientation (same as in mouse genome) | Nucleotide | TTTCCTGTAACGATCGGGAACTGGCA |
| DNA sequence of mouse albumin target site | 4 | target site for mA29-8 guide RNA in reverse orientation (reverse complement of mouse genome) | Nucleotide | TGCCAGTTCCCGATCGTTACAGGAAA |
| DNA sequence of mouse albumin target site | 5 | target site for mA29-12 guide RNA in forward orientation (same as in mouse genome) | Nucleotide | TTTGAGTGTAGCAGAGAGGAACCATT |
| DNA sequence of mouse albumin target site | 6 | target site for mA29-12 guide RNA in reverse orientation (reverse complement of mouse genome) | Nucleotide | AATGGTTCCTCTCTGCTACACTCAAA |
| Spacer | 7 | 20 bp spacer (located between NTDS and cassette) | Nucleotide | AGATATGCTATACCTGATAC |
| DNA sequence of human albumin nucleus targeting sequence and transcriptional enhancer | 8 | hANTS and SV40e | Nucleotide | TGAATTTTGTAATCGGTTGGCAGCCAATGAAATACAAAGATGAG TCTAGTTAATAATCTACAATTATTGGTTAAAGAAGTATATTAGT ATGCTTTGCATACTTCTGCCTGCTGGGGAGCCTGGGGACTTTCC ACACCCTAACTGACACACATTCCAC |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| Splice acceptor | 9 | Splice acceptor | Nucleotide | ACTAAAGAATTATTCTTTTACATTTCAG |
| Human FVIII coding sequence | 10 | Human FVIII coding sequence | Nucleotide | GCCACCAGAAGATATTACCTGGGAGCTGTGGAACTGAGCTGGG<br>ACTACATGCAGTCTGACCTGGGAGAGCTGCCTGTGGATGCTAGA<br>TTTCCTCCAAGAGTGCCCAAGAGCTTCCCCTTCAACACCTCTGTG<br>GTGTACAAGAAAACCCTGTTTGTGGAATTCACAGACCACCTGTT<br>CAATATTGCCAAGCCTAGACCTCCTTGGATGGGACTGCTGGGAC<br>CTACAATTCAGGCTGAGGTGTATGACACAGTGGTCATCACCCTG<br>AAGAACATGGCCAGCCATCCTGTGTCTCTGCATGCTGTGGGAGT<br>GTCTTACTGGAAGGCTTCTGAGGGAGCTGAGTATGATGACCAGA<br>CAAGCCAGAGAGAGAAAGAGGATGACAAGGTTTTCCCTGGAGG<br>CAGCCACACCTATGTCTGGCAGGTCCTGAAAGAAAATGGCCCTA<br>TGGCCTCTGATCCTCTGTGCCTGACATACAGCTACCTGAGCCAT<br>GTGGACCTGGTCAAGGACCTGAATTCTGGCCTGATTGGAGCCCT<br>GCTGGTGTGTAGAGAAGGCAGCCTGGCCAAAGAGAAAACCCAG<br>ACACTGCACAAGTTCATCCTGCTGTTTGCTGTGTTTGATGAGGG<br>CAAGAGCTGGCACTCTGAGACAAAGAACAGCCTGATGCAGGAC<br>AGGGATGCTGCCTCTGCTAGAGCTTGGCCTAAGATGCACACAGT<br>GAATGGCTATGTGAACAGAAGCCTGCCTGGACTGATTGGCTGCC<br>ACAGAAAGTCTGTGTACTGGCATGTGATTGGCATGGGCACAACA<br>CCTGAGGTGCACAGCATCTTTCTGGAAGGACACACCTTCCTGGT<br>GAGAAACCATAGACAGGCCAGCCTGGAAATCAGCCCTATCACC<br>TTCCTGACAGCTCAGACCCTGCTGATGGATCTGGGCCAGTTTCT<br>GCTGTTCTGCCACATCAGCAGCCACCAGCATGATGGCATGGAAG<br>CCTATGTGAAGGTGGACAGCTGCCCTGAAGAACCCCAGCTGAG<br>AATGAAGAACAATGAGGAGGCTGAGGACTATGATGATGACCTG<br>ACAGACTCTGAGATGGATGTGGTCAGATTTGATGATGACAACAG<br>CCCCAGCTTCATCCAGATCAGATCTGTGGCCAAGAAGCACCCCA<br>AGACCTGGGTGCACTATATTGCTGCTGAGGAAGAGGACTGGGA<br>TTATGCTCCTCTGGTGCTGGCCCCTGATGACAGAAGCTACAAGA<br>GCCAGTACCTGAACAATGGCCCTCAGAGAATTGGCAGAAAGTA<br>TAAGAAAGTGAGATTCATGGCCTACACAGATGAGACATTCAAG<br>ACCAGAGAGGCCATTCAGCATGAGTCTGGCATTCTGGGCCCTCT<br>GCTGTATGGAGAAGTGGGAGATACACTGCTGATCATCTTCAAGA<br>ACCAGGCCAGCAGACCCTACAACATCTACCCTCATGGCATCACA<br>GATGTGAGACCCCTGTATTCCAGAAGGCTGCCCAAGGGAGTGA<br>AGCACCTGAAGGACTTCCCTATCCTGCCTGGAGAGATCTTCAAG<br>TACAAGTGGACAGTGACAGTGGAAGATGGCCCCACCAAGTCTG<br>ACCCTAGATGTCTGACAAGATACTACAGCAGCTTTGTGAACATG<br>GAAAGAGACCTGGCCTCTGGCCTGATTGGACCTCTGCTGATCTG<br>CTACAAAGAATCTGTGGACCAGAGAGGCAACCAGATCATGTCT<br>GACAAGAGAAATGTGATCCTGTTTTCTGTGTTTGATGAGAACAG<br>ATCCTGGTATCTGACAGAGAACATCCAGAGATTTCTGCCCAATC<br>CTGCTGGAGTGCAGCTGGAAGATCCTGAGTTCCAGGCCTCCAAC<br>ATCATGCACTCCATCAATGGCTATGTGTTTGACAGCCTGCAGCT<br>GTCTGTGTGCCTGCATGAAGTGGCCTACTGGTACATCCTGAGCA<br>TTGGAGCCCAGACAGACTTCCTGTCTGTGTTCTTCTCTGGCTACA |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | CCTTCAAGCACAAGATGGTGTATGAGGATACCCTGACACTGTTC<br>CCATTCTCTGGAGAGACAGTGTTCATGAGCATGGAAAACCCTGG<br>CCTGTGGATCCTGGGCTGTCACAACTCTGACTTCAGAAACAGAG<br>GCATGACAGCCCTGCTGAAGGTGTCCAGCTGTGACAAGAACAC<br>AGGAGACTACTATGAGGACAGCTATGAGGACATCTCTGCCTACC<br>TGCTGAGCAAGAACAATGCCATTGAGCCCAGAAGCTTCAGCCA<br>GAATGCCACCAATGTGTCCAACAACAGCAACACCAGCAATGAC<br>TCCAATGTGTCCCCTCCAGTGCTGAAGAGACACCAGAGAGAAAT<br>CACCAGAACCACACTGCAGTCTGACCAAGAGGAAATTGACTAT<br>GATGACACCATCTCTGTGGAGATGAAGAAAGAAGATTTTGACAT<br>CTATGATGAGGATGAGAATCAGAGCCCCAGATCCTTTCAGAAA<br>AAGACCAGACACTACTTCATTGCTGCTGTGGAGAGACTGTGGGA<br>CTATGGCATGTCTAGCAGCCCTCATGTGCTGAGAAATAGAGCCC<br>AGTCTGGCTCTGTGCCCCAGTTCAAGAAAGTGGTGTTCCAAGAG<br>TTCACAGATGGCAGCTTCACCCAGCCACTGTATAGAGGAGAGCT<br>GAATGAGCATCTGGGCCTGCTGGGCCCTTATATCAGAGCTGAAG<br>TGGAAGATAACATCATGGTCACCTTCAGAAATCAGGCCTCTAGG<br>CCCTACAGCTTCTACAGCTCCCTGATCAGCTATGAAGAGGACCA<br>GAGACAGGGAGCTGAGCCCAGAAAGAACTTTGTGAAGCCCAAT<br>GAGACTAAGACCTACTTTTGGAAGGTGCAGCACCACATGGCCCC<br>TACAAAGGATGAGTTTGACTGCAAGGCCTGGGCCTACTTTTCTG<br>ATGTGGATCTGGAAAAGGATGTGCACTCTGGACTCATTGGACCA<br>CTGCTTGTGTGCCACACCAACACACTGAACCCTGCTCATGGCAG<br>ACAAGTGACAGTGCAAGAGTTTGCCCTGTTCTTCACCATCTTTG<br>ATGAAACAAAGAGCTGGTACTTCACAGAGAATATGGAGAGAAA<br>CTGCAGGGCCCCTTGCAACATCCAGATGGAAGATCCCACCTTCA<br>AAGAGAACTACAGATTCCATGCCATCAATGGCTACATCATGGAC<br>ACACTGCCTGGCCTGGTTATGGCTCAGGATCAGAGAATCAGATG<br>GTATCTGCTGTCCATGGGCTCCAATGAGAATATCCACAGCATCC<br>ACTTCTCTGGCCATGTGTTCACAGTGAGAAAAAAAGAAGAGTAC<br>AAAATGGCCCTGTACAATCTGTACCCTGGGGTGTTTGAAACAGT<br>GGAAATGCTGCCTTCCAAGGCTGGCATTTGGAGAGTGGAATGTC<br>TGATTGGAGAGCACCTCCATGCTGGAATGAGCACCCTGTTTCTG<br>GTGTACAGCAACAAGTGTCAGACCCCTCTGGGCATGGCCTCTGG<br>ACACATCAGAGACTTCCAGATCACAGCCTCTGGCCAGTATGGAC<br>AGTGGGCTCCTAAACTGGCTAGACTGCACTACTCTGGCAGCATC<br>AATGCCTGGTCCACCAAAGAGCCCTTCAGCTGGATCAAGGTGGA<br>CCTGCTGGCTCCCATGATCATCCATGGAATCAAGACCCAGGGAG<br>CCAGACAGAAGTTCAGCAGCCTGTACATCAGCCAGTTCATCATC<br>ATGTACAGCCTGGATGGCAAGAAGTGGCAGACCTACAGAGGCA<br>ACAGCACAGGCACACTCATGGTGTTCTTTGGCAATGTGGACAGC<br>TCTGGCATTAAGCACAACATCTTCAACCCTCCAATCATTGCCAG<br>ATACATCAGACTGCACCCCACACACTACAGCATCAGATCTACCC<br>TGAGAATGGAACTGATGGGCTGTGACCTGAACAGCTGCAGCAT<br>GCCCCTGGGAATGGAAAGCAAGGCCATCTCTGATGCCCAGATC<br>ACAGCCAGCAGCTACTTCACCAACATGTTTGCCACTTGGAGCCC<br>CTCCAAGGCTAGACTGCATCTGCAGGGCAGAAGCAATGCTTGG |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | AGGCCCCAAGTGAACAACCCCAAAGAGTGGCTGCAGGTGGACT<br>TTCAAAAGACCATGAAAGTGACAGGAGTGACCACACAGGGAGT<br>CAAGTCTCTGCTGACCTCTATGTATGTGAAAGAGTTCCTGATCTC<br>CAGCAGCCAGGATGGCCACCAGTGGACCCTGTTTTTCCAGAATG<br>GCAAAGTGAAAGTGTTCCAGGGCAATCAGGACAGCTTCACACC<br>TGTGGTCAACTCCCTGGATCCTCCACTGCTGACCAGATACCTGA<br>GAATTCACCCTCAGTCTTGGGTGCACCAGATTGCTCTGAGAATG<br>GAAGTGCTGGGCTGTGAAGCTCAGGACCTCTAC |
| Stop codon, spacer and polyadenylation signal | 11 | Stop codon, spacer and polyadenylation signal | Nucleotide | TGATCCTGAATAAAAGATCTTTATTTTCATTAGATCTGTGTGTTG<br>GTTTTTTGTGTG |
| FVIII donor template | 12 | Full non-viral DNA donor template for FVIII with guide sites in F-F orientation (pMG4010) | Nucleotide | ATGCTTTGCATACTTCTGCCTGCTGGGGAGCCTGGGGACTTTCC<br>ACACCCTAACTGACACACATTCCACTGAATTTTGTAATCGGTTG<br>GCAGCCAATGAAATACAAAGATGAGTCTAGTTAATAATCTACA<br>ATTATTGGTTAAAGAAGTATATTAGTTCAGATTCAGAATGTCAA<br>TATTTCCTGTAACGATCGGGAACTGGCATTTGAGTGTAGCAGAG<br>AGGAACCATTTCTCAGTGTTAAGCTTACTAAAGAATTATTCTTTT<br>ACATTTCAGTGGCCACCAGAAGATATTACCTGGGAGCTGTGGAA<br>CTGAGCTGGGACTACATGCAGTCTGACCTGGGAGAGCTGCCTGT<br>GGATGCTAGATTTCCTCCAAGAGTGCCCAAGAGCTTCCCCTTCA<br>ACACCTCTGTGGTGTACAAGAAAACCCTGTTTGTGGAATTCACA<br>GACCACCTGTTCAATATTGCCAAGCCTAGACCTCCTTGGATGGG<br>ACTGCTGGGACCTACAATTCAGGCTGAGGTGTATGACACAGTGG<br>TCATCACCCTGAAGAACATGGCCAGCCATCCTGTGTCTCTGCAT<br>GCTGTGGGAGTGTCTTACTGGAAGGCTTCTGAGGGAGCTGAGTA<br>TGATGACCAGACAAGCCAGAGAGAGAAAGAGGATGACAAGGTT<br>TTCCCTGGAGGCAGCCACACCTATGTCTGGCAGGTCCTGAAAGA<br>AAATGGCCCTATGGCCTCTGATCCTCTGTGCCTGACATACAGCT<br>ACCTGAGCCATGTGGACCTGGTCAAGGACCTGAATTCTGGCCTG<br>ATTGGAGCCCTGCTGGTGTGTAGAGAAGGCAGCCTGGCCAAAG<br>AGAAAACCCAGACACTGCACAAGTTCATCCTGCTGTTTGCTGTG<br>TTTGATGAGGGCAAGAGCTGGCACTCTGAGACAAAGAACAGCC<br>TGATGCAGGACAGGGATGCTGCCTCTGCTAGAGCTTGGCCTAAG<br>ATGCACACAGTGAATGGCTATGTGAACAGAAGCCTGCCTGGACT<br>GATTGGCTGCCACAGAAAGTCTGTGTACTGGCATGTGATTGGCA<br>TGGGCACAACACCTGAGGTGCACAGCATCTTTCTGGAAGGACAC<br>ACCTTCCTGGTGAGAAACCATAGACAGGCCAGCCTGGAAATCA<br>GCCCTATCACCTTCCTGACAGCTCAGACCCTGCTGATGGATCTG<br>GGCCAGTTTCTGCTGTTCTGCCACATCAGCAGCCACCAGCATGA<br>TGGCATGGAAGCCTATGTGAAGGTGGACAGCTGCCCTGAAGAA<br>CCCCAGCTGAGAATGAAGAACAATGAGGAGGCTGAGGACTATG<br>ATGATGACCTGACAGACTCTGAGATGGATGTGGTCAGATTTGAT<br>GATGACAACAGCCCCAGCTTCATCCAGATCAGATCTGTGGCCAA<br>GAAGCACCCCAAGACCTGGGTGCACTATATTGCTGCTGAGGAA |

TABLE 23-continued

Listing of additional protein and nucleic acid sequences referred to herein not included in the sequence listing

| Category | SEQ ID NO: | Description | Type | Sequence |
|---|---|---|---|---|
| | | | | GAGGACTGGGATTATGCTCCTCTGGTGCTGGCCCCTGATGACAG |
| | | | | AAGCTACAAGAGCCAGTACCTGAACAATGGCCCTCAGAGAATT |
| | | | | GGCAGAAAGTATAAGAAAGTGAGATTCATGGCCTACACAGATG |
| | | | | AGACATTCAAGACCAGAGAGGCCATTCAGCATGAGTCTGGCATT |
| | | | | CTGGGCCCTCTGCTGTATGGAGAAGTGGGAGATACACTGCTGAT |
| | | | | CATCTTCAAGAACCAGGCCAGCAGACCCTACAACATCTACCCTC |
| | | | | ATGGCATCACAGATGTGAGACCCCTGTATTCCAGAAGGCTGCCC |
| | | | | AAGGGAGTGAAGCACCTGAAGGACTTCCCTATCCTGCCTGGAG |
| | | | | AGATCTTCAAGTACAAGTGGACAGTGACAGTGGAAGATGGCCC |
| | | | | CACCAAGTCTGACCCTAGATGTCTGACAAGATACTACAGCAGCT |
| | | | | TTGTGAACATGGAAAGAGACCTGGCCTCTGGCCTGATTGGACCT |
| | | | | CTGCTGATCTGCTACAAAGAATCTGTGGACCAGAGAGGCAACC |
| | | | | AGATCATGTCTGACAAGAGAAATGTGATCCTGTTTTCTGTGTTT |
| | | | | GATGAGAACAGATCCTGGTATCTGACAGAGAACATCCAGAGAT |
| | | | | TTCTGCCCAATCCTGCTGGAGTGCAGCTGGAAGATCCTGAGTTC |
| | | | | CAGGCCTCCAACATCATGCACTCCATCAATGGCTATGTGTTTGA |
| | | | | CAGCCTGCAGCTGTCTGTGTGCCTGCATGAAGTGGCCTACTGGT |
| | | | | ACATCCTGAGCATTGGAGCCCAGACAGACTTCCTGTCTGTGTTC |
| | | | | TTCTCTGGCTACACCTTCAAGCACAAGATGGTGTATGAGGATAC |
| | | | | CCTGACACTGTTCCCATTCTCTGGAGAGACAGTGTTCATGAGCA |
| | | | | TGGAAAACCCTGGCCTGTGGATCCTGGGCTGTCACAACTCTGAC |
| | | | | TTCAGAAACAGAGGCATGACAGCCCTGCTGAAGGTGTCCAGCT |
| | | | | GTGACAAGAACACAGGAGACTACTATGAGGACAGCTATGAGGA |
| | | | | CATCTCTGCCTACCTGCTGAGCAAGAACAATGCCATTGAGCCCA |
| | | | | GAAGCTTCAGCCAGAATGCCACCAATGTGTCCAACAACAGCAA |
| | | | | CACCAGCAATGACTCCAATGTGTCCCCTCCAGTGCTGAAGAGAC |
| | | | | ACCAGAGAGAAATCACCAGAACCACACTGCAGTCTGACCAAGA |
| | | | | GGAAATTGACTATGATGACACCATCTCTGTGGAGATGAAGAAA |
| | | | | GAAGATTTTGACATCTATGATGAGGATGAGAATCAGAGCCCCA |
| | | | | GATCCTTTCAGAAAAAGACCAGACACTACTTCATTGCTGCTGTG |
| | | | | GAGAGACTGTGGGACTATGGCATGTCTAGCAGCCCTCATGTGCT |
| | | | | GAGAAATAGAGCCCAGTCTGGCTCTGTGCCCCAGTTCAAGAAA |
| | | | | GTGGTGTTCCAAGAGTTCACAGATGGCAGCTTCACCCAGCCACT |
| | | | | GTATAGAGGAGAGCTGAATGAGCATCTGGGCCTGCTGGGCCCTT |
| | | | | ATATCAGAGCTGAAGTGGAAGATAACATCATGGTCACCTTCAGA |
| | | | | AATCAGGCCTCTAGGCCCTACAGCTTCTACAGCTCCCTGATCAG |
| | | | | CTATGAAGAGGACCAGAGACAGGGAGCTGAGCCCAGAAAGAAC |
| | | | | TTTGTGAAGCCCAATGAGACTAAGACCTACTTTTGGAAGGTGCA |
| | | | | GCACCACATGGCCCCTACAAAGGATGAGTTTGACTGCAAGGCCT |
| | | | | GGGCCTACTTTTCTGATGTGGATCTGGAAAAGGATGTGCACTCT |
| | | | | GGACTCATTGGACCACTGCTTGTGTGCCACACCAACACACTGAA |
| | | | | CCCTGCTCATGGCAGACAAGTGACAGTGCAAGAGTTTGCCCTGT |
| | | | | TCTTCACCATCTTTGATGAAACAAAGAGCTGGTACTTCACAGAG |
| | | | | AATATGGAGAGAAACTGCAGGGCCCCTTGCAACATCCAGATGG |
| | | | | AAGATCCCACCTTCAAAGAGAACTACAGATTCCATGCCATCAAT |
| | | | | GGCTACATCATGGACACACTGCCTGGCCTGGTTATGGCTCAGGA |
| | | | | TCAGAGAATCAGATGGTATCTGCTGTCCATGGGCTCCAATGAGA |

TABLE 23-continued

Listing of additional protein and nucleic acid sequences referred to herein not included in the sequence listing

| Category | SEQ ID NO: | Description | Type | Sequence |
|---|---|---|---|---|
| | | | | ATATCCACAGCATCCACTTCTCTGGCCATGTGTTCACAGTGAGA<br>AAAAAAGAAGAGTACAAAATGGCCCTGTACAATCTGTACCCTG<br>GGGTGTTTGAAACAGTGGAAATGCTGCCTTCCAAGGCTGGCATT<br>TGGAGAGTGGAATGTCTGATTGGAGAGCACCTCCATGCTGGAAT<br>GAGCACCCTGTTTCTGGTGTACAGCAACAAGTGTCAGACCCCTC<br>TGGGCATGGCCTCTGGACACATCAGAGACTTCCAGATCACAGCC<br>TCTGGCCAGTATGGACAGTGGGCTCCTAAACTGGCTAGACTGCA<br>CTACTCTGGCAGCATCAATGCCTGGTCCACCAAAGAGCCCTTCA<br>GCTGGATCAAGGTGGACCTGCTGGCTCCCATGATCATCCATGGA<br>ATCAAGACCCAGGGAGCCAGACAGAAGTTCAGCAGCCTGTACA<br>TCAGCCAGTTCATCATCATGTACAGCCTGGATGGCAAGAAGTGG<br>CAGACCTACAGAGGCAACAGCACAGGCACACTCATGGTGTTCTT<br>TGGCAATGTGGACAGCTCTGGCATTAAGCACAACATCTTCAACC<br>CTCCAATCATTGCCAGATACATCAGACTGCACCCCACACACTAC<br>AGCATCAGATCTACCCTGAGAATGGAACTGATGGGCTGTGACCT<br>GAACAGCTGCAGCATGCCCCTGGGAATGGAAAGCAAGGCCATC<br>TCTGATGCCCAGATCACAGCCAGCAGCTACTTCACCAACATGTT<br>TGCCACTTGGAGCCCCTCCAAGGCTAGACTGCATCTGCAGGGCA<br>GAAGCAATGCTTGGAGGCCCCAAGTGAACAACCCCAAAGAGTG<br>GCTGCAGGTGGACTTTCAAAAGACCATGAAAGTGACAGGAGTG<br>ACCACACAGGGAGTCAAGTCTCTGCTGACCTCTATGTATGTGAA<br>AGAGTTCCTGATCTCCAGCAGCCAGGATGGCCACCAGTGGACCC<br>TGTTTTTCCAGAATGGCAAAGTGAAAGTGTTCCAGGGCAATCAG<br>GACAGCTTCACACCTGTGGTCAACTCCCTGGATCCTCCACTGCT<br>GACCAGATACCTGAGAATTCACCCTCAGTCTTGGGTGCACCAGA<br>TTGCTCTGAGAATGGAAGTGCTGGGCTGTGAAGCTCAGGACCTC<br>TACTGATCCTGAATAAAAGATCTTTATTTTCATTAGATCTGTGTG<br>TTGGTTTTTTGTGTGTATTTAGCTATTTGAGTGTAGCAGAGAGGA<br>ACCATTTTTCCTGTAACGATCGGGAACTGGCAAGATATGCTATA<br>CCTGATACTGAATTTTGTAATCGGTTGGCAGCCAATGAAATACA<br>AAGATGAGTCTAGTTAATAATCTACAATTATTGGTTAAAGAAGT<br>ATATTAGTATGCTTTGCATACTTCTGCCTGCTGGGGAGCCTGGG<br>GACTTTCCACACCCTAACTGACACACATTCCAC |
| FVIII donor template | 13 | Full non-viral DNA donor template for FVIII with guide sites in R-R orientation (pMG4011) | Nucleotide | ATGCTTTGCATACTTCTGCCTGCTGGGGAGCCTGGGGACTTTCC<br>ACACCCTAACTGACACACATTCCACTGAATTTTGTAATCGGTTG<br>GCAGCCAATGAAATACAAAGATGAGTCTAGTTAATAATCTACA<br>ATTATTGGTTAAAGAAGTATATTAGTTCAGATTCAGAATGTCAA<br>TATGCCAGTTCCCGATCGTTACAGGAAAAATGGTTCCTCTCTGC<br>TACACTCAAATCTCAAAGCTTACTAAAGAATTATTCTTTTACATT<br>TCAGTGGCCACCAGAAGATATTACCTGGGAGCTGTGGAACTGA<br>GCTGGGACTACATGCAGTCTGACCTGGGAGAGCTGCCTGTGGAT<br>GCTAGATTTCCTCCAAGAGTGCCCAAGAGCTTCCCCTTCAACAC<br>CTCTGTGGTGTACAAGAAAACCCTGTTTGTGGAATTCACAGACC<br>ACCTGTTCAATATTGCCAAGCCTAGACCTCCTTGGATGGGACTG<br>CTGGGACCTACAATTCAGGCTGAGGTGTATGACACAGTGGTCAT<br>CACCCTGAAGAACATGGCCAGCCATCCTGTGTCTCTGCATGCTG |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | TGGGAGTGTCTTACTGGAAGGCTTCTGAGGGAGCTGAGTATGAT |
| | | | | GACCAGACAAGCCAGAGAGAGAAAGAGGATGACAAGGTTTTCC |
| | | | | CTGGAGGCAGCCACACCTATGTCTGGCAGGTCCTGAAAGAAAA |
| | | | | TGGCCCTATGGCCTCTGATCCTCTGTGCCTGACATACAGCTACCT |
| | | | | GAGCCATGTGGACCTGGTCAAGGACCTGAATTCTGGCCTGATTG |
| | | | | GAGCCCTGCTGGTGTGTAGAGAAGGCAGCCTGGCCAAAGAGAA |
| | | | | AACCCAGACACTGCACAAGTTCATCCTGCTGTTTGCTGTGTTTG |
| | | | | ATGAGGGCAAGAGCTGGCACTCTGAGACAAAGAACAGCCTGAT |
| | | | | GCAGGACAGGGATGCTGCCTCTGCTAGAGCTTGGCCTAAGATGC |
| | | | | ACACAGTGAATGGCTATGTGAACAGAAGCCTGCCTGGACTGATT |
| | | | | GGCTGCCACAGAAAGTCTGTGTACTGGCATGTGATTGGCATGGG |
| | | | | CACAACACCTGAGGTGCACAGCATCTTTCTGGAAGGACACACCT |
| | | | | TCCTGGTGAGAAACCATAGACAGGCCAGCCTGGAAATCAGCCC |
| | | | | TATCACCTTCCTGACAGCTCAGACCCTGCTGATGGATCTGGGCC |
| | | | | AGTTTCTGCTGTTCTGCCACATCAGCAGCCACCAGCATGATGGC |
| | | | | ATGGAAGCCTATGTGAAGGTGGACAGCTGCCCTGAAGAACCCC |
| | | | | AGCTGAGAATGAAGAACAATGAGGAGGCTGAGGACTATGATGA |
| | | | | TGACCTGACAGACTCTGAGATGGATGTGGTCAGATTTGATGATG |
| | | | | ACAACAGCCCCAGCTTCATCCAGATCAGATCTGTGGCCAAGAAG |
| | | | | CACCCCAAGACCTGGGTGCACTATATTGCTGCTGAGGAAGAGG |
| | | | | ACTGGGATTATGCTCCTCTGGTGCTGGCCCCTGATGACAGAAGC |
| | | | | TACAAGAGCCAGTACCTGAACAATGGCCCTCAGAGAATTGGCA |
| | | | | GAAAGTATAAGAAAGTGAGATTCATGGCCTACACAGATGAGAC |
| | | | | ATTCAAGACCAGAGAGGCCATTCAGCATGAGTCTGGCATTCTGG |
| | | | | GCCCTCTGCTGTATGGAGAAGTGGGAGATACACTGCTGATCATC |
| | | | | TTCAAGAACCAGGCCAGCAGACCCTACAACATCTACCCTCATGG |
| | | | | CATCACAGATGTGAGACCCCTGTATTCCAGAAGGCTGCCCAAGG |
| | | | | GAGTGAAGCACCTGAAGGACTTCCCTATCCTGCCTGGAGAGATC |
| | | | | TTCAAGTACAAGTGGACAGTGACAGTGGAAGATGGCCCCACCA |
| | | | | AGTCTGACCCTAGATGTCTGACAAGATACTACAGCAGCTTTGTG |
| | | | | AACATGGAAAGAGACCTGGCCTCTGGCCTGATTGGACCTCTGCT |
| | | | | GATCTGCTACAAAGAATCTGTGGACCAGAGAGGCAACCAGATC |
| | | | | ATGTCTGACAAGAGAAATGTGATCCTGTTTTCTGTGTTTGATGA |
| | | | | GAACAGATCCTGGTATCTGACAGAGAACATCCAGAGATTTCTGC |
| | | | | CCAATCCTGCTGGAGTGCAGCTGGAAGATCCTGAGTTCCAGGCC |
| | | | | TCCAACATCATGCACTCCATCAATGGCTATGTGTTTGACAGCCT |
| | | | | GCAGCTGTCTGTGTGCCTGCATGAAGTGGCCTACTGGTACATCC |
| | | | | TGAGCATTGGAGCCCAGACAGACTTCCTGTCTGTGTTCTTCTCTG |
| | | | | GCTACACCTTCAAGCACAAGATGGTGTATGAGGATACCCTGACA |
| | | | | CTGTTCCCATTCTCTGGAGAGACAGTGTTCATGAGCATGGAAAA |
| | | | | CCCTGGCCTGTGGATCCTGGGCTGTCACAACTCTGACTTCAGAA |
| | | | | ACAGAGGCATGACAGCCCTGCTGAAGGTGTCCAGCTGTGACAA |
| | | | | GAACACAGGAGACTACTATGAGGACAGCTATGAGGACATCTCT |
| | | | | GCCTACCTGCTGAGCAAGAACAATGCCATTGAGCCCAGAAGCTT |
| | | | | CAGCCAGAATGCCACCAATGTGTCCAACAACAGCAACACCAGC |
| | | | | AATGACTCCAATGTGTCCCCTCCAGTGCTGAAGAGACACCAGAG |
| | | | | AGAAATCACCAGAACCACACTGCAGTCTGACCAAGAGGAAATT |

TABLE 23-continued

Listing of additional protein and nucleic acid sequences referred to herein not included in the sequence listing

| Category | SEQ ID NO: | Description | Type | Sequence |
|---|---|---|---|---|
| | | | | GACTATGATGACACCATCTCTGTGGAGATGAAGAAAGAAGATTT |
| | | | | TGACATCTATGATGAGGATGAGAATCAGAGCCCCAGATCCTTTC |
| | | | | AGAAAAAGACCAGACACTACTTCATTGCTGCTGTGGAGAGACT |
| | | | | GTGGGACTATGGCATGTCTAGCAGCCCTCATGTGCTGAGAAATA |
| | | | | GAGCCCAGTCTGGCTCTGTGCCCCAGTTCAAGAAAGTGGTGTTC |
| | | | | CAAGAGTTCACAGATGGCAGCTTCACCCAGCCACTGTATAGAGG |
| | | | | AGAGCTGAATGAGCATCTGGGCCTGCTGGGCCCTTATATCAGAG |
| | | | | CTGAAGTGGAAGATAACATCATGGTCACCTTCAGAAATCAGGCC |
| | | | | TCTAGGCCCTACAGCTTCTACAGCTCCCTGATCAGCTATGAAGA |
| | | | | GGACCAGAGACAGGGAGCTGAGCCCAGAAAGAACTTTGTGAAG |
| | | | | CCCAATGAGACTAAGACCTACTTTTGGAAGGTGCAGCACCACAT |
| | | | | GGCCCCTACAAAGGATGAGTTTGACTGCAAGGCCTGGGCCTACT |
| | | | | TTTCTGATGTGGATCTGGAAAAGGATGTGCACTCTGGACTCATT |
| | | | | GGACCACTGCTTGTGTGCCACACCAACACACTGAACCCTGCTCA |
| | | | | TGGCAGACAAGTGACAGTGCAAGAGTTTGCCCTGTTCTTCACCA |
| | | | | TCTTTGATGAAACAAAGAGCTGGTACTTCACAGAGAATATGGAG |
| | | | | AGAAACTGCAGGGCCCCTTGCAACATCCAGATGGAAGATCCCA |
| | | | | CCTTCAAAGAGAACTACAGATTCCATGCCATCAATGGCTACATC |
| | | | | ATGGACACACTGCCTGGCCTGGTTATGGCTCAGGATCAGAGAAT |
| | | | | CAGATGGTATCTGCTGTCCATGGGCTCCAATGAGAATATCCACA |
| | | | | GCATCCACTTCTCTGGCCATGTGTTCACAGTGAGAAAAAAAGAA |
| | | | | GAGTACAAAATGGCCCTGTACAATCTGTACCCTGGGGTGTTTGA |
| | | | | AACAGTGGAAATGCTGCCTTCCAAGGCTGGCATTTGGAGAGTGG |
| | | | | AATGTCTGATTGGAGAGCACCTCCATGCTGGAATGAGCACCCTG |
| | | | | TTTCTGGTGTACAGCAACAAGTGTCAGACCCCTCTGGGCATGGC |
| | | | | CTCTGGACACATCAGAGACTTCCAGATCACAGCCTCTGGCCAGT |
| | | | | ATGGACAGTGGGCTCCTAAACTGGCTAGACTGCACTACTCTGGC |
| | | | | AGCATCAATGCCTGGTCCACCAAAGAGCCCTTCAGCTGGATCAA |
| | | | | GGTGGACCTGCTGGCTCCCATGATCATCCATGGAATCAAGACCC |
| | | | | AGGGAGCCAGACAGAAGTTCAGCAGCCTGTACATCAGCCAGTT |
| | | | | CATCATCATGTACAGCCTGGATGGCAAGAAGTGGCAGACCTAC |
| | | | | AGAGGCAACAGCACAGGCACACTCATGGTGTTCTTTGGCAATGT |
| | | | | GGACAGCTCTGGCATTAAGCACAACATCTTCAACCCTCCAATCA |
| | | | | TTGCCAGATACATCAGACTGCACCCCACACACTACAGCATCAGA |
| | | | | TCTACCCTGAGAATGGAACTGATGGGCTGTGACCTGAACAGCTG |
| | | | | CAGCATGCCCCTGGGAATGGAAAGCAAGGCCATCTCTGATGCCC |
| | | | | AGATCACAGCCAGCAGCTACTTCACCAACATGTTTGCCACTTGG |
| | | | | AGCCCCTCCAAGGCTAGACTGCATCTGCAGGGCAGAAGCAATG |
| | | | | CTTGGAGGCCCCAAGTGAACAACCCCAAAGAGTGGCTGCAGGT |
| | | | | GGACTTTCAAAAGACCATGAAAGTGACAGGAGTGACCACACAG |
| | | | | GGAGTCAAGTCTCTGCTGACCTCTATGTATGTGAAAGAGTTCCT |
| | | | | GATCTCCAGCAGCCAGGATGGCCACCAGTGGACCCTGTTTTTCC |
| | | | | AGAATGGCAAAGTGAAAGTGTTCCAGGGCAATCAGGACAGCTT |
| | | | | CACACCTGTGGTCAACTCCCTGGATCCTCCACTGCTGACCAGAT |
| | | | | ACCTGAGAATTCACCCTCAGTCTTGGGTGCACCAGATTGCTCTG |
| | | | | AGAATGGAAGTGCTGGGCTGTGAAGCTCAGGACCTCTACTGATC |
| | | | | CTGAATAAAAGATCTTTATTTCATTAGATCTGTGTGTTGGTTTT |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | TTGTGTGTATTTAGCTAAATGGTTCCTCTCTGCTACACTCAAATG CCAGTTCCCGATCGTTACAGGAAAAGATATGCTATACCTGATAC TGAATTTTGTAATCGGTTGGCAGCCAATGAAATACAAAGATGAG TCTAGTTAATAATCTACAATTATTGGTTAAAGAAGTATATTAGT ATGCTTTGCATACTTCTGCCTGCTGGGGAGCCTGGGGACTTTCC ACACCCTAACTGACACACATTCCAC |
| MG29-1 sgRNA targeting mouse albumin | 14 | mA29-8B-50 guide RNA | Nucleotide | mG*mU*mU*GAGAAUC*mG*mA*mA*mAGAUUCUCAAC*mC*mU *mU*U*UAAUUmUmCmUmACU*G*U*U*GUAGAUCUGUAACfGfA fUfCfGfGfGfAfAfC*fU*fG*mG |
| MG29-1 sgRNA targeting mouse albumin | 15 | mA29-12B-50 guide RNA | Nucleotide | mG*mU*mU*GAGAAUC*mG*mA*mA*mAGAUUCUCAAC*mC*mU *mU*U*UAAUUmUmCmUmACU*G*U*U*GUAGAUAGUGUAGfCf AfGfAfGfAfGfGfAfA*fC*fC*mA |
| FVIII donor template | 16 | FVIII donor template with MG29-1 target sites in FF orientation (pMG4006) | Nucleotide | ACGTTTTTCCTGTAACGATCGGGAACTGGCATTTGAGTGTAGCA GAGAGGAACCATTTCTCAAAGCTTACTAAAGAATTATTCTTTTA CATTTCAGTGGCCACCAGAAGATATTACCTGGGAGCTGTGGAAC TGAGCTGGGACTACATGCAGTCTGACCTGGGAGAGCTGCCTGTG GATGCTAGATTTCCTCCAAGAGTGCCCAAGAGCTTCCCCTTCAA CACCTCTGTGGTGTACAAGAAAACCCTGTTTGTGGAATTCACAG ACCACCTGTTCAATATTGCCAAGCCTAGACCTCCTTGGATGGGA CTGCTGGGACCTACAATTCAGGCTGAGGTGTATGACACAGTGGT CATCACCCTGAAGAACATGGCCAGCCATCCTGTGTCTCTGCATG CTGTGGGAGTGTCTTACTGGAAGGCTTCTGAGGGAGCTGAGTAT GATGACCAGACAAGCCAGAGAGAGAAAGAGGATGACAAGGTTT TCCCTGGAGGCAGCCACACCTATGTCTGGCAGGTCCTGAAAGAA AATGGCCCTATGGCCTCTGATCCTCTGTGCCTGACATACAGCTA CCTGAGCCATGTGGACCTGGTCAAGGACCTGAATTCTGGCCTGA TTGGAGCCCTGCTGGTGTGTAGAGAAGGCAGCCTGGCCAAAGA GAAAACCCAGACACTGCACAAGTTCATCCTGCTGTTTGCTGTGT TTGATGAGGGCAAGAGCTGGCACTCTGAGACAAAGAACAGCCT GATGCAGGACAGGGATGCTGCCTCTGCTAGAGCTTGGCCTAAGA TGCACACAGTGAATGGCTATGTGAACAGAAGCCTGCCTGGACTG ATTGGCTGCCACAGAAAGTCTGTGTACTGGCATGTGATTGGCAT GGGCACAACACCTGAGGTGCACAGCATCTTTCTGGAAGGACAC ACCTTCCTGGTGAGAAACCATAGACAGGCCAGCCTGGAAATCA GCCCTATCACCTTCCTGACAGCTCAGACCCTGCTGATGGATCTG GGCCAGTTTCTGCTGTTCTGCCACATCAGCAGCCACCAGCATGA TGGCATGGAAGCCTATGTGAAGGTGGACAGCTGCCCTGAAGAA CCCCAGCTGAGAATGAAGAACAATGAGGAGGCTGAGGACTATG ATGATGACCTGACAGACTCTGAGATGGATGTGGTCAGATTTGAT GATGACAACAGCCCCAGCTTCATCCAGATCAGATCTGTGGCCAA GAAGCACCCCAAGACCTGGGTGCACTATATTGCTGCTGAGGAA GAGGACTGGGATTATGCTCCTCTGGTGCTGGCCCCTGATGACAG AAGCTACAAGAGCCAGTACCTGAACAATGGCCCTCAGAGAATT GGCAGAAAGTATAAGAAAGTGAGATTCATGGCCTACACAGATG |

TABLE 23-continued

Listing of additional protein and nucleic acid sequences referred to herein not included in the sequence listing

| Category | SEQ ID NO: | Description | Type | Sequence |
|---|---|---|---|---|
| | | | | AGACATTCAAGACCAGAGAGGCCATTCAGCATGAGTCTGGCATT |
| | | | | CTGGGCCCTCTGCTGTATGGAGAAGTGGGAGATACACTGCTGAT |
| | | | | CATCTTCAAGAACCAGGCCAGCAGACCCTACAACATCTACCCTC |
| | | | | ATGGCATCACAGATGTGAGACCCCTGTATTCTAGAAGGCTGCCC |
| | | | | AAGGGAGTGAAGCACCTGAAGGACTTCCCTATCCTGCCTGGAG |
| | | | | AGATCTTCAAGTACAAGTGGACAGTGACAGTGGAAGATGGCCC |
| | | | | CACCAAGTCTGACCCTAGATGTCTGACAAGATACTACAGCAGCT |
| | | | | TTGTGAACATGGAAAGAGACCTGGCCTCTGGCCTGATTGGACCT |
| | | | | CTGCTGATCTGCTACAAAGAATCTGTGGACCAGAGAGGCAACC |
| | | | | AGATCATGTCTGACAAGAGAAATGTGATCCTGTTTTCTGTGTTT |
| | | | | GATGAGAACAGATCCTGGTATCTGACAGAGAACATCCAGAGAT |
| | | | | TTCTGCCCAATCCTGCTGGAGTGCAGCTGGAAGATCCTGAGTTC |
| | | | | CAGGCCTCCAACATCATGCACTCCATCAATGGCTATGTGTTTGA |
| | | | | CAGCCTGCAGCTGTCTGTGTGCCTGCATGAAGTGGCCTACTGGT |
| | | | | ACATCCTGAGCATTGGAGCCCAGACAGACTTCCTGTCTGTGTTC |
| | | | | TTCTCTGGCTACACCTTCAAGCACAAGATGGTGTATGAGGATAC |
| | | | | CCTGACACTGTTCCCATTCTCTGGAGAGACAGTGTTCATGAGCA |
| | | | | TGGAAAACCCTGGCCTGTGGATCCTGGGCTGTCACAACTCTGAC |
| | | | | TTCAGAAACAGAGGCATGACAGCCCTGCTGAAGGTGTCCAGCT |
| | | | | GTGACAAGAACACAGGAGACTACTATGAGGACAGCTATGAGGA |
| | | | | CATCTCTGCCTACCTGCTGAGCAAGAACAATGCCATTGAGCCCA |
| | | | | GAAGCTTCAGCCAGAATGCCACCAATGTGTCCAACAACAGCAA |
| | | | | CACCAGCAATGACTCCAATGTGTCCCCTCCAGTGCTGAAGAGAC |
| | | | | ACCAGAGAGAAATCACCAGAACCACACTGCAGTCTGACCAAGA |
| | | | | GGAAATTGACTATGATGACACCATCTCTGTGGAGATGAAGAAA |
| | | | | GAAGATTTTGACATCTATGATGAGGATGAGAATCAGAGCCCCA |
| | | | | GATCCTTTCAGAAAAAGACCAGACACTACTTCATTGCTGCTGTG |
| | | | | GAGAGACTGTGGGACTATGGCATGTCTAGCAGCCCTCATGTGCT |
| | | | | GAGAAATAGAGCCCAGTCTGGCTCTGTGCCCCAGTTCAAGAAA |
| | | | | GTGGTGTTCCAAGAGTTCACAGATGGCAGCTTCACCCAGCCACT |
| | | | | GTATAGAGGAGAGCTGAATGAGCATCTGGGCCTGCTGGGCCCTT |
| | | | | ATATCAGAGCTGAAGTGGAAGATAACATCATGGTCACCTTCAGA |
| | | | | AATCAGGCCTCTAGACCCTACAGCTTCTACAGCTCCCTGATCAG |
| | | | | CTATGAAGAGGACCAGAGACAGGGAGCTGAGCCCAGAAAGAAC |
| | | | | TTTGTGAAGCCCAATGAGACTAAGACCTACTTTTGGAAGGTGCA |
| | | | | GCACCACATGGCCCCTACAAAGGATGAGTTTGACTGCAAGGCCT |
| | | | | GGGCCTACTTTTCTGATGTGGATCTGGAAAAGGATGTGCACTCT |
| | | | | GGACTCATTGGACCACTGCTTGTGTGCCACACCAACACACTGAA |
| | | | | CCCTGCTCATGGCAGACAAGTGACAGTGCAAGAGTTTGCCCTGT |
| | | | | TCTTCACCATCTTTGATGAAACAAAGAGCTGGTACTTCACAGAG |
| | | | | AATATGGAGAGAAACTGCAGGGCCCCTTGCAACATCCAGATGG |
| | | | | AAGATCCCACCTTCAAAGAGAACTACAGATTCCATGCCATCAAT |
| | | | | GGCTACATCATGGACACACTGCCTGGCCTGGTTATGGCTCAGGA |
| | | | | TCAGAGAATCAGATGGTATCTGCTGTCCATGGGCTCCAATGAGA |
| | | | | ATATCCACAGCATCCACTTCTCTGGCCATGTGTTCACAGTGAGA |
| | | | | AAAAAAGAAGAGTACAAAATGGCCCTGTACAATCTGTACCCTG |
| | | | | GGGTGTTTGAAACAGTGGAAATGCTGCCTTCCAAGGCTGGCATT |

TABLE 23-continued

| Category | SEQ ID NO: | Description | Type | Sequence |
|---|---|---|---|---|
| | | | | TGGAGAGTGGAATGTCTGATTGGAGAGCACCTCCATGCTGGAAT GAGCACCCTGTTTCTGGTGTACAGCAACAAGTGTCAGACCCCTC TGGGCATGGCCTCTGGACACATCAGAGACTTCCAGATCACAGCC TCTGGCCAGTATGGACAGTGGGCTCCTAAACTGGCTAGACTGCA CTACTCTGGCAGCATCAATGCCTGGTCCACCAAAGAGCCCTTCA GCTGGATCAAGGTGGACCTGCTGGCTCCCATGATCATCCATGGA ATCAAGACCCAGGGAGCCAGACAGAAGTTCAGCAGCCTGTACA TCAGCCAGTTCATCATCATGTACAGCCTGGATGGCAAGAAGTGG CAGACCTACAGAGGCAACAGCACAGGCACACTCATGGTGTTCTT TGGCAATGTGGACAGCTCTGGCATTAAGCACAACATCTTCAACC CTCCAATCATTGCCAGATACATCAGACTGCACCCCACACACTAC AGCATCAGATCTACCCTGAGAATGGAACTGATGGGCTGTGACCT GAACAGCTGCAGCATGCCCCTGGGAATGGAAAGCAAGGCCATC TCTGATGCCCAGATCACAGCCAGCAGCTACTTCACCAACATGTT TGCCACTTGGAGCCCCTCCAAGGCTAGACTGCATCTGCAGGGCA GAAGCAATGCTTGGAGGCCCCAAGTGAACAACCCCAAAGAGTG GCTGCAGGTGGACTTTCAAAAGACCATGAAAGTGACAGGAGTG ACCACACAGGGAGTCAAGTCTCTGCTGACCTCTATGTATGTGAA AGAGTTCCTGATCTCCAGCAGCCAGGATGGCCACCAGTGGACCC TGTTTTTCCAGAATGGCAAAGTGAAAGTGTTCCAGGGCAATCAG GACAGCTTCACACCTGTGGTCAACTCCCTGGATCCTCCACTGCT GACCAGATACCTGAGAATTCACCCTCAGTCTTGGGTGCACCAGA TTGCTCTGAGAATGGAAGTGCTGGGCTGTGAAGCTCAGGACCTC TACTGATCGCGAATAAAAGATCTTTATTTTCATTAGATCTGTGTG TTGGTTTTTTGTGTGTATTTAGCTATTTGAGTGTAGCAGAGAGGA ACCATTTTTCCTGTAACGATCGGGAACTGGCA |
| FVIII donor template | 17 | FVIII donor template with MG29-1 target sites in RR orientation (pMG4007) | Nucleotide | ACGTTAATGGTTCCTCTCTGCTACACTCAAATGCCAGTTCCCGAT CGTTACAGGAAATCTCAAAGCTTACTAAAGAATTATTCTTTTAC ATTTCAGTGGCCACCAGAAGATATTACCTGGGAGCTGTGGAACT GAGCTGGGACTACATGCAGTCTGACCTGGGAGAGCTGCCTGTGG ATGCTAGATTTCCTCCAAGAGTGCCCAAGAGCTTCCCCTTCAAC ACCTCTGTGGTGTACAAGAAAACCCTGTTTGTGGAATTCACAGA CCACCTGTTCAATATTGCCAAGCCTAGACCTCCTTGGATGGGAC TGCTGGGACCTACAATTCAGGCTGAGGTGTATGACACAGTGGTC ATCACCCTGAAGAACATGGCCAGCCATCCTGTGTCTCTGCATGC TGTGGGAGTGTCTTACTGGAAGGCTTCTGAGGGAGCTGAGTATG ATGACCAGACAAGCCAGAGAGAGAAAGAGGATGACAAGGTTTT CCCTGGAGGCAGCCACACCTATGTCTGGCAGGTCCTGAAAGAA AATGGCCCTATGGCCTCTGATCCTCTGTGCCTGACATACAGCTA CCTGAGCCATGTGGACCTGGTCAAGGACCTGAATTCTGGCCTGA TTGGAGCCCTGCTGGTGTGTAGAGAAGGCAGCCTGGCCAAAGA GAAAACCCAGACACTGCACAAGTTCATCCTGCTGTTTGCTGTGT TTGATGAGGGCAAGAGCTGGCACTCTGAGACAAAGAACAGCCT GATGCAGGACAGGGATGCTGCCTCTGCTAGAGCTTGGCCTAAGA TGCACACAGTGAATGGCTATGTGAACAGAAGCCTGCCTGGACTG ATTGGCTGCCACAGAAAGTCTGTGTACTGGCATGTGATTGGCAT |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | GGGCACAACACCTGAGGTGCACAGCATCTTTCTGGAAGGACAC<br>ACCTTCCTGGTGAGAAACCATAGACAGGCCAGCCTGGAAATCA<br>GCCCTATCACCTTCCTGACAGCTCAGACCCTGCTGATGGATCTG<br>GGCCAGTTTCTGCTGTTCTGCCACATCAGCAGCCACCAGCATGA<br>TGGCATGGAAGCCTATGTGAAGGTGGACAGCTGCCCTGAAGAA<br>CCCCAGCTGAGAATGAAGAACAATGAGGAGGCTGAGGACTATG<br>ATGATGACCTGACAGACTCTGAGATGGATGTGGTCAGATTTGAT<br>GATGACAACAGCCCCAGCTTCATCCAGATCAGATCTGTGGCCAA<br>GAAGCACCCCAAGACCTGGGTGCACTATATTGCTGCTGAGGAA<br>GAGGACTGGGATTATGCTCCTCTGGTGCTGGCCCCTGATGACAG<br>AAGCTACAAGAGCCAGTACCTGAACAATGGCCCTCAGAGAATT<br>GGCAGAAAGTATAAGAAAGTGAGATTCATGGCCTACACAGATG<br>AGACATTCAAGACCAGAGAGGCCATTCAGCATGAGTCTGGCATT<br>CTGGGCCCTCTGCTGTATGGAGAAGTGGGAGATACACTGCTGAT<br>CATCTTCAAGAACCAGGCCAGCAGACCCTACAACATCTACCCTC<br>ATGGCATCACAGATGTGAGACCCCTGTATTCTAGAAGGCTGCCC<br>AAGGGAGTGAAGCACCTGAAGGACTTCCCTATCCTGCCTGGAG<br>AGATCTTCAAGTACAAGTGGACAGTGACAGTGGAAGATGGCCC<br>CACCAAGTCTGACCCTAGATGTCTGACAAGATACTACAGCAGCT<br>TTGTGAACATGGAAAGAGACCTGGCCTCTGGCCTGATTGGACCT<br>CTGCTGATCTGCTACAAAGAATCTGTGGACCAGAGAGGCAACC<br>AGATCATGTCTGACAAGAGAAATGTGATCCTGTTTTCTGTGTTT<br>GATGAGAACAGATCCTGGTATCTGACAGAGAACATCCAGAGAT<br>TTCTGCCCAATCCTGCTGGAGTGCAGCTGGAAGATCCTGAGTTC<br>CAGGCCTCCAACATCATGCACTCCATCAATGGCTATGTGTTTGA<br>CAGCCTGCAGCTGTCTGTGTGCCTGCATGAAGTGGCCTACTGGT<br>ACATCCTGAGCATTGGAGCCCAGACAGACTTCCTGTCTGTGTTC<br>TTCTCTGGCTACACCTTCAAGCACAAGATGGTGTATGAGGATAC<br>CCTGACACTGTTCCCATTCTCTGGAGAGACAGTGTTCATGAGCA<br>TGGAAAACCCTGGCCTGTGGATCCTGGGCTGTCACAACTCTGAC<br>TTCAGAAACAGAGGCATGACAGCCCTGCTGAAGGTGTCCAGCT<br>GTGACAAGAACACAGGAGACTACTATGAGGACAGCTATGAGGA<br>CATCTCTGCCTACCTGCTGAGCAAGAACAATGCCATTGAGCCCA<br>GAAGCTTCAGCCAGAATGCCACCAATGTGTCCAACAACAGCAA<br>CACCAGCAATGACTCCAATGTGTCCCCTCCAGTGCTGAAGAGAC<br>ACCAGAGAGAAATCACCAGAACCACACTGCAGTCTGACCAAGA<br>GGAAATTGACTATGATGACACCATCTCTGTGGAGATGAAGAAA<br>GAAGATTTTGACATCTATGATGAGGATGAGAATCAGAGCCCCA<br>GATCCTTTCAGAAAAAGACCAGACACTACTTCATTGCTGCTGTG<br>GAGAGACTGTGGGACTATGGCATGTCTAGCAGCCCTCATGTGCT<br>GAGAAATAGAGCCCAGTCTGGCTCTGTGCCCCAGTTCAAGAAA<br>GTGGTGTTCCAAGAGTTCACAGATGGCAGCTTCACCCAGCCACT<br>GTATAGAGGAGAGCTGAATGAGCATCTGGGCCTGCTGGGCCCTT<br>ATATCAGAGCTGAAGTGGAAGATAACATCATGGTCACCTTCAGA<br>AATCAGGCCTCTAGACCCTACAGCTTCTACAGCTCCCTGATCAG<br>CTATGAAGAGGACCAGAGACAGGGAGCTGAGCCCAGAAAGAAC<br>TTTGTGAAGCCCAATGAGACTAAGACCTACTTTTGGAAGGTGCA |

TABLE 23-continued

Listing of additional protein and nucleic acid sequences referred to herein not included in the sequence listing

| Category | SEQ ID NO: | Description | Type | Sequence |
|---|---|---|---|---|
| | | | | GCACCACATGGCCCCTACAAAGGATGAGTTTGACTGCAAGGCCT<br>GGGCCTACTTTTCTGATGTGGATCTGGAAAAGGATGTGCACTCT<br>GGACTCATTGGACCACTGCTTGTGTGCCACACCAACACACTGAA<br>CCCTGCTCATGGCAGACAAGTGACAGTGCAAGAGTTTGCCCTGT<br>TCTTCACCATCTTTGATGAAACAAAGAGCTGGTACTTCACAGAG<br>AATATGGAGAGAAACTGCAGGGCCCCTTGCAACATCCAGATGG<br>AAGATCCCACCTTCAAAGAGAACTACAGATTCCATGCCATCAAT<br>GGCTACATCATGGACACACTGCCTGGCCTGGTTATGGCTCAGGA<br>TCAGAGAATCAGATGGTATCTGCTGTCCATGGGCTCCAATGAGA<br>ATATCCACAGCATCCACTTCTCTGGCCATGTGTTCACAGTGAGA<br>AAAAAAGAAGAGTACAAAATGGCCCTGTACAATCTGTACCCTG<br>GGGTGTTTGAAACAGTGGAAATGCTGCCTTCCAAGGCTGGCATT<br>TGGAGAGTGGAATGTCTGATTGGAGAGCACCTCCATGCTGGAAT<br>GAGCACCCTGTTTCTGGTGTACAGCAACAAGTGTCAGACCCCTC<br>TGGGCATGGCCTCTGGACACATCAGAGACTTCCAGATCACAGCC<br>TCTGGCCAGTATGGACAGTGGGCTCCTAAACTGGCTAGACTGCA<br>CTACTCTGGCAGCATCAATGCCTGGTCCACCAAAGAGCCCTTCA<br>GCTGGATCAAGGTGGACCTGCTGGCTCCCATGATCATCCATGGA<br>ATCAAGACCCAGGGAGCCAGACAGAAGTTCAGCAGCCTGTACA<br>TCAGCCAGTTCATCATCATGTACAGCCTGGATGGCAAGAAGTGG<br>CAGACCTACAGAGGCAACAGCACAGGCACACTCATGGTGTTCTT<br>TGGCAATGTGGACAGCTCTGGCATTAAGCACAACATCTTCAACC<br>CTCCAATCATTGCCAGATACATCAGACTGCACCCCACACACTAC<br>AGCATCAGATCTACCCTGAGAATGGAACTGATGGGCTGTGACCT<br>GAACAGCTGCAGCATGCCCCTGGGAATGGAAAGCAAGGCCATC<br>TCTGATGCCCAGATCACAGCCAGCAGCTACTTCACCAACATGTT<br>TGCCACTTGGAGCCCCTCCAAGGCTAGACTGCATCTGCAGGGCA<br>GAAGCAATGCTTGGAGGCCCCAAGTGAACAACCCCAAAGAGTG<br>GCTGCAGGTGGACTTTCAAAAGACCATGAAAGTGACAGGAGTG<br>ACCACACAGGGAGTCAAGTCTCTGCTGACCTCTATGTATGTGAA<br>AGAGTTCCTGATCTCCAGCAGCCAGGATGGCCACCAGTGGACCC<br>TGTTTTTCCAGAATGGCAAAGTGAAAGTGTTCCAGGGCAATCAG<br>GACAGCTTCACACCTGTGGTCAACTCCCTGGATCCTCCACTGCT<br>GACCAGATACCTGAGAATTCACCCTCAGTCTTGGGTGCACCAGA<br>TTGCTCTGAGAATGGAAGTGCTGGGCTGTGAAGCTCAGGACCTC<br>TACTGATCGCGAATAAAAGATCTTTATTTTCATTAGATCTGTGTG<br>TTGGTTTTTTGTGTGTATTTAGCTATGCCAGTTCCCGATCGTTAC<br>AGGAAAAATGGTTCCTCTCTGCTACACTCAAATTCCT |
| FVIII donor template | 18 | FVIII donor template with MG29-1 target sites in FR orientation (pMG4008) | Nucleotide | ACGTTTTTCCTGTAACGATCGGGAACTGGCATTTGAGTGTAGCA<br>GAGAGGAACCATTTCTCAAAGCTTACTAAAGAATTATTCTTTTA<br>CATTTCAGTGGCCACCAGAAGATATTACCTGGGAGCTGTGGAAC<br>TGAGCTGGGACTACATGCAGTCTGACCTGGGAGAGCTGCCTGTG<br>GATGCTAGATTTCCTCCAAGAGTGCCCAAGAGCTTCCCCTTCAA<br>CACCTCTGTGGTGTACAAGAAAACCCTGTTTGTGGAATTCACAG<br>ACCACCTGTTCAATATTGCCAAGCCTAGACCTCCTTGGATGGGA<br>CTGCTGGGACCTACAATTCAGGCTGAGGTGTATGACACAGTGGT |

TABLE 23-continued

Listing of additional protein and nucleic acid sequences referred to herein not included in the sequence listing

| Category | SEQ ID NO: | Description | Type | Sequence |
|---|---|---|---|---|
| | | | | CATCACCCTGAAGAACATGGCCAGCCATCCTGTGTCTCTGCATG<br>CTGTGGGAGTGTCTTACTGGAAGGCTTCTGAGGGAGCTGAGTAT<br>GATGACCAGACAAGCCAGAGAGAGAAAGAGGATGACAAGGTTT<br>TCCCTGGAGGCAGCCACACCTATGTCTGGCAGGTCCTGAAAGAA<br>AATGGCCCTATGGCCTCTGATCCTCTGTGCCTGACATACAGCTA<br>CCTGAGCCATGTGGACCTGGTCAAGGACCTGAATTCTGGCCTGA<br>TTGGAGCCCTGCTGGTGTGTAGAGAAGGCAGCCTGGCCAAAGA<br>GAAAACCCAGACACTGCACAAGTTCATCCTGCTGTTTGCTGTGT<br>TTGATGAGGGCAAGAGCTGGCACTCTGAGACAAAGAACAGCCT<br>GATGCAGGACAGGGATGCTGCCTCTGCTAGAGCTTGGCCTAAGA<br>TGCACACAGTGAATGGCTATGTGAACAGAAGCCTGCCTGGACTG<br>ATTGGCTGCCACAGAAAGTCTGTGTACTGGCATGTGATTGGCAT<br>GGGCACAACACCTGAGGTGCACAGCATCTTTCTGGAAGGACAC<br>ACCTTCCTGGTGAGAAACCATAGACAGGCCAGCCTGGAAATCA<br>GCCCTATCACCTTCCTGACAGCTCAGACCCTGCTGATGGATCTG<br>GGCCAGTTTCTGCTGTTCTGCCACATCAGCAGCCACCAGCATGA<br>TGGCATGGAAGCCTATGTGAAGGTGGACAGCTGCCCTGAAGAA<br>CCCCAGCTGAGAATGAAGAACAATGAGGAGGCTGAGGACTATG<br>ATGATGACCTGACAGACTCTGAGATGGATGTGGTCAGATTTGAT<br>GATGACAACAGCCCCAGCTTCATCCAGATCAGATCTGTGGCCAA<br>GAAGCACCCCAAGACCTGGGTGCACTATATTGCTGCTGAGGAA<br>GAGGACTGGGATTATGCTCCTCTGGTGCTGGCCCCTGATGACAG<br>AAGCTACAAGAGCCAGTACCTGAACAATGGCCCTCAGAGAATT<br>GGCAGAAAGTATAAGAAAGTGAGATTCATGGCCTACACAGATG<br>AGACATTCAAGACCAGAGAGGCCATTCAGCATGAGTCTGGCATT<br>CTGGGCCCTCTGCTGTATGGAGAAGTGGGAGATACACTGCTGAT<br>CATCTTCAAGAACCAGGCCAGCAGACCCTACAACATCTACCCTC<br>ATGGCATCACAGATGTGAGACCCCTGTATTCTAGAAGGCTGCCC<br>AAGGGAGTGAAGCACCTGAAGGACTTCCCTATCCTGCCTGGAG<br>AGATCTTCAAGTACAAGTGGACAGTGACAGTGGAAGATGGCCC<br>CACCAAGTCTGACCCTAGATGTCTGACAAGATACTACAGCAGCT<br>TTGTGAACATGGAAAGAGACCTGGCCTCTGGCCTGATTGGACCT<br>CTGCTGATCTGCTACAAAGAATCTGTGGACCAGAGAGGCAACC<br>AGATCATGTCTGACAAGAGAAATGTGATCCTGTTTTCTGTGTTT<br>GATGAGAACAGATCCTGGTATCTGACAGAGAACATCCAGAGAT<br>TTCTGCCCAATCCTGCTGGAGTGCAGCTGGAAGATCCTGAGTTC<br>CAGGCCTCCAACATCATGCACTCCATCAATGGCTATGTGTTTGA<br>CAGCCTGCAGCTGTCTGTGTGCCTGCATGAAGTGGCCTACTGGT<br>ACATCCTGAGCATTGGAGCCCAGACAGACTTCCTGTCTGTGTTC<br>TTCTCTGGCTACACCTTCAAGCACAAGATGGTGTATGAGGATAC<br>CCTGACACTGTTCCCATTCTCTGGAGAGACAGTGTTCATGAGCA<br>TGGAAAACCCTGGCCTGTGGATCCTGGGCTGTCACAACTCTGAC<br>TTCAGAAACAGAGGCATGACAGCCCTGCTGAAGGTGTCCAGCT<br>GTGACAAGAACACAGGAGACTACTATGAGGACAGCTATGAGGA<br>CATCTCTGCCTACCTGCTGAGCAAGAACAATGCCATTGAGCCCA<br>GAAGCTTCAGCCAGAATGCCACCAATGTGTCCAACAACAGCAA<br>CACCAGCAATGACTCCAATGTGTCCCCTCCAGTGCTGAAGAGAC |

TABLE 23-continued

Listing of additional protein and nucleic acid sequences referred to herein not included in the sequence listing

| Category | SEQ ID NO: | Description | Type | Sequence |
|---|---|---|---|---|
| | | | | ACCAGAGAGAAATCACCAGAACCACACTGCAGTCTGACCAAGA<br>GGAAATTGACTATGATGACACCATCTCTGTGGAGATGAAGAAA<br>GAAGATTTTGACATCTATGATGAGGATGAGAATCAGAGCCCCA<br>GATCCTTTCAGAAAAAGACCAGACACTACTTCATTGCTGCTGTG<br>GAGAGACTGTGGGACTATGGCATGTCTAGCAGCCCTCATGTGCT<br>GAGAAATAGAGCCCAGTCTGGCTCTGTGCCCCAGTTCAAGAAA<br>GTGGTGTTCCAAGAGTTCACAGATGGCAGCTTCACCCAGCCACT<br>GTATAGAGGAGAGCTGAATGAGCATCTGGGCCTGCTGGGCCCTT<br>ATATCAGAGCTGAAGTGGAAGATAACATCATGGTCACCTTCAGA<br>AATCAGGCCTCTAGACCCTACAGCTTCTACAGCTCCCTGATCAG<br>CTATGAAGAGGACCAGAGACAGGGAGCTGAGCCCAGAAAGAAC<br>TTTGTGAAGCCCAATGAGACTAAGACCTACTTTTGGAAGGTGCA<br>GCACCACATGGCCCCTACAAAGGATGAGTTTGACTGCAAGGCCT<br>GGGCCTACTTTTCTGATGTGGATCTGGAAAAGGATGTGCACTCT<br>GGACTCATTGGACCACTGCTTGTGTGCCACACCAACACACTGAA<br>CCCTGCTCATGGCAGACAAGTGACAGTGCAAGAGTTTGCCCTGT<br>TCTTCACCATCTTTGATGAAACAAAGAGCTGGTACTTCACAGAG<br>AATATGGAGAGAAACTGCAGGGCCCCTTGCAACATCCAGATGG<br>AAGATCCCACCTTCAAAGAGAACTACAGATTCCATGCCATCAAT<br>GGCTACATCATGGACACACTGCCTGGCCTGGTTATGGCTCAGGA<br>TCAGAGAATCAGATGGTATCTGCTGTCCATGGGCTCCAATGAGA<br>ATATCCACAGCATCCACTTCTCTGGCCATGTGTTCACAGTGAGA<br>AAAAAAGAAGAGTACAAAATGGCCCTGTACAATCTGTACCCTG<br>GGGTGTTTGAAACAGTGGAAATGCTGCCTTCCAAGGCTGGCATT<br>TGGAGAGTGGAATGTCTGATTGGAGAGCACCTCCATGCTGGAAT<br>GAGCACCCTGTTTCTGGTGTACAGCAACAAGTGTCAGACCCCTC<br>TGGGCATGGCCTCTGGACACATCAGAGACTTCCAGATCACAGCC<br>TCTGGCCAGTATGGACAGTGGGCTCCTAAACTGGCTAGACTGCA<br>CTACTCTGGCAGCATCAATGCCTGGTCCACCAAAGAGCCCTTCA<br>GCTGGATCAAGGTGGACCTGCTGGCTCCCATGATCATCCATGGA<br>ATCAAGACCCAGGGAGCCAGACAGAAGTTCAGCAGCCTGTACA<br>TCAGCCAGTTCATCATCATGTACAGCCTGGATGGCAAGAAGTGG<br>CAGACCTACAGAGGCAACAGCACAGGCACACTCATGGTGTTCTT<br>TGGCAATGTGGACAGCTCTGGCATTAAGCACAACATCTTCAACC<br>CTCCAATCATTGCCAGATACATCAGACTGCACCCCACACACTAC<br>AGCATCAGATCTACCCTGAGAATGGAACTGATGGGCTGTGACCT<br>GAACAGCTGCAGCATGCCCCTGGGAATGGAAAGCAAGGCCATC<br>TCTGATGCCCAGATCACAGCCAGCAGCTACTTCACCAACATGTT<br>TGCCACTTGGAGCCCCTCCAAGGCTAGACTGCATCTGCAGGGCA<br>GAAGCAATGCTTGGAGGCCCCAAGTGAACAACCCCAAAGAGTG<br>GCTGCAGGTGGACTTTCAAAAGACCATGAAAGTGACAGGAGTG<br>ACCACACAGGGAGTCAAGTCTCTGCTGACCTCTATGTATGTGAA<br>AGAGTTCCTGATCTCCAGCAGCCAGGATGGCCACCAGTGGACCC<br>TGTTTTTCCAGAATGGCAAAGTGAAAGTGTTCCAGGGCAATCAG<br>GACAGCTTCACACCTGTGGTCAACTCCCTGGATCCTCCACTGCT<br>GACCAGATACCTGAGAATTCACCCTCAGTCTTGGGTGCACCAGA<br>TTGCTCTGAGAATGGAAGTGCTGGGCTGTGAAGCTCAGGACCTC |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | TACTGATCGCGAATAAAAGATCTTTATTTTCATTAGATCTGTGTG<br>TTGGTTTTTTGTGTGTATTTAGCTATGCCAGTTCCCGATCGTTAC<br>AGGAAAAATGGTTCCTCTCTGCTACACTCAAATTCCT |
| FVIII donor template | 19 | FVIII donor template with MG29-1 target sites in RF orientation (pMG4009) | Nucleotide | ACGTTAATGGTTCCTCTCTGCTACACTCAAATGCCAGTTCCCGAT<br>CGTTACAGGAAATCTCAAAGCTTACTAAAGAATTATTCTTTTAC<br>ATTTCAGTGGCCACCAGAAGATATTACCTGGGAGCTGTGGAACT<br>GAGCTGGGACTACATGCAGTCTGACCTGGGAGAGCTGCCTGTGG<br>ATGCTAGATTTCCTCCAAGAGTGCCCAAGAGCTTCCCCTTCAAC<br>ACCTCTGTGGTGTACAAGAAAACCCTGTTTGTGGAATTCACAGA<br>CCACCTGTTCAATATTGCCAAGCCTAGACCTCCTTGGATGGGAC<br>TGCTGGGACCTACAATTCAGGCTGAGGTGTATGACACAGTGGTC<br>ATCACCCTGAAGAACATGGCCAGCCATCCTGTGTCTCTGCATGC<br>TGTGGGAGTGTCTTACTGGAAGGCTTCTGAGGGAGCTGAGTATG<br>ATGACCAGACAAGCCAGAGAGAGAAAGAGGATGACAAGGTTTT<br>CCCTGGAGGCAGCCACACCTATGTCTGGCAGGTCCTGAAAGAA<br>AATGGCCCTATGGCCTCTGATCCTCTGTGCCTGACATACAGCTA<br>CCTGAGCCATGTGGACCTGGTCAAGGACCTGAATTCTGGCCTGA<br>TTGGAGCCCTGCTGGTGTGTAGAGAAGGCAGCCTGGCCAAAGA<br>GAAAACCCAGACACTGCACAAGTTCATCCTGCTGTTTGCTGTGT<br>TTGATGAGGGCAAGAGCTGGCACTCTGAGACAAAGAACAGCCT<br>GATGCAGGACAGGGATGCTGCCTCTGCTAGAGCTTGGCCTAAGA<br>TGCACACAGTGAATGGCTATGTGAACAGAAGCCTGCCTGGACTG<br>ATTGGCTGCCACAGAAAGTCTGTGTACTGGCATGTGATTGGCAT<br>GGGCACAACACCTGAGGTGCACAGCATCTTTCTGGAAGGACAC<br>ACCTTCCTGGTGAGAAACCATAGACAGGCCAGCCTGGAAATCA<br>GCCCTATCACCTTCCTGACAGCTCAGACCCTGCTGATGGATCTG<br>GGCCAGTTTCTGCTGTTCTGCCACATCAGCAGCCACCAGCATGA<br>TGGCATGGAAGCCTATGTGAAGGTGGACAGCTGCCCTGAAGAA<br>CCCCAGCTGAGAATGAAGAACAATGAGGAGGCTGAGGACTATG<br>ATGATGACCTGACAGACTCTGAGATGGATGTGGTCAGATTTGAT<br>GATGACAACAGCCCCAGCTTCATCCAGATCAGATCTGTGGCCAA<br>GAAGCACCCCAAGACCTGGGTGCACTATATTGCTGCTGAGGAA<br>GAGGACTGGGATTATGCTCCTCTGGTGCTGGCCCCTGATGACAG<br>AAGCTACAAGAGCCAGTACCTGAACAATGGCCCTCAGAGAATT<br>GGCAGAAAGTATAAGAAAGTGAGATTCATGGCCTACACAGATG<br>AGACATTCAAGACCAGAGAGGCCATTCAGCATGAGTCTGGCATT<br>CTGGGCCCTCTGCTGTATGGAGAAGTGGGAGATACACTGCTGAT<br>CATCTTCAAGAACCAGGCCAGCAGACCCTACAACATCTACCCTC<br>ATGGCATCACAGATGTGAGACCCCTGTATTCTAGAAGGCTGCCC<br>AAGGGAGTGAAGCACCTGAAGGACTTCCCTATCCTGCCTGGAG<br>AGATCTTCAAGTACAAGTGGACAGTGACAGTGGAAGATGGCCC<br>CACCAAGTCTGACCCTAGATGTCTGACAAGATACTACAGCAGCT<br>TTGTGAACATGGAAAGAGACCTGGCCTCTGGCCTGATTGGACCT<br>CTGCTGATCTGCTACAAAGAATCTGTGGACCAGAGAGGCAACC<br>AGATCATGTCTGACAAGAGAAATGTGATCCTGTTTTCTGTGTTT<br>GATGAGAACAGATCCTGGTATCTGACAGAGAACATCCAGAGAT |

TABLE 23-continued

Listing of additional protein and nucleic acid sequences referred to herein not included in the sequence listing

| Category | SEQ ID NO: | Description | Type | Sequence |
|---|---|---|---|---|
| | | | | TTCTGCCCAATCCTGCTGGAGTGCAGCTGGAAGATCCTGAGTTC<br>CAGGCCTCCAACATCATGCACTCCATCAATGGCTATGTGTTTGA<br>CAGCCTGCAGCTGTCTGTGTGCCTGCATGAAGTGGCCTACTGGT<br>ACATCCTGAGCATTGGAGCCCAGACAGACTTCCTGTCTGTGTTC<br>TTCTCTGGCTACACCTTCAAGCACAAGATGGTGTATGAGGATAC<br>CCTGACACTGTTCCCATTCTCTGGAGAGACAGTGTTCATGAGCA<br>TGGAAAACCCTGGCCTGTGGATCCTGGGCTGTCACAACTCTGAC<br>TTCAGAAACAGAGGCATGACAGCCCTGCTGAAGGTGTCCAGCT<br>GTGACAAGAACACAGGAGACTACTATGAGGACAGCTATGAGGA<br>CATCTCTGCCTACCTGCTGAGCAAGAACAATGCCATTGAGCCCA<br>GAAGCTTCAGCCAGAATGCCACCAATGTGTCCAACAACAGCAA<br>CACCAGCAATGACTCCAATGTGTCCCCTCCAGTGCTGAAGAGAC<br>ACCAGAGAGAAATCACCAGAACCACACTGCAGTCTGACCAAGA<br>GGAAATTGACTATGATGACACCATCTCTGTGGAGATGAAGAAA<br>GAAGATTTTGACATCTATGATGAGGATGAGAATCAGAGCCCCA<br>GATCCTTTCAGAAAAAGACCAGACACTACTTCATTGCTGCTGTG<br>GAGAGACTGTGGGACTATGGCATGTCTAGCAGCCCTCATGTGCT<br>GAGAAATAGAGCCCAGTCTGGCTCTGTGCCCCAGTTCAAGAAA<br>GTGGTGTTCCAAGAGTTCACAGATGGCAGCTTCACCCAGCCACT<br>GTATAGAGGAGAGCTGAATGAGCATCTGGGCCTGCTGGGCCCTT<br>ATATCAGAGCTGAAGTGGAAGATAACATCATGGTCACCTTCAGA<br>AATCAGGCCTCTAGACCCTACAGCTTCTACAGCTCCCTGATCAG<br>CTATGAAGAGGACCAGAGACAGGGAGCTGAGCCCAGAAAGAAC<br>TTTGTGAAGCCCAATGAGACTAAGACCTACTTTTGGAAGGTGCA<br>GCACCACATGGCCCCTACAAAGGATGAGTTTGACTGCAAGGCCT<br>GGGCCTACTTTTCTGATGTGGATCTGGAAAAGGATGTGCACTCT<br>GGACTCATTGGACCACTGCTTGTGTGCCACACCAACACACTGAA<br>CCCTGCTCATGGCAGACAAGTGACAGTGCAAGAGTTTGCCCTGT<br>TCTTCACCATCTTTGATGAAACAAAGAGCTGGTACTTCACAGAG<br>AATATGGAGAGAAACTGCAGGGCCCCTTGCAACATCCAGATGG<br>AAGATCCCACCTTCAAAGAGAACTACAGATTCCATGCCATCAAT<br>GGCTACATCATGGACACACTGCCTGGCCTGGTTATGGCTCAGGA<br>TCAGAGAATCAGATGGTATCTGCTGTCCATGGGCTCCAATGAGA<br>ATATCCACAGCATCCACTTCTCTGGCCATGTGTTCACAGTGAGA<br>AAAAAAGAAGAGTACAAAATGGCCCTGTACAATCTGTACCCTG<br>GGGTGTTTGAAACAGTGGAAATGCTGCCTTCCAAGGCTGGCATT<br>TGGAGAGTGGAATGTCTGATTGGAGAGCACCTCCATGCTGGAAT<br>GAGCACCCTGTTTCTGGTGTACAGCAACAAGTGTCAGACCCCTC<br>TGGGCATGGCCTCTGGACACATCAGAGACTTCCAGATCACAGCC<br>TCTGGCCAGTATGGACAGTGGGCTCCTAAACTGGCTAGACTGCA<br>CTACTCTGGCAGCATCAATGCCTGGTCCACCAAAGAGCCCTTCA<br>GCTGGATCAAGGTGGACCTGCTGGCTCCCATGATCATCCATGGA<br>ATCAAGACCCAGGGAGCCAGACAGAAGTTCAGCAGCCTGTACA<br>TCAGCCAGTTCATCATCATGTACAGCCTGGATGGCAAGAAGTGG<br>CAGACCTACAGAGGCAACAGCACAGGCACACTCATGGTGTTCTT<br>TGGCAATGTGGACAGCTCTGGCATTAAGCACAACATCTTCAACC<br>CTCCAATCATTGCCAGATACATCAGACTGCACCCCACACACTAC |

TABLE 23-continued

Listing of additional protein and nucleic acid sequences referred to herein not included in the sequence listing

| Category | SEQ ID NO: | Description | Type | Sequence |
|---|---|---|---|---|
| | | | | AGCATCAGATCTACCCTGAGAATGGAACTGATGGGCTGTGACCT<br>GAACAGCTGCAGCATGCCCCTGGGAATGGAAAGCAAGGCCATC<br>TCTGATGCCCAGATCACAGCCAGCAGCTACTTCACCAACATGTT<br>TGCCACTTGGAGCCCCTCCAAGGCTAGACTGCATCTGCAGGGCA<br>GAAGCAATGCTTGGAGGCCCCAAGTGAACAACCCCAAAGAGTG<br>GCTGCAGGTGGACTTTCAAAAGACCATGAAAGTGACAGGAGTG<br>ACCACACAGGGAGTCAAGTCTCTGCTGACCTCTATGTATGTGAA<br>AGAGTTCCTGATCTCCAGCAGCCAGGATGGCCACCAGTGGACCC<br>TGTTTTTCCAGAATGGCAAAGTGAAAGTGTTCCAGGGCAATCAG<br>GACAGCTTCACACCTGTGGTCAACTCCCTGGATCCTCCACTGCT<br>GACCAGATACCTGAGAATTCACCCTCAGTCTTGGGTGCACCAGA<br>TTGCTCTGAGAATGGAAGTGCTGGGCTGTGAAGCTCAGGACCTC<br>TACTGATCGCGAATAAAAGATCTTTATTTTCATTAGATCTGTGTG<br>TTGGTTTTTTGTGTGTATTTAGCTATTTGAGTGTAGCAGAGAGGA<br>ACCATTTTTCCTGTAACGATCGGGAACTGGCATTCCT |
| FVIII donor template | 20 | FVIII donor template with MG3-6/3-4 target sites in FF orientation (pMG4012) | Nucleotide | CATAGTACGCGTACGTTCTTAGGTCAGTGAAGAGAAGAACAAA<br>ATTTATTACGGTCTCATAGGGCCTGCCTTCTCAAAGCTTACTAAA<br>GAATTATTCTTTTACATTTCAGTGGCCACCAGAAGATATTACCTG<br>GGAGCTGTGGAACTGAGCTGGGACTACATGCAGTCTGACCTGG<br>GAGAGCTGCCTGTGGATGCTAGATTTCCTCCAAGAGTGCCCAAG<br>AGCTTCCCCTTCAACACCTCTGTGGTGTACAAGAAAACCCTGTT<br>TGTGGAATTCACAGACCACCTGTTCAATATTGCCAAGCCTAGAC<br>CTCCTTGGATGGGACTGCTGGGACCTACAATTCAGGCTGAGGTG<br>TATGACACAGTGGTCATCACCCTGAAGAACATGGCCAGCCATCC<br>TGTGTCTCTGCATGCTGTGGGAGTGTCTTACTGGAAGGCTTCTG<br>AGGGAGCTGAGTATGATGACCAGACAAGCCAGAGAGAGAAAG<br>AGGATGACAAGGTTTTCCCTGGAGGCAGCCACACCTATGTCTGG<br>CAGGTCCTGAAAGAAAATGGCCCTATGGCCTCTGATCCTCTGTG<br>CCTGACATACAGCTACCTGAGCCATGTGGACCTGGTCAAGGACC<br>TGAATTCTGGCCTGATTGGAGCCCTGCTGGTGTGTAGAGAAGGC<br>AGCCTGGCCAAAGAGAAAACCCAGACACTGCACAAGTTCATCC<br>TGCTGTTTGCTGTGTTTGATGAGGGCAAGAGCTGGCACTCTGAG<br>ACAAAGAACAGCCTGATGCAGGACAGGGATGCTGCCTCTGCTA<br>GAGCTTGGCCTAAGATGCACACAGTGAATGGCTATGTGAACAG<br>AAGCCTGCCTGGACTGATTGGCTGCCACAGAAAGTCTGTGTACT<br>GGCATGTGATTGGCATGGGCACAACACCTGAGGTGCACAGCAT<br>CTTTCTGGAAGGACACACCTTCCTGGTGAGAAACCATAGACAGG<br>CCAGCCTGGAAATCAGCCCTATCACCTTCCTGACAGCTCAGACC<br>CTGCTGATGGATCTGGGCCAGTTTCTGCTGTTCTGCCACATCAGC<br>AGCCACCAGCATGATGGCATGGAAGCCTATGTGAAGGTGGACA<br>GCTGCCCTGAAGAACCCCAGCTGAGAATGAAGAACAATGAGGA<br>GGCTGAGGACTATGATGATGACCTGACAGACTCTGAGATGGAT<br>GTGGTCAGATTTGATGATGACAACAGCCCCAGCTTCATCCAGAT<br>CAGATCTGTGGCCAAGAAGCACCCCAAGACCTGGGTGCACTAT<br>ATTGCTGCTGAGGAAGAGGACTGGGATTATGCTCCTCTGGTGCT<br>GGCCCCTGATGACAGAAGCTACAAGAGCCAGTACCTGAACAAT |

TABLE 23-continued

Listing of additional protein and nucleic acid sequences referred to herein not included in the sequence listing

| Category | SEQ ID NO: | Description | Type | Sequence |
|---|---|---|---|---|
| | | | | GGCCCTCAGAGAATTGGCAGAAAGTATAAGAAAGTGAGATTCA<br>TGGCCTACACAGATGAGACATTCAAGACCAGAGAGGCCATTCA<br>GCATGAGTCTGGCATTCTGGGCCCTCTGCTGTATGGAGAAGTGG<br>GAGATACACTGCTGATCATCTTCAAGAACCAGGCCAGCAGACCC<br>TACAACATCTACCCTCATGGCATCACAGATGTGAGACCCCTGTA<br>TTCTAGAAGGCTGCCCAAGGGAGTGAAGCACCTGAAGGACTTC<br>CCTATCCTGCCTGGAGAGATCTTCAAGTACAAGTGGACAGTGAC<br>AGTGGAAGATGGCCCCACCAAGTCTGACCCTAGATGTCTGACAA<br>GATACTACAGCAGCTTTGTGAACATGGAAAGAGACCTGGCCTCT<br>GGCCTGATTGGACCTCTGCTGATCTGCTACAAAGAATCTGTGGA<br>CCAGAGAGGCAACCAGATCATGTCTGACAAGAGAAATGTGATC<br>CTGTTTTCTGTGTTTGATGAGAACAGATCCTGGTATCTGACAGA<br>GAACATCCAGAGATTTCTGCCCAATCCTGCTGGAGTGCAGCTGG<br>AAGATCCTGAGTTCCAGGCCTCCAACATCATGCACTCCATCAAT<br>GGCTATGTGTTTGACAGCCTGCAGCTGTCTGTGTGCCTGCATGA<br>AGTGGCCTACTGGTACATCCTGAGCATTGGAGCCCAGACAGACT<br>TCCTGTCTGTGTTCTTCTCTGGCTACACCTTCAAGCACAAGATGG<br>TGTATGAGGATACCCTGACACTGTTCCCATTCTCTGGAGAGACA<br>GTGTTCATGAGCATGGAAAACCCTGGCCTGTGGATCCTGGGCTG<br>TCACAACTCTGACTTCAGAAACAGAGGCATGACAGCCCTGCTGA<br>AGGTGTCCAGCTGTGACAAGAACACAGGAGACTACTATGAGGA<br>CAGCTATGAGGACATCTCTGCCTACCTGCTGAGCAAGAACAATG<br>CCATTGAGCCCAGAAGCTTCAGCCAGAATGCCACCAATGTGTCC<br>AACAACAGCAACACCAGCAATGACTCCAATGTGTCCCCTCCAGT<br>GCTGAAGAGACACCAGAGAGAAATCACCAGAACCACACTGCAG<br>TCTGACCAAGAGGAAATTGACTATGATGACACCATCTCTGTGGA<br>GATGAAGAAAGAAGATTTTGACATCTATGATGAGGATGAGAAT<br>CAGAGCCCCAGATCCTTTCAGAAAAAGACCAGACACTACTTCAT<br>TGCTGCTGTGGAGAGACTGTGGGACTATGGCATGTCTAGCAGCC<br>CTCATGTGCTGAGAAATAGAGCCCAGTCTGGCTCTGTGCCCCAG<br>TTCAAGAAAGTGGTGTTCCAAGAGTTCACAGATGGCAGCTTCAC<br>CCAGCCACTGTATAGAGGAGAGCTGAATGAGCATCTGGGCCTG<br>CTGGGCCCTTATATCAGAGCTGAAGTGGAAGATAACATCATGGT<br>CACCTTCAGAAATCAGGCCTCTAGACCCTACAGCTTCTACAGCT<br>CCCTGATCAGCTATGAAGAGGACCAGAGACAGGGAGCTGAGCC<br>CAGAAAGAACTTTGTGAAGCCCAATGAGACTAAGACCTACTTTT<br>GGAAGGTGCAGCACCACATGGCCCCTACAAAGGATGAGTTTGA<br>CTGCAAGGCCTGGGCCTACTTTTCTGATGTGGATCTGGAAAAGG<br>ATGTGCACTCTGGACTCATTGGACCACTGCTTGTGTGCCACACC<br>AACACACTGAACCCTGCTCATGGCAGACAAGTGACAGTGCAAG<br>AGTTTGCCCTGTTCTTCACCATCTTTGATGAAACAAAGAGCTGG<br>TACTTCACAGAGAATATGGAGAGAAACTGCAGGGCCCCTTGCA<br>ACATCCAGATGGAAGATCCCACCTTCAAAGAGAACTACAGATTC<br>CATGCCATCAATGGCTACATCATGGACACACTGCCTGGCCTGGT<br>TATGGCTCAGGATCAGAGAATCAGATGGTATCTGCTGTCCATGG<br>GCTCCAATGAGAATATCCACAGCATCCACTTCTCTGGCCATGTG<br>TTCACAGTGAGAAAAAAAGAAGAGTACAAAATGGCCCTGTACA |

TABLE 23-continued

Listing of additional protein and nucleic acid sequences referred to herein not included in the sequence listing

| Category | SEQ ID NO: | Description | Type | Sequence |
|---|---|---|---|---|
| | | | | ATCTGTACCCTGGGGTGTTTGAAACAGTGGAAATGCTGCCTTCC AAGGCTGGCATTTGGAGAGTGGAATGTCTGATTGGAGAGCACCT CCATGCTGGAATGAGCACCCTGTTTCTGGTGTACAGCAACAAGT GTCAGACCCCTCTGGGCATGGCCTCTGGACACATCAGAGACTTC CAGATCACAGCCTCTGGCCAGTATGGACAGTGGGCTCCTAAACT GGCTAGACTGCACTACTCTGGCAGCATCAATGCCTGGTCCACCA AAGAGCCCTTCAGCTGGATCAAGGTGGACCTGCTGGCTCCCATG ATCATCCATGGAATCAAGACCCAGGGAGCCAGACAGAAGTTCA GCAGCCTGTACATCAGCCAGTTCATCATCATGTACAGCCTGGAT GGCAAGAAGTGGCAGACCTACAGAGGCAACAGCACAGGCACAC TCATGGTGTTCTTTGGCAATGTGGACAGCTCTGGCATTAAGCAC AACATCTTCAACCCTCCAATCATTGCCAGATACATCAGACTGCA CCCCACACACTACAGCATCAGATCTACCCTGAGAATGGAACTGA TGGGCTGTGACCTGAACAGCTGCAGCATGCCCCTGGGAATGGA AAGCAAGGCCATCTCTGATGCCCAGATCACAGCCAGCAGCTACT TCACCAACATGTTTGCCACTTGGAGCCCCTCCAAGGCTAGACTG CATCTGCAGGGCAGAAGCAATGCTTGGAGGCCCCAAGTGAACA ACCCCAAAGAGTGGCTGCAGGTGGACTTTCAAAAGACCATGAA AGTGACAGGAGTGACCACACAGGGAGTCAAGTCTCTGCTGACC TCTATGTATGTGAAAGAGTTCCTGATCTCCAGCAGCCAGGATGG CCACCAGTGGACCCTGTTTTTCCAGAATGGCAAAGTGAAAGTGT TCCAGGGCAATCAGGACAGCTTCACACCTGTGGTCAACTCCCTG GATCCTCCACTGCTGACCAGATACCTGAGAATTCACCCTCAGTC TTGGGTGCACCAGATTGCTCTGAGAATGGAAGTGCTGGGCTGTG AAGCTCAGGACCTCTACTGATCGCGAATAAAAGATCTTTATTTT CATTAGATCTGTGTGTTGGTTTTTTGTGTGTATTTAGCTATTTATT ACGGTCTCATAGGGCCTGCCTCTTAGGTCAGTGAAGAGAAGAAC AAAATTCCTCACGTGCATAGT |
| FVIII donor template | 21 | FVIII donor template with MG3-6/3-4 target sites in RR orientation (pMG4013) | Nucleotide | CATAGTACGCGTACGTTTTTGTTCTTCTCTTCACTGACCTAAGAG GCAGGCCCTATGAGACCGTAATAAATCTCAAAGCTTACTAAAGA ATTATTCTTTTACATTTCAGTGGCCACCAGAAGATATTACCTGGG AGCTGTGGAACTGAGCTGGGACTACATGCAGTCTGACCTGGGA GAGCTGCCTGTGGATGCTAGATTTCCTCCAAGAGTGCCCAAGAG CTTCCCCTTCAACACCTCTGTGGTGTACAAGAAAACCCTGTTTGT GGAATTCACAGACCACCTGTTCAATATTGCCAAGCCTAGACCTC CTTGGATGGGACTGCTGGGACCTACAATTCAGGCTGAGGTGTAT GACACAGTGGTCATCACCCTGAAGAACATGGCCAGCCATCCTGT GTCTCTGCATGCTGTGGGAGTGTCTTACTGGAAGGCTTCTGAGG GAGCTGAGTATGATGACCAGACAAGCCAGAGAGAGAAAGAGG ATGACAAGGTTTTCCCTGGAGGCAGCCACACCTATGTCTGGCAG GTCCTGAAAGAAAATGGCCCTATGGCCTCTGATCCTCTGTGCCT GACATACAGCTACCTGAGCCATGTGGACCTGGTCAAGGACCTGA ATTCTGGCCTGATTGGAGCCCTGCTGGTGTGTAGAGAAGGCAGC CTGGCCAAAGAGAAAACCCAGACACTGCACAAGTTCATCCTGCT GTTTGCTGTGTTTGATGAGGGCAAGAGCTGGCACTCTGAGACAA AGAACAGCCTGATGCAGGACAGGGATGCTGCCTCTGCTAGAGC |

TABLE 23-continued

| Category | SEQ ID NO: | Description | Type | Sequence |
|---|---|---|---|---|
| Listing of additional protein and nucleic acid sequences referred to herein not included in the sequence listing | | | | |
| | | | | TTGGCCTAAGATGCACACAGTGAATGGCTATGTGAACAGAAGC |
| | | | | CTGCCTGGACTGATTGGCTGCCACAGAAAGTCTGTGTACTGGCA |
| | | | | TGTGATTGGCATGGGCACAACACCTGAGGTGCACAGCATCTTTC |
| | | | | TGGAAGGACACACCTTCCTGGTGAGAAACCATAGACAGGCCAG |
| | | | | CCTGGAAATCAGCCCTATCACCTTCCTGACAGCTCAGACCCTGC |
| | | | | TGATGGATCTGGGCCAGTTTCTGCTGTTCTGCCACATCAGCAGC |
| | | | | CACCAGCATGATGGCATGGAAGCCTATGTGAAGGTGGACAGCT |
| | | | | GCCCTGAAGAACCCCAGCTGAGAATGAAGAACAATGAGGAGGC |
| | | | | TGAGGACTATGATGATGACCTGACAGACTCTGAGATGGATGTGG |
| | | | | TCAGATTTGATGATGACAACAGCCCCAGCTTCATCCAGATCAGA |
| | | | | TCTGTGGCCAAGAAGCACCCCAAGACCTGGGTGCACTATATTGC |
| | | | | TGCTGAGGAAGAGGACTGGGATTATGCTCCTCTGGTGCTGGCCC |
| | | | | CTGATGACAGAAGCTACAAGAGCCAGTACCTGAACAATGGCCC |
| | | | | TCAGAGAATTGGCAGAAAGTATAAGAAAGTGAGATTCATGGCC |
| | | | | TACACAGATGAGACATTCAAGACCAGAGAGGCCATTCAGCATG |
| | | | | AGTCTGGCATTCTGGGCCCTCTGCTGTATGGAGAAGTGGGAGAT |
| | | | | ACACTGCTGATCATCTTCAAGAACCAGGCCAGCAGACCCTACAA |
| | | | | CATCTACCCTCATGGCATCACAGATGTGAGACCCCTGTATTCTA |
| | | | | GAAGGCTGCCCAAGGGAGTGAAGCACCTGAAGGACTTCCCTAT |
| | | | | CCTGCCTGGAGAGATCTTCAAGTACAAGTGGACAGTGACAGTG |
| | | | | GAAGATGGCCCCACCAAGTCTGACCCTAGATGTCTGACAAGATA |
| | | | | CTACAGCAGCTTTGTGAACATGGAAAGAGACCTGGCCTCTGGCC |
| | | | | TGATTGGACCTCTGCTGATCTGCTACAAAGAATCTGTGGACCAG |
| | | | | AGAGGCAACCAGATCATGTCTGACAAGAGAAATGTGATCCTGTT |
| | | | | TTCTGTGTTTGATGAGAACAGATCCTGGTATCTGACAGAGAACA |
| | | | | TCCAGAGATTTCTGCCCAATCCTGCTGGAGTGCAGCTGGAAGAT |
| | | | | CCTGAGTTCCAGGCCTCCAACATCATGCACTCCATCAATGGCTA |
| | | | | TGTGTTTGACAGCCTGCAGCTGTCTGTGTGCCTGCATGAAGTGG |
| | | | | CCTACTGGTACATCCTGAGCATTGGAGCCCAGACAGACTTCCTG |
| | | | | TCTGTGTTCTTCTCTGGCTACACCTTCAAGCACAAGATGGTGTAT |
| | | | | GAGGATACCCTGACACTGTTCCCATTCTCTGGAGAGACAGTGTT |
| | | | | CATGAGCATGGAAAACCCTGGCCTGTGGATCCTGGGCTGTCACA |
| | | | | ACTCTGACTTCAGAAACAGAGGCATGACAGCCCTGCTGAAGGT |
| | | | | GTCCAGCTGTGACAAGAACACAGGAGACTACTATGAGGACAGC |
| | | | | TATGAGGACATCTCTGCCTACCTGCTGAGCAAGAACAATGCCAT |
| | | | | TGAGCCCAGAAGCTTCAGCCAGAATGCCACCAATGTGTCCAACA |
| | | | | ACAGCAACACCAGCAATGACTCCAATGTGTCCCCTCCAGTGCTG |
| | | | | AAGAGACACCAGAGAGAAATCACCAGAACCACACTGCAGTCTG |
| | | | | ACCAAGAGGAAATTGACTATGATGACACCATCTCTGTGGAGATG |
| | | | | AAGAAAGAAGATTTTGACATCTATGATGAGGATGAGAATCAGA |
| | | | | GCCCCAGATCCTTTCAGAAAAAGACCAGACACTACTTCATTGCT |
| | | | | GCTGTGGAGAGACTGTGGGACTATGGCATGTCTAGCAGCCCTCA |
| | | | | TGTGCTGAGAAATAGAGCCCAGTCTGGCTCTGTGCCCCAGTTCA |
| | | | | AGAAAGTGGTGTTCCAAGAGTTCACAGATGGCAGCTTCACCCAG |
| | | | | CCACTGTATAGAGGAGAGCTGAATGAGCATCTGGGCCTGCTGG |
| | | | | GCCCTTATATCAGAGCTGAAGTGGAAGATAACATCATGGTCACC |
| | | | | TTCAGAAATCAGGCCTCTAGACCCTACAGCTTCTACAGCTCCCT |

TABLE 23-continued

Listing of additional protein and nucleic acid sequences referred to herein not included in the sequence listing

| Category | SEQ ID NO: | Description | Type | Sequence |
|---|---|---|---|---|
| | | | | GATCAGCTATGAAGAGGACCAGAGACAGGGAGCTGAGCCCAGA AAGAACTTTGTGAAGCCCAATGAGACTAAGACCTACTTTTGGAA GGTGCAGCACCACATGGCCCCTACAAAGGATGAGTTTGACTGCA AGGCCTGGGCCTACTTTTCTGATGTGGATCTGGAAAAGGATGTG CACTCTGGACTCATTGGACCACTGCTTGTGTGCCACACCAACAC ACTGAACCCTGCTCATGGCAGACAAGTGACAGTGCAAGAGTTTG CCCTGTTCTTCACCATCTTTGATGAAACAAAGAGCTGGTACTTC ACAGAGAATATGGAGAGAAACTGCAGGGCCCCTTGCAACATCC AGATGGAAGATCCCACCTTCAAAGAGAACTACAGATTCCATGCC ATCAATGGCTACATCATGGACACACTGCCTGGCCTGGTTATGGC TCAGGATCAGAGAATCAGATGGTATCTGCTGTCCATGGGCTCCA ATGAGAATATCCACAGCATCCACTTCTCTGGCCATGTGTTCACA GTGAGAAAAAAAGAAGAGTACAAAATGGCCCTGTACAATCTGT ACCCTGGGGTGTTTGAAACAGTGGAAATGCTGCCTTCCAAGGCT GGCATTTGGAGAGTGGAATGTCTGATTGGAGAGCACCTCCATGC TGGAATGAGCACCCTGTTTCTGGTGTACAGCAACAAGTGTCAGA CCCCTCTGGGCATGGCCTCTGGACACATCAGAGACTTCCAGATC ACAGCCTCTGGCCAGTATGGACAGTGGGCTCCTAAACTGGCTAG ACTGCACTACTCTGGCAGCATCAATGCCTGGTCCACCAAAGAGC CCTTCAGCTGGATCAAGGTGGACCTGCTGGCTCCCATGATCATC CATGGAATCAAGACCCAGGGAGCCAGACAGAAGTTCAGCAGCC TGTACATCAGCCAGTTCATCATCATGTACAGCCTGGATGGCAAG AAGTGGCAGACCTACAGAGGCAACAGCACAGGCACACTCATGG TGTTCTTTGGCAATGTGGACAGCTCTGGCATTAAGCACAACATC TTCAACCCTCCAATCATTGCCAGATACATCAGACTGCACCCCAC ACACTACAGCATCAGATCTACCCTGAGAATGGAACTGATGGGCT GTGACCTGAACAGCTGCAGCATGCCCCTGGGAATGGAAAGCAA GGCCATCTCTGATGCCCAGATCACAGCCAGCAGCTACTTCACCA ACATGTTTGCCACTTGGAGCCCCTCCAAGGCTAGACTGCATCTG CAGGGCAGAAGCAATGCTTGGAGGCCCCAAGTGAACAACCCCA AAGAGTGGCTGCAGGTGGACTTTCAAAAGACCATGAAAGTGAC AGGAGTGACCACACAGGGAGTCAAGTCTCTGCTGACCTCTATGT ATGTGAAAGAGTTCCTGATCTCCAGCAGCCAGGATGGCCACCAG TGGACCCTGTTTTTCCAGAATGGCAAAGTGAAAGTGTTCCAGGG CAATCAGGACAGCTTCACACCTGTGGTCAACTCCCTGGATCCTC CACTGCTGACCAGATACCTGAGAATTCACCCTCAGTCTTGGGTG CACCAGATTGCTCTGAGAATGGAAGTGCTGGGCTGTGAAGCTCA GGACCTCTACTGATCGCGAATAAAAGATCTTTATTTTCATTAGA TCTGTGTGTTGGTTTTTTGTGTGTATTTAGCTAAGGCAGGCCCTA TGAGACCGTAATAAATTTGTTCTTCTCTTCACTGACCTAAGTTCC TCACGTGCATAGT |
| FVIII donor template | 22 | FVIII donor template with MG3-6/3-4 target sites in FR orientation (pMG4014) | Nucleotide | CATAGTACGCGTACGTTCTTAGGTCAGTGAAGAGAAGAACAAA TTTATTACGGTCTCATAGGGCCTGCCTTCTCAAAGCTTACTAAAG AATTATTCTTTTACATTTCAGTGGCCACCAGAAGATATTACCTGG GAGCTGTGGAACTGAGCTGGGACTACATGCAGTCTGACCTGGG AGAGCTGCCTGTGGATGCTAGATTTCCTCCAAGAGTGCCCAAGA |

TABLE 23-continued

Listing of additional protein and nucleic acid sequences referred to herein not included in the sequence listing

| Category | SEQ ID NO: | Description | Type | Sequence |
|---|---|---|---|---|
| | | | | GCTTCCCCTTCAACACCTCTGTGGTGTACAAGAAAACCCTGTTT<br>GTGGAATTCACAGACCACCTGTTCAATATTGCCAAGCCTAGACC<br>TCCTTGGATGGGACTGCTGGGACCTACAATTCAGGCTGAGGTGT<br>ATGACACAGTGGTCATCACCCTGAAGAACATGGCCAGCCATCCT<br>GTGTCTCTGCATGCTGTGGGAGTGTCTTACTGGAAGGCTTCTGA<br>GGGAGCTGAGTATGATGACCAGACAAGCCAGAGAGAGAAAGA<br>GGATGACAAGGTTTTCCCTGGAGGCAGCCACACCTATGTCTGGC<br>AGGTCCTGAAAGAAAATGGCCCTATGGCCTCTGATCCTCTGTGC<br>CTGACATACAGCTACCTGAGCCATGTGGACCTGGTCAAGGACCT<br>GAATTCTGGCCTGATTGGAGCCCTGCTGGTGTGTAGAGAAGGCA<br>GCCTGGCCAAAGAGAAAACCCAGACACTGCACAAGTTCATCCT<br>GCTGTTTGCTGTGTTTGATGAGGGCAAGAGCTGGCACTCTGAGA<br>CAAAGAACAGCCTGATGCAGGACAGGGATGCTGCCTCTGCTAG<br>AGCTTGGCCTAAGATGCACACAGTGAATGGCTATGTGAACAGA<br>AGCCTGCCTGGACTGATTGGCTGCCACAGAAAGTCTGTGTACTG<br>GCATGTGATTGGCATGGGCACAACACCTGAGGTGCACAGCATCT<br>TTCTGGAAGGACACACCTTCCTGGTGAGAAACCATAGACAGGCC<br>AGCCTGGAAATCAGCCCTATCACCTTCCTGACAGCTCAGACCCT<br>GCTGATGGATCTGGGCCAGTTTCTGCTGTTCTGCCACATCAGCA<br>GCCACCAGCATGATGGCATGGAAGCCTATGTGAAGGTGGACAG<br>CTGCCCTGAAGAACCCCAGCTGAGAATGAAGAACAATGAGGAG<br>GCTGAGGACTATGATGATGACCTGACAGACTCTGAGATGGATGT<br>GGTCAGATTTGATGATGACAACAGCCCCAGCTTCATCCAGATCA<br>GATCTGTGGCCAAGAAGCACCCCAAGACCTGGGTGCACTATATT<br>GCTGCTGAGGAAGAGGACTGGGATTATGCTCCTCTGGTGCTGGC<br>CCCTGATGACAGAAGCTACAAGAGCCAGTACCTGAACAATGGC<br>CCTCAGAGAATTGGCAGAAAGTATAAGAAAGTGAGATTCATGG<br>CCTACACAGATGAGACATTCAAGACCAGAGAGGCCATTCAGCA<br>TGAGTCTGGCATTCTGGGCCCTCTGCTGTATGGAGAAGTGGGAG<br>ATACACTGCTGATCATCTTCAAGAACCAGGCCAGCAGACCCTAC<br>AACATCTACCCTCATGGCATCACAGATGTGAGACCCCTGTATTC<br>TAGAAGGCTGCCCAAGGGAGTGAAGCACCTGAAGGACTTCCCT<br>ATCCTGCCTGGAGAGATCTTCAAGTACAAGTGGACAGTGACAGT<br>GGAAGATGGCCCCACCAAGTCTGACCCTAGATGTCTGACAAGAT<br>ACTACAGCAGCTTTGTGAACATGGAAAGAGACCTGGCCTCTGGC<br>CTGATTGGACCTCTGCTGATCTGCTACAAAGAATCTGTGGACCA<br>GAGAGGCAACCAGATCATGTCTGACAAGAGAAATGTGATCCTG<br>TTTTCTGTGTTTGATGAGAACAGATCCTGGTATCTGACAGAGAA<br>CATCCAGAGATTTCTGCCCAATCCTGCTGGAGTGCAGCTGGAAG<br>ATCCTGAGTTCCAGGCCTCCAACATCATGCACTCCATCAATGGC<br>TATGTGTTTGACAGCCTGCAGCTGTCTGTGTGCCTGCATGAAGT<br>GGCCTACTGGTACATCCTGAGCATTGGAGCCCAGACAGACTTCC<br>TGTCTGTGTTCTTCTCTGGCTACACCTTCAAGCACAAGATGGTGT<br>ATGAGGATACCCTGACACTGTTCCCATTCTCTGGAGAGACAGTG<br>TTCATGAGCATGGAAAACCCTGGCCTGTGGATCCTGGGCTGTCA<br>CAACTCTGACTTCAGAAACAGAGGCATGACAGCCCTGCTGAAG<br>GTGTCCAGCTGTGACAAGAACACAGGAGACTACTATGAGGACA |

TABLE 23-continued

Listing of additional protein and nucleic acid sequences referred to herein not included in the sequence listing

| Category | SEQ ID NO: | Description | Type | Sequence |
|---|---|---|---|---|
| | | | | GCTATGAGGACATCTCTGCCTACCTGCTGAGCAAGAACAATGCC<br>ATTGAGCCCAGAAGCTTCAGCCAGAATGCCACCAATGTGTCCAA<br>CAACAGCAACACCAGCAATGACTCCAATGTGTCCCCTCCAGTGC<br>TGAAGAGACACCAGAGAGAAATCACCAGAACCACACTGCAGTC<br>TGACCAAGAGGAAATTGACTATGATGACACCATCTCTGTGGAGA<br>TGAAGAAAGAAGATTTTGACATCTATGATGAGGATGAGAATCA<br>GAGCCCCAGATCCTTTCAGAAAAAGACCAGACACTACTTCATTG<br>CTGCTGTGGAGAGACTGTGGGACTATGGCATGTCTAGCAGCCCT<br>CATGTGCTGAGAAATAGAGCCCAGTCTGGCTCTGTGCCCCAGTT<br>CAAGAAAGTGGTGTTCCAAGAGTTCACAGATGGCAGCTTCACCC<br>AGCCACTGTATAGAGGAGAGCTGAATGAGCATCTGGGCCTGCT<br>GGGCCCTTATATCAGAGCTGAAGTGGAAGATAACATCATGGTCA<br>CCTTCAGAAATCAGGCCTCTAGACCCTACAGCTTCTACAGCTCC<br>CTGATCAGCTATGAAGAGGACCAGAGACAGGGAGCTGAGCCCA<br>GAAAGAACTTTGTGAAGCCCAATGAGACTAAGACCTACTTTTGG<br>AAGGTGCAGCACCACATGGCCCCTACAAAGGATGAGTTTGACT<br>GCAAGGCCTGGGCCTACTTTTCTGATGTGGATCTGGAAAAGGAT<br>GTGCACTCTGGACTCATTGGACCACTGCTTGTGTGCCACACCAA<br>CACACTGAACCCTGCTCATGGCAGACAAGTGACAGTGCAAGAG<br>TTTGCCCTGTTCTTCACCATCTTTGATGAAACAAAGAGCTGGTAC<br>TTCACAGAGAATATGGAGAGAAACTGCAGGGCCCCTTGCAACA<br>TCCAGATGGAAGATCCCACCTTCAAAGAGAACTACAGATTCCAT<br>GCCATCAATGGCTACATCATGGACACACTGCCTGGCCTGGTTAT<br>GGCTCAGGATCAGAGAATCAGATGGTATCTGCTGTCCATGGGCT<br>CCAATGAGAATATCCACAGCATCCACTTCTCTGGCCATGTGTTC<br>ACAGTGAGAAAAAAAGAAGAGTACAAAATGGCCCTGTACAATC<br>TGTACCCTGGGGTGTTTGAAACAGTGGAAATGCTGCCTTCCAAG<br>GCTGGCATTTGGAGAGTGGAATGTCTGATTGGAGAGCACCTCCA<br>TGCTGGAATGAGCACCCTGTTTCTGGTGTACAGCAACAAGTGTC<br>AGACCCCTCTGGGCATGGCCTCTGGACACATCAGAGACTTCCAG<br>ATCACAGCCTCTGGCCAGTATGGACAGTGGGCTCCTAAACTGGC<br>TAGACTGCACTACTCTGGCAGCATCAATGCCTGGTCCACCAAAG<br>AGCCCTTCAGCTGGATCAAGGTGGACCTGCTGGCTCCCATGATC<br>ATCCATGGAATCAAGACCCAGGGAGCCAGACAGAAGTTCAGCA<br>GCCTGTACATCAGCCAGTTCATCATCATGTACAGCCTGGATGGC<br>AAGAAGTGGCAGACCTACAGAGGCAACAGCACAGGCACACTCA<br>TGGTGTTCTTTGGCAATGTGGACAGCTCTGGCATTAAGCACAAC<br>ATCTTCAACCCTCCAATCATTGCCAGATACATCAGACTGCACCC<br>CACACACTACAGCATCAGATCTACCCTGAGAATGGAACTGATGG<br>GCTGTGACCTGAACAGCTGCAGCATGCCCCTGGGAATGGAAAG<br>CAAGGCCATCTCTGATGCCCAGATCACAGCCAGCAGCTACTTCA<br>CCAACATGTTTGCCACTTGGAGCCCCTCCAAGGCTAGACTGCAT<br>CTGCAGGGCAGAAGCAATGCTTGGAGGCCCCAAGTGAACAACC<br>CCAAAGAGTGGCTGCAGGTGGACTTTCAAAAGACCATGAAAGT<br>GACAGGAGTGACCACACAGGGAGTCAAGTCTCTGCTGACCTCTA<br>TGTATGTGAAAGAGTTCCTGATCTCCAGCAGCCAGGATGGCCAC<br>CAGTGGACCCTGTTTTTCCAGAATGGCAAAGTGAAAGTGTTCCA |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | GGGCAATCAGGACAGCTTCACACCTGTGGTCAACTCCCTGGATC CTCCACTGCTGACCAGATACCTGAGAATTCACCCTCAGTCTTGG GTGCACCAGATTGCTCTGAGAATGGAAGTGCTGGGCTGTGAAGC TCAGGACCTCTACTGATCGCGAATAAAAGATCTTTATTTTCATTA GATCTGTGTGTTGGTTTTTTGTGTGTATTTAGCTAAGGCAGGCCC TATGAGACCGTAATAAATTTGTTCTTCTCTTCACTGACCTAAGTT CCTCACGTGCATAGT |
| FVIII donor template | 23 | FVIII donor template with MG3-6/3-4 target sites in RF orientation (pMG4015) | Nucleotide | CATAGTACGCGTACGTTTTTGTTCTTCTCTTCACTGACCTAAGAG GCAGGCCCTATGAGACCGTAATAAATCTCAAAGCTTACTAAAGA ATTATTCTTTTACATTTCAGTGGCCACCAGAAGATATTACCTGGG AGCTGTGGAACTGAGCTGGGACTACATGCAGTCTGACCTGGGA GAGCTGCCTGTGGATGCTAGATTTCCTCCAAGAGTGCCCAAGAG CTTCCCCTTCAACACCTCTGTGGTGTACAAGAAAACCCTGTTTGT GGAATTCACAGACCACCTGTTCAATATTGCCAAGCCTAGACCTC CTTGGATGGGACTGCTGGGACCTACAATTCAGGCTGAGGTGTAT GACACAGTGGTCATCACCCTGAAGAACATGGCCAGCCATCCTGT GTCTCTGCATGCTGTGGGAGTGTCTTACTGGAAGGCTTCTGAGG GAGCTGAGTATGATGACCAGACAAGCCAGAGAGAGAAAGAGG ATGACAAGGTTTTCCCTGGAGGCAGCCACACCTATGTCTGGCAG GTCCTGAAAGAAAATGGCCCTATGGCCTCTGATCCTCTGTGCCT GACATACAGCTACCTGAGCCATGTGGACCTGGTCAAGGACCTGA ATTCTGGCCTGATTGGAGCCCTGCTGGTGTGTAGAGAAGGCAGC CTGGCCAAAGAGAAAACCCAGACACTGCACAAGTTCATCCTGCT GTTTGCTGTGTTTGATGAGGGCAAGAGCTGGCACTCTGAGACAA AGAACAGCCTGATGCAGGACAGGGATGCTGCCTCTGCTAGAGC TTGGCCTAAGATGCACACAGTGAATGGCTATGTGAACAGAAGC CTGCCTGGACTGATTGGCTGCCACAGAAAGTCTGTGTACTGGCA TGTGATTGGCATGGGCACAACACCTGAGGTGCACAGCATCTTTC TGGAAGGACACACCTTCCTGGTGAGAAACCATAGACAGGCCAG CCTGGAAATCAGCCCTATCACCTTCCTGACAGCTCAGACCCTGC TGATGGATCTGGGCCAGTTTCTGCTGTTCTGCCACATCAGCAGC CACCAGCATGATGGCATGGAAGCCTATGTGAAGGTGGACAGCT GCCCTGAAGAACCCCAGCTGAGAATGAAGAACAATGAGGAGGC TGAGGACTATGATGATGACCTGACAGACTCTGAGATGGATGTGG TCAGATTTGATGATGACAACAGCCCCAGCTTCATCCAGATCAGA TCTGTGGCCAAGAAGCACCCCAAGACCTGGGTGCACTATATTGC TGCTGAGGAAGAGGACTGGGATTATGCTCCTCTGGTGCTGGCCC CTGATGACAGAAGCTACAAGAGCCAGTACCTGAACAATGGCCC TCAGAGAATTGGCAGAAAGTATAAGAAAGTGAGATTCATGGCC TACACAGATGAGACATTCAAGACCAGAGAGGCCATTCAGCATG AGTCTGGCATTCTGGGCCCTCTGCTGTATGGAGAAGTGGGAGAT ACACTGCTGATCATCTTCAAGAACCAGGCCAGCAGACCCTACAA CATCTACCCTCATGGCATCACAGATGTGAGACCCCTGTATTCTA GAAGGCTGCCCAAGGGAGTGAAGCACCTGAAGGACTTCCCTAT CCTGCCTGGAGAGATCTTCAAGTACAAGTGGACAGTGACAGTG GAAGATGGCCCCACCAAGTCTGACCCTAGATGTCTGACAAGATA |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | CTACAGCAGCTTTGTGAACATGGAAAGAGACCTGGCCTCTGGCC<br>TGATTGGACCTCTGCTGATCTGCTACAAAGAATCTGTGGACCAG<br>AGAGGCAACCAGATCATGTCTGACAAGAGAAATGTGATCCTGTT<br>TTCTGTGTTTGATGAGAACAGATCCTGGTATCTGACAGAGAACA<br>TCCAGAGATTTCTGCCCAATCCTGCTGGAGTGCAGCTGGAAGAT<br>CCTGAGTTCCAGGCCTCCAACATCATGCACTCCATCAATGGCTA<br>TGTGTTTGACAGCCTGCAGCTGTCTGTGTGCCTGCATGAAGTGG<br>CCTACTGGTACATCCTGAGCATTGGAGCCCAGACAGACTTCCTG<br>TCTGTGTTCTTCTCTGGCTACACCTTCAAGCACAAGATGGTGTAT<br>GAGGATACCCTGACACTGTTCCCATTCTCTGGAGAGACAGTGTT<br>CATGAGCATGGAAAACCCTGGCCTGTGGATCCTGGGCTGTCACA<br>ACTCTGACTTCAGAAACAGAGGCATGACAGCCCTGCTGAAGGT<br>GTCCAGCTGTGACAAGAACACAGGAGACTACTATGAGGACAGC<br>TATGAGGACATCTCTGCCTACCTGCTGAGCAAGAACAATGCCAT<br>TGAGCCCAGAAGCTTCAGCCAGAATGCCACCAATGTGTCCAACA<br>ACAGCAACACCAGCAATGACTCCAATGTGTCCCCTCCAGTGCTG<br>AAGAGACACCAGAGAGAAATCACCAGAACCACACTGCAGTCTG<br>ACCAAGAGGAAATTGACTATGATGACACCATCTCTGTGGAGATG<br>AAGAAAGAAGATTTTGACATCTATGATGAGGATGAGAATCAGA<br>GCCCCAGATCCTTTCAGAAAAAGACCAGACACTACTTCATTGCT<br>GCTGTGGAGAGACTGTGGGACTATGGCATGTCTAGCAGCCCTCA<br>TGTGCTGAGAAATAGAGCCCAGTCTGGCTCTGTGCCCCAGTTCA<br>AGAAAGTGGTGTTCCAAGAGTTCACAGATGGCAGCTTCACCCAG<br>CCACTGTATAGAGGAGAGCTGAATGAGCATCTGGGCCTGCTGG<br>GCCCTTATATCAGAGCTGAAGTGGAAGATAACATCATGGTCACC<br>TTCAGAAATCAGGCCTCTAGACCCTACAGCTTCTACAGCTCCCT<br>GATCAGCTATGAAGAGGACCAGAGACAGGGAGCTGAGCCCAGA<br>AAGAACTTTGTGAAGCCCAATGAGACTAAGACCTACTTTTGGAA<br>GGTGCAGCACCACATGGCCCCTACAAAGGATGAGTTTGACTGCA<br>AGGCCTGGGCCTACTTTTCTGATGTGGATCTGGAAAAGGATGTG<br>CACTCTGGACTCATTGGACCACTGCTTGTGTGCCACACCAACAC<br>ACTGAACCCTGCTCATGGCAGACAAGTGACAGTGCAAGAGTTTG<br>CCCTGTTCTTCACCATCTTTGATGAAACAAAGAGCTGGTACTTC<br>ACAGAGAATATGGAGAGAAACTGCAGGGCCCCTTGCAACATCC<br>AGATGGAAGATCCCACCTTCAAAGAGAACTACAGATTCCATGCC<br>ATCAATGGCTACATCATGGACACACTGCCTGGCCTGGTTATGGC<br>TCAGGATCAGAGAATCAGATGGTATCTGCTGTCCATGGGCTCCA<br>ATGAGAATATCCACAGCATCCACTTCTCTGGCCATGTGTTCACA<br>GTGAGAAAAAAAGAAGAGTACAAAATGGCCCTGTACAATCTGT<br>ACCCTGGGGTGTTTGAAACAGTGGAAATGCTGCCTTCCAAGGCT<br>GGCATTTGGAGAGTGGAATGTCTGATTGGAGAGCACCTCCATGC<br>TGGAATGAGCACCCTGTTTCTGGTGTACAGCAACAAGTGTCAGA<br>CCCCTCTGGGCATGGCCTCTGGACACATCAGAGACTTCCAGATC<br>ACAGCCTCTGGCCAGTATGGACAGTGGGCTCCTAAACTGGCTAG<br>ACTGCACTACTCTGGCAGCATCAATGCCTGGTCCACCAAAGAGC<br>CCTTCAGCTGGATCAAGGTGGACCTGCTGGCTCCCATGATCATC<br>CATGGAATCAAGACCCAGGGAGCCAGACAGAAGTTCAGCAGCC |

TABLE 23-continued

Listing of additional protein and nucleic acid sequences referred to herein not included in the sequence listing

| Category | SEQ ID NO: | Description | Type | Sequence |
|---|---|---|---|---|
| | | | | TGTACATCAGCCAGTTCATCATCATGTACAGCCTGGATGGCAAG AAGTGGCAGACCTACAGAGGCAACAGCACAGGCACACTCATGG TGTTCTTTGGCAATGTGGACAGCTCTGGCATTAAGCACAACATC TTCAACCCTCCAATCATTGCCAGATACATCAGACTGCACCCCAC ACACTACAGCATCAGATCTACCCTGAGAATGGAACTGATGGGCT GTGACCTGAACAGCTGCAGCATGCCCCTGGGAATGGAAAGCAA GGCCATCTCTGATGCCCAGATCACAGCCAGCAGCTACTTCACCA ACATGTTTGCCACTTGGAGCCCCTCCAAGGCTAGACTGCATCTG CAGGGCAGAAGCAATGCTTGGAGGCCCCAAGTGAACAACCCCA AAGAGTGGCTGCAGGTGGACTTTCAAAAGACCATGAAAGTGAC AGGAGTGACCACACAGGGAGTCAAGTCTCTGCTGACCTCTATGT ATGTGAAAGAGTTCCTGATCTCCAGCAGCCAGGATGGCCACCAG TGGACCCTGTTTTTCCAGAATGGCAAAGTGAAAGTGTTCCAGGG CAATCAGGACAGCTTCACACCTGTGGTCAACTCCCTGGATCCTC CACTGCTGACCAGATACCTGAGAATTCACCCTCAGTCTTGGGTG CACCAGATTGCTCTGAGAATGGAAGTGCTGGGCTGTGAAGCTCA GGACCTCTACTGATCGCGAATAAAAGATCTTTATTTTCATTAGA TCTGTGTGTTGGTTTTTTGTGTGTATTTAGCTATTTATTACGGTCT CATAGGGCCTGCCTCTTAGGTCAGTGAAGAGAAGAACAAATTCC TCACGTGCATAGT |
| MG29-1 sgRNA targeting mouse albumin | 24 | mAlb29-8-50b | Nucleotide | mG*mU*mU*GAGAAUC*mG*mA*mA*mAGAUUCUCAAC*mC*mU *mU*U*UAAUUmUmCmUmACU*G*U*U*GUAGAUCUGUAACfGfA fUfCfGfGfGfAfAfC*fU*fG*mG |
| MG29-1 sgRNA targeting mouse albumin | 25 | mAlb29-12-50b | Nucleotide | mG*mU*mU*GAGAAUC*mG*mA*mA*mAGAUUCUCAAC*mC*mU *mU*U*UAAUUmUmCmUmACU*G*U*U*GUAGAUAGUGUAGfCf AfGfAfGfAfGfGfAfA*fC*fC*mA |
| MG3-6/3-4 sgRNA targeting mouse albumin | 26 | mAlb3634-34 | Nucleotide | mC*mU*mU*AGGUCAGUGAAGAGAAGAAGUUGAGAAUCGAAA GAUUCUUAAUAAGGCAUCCUUCCGAUGCUGACUUCUCACCGU CCGUUUUCCAAUAGGAGCGGGCGGUAUGU*mU*mU*mU |
| MG3-6/3-4 sgRNA targeting mouse albumin | 27 | mAlb3634-59 | Nucleotide | mA*mG*mG*CAGGCCCUAUGAGACCGUAGUUGAGAAUCGAAAG AUUCUUAAUAAGGCAUCCUUCCGAUGCUGACUUCUCACCGUC CGUUAUCCAAUAGGAGCGGGCGGUAUGU*mU*mU*mU |
| PCR primer | 28 | mAlb90F PCR primer | Nucleotide | CTCCTCTTCGTCTCCGGC |
| PCR primer | 29 | mAlb1073R PCR primer | Nucleotide | CTGCCACATTGCTCAGCAC |
| DNA sequence encoding the MG3-6/3-4 mRNA | 30 | DNA sequence encoding the MG3-6/3-4 mRNA | Nucleotide | ATGGCCCCCAAGAAGAAGCGGAAAGTTGGCGGCGGAGGCAGCA GCACCGACATGAAGAACTACCGGATCGGCGTGGACGTGGGCGA TAGATCTGTTGGACTGGCCGCCATCGAGTTCGACGATGATGGAC TGCCCATCCAGAAGCTGGCCCTGGTCACCTTTAGACACGATGGC GGACTGGACCCCACCAAGAACAAGACCCCTATGAGCCGGAAAG |

TABLE 23-continued

Listing of additional protein and nucleic acid sequences referred to herein not included in the sequence listing

| Category | SEQ ID NO: | Description | Type | Sequence |
|---|---|---|---|---|
| | | | | AGACACGGGGAATCGCCAGACGGACCATGCGGATGAACAGAGA<br>GCGGAAGCGGCGGCTGAGAAACCTGGACAACGTGCTGGAAAAC<br>CTGGGCTACTCTGTGCCTGAGGGCCCTGAGCCTGAGACATATGA<br>GGCCTGGACAAGCAGAGCCCTGCTGGCCTCTATCAAACTGGCCT<br>CTGCCGACGAGCTGAACGAACACCTTGTCAGAGCCGTGCGGCA<br>CATGGCCAGACATAGAGGATGGGCCAATCCTTGGTGGTCCCTGG<br>ACCAGCTGGAAAAGGCCAGCCAAGAGCCTAGCGAGACATTCGA<br>GATCATCCTGGCCAGAGCCAGAGAGCTGTTCGGCGAGAAGGTG<br>CCCGCTAATCCTACACTGGGAATGCTGGGAGCCCTGGCCGCTAA<br>CAATGAGGTGCTGCTGAGGCCCAGGGACGAGAAGAAGAGAAAG<br>ACCGGATACGTGCGGGGCACCCCTCTGATGTTTGCTCAAGTTCG<br>ACAGGGCGATCAGCTGGCCGAGCTGCGGAGAATTTGTGAAGTG<br>CAGGGCATCGAGGACCAGTACGAGGCTCTGAGACTGGGCGTGT<br>TCGACCACAAGCACCCCTACGTGCCCAAAGAAAGAGTGGGCAA<br>AGACCCTCTGAACCCCAGCACCAACAGAACCATCAGAGCCAGC<br>CTGGAATTTCAAGAGTTCCGCATCCTGGACAGCGTGGCCAATCT<br>GAGAGTGCGGATCGGCAGCAGAGCCAAGAGGGAACTGACAGA<br>GGCCGAGTATGATGCCGCCGTGGAATTCCTGATGGACTACGCCG<br>ACAAAGAGCAGCCTAGCTGGGCCGATGTGGCCGAGAAAATTGG<br>CGTGCCCGGCAACAGACTGGTGGCCCCTGTTCTGGAAGATGTGC<br>AGCAGAAAACAGCCCCTTACGACAGAAGCAGCGCCGCCTTTGA<br>GAAGGCCATGGGCAAGAAAACCGAGGCCAGACAGTGGTGGGA<br>GTCCACCGATGATGACCAGCTGAGAAGCCTGCTGATTGCCTTCC<br>TGGTGGACGCCACCAACGACACAGAAGAAGCCGCTGCTGAAGC<br>CGGCCTGAGCGAGCTGTATAAGTCTTGGCCTGCCGAGGAAAGA<br>GAGGCCCTGTCCAACATCGACTTCGAGAAGGGCAGAGTGGCCT<br>ACAGCCAAGAAACCCTGAGCAAGCTGAGCGAGTACATGCACGA<br>GTACAGAGTGGGACTGCACGAGGCTAGAAAGGCCGTGTTCGGA<br>GTGGATGATACCTGGCGGCCTCCTCTGGATAAGCTGGAAGAACC<br>TACAGGACAGCCTGCCGTGGACAGAGTGCTGACCATCCTGAGA<br>AGATTCGTGCTGGACTGCGAGCGGCAATGGGGCAGACCTAGAG<br>CCATCACCGTGGAACACACACGGACAGGCCTGATGGGCCCAAC<br>ACAGAGACAGAAGATCCTGAACGAGCAGAAGAAGAACCGGGC<br>CGACAACGAGAGAATCCGGGATGAGCTGAGAGAATCTGGCGTG<br>GACAACCCCTCCAGAGCCGAAGTTCGGAGACACCTGATCGTGC<br>AAGAGCAAGAGTGCCAGTGCCTGTACTGCGGCACCATGATCAC<br>CACCACCACAAGCGAGCTGGACCACATCGTTCCTAGAGCCGGTG<br>GCGGCAGCAGCAGAAGGGAAAATCTGGCCGCTGTGTGCAGAGC<br>CTGCAACGCCAAGAAGAAACGCGAGCTGTTCTACGCCTGGGCT<br>GGCCCAGTGAAGTCCCAAGAGACAATCGAGAGAGTCAGACAGC<br>TGAAGGCCTTTAAGGACAGCAAGAAAGCCAAGATGTTCAAGAA<br>CCAGATCCGCCGGCTGAACCAGACCGAGGCCGATGAGCCTATC<br>GACGAAAGAAGCCTGGCCAGCACATCTTACGCCGCTGTGGCCGT<br>TAGAGAGCGGCTGGAACAGCACTTCAACGAAGGCCTGGCACTG<br>GACGACAAGTCCAGAGTGGTGCTGGATGTGTATGCCGGCGCTGT<br>GACCAGAGAGTCTCGTAGAGCTGGCGGCATCGACGAGCGGATT<br>CTGCTGAGAGGCGAGCGGGACAAGAACAGATTCGATGTGCGGC |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | ATCACGCCGTGGACGCTGCTGTTATGACCCTGCTGAACAGATCC GTGGCTCTGACCCTGGAACAGAGATCACAGCTGAGGCGGGCCTT CTACGAGCTGGAACTGGACAAACTGGACCGGGACCAGCTCAAG CCTGGCGAGGATTGGAGAAACTTCACCGGCCTGTACGAGGCCTC TCAGAACAAGTTCAGCGAGTGGAAGAAAGCCGCCACAGTGCTG GGAGATCTGCTGGCTGAAGCCATCGAGGATGACGCCATTGCCGT GGTGTCTCCACTGAGACTGAGGCCCCAGAATGGCAGCGTGCAC GACGATACCATCAACGCCGTGAAGAAGCTGACACTGGGCTCTG CCTGGCCTGCAGACGCTGTGAAGAGAATCGTGGACCCCGAGAT CTACCTGGCTATGAAGGACGTGCTGGGCAAGCTGAAAGAGCTG CCCGAGGATTCTGCCAGATCTCTGGAACTGTCCGACGGCCGGTA CATCGAAGCCGATGACGAGGTGCTGTTCTTCCCAAAGAAGGCCG CTAGCATCCTGACACCTAGAGGCGCCGCTGAGATCGGCAACTCT ATCCACCATGCCAGACTGTATAGCTGGCTGACCAAGAAGGGCG AGCTGAAGTTTGGCATGCTGAGAGTGTACGGCGCCGAGTTTCCC TGGCTGATGAGAGAGTCTGGAAGCCGCGACGTGCTGCATATGCC TATTCACCCTGGCAGCCAGAGCTTCAGAGGCATGCAGGATGGCG TGCGGAAAGCCGTGGAAAGCGGAGAGGCTGTGGAATTCGGCTG GATCACCCAGGACGATGAGCTGGAATTCGACCCCGAGGACTAC ATTGCCCACGGCGGAGATGACGAACTGAACAGACTGCTGCGAG TGATGCCCGAGAGAAGGTGGCGAGTGGACGGCTTCTATAACGC CGGCACACTGAGAATCAGACCCGCTCTGCTGTCTGCTGAGCAGC TGCCTTCTGAGCTGCAGAAAAAGGTGGCCGACAAGACCCTGAG CGACGTGGAACTGATCCTGCTGAGGGCTGTTCAGCGGGGACTGT TCGTGGCCATCAGCAGCTTTCTGCCCCTGGAAAGCCTGAAAGTG ATCCGGCGGAACAATCTGGGCTTCCCCAGGTGGCGCGGAAACG GAAATCTGCCCACCAGCTTTGAAGTGCGGAGCAGCGCTCTGAGA GCCCTGGGAGTTGAAGGATCTGGCGGAAAAAGACCTGCCGCCA CAAAGAAAGCCGGACAGGCCAAGAAAAAGAAG |
| DNA sequence encoding the MG29-1 mRNA | 31 | DNA sequence encoding the MG29-1 mRNA | Nucleotide | AAAAGCCAGCTCCAGCAGGCGCTGCTCACTCCTCCCCATCCTCT CCCTCTGTCCCTCTGTCCCTCTGACCCTGCACTGTCCCAGCACCA TGGCCCCTAAGAAGAAGAGAAAAGTCGGCGGAGGCGGCAGCTT CAACAACTTCATCAAGAAGTACAGCCTGCAGAAAACCCTGCGCT TCGAGCTGAAGCCTGTGGGCGAGACAGCCGACTACATCGAGGA CTTCAAGAGCGAGTACCTGAAGGACACCGTGCTGAAGGACGAG CAGAGAGCCAAGGACTACCAAGAGATCAAGACCCTGATCGACG ATTACCACCGCGAGTACATCGAAGAGTGCCTGAGAGAACCCGT GGACAAGAAAACCGGCGAGATCCTGGACTTCACCCAGGACCTG GAAGATGCCTTCAGCTACTACCAGAAGCTGAAAGAGAACCCCA CCGAGAACAGAGTCGGCTGGGAGAAAGAGCAAGAGAGCCTGA GGAAGAAGCTGGTCACCTCCTTCGTGGGCAACGACGGCCTGTTC AAGAAAGAGTTCATCACCAGGGACCTGCCTGAGTGGCTGCAGA AGAAAGGACTCTGGGGCGAGTACAAGGACACAGTGGAAAACTT CAAGAAGTTCACCACCTACTTCAGCGGCTTCCACGAGAACCGGA AGAACATGTACACCGCCGAGGCTCAGAGCACCGCTATCGCCAA CAGACTGATGAACGACAACCTGCCTAAGTTCTTTAACAACTACC |

TABLE 23-continued

Listing of additional protein and nucleic acid sequences referred to herein not included in the sequence listing

| Category | SEQ ID NO: | Description | Type | Sequence |
|---|---|---|---|---|
| | | | | TGGCCTACCAGACCATCAAAGAGAAGCACCCCGACCTGGTGTTC |
| | | | | AGACTGGATGATGCTCTGCTGCAGGCCGCTGGCGTGGAACATCT |
| | | | | GGATGAGGCTTTCCAGCCTAGATACTTCAGCAGACTGTTCGCCC |
| | | | | AGAGCGGCATCACCGCTTTCAACGAGCTGATCGGCGGCAGAAC |
| | | | | CACAGAGAACGGCGAGAAGATCCAGGGCCTGAACGAGCAGATC |
| | | | | AACCTGTACAGACAGCAGAACCCCGAGAAGGCCAAGGGCTTCC |
| | | | | CCAGATTCATGCCTCTGTTCAAGCAGATCCTGAGCGACAGAGAG |
| | | | | ACACACAGCTTTCTGCCCGACGCCTTCGAGAACGACAAAGAGCT |
| | | | | GCTCCAGGCTCTGAGAGACTACGTGGACGCCGCCACATCTGAGG |
| | | | | AAGGCATGATCAGCCAGCTGAACAAGGCCATGAACCAGTTCGT |
| | | | | GACCGCCGACCTGAAGAGAGTGTACATCAAGAGCGCCGCTCTG |
| | | | | ACCAGCCTGAGCCAAGAGCTGTTCCACTTCTTCGGCGTGATCAG |
| | | | | CGACGCTATCGCTTGGTACGCCGAGAAGAGACTGAGCCCCAAG |
| | | | | AAGGCCCAAGAGTCTTTCCTGAAGCAAGAGGTGTACGCCATCG |
| | | | | AGGAACTGAACCAGGCTGTCGTGGGCTACATCGACCAGCTGGA |
| | | | | AGATCAGAGCGAGCTGCAGCAACTGCTGGTGGACCTGCCAGAT |
| | | | | CCTCAGAAACCCGTGTCCAGCTTCATCCTGACACACTGGCAGAA |
| | | | | GTCTCAAGAGCCCCTGCAGGCAGTGATCGCCAAGGTGGAACCTC |
| | | | | TGTTCGAACTGGAAGAACTGAGCAAGAACAAGAGGGCCCCAAA |
| | | | | GCACGACAAGGACCAAGGCGGCGAGGGATTTCAGCAGGTCGAC |
| | | | | GCCATCAAGAACATGCTGGACGCCTTCATGGAAGTGTCCCACGC |
| | | | | TATCAAGCCCCTGTACCTGGTCAAGGGAAGAAAGGCCATCGAC |
| | | | | ATGCCCGACGTGGACACCGGCTTCTACGCTGATTTCGCCGAGGC |
| | | | | CTACAGCGCCTACGAGCAAGTGACAGTGTCCCTGTACAACAAG |
| | | | | ACCAGAAACCACCTGTCCAAGAAGCCCTTCAGCAAGGACAAGA |
| | | | | TCAAGATCAACTTCGACGCCCCTACACTGCTGAACGGCTGGGAC |
| | | | | CTGAACAAAGAGAGCGACAACAAGTCCATCATCCTGCGGAAGG |
| | | | | ACGGCAACTTCTACCTGGCAATCATGCACCCCAAGCACACCAAG |
| | | | | GTGTTCGACTGCTACTCTGCCTCTGAGGCTGCCGGCAAGTGCTA |
| | | | | CGAGAAGATGAACTACAAGCTGCTGAGCGGCGCCAACAAGATG |
| | | | | CTGCCTAAGGTGTTCTTTAGCAAGAAGGGCATCGAGACATTCAG |
| | | | | CCCTCCACAAGAAATCCTGGACCTGTACAAGAACAACGAGCAT |
| | | | | AAGAAGGGCGCCACCTTCAAGCTGGAATCCTGCCACAAGCTGA |
| | | | | TCGATTTCTTCAAGCGGAACATCCCCAAGTACAAGGTGCACCCT |
| | | | | ACCGACAACTTTGGCTGGGACGTGTTCGGCTTTCACTTCAGCCC |
| | | | | TACCAGCAGCTACGGCGACCTGTCTGGCTTCTACAGAGAGGTGG |
| | | | | AAGCCCAGGGATACAAGCTGTGGTTCAGCGACGTGTCCGAGGC |
| | | | | TTACATCAACAAATGCGTGGAAGAGGGCAAGCTGTTCCTGTTCC |
| | | | | AAATCTACAACAAGGACTTCTCCCCTAACTCCACCGGCAAGCCC |
| | | | | AACCTGCACACCCTGTATTGGAAGGGCCTGTTCGAGCCCGAGAA |
| | | | | CCTGAAAGACGTGGTGCTGAAGCTGAATGGCGAGGCCGAGATC |
| | | | | TTCTACCGGAAGCACAGCATCAAGCACGAGGACAAGACCATCC |
| | | | | ACAGAGCTAAGGACCCTATCGCTAACAAGAACGCTGACAACCC |
| | | | | CAAGAAACAGAGCGTGTTCGATTACGACATCATCAAGGATAAG |
| | | | | CGGTATACCCAGGACAAGTTCTTCTTCCACGTGCCAATCAGCCT |
| | | | | GAACTTCAAAAGCCAGGGCGTCGTGCGGTTCAACGATAAGATC |
| | | | | AACGGCCTGCTGGCCGCTCAGGACGATGTGCATGTGATCGGCAT |

TABLE 23-continued

Listing of additional protein and nucleic acid sequences referred to herein not included in the sequence listing

| Category | SEQ ID NO: | Description | Type | Sequence |
|---|---|---|---|---|
| | | | | CGACAGAGGCGAGAGACATCTGCTGTACTACACCGTGGTCAAC<br>GGCAAGGGCGAAGTGGTGGAACAGGGCAGCCTGAATCAGGTGG<br>CCACAGATCAGGGCTACGTGGTGGATTACCAGCAGAAGCTGCA<br>CGCCAAAGAGAAAGAACGCGACCAGGCCAGAAAGAACTGGTCC<br>ACCATCGAGAACATCAAAGAACTGAAGGCCGGCTACCTGAGCC<br>AGGTGGTGCATAAGCTGGCTCAGCTGATCGTGAAGCACAACGC<br>CATCGTGTGCCTCGAGGACCTGAATTTCGGCTTCAAGAGGGGCA<br>GATTCAAGGTCGAGAAACAGGTGTACCAGAAGTTCGAGAAGGC<br>TCTGATCGACAAGCTGAACTACCTCGTGTTCAAAGAGAGAGGCG<br>CCACACAGGCTGGCGGATACCTGAATGCTTACCAGCTGGCCGCA<br>CCTTTCGAGAGCTTTGAGAAGCTGGGCAAGCAGACCGGCATCCT<br>GTACTACGTGCGGAGCGACTACACCAGCAAGATCGACCCTGCTA<br>CCGGCTTCGTGGACTTTCTGAAGCCTAAGTACGAGAGCATGGCC<br>AAGAGCAAAGTGTTCTTCGAGTCCTTCGAGCGCATCCAGTGGAA<br>CCAGGCCAAAGGCTACTTCGAGTTCGAGTTTGACTACAAGAAGA<br>TGTGCCCCAGCAGAAAGTTCGGCGACTACAGAACCAGATGGGT<br>CGTGTGCACCTTCGGCGACACCCGCTACCAGAACAGAAGAAAC<br>AAGAGCAGCGGCCAGTGGGAGACAGAGACAATCGATGTGACAG<br>CCCAGCTGAAAGCCCTGTTCGCCGCTTACGGCATCACATACAAT<br>CAAGAGGATAACATCAAGGACGCCATTGCCGCCGTGAAGTACA<br>CCAAGTTCTACAAGCAGCTGTACTGGCTGCTGAGACTGACCCTG<br>AGCCTGAGACACAGCGTGACAGGCACCGACGAGGATTTCATCC<br>TGTCTCCAGTGGCCGACGAGAATGGCGTGTTCTTTGACTCTAGG<br>AAGGCCACCGACAAGCAGCCTAAGGACGCTGATGCTAACGGCG<br>CCTACCATATCGCCCTGAAAGGCCTGTGGAATCTCCAGCAGATC<br>AGACAGCACGACTGGAACGTGGAAAAGCCCAAAAAGCTGAACC<br>TCGCCATGAAGAACGAAGAGTGGTTCGGCTTCGCTCAGAAGAA<br>GAAGTTTAGAGCCAGCGGCGGCAAGAGGCCTGCCGCTACAAAA<br>AAAGCCGGCCAGGCCAAGAAAAAGAAGTGACCACACCCCCATT<br>CCCCCACTCCAGATAGAACTTCAGTTATATCTCACGTGTCTGGA<br>GTT |
| FVIII donor template | 32 | Full non-viral DNA donor template for FVIII with guide sites in F-R orientation (pMG4022) | Nucleotide | ATGCTTTGCATACTTCTGCCTGCTGGGGAGCCTGGGGACTTTCC<br>ACACCCTAACTGACACACATTCCACTGAATTTTGTAATCGGTTG<br>GCAGCCAATGAAATACAAAGATGAGTCTAGTTAATAATCTACA<br>ATTATTGGTTAAAGAAGTATATTAGTTCAGATTCAGAATGTCAA<br>TATTTCCTGTAACGATCGGGAACTGGCATTTGAGTGTAGCAGAG<br>AGGAACCATTTCTCAGTGTTAAGCTTACTAAAGAATTATTCTTTT<br>ACATTTCAGTGGCCACCAGAAGATATTACCTGGGAGCTGTGGAA<br>CTGAGCTGGGACTACATGCAGTCTGACCTGGGAGAGCTGCCTGT<br>GGATGCTAGATTTCCTCCAAGAGTGCCCAAGAGCTTCCCCTTCA<br>ACACCTCTGTGGTGTACAAGAAAACCCTGTTTGTGGAATTCACA<br>GACCACCTGTTCAATATTGCCAAGCCTAGACCTCCTTGGATGGG<br>ACTGCTGGGACCTACAATTCAGGCTGAGGTGTATGACACAGTGG<br>TCATCACCCTGAAGAACATGGCCAGCCATCCTGTGTCTCTGCAT<br>GCTGTGGGAGTGTCTTACTGGAAGGCTTCTGAGGGAGCTGAGTA<br>TGATGACCAGACAAGCCAGAGAGAGAAAGAGGATGACAAGGTT |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | TTCCCTGGAGGCAGCCACACCTATGTCTGGCAGGTCCTGAAAGA |
| | | | | AAATGGCCCTATGGCCTCTGATCCTCTGTGCCTGACATACAGCT |
| | | | | ACCTGAGCCATGTGGACCTGGTCAAGGACCTGAATTCTGGCCTG |
| | | | | ATTGGAGCCCTGCTGGTGTGTAGAGAAGGCAGCCTGGCCAAAG |
| | | | | AGAAAACCCAGACACTGCACAAGTTCATCCTGCTGTTTGCTGTG |
| | | | | TTTGATGAGGGCAAGAGCTGGCACTCTGAGACAAAGAACAGCC |
| | | | | TGATGCAGGACAGGGATGCTGCCTCTGCTAGAGCTTGGCCTAAG |
| | | | | ATGCACACAGTGAATGGCTATGTGAACAGAAGCCTGCCTGGACT |
| | | | | GATTGGCTGCCACAGAAAGTCTGTGTACTGGCATGTGATTGGCA |
| | | | | TGGGCACAACACCTGAGGTGCACAGCATCTTTCTGGAAGGACAC |
| | | | | ACCTTCCTGGTGAGAAACCATAGACAGGCCAGCCTGGAAATCA |
| | | | | GCCCTATCACCTTCCTGACAGCTCAGACCCTGCTGATGGATCTG |
| | | | | GGCCAGTTTCTGCTGTTCTGCCACATCAGCAGCCACCAGCATGA |
| | | | | TGGCATGGAAGCCTATGTGAAGGTGGACAGCTGCCCTGAAGAA |
| | | | | CCCCAGCTGAGAATGAAGAACAATGAGGAGGCTGAGGACTATG |
| | | | | ATGATGACCTGACAGACTCTGAGATGGATGTGGTCAGATTTGAT |
| | | | | GATGACAACAGCCCCAGCTTCATCCAGATCAGATCTGTGGCCAA |
| | | | | GAAGCACCCCAAGACCTGGGTGCACTATATTGCTGCTGAGGAA |
| | | | | GAGGACTGGGATTATGCTCCTCTGGTGCTGGCCCCTGATGACAG |
| | | | | AAGCTACAAGAGCCAGTACCTGAACAATGGCCCTCAGAGAATT |
| | | | | GGCAGAAAGTATAAGAAAGTGAGATTCATGGCCTACACAGATG |
| | | | | AGACATTCAAGACCAGAGAGGCCATTCAGCATGAGTCTGGCATT |
| | | | | CTGGGCCCTCTGCTGTATGGAGAAGTGGGAGATACACTGCTGAT |
| | | | | CATCTTCAAGAACCAGGCCAGCAGACCCTACAACATCTACCCTC |
| | | | | ATGGCATCACAGATGTGAGACCCCTGTATTCCAGAAGGCTGCCC |
| | | | | AAGGGAGTGAAGCACCTGAAGGACTTCCCTATCCTGCCTGGAG |
| | | | | AGATCTTCAAGTACAAGTGGACAGTGACAGTGGAAGATGGCCC |
| | | | | CACCAAGTCTGACCCTAGATGTCTGACAAGATACTACAGCAGCT |
| | | | | TTGTGAACATGGAAAGAGACCTGGCCTCTGGCCTGATTGGACCT |
| | | | | CTGCTGATCTGCTACAAAGAATCTGTGGACCAGAGAGGCAACC |
| | | | | AGATCATGTCTGACAAGAGAAATGTGATCCTGTTTTCTGTGTTT |
| | | | | GATGAGAACAGATCCTGGTATCTGACAGAGAACATCCAGAGAT |
| | | | | TTCTGCCCAATCCTGCTGGAGTGCAGCTGGAAGATCCTGAGTTC |
| | | | | CAGGCCTCCAACATCATGCACTCCATCAATGGCTATGTGTTTGA |
| | | | | CAGCCTGCAGCTGTCTGTGTGCCTGCATGAAGTGGCCTACTGGT |
| | | | | ACATCCTGAGCATTGGAGCCCAGACAGACTTCCTGTCTGTGTTC |
| | | | | TTCTCTGGCTACACCTTCAAGCACAAGATGGTGTATGAGGATAC |
| | | | | CCTGACACTGTTCCCATTCTCTGGAGAGACAGTGTTCATGAGCA |
| | | | | TGGAAAACCCTGGCCTGTGGATCCTGGGCTGTCACAACTCTGAC |
| | | | | TTCAGAAACAGAGGCATGACAGCCCTGCTGAAGGTGTCCAGCT |
| | | | | GTGACAAGAACACAGGAGACTACTATGAGGACAGCTATGAGGA |
| | | | | CATCTCTGCCTACCTGCTGAGCAAGAACAATGCCATTGAGCCCA |
| | | | | GAAGCTTCAGCCAGAATGCCACCAATGTGTCCAACAACAGCAA |
| | | | | CACCAGCAATGACTCCAATGTGTCCCCTCCAGTGCTGAAGAGAC |
| | | | | ACCAGAGAGAAATCACCAGAACCACACTGCAGTCTGACCAAGA |
| | | | | GGAAATTGACTATGATGACACCATCTCTGTGGAGATGAAGAAA |
| | | | | GAAGATTTTGACATCTATGATGAGGATGAGAATCAGAGCCCCA |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | GATCCTTTCAGAAAAAGACCAGACACTACTTCATTGCTGCTGTG |
| | | | | GAGAGACTGTGGGACTATGGCATGTCTAGCAGCCCTCATGTGCT |
| | | | | GAGAAATAGAGCCCAGTCTGGCTCTGTGCCCCAGTTCAAGAAA |
| | | | | GTGGTGTTCCAAGAGTTCACAGATGGCAGCTTCACCCAGCCACT |
| | | | | GTATAGAGGAGAGCTGAATGAGCATCTGGGCCTGCTGGGCCCTT |
| | | | | ATATCAGAGCTGAAGTGGAAGATAACATCATGGTCACCTTCAGA |
| | | | | AATCAGGCCTCTAGGCCCTACAGCTTCTACAGCTCCCTGATCAG |
| | | | | CTATGAAGAGGACCAGAGACAGGGAGCTGAGCCCAGAAAGAAC |
| | | | | TTTGTGAAGCCCAATGAGACTAAGACCTACTTTTGGAAGGTGCA |
| | | | | GCACCACATGGCCCCTACAAAGGATGAGTTTGACTGCAAGGCCT |
| | | | | GGGCCTACTTTTCTGATGTGGATCTGGAAAAGGATGTGCACTCT |
| | | | | GGACTCATTGGACCACTGCTTGTGTGCCACACCAACACACTGAA |
| | | | | CCCTGCTCATGGCAGACAAGTGACAGTGCAAGAGTTTGCCCTGT |
| | | | | TCTTCACCATCTTTGATGAAACAAAGAGCTGGTACTTCACAGAG |
| | | | | AATATGGAGAGAAACTGCAGGGCCCCTTGCAACATCCAGATGG |
| | | | | AAGATCCCACCTTCAAAGAGAACTACAGATTCCATGCCATCAAT |
| | | | | GGCTACATCATGGACACACTGCCTGGCCTGGTTATGGCTCAGGA |
| | | | | TCAGAGAATCAGATGGTATCTGCTGTCCATGGGCTCCAATGAGA |
| | | | | ATATCCACAGCATCCACTTCTCTGGCCATGTGTTCACAGTGAGA |
| | | | | AAAAAAGAAGAGTACAAAATGGCCCTGTACAATCTGTACCCTG |
| | | | | GGGTGTTTGAAACAGTGGAAATGCTGCCTTCCAAGGCTGGCATT |
| | | | | TGGAGAGTGGAATGTCTGATTGGAGAGCACCTCCATGCTGGAAT |
| | | | | GAGCACCCTGTTTCTGGTGTACAGCAACAAGTGTCAGACCCCTC |
| | | | | TGGGCATGGCCTCTGGACACATCAGAGACTTCCAGATCACAGCC |
| | | | | TCTGGCCAGTATGGACAGTGGGCTCCTAAACTGGCTAGACTGCA |
| | | | | CTACTCTGGCAGCATCAATGCCTGGTCCACCAAAGAGCCCTTCA |
| | | | | GCTGGATCAAGGTGGACCTGCTGGCTCCCATGATCATCCATGGA |
| | | | | ATCAAGACCCAGGGAGCCAGACAGAAGTTCAGCAGCCTGTACA |
| | | | | TCAGCCAGTTCATCATCATGTACAGCCTGGATGGCAAGAAGTGG |
| | | | | CAGACCTACAGAGGCAACAGCACAGGCACACTCATGGTGTTCTT |
| | | | | TGGCAATGTGGACAGCTCTGGCATTAAGCACAACATCTTCAACC |
| | | | | CTCCAATCATTGCCAGATACATCAGACTGCACCCCACACACTAC |
| | | | | AGCATCAGATCTACCCTGAGAATGGAACTGATGGGCTGTGACCT |
| | | | | GAACAGCTGCAGCATGCCCCTGGGAATGGAAAGCAAGGCCATC |
| | | | | TCTGATGCCCAGATCACAGCCAGCAGCTACTTCACCAACATGTT |
| | | | | TGCCACTTGGAGCCCCTCCAAGGCTAGACTGCATCTGCAGGGCA |
| | | | | GAAGCAATGCTTGGAGGCCCCAAGTGAACAACCCCAAAGAGTG |
| | | | | GCTGCAGGTGGACTTTCAAAAGACCATGAAAGTGACAGGAGTG |
| | | | | ACCACACAGGGAGTCAAGTCTCTGCTGACCTCTATGTATGTGAA |
| | | | | AGAGTTCCTGATCTCCAGCAGCCAGGATGGCCACCAGTGGACCC |
| | | | | TGTTTTTCCAGAATGGCAAAGTGAAAGTGTTCCAGGGCAATCAG |
| | | | | GACAGCTTCACACCTGTGGTCAACTCCCTGGATCCTCCACTGCT |
| | | | | GACCAGATACCTGAGAATTCACCCTCAGTCTTGGGTGCACCAGA |
| | | | | TTGCTCTGAGAATGGAAGTGCTGGGCTGTGAAGCTCAGGACCTC |
| | | | | TACTGATCCTGAATAAAAGATCTTTATTTTCATTAGATCTGTGTG |
| | | | | TTGGTTTTTTGTGTGTATTTAGCTAACAGTATGATTAAGTGGATA |
| | | | | AATGGTTCCTCTCTGCTACACTCAAATGCCAGTTCCCGATCGTTA |

TABLE 23-continued

Listing of additional protein and nucleic acid sequences referred to herein not included in the sequence listing

| Category | SEQ ID NO: | Description | Type | Sequence |
| --- | --- | --- | --- | --- |
| | | | | CAGGAAAAGATATGCTATACCTGATACTGAATTTTGTAATCGGT<br>TGGCAGCCAATGAAATACAAAGATGAGTCTAGTTAATAATCTAC<br>AATTATTGGTTAAAGAAGTATATTAGTATGCTTTGCATACTTCTG<br>CCTGCTGGGGAGCCTGGGGACTTTCCACACCCTAACTGACACAC<br>ATTCCAC |
| FVIII donor template | 33 | Full non-viral DNA donor template for FVIII with guide sites in R-F orientation (pMG4023) | Nucleotide | ATGCTTTGCATACTTCTGCCTGCTGGGGAGCCTGGGGACTTTCC<br>ACACCCTAACTGACACACATTCCACTGAATTTTGTAATCGGTTG<br>GCAGCCAATGAAATACAAAGATGAGTCTAGTTAATAATCTACA<br>ATTATTGGTTAAAGAAGTATATTAGTTCAGATTCAGAATGTCAA<br>TATGCCAGTTCCCGATCGTTACAGGAAAAAATGGTTCCTCTCTGC<br>TACACTCAAATCTCATATTAAGCTTACTAAAGAATTATTCTTTTA<br>CATTTCAGTGGCCACCAGAAGATATTACCTGGGAGCTGTGGAAC<br>TGAGCTGGGACTACATGCAGTCTGACCTGGGAGAGCTGCCTGTG<br>GATGCTAGATTTCCTCCAAGAGTGCCCAAGAGCTTCCCCTTCAA<br>CACCTCTGTGGTGTACAAGAAAACCCTGTTTGTGGAATTCACAG<br>ACCACCTGTTCAATATTGCCAAGCCTAGACCTCCTTGGATGGGA<br>CTGCTGGGACCTACAATTCAGGCTGAGGTGTATGACACAGTGGT<br>CATCACCCTGAAGAACATGGCCAGCCATCCTGTGTCTCTGCATG<br>CTGTGGGAGTGTCTTACTGGAAGGCTTCTGAGGGAGCTGAGTAT<br>GATGACCAGACAAGCCAGAGAGAGAAAGAGGATGACAAGGTTT<br>TCCCTGGAGGCAGCCACACCTATGTCTGGCAGGTCCTGAAAGAA<br>AATGGCCCTATGGCCTCTGATCCTCTGTGCCTGACATACAGCTA<br>CCTGAGCCATGTGGACCTGGTCAAGGACCTGAATTCTGGCCTGA<br>TTGGAGCCCTGCTGGTGTGTAGAGAAGGCAGCCTGGCCAAAGA<br>GAAAACCCAGACACTGCACAAGTTCATCCTGCTGTTTGCTGTGT<br>TTGATGAGGGCAAGAGCTGGCACTCTGAGACAAAGAACAGCCT<br>GATGCAGGACAGGGATGCTGCCTCTGCTAGAGCTTGGCCTAAGA<br>TGCACACAGTGAATGGCTATGTGAACAGAAGCCTGCCTGGACTG<br>ATTGGCTGCCACAGAAAGTCTGTGTACTGGCATGTGATTGGCAT<br>GGGCACAACACCTGAGGTGCACAGCATCTTTCTGGAAGGACAC<br>ACCTTCCTGGTGAGAAACCATAGACAGGCCAGCCTGGAAATCA<br>GCCCTATCACCTTCCTGACAGCTCAGACCCTGCTGATGGATCTG<br>GGCCAGTTTCTGCTGTTCTGCCACATCAGCAGCCACCAGCATGA<br>TGGCATGGAAGCCTATGTGAAGGTGGACAGCTGCCCTGAAGAA<br>CCCCAGCTGAGAATGAAGAACAATGAGGAGGCTGAGGACTATG<br>ATGATGACCTGACAGACTCTGAGATGGATGTGGTCAGATTTGAT<br>GATGACAACAGCCCCAGCTTCATCCAGATCAGATCTGTGGCCAA<br>GAAGCACCCCAAGACCTGGGTGCACTATATTGCTGCTGAGGAA<br>GAGGACTGGGATTATGCTCCTCTGGTGCTGGCCCCTGATGACAG<br>AAGCTACAAGAGCCAGTACCTGAACAATGGCCCTCAGAGAATT<br>GGCAGAAAGTATAAGAAAGTGAGATTCATGGCCTACACAGATG<br>AGACATTCAAGACCAGAGAGGCCATTCAGCATGAGTCTGGCATT<br>CTGGGCCCTCTGCTGTATGGAGAAGTGGGAGATACACTGCTGAT<br>CATCTTCAAGAACCAGGCCAGCAGACCCTACAACATCTACCCTC<br>ATGGCATCACAGATGTGAGACCCCTGTATTCCAGAAGGCTGCCC<br>AAGGGAGTGAAGCACCTGAAGGACTTCCCTATCCTGCCTGGAG |

TABLE 23-continued

Listing of additional protein and nucleic acid sequences referred to herein not included in the sequence listing

| Category | SEQ ID NO: | Description | Type | Sequence |
|---|---|---|---|---|
| | | | | AGATCTTCAAGTACAAGTGGACAGTGACAGTGGAAGATGGCCC |
| | | | | CACCAAGTCTGACCCTAGATGTCTGACAAGATACTACAGCAGCT |
| | | | | TTGTGAACATGGAAAGAGACCTGGCCTCTGGCCTGATTGGACCT |
| | | | | CTGCTGATCTGCTACAAAGAATCTGTGGACCAGAGAGGCAACC |
| | | | | AGATCATGTCTGACAAGAGAAATGTGATCCTGTTTTCTGTGTTT |
| | | | | GATGAGAACAGATCCTGGTATCTGACAGAGAACATCCAGAGAT |
| | | | | TTCTGCCCAATCCTGCTGGAGTGCAGCTGGAAGATCCTGAGTTC |
| | | | | CAGGCCTCCAACATCATGCACTCCATCAATGGCTATGTGTTTGA |
| | | | | CAGCCTGCAGCTGTCTGTGTGCCTGCATGAAGTGGCCTACTGGT |
| | | | | ACATCCTGAGCATTGGAGCCCAGACAGACTTCCTGTCTGTGTTC |
| | | | | TTCTCTGGCTACACCTTCAAGCACAAGATGGTGTATGAGGATAC |
| | | | | CCTGACACTGTTCCCATTCTCTGGAGAGACAGTGTTCATGAGCA |
| | | | | TGGAAAACCCTGGCCTGTGGATCCTGGGCTGTCACAACTCTGAC |
| | | | | TTCAGAAACAGAGGCATGACAGCCCTGCTGAAGGTGTCCAGCT |
| | | | | GTGACAAGAACACAGGAGACTACTATGAGGACAGCTATGAGGA |
| | | | | CATCTCTGCCTACCTGCTGAGCAAGAACAATGCCATTGAGCCCA |
| | | | | GAAGCTTCAGCCAGAATGCCACCAATGTGTCCAACAACAGCAA |
| | | | | CACCAGCAATGACTCCAATGTGTCCCCTCCAGTGCTGAAGAGAC |
| | | | | ACCAGAGAGAAATCACCAGAACCACACTGCAGTCTGACCAAGA |
| | | | | GGAAATTGACTATGATGACACCATCTCTGTGGAGATGAAGAAA |
| | | | | GAAGATTTTGACATCTATGATGAGGATGAGAATCAGAGCCCCA |
| | | | | GATCCTTTCAGAAAAAGACCAGACACTACTTCATTGCTGCTGTG |
| | | | | GAGAGACTGTGGGACTATGGCATGTCTAGCAGCCCTCATGTGCT |
| | | | | GAGAAATAGAGCCCAGTCTGGCTCTGTGCCCCAGTTCAAGAAA |
| | | | | GTGGTGTTCCAAGAGTTCACAGATGGCAGCTTCACCCAGCCACT |
| | | | | GTATAGAGGAGAGCTGAATGAGCATCTGGGCCTGCTGGGCCCTT |
| | | | | ATATCAGAGCTGAAGTGGAAGATAACATCATGGTCACCTTCAGA |
| | | | | AATCAGGCCTCTAGGCCCTACAGCTTCTACAGCTCCCTGATCAG |
| | | | | CTATGAAGAGGACCAGAGACAGGGAGCTGAGCCCAGAAAGAAC |
| | | | | TTTGTGAAGCCCAATGAGACTAAGACCTACTTTTGGAAGGTGCA |
| | | | | GCACCACATGGCCCCTACAAAGGATGAGTTTGACTGCAAGGCCT |
| | | | | GGGCCTACTTTTCTGATGTGGATCTGGAAAAGGATGTGCACTCT |
| | | | | GGACTCATTGGACCACTGCTTGTGTGCCACACCAACACACTGAA |
| | | | | CCCTGCTCATGGCAGACAAGTGACAGTGCAAGAGTTTGCCCTGT |
| | | | | TCTTCACCATCTTTGATGAAACAAAGAGCTGGTACTTCACAGAG |
| | | | | AATATGGAGAGAAACTGCAGGGCCCCTTGCAACATCCAGATGG |
| | | | | AAGATCCCACCTTCAAAGAGAACTACAGATTCCATGCCATCAAT |
| | | | | GGCTACATCATGGACACACTGCCTGGCCTGGTTATGGCTCAGGA |
| | | | | TCAGAGAATCAGATGGTATCTGCTGTCCATGGGCTCCAATGAGA |
| | | | | ATATCCACAGCATCCACTTCTCTGGCCATGTGTTCACAGTGAGA |
| | | | | AAAAAAGAAGAGTACAAAATGGCCCTGTACAATCTGTACCCTG |
| | | | | GGGTGTTTGAAACAGTGGAAATGCTGCCTTCCAAGGCTGGCATT |
| | | | | TGGAGAGTGGAATGTCTGATTGGAGAGCACCTCCATGCTGGAAT |
| | | | | GAGCACCCTGTTTCTGGTGTACAGCAACAAGTGTCAGACCCCTC |
| | | | | TGGGCATGGCCTCTGGACACATCAGAGACTTCCAGATCACAGCC |
| | | | | TCTGGCCAGTATGGACAGTGGGCTCCTAAACTGGCTAGACTGCA |
| | | | | CTACTCTGGCAGCATCAATGCCTGGTCCACCAAAGAGCCCTTCA |

TABLE 23-continued

Listing of additional protein and nucleic acid sequences referred to herein not included in the sequence listing

| Category | SEQ ID NO: | Description | Type | Sequence |
|---|---|---|---|---|
| | | | | GCTGGATCAAGGTGGACCTGCTGGCTCCCATGATCATCCATGGA<br>ATCAAGACCCAGGGAGCCAGACAGAAGTTCAGCAGCCTGTACA<br>TCAGCCAGTTCATCATCATGTACAGCCTGGATGGCAAGAAGTGG<br>CAGACCTACAGAGGCAACAGCACAGGCACACTCATGGTGTTCTT<br>TGGCAATGTGGACAGCTCTGGCATTAAGCACAACATCTTCAACC<br>CTCCAATCATTGCCAGATACATCAGACTGCACCCCACACACTAC<br>AGCATCAGATCTACCCTGAGAATGGAACTGATGGGCTGTGACCT<br>GAACAGCTGCAGCATGCCCCTGGGAATGGAAAGCAAGGCCATC<br>TCTGATGCCCAGATCACAGCCAGCAGCTACTTCACCAACATGTT<br>TGCCACTTGGAGCCCCTCCAAGGCTAGACTGCATCTGCAGGGCA<br>GAAGCAATGCTTGGAGGCCCCAAGTGAACAACCCCAAAGAGTG<br>GCTGCAGGTGGACTTTCAAAAGACCATGAAAGTGACAGGAGTG<br>ACCACACAGGGAGTCAAGTCTCTGCTGACCTCTATGTATGTGAA<br>AGAGTTCCTGATCTCCAGCAGCCAGGATGGCCACCAGTGGACCC<br>TGTTTTTCCAGAATGGCAAAGTGAAAGTGTTCCAGGGCAATCAG<br>GACAGCTTCACACCTGTGGTCAACTCCCTGGATCCTCCACTGCT<br>GACCAGATACCTGAGAATTCACCCTCAGTCTTGGGTGCACCAGA<br>TTGCTCTGAGAATGGAAGTGCTGGGCTGTGAAGCTCAGGACCTC<br>TACTGATCCTGAATAAAAGATCTTTATTTTCATTAGATCTGTGTG<br>TTGGTTTTTTGTGTGTATTTAGCTATTTGAGTGTAGCAGAGAGGA<br>ACCATTTTTCCTGTAACGATCGGGAACTGGCAAGATATGCTATA<br>CCTGATACTGAATTTTGTAATCGGTTGGCAGCCAATGAAATACA<br>AAGATGAGTCTAGTTAATAATCTACAATTATTGGTTAAAGAAGT<br>ATATTAGTATGCTTTGCATACTTCTGCCTGCTGGGGAGCCTGGG<br>GACTTTCCACACCCTAACTGACACACATTCCAC |
| Transcription factor binding sequence | 34 | OCT1 (POU2F1) TF binding site | Nucleotide | TATGCAAAT |
| Transcription factor binding sequence | 35<br><br>36 | AP1 TF binding site | Nucleotide | TGACTCA |
| Transcription factor binding sequence | | HNF1-A TF binding site | Nucleotide | (G/T)TTAAT(A/T)TT |
| Transcription factor binding sequence | 37<br><br>38 | HNF1-B TF binding site | Nucleotide | TTAATNNTTAAC |
| Transcription factor binding sequence | | CEBPA TF binding site | Nucleotide | TT(G/T)CA(C/T)AA(T/C) |

TABLE 23-continued

Listing of additional protein and nucleic acid sequences referred to herein not included in the sequence listing

| Category | SEQ ID NO: | Description | Type | Sequence |
|---|---|---|---|---|
| Transcription factor binding sequence | 39 | LEF-1 TF binding site | Nucleotide | AAGATCAAAG |
| Transcription factor binding sequence | 40 | FOX D1 TF binding site | Nucleotide | GTAAACA |
| Transcription factor binding sequence | 41 | IRF1 (option 1) TF binding site | Nucleotide | AAA(G/A)(C/T)GAAACC |
| Transcription factor binding sequence | | IRF1 (option 2) TF binding site | Nucleotide | cTTTCnnTTTC |
| MG29-1 sgRNA targeting mouse albumin | 43 | mAlbR1 guide RNA | Nucleotide | mU*mU*mA*GUAUAGCAUGGUCGAGCGUUUUAGAGCUAGAAA UAGCAAGUUAAAAUAAGGCUAGUCCGUUAUCAACUUGAAAAA GUGGCACCGAGUCGGUGCmU*mU*mU*U |
| MG29-1 sgRNA targeting mouse albumin | 44 | mAlbR2 guide RNA | Nucleotide | mU*mU*mC*CUGUAACGAUCGGGAACGUUUUAGAGCUAGAAAU AGCAAGUUAAAAUAAGGCUAGUCCGUUAUCAACUUGAAAAAG UGGCACCGAGUCGGUGCmU*mU*mU*U |
| MG29-1 sgRNA targeting mouse albumin | 45 | mAlbR3 guide RNA | Nucleotide | mU*mG*mC*CAGUUCCCGAUCGUUACGUUUUAGAGCUAGAAAU AGCAAGUUAAAAUAAGGCUAGUCCGUUAUCAACUUGAAAAAG UGGCACCGAGUCGGUGCmU*mU*mU*U |
| PCR Primer | 46 | mAlb90F PCR primer | Nucleotide | CTCCTCTTCGTCTCCGGC |
| PCR Primer | 47 | mAlb1073R PCR primer | Nucleotide | CTGCCACATTGCTCAGCAC |
| PCR Primer | 48 | mAlb282F PCR primer | Nucleotide | TTGCATCTGAGAACCCTTAGG |
| PCR Primer | 49 | mAlb460F PCR primer | Nucleotide | GCCTGCTCGACCATGCTATA |
| MG29-1 sgRNA targeting mouse albumin | 50 | mAlbR2 guide RNA with extensive chemical modifications | Nucleotide | mU*mU*mC*CUGUAACGAUCGGGAACGUUUUAGAmGmCmUmA GAAAmUmAmGmCAAGUUAAAAUAAGGCUAGUCCGUUAUCmA mAmCmUmUGAAAmAmAmGmUmGmGmCmAmCmCmGmAmGmU mCmGmGmUmGmCmU*mU*mU*U |
| DNA sequence encoding the spCas9 mRNA | 51 | Template DNA for spCas9 in vitro transcription | Nucleotide | GCGGCCGCTAATACGACTCACTATAAGAAAAGCCAGCTCCAGC AGGCGCTGCTCACTCCTCCCCATCCTCTCCCTCTGTCCCTCTGTC CCTCTGACCCTGCACTGTCCCAGCACCATGGCCCCCAAGAAGAA GCGGAAAGTTGGCGGCGGAGGCAGCGACAAGAAGTACTCTATC GGCCTGGACATCGGCACCAACTCTGTTGGATGGGCCGTGATCAC |

TABLE 23-continued

Listing of additional protein and nucleic acid sequences referred to herein not included in the sequence listing

| Category | SEQ ID NO: | Description | Type | Sequence |
|---|---|---|---|---|
| | | | | CGACGAGTACAAGGTGCCCAGCAAGAAATTCAAGGTGCTGGGC |
| | | | | AACACCGACCGGCACAGCATCAAGAAGAATCTGATCGGCGCCC |
| | | | | TGCTGTTCGACTCTGGCGAAACAGCCGAAGCCACCAGACTGAA |
| | | | | GAGAACCGCCAGACGGCGGTACACCAGAAGAAAGAACCGGATC |
| | | | | TGCTACCTGCAAGAGATCTTCAGCAACGAGATGGCCAAGGTGG |
| | | | | ACGACAGCTTCTTCCACAGACTGGAAGAGTCCTTCCTGGTGGAA |
| | | | | GAGGACAAGAAGCACGAGCGGCACCCCATCTTCGGCAACATCG |
| | | | | TGGATGAGGTGGCCTACCACGAGAAGTACCCCACCATCTACCAC |
| | | | | CTGAGAAAGAAACTGGTGGACAGCACCGACAAGGCCGACCTGA |
| | | | | GACTGATCTATCTGGCCCTGGCTCACATGATCAAGTTCCGGGGC |
| | | | | CACTTCCTGATCGAGGGCGACCTGAATCCTGACAACAGCGACGT |
| | | | | GGACAAGCTGTTCATCCAGCTGGTGCAGACCTACAACCAGCTGT |
| | | | | TCGAGGAAAACCCCATCAACGCCAGCGGAGTGGATGCCAAGGC |
| | | | | CATCCTGTCTGCCAGACTGAGCAAGAGCAGACGGCTGGAAAAC |
| | | | | CTGATCGCTCAGCTGCCCGGCGAGAAGAAGAATGGCCTGTTCGG |
| | | | | CAACCTGATTGCCCTGAGCCTGGGCCTGACACCTAACTTCAAGA |
| | | | | GCAACTTCGACCTGGCCGAGGACGCCAAACTGCAGCTGTCCAA |
| | | | | GGACACCTACGACGACGACCTGGACAATCTGCTGGCCCAGATC |
| | | | | GGCGATCAGTACGCCGACTTGTTTCTGGCCGCCAAGAACCTGTC |
| | | | | CGACGCCATCCTGCTGAGCGACATCCTGAGAGTGAACACCGAG |
| | | | | ATCACAAAGGCCCCTCTGAGCGCCTCTATGATCAAGAGATACGA |
| | | | | CGAGCACCACCAGGATCTGACCCTGCTGAAGGCCCTCGTTAGAC |
| | | | | AGCAGCTGCCTGAGAAGTACAAAGAGATTTTCTTCGACCAGAGC |
| | | | | AAGAACGGCTACGCCGGCTACATTGATGGCGGAGCCAGCCAAG |
| | | | | AGGAATTCTACAAGTTCATCAAGCCCATCCTCGAGAAGATGGAC |
| | | | | GGCACCGAGGAACTGCTGGTCAAGCTGAACAGAGAGGACCTGC |
| | | | | TGCGGAAGCAGCGGACCTTCGACAATGGCTCTATCCCTCACCAG |
| | | | | ATCCACCTGGGAGAGCTGCACGCCATTCTGCGGAGACAAGAGG |
| | | | | ACTTTTACCCATTCCTGAAGGACAACCGGGAAAAGATTGAGAA |
| | | | | GATCCTGACCTTCAGGATCCCCTACTACGTGGGACCACTGGCCA |
| | | | | GAGGCAATAGCAGATTCGCCTGGATGACCAGAAAGAGCGAGGA |
| | | | | AACCATCACACCCTGGAACTTCGAGGAAGTGGTGGACAAGGGC |
| | | | | GCCAGCGCTCAGTCCTTCATCGAGCGGATGACCAACTTCGATAA |
| | | | | GAACCTGCCTAACGAGAAGGTGCTGCCCAAGCACAGCCTGCTGT |
| | | | | ACGAGTACTTCACCGTGTACAACGAGCTGACCAAAGTGAAATA |
| | | | | CGTGACCGAGGGAATGAGAAAGCCCGCCTTTCTGAGCGGCGAG |
| | | | | CAGAAAAAGGCCATTGTGGATCTGCTGTTCAAGACCAACCGGA |
| | | | | AAGTGACCGTGAAGCAGCTGAAAGAGGACTACTTCAAGAAAAT |
| | | | | CGAGTGCTTCGACAGCGTGGAAATCAGCGGCGTGGAAGATCGG |
| | | | | TTCAATGCCAGCCTGGGCACATACCACGACCTGCTGAAAATTAT |
| | | | | CAAGGACAAGGACTTCCTGGACAACGAAGAGAACGAGGACATC |
| | | | | CTGGAAGATATCGTGCTGACCCTGACACTGTTTGAGGACAGAGA |
| | | | | GATGATCGAGGAACGGCTGAAAACATACGCCCACCTGTTCGAC |
| | | | | GACAAAGTGATGAAGCAACTGAAGCGGCGGAGATACACCGGCT |
| | | | | GGGGCAGACTGTCTCGGAAGCTGATCAACGGCATCCGGGATAA |
| | | | | GCAGTCCGGCAAGACCATCCTGGACTTTCTGAAGTCCGACGGCT |
| | | | | TCGCCAACAGAAACTTCATGCAGCTGATCCACGACGACAGCCTG |

TABLE 23-continued

Listing of additional protein and nucleic acid sequences referred to herein not included in the sequence listing

| Category | SEQ ID NO: | Description | Type | Sequence |
|---|---|---|---|---|
| | | | | ACCTTTAAAGAGGATATCCAGAAAGCCCAGGTGTCCGGCCAGG<br>GCGATTCTCTGCATGAGCACATTGCCAACCTGGCCGGCTCTCCC<br>GCCATTAAGAAGGGCATTCTGCAGACAGTGAAGGTGGTGGACG<br>AGCTGGTCAAAGTCATGGGCAGACACAAGCCCGAGAACATCGT<br>GATCGAAATGGCCAGAGAGAACCAGACCACACAGAAGGGCCAG<br>AAGAACAGCCGCGAGAGAATGAAGCGGATCGAAGAGGGCATC<br>AAAGAGCTGGGCAGCCAGATCCTGAAAGAACACCCCGTGGAAA<br>ACACCCAGCTGCAGAACGAGAAGCTGTACCTGTACTACCTCCAG<br>AACGGCCGGGATATGTACGTGGACCAAGAGCTGGACATCAACC<br>GGCTGTCCGACTACGATGTGGACCATATCGTGCCCCAGTCTTTT<br>CTGAAGGACGACTCCATCGACAACAAGGTCCTGACCAGATCCG<br>ACAAGAATCGGGGCAAGAGCGACAACGTGCCCTCCGAAGAGGT<br>GGTCAAGAAGATGAAGAACTACTGGCGACAGCTGCTGAACGCC<br>AAGCTGATTACCCAGCGGAAGTTCGATAACCTGACCAAGGCCG<br>AGAGAGGCGGCCTGTCTGAACTGGATAAGGCCGGCTTCATCAA<br>GAGACAGCTGGTGGAAACCCGGCAGATCACCAAACACGTGGCA<br>CAGATTCTGGACTCCCGGATGAACACTAAGTACGACGAGAATG<br>ACAAGCTGATCCGGGAAGTGAAAGTGATCACCCTGAAGTCCAA<br>GCTGGTGTCCGATTTCCGGAAGGATTTCCAGTTCTACAAAGTGC<br>GCGAGATCAACAACTACCATCACGCCCACGACGCCTACCTGAAT<br>GCCGTTGTTGGAACAGCCCTGATCAAGAAGTATCCCAAGCTGGA<br>AAGCGAGTTCGTGTACGGCGACTACAAGGTGTACGACGTGCGG<br>AAGATGATCGCCAAGAGCGAGCAAGAGATTGGCAAGGCTACCG<br>CCAAGTACTTTTTCTACAGCAACATCATGAACTTTTTCAAGACC<br>GAGATTACCCTGGCCAACGGCGAGATCAGAAAGCGGCCTCTGA<br>TCGAGACAAACGGCGAAACCGGCGAGATTGTGTGGGATAAGGG<br>CAGAGACTTTGCCACAGTGCGGAAAGTGCTGAGCATGCCCCAA<br>GTGAATATCGTGAAGAAAACCGAGGTGCAGACAGGCGGCTTCA<br>GCAAAGAGTCCATTCTGCCCAAGAGAAACAGCGATAAGCTGAT<br>CGCCCGGAAGAAGGACTGGGACCCTAAGAAGTACGGCGGCTTC<br>GATAGCCCTACCGTGGCCTATTCTGTGCTGGTGGTGGCCAAAGT<br>GGAAAAGGGCAAGTCCAAGAAACTCAAGAGCGTGAAAGAGCTG<br>CTGGGGATCACCATCATGGAAAGAAGCAGCTTCGAGAAGAATC<br>CTATCGATTTCCTCGAGGCCAAGGGCTACAAAGAAGTGAAAAA<br>GGACCTGATCATCAAGCTCCCCAAGTACTCCCTGTTCGAGCTGG<br>AAAATGGCCGGAAGCGGATGCTGGCTTCTGCTGGCGAACTGCA<br>GAAGGGAAACGAACTGGCCCTGCCTAGCAAATATGTGAACTTC<br>CTGTACCTGGCCAGCCACTATGAGAAGCTGAAGGGCAGCCCCG<br>AGGACAATGAGCAAAAGCAGCTGTTTGTGGAACAGCACAAGCA<br>CTACCTGGACGAGATCATCGAGCAGATCAGCGAGTTCTCCAAGA<br>GAGTGATCCTGGCCGACGCTAATCTGGACAAAGTGCTGTCCGCC<br>TACAACAAGCACCGGGACAAGCCTATCAGAGAGCAGGCCGAGA<br>ATATCATCCACCTGTTTACCCTGACCAATCTGGGAGCCCCTGCC<br>GCCTTCAAGTACTTCGACACCACCATCGACCGGAAGCGCTACAC<br>CAGCACCAAAGAGGTGCTGGACGCCACACTGATCCACCAGTCT<br>ATCACCGGCCTGTACGAGACACGGATCGACCTGTCTCAGCTCGG<br>AGGCGATTCTGGCGGAAAAAGACCTGCCGCCACAAAGAAAGCC |

TABLE 23-continued

Listing of additional protein and nucleic acid sequences referred to herein not included in the sequence listing

| Category | SEQ ID NO: | Description | Type | Sequence |
|---|---|---|---|---|
| | | | | GGACAGGCCAAGAAAAAGAAGTGACCACACCCCCATTCCCCCA<br>CTCCAGATAAAGCTTCAGTTATATCTCACGTGTCTGGAGTTAAA<br>AAAAAAAAAAAAAAAAAAAAAAAAAAAAAAAAAAAAAAAAA<br>AAAAAAAAAAAAAAAAAAAAAAAAAAAAAAAAAAAAAAAAA<br>AAAAAAAAAAAAAAAGAAGAGCCCTGCAGG |
| spCas9 amino acid sequence | 52 | Amino acid sequence of spCas9 encoded in mRNA including nuclear localization signals | Protein | MAPKKKRKVGGGGSDKKYSIGLDIGTNSVGWAVITDEYKVPSKKF<br>KVLGNTDRHSIKKNLIGALLFDSGETAEATRLKRTARRRYTRRKNR<br>ICYLQEIFSNEMAKVDDSFFHRLEESFLVEEDKKHERHPIFGNIVDE<br>VAYHEKYPTIYHLRKKLVDSTDKADLRLIYLALAHMIKFRGHFLIE<br>GDLNPDNSDVDKLFIQLVQTYNQLFEENPINASGVDAKAILSARLS<br>KSRRLENLIAQLPGEKKNGLFGNLIALSLGLTPNFKSNFDLAEDAKL<br>QLSKDTYDDDLDNLLAQIGDQYADLFLAAKNLSDAILLSDILRVNT<br>EITKAPLSASMIKRYDEHHQDLTLLKALVRQQLPEKYKEIFFDQSK<br>NGYAGYIDGGASQEEFYKFIKPILEKMDGTEELLVKLNREDLLRKQ<br>RTFDNGSIPHQIHLGELHAILRRQEDFYPFLKDNREKIEKILTFRIPYY<br>VGPLARGNSRFAWMTRKSEETITPWNFEEVVDKGASAQSFIERMT<br>NFDKNLPNEKVLPKHSLLYEYFTVYNELTKVKYVTEGMRKPAFLS<br>GEQKKAIVDLLFKTNRKVTVKQLKEDYFKKIECFDSVEISGVEDRF<br>NASLGTYHDLLKIIKDKDFLDNEENEDILEDIVLTLTLFEDREMIEER<br>LKTYAHLFDDKVMKQLKRRRYTGWGRLSRKLINGIRDKQSGKTIL<br>DFLKSDGFANRNFMQLIHDDSLTFKEDIQKAQVSGQGDSLHEHIAN<br>LAGSPAIKKGILQTVKVVDELVKVMGRHKPENIVIEMARENQTTQ<br>KGQKNSRERMKRIEEGIKELGSQILKEHPVENTQLQNEKLYLYYLQ<br>NGRDMYVDQELDINRLSDYDVDHIVPQSFLKDDSIDNKVLTRSDK<br>NRGKSDNVPSEEVVKKMKNYWRQLLNAKLITQRKFDNLTKAERG<br>GLSELDKAGFIKRQLVETRQITKHVAQILDSRMNTKYDENDKLIRE<br>VKVITLKSKLVSDFRKDFQFYKVREINNYHHAHDAYLNAVVGTAL<br>IKKYPKLESEFVYGDYKVYDVRKMIAKSEQEIGKATAKYFFYSNIM<br>NFFKTEITLANGEIRKRPLIETNGETGEIVWDKGRDFATVRKVLSMP<br>QVNIVKKTEVQTGGFSKESILPKRNSDKLIARKKDWDPKKYGGFDS<br>PTVAYSVLVVAKVEKGKSKKLKSVKELLGITIMERSSFEKNPIDFLE<br>AKGYKEVKKDLIIKLPKYSLFELENGRKRMLASAGELQKGNELALP<br>SKYVNFLYLASHYEKLKGSPEDNEQKQLFVEQHKHYLDEIIEQISEF<br>SKRVILADANLDKVLSAYNKHRDKPIREQAENIIHLFTLTNLGAPA<br>AFKYFDTTIDRKRYTSTKEVLDATLIHQSITGLYETRIDLSQLGGDS<br>GGKRPAATKKAGQAKKKK |
| DNA sequence encoding the MG29-1 mRNA | 53 | Template DNA for MG29-1 in vitro transcription | Nucleotide | TAATACGACTCACTATAAGGAAAAGCCAGCTCCAGCAGGCGCT<br>GCTCACTCCTCCCCATCCTCTCCCTCTGTCCCTCTGTCCCTCTGA<br>CCCTGCACTGTCCCAGCACCATGGCCCCTAAGAAGAAGAGAAA<br>AGTCGGCGGAGGCGGCAGCTTCAACAACTTCATCAAGAAGTAC<br>AGCCTGCAGAAAACCCTGCGCTTCGAGCTGAAGCCTGTGGGCG<br>AGACAGCCGACTACATCGAGGACTTCAAGAGCGAGTACCTGAA<br>GGACACCGTGCTGAAGGACGAGCAGAGAGCCAAGGACTACCAA<br>GAGATCAAGACCCTGATCGACGATTACCACCGCGAGTACATCG<br>AAGAGTGCCTGAGAGAACCCGTGGACAAGAAAACCGGCGAGAT |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | CCTGGACTTCACCCAGGACCTGGAAGATGCCTTCAGCTACTACC |
| | | | | AGAAGCTGAAAGAGAACCCCACCGAGAACAGAGTCGGCTGGGA |
| | | | | GAAAGAGCAAGAGAGCCTGAGGAAGAAGCTGGTCACCTCCTTC |
| | | | | GTGGGCAACGACGGCCTGTTCAAGAAAGAGTTCATCACCAGGG |
| | | | | ACCTGCCTGAGTGGCTGCAGAAGAAAGGACTCTGGGGCGAGTA |
| | | | | CAAGGACACAGTGGAAAACTTCAAGAAGTTCACCACCTACTTCA |
| | | | | GCGGCTTCCACGAGAACCGGAAGAACATGTACACCGCCGAGGC |
| | | | | TCAGAGCACCGCTATCGCCAACAGACTGATGAACGACAACCTG |
| | | | | CCTAAGTTCTTTAACAACTACCTGGCCTACCAGACCATCAAAGA |
| | | | | GAAGCACCCCGACCTGGTGTTCAGACTGGATGATGCTCTGCTGC |
| | | | | AGGCCGCTGGCGTGGAACATCTGGATGAGGCTTTCCAGCCTAGA |
| | | | | TACTTCAGCAGACTGTTCGCCCAGAGCGGCATCACCGCTTTCAA |
| | | | | CGAGCTGATCGGCGGCAGAACCACAGAGAACGGCGAGAAGATC |
| | | | | CAGGGCCTGAACGAGCAGATCAACCTGTACAGACAGCAGAACC |
| | | | | CCGAGAAGGCCAAGGGCTTCCCCAGATTCATGCCTCTGTTCAAG |
| | | | | CAGATCCTGAGCGACAGAGAGACACACAGCTTTCTGCCCGACG |
| | | | | CCTTCGAGAACGACAAAGAGCTGCTCCAGGCTCTGAGAGACTA |
| | | | | CGTGGACGCCGCCACATCTGAGGAAGGCATGATCAGCCAGCTG |
| | | | | AACAAGGCCATGAACCAGTTCGTGACCGCCGACCTGAAGAGAG |
| | | | | TGTACATCAAGAGCGCCGCTCTGACCAGCCTGAGCCAAGAGCTG |
| | | | | TTCCACTTCTTCGGCGTGATCAGCGACGCTATCGCTTGGTACGCC |
| | | | | GAGAAGAGACTGAGCCCCAAGAAGGCCCAAGAGTCTTTCCTGA |
| | | | | AGCAAGAGGTGTACGCCATCGAGGAACTGAACCAGGCTGTCGT |
| | | | | GGGCTACATCGACCAGCTGGAAGATCAGAGCGAGCTGCAGCAA |
| | | | | CTGCTGGTGGACCTGCCAGATCCTCAGAAACCCGTGTCCAGCTT |
| | | | | CATCCTGACACACTGGCAGAAGTCTCAAGAGCCCCTGCAGGCA |
| | | | | GTGATCGCCAAGGTGGAACCTCTGTTCGAACTGGAAGAACTGA |
| | | | | GCAAGAACAAGAGGGCCCCAAAGCACGACAAGGACCAAGGCG |
| | | | | GCGAGGGATTTCAGCAGGTCGACGCCATCAAGAACATGCTGGA |
| | | | | CGCCTTCATGGAAGTGTCCCACGCTATCAAGCCCCTGTACCTGG |
| | | | | TCAAGGGAAGAAAGGCCATCGACATGCCCGACGTGGACACCGG |
| | | | | CTTCTACGCTGATTTCGCCGAGGCCTACAGCGCCTACGAGCAAG |
| | | | | TGACAGTGTCCCTGTACAACAAGACCAGAAACCACCTGTCCAAG |
| | | | | AAGCCCTTCAGCAAGGACAAGATCAAGATCAACTTCGACGCCC |
| | | | | CTACACTGCTGAACGGCTGGGACCTGAACAAAGAGAGCGACAA |
| | | | | CAAGTCCATCATCCTGCGGAAGGACGGCAACTTCTACCTGGCAA |
| | | | | TCATGCACCCCAAGCACACCAAGGTGTTCGACTGCTACTCTGCC |
| | | | | TCTGAGGCTGCCGGCAAGTGCTACGAGAAGATGAACTACAAGC |
| | | | | TGCTGAGCGGCGCCAACAAGATGCTGCCTAAGGTGTTCTTTAGC |
| | | | | AAGAAGGGCATCGAGACATTCAGCCCTCCACAAGAAATCCTGG |
| | | | | ACCTGTACAAGAACAACGAGCATAAGAAGGGCGCCACCTTCAA |
| | | | | GCTGGAATCCTGCCACAAGCTGATCGATTTCTTCAAGCGGAACA |
| | | | | TCCCCAAGTACAAGGTGCACCCTACCGACAACTTTGGCTGGGAC |
| | | | | GTGTTCGGCTTTCACTTCAGCCCTACCAGCAGCTACGGCGACCT |
| | | | | GTCTGGCTTCTACAGAGAGGTGGAAGCCCAGGGATACAAGCTG |
| | | | | TGGTTCAGCGACGTGTCCGAGGCTTACATCAACAAATGCGTGGA |
| | | | | AGAGGGCAAGCTGTTCCTGTTCCAAATCTACAACAAGGACTTCT |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | CCCCTAACTCCACCGGCAAGCCCAACCTGCACACCCTGTATTGG AAGGGCCTGTTCGAGCCCGAGAACCTGAAAGACGTGGTGCTGA AGCTGAATGGCGAGGCCGAGATCTTCTACCGGAAGCACAGCAT CAAGCACGAGGACAAGACCATCCACAGAGCTAAGGACCCTATC GCTAACAAGAACGCTGACAACCCCAAGAAACAGAGCGTGTTCG ATTACGACATCATCAAGGATAAGCGGTATACCCAGGACAAGTTC TTCTTCCACGTGCCAATCAGCCTGAACTTCAAAAGCCAGGGCGT CGTGCGGTTCAACGATAAGATCAACGGCCTGCTGGCCGCTCAGG ACGATGTGCATGTGATCGGCATCGACAGAGGCGAGAGACATCT GCTGTACTACACCGTGGTCAACGGCAAGGGCGAAGTGGTGGAA CAGGGCAGCCTGAATCAGGTGGCCACAGATCAGGGCTACGTGG TGGATTACCAGCAGAAGCTGCACGCCAAAGAGAAAGAACGCGA CCAGGCCAGAAAGAACTGGTCCACCATCGAGAACATCAAAGAA CTGAAGGCCGGCTACCTGAGCCAGGTGGTGCATAAGCTGGCTCA GCTGATCGTGAAGCACAACGCCATCGTGTGCCTCGAGGACCTGA ATTTCGGCTTCAAGAGGGGCAGATTCAAGGTCGAGAAACAGGT GTACCAGAAGTTCGAGAAGGCTCTGATCGACAAGCTGAACTAC CTCGTGTTCAAAGAGAGAGGCGCCACACAGGCTGGCGGATACC TGAATGCTTACCAGCTGGCCGCACCTTTCGAGAGCTTTGAGAAG CTGGGCAAGCAGACCGGCATCCTGTACTACGTGCGGAGCGACT ACACCAGCAAGATCGACCCTGCTACCGGCTTCGTGGACTTTCTG AAGCCTAAGTACGAGAGCATGGCCAAGAGCAAAGTGTTCTTCG AGTCCTTCGAGCGCATCCAGTGGAACCAGGCCAAAGGCTACTTC GAGTTCGAGTTTGACTACAAGAAGATGTGCCCCAGCAGAAAGTT CGGCGACTACAGAACCAGATGGGTCGTGTGCACCTTCGGCGAC ACCCGCTACCAGAACAGAAGAAACAAGAGCAGCGGCCAGTGGG AGACAGAGACAATCGATGTGACAGCCCAGCTGAAAGCCCTGTT CGCCGCTTACGGCATCACATACAATCAAGAGGATAACATCAAG GACGCCATTGCCGCCGTGAAGTACACCAAGTTCTACAAGCAGCT GTACTGGCTGCTGAGACTGACCCTGAGCCTGAGACACAGCGTGA CAGGCACCGACGAGGATTTCATCCTGTCTCCAGTGGCCGACGAG AATGGCGTGTTCTTTGACTCTAGGAAGGCCACCGACAAGCAGCC TAAGGACGCTGATGCTAACGGCGCCTACCATATCGCCCTGAAAG GCCTGTGGAATCTCCAGCAGATCAGACAGCACGACTGGAACGT GGAAAAGCCCAAAAAGCTGAACCTCGCCATGAAGAACGAAGAG TGGTTCGGCTTCGCTCAGAAGAAGAAGTTTAGAGCCAGCGGCG GCAAGAGGCCTGCCGCTACAAAAAAAGCCGGCCAGGCCAAGAA AAAGAAGTGACCACACCCCCATTCCCCCACTCCAGATAGAACTT CAGTTATATCTCACGTGTCTGGAGTTAAAAAAAAAAAAAAAAA AAAAAAAAAAAAAAAAAAAAAAAAAAAAAAAAAAAAAAAA AAAAAAAAAAAAAAAAAAAAAAAAAAAAAAAAAAAAAAAG AAGAGCCCTGCAGG |
| MG29-1 amino acid sequence | 54 | Amino acid sequence of MG29-1 encoded in mRNA including nuclear localization | Protein | MAPKKKRKVGGGGSFNNFIKKYSLQKTLRFELKPVGETADYIEDF KSEYLKDTVLKDEQRAKDYQEIKTLIDDYHREYIEECLREPVDKKT GEILDFTQDLEDAFSYYQKLKENPTENRVGWEKEQESLRKKLVTSF VGNDGLFKKEFITRDLPEWLQKKGLWGEYKDTVENFKKFTTYFSG |

TABLE 23-continued

Listing of additional protein and nucleic acid sequences referred to herein not included in the sequence listing

| Category | SEQ ID NO: | Description | Type | Sequence |
|---|---|---|---|---|
| | | signals | | FHENRKNMYTAEAQSTAIANRLMNDNLPKFFNNYLAYQTIKEKHP<br>DLVFRLDDALLQAAGVEHLDEAFQPRYFSRLFAQSGITAFNELIGG<br>RTTENGEKIQGLNEQINLYRQQNPEKAKGFPRFMPLFKQILSDRETH<br>SFLPDAFENDKELLQALRDYVDAATSEEGMISQLNKAMNQFVTAD<br>LKRVYIKSAALTSLSQELFHFFGVISDAIAWYAEKRLSPKKAQESFL<br>KQEVYAIEELNQAVVGYIDQLEDQSELQQLLVDLPDPQKPVSSFILT<br>HWQKSQEPLQAVIAKVEPLFELEELSKNKRAPKHDKDQGGEGFQQ<br>VDAIKNMLDAFMEVSHAIKPLYLVKGRKAIDMPDVDTGFYADFAE<br>AYSAYEQVTVSLYNKTRNHLSKKPFSKDKIKINFDAPTLLNGWDL<br>NKESDNKSIILRKDGNFYLAIMHPKHTKVFDCYSASEAAGKCYEK<br>MNYKLLSGANKMLPKVFFSKKGIETFSPPQEILDLYKNNEHKKGAT<br>FKLESCHKLIDFFKRNIPKYKVHPTDNFGWDVFGFHFSPTSSYGDLS<br>GFYREVEAQGYKLWFSDVSEAYINKCVEEGKLFLFQIYNKDFSPNS<br>TGKPNLHTLYWKGLFEPENLKDVVLKLNGEAEIFYRKHSIKHEDKT<br>IHRAKDPIANKNADNPKKQSVFDYDIIKDKRYTQDKFFFHVPISLNF<br>KSQGVVRFNDKINGLLAAQDDVHVIGIDRGERHLLYYTVVNGKGE<br>VVEQGSLNQVATDQGYVVDYQQKLHAKEKERDQARKNWSTIENI<br>KELKAGYLSQVVHKLAQLIVKHNAIVCLEDLNFGFKRGRFKVEKQ<br>VYQKFEKALIDKLNYLVFKERGATQAGGYLNAYQLAAPFESFEKL<br>GKQTGILYYVRSDYTSKIDPATGFVDFLKPKYESMAKSKVFFESFE<br>RIQWNQAKGYFEFEFDYKKMCPSRKFGDYRTRWVVCTFGDTRYQ<br>NRRNKSSGQWETETIDVTAQLKALFAAYGITYNQEDNIKDAIAAV<br>KYTKFYKQLYWLLRLTLSLRHSVTGTDEDFILSPVADENGVFFDSR<br>KATDKQPKDADANGAYHIALKGLWNLQQIRQHDWNVEKPKKLN<br>LAMKNEEWFGFAQKKKFRASGGKRPAATKKAGQAKKKK |
| MG29-1 sgRNA targeting mouse albumin | 55 | mAlb29-8-50 guide RNA | Nucleotide | mG*mU*mU*GAGAAUC*mG*mA*mA*mAGAUUCUCAAC*mC*mU<br>*mU*U*UAAUUmUmCmUmACU*G*U*U*GUAGAUCUGUAACfGfA<br>fUfCfGfGfGfAfAfC*fU*fGfG*fC*mA |
| FVIII donor template | 56 | FVIII donor template with MG29-1 target sites in FF orientation (pMG4006) | Nucleotide | ACGTTTTTCCTGTAACGATCGGGAACTGGCATTTGAGTGTAGCA<br>GAGAGGAACCATTTCTCAAAGCTTACTAAAGAATTATTCTTTTA<br>CATTTCAGTGGCCACCAGAAGATATTACCTGGGAGCTGTGGAAC<br>TGAGCTGGGACTACATGCAGTCTGACCTGGGAGAGCTGCCTGTG<br>GATGCTAGATTTCCTCCAAGAGTGCCCAAGAGCTTCCCCTTCAA<br>CACCTCTGTGGTGTACAAGAAAACCCTGTTTGTGGAATTCACAG<br>ACCACCTGTTCAATATTGCCAAGCCTAGACCTCCTTGGATGGGA<br>CTGCTGGGACCTACAATTCAGGCTGAGGTGTATGACACAGTGGT<br>CATCACCCTGAAGAACATGGCCAGCCATCCTGTGTCTCTGCATG<br>CTGTGGGAGTGTCTTACTGGAAGGCTTCTGAGGGAGCTGAGTAT<br>GATGACCAGACAAGCCAGAGAGAGAAAGAGGATGACAAGGTTT<br>TCCCTGGAGGCAGCCACACCTATGTCTGGCAGGTCCTGAAAGAA<br>AATGGCCCTATGGCCTCTGATCCTCTGTGCCTGACATACAGCTA<br>CCTGAGCCATGTGGACCTGGTCAAGGACCTGAATTCTGGCCTGA<br>TTGGAGCCCTGCTGGTGTGTAGAGAAGGCAGCCTGGCCAAAGA<br>GAAAACCCAGACACTGCACAAGTTCATCCTGCTGTTTGCTGTGT<br>TTGATGAGGGCAAGAGCTGGCACTCTGAGACAAAGAACAGCCT |

TABLE 23-continued

Listing of additional protein and nucleic acid sequences referred to herein not included in the sequence listing

| Category | SEQ ID NO: | Description | Type | Sequence |
|---|---|---|---|---|
| | | | | GATGCAGGACAGGGATGCTGCCTCTGCTAGAGCTTGGCCTAAGA<br>TGCACACAGTGAATGGCTATGTGAACAGAAGCCTGCCTGGACTG<br>ATTGGCTGCCACAGAAAGTCTGTGTACTGGCATGTGATTGGCAT<br>GGGCACAACACCTGAGGTGCACAGCATCTTTCTGGAAGGACAC<br>ACCTTCCTGGTGAGAAACCATAGACAGGCCAGCCTGGAAATCA<br>GCCCTATCACCTTCCTGACAGCTCAGACCCTGCTGATGGATCTG<br>GGCCAGTTTCTGCTGTTCTGCCACATCAGCAGCCACCAGCATGA<br>TGGCATGGAAGCCTATGTGAAGGTGGACAGCTGCCCTGAAGAA<br>CCCCAGCTGAGAATGAAGAACAATGAGGAGGCTGAGGACTATG<br>ATGATGACCTGACAGACTCTGAGATGGATGTGGTCAGATTTGAT<br>GATGACAACAGCCCCAGCTTCATCCAGATCAGATCTGTGGCCAA<br>GAAGCACCCCAAGACCTGGGTGCACTATATTGCTGCTGAGGAA<br>GAGGACTGGGATTATGCTCCTCTGGTGCTGGCCCCTGATGACAG<br>AAGCTACAAGAGCCAGTACCTGAACAATGGCCCTCAGAGAATT<br>GGCAGAAAGTATAAGAAAGTGAGATTCATGGCCTACACAGATG<br>AGACATTCAAGACCAGAGAGGCCATTCAGCATGAGTCTGGCATT<br>CTGGGCCCTCTGCTGTATGGAGAAGTGGGAGATACACTGCTGAT<br>CATCTTCAAGAACCAGGCCAGCAGACCCTACAACATCTACCCTC<br>ATGGCATCACAGATGTGAGACCCCTGTATTCTAGAAGGCTGCCC<br>AAGGGAGTGAAGCACCTGAAGGACTTCCCTATCCTGCCTGGAG<br>AGATCTTCAAGTACAAGTGGACAGTGACAGTGGAAGATGGCCC<br>CACCAAGTCTGACCCTAGATGTCTGACAAGATACTACAGCAGCT<br>TTGTGAACATGGAAAGAGACCTGGCCTCTGGCCTGATTGGACCT<br>CTGCTGATCTGCTACAAAGAATCTGTGGACCAGAGAGGCAACC<br>AGATCATGTCTGACAAGAGAAATGTGATCCTGTTTTCTGTGTTT<br>GATGAGAACAGATCCTGGTATCTGACAGAGAACATCCAGAGAT<br>TTCTGCCCAATCCTGCTGGAGTGCAGCTGGAAGATCCTGAGTTC<br>CAGGCCTCCAACATCATGCACTCCATCAATGGCTATGTGTTTGA<br>CAGCCTGCAGCTGTCTGTGTGCCTGCATGAAGTGGCCTACTGGT<br>ACATCCTGAGCATTGGAGCCCAGACAGACTTCCTGTCTGTGTTC<br>TTCTCTGGCTACACCTTCAAGCACAAGATGGTGTATGAGGATAC<br>CCTGACACTGTTCCCATTCTCTGGAGAGACAGTGTTCATGAGCA<br>TGGAAAACCCTGGCCTGTGGATCCTGGGCTGTCACAACTCTGAC<br>TTCAGAAACAGAGGCATGACAGCCCTGCTGAAGGTGTCCAGCT<br>GTGACAAGAACACAGGAGACTACTATGAGGACAGCTATGAGGA<br>CATCTCTGCCTACCTGCTGAGCAAGAACAATGCCATTGAGCCCA<br>GAAGCTTCAGCCAGAATGCCACCAATGTGTCCAACAACAGCAA<br>CACCAGCAATGACTCCAATGTGTCCCCTCCAGTGCTGAAGAGAC<br>ACCAGAGAGAAATCACCAGAACCACACTGCAGTCTGACCAAGA<br>GGAAATTGACTATGATGACACCATCTCTGTGGAGATGAAGAAA<br>GAAGATTTTGACATCTATGATGAGGATGAGAATCAGAGCCCCA<br>GATCCTTTCAGAAAAAGACCAGACACTACTTCATTGCTGCTGTG<br>GAGAGACTGTGGGACTATGGCATGTCTAGCAGCCCTCATGTGCT<br>GAGAAATAGAGCCCAGTCTGGCTCTGTGCCCCAGTTCAAGAAA<br>GTGGTGTTCCAAGAGTTCACAGATGGCAGCTTCACCCAGCCACT<br>GTATAGAGGAGAGCTGAATGAGCATCTGGGCCTGCTGGGCCCTT<br>ATATCAGAGCTGAAGTGGAAGATAACATCATGGTCACCTTCAGA |

TABLE 23-continued

Listing of additional protein and nucleic acid sequences referred to herein not included in the sequence listing

| Category | SEQ ID NO: | Description | Type | Sequence |
|---|---|---|---|---|
| | | | | AATCAGGCCTCTAGACCCTACAGCTTCTACAGCTCCCTGATCAG<br>CTATGAAGAGGACCAGAGACAGGGAGCTGAGCCCAGAAAGAAC<br>TTTGTGAAGCCCAATGAGACTAAGACCTACTTTTGGAAGGTGCA<br>GCACCACATGGCCCCTACAAAGGATGAGTTTGACTGCAAGGCCT<br>GGGCCTACTTTTCTGATGTGGATCTGGAAAAGGATGTGCACTCT<br>GGACTCATTGGACCACTGCTTGTGTGCCACACCAACACACTGAA<br>CCCTGCTCATGGCAGACAAGTGACAGTGCAAGAGTTTGCCCTGT<br>TCTTCACCATCTTTGATGAAACAAAGAGCTGGTACTTCACAGAG<br>AATATGGAGAGAAACTGCAGGGCCCCTTGCAACATCCAGATGG<br>AAGATCCCACCTTCAAAGAGAACTACAGATTCCATGCCATCAAT<br>GGCTACATCATGGACACACTGCCTGGCCTGGTTATGGCTCAGGA<br>TCAGAGAATCAGATGGTATCTGCTGTCCATGGGCTCCAATGAGA<br>ATATCCACAGCATCCACTTCTCTGGCCATGTGTTCACAGTGAGA<br>AAAAAAGAAGAGTACAAAATGGCCCTGTACAATCTGTACCCTG<br>GGGTGTTTGAAACAGTGGAAATGCTGCCTTCCAAGGCTGGCATT<br>TGGAGAGTGGAATGTCTGATTGGAGAGCACCTCCATGCTGGAAT<br>GAGCACCCTGTTTCTGGTGTACAGCAACAAGTGTCAGACCCCTC<br>TGGGCATGGCCTCTGGACACATCAGAGACTTCCAGATCACAGCC<br>TCTGGCCAGTATGGACAGTGGGCTCCTAAACTGGCTAGACTGCA<br>CTACTCTGGCAGCATCAATGCCTGGTCCACCAAAGAGCCCTTCA<br>GCTGGATCAAGGTGGACCTGCTGGCTCCCATGATCATCCATGGA<br>ATCAAGACCCAGGGAGCCAGACAGAAGTTCAGCAGCCTGTACA<br>TCAGCCAGTTCATCATCATGTACAGCCTGGATGGCAAGAAGTGG<br>CAGACCTACAGAGGCAACAGCACAGGCACACTCATGGTGTTCTT<br>TGGCAATGTGGACAGCTCTGGCATTAAGCACAACATCTTCAACC<br>CTCCAATCATTGCCAGATACATCAGACTGCACCCCACACACTAC<br>AGCATCAGATCTACCCTGAGAATGGAACTGATGGGCTGTGACCT<br>GAACAGCTGCAGCATGCCCCTGGGAATGGAAAGCAAGGCCATC<br>TCTGATGCCCAGATCACAGCCAGCAGCTACTTCACCAACATGTT<br>TGCCACTTGGAGCCCCTCCAAGGCTAGACTGCATCTGCAGGGCA<br>GAAGCAATGCTTGGAGGCCCCAAGTGAACAACCCCAAAGAGTG<br>GCTGCAGGTGGACTTTCAAAAGACCATGAAAGTGACAGGAGTG<br>ACCACACAGGGAGTCAAGTCTCTGCTGACCTCTATGTATGTGAA<br>AGAGTTCCTGATCTCCAGCAGCCAGGATGGCCACCAGTGGACCC<br>TGTTTTTCCAGAATGGCAAAGTGAAAGTGTTCCAGGGCAATCAG<br>GACAGCTTCACACCTGTGGTCAACTCCCTGGATCCTCCACTGCT<br>GACCAGATACCTGAGAATTCACCCTCAGTCTTGGGTGCACCAGA<br>TTGCTCTGAGAATGGAAGTGCTGGGCTGTGAAGCTCAGGACCTC<br>TACTGATCGCGAATAAAAGATCTTTATTTTCATTAGATCTGTGTG<br>TTGGTTTTTTGTGTGTATTTAGCTATTTGAGTGTAGCAGAGAGGA<br>ACCATTTTTCCTGTAACGATCGGGAACTGGCA |
| FVIII donor template | 57 | FVIII donor template with MG29-1 target sites in RR orientation (pMG4007) | Nucleotide | ACGTTAATGGTTCCTCTCTGCTACACTCAAATGCCAGTTCCCGAT<br>CGTTACAGGAAATCTCAAAGCTTACTAAAGAATTATTCTTTTAC<br>ATTTCAGTGGCCACCAGAAGATATTACCTGGGAGCTGTGGAACT<br>GAGCTGGGACTACATGCAGTCTGACCTGGGAGAGCTGCCTGTGG<br>ATGCTAGATTTCCTCCAAGAGTGCCCAAGAGCTTCCCCTTCAAC |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | ACCTCTGTGGTGTACAAGAAAACCCTGTTTGTGGAATTCACAGA<br>CCACCTGTTCAATATTGCCAAGCCTAGACCTCCTTGGATGGGAC<br>TGCTGGGACCTACAATTCAGGCTGAGGTGTATGACACAGTGGTC<br>ATCACCCTGAAGAACATGGCCAGCCATCCTGTGTCTCTGCATGC<br>TGTGGGAGTGTCTTACTGGAAGGCTTCTGAGGGAGCTGAGTATG<br>ATGACCAGACAAGCCAGAGAGAGAAAGAGGATGACAAGGTTTT<br>CCCTGGAGGCAGCCACACCTATGTCTGGCAGGTCCTGAAAGAA<br>AATGGCCCTATGGCCTCTGATCCTCTGTGCCTGACATACAGCTA<br>CCTGAGCCATGTGGACCTGGTCAAGGACCTGAATTCTGGCCTGA<br>TTGGAGCCCTGCTGGTGTGTAGAGAAGGCAGCCTGGCCAAAGA<br>GAAAACCCAGACACTGCACAAGTTCATCCTGCTGTTTGCTGTGT<br>TTGATGAGGGCAAGAGCTGGCACTCTGAGACAAAGAACAGCCT<br>GATGCAGGACAGGGATGCTGCCTCTGCTAGAGCTTGGCCTAAGA<br>TGCACACAGTGAATGGCTATGTGAACAGAAGCCTGCCTGGACTG<br>ATTGGCTGCCACAGAAAGTCTGTGTACTGGCATGTGATTGGCAT<br>GGGCACAACACCTGAGGTGCACAGCATCTTTCTGGAAGGACAC<br>ACCTTCCTGGTGAGAAACCATAGACAGGCCAGCCTGGAAATCA<br>GCCCTATCACCTTCCTGACAGCTCAGACCCTGCTGATGGATCTG<br>GGCCAGTTTCTGCTGTTCTGCCACATCAGCAGCCACCAGCATGA<br>TGGCATGGAAGCCTATGTGAAGGTGGACAGCTGCCCTGAAGAA<br>CCCCAGCTGAGAATGAAGAACAATGAGGAGGCTGAGGACTATG<br>ATGATGACCTGACAGACTCTGAGATGGATGTGGTCAGATTTGAT<br>GATGACAACAGCCCCAGCTTCATCCAGATCAGATCTGTGGCCAA<br>GAAGCACCCCAAGACCTGGGTGCACTATATTGCTGCTGAGGAA<br>GAGGACTGGGATTATGCTCCTCTGGTGCTGGCCCCTGATGACAG<br>AAGCTACAAGAGCCAGTACCTGAACAATGGCCCTCAGAGAATT<br>GGCAGAAAGTATAAGAAAGTGAGATTCATGGCCTACACAGATG<br>AGACATTCAAGACCAGAGAGGCCATTCAGCATGAGTCTGGCATT<br>CTGGGCCCTCTGCTGTATGGAGAAGTGGGAGATACACTGCTGAT<br>CATCTTCAAGAACCAGGCCAGCAGACCCTACAACATCTACCCTC<br>ATGGCATCACAGATGTGAGACCCCTGTATTCTAGAAGGCTGCCC<br>AAGGGAGTGAAGCACCTGAAGGACTTCCCTATCCTGCCTGGAG<br>AGATCTTCAAGTACAAGTGGACAGTGACAGTGGAAGATGGCCC<br>CACCAAGTCTGACCCTAGATGTCTGACAAGATACTACAGCAGCT<br>TTGTGAACATGGAAAGAGACCTGGCCTCTGGCCTGATTGGACCT<br>CTGCTGATCTGCTACAAAGAATCTGTGGACCAGAGAGGCAACC<br>AGATCATGTCTGACAAGAGAAATGTGATCCTGTTTTCTGTGTTT<br>GATGAGAACAGATCCTGGTATCTGACAGAGAACATCCAGAGAT<br>TTCTGCCCAATCCTGCTGGAGTGCAGCTGGAAGATCCTGAGTTC<br>CAGGCCTCCAACATCATGCACTCCATCAATGGCTATGTGTTTGA<br>CAGCCTGCAGCTGTCTGTGTGCCTGCATGAAGTGGCCTACTGGT<br>ACATCCTGAGCATTGGAGCCCAGACAGACTTCCTGTCTGTGTTC<br>TTCTCTGGCTACACCTTCAAGCACAAGATGGTGTATGAGGATAC<br>CCTGACACTGTTCCCATTCTCTGGAGAGACAGTGTTCATGAGCA<br>TGGAAAACCCTGGCCTGTGGATCCTGGGCTGTCACAACTCTGAC<br>TTCAGAAACAGAGGCATGACAGCCCTGCTGAAGGTGTCCAGCT<br>GTGACAAGAACACAGGAGACTACTATGAGGACAGCTATGAGGA |

TABLE 23-continued

Listing of additional protein and nucleic acid sequences referred to herein not included in the sequence listing

| Category | SEQ ID NO: | Description | Type | Sequence |
|---|---|---|---|---|
| | | | | CATCTCTGCCTACCTGCTGAGCAAGAACAATGCCATTGAGCCCA |
| | | | | GAAGCTTCAGCCAGAATGCCACCAATGTGTCCAACAACAGCAA |
| | | | | CACCAGCAATGACTCCAATGTGTCCCCTCCAGTGCTGAAGAGAC |
| | | | | ACCAGAGAGAAATCACCAGAACCACACTGCAGTCTGACCAAGA |
| | | | | GGAAATTGACTATGATGACACCATCTCTGTGGAGATGAAGAAA |
| | | | | GAAGATTTTGACATCTATGATGAGGATGAGAATCAGAGCCCCA |
| | | | | GATCCTTTCAGAAAAAGACCAGACACTACTTCATTGCTGCTGTG |
| | | | | GAGAGACTGTGGGACTATGGCATGTCTAGCAGCCCTCATGTGCT |
| | | | | GAGAAATAGAGCCCAGTCTGGCTCTGTGCCCCAGTTCAAGAAA |
| | | | | GTGGTGTTCCAAGAGTTCACAGATGGCAGCTTCACCCAGCCACT |
| | | | | GTATAGAGGAGAGCTGAATGAGCATCTGGGCCTGCTGGGCCCTT |
| | | | | ATATCAGAGCTGAAGTGGAAGATAACATCATGGTCACCTTCAGA |
| | | | | AATCAGGCCTCTAGACCCTACAGCTTCTACAGCTCCCTGATCAG |
| | | | | CTATGAAGAGGACCAGAGACAGGGAGCTGAGCCCAGAAAGAAC |
| | | | | TTTGTGAAGCCCAATGAGACTAAGACCTACTTTTGGAAGGTGCA |
| | | | | GCACCACATGGCCCCTACAAAGGATGAGTTTGACTGCAAGGCCT |
| | | | | GGGCCTACTTTTCTGATGTGGATCTGGAAAAGGATGTGCACTCT |
| | | | | GGACTCATTGGACCACTGCTTGTGTGCCACACCAACACACTGAA |
| | | | | CCCTGCTCATGGCAGACAAGTGACAGTGCAAGAGTTTGCCCTGT |
| | | | | TCTTCACCATCTTTGATGAAACAAAGAGCTGGTACTTCACAGAG |
| | | | | AATATGGAGAGAAACTGCAGGGCCCCTTGCAACATCCAGATGG |
| | | | | AAGATCCCACCTTCAAAGAGAACTACAGATTCCATGCCATCAAT |
| | | | | GGCTACATCATGGACACACTGCCTGGCCTGGTTATGGCTCAGGA |
| | | | | TCAGAGAATCAGATGGTATCTGCTGTCCATGGGCTCCAATGAGA |
| | | | | ATATCCACAGCATCCACTTCTCTGGCCATGTGTTCACAGTGAGA |
| | | | | AAAAAAGAAGAGTACAAAATGGCCCTGTACAATCTGTACCCTG |
| | | | | GGGTGTTTGAAACAGTGGAAATGCTGCCTTCCAAGGCTGGCATT |
| | | | | TGGAGAGTGGAATGTCTGATTGGAGAGCACCTCCATGCTGGAAT |
| | | | | GAGCACCCTGTTTCTGGTGTACAGCAACAAGTGTCAGACCCCTC |
| | | | | TGGGCATGGCCTCTGGACACATCAGAGACTTCCAGATCACAGCC |
| | | | | TCTGGCCAGTATGGACAGTGGGCTCCTAAACTGGCTAGACTGCA |
| | | | | CTACTCTGGCAGCATCAATGCCTGGTCCACCAAAGAGCCCTTCA |
| | | | | GCTGGATCAAGGTGGACCTGCTGGCTCCCATGATCATCCATGGA |
| | | | | ATCAAGACCCAGGGAGCCAGACAGAAGTTCAGCAGCCTGTACA |
| | | | | TCAGCCAGTTCATCATCATGTACAGCCTGGATGGCAAGAAGTGG |
| | | | | CAGACCTACAGAGGCAACAGCACAGGCACACTCATGGTGTTCTT |
| | | | | TGGCAATGTGGACAGCTCTGGCATTAAGCACAACATCTTCAACC |
| | | | | CTCCAATCATTGCCAGATACATCAGACTGCACCCCACACACTAC |
| | | | | AGCATCAGATCTACCCTGAGAATGGAACTGATGGGCTGTGACCT |
| | | | | GAACAGCTGCAGCATGCCCCTGGGAATGGAAAGCAAGGCCATC |
| | | | | TCTGATGCCCAGATCACAGCCAGCAGCTACTTCACCAACATGTT |
| | | | | TGCCACTTGGAGCCCCTCCAAGGCTAGACTGCATCTGCAGGGCA |
| | | | | GAAGCAATGCTTGGAGGCCCCAAGTGAACAACCCCAAAGAGTG |
| | | | | GCTGCAGGTGGACTTTCAAAAGACCATGAAAGTGACAGGAGTG |
| | | | | ACCACACAGGGAGTCAAGTCTCTGCTGACCTCTATGTATGTGAA |
| | | | | AGAGTTCCTGATCTCCAGCAGCCAGGATGGCCACCAGTGGACCC |
| | | | | TGTTTTTCCAGAATGGCAAAGTGAAAGTGTTCCAGGGCAATCAG |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | GACAGCTTCACACCTGTGGTCAACTCCCTGGATCCTCCACTGCT GACCAGATACCTGAGAATTCACCCTCAGTCTTGGGTGCACCAGA TTGCTCTGAGAATGGAAGTGCTGGGCTGTGAAGCTCAGGACCTC TACTGATCGCGAATAAAAGATCTTTATTTTCATTAGATCTGTGTG TTGGTTTTTTGTGTGTATTTAGCTATGCCAGTTCCCGATCGTTAC AGGAAAAATGGTTCCTCTCTGCTACACTCAAATTCCT |
| FVIII donor template | 58 | FVIII donor template with MG29-1 target sites in FR orientation (pMG4008) | Nucleotide | ACGTTTTTCCTGTAACGATCGGGAACTGGCATTTGAGTGTAGCA GAGAGGAACCATTTCTCAAAGCTTACTAAAGAATTATTCTTTTA CATTTCAGTGGCCACCAGAAGATATTACCTGGGAGCTGTGGAAC TGAGCTGGGACTACATGCAGTCTGACCTGGGAGAGCTGCCTGTG GATGCTAGATTTCCTCCAAGAGTGCCCAAGAGCTTCCCCTTCAA CACCTCTGTGGTGTACAAGAAAACCCTGTTTGTGGAATTCACAG ACCACCTGTTCAATATTGCCAAGCCTAGACCTCCTTGGATGGGA CTGCTGGGACCTACAATTCAGGCTGAGGTGTATGACACAGTGGT CATCACCCTGAAGAACATGGCCAGCCATCCTGTGTCTCTGCATG CTGTGGGAGTGTCTTACTGGAAGGCTTCTGAGGGAGCTGAGTAT GATGACCAGACAAGCCAGAGAGAGAAAGAGGATGACAAGGTTT TCCCTGGAGGCAGCCACACCTATGTCTGGCAGGTCCTGAAAGAA AATGGCCCTATGGCCTCTGATCCTCTGTGCCTGACATACAGCTA CCTGAGCCATGTGGACCTGGTCAAGGACCTGAATTCTGGCCTGA TTGGAGCCCTGCTGGTGTGTAGAGAAGGCAGCCTGGCCAAAGA GAAAACCCAGACACTGCACAAGTTCATCCTGCTGTTTGCTGTGT TTGATGAGGGCAAGAGCTGGCACTCTGAGACAAAGAACAGCCT GATGCAGGACAGGGATGCTGCCTCTGCTAGAGCTTGGCCTAAGA TGCACACAGTGAATGGCTATGTGAACAGAAGCCTGCCTGGACTG ATTGGCTGCCACAGAAAGTCTGTGTACTGGCATGTGATTGGCAT GGGCACAACACCTGAGGTGCACAGCATCTTTCTGGAAGGACAC ACCTTCCTGGTGAGAAACCATAGACAGGCCAGCCTGGAAATCA GCCCTATCACCTTCCTGACAGCTCAGACCCTGCTGATGGATCTG GGCCAGTTTCTGCTGTTCTGCCACATCAGCAGCCACCAGCATGA TGGCATGGAAGCCTATGTGAAGGTGGACAGCTGCCCTGAAGAA CCCCAGCTGAGAATGAAGAACAATGAGGAGGCTGAGGACTATG ATGATGACCTGACAGACTCTGAGATGGATGTGGTCAGATTTGAT GATGACAACAGCCCCAGCTTCATCCAGATCAGATCTGTGGCCAA GAAGCACCCCAAGACCTGGGTGCACTATATTGCTGCTGAGGAA GAGGACTGGGATTATGCTCCTCTGGTGCTGGCCCCTGATGACAG AAGCTACAAGAGCCAGTACCTGAACAATGGCCCTCAGAGAATT GGCAGAAAGTATAAGAAAGTGAGATTCATGGCCTACACAGATG AGACATTCAAGACCAGAGAGGCCATTCAGCATGAGTCTGGCATT CTGGGCCCTCTGCTGTATGGAGAAGTGGGAGATACACTGCTGAT CATCTTCAAGAACCAGGCCAGCAGACCCTACAACATCTACCCTC ATGGCATCACAGATGTGAGACCCCTGTATTCTAGAAGGCTGCCC AAGGGAGTGAAGCACCTGAAGGACTTCCCTATCCTGCCTGGAG AGATCTTCAAGTACAAGTGGACAGTGACAGTGGAAGATGGCCC CACCAAGTCTGACCCTAGATGTCTGACAAGATACTACAGCAGCT TTGTGAACATGGAAAGAGACCTGGCCTCTGGCCTGATTGGACCT |

TABLE 23-continued

Listing of additional protein and nucleic acid sequences referred to herein not included in the sequence listing

| Category | SEQ ID NO: | Description | Type | Sequence |
|---|---|---|---|---|
| | | | | CTGCTGATCTGCTACAAAGAATCTGTGGACCAGAGAGGCAACC<br>AGATCATGTCTGACAAGAGAAATGTGATCCTGTTTTCTGTGTTT<br>GATGAGAACAGATCCTGGTATCTGACAGAGAACATCCAGAGAT<br>TTCTGCCCAATCCTGCTGGAGTGCAGCTGGAAGATCCTGAGTTC<br>CAGGCCTCCAACATCATGCACTCCATCAATGGCTATGTGTTTGA<br>CAGCCTGCAGCTGTCTGTGTGCCTGCATGAAGTGGCCTACTGGT<br>ACATCCTGAGCATTGGAGCCCAGACAGACTTCCTGTCTGTGTTC<br>TTCTCTGGCTACACCTTCAAGCACAAGATGGTGTATGAGGATAC<br>CCTGACACTGTTCCCATTCTCTGGAGAGACAGTGTTCATGAGCA<br>TGGAAAACCCTGGCCTGTGGATCCTGGGCTGTCACAACTCTGAC<br>TTCAGAAACAGAGGCATGACAGCCCTGCTGAAGGTGTCCAGCT<br>GTGACAAGAACACAGGAGACTACTATGAGGACAGCTATGAGGA<br>CATCTCTGCCTACCTGCTGAGCAAGAACAATGCCATTGAGCCCA<br>GAAGCTTCAGCCAGAATGCCACCAATGTGTCCAACAACAGCAA<br>CACCAGCAATGACTCCAATGTGTCCCCTCCAGTGCTGAAGAGAC<br>ACCAGAGAGAAATCACCAGAACCACACTGCAGTCTGACCAAGA<br>GGAAATTGACTATGATGACACCATCTCTGTGGAGATGAAGAAA<br>GAAGATTTTGACATCTATGATGAGGATGAGAATCAGAGCCCCA<br>GATCCTTTCAGAAAAAGACCAGACACTACTTCATTGCTGCTGTG<br>GAGAGACTGTGGGACTATGGCATGTCTAGCAGCCCTCATGTGCT<br>GAGAAATAGAGCCCAGTCTGGCTCTGTGCCCCAGTTCAAGAAA<br>GTGGTGTTCCAAGAGTTCACAGATGGCAGCTTCACCCAGCCACT<br>GTATAGAGGAGAGCTGAATGAGCATCTGGGCCTGCTGGGCCCTT<br>ATATCAGAGCTGAAGTGGAAGATAACATCATGGTCACCTTCAGA<br>AATCAGGCCTCTAGACCCTACAGCTTCTACAGCTCCCTGATCAG<br>CTATGAAGAGGACCAGAGACAGGGAGCTGAGCCCAGAAAGAAC<br>TTTGTGAAGCCCAATGAGACTAAGACCTACTTTTGGAAGGTGCA<br>GCACCACATGGCCCCTACAAAGGATGAGTTTGACTGCAAGGCCT<br>GGGCCTACTTTTCTGATGTGGATCTGGAAAAGGATGTGCACTCT<br>GGACTCATTGGACCACTGCTTGTGTGCCACACCAACACACTGAA<br>CCCTGCTCATGGCAGACAAGTGACAGTGCAAGAGTTTGCCCTGT<br>TCTTCACCATCTTTGATGAAACAAAGAGCTGGTACTTCACAGAG<br>AATATGGAGAGAAACTGCAGGGCCCCTTGCAACATCCAGATGG<br>AAGATCCCACCTTCAAAGAGAACTACAGATTCCATGCCATCAAT<br>GGCTACATCATGGACACACTGCCTGGCCTGGTTATGGCTCAGGA<br>TCAGAGAATCAGATGGTATCTGCTGTCCATGGGCTCCAATGAGA<br>ATATCCACAGCATCCACTTCTCTGGCCATGTGTTCACAGTGAGA<br>AAAAAAGAAGAGTACAAAATGGCCCTGTACAATCTGTACCCTG<br>GGGTGTTTGAAACAGTGGAAATGCTGCCTTCCAAGGCTGGCATT<br>TGGAGAGTGGAATGTCTGATTGGAGAGCACCTCCATGCTGGAAT<br>GAGCACCCTGTTTCTGGTGTACAGCAACAAGTGTCAGACCCCTC<br>TGGGCATGGCCTCTGGACACATCAGAGACTTCCAGATCACAGCC<br>TCTGGCCAGTATGGACAGTGGGCTCCTAAACTGGCTAGACTGCA<br>CTACTCTGGCAGCATCAATGCCTGGTCCACCAAAGAGCCCTTCA<br>GCTGGATCAAGGTGGACCTGCTGGCTCCCATGATCATCCATGGA<br>ATCAAGACCCAGGGAGCCAGACAGAAGTTCAGCAGCCTGTACA<br>TCAGCCAGTTCATCATCATGTACAGCCTGGATGGCAAGAAGTGG |

TABLE 23-continued

Listing of additional protein and nucleic acid sequences referred to herein not included in the sequence listing

| Category | SEQ ID NO: | Description | Type | Sequence |
|---|---|---|---|---|
| | | | | CAGACCTACAGAGGCAACAGCACAGGCACACTCATGGTGTTCTT<br>TGGCAATGTGGACAGCTCTGGCATTAAGCACAACATCTTCAACC<br>CTCCAATCATTGCCAGATACATCAGACTGCACCCCACACACTAC<br>AGCATCAGATCTACCCTGAGAATGGAACTGATGGGCTGTGACCT<br>GAACAGCTGCAGCATGCCCCTGGGAATGGAAAGCAAGGCCATC<br>TCTGATGCCCAGATCACAGCCAGCAGCTACTTCACCAACATGTT<br>TGCCACTTGGAGCCCCTCCAAGGCTAGACTGCATCTGCAGGGCA<br>GAAGCAATGCTTGGAGGCCCCAAGTGAACAACCCCAAAGAGTG<br>GCTGCAGGTGGACTTTCAAAAGACCATGAAAGTGACAGGAGTG<br>ACCACACAGGGAGTCAAGTCTCTGCTGACCTCTATGTATGTGAA<br>AGAGTTCCTGATCTCCAGCAGCCAGGATGGCCACCAGTGGACCC<br>TGTTTTTCCAGAATGGCAAAGTGAAAGTGTTCCAGGGCAATCAG<br>GACAGCTTCACACCTGTGGTCAACTCCCTGGATCCTCCACTGCT<br>GACCAGATACCTGAGAATTCACCCTCAGTCTTGGGTGCACCAGA<br>TTGCTCTGAGAATGGAAGTGCTGGGCTGTGAAGCTCAGGACCTC<br>TACTGATCGCGAATAAAAGATCTTTATTTTCATTAGATCTGTGTG<br>TTGGTTTTTTGTGTGTATTTAGCTATGCCAGTTCCCGATCGTTAC<br>AGGAAAAATGGTTCCTCTCTGCTACACTCAAATTCCT |
| FVIII donor template | 59 | FVIII donor template with MG29-1 target sites in RF orientation (pMG4009) | Nucleotide | ACGTTAATGGTTCCTCTCTGCTACACTCAAATGCCAGTTCCCGAT<br>CGTTACAGGAAATCTCAAAGCTTACTAAAGAATTATTCTTTTAC<br>ATTTCAGTGGCCACCAGAAGATATTACCTGGGAGCTGTGGAACT<br>GAGCTGGGACTACATGCAGTCTGACCTGGGAGAGCTGCCTGTGG<br>ATGCTAGATTTCCTCCAAGAGTGCCCAAGAGCTTCCCCTTCAAC<br>ACCTCTGTGGTGTACAAGAAAACCCTGTTTGTGGAATTCACAGA<br>CCACCTGTTCAATATTGCCAAGCCTAGACCTCCTTGGATGGGAC<br>TGCTGGGACCTACAATTCAGGCTGAGGTGTATGACACAGTGGTC<br>ATCACCCTGAAGAACATGGCCAGCCATCCTGTGTCTCTGCATGC<br>TGTGGGAGTGTCTTACTGGAAGGCTTCTGAGGGAGCTGAGTATG<br>ATGACCAGACAAGCCAGAGAGAGAAAGAGGATGACAAGGTTTT<br>CCCTGGAGGCAGCCACACCTATGTCTGGCAGGTCCTGAAAGAA<br>AATGGCCCTATGGCCTCTGATCCTCTGTGCCTGACATACAGCTA<br>CCTGAGCCATGTGGACCTGGTCAAGGACCTGAATTCTGGCCTGA<br>TTGGAGCCCTGCTGGTGTGTAGAGAAGGCAGCCTGGCCAAAGA<br>GAAAACCCAGACACTGCACAAGTTCATCCTGCTGTTTGCTGTGT<br>TTGATGAGGGCAAGAGCTGGCACTCTGAGACAAAGAACAGCCT<br>GATGCAGGACAGGGATGCTGCCTCTGCTAGAGCTTGGCCTAAGA<br>TGCACACAGTGAATGGCTATGTGAACAGAAGCCTGCCTGGACTG<br>ATTGGCTGCCACAGAAAGTCTGTGTACTGGCATGTGATTGGCAT<br>GGGCACAACACCTGAGGTGCACAGCATCTTTCTGGAAGGACAC<br>ACCTTCCTGGTGAGAAACCATAGACAGGCCAGCCTGGAAATCA<br>GCCCTATCACCTTCCTGACAGCTCAGACCCTGCTGATGGATCTG<br>GGCCAGTTTCTGCTGTTCTGCCACATCAGCAGCCACCAGCATGA<br>TGGCATGGAAGCCTATGTGAAGGTGGACAGCTGCCCTGAAGAA<br>CCCCAGCTGAGAATGAAGAACAATGAGGAGGCTGAGGACTATG<br>ATGATGACCTGACAGACTCTGAGATGGATGTGGTCAGATTTGAT<br>GATGACAACAGCCCCAGCTTCATCCAGATCAGATCTGTGGCCAA |

TABLE 23-continued

Listing of additional protein and nucleic acid sequences referred to herein not included in the sequence listing

| Category | SEQ ID NO: | Description | Type | Sequence |
|---|---|---|---|---|
| | | | | GAAGCACCCCAAGACCTGGGTGCACTATATTGCTGCTGAGGAA |
| | | | | GAGGACTGGGATTATGCTCCTCTGGTGCTGGCCCCTGATGACAG |
| | | | | AAGCTACAAGAGCCAGTACCTGAACAATGGCCCTCAGAGAATT |
| | | | | GGCAGAAAGTATAAGAAAGTGAGATTCATGGCCTACACAGATG |
| | | | | AGACATTCAAGACCAGAGAGGCCATTCAGCATGAGTCTGGCATT |
| | | | | CTGGGCCCTCTGCTGTATGGAGAAGTGGGAGATACACTGCTGAT |
| | | | | CATCTTCAAGAACCAGGCCAGCAGACCCTACAACATCTACCCTC |
| | | | | ATGGCATCACAGATGTGAGACCCCTGTATTCTAGAAGGCTGCCC |
| | | | | AAGGGAGTGAAGCACCTGAAGGACTTCCCTATCCTGCCTGGAG |
| | | | | AGATCTTCAAGTACAAGTGGACAGTGACAGTGGAAGATGGCCC |
| | | | | CACCAAGTCTGACCCTAGATGTCTGACAAGATACTACAGCAGCT |
| | | | | TTGTGAACATGGAAAGAGACCTGGCCTCTGGCCTGATTGGACCT |
| | | | | CTGCTGATCTGCTACAAAGAATCTGTGGACCAGAGAGGCAACC |
| | | | | AGATCATGTCTGACAAGAGAAATGTGATCCTGTTTTCTGTGTTT |
| | | | | GATGAGAACAGATCCTGGTATCTGACAGAGAACATCCAGAGAT |
| | | | | TTCTGCCCAATCCTGCTGGAGTGCAGCTGGAAGATCCTGAGTTC |
| | | | | CAGGCCTCCAACATCATGCACTCCATCAATGGCTATGTGTTTGA |
| | | | | CAGCCTGCAGCTGTCTGTGTGCCTGCATGAAGTGGCCTACTGGT |
| | | | | ACATCCTGAGCATTGGAGCCCAGACAGACTTCCTGTCTGTGTTC |
| | | | | TTCTCTGGCTACACCTTCAAGCACAAGATGGTGTATGAGGATAC |
| | | | | CCTGACACTGTTCCCATTCTCTGGAGAGACAGTGTTCATGAGCA |
| | | | | TGGAAAACCCTGGCCTGTGGATCCTGGGCTGTCACAACTCTGAC |
| | | | | TTCAGAAACAGAGGCATGACAGCCCTGCTGAAGGTGTCCAGCT |
| | | | | GTGACAAGAACACAGGAGACTACTATGAGGACAGCTATGAGGA |
| | | | | CATCTCTGCCTACCTGCTGAGCAAGAACAATGCCATTGAGCCCA |
| | | | | GAAGCTTCAGCCAGAATGCCACCAATGTGTCCAACAACAGCAA |
| | | | | CACCAGCAATGACTCCAATGTGTCCCCTCCAGTGCTGAAGAGAC |
| | | | | ACCAGAGAGAAATCACCAGAACCACACTGCAGTCTGACCAAGA |
| | | | | GGAAATTGACTATGATGACACCATCTCTGTGGAGATGAAGAAA |
| | | | | GAAGATTTTGACATCTATGATGAGGATGAGAATCAGAGCCCCA |
| | | | | GATCCTTTCAGAAAAAGACCAGACACTACTTCATTGCTGCTGTG |
| | | | | GAGAGACTGTGGGACTATGGCATGTCTAGCAGCCCTCATGTGCT |
| | | | | GAGAAATAGAGCCCAGTCTGGCTCTGTGCCCCAGTTCAAGAAA |
| | | | | GTGGTGTTCCAAGAGTTCACAGATGGCAGCTTCACCCAGCCACT |
| | | | | GTATAGAGGAGAGCTGAATGAGCATCTGGGCCTGCTGGGCCCTT |
| | | | | ATATCAGAGCTGAAGTGGAAGATAACATCATGGTCACCTTCAGA |
| | | | | AATCAGGCCTCTAGACCCTACAGCTTCTACAGCTCCCTGATCAG |
| | | | | CTATGAAGAGGACCAGAGACAGGGAGCTGAGCCCAGAAAGAAC |
| | | | | TTTGTGAAGCCCAATGAGACTAAGACCTACTTTTGGAAGGTGCA |
| | | | | GCACCACATGGCCCCTACAAAGGATGAGTTTGACTGCAAGGCCT |
| | | | | GGGCCTACTTTTCTGATGTGGATCTGGAAAAGGATGTGCACTCT |
| | | | | GGACTCATTGGACCACTGCTTGTGTGCCACACCAACACACTGAA |
| | | | | CCCTGCTCATGGCAGACAAGTGACAGTGCAAGAGTTTGCCCTGT |
| | | | | TCTTCACCATCTTTGATGAAACAAAGAGCTGGTACTTCACAGAG |
| | | | | AATATGGAGAGAAACTGCAGGGCCCCTTGCAACATCCAGATGG |
| | | | | AAGATCCCACCTTCAAAGAGAACTACAGATTCCATGCCATCAAT |
| | | | | GGCTACATCATGGACACACTGCCTGGCCTGGTTATGGCTCAGGA |

TABLE 23-continued

Listing of additional protein and nucleic acid sequences referred to herein not included in the sequence listing

| Category | SEQ ID NO: | Description | Type | Sequence |
|---|---|---|---|---|
| | | | | TCAGAGAATCAGATGGTATCTGCTGTCCATGGGCTCCAATGAGA ATATCCACAGCATCCACTTCTCTGGCCATGTGTTCACAGTGAGA AAAAAAGAAGAGTACAAAATGGCCCTGTACAATCTGTACCCTG GGGTGTTTGAAACAGTGGAAATGCTGCCTTCCAAGGCTGGCATT TGGAGAGTGGAATGTCTGATTGGAGAGCACCTCCATGCTGGAAT GAGCACCCTGTTTCTGGTGTACAGCAACAAGTGTCAGACCCCTC TGGGCATGGCCTCTGGACACATCAGAGACTTCCAGATCACAGCC TCTGGCCAGTATGGACAGTGGGCTCCTAAACTGGCTAGACTGCA CTACTCTGGCAGCATCAATGCCTGGTCCACCAAAGAGCCCTTCA GCTGGATCAAGGTGGACCTGCTGGCTCCCATGATCATCCATGGA ATCAAGACCCAGGGAGCCAGACAGAAGTTCAGCAGCCTGTACA TCAGCCAGTTCATCATCATGTACAGCCTGGATGGCAAGAAGTGG CAGACCTACAGAGGCAACAGCACAGGCACACTCATGGTGTTCTT TGGCAATGTGGACAGCTCTGGCATTAAGCACAACATCTTCAACC CTCCAATCATTGCCAGATACATCAGACTGCACCCCACACACTAC AGCATCAGATCTACCCTGAGAATGGAACTGATGGGCTGTGACCT GAACAGCTGCAGCATGCCCCTGGGAATGGAAAGCAAGGCCATC TCTGATGCCCAGATCACAGCCAGCAGCTACTTCACCAACATGTT TGCCACTTGGAGCCCCTCCAAGGCTAGACTGCATCTGCAGGGCA GAAGCAATGCTTGGAGGCCCCAAGTGAACAACCCCAAAGAGTG GCTGCAGGTGGACTTTCAAAAGACCATGAAAGTGACAGGAGTG ACCACACAGGGAGTCAAGTCTCTGCTGACCTCTATGTATGTGAA AGAGTTCCTGATCTCCAGCAGCCAGGATGGCCACCAGTGGACCC TGTTTTTCCAGAATGGCAAAGTGAAAGTGTTCCAGGGCAATCAG GACAGCTTCACACCTGTGGTCAACTCCCTGGATCCTCCACTGCT GACCAGATACCTGAGAATTCACCCTCAGTCTTGGGTGCACCAGA TTGCTCTGAGAATGGAAGTGCTGGGCTGTGAAGCTCAGGACCTC TACTGATCGCGAATAAAAGATCTTTATTTTCATTAGATCTGTGTG TTGGTTTTTTGTGTGTATTTAGCTATTTGAGTGTAGCAGAGAGGA ACCATTTTTCCTGTAACGATCGGGAACTGGCATTCCT |
| MG29-1 sgRNA targeting mouse albumin | 60 | mA29-8b-50 guide RNA | Nucleotide | mG*mU*mU*GAGAAUC*mG*mA*mA*mAGAUUCUCAAC*mC*mU *mU*U*UAAUUmUmCmUmACU*G*U*U*GUAGAUCUGUAACfGfA fUfCfGfGfGfAfAfC*fU*fG*mG |
| MG29-1 sgRNA targeting mouse albumin | 61 | mA29-12b-50 guide RNA | Nucleotide | mG*mU*mU*GAGAAUC*mG*mA*mA*mAGAUUCUCAAC*mC*mU *mU*U*UAAUUmUmCmUmACU*G*U*U*GUAGAUAGUGUAGfCf AfGfAfGfAfGfGfAfA*fC*fC*mA |
| MG29-1 sgRNA targeting mouse albumin | 62 | mA29-8-37 guide RNA | Nucleotide | mC*mU*mU*U*UAAUUmUmCmUmACU*G*U*U*GUAGAUCUGUA ACfGfAfUfCfGfGfGfAfAfC*fU*fGfG*fC*mA |
| MG29-1 sgRNA targeting mouse albumin | 63 | mA29-12-37 guide RNA | Nucleotide | mC*mU*mU*U*UAAUUmUmCmUmACU*G*U*U*GUAGAUAGUGU AGfCfAfGfAfGfAfGfGfAfA*fC*fCfA*fU*mU |

TABLE 23-continued

| Category | SEQ ID NO: | Description | Type | Sequence |
|---|---|---|---|---|
| Listing of additional protein and nucleic acid sequences referred to herein not included in the sequence listing | | | | |
| MG29-1 sgRNA targeting human albumin intron 1 | 64 | chA29-74B-50 | Nucleotide | mG*mU*mU*GAGAAUC*mG*mA*mA*mAGAUUCUCAAC*mC*mU *mU*U*UAAUUmUmCmUmACU*G*U*U*GUAGAUAAUAAAGfCf AfUfAfGfUfGfCfAfA*fU*fG*mG |
| MG29-1 sgRNA targeting human albumin intron 1 | 65 | CA29-78B-50 | Nucleotide | mG*mU*mU*GAGAAUC*mG*mA*mA*mAGAUUCUCAAC*mC*mU *mU*U*UAAUUmUmCmUmACU*G*U*U*GUAGAUUUUUGCCfCfA fCfUfAfAfGfGfAfA*fA*fG*mU |
| MG29-1 sgRNA targeting human albumin intron 1 | 66 | chA29-83B-50 | Nucleotide | mG*mU*mU*GAGAAUC*mG*mA*mA*mAGAUUCUCAAC*mC*mU *mU*U*UAAUUmUmCmUmACU*G*U*U*GUAGAUUGAGAUCfAf AfCfAfGfCfAfCfAfG*fG*fU*mU |
| MG29-1 sgRNA targeting human albumin intron 1 | 67 | cA29-84B-50 | Nucleotide | mG*mU*mU*GAGAAUC*mG*mA*mA*mAGAUUCUCAAC*mC*mU *mU*U*UAAUUmUmCmUmACU*G*U*U*GUAGAUCACUUUCfCfU fUfAfGfUfGfGfGfC*fA*fA*mA |
| MG29-1 sgRNA targeting human albumin intron 1 | 68 | cA29-87B-50 | Nucleotide | mG*mU*mU*GAGAAUC*mG*mA*mA*mAGAUUCUCAAC*mC*mU *mU*U*UAAUUmUmCmUmACU*G*U*U*GUAGAUCCCACUAfAfG fGfAfAfAfGfUfGfC*fA*fA*mA |
| Protease recognition site | 69 | Native furin cleavage site of FVIII | Protein | RHQR |
| Artificial protein sequence derived from human FVIII B-domain | 101 | Protein sequence containing 6 potential N-linked glycosylation sites derived from the B-domain of FVIII as described in McIntosh et al 2013 (BLOOD, VOLUME 121, NUMBER 17, DOI 10.1182/blood-2012-10-462200) | Protein | ENRSFSQNATNVSNNSNTSNDSNVSPPVLKRHQR |
| Novel protein sequence to replace the B-domain of FVIII | 71 | var1 B-domain replacement | Protein | ENRSFSQNPPVLKRHQR |
| Novel protein sequence to replace the B-domain of FVIII | 72 | var2 B-domain replacement | Protein | ENRSFSQNPPVLKRHQR |

TABLE 23-continued

Listing of additional protein and nucleic acid sequences referred to herein not included in the sequence listing

| Category | SEQ ID NO: | Description | Type | Sequence |
|---|---|---|---|---|
| Novel protein sequence to replace the B-domain of FVIII | 73 | var3 B-domain replacement | Protein | EPRSFSQNCSQNPPVLKRHQR |
| Novel protein sequence to replace the B-domain of FVIII | 74 | var4 B-domain replacement | Protein | EPRNFSQNCSQNPPVLKRHQR |
| Novel protein sequence to replace the B-domain of FVIII | 75 | var5 B-domain replacement | Protein | ENRSFSQNCSQNPPVLKRHQR |
| Novel protein sequence to replace the B-domain of FVIII | 76 | var6 B-domain replacement | Protein | EPRNFSQNATPPVLKRHQR |
| Novel protein sequence to replace the B-domain of FVIII | 77 | var7 B-domain replacement | Protein | ENRSNFSQNPPVLKRHQR |
| Novel protein sequence to replace the B-domain of FVIII | 78 | var8 B-domain replacement | Protein | ENRSNFSQNCSQNPPVLKRHQR |
| Novel protein sequence to replace the B-domain of FVIII | 79 | var9 B-domain replacement | Protein | ENRSNFSQNATPPVLKRHQR |
| Artificial protein sequence derived by combining the N and C terminal junctions of the B-domain as described by Lind et al (Eur J Biochem. 1995; 232(1): 19-27) | 80 | SQ Linker | Protein | EPRSFSQNPPVLKRHQR |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| Human FVIII donor cassette pMG4017 | 81 | pMG4017 insert (FVIII donor in which the B-domain is replaced by the SQ linker) | Nucleotide | ACGCGTACGTTTTTCCTGTAACGATCGGGAACTGGCATTTGAGT GTAGCAGAGAGGAACCATTTCTCAGTGTTAAGCTTACTAAAGAA TTATTCTTTTACATTTCAGTGGCCACCAGAAGATATTACCTGGGA GCTGTGGAACTGAGCTGGGACTACATGCAGTCTGACCTGGGAG AGCTGCCTGTGGATGCTAGATTTCCTCCAAGAGTGCCCAAGAGC TTCCCCTTCAACACCTCTGTGGTGTACAAGAAAACCCTGTTTGTG GAATTCACAGACCACCTGTTCAATATTGCCAAGCCTAGACCTCC TTGGATGGGACTGCTGGGACCTACAATTCAGGCTGAGGTGTATG ACACAGTGGTCATCACCCTGAAGAACATGGCCAGCCATCCTGTG TCTCTGCATGCTGTGGGAGTGTCTTACTGGAAGGCTTCTGAGGG AGCTGAGTATGATGACCAGACAAGCCAGAGAGAGAAAGAGGAT GACAAGGTTTTCCCTGGAGGCAGCCACACCTATGTCTGGCAGGT CCTGAAAGAAAATGGCCCTATGGCCTCTGATCCTCTGTGCCTGA CATACAGCTACCTGAGCCATGTGGACCTGGTCAAGGACCTGAAT TCTGGCCTGATTGGAGCCCTGCTGGTGTGTAGAGAAGGCAGCCT GGCCAAAGAGAAAACCCAGACACTGCACAAGTTCATCCTGCTG TTTGCTGTGTTTGATGAGGGCAAGAGCTGGCACTCTGAGACAAA GAACAGCCTGATGCAGGACAGGGATGCTGCCTCTGCTAGAGCTT GGCCTAAGATGCACACAGTGAATGGCTATGTGAACAGAAGCCT GCCTGGACTGATTGGCTGCCACAGAAAGTCTGTGTACTGGCATG TGATTGGCATGGGCACAACACCTGAGGTGCACAGCATCTTTCTG GAAGGACACACCTTCCTGGTGAGAAACCATAGACAGGCCAGCC TGGAAATCAGCCCTATCACCTTCCTGACAGCTCAGACCCTGCTG ATGGATCTGGGCCAGTTTCTGCTGTTCTGCCACATCAGCAGCCA CCAGCATGATGGCATGGAAGCCTATGTGAAGGTGGACAGCTGC CCTGAAGAACCCCAGCTGAGAATGAAGAACAATGAGGAGGCTG AGGACTATGATGATGACCTGACAGACTCTGAGATGGATGTGGTC AGATTTGATGATGACAACAGCCCCAGCTTCATCCAGATCAGATC TGTGGCCAAGAAGCACCCCAAGACCTGGGTGCACTATATTGCTG CTGAGGAAGAGGACTGGGATTATGCTCCTCTGGTGCTGGCCCCT GATGACAGAAGCTACAAGAGCCAGTACCTGAACAATGGCCCTC AGAGAATTGGCAGAAAGTATAAGAAAGTGAGATTCATGGCCTA CACAGATGAGACATTCAAGACCAGAGAGGCCATTCAGCATGAG TCTGGCATTCTGGGCCCTCTGCTGTATGGAGAAGTGGGAGATAC ACTGCTGATCATCTTCAAGAACCAGGCCAGCAGACCCTACAACA TCTACCCTCATGGCATCACAGATGTGAGACCCCTGTATTCTAGA AGGCTGCCCAAGGGAGTGAAGCACCTGAAGGACTTCCCTATCCT GCCTGGAGAGATCTTCAAGTACAAGTGGACAGTGACAGTGGAA GATGGCCCCACCAAGTCTGACCCTAGATGTCTGACAAGATACTA CAGCAGCTTTGTGAACATGGAAAGAGACCTGGCCTCTGGCCTGA TTGGACCTCTGCTGATCTGCTACAAAGAATCTGTGGACCAGAGA GGCAACCAGATCATGTCTGACAAGAGAAATGTGATCCTGTTTTC TGTGTTTGATGAGAACAGATCCTGGTATCTGACAGAGAACATCC AGAGATTTCTGCCCAATCCTGCTGGAGTGCAGCTGGAAGATCCT GAGTTCCAGGCCTCCAACATCATGCACTCCATCAATGGCTATGT GTTTGACAGCCTGCAGCTGTCTGTGTGCCTGCATGAAGTGGCCT |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | ACTGGTACATCCTGAGCATTGGAGCCCAGACAGACTTCCTGTCT<br>GTGTTCTTCTCTGGCTACACCTTCAAGCACAAGATGGTGTATGA<br>GGATACCCTGACACTGTTCCCATTCTCTGGAGAGACAGTGTTCA<br>TGAGCATGGAAAACCCTGGCCTGTGGATCCTGGGCTGTCACAAC<br>TCTGACTTCAGAAACAGAGGCATGACAGCCCTGCTGAAGGTGTC<br>CAGCTGTGACAAGAACACAGGAGACTACTATGAGGACAGCTAT<br>GAGGACATCTCTGCCTACCTGCTGAGCAAGAACAATGCCATTGA<br>GCCCAGAAGCTTCAGCCAGAATCCTCCAGTGCTGAAGAGACAC<br>CAGAGAGAAATCACCAGAACCACACTGCAGTCTGACCAAGAGG<br>AAATTGACTATGATGACACCATCTCTGTGGAGATGAAGAAAGA<br>AGATTTTGACATCTATGATGAGGATGAGAATCAGAGCCCCAGAT<br>CCTTTCAGAAAAAGACCAGACACTACTTCATTGCTGCTGTGGAG<br>AGACTGTGGGACTATGGCATGTCTAGCAGCCCTCATGTGCTGAG<br>AAATAGAGCCCAGTCTGGCTCTGTGCCCCAGTTCAAGAAAGTGG<br>TGTTCCAAGAGTTCACAGATGGCAGCTTCACCCAGCCACTGTAT<br>AGAGGAGAGCTGAATGAGCATCTGGGCCTGCTGGGCCCTTATAT<br>CAGAGCTGAAGTGGAAGATAACATCATGGTCACCTTCAGAAAT<br>CAGGCCTCTAGACCCTACAGCTTCTACAGCTCCCTGATCAGCTA<br>TGAAGAGGACCAGAGACAGGGAGCTGAGCCCAGAAAGAACTTT<br>GTGAAGCCCAATGAGACTAAGACCTACTTTTGGAAGGTGCAGC<br>ACCACATGGCCCCTACAAAGGATGAGTTTGACTGCAAGGCCTGG<br>GCCTACTTTTCTGATGTGGATCTGGAAAAGGATGTGCACTCTGG<br>ACTCATTGGACCACTGCTTGTGTGCCACACCAACACACTGAACC<br>CTGCTCATGGCAGACAAGTGACAGTGCAAGAGTTTGCCCTGTTC<br>TTCACCATCTTTGATGAAACAAAGAGCTGGTACTTCACAGAGAA<br>TATGGAGAGAAACTGCAGGGCCCCTTGCAACATCCAGATGGAA<br>GATCCCACCTTCAAAGAGAACTACAGATTCCATGCCATCAATGG<br>CTACATCATGGACACACTGCCTGGCCTGGTTATGGCTCAGGATC<br>AGAGAATCAGATGGTATCTGCTGTCCATGGGCTCCAATGAGAAT<br>ATCCACAGCATCCACTTCTCTGGCCATGTGTTCACAGTGAGAAA<br>AAAAGAAGAGTACAAAATGGCCCTGTACAATCTGTACCCTGGG<br>GTGTTTGAAACAGTGGAAATGCTGCCTTCCAAGGCTGGCATTTG<br>GAGAGTGGAATGTCTGATTGGAGAGCACCTCCATGCTGGAATG<br>AGCACCCTGTTTCTGGTGTACAGCAACAAGTGTCAGACCCCTCT<br>GGGCATGGCCTCTGGACACATCAGAGACTTCCAGATCACAGCCT<br>CTGGCCAGTATGGACAGTGGGCTCCTAAACTGGCTAGACTGCAC<br>TACTCTGGCAGCATCAATGCCTGGTCCACCAAAGAGCCCTTCAG<br>CTGGATCAAGGTGGACCTGCTGGCTCCCATGATCATCCATGGAA<br>TCAAGACCCAGGGAGCCAGACAGAAGTTCAGCAGCCTGTACAT<br>CAGCCAGTTCATCATCATGTACAGCCTGGATGGCAAGAAGTGGC<br>AGACCTACAGAGGCAACAGCACAGGCACACTCATGGTGTTCTTT<br>GGCAATGTGGACAGCTCTGGCATTAAGCACAACATCTTCAACCC<br>TCCAATCATTGCCAGATACATCAGACTGCACCCCACACACTACA<br>GCATCAGATCTACCCTGAGAATGGAACTGATGGGCTGTGACCTG<br>AACAGCTGCAGCATGCCCCTGGGAATGGAAAGCAAGGCCATCT<br>CTGATGCCCAGATCACAGCCAGCAGCTACTTCACCAACATGTTT<br>GCCACTTGGAGCCCCTCCAAGGCTAGACTGCATCTGCAGGGCAG |

TABLE 23-continued

Listing of additional protein and nucleic acid sequences referred to herein not included in the sequence listing

| Category | SEQ ID NO: | Description | Type | Sequence |
|---|---|---|---|---|
| | | | | AAGCAATGCTTGGAGGCCCCAAGTGAACAACCCCAAAGAGTGG CTGCAGGTGGACTTTCAAAAGACCATGAAAGTGACAGGAGTGA CCACACAGGGAGTCAAGTCTCTGCTGACCTCTATGTATGTGAAA GAGTTCCTGATCTCCAGCAGCCAGGATGGCCACCAGTGGACCCT GTTTTTCCAGAATGGCAAAGTGAAAGTGTTCCAGGGCAATCAGG ACAGCTTCACACCTGTGGTCAACTCCCTGGATCCTCCACTGCTG ACCAGATACCTGAGAATTCACCCTCAGTCTTGGGTGCACCAGAT TGCTCTGAGAATGGAAGTGCTGGGCTGTGAAGCTCAGGACCTCT ACTGATCGCGAATAAAAGATCTTTATTTTCATTAGATCTGTGTGT TGGTTTTTTGTGTGTATTTAGCTAACAGTATGATTAAGTGGATAA ATGGTTCCTCTCTGCTACACTCAAATGCCAGTTCCCGATCGTTAC AGGAAATTCCTCACGTG |
| Human FVIII donor cassette pMG4018 | 82 | pMG4018 insert (FVIII donor with B domain replaced by the var2 sequence) | Nucleotide | ACGCGTACGTTTTTCCTGTAACGATCGGGAACTGGCATTTGAGT GTAGCAGAGAGGAACCATTTCTCAGTGTTAAGCTTACTAAAGAA TTATTCTTTTACATTTCAGTGGCCACCAGAAGATATTACCTGGGA GCTGTGGAACTGAGCTGGGACTACATGCAGTCTGACCTGGGAG AGCTGCCTGTGGATGCTAGATTTCCTCCAAGAGTGCCCAAGAGC TTCCCCTTCAACACCTCTGTGGTGTACAAGAAAACCCTGTTTGTG GAATTCACAGACCACCTGTTCAATATTGCCAAGCCTAGACCTCC TTGGATGGGACTGCTGGGACCTACAATTCAGGCTGAGGTGTATG ACACAGTGGTCATCACCCTGAAGAACATGGCCAGCCATCCTGTG TCTCTGCATGCTGTGGGAGTGTCTTACTGGAAGGCTTCTGAGGG AGCTGAGTATGATGACCAGACAAGCCAGAGAGAGAAAGAGGAT GACAAGGTTTTCCCTGGAGGCAGCCACACCTATGTCTGGCAGGT CCTGAAAGAAAATGGCCCTATGGCCTCTGATCCTCTGTGCCTGA CATACAGCTACCTGAGCCATGTGGACCTGGTCAAGGACCTGAAT TCTGGCCTGATTGGAGCCCTGCTGGTGTGTAGAGAAGGCAGCCT GGCCAAAGAGAAAACCCAGACACTGCACAAGTTCATCCTGCTG TTTGCTGTGTTTGATGAGGGCAAGAGCTGGCACTCTGAGACAAA GAACAGCCTGATGCAGGACAGGGATGCTGCCTCTGCTAGAGCTT GGCCTAAGATGCACACAGTGAATGGCTATGTGAACAGAAGCCT GCCTGGACTGATTGGCTGCCACAGAAAGTCTGTGTACTGGCATG TGATTGGCATGGGCACAACACCTGAGGTGCACAGCATCTTTCTG GAAGGACACACCTTCCTGGTGAGAAACCATAGACAGGCCAGCC TGGAAATCAGCCCTATCACCTTCCTGACAGCTCAGACCCTGCTG ATGGATCTGGGCCAGTTTCTGCTGTTCTGCCACATCAGCAGCCA CCAGCATGATGGCATGGAAGCCTATGTGAAGGTGGACAGCTGC CCTGAAGAACCCCAGCTGAGAATGAAGAACAATGAGGAGGCTG AGGACTATGATGATGACCTGACAGACTCTGAGATGGATGTGGTC AGATTTGATGATGACAACAGCCCCAGCTTCATCCAGATCAGATC TGTGGCCAAGAAGCACCCCAAGACCTGGGTGCACTATATTGCTG CTGAGGAAGAGGACTGGGATTATGCTCCTCTGGTGCTGGCCCCT GATGACAGAAGCTACAAGAGCCAGTACCTGAACAATGGCCCTC AGAGAATTGGCAGAAAGTATAAGAAAGTGAGATTCATGGCCTA CACAGATGAGACATTCAAGACCAGAGAGGCCATTCAGCATGAG TCTGGCATTCTGGGCCCTCTGCTGTATGGAGAAGTGGGAGATAC |

TABLE 23-continued

Listing of additional protein and nucleic acid sequences referred to herein not included in the sequence listing

| Category | SEQ ID NO: | Description | Type | Sequence |
|---|---|---|---|---|
| | | | | ACTGCTGATCATCTTCAAGAACCAGGCCAGCAGACCCTACAACA |
| | | | | TCTACCCTCATGGCATCACAGATGTGAGACCCCTGTATTCTAGA |
| | | | | AGGCTGCCCAAGGGAGTGAAGCACCTGAAGGACTTCCCTATCCT |
| | | | | GCCTGGAGAGATCTTCAAGTACAAGTGGACAGTGACAGTGGAA |
| | | | | GATGGCCCCACCAAGTCTGACCCTAGATGTCTGACAAGATACTA |
| | | | | CAGCAGCTTTGTGAACATGGAAAGAGACCTGGCCTCTGGCCTGA |
| | | | | TTGGACCTCTGCTGATCTGCTACAAAGAATCTGTGGACCAGAGA |
| | | | | GGCAACCAGATCATGTCTGACAAGAGAAATGTGATCCTGTTTTC |
| | | | | TGTGTTTGATGAGAACAGATCCTGGTATCTGACAGAGAACATCC |
| | | | | AGAGATTTCTGCCCAATCCTGCTGGAGTGCAGCTGGAAGATCCT |
| | | | | GAGTTCCAGGCCTCCAACATCATGCACTCCATCAATGGCTATGT |
| | | | | GTTTGACAGCCTGCAGCTGTCTGTGTGCCTGCATGAAGTGGCCT |
| | | | | ACTGGTACATCCTGAGCATTGGAGCCCAGACAGACTTCCTGTCT |
| | | | | GTGTTCTTCTCTGGCTACACCTTCAAGCACAAGATGGTGTATGA |
| | | | | GGATACCCTGACACTGTTCCCATTCTCTGGAGAGACAGTGTTCA |
| | | | | TGAGCATGGAAAACCCTGGCCTGTGGATCCTGGGCTGTCACAAC |
| | | | | TCTGACTTCAGAAACAGAGGCATGACAGCCCTGCTGAAGGTGTC |
| | | | | CAGCTGTGACAAGAACACAGGAGACTACTATGAGGACAGCTAT |
| | | | | GAGGACATCTCTGCCTACCTGCTGAGCAAGAACAATGCCATTGA |
| | | | | GCCCAGAAACTTCAGCCAGAATCCTCCAGTGCTGAAGAGACAC |
| | | | | CAGAGAGAAATCACCAGAACCACACTGCAGTCTGACCAAGAGG |
| | | | | AAATTGACTATGATGACACCATCTCTGTGGAGATGAAGAAAGA |
| | | | | AGATTTTGACATCTATGATGAGGATGAGAATCAGAGCCCCAGAT |
| | | | | CCTTTCAGAAAAAGACCAGACACTACTTCATTGCTGCTGTGGAG |
| | | | | AGACTGTGGGACTATGGCATGTCTAGCAGCCCTCATGTGCTGAG |
| | | | | AAATAGAGCCCAGTCTGGCTCTGTGCCCCAGTTCAAGAAAGTGG |
| | | | | TGTTCCAAGAGTTCACAGATGGCAGCTTCACCCAGCCACTGTAT |
| | | | | AGAGGAGAGCTGAATGAGCATCTGGGCCTGCTGGGCCCTTATAT |
| | | | | CAGAGCTGAAGTGGAAGATAACATCATGGTCACCTTCAGAAAT |
| | | | | CAGGCCTCTAGACCCTACAGCTTCTACAGCTCCCTGATCAGCTA |
| | | | | TGAAGAGGACCAGAGACAGGGAGCTGAGCCCAGAAAGAACTTT |
| | | | | GTGAAGCCCAATGAGACTAAGACCTACTTTTGGAAGGTGCAGC |
| | | | | ACCACATGGCCCCTACAAAGGATGAGTTTGACTGCAAGGCCTGG |
| | | | | GCCTACTTTTCTGATGTGGATCTGGAAAAGGATGTGCACTCTGG |
| | | | | ACTCATTGGACCACTGCTTGTGTGCCACACCAACACACTGAACC |
| | | | | CTGCTCATGGCAGACAAGTGACAGTGCAAGAGTTTGCCCTGTTC |
| | | | | TTCACCATCTTTGATGAAACAAAGAGCTGGTACTTCACAGAGAA |
| | | | | TATGGAGAGAAACTGCAGGGCCCCTTGCAACATCCAGATGGAA |
| | | | | GATCCCACCTTCAAAGAGAACTACAGATTCCATGCCATCAATGG |
| | | | | CTACATCATGGACACACTGCCTGGCCTGGTTATGGCTCAGGATC |
| | | | | AGAGAATCAGATGGTATCTGCTGTCCATGGGCTCCAATGAGAAT |
| | | | | ATCCACAGCATCCACTTCTCTGGCCATGTGTTCACAGTGAGAAA |
| | | | | AAAAGAAGAGTACAAAATGGCCCTGTACAATCTGTACCCTGGG |
| | | | | GTGTTTGAAACAGTGGAAATGCTGCCTTCCAAGGCTGGCATTTG |
| | | | | GAGAGTGGAATGTCTGATTGGAGAGCACCTCCATGCTGGAATG |
| | | | | AGCACCCTGTTTCTGGTGTACAGCAACAAGTGTCAGACCCCTCT |
| | | | | GGGCATGGCCTCTGGACACATCAGAGACTTCCAGATCACAGCCT |

TABLE 23-continued

| Category | SEQ ID NO: | Description | Type | Sequence |
|---|---|---|---|---|
| | | | | CTGGCCAGTATGGACAGTGGGCTCCTAAACTGGCTAGACTGCAC<br>TACTCTGGCAGCATCAATGCCTGGTCCACCAAAGAGCCCTTCAG<br>CTGGATCAAGGTGGACCTGCTGGCTCCCATGATCATCCATGGAA<br>TCAAGACCCAGGGAGCCAGACAGAAGTTCAGCAGCCTGTACAT<br>CAGCCAGTTCATCATCATGTACAGCCTGGATGGCAAGAAGTGGC<br>AGACCTACAGAGGCAACAGCACAGGCACACTCATGGTGTTCTTT<br>GGCAATGTGGACAGCTCTGGCATTAAGCACAACATCTTCAACCC<br>TCCAATCATTGCCAGATACATCAGACTGCACCCCACACACTACA<br>GCATCAGATCTACCCTGAGAATGGAACTGATGGGCTGTGACCTG<br>AACAGCTGCAGCATGCCCCTGGGAATGGAAAGCAAGGCCATCT<br>CTGATGCCCAGATCACAGCCAGCAGCTACTTCACCAACATGTTT<br>GCCACTTGGAGCCCCTCCAAGGCTAGACTGCATCTGCAGGGCAG<br>AAGCAATGCTTGGAGGCCCCAAGTGAACAACCCCAAAGAGTGG<br>CTGCAGGTGGACTTTCAAAAGACCATGAAAGTGACAGGAGTGA<br>CCACACAGGGAGTCAAGTCTCTGCTGACCTCTATGTATGTGAAA<br>GAGTTCCTGATCTCCAGCAGCCAGGATGGCCACCAGTGGACCCT<br>GTTTTTCCAGAATGGCAAAGTGAAAGTGTTCCAGGGCAATCAGG<br>ACAGCTTCACACCTGTGGTCAACTCCCTGGATCCTCCACTGCTG<br>ACCAGATACCTGAGAATTCACCCTCAGTCTTGGGTGCACCAGAT<br>TGCTCTGAGAATGGAAGTGCTGGGCTGTGAAGCTCAGGACCTCT<br>ACTGATCGCGAATAAAAGATCTTTATTTTCATTAGATCTGTGTGT<br>TGGTTTTTTGTGTGTATTTAGCTAACAGTATGATTAAGTGGATAA<br>ATGGTTCCTCTCTGCTACACTCAAATGCCAGTTCCCGATCGTTAC<br>AGGAAATTCCTCACGTG |
| Human FVIII donor cassette pMG4019 | 83 | pMG4019 (FVIII donor with B domain replaced by the var3 sequence) | Nucleotide | ACGCGTACGTTTTTCCTGTAACGATCGGGAACTGGCATTTGAGT<br>GTAGCAGAGAGGAACCATTTCTCAGTGTTAAGCTTACTAAAGAA<br>TTATTCTTTTACATTTCAGTGGCCACCAGAAGATATTACCTGGGA<br>GCTGTGGAACTGAGCTGGGACTACATGCAGTCTGACCTGGGAG<br>AGCTGCCTGTGGATGCTAGATTTCCTCCAAGAGTGCCCAAGAGC<br>TTCCCCTTCAACACCTCTGTGGTGTACAAGAAAACCCTGTTTGTG<br>GAATTCACAGACCACCTGTTCAATATTGCCAAGCCTAGACCTCC<br>TTGGATGGGACTGCTGGGACCTACAATTCAGGCTGAGGTGTATG<br>ACACAGTGGTCATCACCCTGAAGAACATGGCCAGCCATCCTGTG<br>TCTCTGCATGCTGTGGGAGTGTCTTACTGGAAGGCTTCTGAGGG<br>AGCTGAGTATGATGACCAGACAAGCCAGAGAGAGAAAGAGGAT<br>GACAAGGTTTTCCCTGGAGGCAGCCACACCTATGTCTGGCAGGT<br>CCTGAAAGAAAATGGCCCTATGGCCTCTGATCCTCTGTGCCTGA<br>CATACAGCTACCTGAGCCATGTGGACCTGGTCAAGGACCTGAAT<br>TCTGGCCTGATTGGAGCCCTGCTGGTGTGTAGAGAAGGCAGCCT<br>GGCCAAAGAGAAAACCCAGACACTGCACAAGTTCATCCTGCTG<br>TTTGCTGTGTTTGATGAGGGCAAGAGCTGGCACTCTGAGACAAA<br>GAACAGCCTGATGCAGGACAGGGATGCTGCCTCTGCTAGAGCTT<br>GGCCTAAGATGCACACAGTGAATGGCTATGTGAACAGAAGCCT<br>GCCTGGACTGATTGGCTGCCACAGAAAGTCTGTGTACTGGCATG<br>TGATTGGCATGGGCACAACACCTGAGGTGCACAGCATCTTTCTG<br>GAAGGACACACCTTCCTGGTGAGAAACCATAGACAGGCCAGCC |

TABLE 23-continued

Listing of additional protein and nucleic acid sequences referred to herein not included in the sequence listing

| Category | SEQ ID NO: | Description | Type | Sequence |
|---|---|---|---|---|
| | | | | TGGAAATCAGCCCTATCACCTTCCTGACAGCTCAGACCCTGCTG<br>ATGGATCTGGGCCAGTTTCTGCTGTTCTGCCACATCAGCAGCCA<br>CCAGCATGATGGCATGGAAGCCTATGTGAAGGTGGACAGCTGC<br>CCTGAAGAACCCCAGCTGAGAATGAAGAACAATGAGGAGGCTG<br>AGGACTATGATGATGACCTGACAGACTCTGAGATGGATGTGGTC<br>AGATTTGATGATGACAACAGCCCCAGCTTCATCCAGATCAGATC<br>TGTGGCCAAGAAGCACCCCAAGACCTGGGTGCACTATATTGCTG<br>CTGAGGAAGAGGACTGGGATTATGCTCCTCTGGTGCTGGCCCCT<br>GATGACAGAAGCTACAAGAGCCAGTACCTGAACAATGGCCCTC<br>AGAGAATTGGCAGAAAGTATAAGAAAGTGAGATTCATGGCCTA<br>CACAGATGAGACATTCAAGACCAGAGAGGCCATTCAGCATGAG<br>TCTGGCATTCTGGGCCCTCTGCTGTATGGAGAAGTGGGAGATAC<br>ACTGCTGATCATCTTCAAGAACCAGGCCAGCAGACCCTACAACA<br>TCTACCCTCATGGCATCACAGATGTGAGACCCCTGTATTCTAGA<br>AGGCTGCCCAAGGGAGTGAAGCACCTGAAGGACTTCCCTATCCT<br>GCCTGGAGAGATCTTCAAGTACAAGTGGACAGTGACAGTGGAA<br>GATGGCCCCACCAAGTCTGACCCTAGATGTCTGACAAGATACTA<br>CAGCAGCTTTGTGAACATGGAAAGAGACCTGGCCTCTGGCCTGA<br>TTGGACCTCTGCTGATCTGCTACAAAGAATCTGTGGACCAGAGA<br>GGCAACCAGATCATGTCTGACAAGAGAAATGTGATCCTGTTTTC<br>TGTGTTTGATGAGAACAGATCCTGGTATCTGACAGAGAACATCC<br>AGAGATTTCTGCCCAATCCTGCTGGAGTGCAGCTGGAAGATCCT<br>GAGTTCCAGGCCTCCAACATCATGCACTCCATCAATGGCTATGT<br>GTTTGACAGCCTGCAGCTGTCTGTGTGCCTGCATGAAGTGGCCT<br>ACTGGTACATCCTGAGCATTGGAGCCCAGACAGACTTCCTGTCT<br>GTGTTCTTCTCTGGCTACACCTTCAAGCACAAGATGGTGTATGA<br>GGATACCCTGACACTGTTCCCATTCTCTGGAGAGACAGTGTTCA<br>TGAGCATGGAAAACCCTGGCCTGTGGATCCTGGGCTGTCACAAC<br>TCTGACTTCAGAAACAGAGGCATGACAGCCCTGCTGAAGGTGTC<br>CAGCTGTGACAAGAACACAGGAGACTACTATGAGGACAGCTAT<br>GAGGACATCTCTGCCTACCTGCTGAGCAAGAACAATGCCATTGA<br>GCCCAGAAGCTTCAGCCAGAATTGCAGCCAGAACCCTCCAGTGC<br>TGAAGAGACACCAGAGAGAAATCACCAGAACCACACTGCAGTC<br>TGACCAAGAGGAAATTGACTATGATGACACCATCTCTGTGGAGA<br>TGAAGAAAGAAGATTTTGACATCTATGATGAGGATGAGAATCA<br>GAGCCCCAGATCCTTTCAGAAAAAGACCAGACACTACTTCATTG<br>CTGCTGTGGAGAGACTGTGGGACTATGGCATGTCTAGCAGCCCT<br>CATGTGCTGAGAAATAGAGCCCAGTCTGGCTCTGTGCCCCAGTT<br>CAAGAAAGTGGTGTTCCAAGAGTTCACAGATGGCAGCTTCACCC<br>AGCCACTGTATAGAGGAGAGCTGAATGAGCATCTGGGCCTGCT<br>GGGCCCTTATATCAGAGCTGAAGTGGAAGATAACATCATGGTCA<br>CCTTCAGAAATCAGGCCTCTAGACCCTACAGCTTCTACAGCTCC<br>CTGATCAGCTATGAAGAGGACCAGAGACAGGGAGCTGAGCCCA<br>GAAAGAACTTTGTGAAGCCCAATGAGACTAAGACCTACTTTTGG<br>AAGGTGCAGCACCACATGGCCCCTACAAAGGATGAGTTTGACT<br>GCAAGGCCTGGGCCTACTTTTCTGATGTGGATCTGGAAAAGGAT<br>GTGCACTCTGGACTCATTGGACCACTGCTTGTGTGCCACACCAA |

TABLE 23-continued

Listing of additional protein and nucleic acid sequences referred to herein not included in the sequence listing

| Category | SEQ ID NO: | Description | Type | Sequence |
|---|---|---|---|---|
| | | | | CACACTGAACCCTGCTCATGGCAGACAAGTGACAGTGCAAGAG<br>TTTGCCCTGTTCTTCACCATCTTTGATGAAACAAAGAGCTGGTAC<br>TTCACAGAGAATATGGAGAGAAACTGCAGGGCCCCTTGCAACA<br>TCCAGATGGAAGATCCCACCTTCAAAGAGAACTACAGATTCCAT<br>GCCATCAATGGCTACATCATGGACACACTGCCTGGCCTGGTTAT<br>GGCTCAGGATCAGAGAATCAGATGGTATCTGCTGTCCATGGGCT<br>CCAATGAGAATATCCACAGCATCCACTTCTCTGGCCATGTGTTC<br>ACAGTGAGAAAAAAAGAAGAGTACAAAATGGCCCTGTACAATC<br>TGTACCCTGGGGTGTTTGAAACAGTGGAAATGCTGCCTTCCAAG<br>GCTGGCATTTGGAGAGTGGAATGTCTGATTGGAGAGCACCTCCA<br>TGCTGGAATGAGCACCCTGTTTCTGGTGTACAGCAACAAGTGTC<br>AGACCCCTCTGGGCATGGCCTCTGGACACATCAGAGACTTCCAG<br>ATCACAGCCTCTGGCCAGTATGGACAGTGGGCTCCTAAACTGGC<br>TAGACTGCACTACTCTGGCAGCATCAATGCCTGGTCCACCAAAG<br>AGCCCTTCAGCTGGATCAAGGTGGACCTGCTGGCTCCCATGATC<br>ATCCATGGAATCAAGACCCAGGGAGCCAGACAGAAGTTCAGCA<br>GCCTGTACATCAGCCAGTTCATCATCATGTACAGCCTGGATGGC<br>AAGAAGTGGCAGACCTACAGAGGCAACAGCACAGGCACACTCA<br>TGGTGTTCTTTGGCAATGTGGACAGCTCTGGCATTAAGCACAAC<br>ATCTTCAACCCTCCAATCATTGCCAGATACATCAGACTGCACCC<br>CACACACTACAGCATCAGATCTACCCTGAGAATGGAACTGATGG<br>GCTGTGACCTGAACAGCTGCAGCATGCCCCTGGGAATGGAAAG<br>CAAGGCCATCTCTGATGCCCAGATCACAGCCAGCAGCTACTTCA<br>CCAACATGTTTGCCACTTGGAGCCCCTCCAAGGCTAGACTGCAT<br>CTGCAGGGCAGAAGCAATGCTTGGAGGCCCCAAGTGAACAACC<br>CCAAAGAGTGGCTGCAGGTGGACTTTCAAAAGACCATGAAAGT<br>GACAGGAGTGACCACACAGGGAGTCAAGTCTCTGCTGACCTCTA<br>TGTATGTGAAAGAGTTCCTGATCTCCAGCAGCCAGGATGGCCAC<br>CAGTGGACCCTGTTTTTCCAGAATGGCAAAGTGAAAGTGTTCCA<br>GGGCAATCAGGACAGCTTCACACCTGTGGTCAACTCCCTGGATC<br>CTCCACTGCTGACCAGATACCTGAGAATTCACCCTCAGTCTTGG<br>GTGCACCAGATTGCTCTGAGAATGGAAGTGCTGGGCTGTGAAGC<br>TCAGGACCTCTACTGATCGCGAATAAAAGATCTTTATTTTCATTA<br>GATCTGTGTGTTGGTTTTTTGTGTGTATTTAGCTAACAGTATGAT<br>TAAGTGGATAAATGGTTCCTCTCTGCTACACTCAAATGCCAGTT<br>CCCGATCGTTACAGGAAATTCCTCACGTG |
| Human FVIII donor cassette pMG4020 | 84 | pMG4020 (FVIII donor with the B-domain replaced by the var4 sequence) | Nucleotide | ACGCGTACGTTTTTCCTGTAACGATCGGGAACTGGCATTTGAGT<br>GTAGCAGAGAGGAACCATTTCTCAGTGTTAAGCTTACTAAAGAA<br>TTATTCTTTTACATTTCAGTGGCCACCAGAAGATATTACCTGGGA<br>GCTGTGGAACTGAGCTGGGACTACATGCAGTCTGACCTGGGAG<br>AGCTGCCTGTGGATGCTAGATTTCCTCCAAGAGTGCCCAAGAGC<br>TTCCCCTTCAACACCTCTGTGGTGTACAAGAAAACCCTGTTTGTG<br>GAATTCACAGACCACCTGTTCAATATTGCCAAGCCTAGACCTCC<br>TTGGATGGGACTGCTGGGACCTACAATTCAGGCTGAGGTGTATG<br>ACACAGTGGTCATCACCCTGAAGAACATGGCCAGCCATCCTGTG<br>TCTCTGCATGCTGTGGGAGTGTCTTACTGGAAGGCTTCTGAGGG |

TABLE 23-continued

| Category | SEQ ID NO: | Description | Type | Sequence |
|---|---|---|---|---|
| Listing of additional protein and nucleic acid sequences referred to herein not included in the sequence listing | | | | |
| | | | | AGCTGAGTATGATGACCAGACAAGCCAGAGAGAGAAAGAGGAT |
| | | | | GACAAGGTTTTCCCTGGAGGCAGCCACACCTATGTCTGGCAGGT |
| | | | | CCTGAAAGAAAATGGCCCTATGGCCTCTGATCCTCTGTGCCTGA |
| | | | | CATACAGCTACCTGAGCCATGTGGACCTGGTCAAGGACCTGAAT |
| | | | | TCTGGCCTGATTGGAGCCCTGCTGGTGTGTAGAGAAGGCAGCCT |
| | | | | GGCCAAAGAGAAAACCCAGACACTGCACAAGTTCATCCTGCTG |
| | | | | TTTGCTGTGTTTGATGAGGGCAAGAGCTGGCACTCTGAGACAAA |
| | | | | GAACAGCCTGATGCAGGACAGGGATGCTGCCTCTGCTAGAGCTT |
| | | | | GGCCTAAGATGCACACAGTGAATGGCTATGTGAACAGAAGCCT |
| | | | | GCCTGGACTGATTGGCTGCCACAGAAAGTCTGTGTACTGGCATG |
| | | | | TGATTGGCATGGGCACAACACCTGAGGTGCACAGCATCTTTCTG |
| | | | | GAAGGACACACCTTCCTGGTGAGAAACCATAGACAGGCCAGCC |
| | | | | TGGAAATCAGCCCTATCACCTTCCTGACAGCTCAGACCCTGCTG |
| | | | | ATGGATCTGGGCCAGTTTCTGCTGTTCTGCCACATCAGCAGCCA |
| | | | | CCAGCATGATGGCATGGAAGCCTATGTGAAGGTGGACAGCTGC |
| | | | | CCTGAAGAACCCCAGCTGAGAATGAAGAACAATGAGGAGGCTG |
| | | | | AGGACTATGATGATGACCTGACAGACTCTGAGATGGATGTGGTC |
| | | | | AGATTTGATGATGACAACAGCCCCAGCTTCATCCAGATCAGATC |
| | | | | TGTGGCCAAGAAGCACCCCAAGACCTGGGTGCACTATATTGCTG |
| | | | | CTGAGGAAGAGGACTGGGATTATGCTCCTCTGGTGCTGGCCCCT |
| | | | | GATGACAGAAGCTACAAGAGCCAGTACCTGAACAATGGCCCTC |
| | | | | AGAGAATTGGCAGAAAGTATAAGAAAGTGAGATTCATGGCCTA |
| | | | | CACAGATGAGACATTCAAGACCAGAGAGGCCATTCAGCATGAG |
| | | | | TCTGGCATTCTGGGCCCTCTGCTGTATGGAGAAGTGGGAGATAC |
| | | | | ACTGCTGATCATCTTCAAGAACCAGGCCAGCAGACCCTACAACA |
| | | | | TCTACCCTCATGGCATCACAGATGTGAGACCCCTGTATTCTAGA |
| | | | | AGGCTGCCCAAGGGAGTGAAGCACCTGAAGGACTTCCCTATCCT |
| | | | | GCCTGGAGAGATCTTCAAGTACAAGTGGACAGTGACAGTGGAA |
| | | | | GATGGCCCCACCAAGTCTGACCCTAGATGTCTGACAAGATACTA |
| | | | | CAGCAGCTTTGTGAACATGGAAAGAGACCTGGCCTCTGGCCTGA |
| | | | | TTGGACCTCTGCTGATCTGCTACAAAGAATCTGTGGACCAGAGA |
| | | | | GGCAACCAGATCATGTCTGACAAGAGAAATGTGATCCTGTTTTC |
| | | | | TGTGTTTGATGAGAACAGATCCTGGTATCTGACAGAGAACATCC |
| | | | | AGAGATTTCTGCCCAATCCTGCTGGAGTGCAGCTGGAAGATCCT |
| | | | | GAGTTCCAGGCCTCCAACATCATGCACTCCATCAATGGCTATGT |
| | | | | GTTTGACAGCCTGCAGCTGTCTGTGTGCCTGCATGAAGTGGCCT |
| | | | | ACTGGTACATCCTGAGCATTGGAGCCCAGACAGACTTCCTGTCT |
| | | | | GTGTTCTTCTCTGGCTACACCTTCAAGCACAAGATGGTGTATGA |
| | | | | GGATACCCTGACACTGTTCCCATTCTCTGGAGAGACAGTGTTCA |
| | | | | TGAGCATGGAAAACCCTGGCCTGTGGATCCTGGGCTGTCACAAC |
| | | | | TCTGACTTCAGAAACAGAGGCATGACAGCCCTGCTGAAGGTGTC |
| | | | | CAGCTGTGACAAGAACACAGGAGACTACTATGAGGACAGCTAT |
| | | | | GAGGACATCTCTGCCTACCTGCTGAGCAAGAACAATGCCATTGA |
| | | | | GCCCAGAAACTTCAGCCAGAATTGCAGCCAGAACCCTCCAGTGC |
| | | | | TGAAGAGACACCAGAGAGAAATCACCAGAACCACACTGCAGTC |
| | | | | TGACCAAGAGGAAATTGACTATGATGACACCATCTCTGTGGAGA |
| | | | | TGAAGAAAGAAGATTTTGACATCTATGATGAGGATGAGAATCA |

TABLE 23-continued

Listing of additional protein and nucleic acid sequences referred to herein not included in the sequence listing

| Category | SEQ ID NO: | Description | Type | Sequence |
|---|---|---|---|---|
| | | | | GAGCCCCAGATCCTTTCAGAAAAAGACCAGACACTACTTCATTG<br>CTGCTGTGGAGAGACTGTGGGACTATGGCATGTCTAGCAGCCCT<br>CATGTGCTGAGAAATAGAGCCCAGTCTGGCTCTGTGCCCCAGTT<br>CAAGAAAGTGGTGTTCCAAGAGTTCACAGATGGCAGCTTCACCC<br>AGCCACTGTATAGAGGAGAGCTGAATGAGCATCTGGGCCTGCT<br>GGGCCCTTATATCAGAGCTGAAGTGGAAGATAACATCATGGTCA<br>CCTTCAGAAATCAGGCCTCTAGACCCTACAGCTTCTACAGCTCC<br>CTGATCAGCTATGAAGAGGACCAGAGACAGGGAGCTGAGCCCA<br>GAAAGAACTTTGTGAAGCCCAATGAGACTAAGACCTACTTTTGG<br>AAGGTGCAGCACCACATGGCCCCTACAAAGGATGAGTTTGACT<br>GCAAGGCCTGGGCCTACTTTTCTGATGTGGATCTGGAAAAGGAT<br>GTGCACTCTGGACTCATTGGACCACTGCTTGTGTGCCACACCAA<br>CACACTGAACCCTGCTCATGGCAGACAAGTGACAGTGCAAGAG<br>TTTGCCCTGTTCTTCACCATCTTTGATGAAACAAAGAGCTGGTAC<br>TTCACAGAGAATATGGAGAGAAACTGCAGGGCCCCTTGCAACA<br>TCCAGATGGAAGATCCCACCTTCAAAGAGAACTACAGATTCCAT<br>GCCATCAATGGCTACATCATGGACACACTGCCTGGCCTGGTTAT<br>GGCTCAGGATCAGAGAATCAGATGGTATCTGCTGTCCATGGGCT<br>CCAATGAGAATATCCACAGCATCCACTTCTCTGGCCATGTGTTC<br>ACAGTGAGAAAAAAAGAAGAGTACAAAATGGCCCTGTACAATC<br>TGTACCCTGGGGTGTTTGAAACAGTGGAAATGCTGCCTTCCAAG<br>GCTGGCATTTGGAGAGTGGAATGTCTGATTGGAGAGCACCTCCA<br>TGCTGGAATGAGCACCCTGTTTCTGGTGTACAGCAACAAGTGTC<br>AGACCCCTCTGGGCATGGCCTCTGGACACATCAGAGACTTCCAG<br>ATCACAGCCTCTGGCCAGTATGGACAGTGGGCTCCTAAACTGGC<br>TAGACTGCACTACTCTGGCAGCATCAATGCCTGGTCCACCAAAG<br>AGCCCTTCAGCTGGATCAAGGTGGACCTGCTGGCTCCCATGATC<br>ATCCATGGAATCAAGACCCAGGGAGCCAGACAGAAGTTCAGCA<br>GCCTGTACATCAGCCAGTTCATCATCATGTACAGCCTGGATGGC<br>AAGAAGTGGCAGACCTACAGAGGCAACAGCACAGGCACACTCA<br>TGGTGTTCTTTGGCAATGTGGACAGCTCTGGCATTAAGCACAAC<br>ATCTTCAACCCTCCAATCATTGCCAGATACATCAGACTGCACCC<br>CACACACTACAGCATCAGATCTACCCTGAGAATGGAACTGATGG<br>GCTGTGACCTGAACAGCTGCAGCATGCCCCTGGGAATGGAAAG<br>CAAGGCCATCTCTGATGCCCAGATCACAGCCAGCAGCTACTTCA<br>CCAACATGTTTGCCACTTGGAGCCCCTCCAAGGCTAGACTGCAT<br>CTGCAGGGCAGAAGCAATGCTTGGAGGCCCCAAGTGAACAACC<br>CCAAAGAGTGGCTGCAGGTGGACTTTCAAAAGACCATGAAAGT<br>GACAGGAGTGACCACACAGGGAGTCAAGTCTCTGCTGACCTCTA<br>TGTATGTGAAAGAGTTCCTGATCTCCAGCAGCCAGGATGGCCAC<br>CAGTGGACCCTGTTTTTCCAGAATGGCAAAGTGAAAGTGTTCCA<br>GGGCAATCAGGACAGCTTCACACCTGTGGTCAACTCCCTGGATC<br>CTCCACTGCTGACCAGATACCTGAGAATTCACCCTCAGTCTTGG<br>GTGCACCAGATTGCTCTGAGAATGGAAGTGCTGGGCTGTGAAGC |

TABLE 23-continued

| Category | SEQ ID NO: | Description | Type | Sequence |
|---|---|---|---|---|
| | | | | TCAGGACCTCTACTGATCGCGAATAAAAGATCTTTATTTTCATTA<br>GATCTGTGTGTTGGTTTTTTGTGTGTATTTAGCTAACAGTATGAT<br>TAAGTGGATAAATGGTTCCTCTCTGCTACACTCAAATGCCAGTT<br>CCCGATCGTTACAGGAAATTCCTCACGTG |
| Human FVIII donor cassette pMG4021 | 85 | pMG4021 (FVIII donor with the B-domain replaced by the var 8 sequence ) | Nucleotide | ACGCGTACGTTTTTCCTGTAACGATCGGGAACTGGCATTTGAGT<br>GTAGCAGAGAGGAACCATTTCTCAGTGTTAAGCTTACTAAAGAA<br>TTATTCTTTTACATTTCAGTGGCCACCAGAAGATATTACCTGGGA<br>GCTGTGGAACTGAGCTGGGACTACATGCAGTCTGACCTGGGAG<br>AGCTGCCTGTGGATGCTAGATTTCCTCCAAGAGTGCCCAAGAGC<br>TTCCCCTTCAACACCTCTGTGGTGTACAAGAAAACCCTGTTTGTG<br>GAATTCACAGACCACCTGTTCAATATTGCCAAGCCTAGACCTCC<br>TTGGATGGGACTGCTGGGACCTACAATTCAGGCTGAGGTGTATG<br>ACACAGTGGTCATCACCCTGAAGAACATGGCCAGCCATCCTGTG<br>TCTCTGCATGCTGTGGGAGTGTCTTACTGGAAGGCTTCTGAGGG<br>AGCTGAGTATGATGACCAGACAAGCCAGAGAGAGAAAGAGGAT<br>GACAAGGTTTTCCCTGGAGGCAGCCACACCTATGTCTGGCAGGT<br>CCTGAAAGAAAATGGCCCTATGGCCTCTGATCCTCTGTGCCTGA<br>CATACAGCTACCTGAGCCATGTGGACCTGGTCAAGGACCTGAAT<br>TCTGGCCTGATTGGAGCCCTGCTGGTGTGTAGAGAAGGCAGCCT<br>GGCCAAAGAGAAAACCCAGACACTGCACAAGTTCATCCTGCTG<br>TTTGCTGTGTTTGATGAGGGCAAGAGCTGGCACTCTGAGACAAA<br>GAACAGCCTGATGCAGGACAGGGATGCTGCCTCTGCTAGAGCTT<br>GGCCTAAGATGCACACAGTGAATGGCTATGTGAACAGAAGCCT<br>GCCTGGACTGATTGGCTGCCACAGAAAGTCTGTGTACTGGCATG<br>TGATTGGCATGGGCACAACACCTGAGGTGCACAGCATCTTTCTG<br>GAAGGACACACCTTCCTGGTGAGAAACCATAGACAGGCCAGCC<br>TGGAAATCAGCCCTATCACCTTCCTGACAGCTCAGACCCTGCTG<br>ATGGATCTGGGCCAGTTTCTGCTGTTCTGCCACATCAGCAGCCA<br>CCAGCATGATGGCATGGAAGCCTATGTGAAGGTGGACAGCTGC<br>CCTGAAGAACCCCAGCTGAGAATGAAGAACAATGAGGAGGCTG<br>AGGACTATGATGATGACCTGACAGACTCTGAGATGGATGTGGTC<br>AGATTTGATGATGACAACAGCCCCAGCTTCATCCAGATCAGATC<br>TGTGGCCAAGAAGCACCCCAAGACCTGGGTGCACTATATTGCTG<br>CTGAGGAAGAGGACTGGGATTATGCTCCTCTGGTGCTGGCCCCT<br>GATGACAGAAGCTACAAGAGCCAGTACCTGAACAATGGCCCTC<br>AGAGAATTGGCAGAAAGTATAAGAAAGTGAGATTCATGGCCTA<br>CACAGATGAGACATTCAAGACCAGAGAGGCCATTCAGCATGAG<br>TCTGGCATTCTGGGCCCTCTGCTGTATGGAGAAGTGGGAGATAC<br>ACTGCTGATCATCTTCAAGAACCAGGCCAGCAGACCCTACAACA<br>TCTACCCTCATGGCATCACAGATGTGAGACCCCTGTATTCTAGA<br>AGGCTGCCCAAGGGAGTGAAGCACCTGAAGGACTTCCCTATCCT<br>GCCTGGAGAGATCTTCAAGTACAAGTGGACAGTGACAGTGGAA<br>GATGGCCCCACCAAGTCTGACCCTAGATGTCTGACAAGATACTA<br>CAGCAGCTTTGTGAACATGGAAAGAGACCTGGCCTCTGGCCTGA<br>TTGGACCTCTGCTGATCTGCTACAAAGAATCTGTGGACCAGAGA<br>GGCAACCAGATCATGTCTGACAAGAGAAATGTGATCCTGTTTTC |

Listing of additional protein and nucleic acid sequences referred to herein not included in the sequence listing TABLE 23-continued Listing of additional protein and nucleic acid sequences referred to herein not included in the sequence listing

| Category | SEQ ID NO: | Description | Type | Sequence |
|---|---|---|---|---|
| | | | | TGTGTTTGATGAGAACAGATCCTGGTATCTGACAGAGAACATCC<br>AGAGATTTCTGCCCAATCCTGCTGGAGTGCAGCTGGAAGATCCT<br>GAGTTCCAGGCCTCCAACATCATGCACTCCATCAATGGCTATGT<br>GTTTGACAGCCTGCAGCTGTCTGTGTGCCTGCATGAAGTGGCCT<br>ACTGGTACATCCTGAGCATTGGAGCCCAGACAGACTTCCTGTCT<br>GTGTTCTTCTCTGGCTACACCTTCAAGCACAAGATGGTGTATGA<br>GGATACCCTGACACTGTTCCCATTCTCTGGAGAGACAGTGTTCA<br>TGAGCATGGAAAACCCTGGCCTGTGGATCCTGGGCTGTCACAAC<br>TCTGACTTCAGAAACAGAGGCATGACAGCCCTGCTGAAGGTGTC<br>CAGCTGTGACAAGAACACAGGAGACTACTATGAGGACAGCTAT<br>GAGGACATCTCTGCCTACCTGCTGAGCAAGAACAATGCCATTGA<br>GAACAGAAGCAACTTCAGCCAGAATTGCAGCCAGAACCCTCCA<br>GTGCTGAAGAGACACCAGAGAGAAATCACCAGAACCACACTGC<br>AGTCTGACCAAGAGGAAATTGACTATGATGACACCATCTCTGTG<br>GAGATGAAGAAAGAAGATTTTGACATCTATGATGAGGATGAGA<br>ATCAGAGCCCCAGATCCTTTCAGAAAAAGACCAGACACTACTTC<br>ATTGCTGCTGTGGAGAGACTGTGGGACTATGGCATGTCTAGCAG<br>CCCTCATGTGCTGAGAAATAGAGCCCAGTCTGGCTCTGTGCCCC<br>AGTTCAAGAAAGTGGTGTTCCAAGAGTTCACAGATGGCAGCTTC<br>ACCCAGCCACTGTATAGAGGAGAGCTGAATGAGCATCTGGGCC<br>TGCTGGGCCCTTATATCAGAGCTGAAGTGGAAGATAACATCATG<br>GTCACCTTCAGAAATCAGGCCTCTAGACCCTACAGCTTCTACAG<br>CTCCCTGATCAGCTATGAAGAGGACCAGAGACAGGGAGCTGAG<br>CCCAGAAAGAACTTTGTGAAGCCCAATGAGACTAAGACCTACTT<br>TTGGAAGGTGCAGCACCACATGGCCCCTACAAAGGATGAGTTTG<br>ACTGCAAGGCCTGGGCCTACTTTTCTGATGTGGATCTGGAAAAG<br>GATGTGCACTCTGGACTCATTGGACCACTGCTTGTGTGCCACAC<br>CAACACACTGAACCCTGCTCATGGCAGACAAGTGACAGTGCAA<br>GAGTTTGCCCTGTTCTTCACCATCTTTGATGAAACAAAGAGCTG<br>GTACTTCACAGAGAATATGGAGAGAAACTGCAGGGCCCCTTGC<br>AACATCCAGATGGAAGATCCCACCTTCAAAGAGAACTACAGAT<br>TCCATGCCATCAATGGCTACATCATGGACACACTGCCTGGCCTG<br>GTTATGGCTCAGGATCAGAGAATCAGATGGTATCTGCTGTCCAT<br>GGGCTCCAATGAGAATATCCACAGCATCCACTTCTCTGGCCATG<br>TGTTCACAGTGAGAAAAAAAGAAGAGTACAAAATGGCCCTGTA<br>CAATCTGTACCCTGGGGTGTTTGAAACAGTGGAAATGCTGCCTT<br>CCAAGGCTGGCATTTGGAGAGTGGAATGTCTGATTGGAGAGCA<br>CCTCCATGCTGGAATGAGCACCCTGTTTCTGGTGTACAGCAACA<br>AGTGTCAGACCCCTCTGGGCATGGCCTCTGGACACATCAGAGAC<br>TTCCAGATCACAGCCTCTGGCCAGTATGGACAGTGGGCTCCTAA<br>ACTGGCTAGACTGCACTACTCTGGCAGCATCAATGCCTGGTCCA<br>CCAAAGAGCCCTTCAGCTGGATCAAGGTGGACCTGCTGGCTCCC<br>ATGATCATCCATGGAATCAAGACCCAGGGAGCCAGACAGAAGT<br>TCAGCAGCCTGTACATCAGCCAGTTCATCATCATGTACAGCCTG<br>GATGGCAAGAAGTGGCAGACCTACAGAGGCAACAGCACAGGCA<br>CACTCATGGTGTTCTTTGGCAATGTGGACAGCTCTGGCATTAAG<br>CACAACATCTTCAACCCTCCAATCATTGCCAGATACATCAGACT |

TABLE 23-continued

Listing of additional protein and nucleic acid sequences referred to herein not included in the sequence listing

| Category | SEQ ID NO: | Description | Type | Sequence |
|---|---|---|---|---|
| | | | | GCACCCCACACACTACAGCATCAGATCTACCCTGAGAATGGAAC<br>TGATGGGCTGTGACCTGAACAGCTGCAGCATGCCCCTGGGAATG<br>GAAAGCAAGGCCATCTCTGATGCCCAGATCACAGCCAGCAGCT<br>ACTTCACCAACATGTTTGCCACTTGGAGCCCCTCCAAGGCTAGA<br>CTGCATCTGCAGGGCAGAAGCAATGCTTGGAGGCCCCAAGTGA<br>ACAACCCCAAAGAGTGGCTGCAGGTGGACTTTCAAAAGACCAT<br>GAAAGTGACAGGAGTGACCACACAGGGAGTCAAGTCTCTGCTG<br>ACCTCTATGTATGTGAAAGAGTTCCTGATCTCCAGCAGCCAGGA<br>TGGCCACCAGTGGACCCTGTTTTTCCAGAATGGCAAAGTGAAAG<br>TGTTCCAGGGCAATCAGGACAGCTTCACACCTGTGGTCAACTCC<br>CTGGATCCTCCACTGCTGACCAGATACCTGAGAATTCACCCTCA<br>GTCTTGGGTGCACCAGATTGCTCTGAGAATGGAAGTGCTGGGCT<br>GTGAAGCTCAGGACCTCTACTGATCGCGAATAAAAGATCTTTAT<br>TTTCATTAGATCTGTGTGTTGGTTTTTTGTGTGTATTTAGCTAAC<br>AGTATGATTAAGTGGATAAATGGTTCCTCTCTGCTACACTCAAA<br>TGCCAGTTCCCGATCGTTACAGGAAATTCCTCACGTG |
| Cynomolgus macaque FVIII protein sequence in which the B-domain was replaced with the SQ linker and residue F2196 was changed to K | 86 | Cynomolgus FVIII in which the B-domain was replaced by the SQ linker sequence and residue F2196 was changed to K. Residues 1 to 20 encode the native signal peptide | Protein | MQIELSTYFFLCLLRFCFSATRRYYLGAVELSWDYMQSDLGELPVD<br>TRFPPRVPRSFPFNTSVMYKKTVFVEFTDHLFNIAKPRPPWMGLLG<br>PTIQAEVYDTVVITLKNMASHPVSLHAVGVSYWKASEGAEYDDQT<br>SQREKEDDKVFPGGSHTYVWQVLKENGPMASDPLCLTYSYLSHV<br>DLVKDLNSGLIGALLVCREGSLAKEKTQTLHKFVLLFAVFDEGKS<br>WHSETKNSLMQDRDDASARAWPKMHTVNGYVNRSLPGLIGCHRK<br>SVYWHVIGMGTTPEVHSIFLEGHTFLVRNHRQASLEISPITFLTAQT<br>LLMDLGQFLLFCHISSHQHDGMEAYVKVDSCPEEPQLRMKNNEEA<br>EDYDDDLADSEMDVVRFDDDNSPSFIQIRSVAKKHPKTWVHYIAA<br>EEEVWDYAPSVLAPDDRSYKSQYLNNGSQRIGRKYKKVRFMAYT<br>DETFKTREAIQYESGILGPLLYGEVGDTLLIIFKNQASRPYNIYPHGI<br>TDVRPLYSRRLPKGVKHLKDFPILPGEIFKYKWTVTVEDGPTKSDP<br>RCLTRYYSSFINMERDLASGLIGPLLICYKESVDQRGNQIMSDKRN<br>VILFSVFDENQSWYLTENIQRFLPNPVGVQLEDPEFQASNIMHSING<br>YVFDSLQLSVCLHEVAYWYILSIGAQTDFLSVFFSGYTFKHKMVYE<br>DTLTLFPFSGETVFMSMENPGLWILGCHNSDFRNRGMTALLKVSSC<br>DKNTGDYYEDSYEDISTYLLSKNNAIEPRSFSQNPPVLKRHQREITL<br>NTLQSDQEEIDYDDTISVEMKKEDFDIYGEDENQSPRSFQKKTRHY<br>FIAAVERLWDYGMSSSPHVLRNRAQSGSVPQFKKVVFQEFTDGSF<br>TQPLYRGELNEHLGLLGPYIRAEVEDNIMVTFKNQASRPYSFYSSLI<br>SYEEDQRQGAEPRKNFVKPNETKTYFWKVQHHMAPTKDEFDCKA<br>WAYFSDVDLEKDVHSGLIGPLLVCHTNTLNPAHGRQVTVQEFALF<br>FTIFDETKSWYFTENTERNCRAPCNIQMEDPTFKENYRFHAINGYIM<br>DTLPGLVMAQDQRIRWYLLSMGSNENIHSIHFSGHVFTVRKKEEY<br>KMAVYNLYPGVFETVEMLPSKAGIWRVECLIGEHLHAGMSTLFLV<br>YSNKCQTPLGMASGRIRDFQITASGQYGQWAPKLARLHYSGSINA<br>WSTKEPFSWIKVDLLAPMIIHGIKTQGARQKFSSLYISQFIIMYSLDG<br>KKWQTYRGNSTGTLMVFFGNVDSSGIKHNIFNPPIIARYIRLHPTHY<br>SIRSTLRMELMGCDLNSCSMPLGMESKAISDAQITASSYKTNMFAT<br>WSPSKARLNLQGRSNAWRPQVNNPKEWLQVDFQKTMKVTGITTQ |

TABLE 23-continued

Listing of additional protein and nucleic acid sequences referred to herein not included in the sequence listing

| Category | SEQ ID NO: | Description | Type | Sequence |
|---|---|---|---|---|
| | | | | GVKSLLTSMYVKEFLISSSQDGHHWTLFFQNGKVKVFQGNQDSFT<br>PVVNSLDSPLLTRYLRIHPQSWVHQIALRIEVLGCEAQELY |
| Cynomolgus macaque FVIII protein sequence in which the B-domain was replaced with the var 4 B-domain replacement and residue F2196 was changed to K and the signal peptide was removed | 87 | Cynomolgus FVIII in which the B domain was replaced by the var 4 B domain replacement and residue F2196 was changed to K and the native signal peptide was deleted | Protein | ATRRYYLGAVELSWDYMQSDLGELPVDTRFPPRVPRSFPFNTSVM<br>YKKTVFVEFTDHLFNIAKPRPPWMGLLGPTIQAEVYDTVVITLKNM<br>ASHPVSLHAVGVSYWKASEGAEYDDQTSQREKEDDKVFPGGSHT<br>YVWQVLKENGPMASDPLCLTYSYLSHVDLVKDLNSGLIGALLVCR<br>EGSLAKEKTQTLHKFVLLFAVFDEGKSWHSETKNSLMQDRDDASA<br>RAWPKMHTVNGYVNRSLPGLIGCHRKSVYWHVIGMGTTPEVHSIF<br>LEGHTFLVRNHRQASLEISPITFLTAQTLLMDLGQFLLFCHISSHQH<br>DGMEAYVKVDSCPEEPQLRMKNNEEAEDYDDDLADSEMDVVRF<br>DDDNSPSFIQIRSVAKKHPKTWVHYIAAEEEVWDYAPSVLAPDDRS<br>YKSQYLNNGSQRIGRKYKKVRFMAYTDETFKTREAIQYESGILGPL<br>LYGEVGDTLLIIFKNQASRPYNIYPHGITDVRPLYSRRLPKGVKHLK<br>DFPILPGEIFKYKWTVTVEDGPTKSDPRCLTRYYSSFINMERDLASG<br>LIGPLLICYKESVDQRGNQIMSDKRNVILFSVFDENQSWYLTENIQR<br>FLPNPVGVQLEDPEFQASNIMHSINGYVFDSLQLSVCLHEVAYWYI<br>LSIGAQTDFLSVFFSGYTFKHKMVYEDTLTLFPFSGETVFMSMENP<br>GLWILGCHNSDFRNRGMTALLKVSSCDKNTGDYYEDSYEDISTYL<br>LSKNNAIEPRNFSQNCSQNPPVLKRHQREITLNTLQSDQEEIDYDDT<br>ISVEMKKEDFDIYGEDENQSPRSFQKKTRHYFIAAVERLWDYGMSS<br>SPHVLRNRAQSGSVPQFKKVVFQEFTDGSFTQPLYRGELNEHLGLL<br>GPYIRAEVEDNIMVTFKNQASRPYSFYSSLISYEEDQRQGAEPRKNF<br>VKPNETKTYFWKVQHHMAPTKDEFDCKAWAYFSDVDLEKDVHS<br>GLIGPLLVCHTNTLNPAHGRQVTVQEFALFFTIFDETKSWYFTENTE<br>RNCRAPCNIQMEDPTFKENYRFHAINGYIMDTLPGLVMAQDQRIR<br>WYLLSMGSNENIHSIHFSGHVFTVRKKEEYKMAVYNLYPGVFETV<br>EMLPSKAGIWRVECLIGEHLHAGMSTLFLVYSNKCQTPLGMASGRI<br>RDFQITASGQYGQWAPKLARLHYSGSINAWSTKEPFSWIKVDLLAP<br>MIIHGIKTQGARQKFSSLYISQFIIMYSLDGKKWQTYRGNSTGTLM<br>VFFGNVDSSGIKHNIFNPPIIARYIRLHPTHYSIRSTLRMELMGCDLN<br>SCSMPLGMESKAISDAQITASSYKTNMFATWSPSKARLNLQGRSN<br>AWRPQVNNPKEWLQVDFQKTMKVTGITTQGVKSLLTSMYVKEFLI<br>SSSQDGHHWTLFFQNGKVKVFQGNQDSFTPVVNSLDSPLLTRYLRI<br>HPQSWVHQIALRIEVLGCEAQELY |
| Cyno FVIII donor cassette pMG4016 | 88 | pMG4016 (Cyno FVIII donor cassette that encodes cyno FVIII with var4 B-domain replacement and F2196K and associated guide target sites, splice acceptor and polyA signal) | Nucleotide | CATAGTACGCGTACGTTTTTTCTTTTGCCCACTAAGGAAAGTGC<br>AAAATATTGGGCTCTGATTCCTACAGAAAAATCTCAGCATCAAG<br>CTTACTAAAGAATTATTCTTTTACATTTCAGTGGCCACCAGAAG<br>ATATTACCTGGGAGCTGTGGAACTGAGCTGGGACTACATGCAGT<br>CTGACCTGGGAGAGCTGCCTGTGGATACCAGATTTCCTCCAAGA<br>GTGCCCAGAAGCTTCCCCTTCAACACCTCTGTGATGTACAAGAA<br>AACAGTGTTTGTGGAATTCACAGACCACCTGTTCAATATTGCCA<br>AGCCTAGACCTCCTTGGATGGGACTGCTGGGACCTACAATTCAG<br>GCTGAGGTGTATGACACAGTGGTCATCACCCTGAAGAACATGGC<br>CAGCCATCCTGTGTCTCTGCATGCTGTGGGAGTGTCTTACTGGA<br>AGGCTTCTGAGGGAGCTGAGTATGATGACCAGACAAGCCAGAG |

TABLE 23-continued

| Category | SEQ ID NO: | Description | Type | Sequence |
|---|---|---|---|---|
| Listing of additional protein and nucleic acid sequences referred to herein not included in the sequence listing | | | | |
| | | | | AGAGAAAGAGGATGACAAGGTTTTCCCTGGAGGCAGCCACACC<br>TATGTCTGGCAGGTCCTGAAAGAAAATGGCCCTATGGCCTCTGA<br>TCCTCTGTGCCTGACATACAGCTACCTGAGCCATGTGGACCTGG<br>TCAAGGACCTGAATTCTGGCCTGATTGGAGCCCTGCTGGTGTGT<br>AGAGAAGGCAGCCTGGCCAAAGAGAAAACCCAGACACTGCACA<br>AGTTTGTGCTGCTGTTTGCTGTGTTTGATGAGGGCAAGAGCTGG<br>CACTCTGAGACAAAGAACAGCCTGATGCAGGACAGGGATGATG<br>CCTCTGCTAGAGCTTGGCCTAAGATGCACACAGTGAATGGCTAT<br>GTGAACAGAAGCCTGCCTGGACTGATTGGCTGCCACAGAAAGT<br>CTGTGTACTGGCATGTGATTGGCATGGGCACAACACCTGAGGTG<br>CACAGCATCTTTCTGGAAGGACACACCTTCCTGGTGAGAAACCA<br>TAGACAGGCCAGCCTGGAAATCAGCCCTATCACCTTCCTGACAG<br>CTCAGACCCTGCTGATGGATCTGGGCCAGTTTCTGCTGTTCTGCC<br>ACATCAGCAGCCACCAGCATGATGGCATGGAAGCCTATGTGAA<br>GGTGGACAGCTGCCCTGAAGAACCCCAGCTGAGAATGAAGAAC<br>AATGAGGAGGCTGAGGACTATGATGATGACCTGGCTGACTCTG<br>AGATGGATGTGGTCAGATTTGATGATGACAACAGCCCCAGCTTC<br>ATCCAGATCAGATCTGTGGCCAAGAAGCACCCCAAGACCTGGG<br>TGCACTATATTGCTGCTGAGGAAGAGGTGTGGGATTATGCTCCT<br>AGTGTGCTGGCCCCTGATGACAGAAGCTACAAGAGCCAGTACCT<br>GAACAATGGCAGCCAGAGAATTGGCAGAAAGTATAAGAAAGTG<br>AGATTCATGGCCTACACAGATGAGACATTCAAGACCAGAGAGG<br>CCATTCAGTATGAGTCTGGCATTCTGGGCCCTCTGCTGTATGGA<br>GAAGTGGGAGATACACTGCTGATCATCTTCAAGAACCAGGCCA<br>GCAGACCCTACAACATCTACCCTCATGGCATCACAGATGTGAGA<br>CCCCTGTATTCTAGAAGGCTGCCCAAGGGAGTGAAGCACCTGAA<br>GGACTTCCCTATCCTGCCTGGAGAGATCTTCAAGTACAAGTGGA<br>CAGTGACAGTGGAAGATGGCCCCACCAAGTCTGACCCTAGATGT<br>CTGACAAGATACTACAGCAGCTTTATCAACATGGAAAGAGACCT<br>GGCCTCTGGCCTGATTGGACCTCTGCTGATCTGCTACAAAGAAT<br>CTGTGGACCAGAGAGGCAACCAGATCATGTCTGACAAGAGAAA<br>TGTGATCCTGTTTTCTGTGTTTGATGAGAACCAGTCCTGGTATCT<br>GACAGAGAACATCCAGAGATTTCTGCCCAATCCTGTGGGAGTGC<br>AGCTGGAAGATCCTGAGTTCCAGGCCTCCAACATCATGCACTCC<br>ATCAATGGCTATGTGTTTGACAGCCTGCAGCTGTCTGTGTGCCT<br>GCATGAAGTGGCCTACTGGTACATCCTGAGCATTGGAGCCCAGA<br>CAGACTTCCTGTCTGTGTTCTTCTCTGGCTACACCTTCAAGCACA<br>AGATGGTGTATGAGGATACCCTGACACTGTTCCCATTCTCTGGA<br>GAGACAGTGTTCATGAGCATGGAAAACCCTGGCCTGTGGATCCT<br>GGGCTGTCACAACTCTGACTTCAGAAACAGAGGCATGACAGCC<br>CTGCTGAAGGTGTCCAGCTGTGACAAGAACACAGGAGACTACT<br>ATGAGGACAGCTATGAGGACATCTCTACCTACCTGCTGAGCAAG<br>AACAATGCCATTGAGCCCAGAAACTTCAGCCAGAATTGCTCCCA<br>GAACCCTCCAGTGCTGAAGAGACACCAGAGAGAAATCACCCTG<br>AACACACTGCAGTCTGACCAAGAGGAAATTGACTATGATGACA<br>CCATCTCTGTGGAGATGAAGAAAGAAGATTTTGACATCTATGGA<br>GAGGATGAGAATCAGAGCCCCAGATCCTTTCAGAAAAAGACCA |

TABLE 23-continued

Listing of additional protein and nucleic acid sequences referred to herein not included in the sequence listing

| Category | SEQ ID NO: | Description | Type | Sequence |
|---|---|---|---|---|
| | | | | GACACTACTTCATTGCTGCTGTGGAGAGACTGTGGGACTATGGC<br>ATGTCTAGCAGCCCTCATGTGCTGAGAAATAGAGCCCAGTCTGG<br>CTCTGTGCCCCAGTTCAAGAAAGTGGTGTTCCAAGAGTTCACAG<br>ATGGCAGCTTCACCCAGCCACTGTATAGAGGAGAGCTGAATGA<br>GCATCTGGGCCTGCTGGGCCCTTATATCAGAGCTGAAGTGGAAG<br>ATAACATCATGGTCACCTTCAAGAATCAGGCCTCTAGACCCTAC<br>AGCTTCTACAGCTCCCTGATCAGCTATGAAGAGGACCAGAGACA<br>GGGAGCTGAGCCCAGAAAGAACTTTGTGAAGCCCAATGAGACT<br>AAGACCTACTTTTGGAAGGTGCAGCACCACATGGCCCCTACAAA<br>GGATGAGTTTGACTGCAAGGCCTGGGCCTACTTTTCTGATGTGG<br>ATCTGGAAAAGGATGTGCACTCTGGACTCATTGGACCACTGCTT<br>GTGTGCCACACCAACACACTGAACCCTGCTCATGGCAGACAAGT<br>GACAGTGCAAGAGTTTGCCCTGTTCTTCACCATCTTTGATGAAA<br>CAAAGAGCTGGTACTTCACAGAGAATACAGAGAGAAACTGCAG<br>GGCCCCTTGCAACATCCAGATGGAAGATCCCACCTTCAAAGAGA<br>ACTACAGATTCCATGCCATCAATGGCTACATCATGGACACACTG<br>CCTGGCCTGGTTATGGCTCAGGATCAGAGAATCAGATGGTATCT<br>GCTGTCCATGGGCTCCAATGAGAATATCCACAGCATCCACTTCT<br>CTGGCCATGTGTTCACAGTGAGAAAAAAAGAAGAGTACAAAAT<br>GGCTGTGTACAATCTGTACCCTGGGGTGTTTGAAACAGTGGAAA<br>TGCTGCCTTCCAAGGCTGGCATTTGGAGAGTGGAATGTCTGATT<br>GGAGAGCACCTCCATGCTGGAATGAGCACCCTGTTTCTGGTGTA<br>CAGCAACAAGTGTCAGACCCCTCTGGGCATGGCCTCTGGAAGA<br>ATCAGAGACTTCCAGATCACAGCCTCTGGCCAGTATGGACAGTG<br>GGCTCCTAAACTGGCTAGACTGCACTACTCTGGCAGCATCAATG<br>CCTGGTCCACCAAAGAGCCCTTCAGCTGGATCAAGGTGGACCTG<br>CTGGCTCCCATGATCATCCATGGAATCAAGACCCAGGGAGCCAG<br>ACAGAAGTTCAGCAGCCTGTACATCAGCCAGTTCATCATCATGT<br>ACAGCCTGGATGGCAAGAAGTGGCAGACCTACAGAGGCAACAG<br>CACAGGCACACTCATGGTGTTCTTTGGCAATGTGGACAGCTCTG<br>GCATTAAGCACAACATCTTCAACCCTCCAATCATTGCCAGATAC<br>ATCAGACTGCACCCCACACACTACAGCATCAGATCTACCCTGAG<br>AATGGAACTGATGGGCTGTGACCTGAACAGCTGCAGCATGCCCC<br>TGGGAATGGAAAGCAAGGCCATCTCTGATGCCCAGATCACAGC<br>CAGCAGCTACAAGACCAACATGTTTGCCACTTGGAGCCCCTCCA<br>AGGCTAGACTGAACCTGCAGGGCAGAAGCAATGCTTGGAGGCC<br>CCAAGTGAACAACCCCAAAGAGTGGCTGCAGGTGGACTTTCAA<br>AAGACCATGAAAGTGACAGGAATCACCACACAGGGAGTCAAGT<br>CTCTGCTGACCTCTATGTATGTGAAAGAGTTCCTGATCTCCAGC<br>AGCCAGGATGGCCACCACTGGACCCTGTTTTTCCAGAATGGCAA<br>AGTGAAAGTGTTCCAGGGCAATCAGGACAGCTTCACACCTGTGG<br>TCAACTCCCTGGATAGCCCACTGCTGACCAGATACCTGAGAATT<br>CACCCTCAGTCTTGGGTGCACCAGATTGCTCTGAGAATTGAAGT<br>GCTGGGCTGTGAAGCTCAGGAGCTCTACTGATCGCGAATAAAA<br>GATCTTTATTTTCATTAGATCTGTGTGTTGGTTTTTTGTGTGTATT<br>TAGCTAATATTGGGCTCTGATTCCTACAGAAAAATTTGCACTTTC<br>CTTAGTGGGCAAAAGAAAATTCCTCACGTGCATAGT |

TABLE 23-continued

Listing of additional protein and nucleic acid sequences referred to herein not included in the sequence listing

| Category | SEQ ID NO: | Description | Type | Sequence |
|---|---|---|---|---|
| Novel protein sequence to replace the B-domain of FVIII | 102 | var4sc (B-domain replacement encoding 2 N-linked glycosylation sites and deletion of 3 of the 4 residues of the furin recognition site) | Protein | EPRNFSQNCSQNPPVLKR |
| Human FVIII in which the B-domain is replaced with the var4sc B-domain replacement thereby generating a single chain FVIII containing 2 N-linked glycosylation sites | 90 | Human single chain B-domain deleted FVIII containing the var4sc B-domain replacement (lacks the native signal peptide). Protein is encoded in pMG4026 | Protein | ATRRYYLGAVELSWDYMQSDLGELPVDARFPPRVPKSFPFNTSVV<br>YKKTLFVEFTDHLFNIAKPRPPWMGLLGPTIQAEVYDTVVITLKNM<br>ASHPVSLHAVGVSYWKASEGAEYDDQTSQREKEDDKVFPGGSHT<br>YVWQVLKENGPMASDPLCLTYSYLSHVDLVKDLNSGLIGALLVCR<br>EGSLAKEKTQTLHKFILLFAVFDEGKSWHSETKNSLMQDRDAASA<br>RAWPKMHTVNGYVNRSLPGLIGCHRKSVYWHVIGMGTTPEVHSIF<br>LEGHTFLVRNHRQASLEISPITFLTAQTLLMDLGQFLLFCHISSHQH<br>DGMEAYVKVDSCPEEPQLRMKNNEEAEDYDDDLTDSEMDVVRFD<br>DDNSPSFIQIRSVAKKHPKTWVHYIAAEEEDWDYAPLVLAPDDRSY<br>KSQYLNNGPQRIGRKYKKVRFMAYTDETFKTREAIQHESGILGPLL<br>YGEVGDTLLIIFKNQASRPYNIYPHGITDVRPLYSRRLPKGVKHLKD<br>FPILPGEIFKYKWTVTVEDGPTKSDPRCLTRYYSSFVNMERDLASG<br>LIGPLLICYKESVDQRGNQIMSDKRNVILFSVFDENRSWYLTENIQR<br>FLPNPAGVQLEDPEFQASNIMHSINGYVFDSLQLSVCLHEVAYWYI<br>LSIGAQTDFLSVFFSGYTFKHKMVYEDTLTLFPFSGETVFMSMENP<br>GLWILGCHNSDFRNRGMTALLKVSSCDKNTGDYYEDSYEDISAYL<br>LSKNNAIEPRNFSQNCSQNPPVLKREITRTTLQSDQEEIDYDDTISVE<br>MKKEDFDIYDEDENQSPRSFQKKTRHYFIAAVERLWDYGMSSSPH<br>VLRNRAQSGSVPQFKKVVFQEFTDGSFTQPLYRGELNEHLGLLGPY<br>IRAEVEDNIMVTFRNQASRPYSFYSSLISYEEDQRQGAEPRKNFVKP<br>NETKTYFWKVQHHMAPTKDEFDCKAWAYFSDVDLEKDVHSGLIG<br>PLLVCHTNTLNPAHGRQVTVQEFALFFTIFDETKSWYFTENMERNC<br>RAPCNIQMEDPTFKENYRFHAINGYIMDTLPGLVMAQDQRIRWYL<br>LSMGSNENIHSIHFSGHVFTVRKKEEYKMALYNLYPGVFETVEMLP<br>SKAGIWRVECLIGEHLHAGMSTLFLVYSNKCQTPLGMASGHIRDFQ<br>ITASGQYGQWAPKLARLHYSGSINAWSTKEPFSWIKVDLLAPMIIH<br>GIKTQGARQKFSSLYISQFIIMYSLDGKKWQTYRGNSTGTLMVFFG<br>NVDSSGIKHNIFNPPIIARYIRLHPTHYSIRSTLRMELMGCDLNSCSM<br>PLGMESKAISDAQITASSYFTNMFATWSPSKARLHLQGRSNAWRP<br>QVNNPKEWLQVDFQKTMKVTGVTTQGVKSLLTSMYVKEFLISSSQ<br>DGHQWTLFFQNGKVKVFQGNQDSFTPVVNSLDPPLLTRYLRIHPQ<br>SWVHQIALRMEVLGCEAQDLY |
| Human FVIII donor cassette pMG4026 | 91 | pMG4026 (human FVIII donor containing the FVIII coding sequence in which the B-domain was replaced | Nucleotide | ACGCGTACGTTAAAGCTTACGTTTTTCCTGTAACGATCGGGAAC<br>TGGCACTTAGGTCAGTGAAGAGAAGAACAAAAATATTTAGCTA<br>CTCAAAGCTTACTAAAGAATTATTCTTTTACATTTCAGTGGCCAC<br>CAGAAGATATTACCTGGGAGCTGTGGAACTGAGCTGGGACTAC<br>ATGCAGTCTGACCTGGGAGAGCTGCCTGTGGATGCTAGATTTCC |

TABLE 23-continued

Listing of additional protein and nucleic acid sequences referred to herein not included in the sequence listing

| Category | SEQ ID NO: | Description | Type | Sequence |
|---|---|---|---|---|
| | | with the var4sc B-<br>domain replacement.<br>The DNA sequence<br>was codon optimized<br>with the copt1 codon<br>optimization. Includes<br>flanking guide target<br>sites, splice acceptor<br>and polyA signal) | | TCCAAGAGTGCCCAAGAGCTTCCCCTTCAACACCTCTGTGGTGT<br>ACAAGAAAACCCTGTTTGTGGAATTCACAGACCACCTGTTCAAT<br>ATTGCCAAGCCTAGACCTCCTTGGATGGGACTGCTGGGACCTAC<br>AATTCAGGCTGAGGTGTATGACACAGTGGTCATCACCCTGAAGA<br>ACATGGCCAGCCATCCTGTGTCTCTGCATGCTGTGGGAGTGTCT<br>TACTGGAAGGCTTCTGAGGGAGCTGAGTATGATGACCAGACAA<br>GCCAGAGAGAGAAAGAGGATGACAAGGTTTTCCCTGGAGGCAG<br>CCACACCTATGTCTGGCAGGTCCTGAAAGAAAATGGCCCTATGG<br>CCTCTGATCCTCTGTGCCTGACATACAGCTACCTGAGCCATGTG<br>GACCTGGTCAAGGACCTGAATTCTGGCCTGATTGGAGCCCTGCT<br>GGTGTGTAGAGAAGGCAGCCTGGCCAAAGAGAAAACCCAGACA<br>CTGCACAAGTTCATCCTGCTGTTTGCTGTGTTTGATGAGGGCAA<br>GAGCTGGCACTCTGAGACAAAGAACAGCCTGATGCAGGACAGG<br>GATGCTGCCTCTGCTAGAGCTTGGCCTAAGATGCACACAGTGAA<br>TGGCTATGTGAACAGAAGCCTGCCTGGACTGATTGGCTGCCACA<br>GAAAGTCTGTGTACTGGCATGTGATTGGCATGGGCACAACACCT<br>GAGGTGCACAGCATCTTTCTGGAAGGACACACCTTCCTGGTGAG<br>AAACCATAGACAGGCCAGCCTGGAAATCAGCCCTATCACCTTCC<br>TGACAGCTCAGACCCTGCTGATGGATCTGGGCCAGTTTCTGCTG<br>TTCTGCCACATCAGCAGCCACCAGCATGATGGCATGGAAGCCTA<br>TGTGAAGGTGGACAGCTGCCCTGAAGAACCCCAGCTGAGAATG<br>AAGAACAATGAGGAGGCTGAGGACTATGATGATGACCTGACAG<br>ACTCTGAGATGGATGTGGTCAGATTTGATGATGACAACAGCCCC<br>AGCTTCATCCAGATCAGATCTGTGGCCAAGAAGCACCCCAAGAC<br>CTGGGTGCACTATATTGCTGCTGAGGAAGAGGACTGGGATTATG<br>CTCCTCTGGTGCTGGCCCCTGATGACAGAAGCTACAAGAGCCAG<br>TACCTGAACAATGGCCCTCAGAGAATTGGCAGAAAGTATAAGA<br>AAGTGAGATTCATGGCCTACACAGATGAGACATTCAAGACCAG<br>AGAGGCCATTCAGCATGAGTCTGGCATTCTGGGCCCTCTGCTGT<br>ATGGAGAAGTGGGAGATACACTGCTGATCATCTTCAAGAACCA<br>GGCCAGCAGACCCTACAACATCTACCCTCATGGCATCACAGATG<br>TGAGACCCCTGTATTCTAGAAGGCTGCCCAAGGGAGTGAAGCA<br>CCTGAAGGACTTCCCTATCCTGCCTGGAGAGATCTTCAAGTACA<br>AGTGGACAGTGACAGTGGAAGATGGCCCCACCAAGTCTGACCC<br>TAGATGTCTGACAAGATACTACAGCAGCTTTGTGAACATGGAAA<br>GAGACCTGGCCTCTGGCCTGATTGGACCTCTGCTGATCTGCTAC<br>AAAGAATCTGTGGACCAGAGAGGCAACCAGATCATGTCTGACA<br>AGAGAAATGTGATCCTGTTTTCTGTGTTTGATGAGAACAGATCC<br>TGGTATCTGACAGAGAACATCCAGAGATTTCTGCCCAATCCTGC<br>TGGAGTGCAGCTGGAAGATCCTGAGTTCCAGGCCTCCAACATCA<br>TGCACTCCATCAATGGCTATGTGTTTGACAGCCTGCAGCTGTCT<br>GTGTGCCTGCATGAAGTGGCCTACTGGTACATCCTGAGCATTGG<br>AGCCCAGACAGACTTCCTGTCTGTGTTCTTCTCTGGCTACACCTT<br>CAAGCACAAGATGGTGTATGAGGATACCCTGACACTGTTCCCAT<br>TCTCTGGAGAGACAGTGTTCATGAGCATGGAAAACCCTGGCCTG<br>TGGATCCTGGGCTGTCACAACTCTGACTTCAGAAACAGAGGCAT<br>GACAGCCCTGCTGAAGGTGTCCAGCTGTGACAAGAACACAGGA |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | GACTACTATGAGGACAGCTATGAGGACATCTCTGCCTACCTGCT<br>GAGCAAGAACAATGCCATTGAGCCCAGAAACTTCAGCCAGAAT<br>TGCTCCCAGAACCCTCCAGTGCTGAAGAGAGAAATCACCAGAA<br>CCACACTGCAGTCTGACCAAGAGGAAATTGACTATGATGACACC<br>ATCTCTGTGGAGATGAAGAAAGAAGATTTTGACATCTATGATGA<br>GGATGAGAATCAGAGCCCCAGATCCTTTCAGAAAAAGACCAGA<br>CACTACTTCATTGCTGCTGTGGAGAGACTGTGGGACTATGGCAT<br>GTCTAGCAGCCCTCATGTGCTGAGAAATAGAGCCCAGTCTGGCT<br>CTGTGCCCCAGTTCAAGAAAGTGGTGTTCCAAGAGTTCACAGAT<br>GGCAGCTTCACCCAGCCACTGTATAGAGGAGAGCTGAATGAGC<br>ATCTGGGCCTGCTGGGCCCTTATATCAGAGCTGAAGTGGAAGAT<br>AACATCATGGTCACCTTCAGAAATCAGGCCTCTAGACCCTACAG<br>CTTCTACAGCTCCCTGATCAGCTATGAAGAGGACCAGAGACAGG<br>GAGCTGAGCCCAGAAAGAACTTTGTGAAGCCCAATGAGACTAA<br>GACCTACTTTTGGAAGGTGCAGCACCACATGGCCCCTACAAAGG<br>ATGAGTTTGACTGCAAGGCCTGGGCCTACTTTTCTGATGTGGAT<br>CTGGAAAAGGATGTGCACTCTGGACTCATTGGACCACTGCTTGT<br>GTGCCACACCAACACACTGAACCCTGCTCATGGCAGACAAGTG<br>ACAGTGCAAGAGTTTGCCCTGTTCTTCACCATCTTTGATGAAAC<br>AAAGAGCTGGTACTTCACAGAGAATATGGAGAGAAACTGCAGG<br>GCCCCTTGCAACATCCAGATGGAAGATCCCACCTTCAAAGAGAA<br>CTACAGATTCCATGCCATCAATGGCTACATCATGGACACACTGC<br>CTGGCCTGGTTATGGCTCAGGATCAGAGAATCAGATGGTATCTG<br>CTGTCCATGGGCTCCAATGAGAATATCCACAGCATCCACTTCTC<br>TGGCCATGTGTTCACAGTGAGAAAAAAAGAAGAGTACAAAATG<br>GCCCTGTACAATCTGTACCCTGGGGTGTTTGAAACAGTGGAAAT<br>GCTGCCTTCCAAGGCTGGCATTTGGAGAGTGGAATGTCTGATTG<br>GAGAGCACCTCCATGCTGGAATGAGCACCCTGTTTCTGGTGTAC<br>AGCAACAAGTGTCAGACCCCTCTGGGCATGGCCTCTGGACACAT<br>CAGAGACTTCCAGATCACAGCCTCTGGCCAGTATGGACAGTGGG<br>CTCCTAAACTGGCTAGACTGCACTACTCTGGCAGCATCAATGCC<br>TGGTCCACCAAAGAGCCCTTCAGCTGGATCAAGGTGGACCTGCT<br>GGCTCCCATGATCATCCATGGAATCAAGACCCAGGGAGCCAGA<br>CAGAAGTTCAGCAGCCTGTACATCAGCCAGTTCATCATCATGTA<br>CAGCCTGGATGGCAAGAAGTGGCAGACCTACAGAGGCAACAGC<br>ACAGGCACACTCATGGTGTTCTTTGGCAATGTGGACAGCTCTGG<br>CATTAAGCACAACATCTTCAACCCTCCAATCATTGCCAGATACA<br>TCAGACTGCACCCCACACACTACAGCATCAGATCTACCCTGAGA<br>ATGGAACTGATGGGCTGTGACCTGAACAGCTGCAGCATGCCCCT<br>GGGAATGGAAAGCAAGGCCATCTCTGATGCCCAGATCACAGCC<br>AGCAGCTACTTCACCAACATGTTTGCCACTTGGAGCCCCTCCAA<br>GGCTAGACTGCATCTGCAGGGCAGAAGCAATGCTTGGAGGCCC<br>CAAGTGAACAACCCCAAAGAGTGGCTGCAGGTGGACTTTCAAA<br>AGACCATGAAAGTGACAGGAGTGACCACACAGGGAGTCAAGTC<br>TCTGCTGACCTCTATGTATGTGAAAGAGTTCCTGATCTCCAGCA<br>GCCAGGATGGCCACCAGTGGACCCTGTTTTTCCAGAATGGCAAA<br>GTGAAAGTGTTCCAGGGCAATCAGGACAGCTTCACACCTGTGGT |

TABLE 23-continued

| Category | SEQ ID NO: | Description | Type | Sequence |
|---|---|---|---|---|
| Listing of additional protein and nucleic acid sequences referred to herein not included in the sequence listing | | | | |
| | | | | CAACTCCCTGGATCCTCCACTGCTGACCAGATACCTGAGAATTC<br>ACCCTCAGTCTTGGGTGCACCAGATTGCTCTGAGAATGGAAGTG<br>CTGGGCTGTGAAGCTCAGGACCTCTACTGATCGCGAATAAAAGA<br>TCTTTATTTTCATTAGATCTGTGTGTTGGTTTTTTGTGTGTATTAC<br>AGTATGATAGCTACTCAAAGCACTTTTTGTTCTTCTCTTCACTGA<br>CCTAAGTGCCAGTTCCCGATCGTTACAGGAAATTCAACTATAGC<br>TACACGTG |
| Human FVIII donor cassette pMG4029 | 92 | pMG4029 (DNA sequence that encodes human FVIII in which the B-domain was replaced by the var4 B-domain replacement. The DNA sequence was codon optimized using the copt4 codon optimization. Flanking guide target sites, splice acceptor and polyA signal are included) | Nucleotide | ACGCGTACGTTAAAGCTTACGTTTTTCCTGTAACGATCGGGAAC<br>TGGCACTTAGGTCAGTGAAGAGAAGAACAAAAATATTTAGCTA<br>CTCAAAGCTTACTAAAGAATTATTCTTTTACATTTCAGTGGCCAC<br>CAGGAGATACTACCTGGGGGCTGTGGAGCTTAGCTGGGACTAC<br>ATGCAGTCTGACCTGGGGGAGCTGCCTGTGGATGCCAGATTCCC<br>ACCCAGAGTGCCCAAATCCTTCCCATTCAACACCAGCGTGGTCT<br>ACAAGAAGACCCTCTTTGTGGAGTTCACTGACCACCTGTTCAAC<br>ATTGCCAAACCCAGGCCACCCTGGATGGGACTCCTGGGACCCAC<br>CATTCAGGCTGAGGTCTATGACACTGTGGTCATCACCCTCAAGA<br>ACATGGCCTCCCACCCTGTGAGCCTGCATGCTGTGGGGGTCAGC<br>TACTGGAAGGCCTCTGAGGGGGCTGAGTATGATGACCAGACCTC<br>CCAGAGGGAGAAGGAGGATGACAAAGTGTTCCCTGGGGGCAGC<br>CACACCTATGTGTGGCAGGTCCTCAAGGAGAATGGCCCCATGGC<br>CTCTGACCCACTCTGCCTGACCTACTCCTACCTTTCTCATGTGGA<br>CCTGGTCAAGGACCTCAACTCTGGACTGATTGGGGCCCTGCTGG<br>TGTGCAGAGAGGGCTCCCTGGCCAAAGAGAAGACCCAGACCCT<br>GCACAAGTTCATTCTCCTGTTTGCTGTCTTTGATGAGGGCAAGA<br>GCTGGCACTCTGAAACCAAGAACTCCCTGATGCAGGACAGGGA<br>TGCTGCCTCTGCCAGAGCCTGGCCCAAGATGCACACTGTGAATG<br>GCTATGTCAACAGGAGCCTGCCTGGACTCATTGGCTGCCACAGG<br>AAAAGCGTCTACTGGCATGTGATTGGCATGGGGACAACCCCTGA<br>GGTGCACTCCATTTTCCTGGAGGGCCACACCTTCCTGGTCAGAA<br>ACCACAGACAGGCCAGCCTGGAGATCAGCCCCATCACCTTCCTC<br>ACTGCCCAGACCCTGCTGATGGACCTCGGACAGTTCCTGCTGTT<br>CTGCCACATCAGCTCCCACCAGCATGATGGCATGGAGGCCTATG<br>TCAAGGTGGACAGCTGCCCTGAGGAGCCACAGCTCAGAATGAA<br>GAACAATGAGGAGGCTGAGGACTATGATGATGACCTGACTGAC<br>TCTGAGATGGATGTGGTCCGCTTTGATGATGACAACAGCCCATC<br>CTTCATTCAGATCAGGTCTGTGGCCAAGAAACACCCCAAGACCT<br>GGGTGCACTACATTGCTGCTGAGGAGGAGGACTGGGACTATGC<br>CCCACTGGTCCTGGCCCCTGATGACAGAAGCTACAAGAGCCAGT<br>ACCTCAACAATGGCCCACAGAGGATTGGACGGAAGTACAAGAA<br>AGTCAGGTTCATGGCCTACACTGATGAAACCTTCAAGACCAGAG<br>AGGCCATTCAGCATGAGTCTGGCATCCTGGGCCCACTCCTGTAT<br>GGGGAGGTGGGGGACACCCTGCTCATCATCTTCAAGAACCAGG<br>CCTCCAGGCCCTACAACATCTACCCACATGGCATCACTGATGTC<br>AGACCCCTGTACAGCCGCAGGCTGCCAAAGGGGGTCAAACACC<br>TCAAGGACTTCCCCATTCTGCCTGGGGAGATCTTCAAGTACAAG<br>TGGACTGTCACTGTGGAGGATGGACCAACCAAATCTGACCCCAG |

TABLE 23-continued

Listing of additional protein and nucleic acid sequences referred to herein not included in the sequence listing

| Category | SEQ ID NO: | Description | Type | Sequence |
|---|---|---|---|---|
| | | | | ATGCCTCACCAGATACTACTCCAGCTTTGTGAACATGGAGAGGG<br>ACCTGGCCTCTGGCCTGATTGGCCCACTGCTCATCTGCTACAAG<br>GAGAGCGTGGACCAGAGGGGAAACCAGATCATGTCTGACAAGA<br>GGAATGTGATTCTGTTCTCTGTCTTTGATGAGAACAGGAGCTGG<br>TACCTGACTGAGAACATTCAGCGCTTCCTGCCCAACCCTGCTGG<br>GGTGCAGCTGGAGGACCCTGAGTTCCAGGCCAGCAACATCATG<br>CACTCCATCAATGGCTATGTCTTTGACAGCCTCCAGCTTTCTGTC<br>TGCCTGCATGAGGTGGCCTACTGGTACATTCTTTCCATTGGGGC<br>CCAGACTGACTTCCTTTCTGTCTTCTTCAGCGGCTACACCTTCAA<br>ACACAAGATGGTGTATGAGGACACCCTGACCCTCTTCCCATTCT<br>CTGGGGAGACTGTGTTCATGAGCATGGAGAACCCTGGCCTGTGG<br>ATTCTGGGATGCCACAACTCTGACTTCCGGAACAGAGGCATGAC<br>TGCCCTGCTCAAAGTCTCCTCCTGTGACAAGAACACTGGGGACT<br>ACTATGAGGACAGCTATGAGGACATCTCTGCCTACCTGCTCAGC<br>AAGAACAATGCCATTGAGCCCAGGAACTTCAGCCAGAATTGCTC<br>CCAGAACCCTCCAGTCCTGAAGAGAGAGATCACCAGAACCACC<br>CTCCAGTCTGACCAGGAGGAGATTGACTATGATGACACCATTTC<br>TGTGGAGATGAAGAAAGAGGACTTTGACATCTATGACGAGGAC<br>GAGAACCAGAGCCCAAGGAGCTTCCAGAAGAAGACCAGGCACT<br>ACTTCATTGCTGCTGTGGAGCGCCTGTGGGACTATGGCATGAGC<br>TCCAGCCCCCATGTCCTCAGAAACAGGGCCCAGTCTGGCTCTGT<br>CCCACAGTTCAAGAAAGTGGTCTTCCAAGAGTTCACTGATGGCA<br>GCTTCACCCAGCCCCTGTACAGAGGGGAGCTGAATGAGCACCTG<br>GGACTCCTGGGCCCATACATCAGGGCTGAGGTGGAGGACAACA<br>TCATGGTCACCTTCCGCAACCAGGCCTCCAGACCCTACAGCTTC<br>TACAGCTCCCTCATCAGCTATGAGGAGGACCAGAGGCAGGGG<br>CTGAGCCACGGAAGAACTTTGTCAAACCCAATGAAACCAAGAC<br>CTACTTCTGGAAAGTCCAGCACCACATGGCCCCCACCAAGGATG<br>AGTTTGACTGCAAGGCCTGGGCCTACTTCAGCGATGTGGACCTG<br>GAGAAGGATGTCCACTCTGGCCTGATTGGCCCACTCCTGGTCTG<br>CCACACCAACACCCTGAACCCTGCCCATGGAAGACAAGTCACT<br>GTGCAGGAGTTTGCCCTCTTCTTCACCATCTTTGATGAAACCAA<br>GAGCTGGTACTTCACTGAGAACATGGAGCGCAACTGCAGAGCC<br>CCATGCAACATTCAGATGGAGGACCCCACCTTCAAAGAGAACT<br>ACCGGTTCCATGCCATCAATGGCTACATCATGGACACCCTGCCT<br>GGGCTTGTCATGGCCCAGGACCAGAGGATCAGATGGTACCTGCT<br>TAGCATGGGCTCCAATGAGAACATTCACTCCATCCACTTCAGCG<br>GGCATGTCTTCACTGTGCGCAAGAAGGAGGAGTACAAGATGGC<br>CCTGTACAACCTCTACCCTGGGGTCTTTGAGACTGTGGAGATGC<br>TGCCCTCCAAAGCTGGCATCTGGAGGGTGGAGTGCCTCATTGGG<br>GAGCACCTGCATGCTGGCATGAGCACCCTGTTCCTGGTCTACAG<br>CAACAAGTGCCAGACCCCCCTGGGAATGGCCTCTGGCCACATCA<br>GGGACTTCCAGATCACTGCCTCTGGCCAGTATGGCCAGTGGGCC<br>CCCAAGCTGGCCAGACTCCACTACTCTGGATCCATCAATGCCTG<br>GAGCACCAAGGAGCCATTCAGCTGGATCAAAGTGGACCTGCTG<br>GCCCCCATGATCATCCATGGCATCAAGACCCAGGGGGCCAGGC<br>AGAAGTTCTCCAGCCTGTACATCAGCCAGTTCATCATCATGTAC |

TABLE 23-continued

Listing of additional protein and nucleic acid sequences referred to herein not included in the sequence listing

| Category | SEQ ID NO: | Description | Type | Sequence |
|---|---|---|---|---|
| | | | | AGCCTGGATGGCAAGAAATGGCAGACCTACAGAGGCAACTCCA CTGGAACACTCATGGTCTTCTTTGGCAATGTGGACAGCTCTGGC ATCAAGCACAACATCTTCAACCCCCCAATCATCGCCAGATACAT CAGGCTGCACCCCACCCACTACAGCATCCGGAGCACCCTCAGA ATGGAGCTGATGGGCTGTGACCTGAACTCCTGCAGCATGCCCCT GGGCATGGAGAGCAAGGCCATTTCTGATGCCCAGATCACTGCCT CCAGCTACTTCACCAACATGTTTGCCACCTGGAGCCCAAGCAAG GCCAGGCTGCACCTCCAGGGAAGGAGCAATGCCTGGAGACCCC AGGTCAACAACCCAAAGGAGTGGCTGCAGGTGGACTTCCAGAA GACCATGAAGGTCACTGGGGTCACCACCCAGGGGGTCAAGAGC CTGCTCACCAGCATGTATGTGAAGGAGTTCCTGATCAGCTCCAG CCAGGATGGCCACCAGTGGACCCTCTTCTTCCAGAATGGCAAGG TCAAGGTGTTCCAGGGCAACCAGGACAGCTTCACCCCTGTGGTG AACAGCCTGGACCCCCCCCTCCTGACCAGATACCTGAGGATTCA CCCCCAGAGCTGGGTCCACCAGATTGCCCTGAGAATGGAGGTCC TGGGATGTGAGGCCCAGGACCTGTACTGATCGCGAATAAAAGA TCTTTATTTTCATTAGATCTGTGTGTTGGTTTTTTGTGTGTATTAC AGTATGATAGCTACTCAAAGCACTTTTTGTTCTTCTCTTCACTGA CCTAAGTGCCAGTTCCCGATCGTTACAGGAAATTCAACTATAGC TACACGTG |
| Human FVIII donor cassette pMG4027_c02 F309S | 93 | pMG4027_co2_F309S (DNA sequence that encodes human FVIII in which the B-domain was replaced by the var4 B-domain replacement and F309 was changed to S. The DNA sequence was codon optimization using copt2 codon optimization. Flanking guide target sites, splice acceptor and polyA signal are included | Nucleotide | ACGCGTACGTTAAAGCTTACGTTTTTCCTGTAACGATCGGGAAC TGGCACTTAGGTCAGTGAAGAGAAGAACAAAAATATTTAGCTA CTCAAAGCTTACTAAAGAATTATTCTTTTACATTTCAGTGGCCAC CAGGAGATACTACCTGGGGGCTGTGGAGCTGAGCTGGGACTAC ATGCAGTCTGACCTGGGGGAGCTGCCTGTGGATGCCAGGTTCCC CCCCAGAGTGCCCAAGAGCTTCCCCTTCAACACCTCTGTGGTGT ACAAGAAGACCCTGTTTGTGGAGTTCACTGACCACCTGTTCAAC ATTGCCAAGCCCAGGCCCCCCTGGATGGGCCTGCTGGGCCCCAC CATCCAGGCTGAGGTGTATGACACTGTGGTGATCACCCTGAAGA ACATGGCCAGCCACCCTGTGAGCCTGCATGCTGTGGGGGTGAGC TACTGGAAGGCCTCTGAGGGGGCTGAGTATGATGACCAGACCA GCCAGAGGGAGAAGGAGGATGACAAGGTGTTCCCTGGGGGCAG CCACACCTATGTGTGGCAGGTGCTGAAGGAGAATGGCCCCATG GCCTCTGACCCCCTGTGCCTGACCTACAGCTACCTGAGCCATGT GGACCTGGTGAAGGACCTGAACTCTGGCCTGATTGGGGCCCTGC TGGTGTGCAGGGAGGGCAGCCTGGCCAAGGAGAAGACCCAGAC CCTGCACAAGTTCATCCTGCTGTTTGCTGTGTTTGATGAGGGCA AGAGCTGGCACTCTGAAACCAAGAACAGCCTGATGCAGGACAG GGATGCTGCCTCTGCCAGGGCCTGGCCCAAGATGCACACTGTGA ATGGCTATGTGAACAGGAGCCTGCCTGGCCTGATTGGCTGCCAC AGGAAGTCTGTGTACTGGCATGTGATTGGCATGGGCACCACCCC TGAGGTGCACAGCATCTTCCTGGAGGGCCACACCTTCCTGGTCA GGAACCACAGGCAGGCCAGCCTGGAGATCAGCCCCATCACCTT CCTGACTGCCCAGACCCTGCTGATGGACCTGGGCCAGTTCCTGC TGTCTTGCCACATCAGCAGCCACCAGCATGATGGCATGGAGGCC TATGTGAAGGTGGACAGCTGCCCTGAGGAGCCCCAGCTGAGGA |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | TGAAGAACAATGAGGAGGCTGAGGACTATGATGATGACCTGAC<br>TGACTCTGAGATGGATGTGGTGAGGTTTGATGATGACAACAGCC<br>CCAGCTTCATCCAGATCAGGTCTGTGGCCAAGAAGCACCCCAAG<br>ACCTGGGTGCACTACATTGCTGCTGAGGAGGAGGACTGGGACT<br>ATGCCCCCCTGGTGCTGGCCCCTGATGACAGGAGCTACAAGAGC<br>CAGTACCTGAACAATGGCCCCCAGAGGATTGGCAGGAAGTACA<br>AGAAGGTCAGGTTCATGGCCTACACTGATGAAACCTTCAAGACC<br>AGGGAGGCCATCCAGCATGAGTCTGGCATCCTGGGCCCCCTGCT<br>GTATGGGGAGGTGGGGGACACCCTGCTGATCATCTTCAAGAACC<br>AGGCCAGCAGGCCCTACAACATCTACCCCCATGGCATCACTGAT<br>GTGAGGCCCCTGTACAGCAGGAGGCTGCCCAAGGGGGTGAAGC<br>ACCTGAAGGACTTCCCCATCCTGCCTGGGGAGATCTTCAAGTAC<br>AAGTGGACTGTGACTGTGGAGGATGGCCCCACCAAGTCTGACCC<br>CAGGTGCCTGACCAGATACTACAGCAGCTTTGTGAACATGGAGA<br>GGGACCTGGCCTCTGGCCTGATTGGCCCCCTGCTGATCTGCTAC<br>AAGGAGTCTGTGGACCAGAGGGGCAACCAGATCATGTCTGACA<br>AGAGGAATGTGATCCTGTTCTCTGTGTTTGATGAGAACAGGAGC<br>TGGTACCTGACTGAGAACATCCAGAGGTTCCTGCCCAACCCTGC<br>TGGGGTGCAGCTGGAGGACCCTGAGTTCCAGGCCAGCAACATC<br>ATGCACAGCATCAATGGCTATGTGTTTGACAGCCTGCAGCTGTC<br>TGTGTGCCTGCATGAGGTGGCCTACTGGTACATCCTGAGCATTG<br>GGGCCCAGACTGACTTCCTGTCTGTGTTCTTCTCTGGCTACACCT<br>TCAAGCACAAGATGGTGTATGAGGACACCCTGACCCTGTTCCCC<br>TTCTCTGGGGAGACTGTGTTCATGAGCATGGAGAACCCTGGCCT<br>GTGGATTCTGGGCTGCCACAACTCTGACTTCAGGAACAGGGGCA<br>TGACTGCCCTGCTGAAAGTCTCCAGCTGTGACAAGAACACTGGG<br>GACTACTATGAGGACAGCTATGAGGACATCTCTGCCTACCTGCT<br>GAGCAAGAACAATGCCATTGAGCCCAGGAACTTCAGCCAGAAT<br>TGCTCCCAGAACCCTCCAGTGCTGAAGAGAGAGATCACCAGGA<br>CCACCCTGCAGTCTGACCAGGAGGAGATTGACTATGATGACACC<br>ATCTCTGTGGAGATGAAGAAGGAGGACTTTGACATCTACGACG<br>AGGACGAGAACCAGAGCCCCAGGAGCTTCCAGAAGAAGACCAG<br>GCACTACTTCATTGCTGCTGTGGAGAGGCTGTGGGACTATGGCA<br>TGAGCAGCAGCCCCCATGTGCTGAGGAACAGGGCCCAGTCTGG<br>CTCTGTGCCCCAGTTCAAGAAGGTGGTGTTCCAGGAGTTCACTG<br>ATGGCAGCTTCACCCAGCCCCTGTACAGAGGGGAGCTGAATGA<br>GCACCTGGGCCTGCTGGGCCCCTACATCAGGGCTGAGGTGGAG<br>GACAACATCATGGTGACCTTCAGGAACCAGGCCAGCAGGCCCT<br>ACAGCTTCTACAGCAGCCTGATCAGCTATGAGGAGGACCAGAG<br>GCAGGGGGCTGAGCCCAGGAAGAACTTTGTGAAGCCCAATGAA<br>ACCAAGACCTACTTCTGGAAGGTGCAGCACCACATGGCCCCCAC<br>CAAGGATGAGTTTGACTGCAAGGCCTGGGCCTACTTCTCTGATG<br>TGGACCTGGAGAAGGATGTGCACTCTGGCCTGATTGGCCCCCTG<br>CTGGTGTGCCACACCAACACCCTGAACCCTGCCCATGGCAGGCA<br>GGTGACTGTGCAGGAGTTTGCCCTGTTCTTCACCATCTTTGATGA<br>AACCAAGAGCTGGTACTTCACTGAGAACATGGAGAGGAACTGC<br>AGGGCCCCCTGCAACATCCAGATGGAGGACCCCACCTTCAAGG |

TABLE 23-continued

Listing of additional protein and nucleic acid sequences referred to herein not included in the sequence listing

| Category | SEQ ID NO: | Description | Type | Sequence |
|---|---|---|---|---|
| | | | | AGAACTACAGGTTCCATGCCATCAATGGCTACATCATGGACACC<br>CTGCCTGGCCTGGTGATGGCCCAGGACCAGAGGATCAGGTGGT<br>ACCTGCTGAGCATGGGCAGCAATGAGAACATCCACAGCATCCA<br>CTTCTCTGGCCATGTGTTCACTGTGAGGAAGAAGGAGGAGTACA<br>AGATGGCCCTGTACAACCTGTACCCTGGGGTGTTTGAGACTGTG<br>GAGATGCTGCCCAGCAAGGCTGGCATCTGGAGGGTGGAGTGCC<br>TGATTGGGGAGCACCTGCATGCTGGCATGAGCACCCTGTTCCTG<br>GTGTACAGCAACAAGTGCCAGACCCCCCTGGGCATGGCCTCTGG<br>CCACATCAGGGACTTCCAGATCACTGCCTCTGGCCAGTATGGCC<br>AGTGGGCCCCCAAGCTGGCCAGGCTGCACTACTCTGGCAGCATC<br>AATGCCTGGAGCACCAAGGAGCCCTTCAGCTGGATCAAGGTGG<br>ACCTGCTGGCCCCCATGATCATCCATGGCATCAAGACCCAGGGG<br>GCCAGGCAGAAGTTCAGCAGCCTGTACATCAGCCAGTTCATCAT<br>CATGTACAGCCTGGATGGCAAGAAGTGGCAGACCTACAGGGGC<br>AACAGCACTGGCACCCTGATGGTGTTCTTTGGCAATGTGGACAG<br>CTCTGGCATCAAGCACAACATCTTCAACCCCCCCATCATTGCCA<br>GATACATCAGGCTGCACCCCACCCACTACAGCATCAGGAGCAC<br>CCTGAGGATGGAGCTGATGGGCTGTGACCTGAACAGCTGCAGC<br>ATGCCCCTGGGCATGGAGAGCAAGGCCATCTCTGATGCCCAGAT<br>CACTGCCAGCAGCTACTTCACCAACATGTTTGCCACCTGGAGCC<br>CCAGCAAGGCCAGGCTGCACCTGCAGGGCAGGAGCAATGCCTG<br>GAGGCCCCAGGTCAACAACCCCAAGGAGTGGCTGCAGGTGGAC<br>TTCCAGAAGACCATGAAGGTGACTGGGGTGACCACCCAGGGGG<br>TGAAGAGCCTGCTGACCAGCATGTATGTGAAGGAGTTCCTGATC<br>AGCAGCAGCCAGGATGGCCACCAGTGGACCCTGTTCTTCCAGAA<br>TGGCAAGGTGAAGGTGTTCCAGGGCAACCAGGACAGCTTCACC<br>CCTGTGGTGAACAGCCTGGACCCCCCCCTGCTGACCAGATACCT<br>GAGGATTCACCCCCAGAGCTGGGTGCACCAGATTGCCCTGAGG<br>ATGGAGGTGCTGGGCTGTGAGGCCCAGGACCTGTACTGATCGCG<br>AATAAAAGATCTTTATTTTCATTAGATCTGTGTGTTGGTTTTTTG<br>TGTGTATTACAGTATGATAGCTACTCAAAGCACTTTTTGTTCTTC<br>TCTTCACTGACCTAAGTGCCAGTTCCCGATCGTTACAGGAAATT<br>CAACTATAGCTACACGTG |
| Human FVIII donor cassette pMG4029_co4 F309S | 94 | pMG4029_co4_F309S (DNA sequence that encodes human FVIII in which the B-domain was replaced by the var4 B-domain replacement and F309 residue was changed to S. The DNA sequence was codon optimized using codon optimization copt4.Flanking guide | Nucleotide | ACGCGTACGTTAAAGCTTACGTTTTTCCTGTAACGATCGGGAAC<br>TGGCACTTAGGTCAGTGAAGAGAAGAACAAAAATATTTAGCTA<br>CTCAAAGCTTACTAAAGAATTATTCTTTTACATTTCAGTGGCCAC<br>CAGGAGATACTACCTGGGGGCTGTGGAGCTTAGCTGGGACTAC<br>ATGCAGTCTGACCTGGGGGAGCTGCCTGTGGATGCCAGATTCCC<br>ACCCAGAGTGCCCAAATCCTTCCCATTCAACACCAGCGTGGTCT<br>ACAAGAAGACCCTCTTTGTGGAGTTCACTGACCACCTGTTCAAC<br>ATTGCCAAACCCAGGCCACCCTGGATGGGACTCCTGGGACCCAC<br>CATTCAGGCTGAGGTCTATGACACTGTGGTCATCACCCTCAAGA<br>ACATGGCCTCCCACCCTGTGAGCCTGCATGCTGTGGGGGTCAGC<br>TACTGGAAGGCCTCTGAGGGGGCTGAGTATGATGACCAGACCTC<br>CCAGAGGGAGAAGGAGGATGACAAAGTGTTCCCTGGGGGCAGC<br>CACACCTATGTGTGGCAGGTCCTCAAGGAGAATGGCCCCATGGC |

TABLE 23-continued

Listing of additional protein and nucleic acid sequences referred to herein not included in the sequence listing

| Category | SEQ ID NO: | Description | Type | Sequence |
|---|---|---|---|---|
| | | target sites, splice acceptor and polyA signal are included | | CTCTGACCCACTCTGCCTGACCTACTCCTACCTTTCTCATGTGGA<br>CCTGGTCAAGGACCTCAACTCTGGACTGATTGGGGCCCTGCTGG<br>TGTGCAGAGAGGGCTCCCTGGCCAAAGAGAAGACCCAGACCCT<br>GCACAAGTTCATTCTCCTGTTTGCTGTCTTTGATGAGGGCAAGA<br>GCTGGCACTCTGAAACCAAGAACTCCCTGATGCAGGACAGGGA<br>TGCTGCCTCTGCCAGAGCCTGGCCCAAGATGCACACTGTGAATG<br>GCTATGTCAACAGGAGCCTGCCTGGACTCATTGGCTGCCACAGG<br>AAAAGCGTCTACTGGCATGTGATTGGCATGGGGACAACCCCTGA<br>GGTGCACTCCATTTTCCTGGAGGGCCACACCTTCCTGGTCAGAA<br>ACCACAGACAGGCCAGCCTGGAGATCAGCCCCATCACCTTCCTC<br>ACTGCCCAGACCCTGCTGATGGACCTCGGACAGTTCCTGCTGTC<br>TTGCCACATCAGCTCCCACCAGCATGATGGCATGGAGGCCTATG<br>TCAAGGTGGACAGCTGCCCTGAGGAGCCACAGCTCAGAATGAA<br>GAACAATGAGGAGGCTGAGGACTATGATGATGACCTGACTGAC<br>TCTGAGATGGATGTGGTCCGCTTTGATGATGACAACAGCCCATC<br>CTTCATTCAGATCAGGTCTGTGGCCAAGAAACACCCCAAGACCT<br>GGGTGCACTACATTGCTGCTGAGGAGGAGGACTGGGACTATGC<br>CCCACTGGTCCTGGCCCCTGATGACAGAAGCTACAAGAGCCAGT<br>ACCTCAACAATGGCCCACAGAGGATTGGACGGAAGTACAAGAA<br>AGTCAGGTTCATGGCCTACACTGATGAAACCTTCAAGACCAGAG<br>AGGCCATTCAGCATGAGTCTGGCATCCTGGGCCCACTCCTGTAT<br>GGGGAGGTGGGGGACACCCTGCTCATCATCTTCAAGAACCAGG<br>CCTCCAGGCCCTACAACATCTACCCACATGGCATCACTGATGTC<br>AGACCCCTGTACAGCCGCAGGCTGCCAAAGGGGGTCAAACACC<br>TCAAGGACTTCCCCATTCTGCCTGGGGAGATCTTCAAGTACAAG<br>TGGACTGTCACTGTGGAGGATGGACCAACCAAATCTGACCCCAG<br>ATGCCTCACCAGATACTACTCCAGCTTTGTGAACATGGAGAGGG<br>ACCTGGCCTCTGGCCTGATTGGCCCACTGCTCATCTGCTACAAG<br>GAGAGCGTGGACCAGAGGGGAAACCAGATCATGTCTGACAAGA<br>GGAATGTGATTCTGTTCTCTGTCTTTGATGAGAACAGGAGCTGG<br>TACCTGACTGAGAACATTCAGCGCTTCCTGCCCAACCCTGCTGG<br>GGTGCAGCTGGAGGACCCTGAGTTCCAGGCCAGCAACATCATG<br>CACTCCATCAATGGCTATGTCTTTGACAGCCTCCAGCTTTCTGTC<br>TGCCTGCATGAGGTGGCCTACTGGTACATTCTTTCCATTGGGGC<br>CCAGACTGACTTCCTTTCTGTCTTCTTCAGCGGCTACACCTTCAA<br>ACACAAGATGGTGTATGAGGACACCCTGACCCTCTTCCCATTCT<br>CTGGGGAGACTGTGTTCATGAGCATGGAGAACCCTGGCCTGTGG<br>ATTCTGGGATGCCACAACTCTGACTTCCGGAACAGAGGCATGAC<br>TGCCCTGCTCAAAGTCTCCTCCTGTGACAAGAACACTGGGGACT<br>ACTATGAGGACAGCTATGAGGACATCTCTGCCTACCTGCTCAGC<br>AAGAACAATGCCATTGAGCCCAGGAACTTCAGCCAGAATTGCTC<br>CCAGAACCCTCCAGTCCTGAAGAGAGAGATCACCAGAACCACC<br>CTCCAGTCTGACCAGGAGGAGATTGACTATGATGACACCATTTC<br>TGTGGAGATGAAGAAAGAGGACTTTGACATCTATGACGAGGAC<br>GAGAACCAGAGCCCAAGGAGCTTCCAGAAGAAGACCAGGCACT<br>ACTTCATTGCTGCTGTGGAGCGCCTGTGGGACTATGGCATGAGC<br>TCCAGCCCCCATGTCCTCAGAAACAGGGCCCAGTCTGGCTCTGT |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| | | | | CCCACAGTTCAAGAAAGTGGTCTTCCAAGAGTTCACTGATGGCA<br>GCTTCACCCAGCCCCTGTACAGAGGGGAGCTGAATGAGCACCTG<br>GGACTCCTGGGCCCATACATCAGGGCTGAGGTGGAGGACAACA<br>TCATGGTCACCTTCCGCAACCAGGCCTCCAGACCCTACAGCTTC<br>TACAGCTCCCTCATCAGCTATGAGGAGGACCAGAGGCAGGGGG<br>CTGAGCCACGGAAGAACTTTGTCAAACCCAATGAAACCAAGAC<br>CTACTTCTGGAAAGTCCAGCACCACATGGCCCCCACCAAGGATG<br>AGTTTGACTGCAAGGCCTGGGCCTACTTCAGCGATGTGGACCTG<br>GAGAAGGATGTCCACTCTGGCCTGATTGGCCCACTCCTGGTCTG<br>CCACACCAACACCCTGAACCCTGCCCATGGAAGACAAGTCACT<br>GTGCAGGAGTTTGCCCTCTTCTTCACCATCTTTGATGAAACCAA<br>GAGCTGGTACTTCACTGAGAACATGGAGCGCAACTGCAGAGCC<br>CCATGCAACATTCAGATGGAGGACCCCACCTTCAAAGAGAACT<br>ACCGGTTCCATGCCATCAATGGCTACATCATGGACACCCTGCCT<br>GGGCTTGTCATGGCCCAGGACCAGAGGATCAGATGGTACCTGCT<br>TAGCATGGGCTCCAATGAGAACATTCACTCCATCCACTTCAGCG<br>GGCATGTCTTCACTGTGCGCAAGAAGGAGGAGTACAAGATGGC<br>CCTGTACAACCTCTACCCTGGGGTCTTTGAGACTGTGGAGATGC<br>TGCCCTCCAAAGCTGGCATCTGGAGGGTGGAGTGCCTCATTGGG<br>GAGCACCTGCATGCTGGCATGAGCACCCTGTTCCTGGTCTACAG<br>CAACAAGTGCCAGACCCCCCTGGGAATGGCCTCTGGCCACATCA<br>GGGACTTCCAGATCACTGCCTCTGGCCAGTATGGCCAGTGGGCC<br>CCCAAGCTGGCCAGACTCCACTACTCTGGATCCATCAATGCCTG<br>GAGCACCAAGGAGCCATTCAGCTGGATCAAAGTGGACCTGCTG<br>GCCCCCATGATCATCCATGGCATCAAGACCCAGGGGGCCAGGC<br>AGAAGTTCTCCAGCCTGTACATCAGCCAGTTCATCATCATGTAC<br>AGCCTGGATGGCAAGAAATGGCAGACCTACAGAGGCAACTCCA<br>CTGGAACACTCATGGTCTTCTTTGGCAATGTGGACAGCTCTGGC<br>ATCAAGCACAACATCTTCAACCCCCCAATCATCGCCAGATACAT<br>CAGGCTGCACCCCACCCACTACAGCATCCGGAGCACCCTCAGA<br>ATGGAGCTGATGGGCTGTGACCTGAACTCCTGCAGCATGCCCCT<br>GGGCATGGAGAGCAAGGCCATTTCTGATGCCCAGATCACTGCCT<br>CCAGCTACTTCACCAACATGTTTGCCACCTGGAGCCCAAGCAAG<br>GCCAGGCTGCACCTCCAGGGAAGGAGCAATGCCTGGAGACCCC<br>AGGTCAACAACCCAAAGGAGTGGCTGCAGGTGGACTTCCAGAA<br>GACCATGAAGGTCACTGGGGTCACCACCCAGGGGGTCAAGAGC<br>CTGCTCACCAGCATGTATGTGAAGGAGTTCCTGATCAGCTCCAG<br>CCAGGATGGCCACCAGTGGACCCTCTTCTTCCAGAATGGCAAGG<br>TCAAGGTGTTCCAGGGCAACCAGGACAGCTTCACCCCTGTGGTG<br>AACAGCCTGGACCCCCCCCTCCTGACCAGATACCTGAGGATTCA<br>CCCCCAGAGCTGGGTCCACCAGATTGCCCTGAGAATGGAGGTCC<br>TGGGATGTGAGGCCCAGGACCTGTACTGATCGCGAATAAAAGA<br>TCTTTATTTTCATTAGATCTGTGTGTTGGTTTTTTGTGTGTATTAC<br>AGTATGATAGCTACTCAAAGCACTTTTTGTTCTTCTCTTCACTGA<br>CCTAAGTGCCAGTTCCCGATCGTTACAGGAAATTCAACTATAGC<br>TACACGTG |

TABLE 23-continued

| Listing of additional protein and nucleic acid sequences referred to herein not included in the sequence listing | | | | |
|---|---|---|---|---|
| Category | SEQ ID NO: | Description | Type | Sequence |
| Messenger RNA encoding the MG3-6/3-4 nuclease with nuclear localization signal added at both the N and C termini | 95 | MG3-6/3-4 mRNA sequence (includes 5' and 3' UTR and NLS sequences) | Nucleotide | ATGCATGCGCGGCCGCAAGCTTTAATACGACTCACTATAAGGAA AAGCCAGCTCCAGCAGGCGCTGCTCACTCCTCCCCATCCTCTCC CTCTGTCCCTCTGTCCCTCTGACCCTGCACTGTCCCAGCACCATG GCCCCCAAGAAGAAGCGGAAAGTTGGCGGCGGAGGCAGCAGCA CCGACATGAAGAACTACCGGATCGGCGTGGACGTGGGCGATAG ATCTGTTGGACTGGCCGCCATCGAGTTCGACGATGATGGACTGC CCATCCAGAAGCTGGCCCTGGTCACCTTTAGACACGATGGCGGA CTGGACCCCACCAAGAACAAGACCCCTATGAGCCGGAAAGAGA CACGGGGAATCGCCAGACGGACCATGCGGATGAACAGAGAGCG GAAGCGGCGGCTGAGAAACCTGGACAACGTGCTGGAAAACCTG GGCTACTCTGTGCCTGAGGGCCCTGAGCCTGAGACATATGAGGC CTGGACAAGCAGAGCCCTGCTGGCCTCTATCAAACTGGCCTCTG CCGACGAGCTGAACGAACACCTTGTCAGAGCCGTGCGGCACAT GGCCAGACATAGAGGATGGGCCAATCCTTGGTGGTCCCTGGACC AGCTGGAAAAGGCCAGCCAAGAGCCTAGCGAGACATTCGAGAT CATCCTGGCCAGAGCCAGAGAGCTGTTCGGCGAGAAGGTGCCC GCTAATCCTACACTGGGAATGCTGGGAGCCCTGGCCGCTAACAA TGAGGTGCTGCTGAGGCCCAGGGACGAGAAGAAGAGAAAGACC GGATACGTGCGGGGCACCCCTCTGATGTTTGCTCAAGTTCGACA GGGCGATCAGCTGGCCGAGCTGCGGAGAATTTGTGAAGTGCAG GGCATCGAGGACCAGTACGAGGCTCTGAGACTGGGCGTGTTCG ACCACAAGCACCCCTACGTGCCCAAAGAAAGAGTGGGCAAAGA CCCTCTGAACCCCAGCACCAACAGAACCATCAGAGCCAGCCTG GAATTTCAAGAGTTCCGCATCCTGGACAGCGTGGCCAATCTGAG AGTGCGGATCGGCAGCAGAGCCAAGAGGGAACTGACAGAGGCC GAGTATGATGCCGCCGTGGAATTCCTGATGGACTACGCCGACAA AGAGCAGCCTAGCTGGGCCGATGTGGCCGAGAAAATTGGCGTG CCCGGCAACAGACTGGTGGCCCCTGTTCTGGAAGATGTGCAGCA GAAAACAGCCCCTTACGACAGAAGCAGCGCCGCCTTTGAGAAG GCCATGGGCAAGAAAACCGAGGCCAGACAGTGGTGGGAGTCCA CCGATGATGACCAGCTGAGAAGCCTGCTGATTGCCTTCCTGGTG GACGCCACCAACGACACAGAAGAAGCCGCTGCTGAAGCCGGCC TGAGCGAGCTGTATAAGTCTTGGCCTGCCGAGGAAAGAGAGGC CCTGTCCAACATCGACTTCGAGAAGGGCAGAGTGGCCTACAGCC AAGAAACCCTGAGCAAGCTGAGCGAGTACATGCACGAGTACAG AGTGGGACTGCACGAGGCTAGAAAGGCCGTGTTCGGAGTGGAT GATACCTGGCGGCCTCCTCTGGATAAGCTGGAAGAACCTACAGG ACAGCCTGCCGTGGACAGAGTGCTGACCATCCTGAGAAGATTCG TGCTGGACTGCGAGCGGCAATGGGGCAGACCTAGAGCCATCAC CGTGGAACACACACGGACAGGCCTGATGGGCCCAACACAGAGA CAGAAGATCCTGAACGAGCAGAAGAAGAACCGGGCCGACAACG AGAGAATCCGGGATGAGCTGAGAGAATCTGGCGTGGACAACCC CTCCAGAGCCGAAGTTCGGAGACACCTGATCGTGCAAGAGCAA GAGTGCCAGTGCCTGTACTGCGGCACCATGATCACCACCACCAC AAGCGAGCTGGACCACATCGTTCCTAGAGCCGGTGGCGGCAGC AGCAGAAGGGAAAATCTGGCCGCTGTGTGCAGAGCCTGCAACG CCAAGAAGAAACGCGAGCTGTTCTACGCCTGGGCTGGCCCAGT |

TABLE 23-continued

Listing of additional protein and nucleic acid sequences referred to herein not included in the sequence listing

| Category | SEQ ID NO: | Description | Type | Sequence |
|---|---|---|---|---|
| | | | | GAAGTCCCAAGAGACAATCGAGAGAGTCAGACAGCTGAAGGCC<br>TTTAAGGACAGCAAGAAAGCCAAGATGTTCAAGAACCAGATCC<br>GCCGGCTGAACCAGACCGAGGCCGATGAGCCTATCGACGAAAG<br>AAGCCTGGCCAGCACATCTTACGCCGCTGTGGCCGTTAGAGAGC<br>GGCTGGAACAGCACTTCAACGAAGGCCTGGCACTGGACGACAA<br>GTCCAGAGTGGTGCTGGATGTGTATGCCGGCGCTGTGACCAGAG<br>AGTCTCGTAGAGCTGGCGGCATCGACGAGCGGATTCTGCTGAGA<br>GGCGAGCGGGACAAGAACAGATTCGATGTGCGGCATCACGCCG<br>TGGACGCTGCTGTTATGACCCTGCTGAACAGATCCGTGGCTCTG<br>ACCCTGGAACAGAGATCACAGCTGAGGCGGGCCTTCTACGAGC<br>TGGAACTGGACAAACTGGACCGGGACCAGCTCAAGCCTGGCGA<br>GGATTGGAGAAACTTCACCGGCCTGTACGAGGCCTCTCAGAACA<br>AGTTCAGCGAGTGGAAGAAAGCCGCCACAGTGCTGGGAGATCT<br>GCTGGCTGAAGCCATCGAGGATGACGCCATTGCCGTGGTGTCTC<br>CACTGAGACTGAGGCCCCAGAATGGCAGCGTGCACGACGATAC<br>CATCAACGCCGTGAAGAAGCTGACACTGGGCTCTGCCTGGCCTG<br>CAGACGCTGTGAAGAGAATCGTGGACCCCGAGATCTACCTGGCT<br>ATGAAGGACGTGCTGGGCAAGCTGAAAGAGCTGCCCGAGGATT<br>CTGCCAGATCTCTGGAACTGTCCGACGGCCGGTACATCGAAGCC<br>GATGACGAGGTGCTGTTCTTCCCAAAGAAGGCCGCTAGCATCCT<br>GACACCTAGAGGCGCCGCTGAGATCGGCAACTCTATCCACCATG<br>CCAGACTGTATAGCTGGCTGACCAAGAAGGGCGAGCTGAAGTT<br>TGGCATGCTGAGAGTGTACGGCGCCGAGTTTCCCTGGCTGATGA<br>GAGAGTCTGGAAGCCGCGACGTGCTGCATATGCCTATTCACCCT<br>GGCAGCCAGAGCTTCAGAGGCATGCAGGATGGCGTGCGGAAAG<br>CCGTGGAAAGCGGAGAGGCTGTGGAATTCGGCTGGATCACCCA<br>GGACGATGAGCTGGAATTCGACCCCGAGGACTACATTGCCCAC<br>GGCGGAGATGACGAACTGAACAGACTGCTGCGAGTGATGCCCG<br>AGAGAAGGTGGCGAGTGGACGGCTTCTATAACGCCGGCACACT<br>GAGAATCAGACCCGCTCTGCTGTCTGCTGAGCAGCTGCCTTCTG<br>AGCTGCAGAAAAAGGTGGCCGACAAGACCCTGAGCGACGTGGA<br>ACTGATCCTGCTGAGGGCTGTTCAGCGGGGACTGTTCGTGGCCA<br>TCAGCAGCTTTCTGCCCCTGGAAAGCCTGAAAGTGATCCGGCGG<br>AACAATCTGGGCTTCCCCAGGTGGCGCGGAAACGGAAATCTGC<br>CCACCAGCTTTGAAGTGCGGAGCAGCGCTCTGAGAGCCCTGGG<br>AGTTGAAGGATCTGGCGGAAAAAGACCTGCCGCCACAAAGAAA<br>GCCGGACAGGCCAAGAAAAAGAAGTGACCACACCCCCATTCCC<br>CCACTCCAGATAGAACTTCAGTTATATCTCACGTGTCTGGAGTT<br>GGATCCATGCATGC |
| Protein sequence of the MG3-6/3-4 nuclease with nuclear localization signal added at | 96 | MG3-6/3-4 protein sequence (includes NLS sequences) | Protein | MAPKKKRKVGGGGSSTDMKNYRIGVDVGDRSVGLAAIEFDDDGL<br>PIQKLALVTFRHDGGLDPTKNKTPMSRKETRGIARRTMRMNRERK<br>RRLRNLDNVLENLGYSVPEGPEPETYEAWTSRALLASIKLASADEL<br>NEHLVRAVRHMARHRGWANPWWSLDQLEKASQEPSETFEIILARA<br>RELFGEKVPANPTLGMLGALAANNEVLLRPRDEKKRKTGYVRGTP<br>LMFAQVRQGDQLAELRRICEVQGIEDQYEALRLGVFDHKHPYVPK |

TABLE 23-continued

| Category | SEQ ID NO: | Description | Type | Sequence |
|---|---|---|---|---|
| Listing of additional protein and nucleic acid sequences referred to herein not included in the sequence listing | | | | |
| both the N and C termini | | | | ERVGKDPLNPSTNRTIRASLEFQEFRILDSVANLRVRIGSRAKRELTEAEYDAAVEFLMDYADKEQPSWADVAEKIGVPGNRLVAPVLEDVQQKTAPYDRSSAAFEKAMGKKTEARQWWESTDDDQLRSLLIAFLVDATNDTEEAAAEAGLSELYKSWPAEEREALSNIDFEKGRVAYSQETLSKLSEYMHEYRVGLHEARKAVFGVDDTWRPPLDKLEEPTGQPAVDRVLTILRRFVLDCERQWGRPRAITVEHTRTGLMGPTQRQKILNEQKKNRADNERIRDELRESGVDNPSRAEVRRHLIVQEQECQCLYCGTMITTTTSELDHIVPRAGGGSSRRENLAAVCRACNAKKKRELFYAWAGPVKSQETIERVRQLKAFKDSKKAKMFKNQIRRLNQTEADEPIDERSLASTSYAAVAVRERLEQHFNEGLALDDKSRVVLDVYAGAVTRESRRAGGIDERILLRGERDKNRFDVRHHAVDAAVMTLLNRSVALTLEQRSQLRRAFYELELDKLDRDQLKPGEDWRNFTGLYEASQNKFSEWKKAATVLGDLLAEAIEDDAIAVVSPLRLRPQNGSVHDDTINAVKKLTLGSAWPADAVKRIVDPEIYLAMKDVLGKLKELPEDSARSLELSDGRYIEADDEVLFFPKKAASILTPRGAAEIGNSIHHARLYSWLTKKGELKFGMLRVYGAEFPWLMRESGSRDVLHMPIHPGSQSFRGMQDGVRKAVESGEAVEFGWITQDDELEFDPEDYIAHGGDDELNRLLRVMPERRWRVDGFYNAGTLRIRPALLSAEQLPSELQKKVADKTLSDVELILLRAVQRGLFVAISSFLPLESLKVIRRNNLGFPRWRGNGNLPTSFEVRSSALRALGVEGSGGKRPAATKKAGQAKKKK |
| Single guide RNA (sgRNA) mA364-34-1 with chemical modifications | 97 | sgRNA mA364-34-1 that targets mouse albumin intron 1 when combined with the MG3-6/3-4 nuclease (m: 2'-O-methyl modified base, *: Phosphorothioate bond) | Nucleotide | mC*mU*mU*AGGUCAGUGAAGAGAAGAAGUUGAGAAUCGAAAGAUUCUUAAUAAGGCAUCCUUCCGAUGCUGACUUCUCACCGUCCGUUAUCCAAUAGGAGCGGGCGGUAUGU*mU*mU*mU |
| Single guide RNA (sgRNA) mA364-59-1 with chemical modifications | 98 | sgRNA mA364-59-1 that targets mouse albumin intron 1 when combined with the MG3-6/3-4 nuclease (m: 2'-O-methyl modified base, *: Phosphorothioate bond) | Nucleotide | mA*mG*mG*CAGGCCCUAUGAGACCGUAGUUGAGAAUCGAAAGAUUCUUAAUAAGGCAUCCUUCCGAUGCUGACUUCUCACCGUCCGUUAUCCAAUAGGAGCGGGCGGUAUGU*mU*mU*mU |

mN: 2'-O-Methyl modified base N; fN: 2'-Fluoro modified base N; *: phosphorothioate linkage; N: standard ribonucleotide base While preferred embodiments of the present disclosure have been shown and described herein, it will be obvious to those skilled in the art that such embodiments are provided by way of example only. It is not intended that the disclosure be limited by the specific examples provided within the specification. While the disclosure has been described with reference to the aforementioned specification, the descriptions and illustrations of the embodiments herein are not meant to be construed in a limiting sense. Numerous variations, changes, and substitutions will now occur to those skilled in the art without departing from the disclosure. Furthermore, it shall be understood that all aspects of the disclosure are not limited to the specific depictions, configurations or relative proportions set forth herein which depend upon a variety of conditions and variables. It should be understood that various alternatives to the embodiments of the disclosure described herein may be employed in practicing the disclosure. It is therefore contemplated that the disclosure shall also cover any such alternatives, modifications, variations or equivalents. It is intended that the following claims define the scope of the disclosure and that methods and structures within the scope of these claims and their equivalents be covered thereby.

What is claimed is:

1. A method for supplementing liver enzyme expression in a subject in need thereof, comprising administering to the subject:

a) an endonuclease having the amino acid sequence of SEQ ID NO: 54;

b) an engineered guide polynucleotide capable of i) forming a complex with the endonuclease and ii) hybridizing to a target nucleic acid sequence within intron 1 of an albumin gene; and c) a donor template polynucleotide comprising a nucleic acid encoding a Factor VIII (FVIII) gene or a functional fragment thereof, thereby supplementing liver enzyme expression of Factor VIII in said subject, the nucleic acid having at least 98% sequence identity to any one of SEQ ID NOs: 12, 13, 16-23, 32, 33, or 56-59.

2. The method of claim 1, wherein the endonuclease is encoded by a nucleic acid having 100% sequence identity to any one of SEQ ID NOs: 31 or 53.

3. The method of claim 1, wherein the engineered guide polynucleotide has at least 90% sequence identity to any one of SEQ ID NOs: 14, 15, 24-27, 43-45, 50, 55, or 60-68.

4. The method of claim 1, wherein the target nucleic acid sequence has at least 90% or 100% sequence identity to any one of SEQ ID NOs: 1, 2-6, or 8.

5. The method of claim 1, wherein the nucleic acid has at least 90100% sequence identity to any one of SEQ ID NOs: 12, 13, 16-23, 32, 33, or 56-59.

6. The method of claim 1, wherein the FVIII gene or functional fragment thereof is codon-optimized to remove at least one cytosine-guanine (CG or CpG) motif.

7. The method of claim 1, wherein the FVIII gene or functional fragment thereof has at least 98% identity to SEQ ID NO: 10 and is modified to comprise a B-domain.

* * * * *